US011384144B2

(12) United States Patent
Scheinberg et al.

(10) Patent No.: US 11,384,144 B2
(45) Date of Patent: Jul. 12, 2022

(54) T CELL RECEPTOR-LIKE ANTIBODIES SPECIFIC FOR A PRAME PEPTIDE

(71) Applicants: MEMORIAL SLOAN-KETTERING CANCER CENTER, New York, NY (US); EUREKA THERAPEUTICS, INC., Emeryville, CA (US)

(72) Inventors: David A. Scheinberg, New York, NY (US); Tao Dao, New York, NY (US); Cheng Liu, Emeryville, CA (US); Hong Liu, El Sobrante, CA (US); Yiyang Xu, Pleasanton, CA (US); Su Yan, State College, PA (US)

(73) Assignees: MEMORIAL SLOAN-KETTERING CANCER CENTER, New York, NY (US); EUREKA THERAPEUTICS, INC., Emeryville, CA (US)

(*) Notice: Subject to any disclaimer, the term of this patent is extended or adjusted under 35 U.S.C. 154(b) by 213 days.

(21) Appl. No.: 15/817,673

(22) Filed: Nov. 20, 2017

(65) Prior Publication Data
US 2018/0148503 A1 May 31, 2018

Related U.S. Application Data

(63) Continuation of application No. PCT/US2016/033430, filed on May 20, 2016.

(60) Provisional application No. 62/165,603, filed on May 22, 2015.

(51) Int. Cl.
| C07K 16/30 | (2006.01) |
| C07K 16/46 | (2006.01) |
| C07K 16/28 | (2006.01) |
| A61K 47/68 | (2017.01) |
| G01N 33/574 | (2006.01) |
| A61K 39/00 | (2006.01) |
| C07K 14/00 | (2006.01) |

(52) U.S. Cl.
CPC .......... *C07K 16/28* (2013.01); *A61K 47/6849* (2017.08); *C07K 16/2809* (2013.01); *C07K 16/2833* (2013.01); *C07K 16/30* (2013.01); *C07K 16/3053* (2013.01); *G01N 33/57492* (2013.01); *A61K 39/0011* (2013.01); *A61K 2039/505* (2013.01); *A61K 2039/5156* (2013.01); *A61K 2039/5158* (2013.01); *C07K 14/00* (2013.01); *C07K 2317/21* (2013.01); *C07K 2317/31* (2013.01); *C07K 2317/32* (2013.01); *C07K 2317/34* (2013.01); *C07K 2317/41* (2013.01); *C07K 2317/56* (2013.01); *C07K 2317/565* (2013.01); *C07K 2317/622* (2013.01); *C07K 2317/732* (2013.01); *C07K 2319/03* (2013.01); *C07K 2319/33* (2013.01); *C07K 2319/74* (2013.01); *G01N 2333/705* (2013.01)

(58) Field of Classification Search
None
See application file for complete search history.

(56) References Cited

U.S. PATENT DOCUMENTS

| 4,956,778 A | 9/1990 | Naito |
| 5,091,513 A | 2/1992 | Huston et al. |
| 5,132,405 A | 7/1992 | Huston et al. |
| 5,225,539 A | 7/1993 | Winter |
| 5,530,101 A | 6/1996 | Queen et al. |
| 5,585,089 A | 12/1996 | Queen et al. |
| 5,677,425 A | 10/1997 | Bodmer et al. |
| 5,693,762 A | 12/1997 | Queen et al. |
| 5,714,350 A | 2/1998 | Co et al. |
| 5,869,046 A | 2/1999 | Presta et al. |

(Continued)

FOREIGN PATENT DOCUMENTS

| EP | 0 154 316 A2 | 9/1985 |
| EP | 0 401 384 A1 | 12/1990 |

(Continued)

OTHER PUBLICATIONS

Beiboer (J. Mol. Biol. (2000) 296:833-849) (Year: 2000).*
Johnson and Wu (Methods in Molecular Biology, Antibody Engineering: Methods and Protocols, vol. 248, p. 11-25, 2004) (Year: 2004).*
Chang (Blood, vol. 126, No. 23, p. 2527, 2015) (Year: 2015).*
Weidanz (Int. Rev. Immunol, vol. 30, No. 5-6, p. 328-340, 2011) (Year: 2011).*

(Continued)

*Primary Examiner* — Michael Allen
(74) *Attorney, Agent, or Firm* — Baker Botts L.L.P.

(57) ABSTRACT

The presently disclosed subject matter provides antigen-binding proteins that specifically bind to Preferentially expressed antigen of melanoma (PRAME), including humanized, chimeric and fully human antibodies against PRAME, antibody fragments (e.g., scFv, Fab and F(ab)$_2$), chimeric antigen receptors (CARs), fusion proteins, and conjugates thereof. The antigen-binding proteins and antibodies bind to a PRAME peptide/HLA class I molecule complex. Such antibodies, fragments, fusion proteins and conjugates thereof are useful for the treatment of PRAME associated diseases, including for example, breast cancer, ovarian cancer, melanoma, lung cancer, gastrointestinal cancer, brain tumor, head and neck cancer, renal cancer, myeloma, neuroblastoma, mantle cell lymphoma, chronic myelocytic leukemia, multiple myeloma, acute lymphoblastic leukemia (ALL), acute myeloid/myelogenous leukemia (AML), Non-Hodgkin lymphoma (NHL), and Chronic lymphocytic leukemia (CLL). The antibodies or antigen binding proteins may comprise one or more framework region amino acid substitutions designed to improve protein stability, antibody binding and/or expression levels.

46 Claims, 26 Drawing Sheets
Specification includes a Sequence Listing.

(56) References Cited

U.S. PATENT DOCUMENTS

| | | | |
|---|---|---|---|
| 6,121,022 | A | 9/2000 | Presta et al. |
| 6,165,745 | A | 12/2000 | Ward et al. |
| 6,180,370 | B1 | 1/2001 | Queen et al. |
| 6,350,861 | B1 | 2/2002 | Co et al. |
| 2003/0153043 | A1 | 8/2003 | Carr et al. |
| 2003/0157109 | A1 | 8/2003 | Corvalan et al. |
| 2003/0186355 | A1* | 10/2003 | Ossendorp ............ A61K 39/00 435/68.1 |
| 2004/0023864 | A1 | 2/2004 | Roczniak et al. |
| 2004/0141969 | A1 | 7/2004 | Floege et al. |
| 2005/0196754 | A1 | 9/2005 | Drmanac et al. |
| 2007/0004910 | A1 | 1/2007 | Sexton et al. |
| 2008/0095775 | A1 | 4/2008 | Lewis et al. |
| 2008/0124352 | A1* | 5/2008 | Diamond ........... A61K 39/0011 424/188.1 |
| 2010/0303801 | A1 | 12/2010 | Throsby et al. |
| 2011/0064726 | A1 | 3/2011 | Liu et al. |
| 2013/0029359 | A1* | 1/2013 | Kertesz ................ C07K 14/47 435/7.92 |
| 2013/0058936 | A1* | 3/2013 | Bruenker ............ C07K 16/468 424/136.1 |
| 2013/0171096 | A1 | 7/2013 | Hsieh et al. |
| 2013/0205102 | A1 | 11/2013 | Jones et al. |
| 2014/0348862 | A1 | 11/2014 | Kessler et al. |

FOREIGN PATENT DOCUMENTS

| | | |
|---|---|---|
| WO | WO 00/42072 A2 | 7/2000 |
| WO | WO 2004/022709 A2 | 3/2004 |
| WO | WO 2011/062634 A2 | 5/2011 |
| WO | WO 2011/147982 A2 | 12/2011 |

OTHER PUBLICATIONS

Paul (Fundamental Immunology, 3rd Edition, 1993, pp. 292-295) (Year: 1993).*
Bendig M. M. (Methods: A Companion to Methods in Enzymology, 1995; 8:83-93) (Year: 1995).*
Rudikoff et al. (Proceedings of the National Academy of Sciences USA, vol. 79, p. 1979-1983, 1982) (Year: 1982).*
Portolano (The Journal of Immunology, vol. 150, No. 3, p. 880-887, 1993) (Year: 1993).*
A2NYV5, UniProtKB/TrEMBL entry A2NYV5_HUMAN, Apr. 1, 2015 [online]. [Retrieved on Nov. 15, 2016]. Retrieved from the internet URL:http://www.uniprot.org/uniprot/A2NYV5.txt?version=31.
Allen, "Ligand-Targeted Therapeutics in Anticancer Therapy," Nat. Rev. Cancer 2:750-763 (2002).
Altschul et al., "Gapped BLAST and PSI-BLAST: a new generation of protein database search programs," Nucleic Acids Res. 25(17):3389-3402 (1997).
Altschul, et al., "Basic Local Alignment Search Tool," J. Mol. Biol. 215:403-410 (1990).
Arnon et al., "Monoclonal Antibodies for Immunotargeting of Drugs in Cancer Therapy," Monoclonal Antibodies and Cancer Therapy, pp. 243-256 (1985).
Asano et al., "Cytotoxic Enhancement of a Bispecific Diabody by Format Conversion to Tandem Single-chain Variable Fragment (taFv) The Case of the hEx3 Diabody," J. Biol. Chem 286(3):1812-1818 (2011).
Azinovic et al., "Survival benefit associated with human anti-mouse antibody (HAMA) in patients with B-cell malignancies," Cancer Immunol Immunother 55:1451-1458 (2006).
Benton et al., "Screening λgt Recombinant Clones by Hybridization to Single Plaques in situ," Science 196(4286):180-182 (1977).
Bird et al., "Single-Chain Antigen-Binding Proteins," Science 242(4877):423-426 (1988).
Bregni et al., "Human Peripheral Blood Hematopoietic Progenitors are Optimal Targets of Retroviral-Mediated Gene Transfer," Blood 80(6):1418-1422 (1992).

Brennan et al., "Preparation of Bispecific Antibodies by Chemical Recombination of Monoclonal Immunoglobulin G1 Fragments," Science 229:81-83 (1985).
Brentjens et al., "Safety and persistence of adoptively transferred autologous CD19-targeted T cells in patients with relapsed or chemotherapy refractory B-cell leukemias," Blood 118(18):4817-4828 (2011).
Brigham et al., "Rapid Communication: In vivo Transfection of Murine Lungs with a Functioning Prokaryotic Gene Using a Liposome Vehicle," Am. J. Med. Sci. 298(4):278-281 (1989).
Brocks et al., "A TNF receptor antagonistic scFv, which is not secreted in mammalian cells, is expressed as a soluble mono- and bivalent scFv derivative in insect cells," Immunotechnology 3:173-184 (1997).
Caron et al., "Engineered Humanized Dimeric Forms of IgG are More Effective Antibodies," J Exp. Med 176:1191-1195 (1992).
Chames et al., "Direct selection of a human antibody fragment directed against the tumor T-cell epitope HLA-A1-MAGE-A1 from a nonimmunized phage-Fab library," PNAS USA 97(14):7969-7974 (2000).
Chen et al., "Selection and Analysis of an Optimized Anti-VEGF Antibody: Crystal Structure of an Affinity-matured Fab in Complex with Antigen," J. Mol. Biol. 293:865-881(1999).
Cox et al., "A Directory of Human Germ-line $V_\chi$ Segments Reveals a Strong Bias in their Usage," Eur. J. Immunol. 24:827-836 (1994).
Cuesta et al., "Multivalent antibodies: when design surpasses evolution," Trends in Biotechnology 28(7):355-362 (2010).
Danos et al., "Safe and efficient generation of recombinant retroviruses with amphotropic and ecotropic host ranges," PNAS USA 85:6460-6464 (1988).
Doolan et al., "Prevalence and prognostic and predictive relevance of PRAME in breast cancer," Breast Cancer Res Treat. 109:359-365 (2008).
Doronina et al., "Development of potent monoclonal antibody auristatin conjugates for cancer therapy," Nat Biotechnol. 21(7):778-784 (2003).
Epel et al., "Targeting TARP, a novel breast and prostate tumor-associated antigen, with T cell receptor-like human recombinant antibodies," Eur J Immunol. 3 8(6):1706-1720 (2008).
Epping et al., "The Human Tumor Antigen PRAME is a Dominant Repressor of Retinoic Acid Receptor Signaling," Cell 122:835-847 (2005).
Felgner et al., "Lipofection: A highly efficient, lipid-mediated DNA-transfection procedure," PNAS USA 84:7413-7417 (1987).
Fife et al., "Inhibition of T cell activation and autoimmune diabetes using a B cell surface-linked CTLA-4 agonist," J Clin Invest 116(8):2252-2261 (2006).
Gerber et al., "Characterization of chronic myeloid leukemia stem cells," Am J Hematol. 86(1):31-37 (2011).
Giomarelli et al., "Inhibition of thrombin-induced platelet aggregation using human single-chain Fv antibodies specific for TREM-like transcript-I," Thromb Haemost 97:955-963 (2007).
Glennie et al., "Preparation and performance of bispecific F(ab' gamma)2 antibody containing thioether-linked Fab' gamma fragments," J. Immunol. 139:2367-2375 (1987).
Greiner et al., "Simultaneous expression of different immunogenic antigens in acute myeloid leukemia," Exp Hematol. 28:1413-1422 (2000).
Griffioen et al., "Detection and Functional Analysis of CD8+ T cells Specific for PRAME: a Target for T-cell Therapy," Clin Cancer Res 12(10):3130-3136 (2006).
Grunstein et al., "Colony hybridization: A method for the isolation of cloned DNAs that contain a specific gene," PNAS USA 72(10):3961-3965 (1975).
Gunasekaran et al., "Enhancing Antibody Fc Heterodimer Formation through Electrostatic Steering Effects," J Biol. Chem. 285(25):19637-19646 (2010).
Harris et al., "Crystallographic Structure of an Intact IgG1 Monoclonal Antibody," Journal of Molecular Biology 275:861-872 (1998).
Held et al., "Dissecting cytotoxic T cell responses towards the NY-ESO-1 protein by peptide/MHC-specific antibody fragments," Eur J. Immunol. 34:2919-2929 (2004).

(56) References Cited

OTHER PUBLICATIONS

Hellstrom et al., "Antibodies for Drug Delivery," in Controlled Drug Delivery (2nd Ed.), Robinson et al. (eds.), pp. 623-653 (1987).
Ho et al., "Inhibition of Cocaine Binding to the Human Dopamine Transporter by a Single Chain Anti-Idiotypic Antibody: Its Cloning, Expression and Functional Properties," BioChim Biophys Acta 1638(3):257-266 (2003).
Hughes et al., "Retroviral Gene Transfer to Primitive Normal and Leukemic Hematopoietic Cells Using Clinically Applicable Procedures," J. Clin. Invest. 89:1817-1824 (1992).
Huston et al., "Protein engineering of antibody binding sites: Recovery of specific activity in an anti-digoxin single-chain Fv analogue produced in *Escherichia coli*," PNAS USA 85:5879-5883 (1988).
Ikeda et al., "Characterization of an Antigen that is Recognized on a Melanoma Showing Partial HLA Loss by CTL Expressing an NK Inhibitory Receptor," Immunity 6:199-208 (1997).
International Search Report dated Mar. 13, 2017 in International Application No. PCT/US16/33430.
Jones et al., "Replacing the complementarity-determining regions in a human antibody with those from a mouse," Nature 321:522-525 (1986).
Kabat et al., Sequences of Proteins of Immunological Interest, vol. 1, Fifth Edition, U.S. Department of Health and Human Services, NIH Publication No. 91-3242 (1991).
Karpovsky et al., "Production of Target-Specific Effector Cells Using Hetero-Cross-Linked Aggregates Containing Anti-Target Cell and Anti-Fcγ Receptor Antibodies," J. Exp. Med. 160:1686-1701 (1984).
Kessler et al., "Efficient Identification of Novel HLA-A*0201-Presented Cytotoxic T Lymphocyte Epitopes in the Widely Expressed Tumor Antigen PRAME by Proteasome-mediated Digestion Analysis," J Exp. Med. 193(1):73-88 (2001).
Kimmel, "[54] Identification and Characterization of Specific Clones: Strategy for Confirming the Validity of Presumptive Clones," Methods Enzymol. 152:507-511 (1987).
Klechevsky et al., "Antitumor activity of immunotoxins with T-cell receptor-like specificity against human melanoma xenografts," Cancer Res 68(15):6360-6367 (2008).
Kobayashi et al., "Defining MHC class II T helper epitopes for WT1 tumor antigen," Cancer Immunol. Immunother. 55:850-860 (2006).
Ledbetter et al., "Agonistic Activity of a CD40-Specific Single-Chain Fv Constructed from the Variable Regions of mAb G28-5," Crit Rev Immunol 17:427-435 (1997).
Lev et al., "Isolation and Characterization of Human Recombinant Antibodies Endowed with the Antigen-specific, Major Histocompatibility Complex-restricted Specificity of T Cells Directed toward the Widely Expressed Tumor T-cell Epitopes of the Telomerase Catalytic Subunit," Cancer Res 62:3184-3194 (2002).
Li et al., "Immunotherapy for patients with acute myeloid leukemia using autologous dendritic cells generated from leukemic blasts," Int J Oncol. 28:855-861 (2006).
Liu et al., "Heteroantibody duplexes target cells for lysis by cytotoxic T lymphocytes," Proc. Natl. Acad. Sci. USA 82:8648-8652 (1985).
Loffler et al., "A recombinant bispecific single-chain antibody, CD19 3 CD3, induces rapid and high lymphoma-directed cytotoxicity by unstimulated T lymphocytes," Blood 95:2098-2103 (2000).
Luetkens et al., "Expression, epigenetic regulation, and humoral immunogenicity of cancer-testis antigens in chronic myeloid leukemia," Leuk Res. 34:1647-1655 (2010).
Martin et al., "Application of AlMe3-Mediated Amidation Reactions to Solution Phase Peptide Synthesis," Tetrahedron Letters 39:1517-1520 (1998).
Matsushita et al., "Preferentially Expressed Antigen of Melanoma (PRAME) in the Development of Diagnostic and Therapeutic Methods for Hematological Malignancies," Leuk Lymphoma. 44(3):439-444 (2003).
McCafferty et al., "Phage antibodies: filamentous phage displaying antibody variable domains," Nature 348:552-554 (1990).

Meyers et al., "Optimal alignments in linear space," Cabios 4(1):11-17 (1988).
Miederer et al., "Realizing the potential of the Actinium-225 radionuclide generator in targeted alpha-particle therapy applications," Adv Drug Deliv Rev 60(12):1371-1382 (2008).
Miller et al., "Generation of Helper-Free Amphotropic Retroviruses That Transduce a Dominant-Acting, Methotrexate-Resistant Dihydrofolate Reductase Gene," Mol. Cell. Biol. 5(3):431-437 (1985).
Miller et al., "Redesign of Retrovirus Packaging Cell Lines to Avoid Recombination Leading to Helper Virus Production," Mol. Cell. Biol. 6(8):2895-2902 (1986).
Molecular Cloning: a Laboratory Manual 3rd edition, J.F. Sambrook and D.W. Russell, ed. Cold Spring Harbor Laboratory Press 2001.
Moosmayer et al., "A single-chain TNF receptor antagonist is an effective inhibitor of TNF mediated cytotoxicity," Thera Immunol. 2:31-40 (1995).
Muller et al., "Improved Pharmacokinetics of Recombinant Bispecific Antibody Molecules by Fusion to Human Serum Albumin," J Biol. Chem 282(17):12650-12660 (2007).
Needleman et al., "A General Method Applicable to the Search for Similarities in the Amino Acid Sequence of Two Proteins," J. Mol. Biol. 48:443-453 (1970).
Neumann et al., "Fab antibodies capable of blocking T cells by competitive binding have the identical specificity but a higher affinity to the MHC-peptide-complex than the T cell receptor," Immunol Lett. 125:86-92 (2009).
Noy et al., "T-cell receptor-like antibodies: novel reagents for clinical cancer immunology and immunotherapy," Expert Rev. Anticancer Ther. 5(3):523-536 (2005).
Oehler et al., "The preferentially expressed antigen in melanoma (PRAME) inhibits myeloid differentiation in normal hematopoietic and leukemic progenitor cells," Blood 114:3299-3308 (2009).
Oka et al., "WT1 Peptide Cancer Vaccine for Patients with Hematopoietic Malignancies and Solid Cancers," The Scientific World Journal 7:649-665 (2007).
Ono et al., "Plasmid DNAs directly injected into mouse brain with lipofectin can be incorporated and expressed by brain cells," Neuroscience Letters 117:259-263 (1990).
Pastan et al., "Immunotoxins in cancer therapy," Curr. Opin. Investig. Drugs 3(7):1089-1091 (2002).
Paulus, "Preparation and Biomedical Applications of Bispecific Antibodies," Behring Ins. Mitt. 78:118-132 (1985).
Payne, "Progress in immunoconjugate cancer therapeutics," Cancer Cell 3:207-212 (2003).
Persic et al., "An integrated vector system for the eukaryotic expression of antibodies or their fragments after selection from phage display libraries," Gene 187:9-18 (1997).
Peter et al., "Protective effects of an anti-melanocortin-4 receptor scfV derivative in lipopolysaccharide-induced cachexia in rats," J Cachexia Sarcopenia Muscle 4:79-88 (2013).
Peter et al., "scFv Single Chain Antibody Variable Fragment as Inverse Agonist of the β2-Adrenergic Receptor," J Biol. Chem. 278(38):36740-36747 (2003).
Proto-Siqueira et al., "PRAME is a membrane and cytoplasmic protein aberrantly expressed in chronic lymphocytic leukemia and mantle cell lymphoma," Leuk Res. 30:1333-1339 (2006).
Proto-Siqueira et al., "The expression of PRAME in chronic lymphoproliferative disorders," Leuk Res. 27:393-396 (2003).
Qin et al., "Expression patterns of WT1 and PRAME in acute myeloid leukemia patients and their usefulness for monitoring minimal residual disease," Leuk Res. 33:384-390 (2009).
Queen et al., "A humanized antibody that binds to the interleukin 2 receptor," Proc Natl Acad Sci USA 86:10029-10033 (1989).
Quintarelli et al., "Cytotoxic T lymphocytes directed to the preferentially expressed antigen of melanoma (PRAME) target chronic myeloid leukemia," Blood 112:1876-1885 (2008).
Quintarelli et al., "High-avidity cytotoxic T lymphocytes specific for a new PRAME-derived peptide can target leukemic and leukemic-precursor cells," Blood 117(12):3353-3362 (2011).
Rezvani et al., "Ex vivo characterization of polyclonal memory CD8+ T-cell responses to PRAME-specific peptides in patients with

(56) References Cited

OTHER PUBLICATIONS acute lymphoblastic leukemia and acute and chronic myeloid leukemia," Blood 113:2245-2255 (2009).
Riechmann et al., "Reshaping human antibodies for therapy," Nature 332:323-327 (1988).
Ritter et al., "Serological Analysis of Human Anti-Human Antibody Responses in Colon Cancer Patients Treated with Repeated Doses of Humanized Monoclonal Antibody A33," Cancer Res 61:6851-6859 (2001).
Roberts et al., "Vaccination with CD20 peptides induces a biologically active, specific immune response in mice," Blood 99:3748-3755 (2002).
Roman-Gomez et al., "Epigenetic regulation of PRAME gene in chronic myeloid leukemia," Leuk Res. 31:1521-1528 (2007).
Rossi et al., "Stably tethered multifunctional structures of defined composition made by the dock and lock method for use in cancer targeting," PNAS USA 103(18):6841-6846 (2006).
S25754, GenPept Accession No. S25754, Ig lambda chain—human (fragment), Jan. 21, 2000 [online]. [Retrieved on Nov. 15, 2016]. Retrieved from the internet <URL: https //www.ncbi.nlm.nih.gov/protein/S25754>.
Saito et al., "Drug delivery strategy utilizing conjugation via reversible disulfide linkages: role and site of cellular reducing activities," Adv. Drug Deliv. Rev. 55:199-215 (2003).
Saito et al., "Induction of cell cycle entry eliminates human leukemia stem cells in a mouse model of AML," Nat Biotechnol. 28(3):275-280 (2010).
Sakashita et al., "9-cis-Retinoic Acid: Effects on Normal and Leukemic Hematopoiesis In Vitro," Blood 81(4):1009-1016 (1993).
Sambrook et al., Molecular Cloning: A Laboratory Manual, $2^{nd}$ Edition, Cold Spring Harbor Laboratory Press, New York (1989).
Schuler et al., "SYFPEITHI Database for Searching and T-Cell Epitope Prediction," Methods in Molecular Biology 409:75-93 (2007).
Segal et al., "Identification of cancer-testis genes expressed by melanoma and soft tissue sarcoma using bioinformatics," Cancer Immun. 5:2 (2005).
Senter et al., "Selective activation of anticancer prodrugs by monoclonal antibody—enzyme conjugates," Adv. Drug Deliv. Rev. 53:247-264 (2001).
Sergeeva et al., "An anti-PR1/HLA-A2 T-cell receptor-like antibody mediates complement-dependent cytotoxicity against acute myeloid leukemia progenitor cells," Blood 117(16):4262-4272 (2011).
Shieh et al., "Transgenic Expression of Single-Chain Anti-CTLA-4 Fv on β Cells Protects Nonobese Diabetic Mice from Autoimmune Diabetes," J Immunol., 183:2277-2285 (2009).
Singh et al., "ProPred: prediction of HLA-DR binding site," Bioinformatics 17(12):1236-1237 (2001).
Straubinger et al., "Liposomes as Carriers for Intracellular Delivery of Nucleic Acids," Methods in Enzymology 101:512-527 (1983).
Sutherland et al., "Anti- leukemic activity of lintuzumab (SGN-33) in preclinical models of acute myeloid leukemia," mAbs 1(5):481-490 (2009).
Thorpe et al., "The Preparation and Cytotoxic Properties of Antibody-Toxin Conjugates," Immunol. Rev., 62:119-158 (1982).
Thorpe, "Antibody Carriers of Cytotoxic Agents in Cancer Therapy: A Review," in Monoclonal Antibodies 84: Biological and Clinical Applications, Pinchera et al. (eds.), pp. 475-506 (1985).
Tjandra et al., "Development of human anti-murine antibody (HAMA) response in patients," Immunol Cell Biol. 68:367-376 (1990).
Tomimatsu et al., "Production of Human Monoclonal Antibodies against FcεRIα by a Method Combining in-vitro Immunization with Phage Display," Biosci Biotechnol Biochem 73(7):1465-1469 (2009).
Tomlinson et al., "The Repertoire of Human Germline VH Sequences Reveals about Fifty Groups of VH Segments with Different Hypervariable Loops," J. Mol. Biol. 227:776-798 (1992).
Trail et al., "Monoclonal antibody drug immunoconjugates for targeted treatment of cancer," Cancer Immunol. Immunother. 52:328-337 (2003).
Van Baren et al., "PRAME, a gene encoding an antigen recognized on a human melanoma by cytolytic T cells, is expressed in acute leukaemia cells," Br J Haematol. 102:1376-1379 (1998).
Verma et al., "TCR Mimic Monoclonal Antibodies Induce Apoptosis of Tumor Cells via Immune Effector-Independent Mechanisms," J Immunol. 186:3265-3276 (2011).
Vulcani-Freitas et al., "PRAME gene expression profile in medulloblastoma," Arq Neuropsiquiatr. 69(1):9-12 (2011).
Wadelin et al., "Leucine-rich repeat protein PRAME: expression, potential functions and clinical implications for leukaemia," Mol. Cancer 9:226 (2010).
Wahl et al., "[43] Molecular Hybridization of Immobilized Nucleic Acids: Theoretical Concepts and Practical Considerations," Methods Enzymol. 152:399-407 (1987).
Wahl et al., "Improved Radioimaging and Tumor Localization with Monoclonal F(ab')2," J. Nucl. Med. 24:316-325 (1983).
Ward et al., "Binding activities of a repertoire of single immunoglobulin variable domains secreted from *Escherichia coli*," Nature 341:544-546 (1989).
Weiner et al., "The role of T cell activation in anti-CD3 x antitumor bispecific antibody therapy," J Immunology 152:2385-2392 (1994).
Wittman et al., "Antibody Targeting to a Class I MHC-Peptide Epitope Promotes Tumor Cell Death," J Immunol. 177:4187-4195 (2006).
Wolff et al., "Direct Gene Transfer into Mouse Muscle in Vivo," Science 247(4949):1465-1468 (1990).
Wu et al., "Receptor-mediated Gene Delivery and Expression in Vivo," Journal of Biological Chemistry 263(29):14621-14624 (1988).
Wu et al., "Targeting Genes: Delivery and Persistent Expression of a Foreign Gene Driven by Mammalian Regulatory Elements in Vivo," Journal of Biological Chemistry 264(29):16985-16987 (1989).
Xie et al., "Direct demonstration of MuSK involvement in acetylcholine receptor clustering through identification of agonist ScFv," Nat Biotech 15:768-771 (1997).
Xu et al., "Correction of the enzyme deficiency in hematopoietic cells of Gaucher patients using a clinically acceptable retroviral supernatant transduction protocol," Exp. Hemat. 22:223-230 (1994).
Yasmina et al., "Probing the binding mechanism and affinity of tanezumab, a recombinant humanized anti-NGF monoclonal antibody, using a repertoire of biosensors," Protein Science 17:1326-1335 (2008).
Zarrinkar et al., "AC220 is a uniquely potent and selective inhibitor of FLT3 for the treatment of acute myeloid leukemia (AML)," Blood 114:2984-2992 (2009).
Zhao et al., "Characteristics of an scFv Antibody Fragment That Binds to Immunoglobulin G of Graves' Disease Patients and Inhibits Autoantibody-Mediated Thyroid-Stimulating Activity," Hybridoma 27(6):445-451 (2008).
Amir et al., "PRAME-specific Allo-HLA-Restricted T cells with Potent Antitumor Reactivity Useful for Therapeutic T-cell Receptor Gene Transfer," Clinical Cancer Research 17(17):5615-5625 (2011).
Chang et al., "A therapeutic T cell receptor mimic antibody targets tumor-associated PRAME peptide/HLA-I antigens," Journal of Clinical Investigation, 127(7):2705-2718 (2017).
Costessi et al., "The tumour antigen PRAME is a subunit of a Cul2 ubiquitin ligase and associates with active NFY promoters," The EMBO Journal, 30:3786-3798 (2011).
Supplementary Partial European Search Report dated Nov. 23, 2018 in EP Application No. 16800529.
Yao et al., "Increased PRAME-Specific CTL Killing of Acute Myeloid Leukemia Cells by Either a Novel Histone Deacetylase Inhibitor Chidamide Alone or Combined Treatment with Decitabine," PLoS ONE, 8(8):e70522 (2013).

* cited by examiner

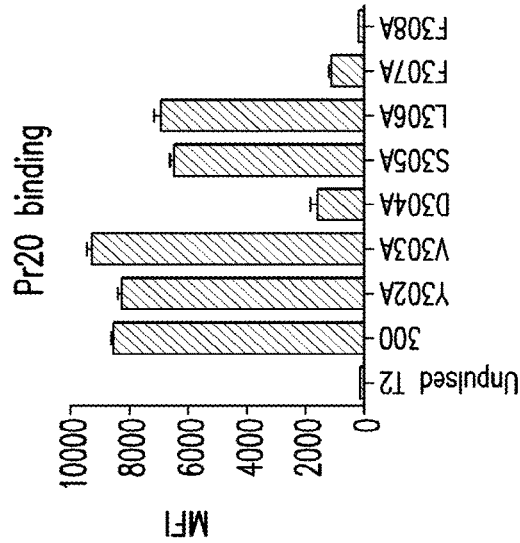
FIG. 6A
PRAME300: ALYVDSLFFL (SEQ ID NO: 678)
Y302A: ALAVDSLFFL (SEQ ID NO: 679)
V303A: ALYADSLFFL (SEQ ID NO: 680)
D304A: ALYVASLFFL (SEQ ID NO: 681)
S305A: ALYVDALFFL (SEQ ID NO: 682)
L306A: ALYVDSAFFL (SEQ ID NO: 683)
F307A: ALYVDSLAFL (SEQ ID NO: 684)
F308A: ALYVDSLFAL (SEQ ID NO: 685)
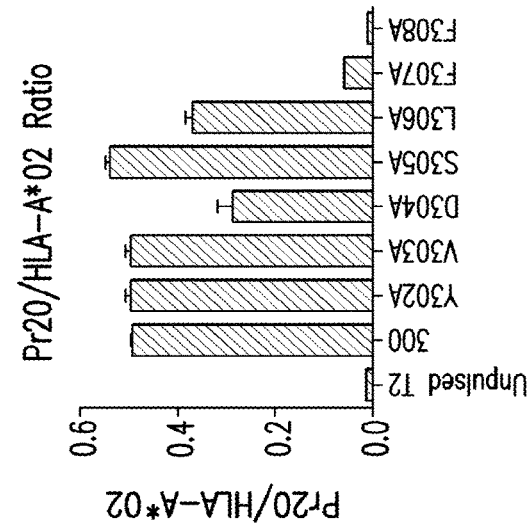
FIG. 6B
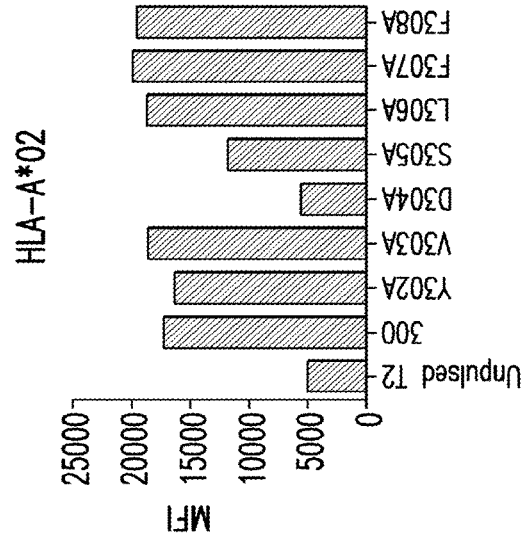
FIG. 6C
FIG. 6D

| Sample | Median:<APC-A> |
|---|---|
| ——— BV173_#29_Cold#20_APC.fcs | 1375 |
| -------- BV173_#20_Cold+hIgG_APC.fcs | 201 |
| —·—·— BV173_#20_Cold+#20_APC.fcs | 220 |
| ——— BV173_Pr300-hIgG_APC 3µg_ml.fcs | 210 |
| ——— BV173_Pr300-#20_APC 3µg_ml.fcs | 1650 |

| Sample | Median:<APC-A> |
|---|---|
| ——— HL-60_#29_Cold#20_APC.fcs | 137 |
| -------- HL-60_#20_Cold+hIgG_APC.fcs | 140 |
| —·—·— HL-60_#20_Cold+#20_APC.fcs | 121 |
| ——— HL-60_Pr300-hIgG_APC 3µg_ml.fcs | 139 |
| ——— HL-60_Pr300-#20_APC 3µg_ml.fcs | 150 |

T CELL RECEPTOR-LIKE ANTIBODIES SPECIFIC FOR A PRAME PEPTIDE

CROSS REFERENCE TO RELATED APPLICATIONS

This application is a Continuation of International Patent Application No. PCT/US16/33430 filed May 20, 2016, which claims priority to U.S. Provisional Application No. 62/165,603, filed May 22, 2015, priority to each of which is claimed, and the contents of each of which are incorporated by reference in their entireties.

GRANT INFORMATION

This invention was made with government support under Grant No. P30 CA008748 from National Institutes of Health. The government has certain rights in the presently disclosed subject matter.

SEQUENCE LISTING

The specification further incorporates by reference the Sequence Listing submitted herewith via EFS on Nov. 20, 2017. Pursuant to 37 C.F.R. § 1.52(e)(5), the Sequence Listing text file, identified as 0727340398CONSEQ.txt, is 464,160 bytes and was created on Nov. 20, 2017. The entire contents of the Sequence Listing are hereby incorporated by reference. The Sequence Listing does not extend beyond the scope of the specification and thus does not contain new matter.

TECHNICAL FIELD

The presently disclosed subject matter relates generally to antibodies against cytosolic proteins. More particularly, the presently disclosed subject matter relates to antibodies against preferentially expressed antigen of melanoma (PRAME), specifically antibodies that recognize a PRAME peptide in conjunction with a major histocompatibility complex ("MHC").

BACKGROUND OF THE PRESENTLY DISCLOSED SUBJECT MATTER

For induction of CTL responses, intracellular proteins are usually degraded by the proteasome or endo/lysosomes, and the resulting peptide fragments bind to MHC class I or II molecules. These peptide-MHC complexes are displayed at the cell surface where they provide targets for T cell recognition via a peptide-MHC (pMHC)-T cell receptor (TCR) interaction (Oka et al., *The Scientific World Journal* 2007; 7: 649-665; Kobayashi et al., *Cancer Immunol. Immunother.* 2006; 55 (7): 850-860).

To improve efficacy, cancer antigens can be targeted with monoclonal antibody therapy. Monoclonal antibody (mAb) therapy has been shown to exert powerful antitumor effects by multiple mechanisms, including complement-dependent cytotoxicity (CDC), antibody-dependent cellular cytotoxicity (ADCC) and direct cell inhibition or apoptosis-inducing effects on tumor cells that over-express the target molecules. Furthermore, mAb can be used as carriers to specifically deliver a cytotoxic moiety such as a radionuclide, cytotoxic drug or toxin to the tumor cells (Miederer et al., *Adv Drug Deliv Rev* 2008; 60 (12): 1371-1382).

A tremendous benefit would exist if, in addition to a cellular immunotherapy approach, a humoral immunotherapy approach was available to target non-cell surface tumor antigens. Therefore, a monoclonal antibody (mAb) that mimics a T cell receptor in that it is specific for a target comprising a fragment of an intracellular protein in conjunction with an MHC molecule, for example, a PRAME peptide/HLA-A2 complex, would be a novel and effective therapeutic agent alone or as a vehicle capable of delivering potent anti-cancer reagents, such as drugs, toxins and radioactive elements. Such mAbs would also be useful as diagnostic or prognostic tools. PRAME is expressed in more than 80% of acute and chronic leukemias, Myelodysplastic syndrome (MDS) and a fraction of melanoma, sarcoma, gastrointestinal cancer, renal cancer, breast cancer, lung cancer, among others. PRAME is expressed in the cancer stem cell as documented in some systems. 40% of people in the United States express HLA-A2. Therefore, there is a large unmet need and large patient population for this drug.

SUMMARY OF THE PRESENTLY DISCLOSED SUBJECT MATTER

The presently disclosed subject matter identifies and characterizes antigen-binding proteins, such as antibodies, that are able to target cytosolic/intracellular proteins, for example, the PRAME oncoprotein. The disclosed antibodies target a peptide/MHC complex as it would typically appear on the surface of a cell following antigen processing of PRAME protein and presentation by the cell. In that regard, the antibodies mimic T-cell receptors in that the antibodies have the ability to specifically recognize and bind to a peptide in an MHC-restricted fashion, that is, when the peptide is bound to an MHC antigen. The peptide/MHC complex recapitulates the antigen as it would typically appear on the surface of a cell following antigen processing and presentation of the PRAME protein to a T-cell.

The antibodies disclosed herein specifically recognize and bind to epitopes of a peptide/MHC complex (e.g., a PRAME/HLA complex, more specifically, a PRAME/HLA class I complex, more specifically, a PRAME/HLA-A complex, and more specifically, a PRAME/HLA-A2 complex, even more specifically, a PRAME/HLA-A*0201 complex. Examples of PRAME peptides that are recognized by the antigen-binding proteins of the presently disclosed subject matter as part of an MHC-peptide complex include, but are not limited to, $PRA^{100-108}$ (SEQ ID NO: 2), $PRA^{142-151}$ (SEQ ID NO: 3), $PRA^{300-309}$ (SEQ ID NO: 4), $PRA^{425-433}$ (SEQ ID NO: 5), and $PRA^{435-443}$ (SEQ ID NO: 6).

In certain embodiments, therefore, the presently disclosed subject matter provides for an isolated antibody, or an antigen-binding portion thereof, which binds to a PRAME peptide bound to an MHC molecule. The PRAME peptide binds to the MHC molecule to form a PRAME/MHC complex. In certain embodiments, the MHC molecule is an HLA molecule. In certain embodiments, the HLA molecule is an HLA class I molecule. In certain embodiments, the HLA class I molecule is HLA-A. In certain embodiments, the HLA-A is HLA-A2. In certain embodiments, the HLA-A2 is HLA-A*0201.

In certain embodiment, the antibody or antigen-binding portion binds to $PRA^{300-309}$ (SEQ ID NO: 4). In certain embodiments, the antibody or antigen-binding portion thereof comprises a heavy chain variable region CDR3 sequence and a light chain variable region CDR3 sequence selected from the group consisting of:

(a) a heavy chain variable region CDR3 sequence comprising amino acid sequence set forth in SEQ ID NO: 9 or a modification thereof, and a light chain variable region CDR3 sequence comprising amino acid sequence set forth in SEQ ID NO: 12 or a modification thereof;

(b) a heavy chain variable region CDR3 sequence comprising an amino acid sequence set forth in SEQ ID NO: 15 or a modification thereof, and a light chain variable region CDR3 sequence comprising amino an acid sequence set forth in SEQ ID NO: 18 or a modification thereof;

(c) a heavy chain variable region CDR3 sequence comprising an amino acid sequence set forth in SEQ ID NO: 21 or a modification thereof, and a light chain variable region CDR3 sequence comprising an amino acid sequence set forth in SEQ ID NO: 24 or a modification thereof; and (d) a heavy chain variable region CDR3 sequence comprising an amino acid sequence set forth in SEQ ID NO: 27 or a modification thereof, and a light chain variable region CDR3 sequence comprising an amino acid sequence set forth in SEQ ID NO: 30 or a modification thereof.

Further, the antibody or antigen-binding portion thereof comprises a heavy chain variable region CDR2 sequence and a light chain variable region CDR2 sequence selected from the group consisting of:

(a) a heavy chain variable region CDR2 sequence comprising an amino acid sequence set forth in SEQ ID NO: 8 or a modification thereof, and a light chain variable region CDR2 sequence comprising an amino acid sequence set forth in SEQ ID NO: 11 or a modification thereof;

(b) a heavy chain variable region CDR2 sequence comprising an amino acid sequence set forth in SEQ ID NO: 14 or a modification thereof, and a light chain variable region CDR2 sequence comprising an amino acid sequence set forth in SEQ ID NO: 17 or a modification thereof;

(c) a heavy chain variable region CDR2 sequence comprising an amino acid sequence set forth in SEQ ID NO: 20 or a modification thereof, and a light chain variable region CDR2 sequence comprising an amino acid sequence set forth in SEQ ID NO: 23 or a modification thereof; and (d) a heavy chain variable region CDR2 sequence comprising an amino acid sequence set forth in SEQ ID NO: 26 or a modification thereof, and a light chain variable region CDR2 sequence comprising an amino acid sequence set forth in SEQ ID NO: 29 or a modification thereof.

Further, the antibody or antigen-binding portion thereof comprises a heavy chain variable region CDR1 sequence and a light chain variable region CDR1 sequence selected from the group consisting of:

(a) a heavy chain variable region CDR1 sequence comprising an amino acid sequence set forth in SEQ ID NO: 7 or a modification thereof, and a light chain variable region CDR1 sequence comprising an amino acid sequence set forth in SEQ ID NO: 10 or a modification thereof;

(b) a heavy chain variable region CDR1 sequence comprising an amino acid sequence set forth in SEQ ID NO: 13 or a modification thereof, and a light chain variable region CDR1 sequence comprising an amino acid sequence set forth in SEQ ID NO: 16 or a modification thereof;

(c) a heavy chain variable region CDR1 sequence comprising an amino acid sequence set forth in SEQ ID NO: 19 or a modification thereof, and a light chain variable region CDR1 sequence comprising an amino acid sequence set forth in SEQ ID NO: 22 or a modification thereof; and (d) a heavy chain variable region CDR1 sequence comprising an amino acid sequence set forth in SEQ ID NO: 25 or a modification thereof, and a light chain variable region CDR1 sequence comprising an amino acid sequence set forth in SEQ ID NO: 28 or a modification thereof.

In certain embodiments, the antibody or antigen-binding portion thereof comprises:

(a) a heavy chain variable region CDR1 comprising an amino acid sequence set forth in SEQ ID NO: 7; a heavy chain variable region CD22 comprising an amino acid sequence set forth in SEQ ID NO: 8; a heavy chain variable region CDR3 comprising an amino acid sequence set forth in SEQ ID NO: 9; a light chain variable region CDR1 comprising an amino acid sequence set forth in SEQ ID NO: 10; a light chain variable region CDR2 comprising an amino acid sequence set forth in SEQ ID NO: 11; and a light chain variable region CDR3 comprising an amino acid sequence set forth in SEQ ID NO: 12;

(b) a heavy chain variable region CDR1 comprising an amino acid sequence set forth in SEQ ID NO: 13; a heavy chain variable region CDR2 comprising an amino acid sequence set forth in SEQ ID NO: 14; a heavy chain variable region CDR3 comprising an amino acid sequence set forth in SEQ ID NO: 15; a light chain variable region CDR1 comprising an amino acid sequence set forth in SEQ ID NO: 16; a light chain variable region CDR2 comprising an amino acid sequence set forth in SEQ ID NO: 17; and a light chain variable region CDR3 comprising an amino acid sequence set forth in SEQ ID NO: 18;

(c) a heavy chain variable region CDR1 comprising an amino acid sequence set forth in SEQ ID NO: 19; a heavy chain variable region CDR2 comprising an amino acid sequence set forth in SEQ ID NO: 20; a heavy chain variable region CDR3 comprising an amino acid sequence set forth in SEQ ID NO: 21; a light chain variable region CDR1 comprising an amino acid sequence set forth in SEQ ID NO: 22; a light chain variable region CDR2 comprising an amino acid sequence set forth in SEQ ID NO: 23; and a light chain variable region CDR3 comprising an amino acid sequence set forth in SEQ ID NO: 24; or (d) a heavy chain variable region CDR1 comprising an amino acid sequence set forth in SEQ ID NO: 25; a heavy chain variable region CDR2 comprising an amino acid sequence set forth in SEQ ID NO: 26; a heavy chain variable region CDR3 comprising an amino acid sequence set forth in SEQ ID NO: 27; a light chain variable region CDR1 comprising an amino acid sequence set forth in SEQ ID NO: 28; a light chain variable region CDR2 comprising an amino acid sequence set forth in SEQ ID NO: 29; and a light chain variable region CDR3 comprising an amino acid sequence set forth in SEQ ID NO: 30.

In certain embodiments, the antibody or antigen-binding portion thereof comprises a heavy chain variable region CDR1 comprising an amino acid sequence set forth in SEQ ID NO: 7; a heavy chain variable region CD22 comprising an amino acid sequence set forth in SEQ ID NO: 8; a heavy chain variable region CDR3 comprising an amino acid sequence set forth in SEQ ID NO: 9; a light chain variable region CDR1 comprising an amino acid sequence set forth in SEQ ID NO: 10; a light chain variable region CDR2 comprising an amino acid sequence set forth in SEQ ID NO: 11; and a light chain variable region CDR3 comprising an amino acid sequence set forth in SEQ ID NO: 12.

In certain embodiments, the antibody or antigen-binding portion thereof comprises a heavy chain variable region that comprises an amino acid sequence that is at least 80% homologous to the sequence selected from the group consisting of SEQ ID NOS: 49, 51, 53, and 55. In certain embodiments, the antibody or antigen-binding portion thereof comprises a heavy chain variable region that comprises an amino acid sequence set forth in SEQ ID NO: 49, SEQ ID NO: 51, SEQ ID NO: 53, or SEQ ID NO: 55.

In certain embodiments, the antibody or antigen-binding portion thereof comprises a light chain variable region that comprises an amino acid sequence that is at least 80% homologous to the sequence selected from the group consisting of SEQ ID NOS: 50, 52, 54, and 56. In certain embodiments, the antibody or antigen-binding portion thereof comprises a light chain variable region that comprises an amino acid sequence set forth in SEQ ID NO: 50, SEQ ID NO: 52, SEQ ID NO: 54, or SEQ ID NO: 56.

In certain embodiments, the antibody or antigen-binding portion thereof comprises:

(a) a heavy chain variable region comprising an amino acid sequence set forth in SEQ ID NO: 49, and a light chain variable region comprising an amino acid sequence set forth in SEQ ID NO: 50;

(b) a heavy chain variable region comprising an amino acid sequence set forth in SEQ ID NO: 51, and a light chain variable region comprising an amino acid sequence set forth in SEQ ID NO: 52;

(c) a heavy chain variable region comprising an amino acid sequence set forth in SEQ ID NO: 53, and a light chain variable region comprising an amino acid sequence set forth in SEQ ID NO: 54; or (d) a heavy chain variable region comprising an amino acid sequence set forth in SEQ ID NO: 55, and a light chain variable region comprising an amino acid sequence set forth in SEQ ID NO: 56.

In certain embodiments, the antibody or antigen-binding portion thereof comprises a heavy chain variable region comprising an amino acid sequence set forth in SEQ ID NO: 49, and a light chain variable region comprising an amino acid sequence set forth in SEQ ID NO: 50.

In certain embodiments, the antibody or antigen-binding portion binds to PRA$^{435-443}$ (SEQ ID NO: 6). In certain embodiments, the antibody or antigen-binding portion thereof comprises a heavy chain variable region CDR3 sequence and a light chain variable region CDR3 sequence selected from the group consisting of:

(a) a heavy chain variable region CDR3 sequence comprising an amino acid sequence set forth in SEQ ID NO: 33 or a modification thereof, and a light chain variable region CDR3 sequence comprising an amino acid sequence set forth in SEQ ID NO: 36 or a modification thereof;

(b) a heavy chain variable region CDR3 sequence comprising an amino acid sequence set forth in SEQ ID NO: 39 or a modification thereof, and a light chain variable region CDR3 sequence comprising an amino acid sequence set forth in SEQ ID NO: 42 or a modification thereof; and (c) a heavy chain variable region CDR3 sequence comprising an amino acid sequence set forth in SEQ ID NO: 45 or a modification thereof, and a light chain variable region CDR3 sequence comprising an amino acid sequence set forth in SEQ ID NO: 48 or a modification thereof.

Further, the antibody or antigen-binding portion thereof comprises a heavy chain variable region CDR2 sequence and a light chain variable region CDR2 sequence selected from the group consisting of:

(a) a heavy chain variable region CDR2 sequence comprising an amino acid sequence set forth in SEQ ID NO: 32 or a modification thereof, and a light chain variable region CDR2 sequence comprising an amino acid sequence set forth in SEQ ID NO: 35 or a modification thereof;

(b) a heavy chain variable region CDR2 sequence comprising an amino acid sequence set forth in SEQ ID NO: 38 or a modification thereof, and a light chain variable region CDR2 sequence comprising an amino acid sequence set forth in SEQ ID NO: 41 or a modification thereof; and (c) a heavy chain variable region CDR2 sequence comprising an amino acid sequence set forth in SEQ ID NO: 44 or a modification thereof, and a light chain variable region CDR2 sequence comprising an amino acid sequence set forth in SEQ ID NO: 47 or a modification thereof.

Further, the antibody or antigen-binding portion thereof comprises a heavy chain variable region CDR1 sequence and a light chain variable region CDR1 sequence selected from the group consisting of:

(a) a heavy chain variable region CDR1 sequence comprising an amino acid sequence set forth in SEQ ID NO: 31 or a modification thereof, and a light chain variable region CDR1 sequence comprising an amino acid sequence set forth in SEQ ID NO: 34 or a modification thereof;

(b) a heavy chain variable region CDR1 sequence comprising an amino acid sequence set forth in SEQ ID NO: 37 or a modification thereof, and a light chain variable region CDR1 sequence comprising an amino acid sequence set forth in SEQ ID NO: 40 or a modification thereof; and (c) a heavy chain variable region CDR1 sequence comprising an amino acid sequence set forth in SEQ ID NO: 43 or a modification thereof, and a light chain variable region CDR1 sequence comprising an amino acid sequence set forth in SEQ ID NO: 46 or a modification thereof.

In certain embodiments, the antibody or antigen-binding portion thereof comprises:

(a) a heavy chain variable region CDR1 comprising an amino acid sequence set forth in SEQ ID NO: 31; a heavy chain variable region CDR2 comprising an amino acid sequence set forth in SEQ ID NO: 32; a heavy chain variable region CDR3 comprising an amino acid sequence set forth in SEQ ID NO: 33; a light chain variable region CDR1 comprising an amino acid sequence set forth in SEQ ID NO: 34; a light chain variable region CDR2 comprising an amino acid sequence set forth in SEQ ID NO: 35; and a light chain variable region CDR3 comprising an amino acid sequence set forth in SEQ ID NO: 36;

(b) a heavy chain variable region CDR1 comprising an amino acid sequence set forth in SEQ ID NO: 37; a heavy chain variable region CDR2 comprising an amino acid sequence set forth in SEQ ID NO: 38; a heavy chain variable region CDR3 comprising an amino acid sequence set forth in SEQ ID NO: 39; a light chain variable region CDR1 comprising an amino acid sequence set forth in SEQ ID NO: 40; a light chain variable region CDR2 comprising an amino acid sequence set forth in SEQ ID NO: 41; and a light chain variable region CDR3 comprising an amino acid sequence set forth in SEQ ID NO: 42; or (c) a heavy chain variable region CDR1 comprising an amino acid sequence set forth in SEQ ID NO: 43; a heavy chain variable region CDR2 comprising an amino acid sequence set forth in SEQ ID NO: 44; a heavy chain variable region CDR3 comprising an amino acid sequence set forth in SEQ ID NO: 45; a light chain variable region CDR1 comprising an amino acid sequence set forth in SEQ ID NO: 46; a light chain variable region CDR2 comprising an amino acid sequence set forth in SEQ ID NO: 47; and a light chain variable region CDR3 comprising an amino acid sequence set forth in SEQ ID NO: 48.

In certain embodiments, the antibody or antigen-binding portion thereof comprises a heavy chain variable region CDR1 comprising an amino acid sequence set forth in SEQ ID NO: 31; a heavy chain variable region CDR2 comprising an amino acid sequence set forth in SEQ ID NO: 32; a heavy chain variable region CDR3 comprising an amino acid sequence set forth in SEQ ID NO: 33; a light chain variable region CDR1 comprising an amino acid sequence set forth in SEQ ID NO: 34; a light chain variable region CDR2 comprising an amino acid sequence set forth in SEQ ID NO:

35; and a light chain variable region CDR3 comprising an amino acid sequence set forth in SEQ ID NO: 36.

In certain embodiments, the antibody or antigen-binding portion thereof comprises a heavy chain variable region that comprises an amino acid sequence that is at least 80% homologous to the sequence selected from the group consisting of SEQ ID NOS: 57, 59, and 61. In certain embodiments, the antibody or antigen-binding portion thereof comprises a heavy chain variable region that comprises an amino acid sequence set forth in SEQ ID NO: 57, SEQ ID NO: 59, or SEQ ID NO: 61.

In certain embodiments, the antibody or antigen-binding portion thereof comprises a light chain variable region that comprises an amino acid sequence that is at least 80% homologous to the sequence selected from the group consisting of SEQ ID NOS: 58, 60, and 62. In certain embodiments, the antibody or antigen-binding portion thereof comprises a light chain variable region that comprises an amino acid sequence set forth in SEQ ID NO: 58, SEQ ID NO: 60, or SEQ ID NO: 62.

In certain embodiments, the antibody or antigen-binding portion thereof comprises:

(a) a heavy chain variable region comprising an amino acid sequence set forth in SEQ ID NO: 57, and a light chain variable region comprising an amino acid sequence set forth in SEQ ID NO: 58;

(b) a heavy chain variable region comprising an amino acid sequence set forth in SEQ ID NO: 59, and a light chain variable region comprising an amino acid sequence set forth in SEQ ID NO: 60; or (c) a heavy chain variable region comprising an amino acid sequence set forth in SEQ ID NO: 61, and a light chain variable region comprising an amino acid sequence set forth in SEQ ID NO: 62.

The modification can be one or more deletions, insertions, substitutions, and/or combinations therefore. The modification thereof can consist of no more than 2, no more than 3, no more than 4, or no more than 5 modifications.

In certain embodiments, the antibody or antigen-binding portion thereof binds to the N-terminal of the PRAME peptide that is bound to the MHC molecule. In certain embodiments, the antibody or antigen-binding portion thereof binds to C-terminal of the PRAME peptide that is bound to the MHC molecule. In certain embodiments, the antibody or antigen-binding portion thereof binds to the PRAME peptide that is bound to the MHC molecule with a binding affinity ($K_D$) of about $1 \times 10^{-7}$ M or less. In certain embodiments, the antibody or antigen-binding portion thereof specifically binds to the PRAME peptide, e.g., binds to the PRAME peptide with a binding affinity ($K_D$) of about 1-5 nM, e.g., about 2.4 nM.

The presently disclosed subject matter also provides for an isolated antibody or antigen-binding portion thereof that cross-competes for binding to a PRAME peptide bound to an MHC molecule with a reference antibody or antigen-binding portion thereof comprising:

(a) a heavy chain variable region comprising an amino acid sequence set forth in SEQ ID NO: 49, and a light chain variable region comprising an amino acid sequence set forth in SEQ ID NO: 50;

(b) a heavy chain variable region comprising an amino acid sequence set forth in SEQ ID NO: 51, and a light chain variable region comprising an amino acid sequence set forth in SEQ ID NO: 52;

(c) a heavy chain variable region comprising an amino acid sequence set forth in SEQ ID NO: 53, and a light chain variable region comprising an amino acid sequence set forth in SEQ ID NO: 54;

(d) a heavy chain variable region comprising an amino acid sequence set forth in SEQ ID NO: 55, and a light chain variable region comprising an amino acid sequence set forth in SEQ ID NO: 56;

(e) a heavy chain variable region comprising an amino acid sequence set forth in SEQ ID NO: 57, and a light chain variable region comprising an amino acid sequence set forth in SEQ ID NO: 58;

(f) a heavy chain variable region comprising an amino acid sequence set forth in SEQ ID NO: 59, and a light chain variable region comprising an amino acid sequence set forth in SEQ ID NO: 60; or (g) a heavy chain variable region comprising an amino acid sequence set forth in SEQ ID NO: 61, and a light chain variable region comprising an amino acid sequence set forth in SEQ ID NO: 62.

In certain embodiments, the reference antibody or antigen-binding portion thereof comprises a heavy chain variable region comprising an amino acid sequence set forth in SEQ ID NO: 49, and a light chain variable region comprising an amino acid sequence set forth in SEQ ID NO: 50.

In certain embodiments, the MHC molecule is a HLA molecule. In certain embodiments, the HLA molecule is an HLA class I molecule. In certain embodiments, the HLA class I molecule is HLA-A. In certain embodiments, the HLA-A is HLA-A2. In certain embodiments, the HLA-A2 is HLA-A*0201. In certain embodiments, the PRAME peptide is selected from the group consisting of $PRA^{100-108}$ (SEQ ID NO: 2), $PRA^{142-151}$ (SEQ ID NO: 3), $PRA^{300-309}$ (SEQ ID NO: 4), $PRA^{425-433}$ (SEQ ID NO: 5), and $PRA^{435-443}$ (SEQ ID NO: 6). In certain embodiments, the PRAME peptide is $PRA^{300-309}$ (SEQ ID NO: 4). In certain embodiments, the PRAME peptide is $PRA^{435-443}$ (SEQ ID NO: 6).

In certain embodiments, the above-described antibody comprises a human variable region framework region. In certain embodiments, the above-described antibody is a fully human or an antigen-binding portion thereof. In certain embodiments, the above-described antibody is a chimeric antibody or an antigen-binding portion thereof. In certain embodiments, the above-described antibody is a humanized antibody or an antigen-binding portion thereof. In certain embodiments, the above-described antibody is of an IgG1, IgG2, IgG3, or IgG4 isotype. In certain embodiments, the above-described antibody is of an IgG1 isotype In certain embodiments, the above-described antibody or antigen-binding portion thereof comprises one or more post-translational modifications. In certain embodiments, the one or more post-translational modifications comprise afucosylation. In certain embodiments, the above-described antibody or antigen-binding portion thereof comprises an afucosylated Fc region.

The presently disclosed subject matter further provides for compositions comprising the above-described antibodies or antigen-binding portions thereof and a pharmaceutically acceptable carrier.

In another aspect, the presently disclosed subject matter provides for an immunoconjugate comprising a first component which is an antigen-binding protein, antibody or antigen-binding portion thereof as disclosed herein. The immunoconjugate comprises a second component that is a therapeutic moiety, e.g., a drug, a cytotoxin, or a radioisotope. The presently disclosed subject matter further provides for compositions comprising the above-described immunoconjugates and a pharmaceutically acceptable carrier.

The presently disclosed subject matter also provides for a bispecific antibody comprising above-described antibody or antigen-binding portion thereof linked to a second functional moiety. In certain embodiments, the second functional moiety has a different binding specificity than said antibody or antigen binding portion thereof. In certain embodiments, the bispecific antibody recognizes CD3 and the PRAME peptide bound to the MHC molecule (PRAME/MEIC complex). The presently disclosed subject matter further provides for compositions comprising the above-described bispecific antibodies and a pharmaceutically acceptable carrier. Furthermore, the presently disclosed subject matter provides for chimeric antigen receptors (CARs) specific for a PRAME peptide bound to an MHC molecule. In certain embodiments, the CAR comprises an antigen-binding portion comprising a heavy chain variable region and a light chain variable region. In certain embodiments, the CAR comprises a linker between the heavy chain variable region and the light chain variable region. In certain embodiments, the linker comprises the amino acid sequence set forth in SEQ ID NO: 70. In certain embodiments, the CAR comprises one of the above-described antigen-binding portion. In certain embodiments, the antigen-binding portion comprises a single-chain variable fragment (scFv). In certain embodiments, the scFv is a human scFv. In certain embodiments, the human scFv comprises the amino acid sequence selected from the group consisting of SEQ ID NOS: 63, 64, 65, 66, 67, 68, and 69. In certain embodiments, the human scFv comprises the amino acid sequence set forth in SEQ ID NO: 63. In certain embodiments, the antigen-binding portion comprises a Fab, which is optionally crosslinked. In certain embodiments, the antigen-binding portion comprises a $F(ab)_2$. The presently disclosed subject matter further provides for compositions comprising the above-described CARs and a pharmaceutically acceptable carrier.

In yet another aspect, the presently disclosed subject matter provides for nucleic acids that encode antigen-binding proteins, including antibodies and chimeric antigen receptors (CARs) specific for a PRAME peptide/HLA complex, e.g., a PRAME/HLA class I complex, more specifically, a PRAME/HLA-A complex, and more specifically, a PRAME/HLA-A2 complex, even more specifically, a PRAME/HLA-A*0201 complex. The presently disclosed subject matter also provides for vectors comprising such nucleic acids, including vectors to facilitate expression and/or secretion of an antigen-binding protein (e.g., an antibody or CAR) in accordance with the presently disclosed subject matter.

In another related aspect, the presently disclosed subject matter provides for cells comprising the nucleic acids or antigen-binding proteins disclosed herein, including recombinant immune effector cells, such as, T-cells genetically modified to express a CAR comprising an antigen-binding region in accordance with the presently disclosed subject matter. Cells which have been engineered to produce antibodies in accordance with the disclosure are also encompassed by the presently disclosed subject matter.

In a related aspect, the presently disclosed subject matter provides for pharmaceutical compositions comprising the antigen-binding proteins, antibodies, nucleic acids, vectors or cells comprising the nucleic acids or antigen-binding proteins disclosed herein, together with a pharmaceutically acceptable carrier.

In another aspect, the presently disclosed subject matter provides for a method for detecting PRAME on the surface of cells or tissues using PRAME antibodies of the presently disclosed subject matter. In certain embodiments, the method comprises: (a) contacting a cell or tissue with an antibody or an antigen-binding portion thereof that binds to a PRAME peptide that is bound to an MHC molecule, wherein the antibody or antigen-binding portion thereof comprises a detectable label; and (b) determining the amount of the labeled antibody or antigen-binding portion thereof bound to the cell or tissue by measuring the amount of detectable label associated with the cell or tissue, wherein the amount of bound antibody or antigen-binding portion thereof indicates the amount of PRAME in the cell or tissue.

In certain embodiments, the antibody or antigen-binding portion thereof is one of the above-described antibodies or antigen-binding portions thereof.

In yet another aspect, the presently disclosed subject matter provides for methods for treating a subject having a PRAME-positive disease, comprising administering to the subject a therapeutically effective amount of an antigen-binding protein (e.g., CAR) or a composition comprising thereof as described above, an antibody or antigen-binding portion thereof (including bispecific antibody) or a composition comprising thereof as described above, an immunoconjugate or a composition comprising thereof as described above, a nucleic acid encoding the antigen-binding protein or antibody, or a cell comprising the nucleic acids or proteins as described above. In certain embodiments, the method further comprises administering one or more compound selected from the group consisting of compounds that are capable of killing the tumor cell, compounds that are capable of enhancing the killing effect by an effector cell, and compounds that are capable of upregulating the antigen targets on the tumor cell.

In yet another aspect, the presently disclosed subject matter provides for kits for treating a PRAME-positive disease. In certain embodiments, the kit comprises an antibody or antigen-binding portion as described above. In certain embodiments, the kit comprises a CAR as described above. In certain embodiments, the kit comprises a bispecific antibody as described above. In certain embodiments, the kit further comprises written instructions for using the antibody or antigen-binding portion thereof, the CAR, or the bispecific antibody for treating a subject having a PRAME-positive disease.

The PRAME-positive disease is selected from the group consisting of breast cancer, ovarian cancer, melanoma, lung cancer, gastrointestinal cancers, brain tumors, head and neck cancer, renal cancer, myeloma, neuroblastoma, mantle cell lymphoma, chronic myelocytic leukemia, multiple myeloma, acute lymphoblastic leukemia (ALL), acute myeloid/myelogenous leukemia (AML), Non-Hodgkin lymphoma (NHL), and Chronic lymphocytic leukemia (CLL).

BRIEF DESCRIPTION OF THE DRAWINGS

FIGS. 6A-6F represent binding location of Pr300#20 to T2 cells pulsed with PRA$^{300-309}$ or PRA$^{300-309}$ substituted with alanine. (A) (SEQ ID NOS: 678-685) PRAME300 peptides including alanine mutations. (B) Binding of Pr300#20 to T2 pulsed cells with peptides listed in (A). (C) HLA-A02 binding. (D) Pr#20/HLA-A02 ratio. (E and F) Binding of Pr300#20 to T2 cells pulsed with PRAME300 or PRAME300 substituted with alanine.

DETAILED DESCRIPTION

I. Definitions

Figure 1A:
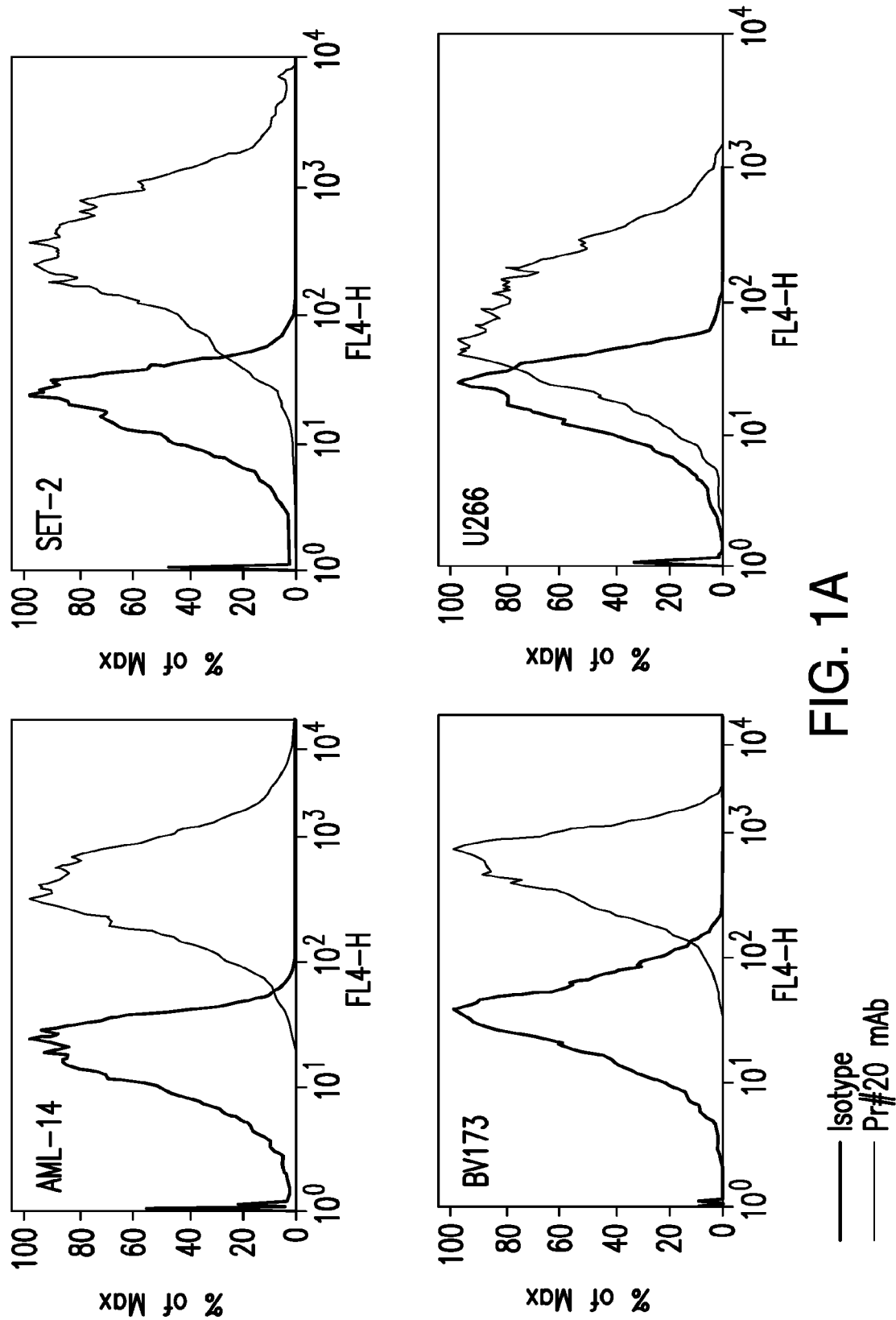
FIGS. 1A-1D represent binding of Pr300#20 human IgG1 antibody to PRAME-expressing tumor cell lines. (A) binding of Pr300-#20 to PRAME$^-$/HLA-A*02$^+$ cancer cells. (B) Binding of Pr300-#20 to PRAME300 pulsed and unpulsed T2 cells. (C) binding of Pr300-#20 to PRAME$^+$/HLA-A*0201$^+$ leukemias AML14, BV173, and SET2 and to PRAME$^+$/HLA-A*0201$^-$ leukemia HL60. (D) HLA-A2 expression (upper panel) and binding of Pr300#20 to a HLA-A2$^+$ melanoma cell line SK-MEL-5 (lower panel).

Unless defined otherwise, all technical and scientific terms used herein have the meaning commonly understood by a person skilled in the art to which this invention belongs. The following references provide one of ordinary skill in the art with a general definition of many of the terms used in the presently disclosed subject matter: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991); Molecular Cloning: a Laboratory Manual 3rd edition, J. F. Sambrook and D. W. Russell, ed. Cold Spring Harbor Laboratory Press 2001; Recombinant Antibodies for Immunotherapy, Melvyn Little, ed. Cambridge University Press 2009; "Oligonucleotide Synthesis" (M. J. Gait, ed., 1984); "Animal Cell Culture" (R. I. Freshney, ed., 1987); "Methods in Enzymology" (Academic Press, Inc.); "Current Protocols in Molecular Biology" (F. M. Ausubel et al., eds., 1987, and periodic updates); "PCR: The Polymerase Chain Reaction", (Mullis et al., ed., 1994); "A Practical Guide to Molecular Cloning" (Perbal Bernard V., 1988); "Phage Display: A Laboratory Manual" (Barbas et al., 2001). The contents of these references and other references containing standard protocols, widely known to and relied upon by those of skill in the art, including manufacturers' instructions are hereby incorporated by reference as part of the presently disclosed subject matter. As used herein, the following terms have the meanings ascribed to them below, unless specified otherwise.

The following abbreviations are used throughout the present application:

Ab: Antibody
ADCC: Antibody-dependent cellular cytotoxicity
ALL: Acute lymphocytic leukemia
AML: Acute myeloid leukemia
APC: Antigen presenting cell
β2M: Beta-2-microglobulin
BiTE: Bi-specific T cell engaging antibody
CAR: Chimeric antigen receptor
CDC: Complement dependent cytotoxicity
CMC: Complement mediated cytotoxicity
CDR: Complementarity determining region (see also HVR below)
$C_L$: Constant domain of the light chain
$CH_1$: $1^{st}$ constant domain of the heavy chain
$CH_{1, 2, 3}$: $1^{st}$, $2^{nd}$ and $3^{rd}$ constant domains of the heavy chain
$CH_{2, 3}$: $2^{nd}$ and $3^{rd}$ constant domains of the heavy chain
CHO: Chinese hamster ovary
CTL: Cytotoxic T cell
E:T Ratio: Effector:Target ratio
Fab: Antibody binding fragment
FACS: Flow assisted cytometric cell sorting
FBS: Fetal bovine serum
FR: Framework region
HC: Heavy chain
HLA: Human leukocyte antigen
HVR-H: Hypervariable region-heavy chain (see also CDR)
HVR-L: Hypervariable region-light chain (see also CDR)
Ig: Immunoglobulin
IRES: Internal ribosome entry site
$K_D$: Dissociation constant
$k_{off}$: Dissociation rate
$k_{on}$: Association rate
MHC: Major histocompatibility complex
MM: Multiple myeloma
scFv: Single-chain variable fragment
TCR: T cell receptor
$V_H$: Variable heavy chain includes heavy chain hypervariable region and heavy chain variable framework region
$V_L$: Variable light chain includes light chain hypervariable region and light chain variable framework region
PRAME: Preferentially expressed antigen of melanoma As used herein, the term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

As used herein, the term "cell population" refers to a group of at least two cells expressing similar or different phenotypes. In non-limiting examples, a cell population can include at least about 10, at least about 100, at least about 200, at least about 300, at least about 400, at least about 500, at least about 600, at least about 700, at least about 800, at least about 900, at least about 1000 cells expressing similar or different phenotypes.

As used herein, the term "antigen-binding protein" refers to a protein or polypeptide that comprises an antigen-binding region or antigen-binding portion, that is, has a strong affinity to another molecule to which it binds. Antigen-binding proteins encompass antibodies, chimeric antigen receptors (CARs) and fusion proteins.

The terms "antibody" and "antibodies" refer to antigen-binding proteins of the immune system. As used herein, the term "antibody" includes whole, full length antibodies having an antigen-binding region, and any fragment thereof in which the "antigen-binding portion" or "antigen-binding region" is retained, or single chains, for example, single chain variable fragment (scFv), thereof. The term "antibody" means not only intact antibody molecules, but also fragments of antibody molecules that retain immunogen-binding ability. Such fragments are also well known in the art and are regularly employed both in vitro and in vivo. Accordingly, as used herein, the term "antibody" means not only intact immunoglobulin molecules but also the well-known active fragments F(ab')$_2$, and Fab. F(ab')$_2$, and Fab fragments that lack the Fc fragment of intact antibody, clear more rapidly from the circulation, and may have less non-specific tissue binding of an intact antibody (Wahl et al., *J. Nucl. Med.* 24:316-325 (1983). In certain embodiments, an antibody is a glycoprotein comprising at least two heavy (H) chains and two light (L) chains inter-connected by disulfide bonds. Each heavy chain is comprised of a heavy chain variable region (abbreviated herein as $V_H$) and a heavy chain constant ($C_H$) region. The heavy chain constant region is comprised of three domains, CH1, CH2 and CH3. Each light chain is comprised of a light chain variable region (abbreviated herein as $V_L$) and a light chain constant $C_L$ region. The light chain constant region is comprised of one domain, $C_L$. The $V_H$ and $V_L$ regions can be further sub-divided into regions of hypervariability, termed complementarity determining regions (CDR), interspersed with regions that are more conserved, termed framework regions (FR). Each $V_H$ and $V_L$ is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "antigen-binding portion", "antigen-binding fragment", or "antigen-binding region" of an antibody, as used herein, refers to that region or portion of an antibody that binds to the antigen and which confers antigen specificity to the antibody; fragments of antigen-binding proteins, for example, antibodies includes one or more fragments of an antibody that retain the ability to specifically bind to an antigen (e.g., an peptide/HLA complex). It has been shown that the antigen-binding function of an antibody can be performed by fragments of a full-length antibody. Examples of antigen-binding portions encompassed within the term "antibody fragments" of an antibody include a Fab fragment, a monovalent fragment consisting of the $V_L$, $V_H$, $C_L$ and CH1 domains; a F(ab)$_2$ fragment, a bivalent fragment comprising two Fab fragments linked by a disulfide bridge at the hinge region; a Fd fragment consisting of the $V_H$ and CH1 domains; a Fv fragment consisting of the $V_L$ and $V_H$ domains of a single arm of an antibody; a dAb fragment (Ward et al., 1989 Nature 341:544-546), which consists of a $V_H$ domain; and an isolated complementarity determining region (CDR).

Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules. These are known as single chain Fv (scFv); see e.g., Bird et al., 1988 Science 242:423-426; and Huston et al., 1988 Proc. Natl. Acad. Sci. 85:5879-5883. These antibody fragments are obtained using conventional techniques known to those of ordinary skill in the art, and the fragments are screened for utility in the same manner as are intact antibodies.

An "isolated antibody" or "isolated antigen-binding protein" is one which has been identified and separated and/or recovered from a component of its natural environment. "Synthetic antibodies" or "recombinant antibodies" are generally generated using recombinant technology or using peptide synthetic techniques known to those of skill in the art.

As used herein, the term "single-chain variable fragment" or "scFv" is a fusion protein of the variable regions of the heavy ($V_H$) and light chains ($V_L$) of an immunoglobulin (e.g., mouse or human) covalently linked to form a $V_H$::VL heterodimer. The heavy ($V_H$) and light chains ($V_L$) are either joined directly or joined by a peptide-encoding linker (e.g., 10, 15, 20, 25 amino acids), which connects the N-terminus of the $V_H$ with the C-terminus of the $V_L$, or the C-terminus of the $V_H$ with the N-terminus of the $V_L$. The linker is usually rich in glycine for flexibility, as well as serine or threonine for solubility. Despite removal of the constant regions and the introduction of a linker, scFv proteins retain the specificity of the original immunoglobulin. Single chain Fv polypeptide antibodies can be expressed from a nucleic acid comprising $V_H$- and $V_L$-encoding sequences as described by Huston, et al. (Proc. Nat. Acad. Sci. USA, 85:5879-5883, 1988). See, also, U.S. Pat. Nos. 5,091,513, 5,132,405 and 4,956,778; and U.S. Patent Publication Nos. 20050196754 and 20050196754. Antagonistic scFvs having inhibitory activity have been described (see, e.g., Zhao et al., Hyrbidoma (Larchmt) 2008 27(6):455-51; Peter et al., J Cachexia Sarcopenia Muscle 2012 Aug. 12; Shieh et al., J Immunol 2009 183(4):2277-85; Giomarelli et al., Thromb Haemost 2007 97(6):955-63; Fife eta., J Clin Invst 2006 116(8):2252-61; Brocks et al., Immunotechnology 1997 3(3):173-84; Moosmayer et al., Ther Immunol 1995 2(10:31-40). Agonistic scFvs having stimulatory activity have been described (see, e.g., Peter et al., J Biol Chem 2003 25278(38):36740-7; Xie et al., Nat Biotech 1997 15(8):768-71; Ledbetter et al., Crit Rev Immunol 1997 17(5-6):427-55; Ho et al., BioChim Biophys Acta 2003 1638(3):257-66).

As used herein, "F(ab)" refers to a fragment of an antibody structure that binds to an antigen but is monovalent and does not have a Fc portion, for example, an antibody digested by the enzyme papain yields two F(ab) fragments and an Fc fragment (e.g., a heavy (H) chain constant region; Fc region that does not bind to an antigen).

As used herein, "F(ab')$_2$" refers to an antibody fragment generated by pepsin digestion of whole IgG antibodies, wherein this fragment has two antigen binding (ab') (bivalent) regions, wherein each (ab') region comprises two separate amino acid chains, a part of a H chain and a light (L) chain linked by an S—S bond for binding an antigen and where the remaining H chain portions are linked together. A "F(ab')2" fragment can be split into two individual Fab' fragments.

As used herein, the term "vector" refers to any genetic element, such as a plasmid, phage, transposon, cosmid, chromosome, virus, virion, etc., which is capable of replication when associated with the proper control elements and which can transfer gene sequences into cells. Thus, the term includes cloning and expression vehicles, as well as viral vectors and plasmid vectors.

As used herein, the term "expression vector" refers to a recombinant nucleic acid sequence, e.g., a recombinant DNA molecule, containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

As used herein, "CDRs" are defined as the complementarity determining region amino acid sequences of an antibody which are the hypervariable regions of immunoglobulin heavy and light chains. See, e.g., Kabat et al., Sequences of Proteins of Immunological Interest, 4th U.S. Department of Health and Human Services, National Institutes of Health (1987). Generally, antibodies comprise three heavy chain and three light chain CDRs or CDR regions in the variable region. CDRs provide the majority of contact residues for the binding of the antibody to the antigen or epitope. In certain embodiments, the CDRs regions are delineated using the Kabat system (Kabat, E. A., et al. (1991) Sequences of Proteins of Immunological Interest, Fifth Edition, U.S. Department of Health and Human Services, NIH Publication No. 91-3242).

As used herein, the term "affinity" is meant a measure of binding strength. Without being bound to theory, affinity depends on the closeness of stereochemical fit between antibody combining sites and antigen determinants, on the size of the area of contact between them, and on the distribution of charged and hydrophobic groups. Affinity also includes the term "avidity," which refers to the strength of the antigen-antibody bond after formation of reversible complexes. Methods for calculating the affinity of an antibody for an antigen are known in the art, comprising use of binding experiments to calculate affinity. Antibody activity in functional assays (e.g., flow cytometry assay) is also reflective of antibody affinity. Antibodies and affinities can be phenotypically characterized and compared using functional assays (e.g., flow cytometry assay).

Nucleic acid molecules useful in the presently disclosed subject matter include any nucleic acid molecule that encodes an antibody or an antigen-binding portion thereof. Such nucleic acid molecules need not be 100% identical with an endogenous nucleic acid sequence, but will typically exhibit substantial identity. Polynucleotides having "substantial homology" or "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152: 507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 μg/ml denatured salmon sperm DNA (ssDNA). In a most preferred embodiment, hybridization will occur at 42° C. in 250 mM NaCl, 25 mM trisodium citrate, 1% SDS, 50% formamide, and 200 μg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM tri sodium citrate, and 0.1% SDS. In a more preferred embodiment, wash steps will occur at 42° C. in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Rogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

As used herein, the term "cross-compete" or "compete" refers to the situation where binding of a presently disclosed antibody or an antigen-binding portion thereof to a given antigen, e.g., a PRAME peptide or a PRAME/HLA class I complex (e.g., a PRAME/HLA-A complex, e.g., a PRAME/HLA-A2 complex, e.g., a PRAME/HLA-A*0201 complex), decreases or reduces binding of a reference antibody or an antigen-binding portion thereof, e.g., that comprises the $V_H$ and $V_L$ CDR1, CDR2, and CDR3 sequences or $V_H$ and $V_L$ sequences of any of the presently disclosed antibodies or antigen-binding portions thereof to the same antigen. The term "cross-compete" or "compete" also refers to the situation where binding of a reference antibody or an antigen-binding portion thereof to a given antigen, e.g., a PRAME peptide or a PRAME/HLA class I complex (e.g., a PRAME/HLA-A complex, e.g., a PRAME/HLA-A2 complex, e.g., a PRAME/HLA-A*0201 complex), decreases or reduces binding of a presently disclosed antibody or an antigen-binding portion thereof to the same antigen. The "cross-competing" or "competing" antibodies or antigen-binding portions thereof bind to the same or substantially the same epitope, an overlapping epitope, or an adjacent epitope on the antigen (e.g., a PRAME peptide or a PRAME/HLA class I complex (e.g., a PRAME/HLA-A complex, e.g., a PRAME/HLA-A2 complex, e.g., a PRAME/HLA-A*0201 complex)) as the reference antibody or antigen-binding portion thereof.

As used herein, an "effective amount" or "therapeutically effective amount" is an amount sufficient to affect a beneficial or desired clinical result upon treatment. An effective amount can be administered to a subject in one or more doses. In terms of treatment, an effective amount is an amount that is sufficient to palliate, ameliorate, stabilize, reverse or slow the progression of the disease, or otherwise reduce the pathological consequences of the disease. The effective amount is generally determined by the physician on a case-by-case basis and is within the skill of one in the art. Several factors are typically taken into account when determining an appropriate dosage to achieve an effective amount. These factors include age, sex and weight of the subject, the condition being treated, the severity of the condition and the form and effective concentration of the immunoresponsive cells administered.

As used herein, the term "heterologous nucleic acid molecule or polypeptide" refers to a nucleic acid molecule (e.g., a cDNA, DNA or RNA molecule) or polypeptide that is not normally present in a cell or sample obtained from a cell. This nucleic acid may be from another organism, or it may be, for example, an mRNA molecule that is not normally expressed in a cell or sample.

As used herein, the term "increase" refers to alter positively by at least about 5%, including, but not limited to, alter positively by about 5%, by about 10%, by about 25%, by about 30%, by about 50%, by about 75%, or by about 100%.

As used herein, the term "reduce" refers to alter negatively by at least about 5% including, but not limited to, alter negatively by about 5%, by about 10%, by about 25%, by about 30%, by about 50%, by about 75%, or by about 100%.

As used herein, the term "isolated," "purified," or "biologically pure" refers to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or polypeptide of the presently disclosed subject matter is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

As used herein, the term "specifically binds" or "specifically binds to" or "specifically target" is meant a polypeptide or fragment thereof (including an antibody or an antigen-binding portion thereof) that recognizes and binds a biological molecule of interest (e.g., a PRAME/MHC complex, (e.g., a PRAME/HLA complex, more specifically, a PRAME/HLA class I complex, more specifically, a PRAME/HLA-A complex, more specifically, a PRAME/HLA-A2 complex, and more specifically, a PRAME/HLA-A*0201 complex), but which does not substantially recognize and bind other molecules in a sample, for example, a biological sample. In certain embodiments, an antibody or an antigen-binding portion thereof that "specifically binds to a PRAME/MHC complex" refers to an antibody or an antigen-binding portion thereof that binds to a PRAME/MHC complex with a $K_D$ of $5\times10^{-7}$ M or less, $1\times10^{-7}$ M or less, $5\times10^{-8}$ M or less, $1\times10^{-8}$ M or less, $5\times10^{-9}$ M or less, $1\times10^{-9}$ M or less, $5\times10^{-10}$ M or less, or $1\times10^{-10}$ M or less.

As used herein, the term "treating" or "treatment" refers to clinical intervention in an attempt to alter the disease course of the individual or cell being treated, and can be performed either for prophylaxis or during the course of clinical pathology. Therapeutic effects of treatment include, without limitation, preventing occurrence or recurrence of disease, alleviation of symptoms, diminishment of any direct or indirect pathological consequences of the disease, preventing metastases, decreasing the rate of disease progression, amelioration or palliation of the disease state, and remission or improved prognosis. By preventing progression of a disease or disorder, a treatment can prevent deterioration due to a disorder in an affected or diagnosed subject or a subject suspected of having the disorder, but also a treatment may prevent the onset of the disorder or a symptom of the disorder in a subject at risk for the disorder or suspected of having the disorder.

As used herein, the term "subject" refers to any animal (e.g., a mammal), including, but not limited to, humans, non-human primates, rodents, and the like (e.g., which is to be the recipient of a particular treatment, or from whom cells are harvested).

II. PRAME

PRAME is a cancer-testis antigen (CTA), that is not expressed in adult tissue (outside of testis)[1], but is widely expressed on many different types of cancers (e.g., renal cancer, breast cancer, lung cancer, gastrointestinal cancer, brain tumor, myeloma, Chronic Myelogenous Leukemia (CML), acute myeloid leukemia (AML), Non-Hodgkin lymphoma (also known as non-Hodgkin's lymphoma, NHL, or lymphoma), melanoma, ovary cancer, medulloblastoma, Chronic lymphocytic leukemia (CLL), mantle cell lymphoma, head and neck cancer, neuroblastoma and others) often in about >80-90% of specimens[1-12]. Table 1 lists certain key features that Key features make PRAME an attractive target.

TABLE 1

Characteristics of PRAME: an Optimal, Validated Cancer Target

Important Characteristics for a cancer target antigen
Expression in cancer cells
Expression on surface of cancer cell (in MHC context)
Limited to no expression on adult cells
Expressed on multiple cancer types
Expression on cancer stem cell or progenitor cell
Target is involved in oncogenic process
Multiple epitopes presented by multiple HLA types
Target epitope generates T cell response to cancer cell
T cell response is cytolytic to natural cancer cell
Vaccination of humans generates PRAME reactive T cells
May be used as surrogate for disease progression or diagnosis as biomarker in leukemia or cancers For example, the key features of PRAME include its limited expression on normal cells, but, importantly, its presence on leukemia stem cells[3, 13, 14], and its involvement in the oncogenic process[3, 14]-16. PRAME regulates the retinoic acid receptor pathway and has been shown to affect growth and differentiation of leukemia, solid tumor and hematopoietic cells in several systems. PRAME can be upregulated by FDA approved demethylating agents[1, 12, 17]. Several studies have described multiple distinct peptide epitopes of PRAME that elicit specific human CTL's capable of killing fresh cancer cells, thus validating the protein as being highly expressed, processed, and presented on the cell surface to a degree adequate for recognition[14, 18-22]. PRAME has also been identified as a prognostic marker[1, 12, 23, 24]. Moreover, healthy donors and patients bear PRAME reactive CTL's, showing that the antigen was not tolerating, which confirms that PRAME is unlikely to be found in adult tissues[14, 18, 25]. In this way, a cytotoxic agent directed to this antigen could provide wide, cancer selective applications.

PRAME is a nuclear protein and is inaccessible to classical antibody therapy, and has been the subject of T cell therapy[15-22]. Others have extensively studied two PRAME-derived peptides (PRA300-[309] and PRA[435-443]), that have been shown to be processed and presented by HLA-A*0201 molecules to induce cytotoxic CD8 T cells, capable of killing PRAME-positive tumor cells[18-22]. The PRAME peptide vaccines were shown to be able to induce CD8 T cell responses in a high proportion of patients with AML, which correlated with clinical benefit in some patients[21]. These results have provided strong evidence and a rational for therapeutic targeting of the PRAME derived T cell epitopes for leukemias and a wide range of human cancers.

III. Anti-PRAME Antibodies Targeting PRAME/MHC Peptide Complex

The presently disclosed subject matter employs an approach to obtaining therapeutic antibodies to any protein, including those proteins that are inaccessible because they are not expressed on the cell surface.

In order to target tumor antigens derived from intracellular or nuclear proteins, development of a therapeutic antibody an uncommon approach is required. This approach is to generate recombinant mAbs that recognize the peptide/MHC complex expressed on the cell surface, with the same specificity as a T-cell receptor (TCR). Such mAbs share functional homology with TCRs regarding target recognition, but confer higher affinity and capabilities of arming with potent cytotoxic agents that antibodies feature. Technically, TCR-like mAbs may be generated by conventional hybridoma techniques or by in vitro antibody library techniques known to those of skill in the art, to produce human, humanized or chimeric antibodies.

Only 10% of a cell's proteins are destined for expression on the cell surface; fewer still are cell surface proteins containing epitopes selective to malignant cells. Therefore, monoclonal antibodies do not exist for the vast majority of proteins, especially those uniquely expressed by cancer cells. In contrast, nearly all proteins within the cell are processed and presented on the cell surface as peptides within the context of MHC molecules for recognition by T cell receptors. Traditionally, the MHC-peptide complex could only be recognized by a T-cell receptor (TCR), limiting the ability to detect an epitope of interest using T cell-based readout assays. Phage display methodology now has enabled the reliable generation of monoclonal antibodies to these unique epitopes, thus opening the door to a new universe of antigens that were previously inaccessible. Many of these epitopes have the potential to be truly tumor-specific and largely absent on normal tissues. The use of phage display libraries has made it possible to select large numbers of antibody repertoires for unique and rare antibodies against very defined epitopes (for more details on phage display (see McCafferty et al., Nature, 348: 552-554.). The rapid identification of human Fab or scFv fragments highly specific for tumor antigen-derived peptide-MHC complex molecules has thus become possible (Noy, Expert Rev Anticancer Ther 2005:5 (3): 523-536. Chames et al., Proc Natl Acad Sci USA 2000; 97: 7969-7974; Held et al., Eur J. Immunol. 2004: 34:2919-2929; Lev et al., Cancer Res 2002; 62: 3184-3194). Immuno-toxins, generated by fusing TCR-like Fab specific for melanoma Ag MART-1 26-35/A2 or gp100 280-288/A2 to a truncated form of Pseudomonas endotoxin, have been shown to inhibit human melanoma growth both in vitro and in vivo (Klechevsky et al., Cancer Res 2008; 68 (15): 6360-6367). The present presently disclosed subject matter involves the development of a TCR-like, fully human mAb that recognizes, for example, the PRAME peptide/HLA-A2 complex for cancer therapy. Therefore, the presently disclosed subject matter provides for methods and compositions to construct phage-antibody reagents that will recognize specific MHC/peptide complexes on the cell surface in order to vastly expand our repertoire of tumor-associated, and perhaps more importantly, tumor-specific targets. The presently disclosed subject matter provides for antibodies (e.g., monoclonal antibodies) to the neo-epitopes of peptide/MHC complexes derived from the prototypical intracellular tumor antigen, PRAME.

In certain embodiments, a presently disclosed antibody or antigen-binding portion thereof binds to a PRAME/MHC complex with high affinity, for example with a $K_D$ of $1 \times 10^{-7}$ M or less, e.g., about $1 \times 10^{-8}$ M or less, about $1 \times 10^{-9}$ M or less, or about $1 \times 10^{-10}$ M or less. In certain embodiments, a presently disclosed antibody or antigen-binding portion thereof binds to a PRAME/MHC complex with a $K_D$ of from about $1 \times 10^{-10}$ M to about $1 \times 10^{-7}$ M, e.g., about from about $1 \times 10^{-10}$ M to about $1 \times 10^{-9}$ M, from $1 \times 10^{-9}$ M to about $1 \times 10^{-8}$ M, or from about $1 \times 10^{-8}$ M to about $1 \times 10^{-7}$ M. In certain embodiments, a presently disclosed antibody or antigen-binding portion thereof binds to a PRAME/MHC complex with a $K_D$ of about 1-10 nM, e.g., about 1-9 nM, about 1-8 nM, about 1-7 nM, about 1-6 nM, about 1-5 nM, about 1-4 nM, about 1-3 nM, about 1-2 nM, about 2-3 nM, about 2-4 nM, about 2-5 nM, about 2-6 nM, about 2-7 nM, about 2-8 nM, about 2-9 nM, about 2-10 nM, about 3-4 nM, about 3-5 nM, about 3-6 nM, about 3-7 nM, about 3-8 nM, about 3-9 nM, about 3-10 nM, about 4-5 nM, about 4-6 nM, about 4-7 nM, about 4-8 nM, about 4-9 nM, about 4-10 nM, about 5-6 nM, about 5-7 nM, about 5-8 nM, about 5-9 nM, about 5-10 nM, about 6-7 nM, about 6-8 nM, about 6-9 nM, about 6-10 nM, about 7-8 nM, about 7-9 nM, about 7-10 nM, about 8-9 nM, about 8-10 nM, or about 9-10 nM. In one non-limiting embodiment, the $K_D$ is 2.4 nM.

In the presently disclosed subject matter, antigen-binding proteins, including antibodies, having an antigen-binding region based on scFvs that are selected from human scFv phage display libraries using recombinant HLA-peptide complexes are described. These molecules demonstrated exquisite specificity, for example as shown with anti-PRAME antibodies that recognize only PRAME/MHC complexes (e.g., PRAME/HLA complexes, more specifically, PRAME/HLA class I complexes, more specifically, PRAME/HLA-A complexes, more specifically, PRAME/HLA-A2 complexes, and more specifically, PRAME/HLA-A*0201 complexes). In addition, along with their inability to bind to MHC-complexes containing other peptides, the molecules are also unable to bind to the peptides themselves, further demonstrating their TCR-like specificity.

Recombinant antibodies with TCR-like specificity represent a new and valuable tool for research and therapeutic applications in tumor immunology and immunotherapy. PRAME is a well-established and validated tumor antigen that has been investigated as a marker, prognostic factor and therapeutic target.

The presently disclosed antigen-binding portion can be a Fab, Fab', F(ab')$_2$, Fv or a single chain variable fragment (scFv). In certain non-limiting embodiments, the presently disclosed antigen-binding portion thereof is a scFv. In certain embodiments, the scFv is a human scFv. The scFvs of the presently disclosed subject matter selected by phage display are initially tested for their ability to bind to peptide presented on the surface of HLA-positive cells. After T2 cells are incubated in the presence of peptide, fluorescently labeled antibodies can be used to selectively recognize the antigen pulsed cells using flow cytometry.

In certain embodiments, the presently disclosed subject matter provides for antibodies that have the scFv sequence fused to one or more constant domains of the heavy or light chain variable region of the antibodies to form an antibody with an Fc region of a human immunoglobulin to yield a bivalent protein, increasing the overall avidity and stability of the antibody. In addition, the Fc portion allows the direct conjugation of other molecules, including but not limited to fluorescent dyes, cytotoxins, radioisotopes, etc. to the antibody for example, for use in antigen quantitation studies, to immobilize the antibody for affinity measurements, for targeted delivery of a therapeutic agent, and/or to test for Fc-mediated cytotoxicity using immune effector cells and many other applications.

The molecules of the presently disclosed subject matter are based on the identification and selection of scFv using phage display, the amino acid sequence of which confers the molecules' specificity for the MHC restricted peptide of interest and forms the basis of all antigen-binding proteins of the disclosure. The scFv, therefore, can be used to design a diverse array of "antibody" molecules, including, for example, full length antibodies, fragments thereof, such as Fab and F(ab')$_2$, minibodies, fusion proteins, including scFv-Fc fusions, multivalent antibodies, that is, antibodies that have more than one specificity for the same antigen or different antigens, for example, bispecific T-cell engaging antibodies (BiTe), tribodies, etc. (see Cuesta et al., *Multivalent antibodies: when design surpasses evolution. Trends in Biotechnology* 28:355-362 2010).

In constructing a recombinant immunoglobulin, appropriate amino acid sequences for constant regions of various immunoglobulin isotypes and methods for the production of a wide array of antibodies are known to those of skill in the art.

Phage display technology allows for the rapid selection and production of antigen-specific scFv and Fab fragments, which are useful in and of themselves, or which can be further developed to provide complete antibodies, antigen binding proteins or antigen binding fragments thereof. Complete mAbs with Fc domains have a number of advantages over the scFv and Fab antibodies. First, only full length Abs exert immunological function such as CDC and ADCC mediated via Fc domain. Second, bivalent mAbs offer stronger antigen-binding affinity than monomeric Fab Abs. Third, plasma half-life and renal clearance will be different with the Fab and bivalent mAb. The particular features and advantages of each can be matched to the planned effector strategy. Fourth, bivalent mAb may be internalized at different rates than scFv and Fab, altering immune function or carrier function. Alpha emitters, for example, do not need to be internalized to kill the targets, but many drugs and toxins will benefit from internalization of the immune complex. In one embodiment, therefore, once scFv clones specific for a PRAME peptide-HLA complex are obtained from phage display libraries, a full length IgG mAb using the scFv fragments is produced.

To produce recombinant human monoclonal IgG in Chinese hamster ovary (CHO) cells, a full length IgG mAb can be engineered based on a method known to those of skill in the art (Tomomatsu et al., Production of human monoclonal antibodies against FceRIa by a method combining in vitro immunization with phage display. Biosci Biotechnol Biochem 73(7): 1465-1469 2009). Briefly, antibody variable regions can be sub-cloned into mammalian expression vectors, with matching Lambda or Kappa light chain constant sequences and IgG1 subclass Fc (for example) (Lidij a P, et al. An integrated vector system for the eukaryotic expression of antibodies or their fragments after selection from phage display libraries. Gene 1997; 187(1): 9-18; Lisa J H, et al. Crystallographic structure of an intact IgG1 monoclonal antibody. Journal of Molecular Biology 1998; 275 (5): 861-872). Kinetic binding analysis (Yasmina N A, et al. Probing the binding mechanism and affinity of tanezumab, a recombinant humanized anti-NGF monoclonal antibody, using a repertoire of biosensors. Protein Science 2008; 17(8): 1326-1335) can be used to confirm specific binding of full length IgG to a PRAME/HLA class I complex with a $K_D$ in nanomolar range.

In certain embodiments, the presently disclosed subject matter provides for an antigen-binding protein that is a full length antibody (anti-PRAME antibody), the heavy and light chains of an antibody of the presently disclosed subject matter may be full-length (e.g., an antibody including at least one, and preferably two, complete heavy chains, and at least one, and preferably two, complete light chains). The antibody can be of an IgG1, IgG2, IgG3, IgG4, IgM, IgA1, IgA2, IgD, or IgE isotype. In certain embodiments, the antibody is of an IgG1, IgG2, IgG3, or IgG4 isotype. In one non-limiting embodiment, the antibody is of an IgG1 isotype (e.g., a human IgG1 antibody). The choice of antibody type may depend on the immune effector function that the antibody is designed to elicit. The light chain constant region can be a kappa or lambda constant region, preferably is a kappa constant region.

In certain embodiments, a presently disclosed antibody or other antigen-binding protein specifically binds to a PRAME peptide bound to an MHC molecule, e.g., a HLA molecule, more specifically, a HLA class I molecule, more specifically, a HLA-A molecule, more specifically, a HLA-A2, even more specifically, HLA-A*0201. The PRAME peptide can include 8-11 amino acids, e.g., 8, 9, 10, and 11 amino acids. In certain embodiment, the PRAME peptide is a 9-mer peptide. In certain embodiments, the PRAME peptide is a 10-mer peptide. The PRAME peptide can be one known in the art, including, but not limited to, PRA$^{100-108}$ (SEQ ID NO: 2), PRA$^{142-151}$ (SEQ ID NO: 3), PRA$^{300-309}$ (SEQ ID NO: 4), PRA$^{425-433}$ (SEQ ID NO: 5), and PRA$^{435-443}$ (SEQ ID NO: 6).[18-22] The sequences of SEQ ID NOS: 2-6 are provided below.

using the Kabat system (Kabat, E. A., et al. (1991) Sequences of Proteins of Immunological Interest, Fifth Edition, U.S. Department of Health and Human Services, NIH Publication No. 91-3242). The full length amino acid sequences and nucleotides encoding thereof, the heavy chain variable region sequences and nucleotides encoding thereof, and the light chain variable region sequences and nucleotides encoding thereof, of EXT009-08, EXT009-17, EXT009-20, and EXT009-29 are shown in Appendix A.

TABLE 2

| clones | HCDR1 | HCDR2 | HCDR3 | LCDR1 | LCDR2 | LCDR3 |
|---|---|---|---|---|---|---|
| EXT009-20 | GGTFSSYA (SEQ ID NO: 7) | IIPILGIA (SEQ ID NO: 8) | ARHYGQWWDY (SEQ ID NO: 9) | SSNIGSNT (SEQ ID NO: 10) | SNN (SEQ ID NO: 11) | AAWDDSLN GSYV (SEQ ID NO: 12) |
| EXT009-08 | GGTFSSHP (SEQ ID NO: 13) | IIPMLDIP (SEQ ID NO: 14) | ARGLYYYDY (SEQ ID NO: 15) | TSNIGAGFD (SEQ ID NO: 16) | GNT (SEQ ID NO: 17) | QSYDRSLST IL (SEQ ID NO: 18) |
| EXT009-17 | GGTFSSYA (SEQ ID NO: 19) | IIPIFGIA (SEQ ID NO: 20) | ARSMWYMDS (SEQ ID NO: 21) | SSNIGAGFD (SEQ ID NO: 22) | GNS (SEQ ID NO: 23) | QSYDSSLSG YV (SEQ ID NO: 24) |
| EXT009-29 | GYTFSSYG (SEQ ID NO: 25) | ISPYNGNT (SEQ ID NO: 26) | ARYSGYYYVDY (SEQ ID NO: 27) | QSISSY (SEQ ID NO: 28) | AAS (SEQ ID NO: 29) | QQSYSTPRT (SEQ ID NO: 30) |

```
                                    (SEQ ID NO: 2)
VLDGLDVLL (SEQ ID NO: 3)
SLYSFPEPEA, (SEQ ID NO: 4)
ALYVDSLFFL (SEQ ID NO: 5)
SLLQHLIGL (SEQ ID NO: 6)
NLTHVLYPV
```

In certain embodiments, the PRAME peptide is PRA$^{300-309}$. In certain embodiments, the PRAME peptide is PRA$^{435-443}$. In certain embodiments, the antibody or other antigen-binding protein binds to the C-terminal of the PRAME peptide in the PRAME/MHC complex. In certain embodiments, the antibody or other antigen-binding protein binds to the N-terminal of the PRAME peptide in the PRAME/MHC complex.

In certain embodiments, the antibody or other antigen-binding protein binds to PRA$^{300-309}$ in conjunction with HLA-A*0201. Non-limiting examples of scFvs that bind to PRA$^{300-309}$ include EXT009-01, EXT009-03, EXT009-04, EXT009-05, EXT009-07, EXT009-08, EXT009-09, EXT009-10, EXT009-12, EXT009-13, EXT009-14, EXT009-15, EXT009-17, EXT009-18, EXT009-19, EXT009-20, EXT009-21, EXT009-23, EXT009-25, EXT009-27, EXT009-29, EXT009-30, EXT009-31, EXT009-32, and EXT009-33. The heavy chain and light chain variable region CDR1, CD22, and CDR3 sequences of EXT009-08, EXT009-17, EXT009-20, and EXT009-29 are shown in Table 2 below. The CDR regions are delineated The heavy chain and light chain variable region CDR1, CD22, and CDR3 sequences of EXT009-01, EXT009-03, EXT009-04, EXT009-05, EXT009-07, EXT009-09, EXT009-10, EXT009-12, EXT009-13, EXT009-14, EXT009-15, EXT009-18, EXT009-19, EXT009-21, EXT009-23, EXT009-25, EXT009-27, EXT009-30, EXT009-31, EXT009-32, and EXT009-33 are shown in Appendix B. The full length amino acid sequences and nucleotides encoding thereof, the heavy chain variable region sequences and nucleotides encoding thereof, and the light chain variable region sequences and nucleotides encoding thereof, of EXT009-01, EXT009-03, EXT009-04, EXT009-05, EXT009-07, EXT009-09, EXT009-10, EXT009-12, EXT009-13, EXT009-14, EXT009-15, EXT009-18, EXT009-19, EXT009-21, EXT009-23, EXT009-25, EXT009-27, EXT009-30, EXT009-31, EXT009-32, and EXT009-33 are shown in Appendix C.

In certain embodiments, the antibody or other antigen-binding protein binds to PRA$^{435-443}$ in conjunction with HLA-A*0201. Non-limiting examples of scFvs that bind to PRA$^{435-443}$ include EXT010-01, EXT010-03, EXT010-04, EXT010-06, EXT010-07, EXT010-08, EXT010-10, EXT010-12, EXT010-13, EXT010-15, EXT010-17, EXT010-23, EXT010-24, EXT010-25, EXT010-26, EXT010-27, EXT010-28, EXT010-29, EXT010-30, EXT010-31, EXT010-32, EXT010-33, EXT010-34, EXT010-37, EXT010-40, EXT010-42, EXT010-44, EXT010-47, EXT010-48, EXT010-49, EXT010-55, EXT010-56, EXT010-59, and EXT010-60. The heavy chain and light chain variable region CDR1, CDR2, and CDR3 sequences of EXT010-12, EXT010-37, and EXT010-40, are shown in Table 3 below. The full length amino acid sequences and nucleotides encoding thereof, the heavy chain variable region sequences and nucleotides encoding thereof, and the light chain variable region sequences and nucleotides encoding thereof, of EXT010-12, EXT010-37, and EXT010-40 are shown in Appendix A.

TABLE 3

| clones | HCDR1 | HCDR2 | HCDR3 | LCDR1 | LCDR2 | LCDR3 |
|---|---|---|---|---|---|---|
| EXT010-12 | GGTFSSYA (SEQ ID NO: 31) | IIPILGIA (SEQ ID NO: 32) | ARQGYVWSEMDF (SEQ ID NO: 33) | NIGSKS (SEQ ID NO: 34) | YDS (SEQ ID NO: 35) | QVWDSIT DHYV (SEQ ID NO: 36) |
| EXT010-37 | GYTFTSYY (SEQ ID NO: 37) | INPSGGST (SEQ ID NO: 38) | AAGSYYSLDI (SEQ ID NO: 39) | SGSIASNF (SEQ ID NO: 40) | DDN (SEQ ID NO: 41) | QSYDGSN VI (SEQ ID NO: 42) |
| EXT010-40 | GYTFSSYY (SEQ ID NO: 43) | INPTSGST (SEQ ID NO: 44) | ARSGGGYGDS (SEQ ID ) NO: 45 | NFGSQS (SEQ ID NO: 46) | YDQ (SEQ ID NO: 47) | QVWDTY TDHVV (SEQ ID NO: 48) |

The heavy chain and light chain variable region CDR1, CDR2, and CDR3 sequences of EXT010-01, EXT010-03, EXT010-04, EXT010-06, EXT010-07, EXT010-08, EXT010-10, EXT010-13, EXT010-15, EXT010-17, EXT010-23, EXT010-24, EXT010-25, EXT010-26, EXT010-27, EXT010-28, EXT010-29, EXT010-30, EXT010-31, EXT010-32, EXT010-33, EXT010-34, EXT010-42, EXT010-44, EXT010-47, EXT010-48, EXT010-49, EXT010-55, EXT010-56, EXT010-59, and EXT010-60 are shown in Appendix D. The full length amino acid sequences and nucleotides encoding thereof, the heavy chain variable region sequences and nucleotides encoding thereof, and the light chain variable region sequences and nucleotides encoding thereof, of EXT010-01, EXT010-03, EXT010-04, EXT010-06, EXT010-07, EXT010-08, EXT010-10, EXT010-13, EXT010-15, EXT010-17, EXT010-23, EXT010-24, EXT010-25, EXT010-26, EXT010-27, EXT010-28, EXT010-29, EXT010-30, EXT010-31, EXT010-32, EXT010-33, EXT010-34, EXT010-42, EXT010-44, EXT010-47, EXT010-48, EXT010-49, EXT010-55, EXT010-56, EXT010-59, and EXT010-60 are shown in Appendix C.

Given that each of EXT009-01, EXT009-03, EXT009-04, EXT009-05, EXT009-07, EXT009-08, EXT009-09, EXT009-10, EXT009-12, EXT009-13, EXT009-14, EXT009-15, EXT009-17, EXT009-18, EXT009-19, EXT009-20, EXT009-21, EXT009-23, EXT009-25, EXT009-27, EXT009-29, EXT009-30, EXT009-31, EXT009-32, and EXT009-33 can bind to PRA$^{300-309}$ in conjunction with HLA-A*0201, the V$_H$ and V$_L$ sequences of EXT009-01, EXT009-03, EXT009-04, EXT009-05, EXT009-07, EXT009-08, EXT009-09, EXT009-10, EXT009-12, EXT009-13, EXT009-14, EXT009-15, EXT009-17, EXT009-18, EXT009-19, EXT009-20, EXT009-21, EXT009-23, EXT009-25, EXT009-27, EXT009-29, EXT009-30, EXT009-31, EXT009-32, and EXT009-33 can be "mixed and matched" to create other antibodies or other antigen-binding proteins that bind to PRA$^{300-309}$ in conjunction with HLA-A*0201.

Similarly, given that each of EXT010-01, EXT010-03, EXT010-04, EXT010-06, EXT010-07, EXT010-08, EXT010-10, EXT010-12, EXT010-13, EXT010-15, EXT010-17, EXT010-23, EXT010-24, EXT010-25, EXT010-26, EXT010-27, EXT010-28, EXT010-29, EXT010-30, EXT010-31, EXT010-32, EXT010-33, EXT010-34, EXT010-37, EXT010-40, EXT010-42, EXT010-44, EXT010-47, EXT010-48, EXT010-49, EXT010-55, EXT010-56, EXT010-59, and EXT010-60 can bind to PRA$^{435-443}$ in conjunction with HLA-A*0201, the V$_H$ and V$_L$ sequences of EXT010-01, EXT010-03, EXT010-04, EXT010-06, EXT010-07, EXT010-08, EXT010-10, EXT010-12, EXT010-13, EXT010-15, EXT010-17, EXT010-23, EXT010-24, EXT010-25, EXT010-26, EXT010-27, EXT010-28, EXT010-29, EXT010-30, EXT010-31, EXT010-32, EXT010-33, EXT010-34, EXT010-37, EXT010-40, EXT010-42, EXT010-44, EXT010-47, EXT010-48, EXT010-49, EXT010-55, EXT010-56, EXT010-59, and EXT010-60 can be "mixed and matched" to create other antibodies or other antigen-binding proteins that bind to PRA$^{435-443}$ in conjunction with HLA-A*0201.

Such "mixed and matched" antibodies can be tested using the binding assays known in the art, including for example, ELISAs, Western blots, RIAs, Biacore analysis. Preferably, when V$_H$ and V$_L$ chains are mixed and matched, a V$_H$ sequence from a particular V$_H$/V$_L$ pairing is replaced with a structurally similar V$_H$ sequence. Likewise, a V$_L$ sequence from a particular V$_H$/V$_L$ pairing is replaced with a structurally similar V$_L$ sequence.

In certain embodiments, a presently disclosed antibody or other antigen-binding protein comprises: (a) the V$_H$ of EXT009-01, EXT009-03, EXT009-04, EXT009-05, EXT009-07, EXT009-08, EXT009-09, EXT009-10, EXT009-12, EXT009-13, EXT009-14, EXT009-15, EXT009-17, EXT009-18, EXT009-19, EXT009-20, EXT009-21, EXT009-23, EXT009-25, EXT009-27, EXT009-29, EXT009-30, EXT009-31, EXT009-32, or EXT009-33, as shown in Appendices A and C, and/or (b) the V$_L$ of EXT009-01, EXT009-03, EXT009-04, EXT009-05, EXT009-07, EXT009-08, EXT009-09, EXT009-10, EXT009-12, EXT009-13, EXT009-14, EXT009-15, EXT009-17, EXT009-18, EXT009-19, EXT009-20, EXT009-21, EXT009-23, EXT009-25, EXT009-27, EXT009-29, EXT009-30, EXT009-31, EXT009-32, or EXT009-33, as shown in Appendices A and C.

For example, the antibody or other antigen-binding protein comprises (a) a V$_H$ comprising an amino acid sequence selected from the group consisting of SEQ ID NO: 49, SEQ ID NO: 51, SEQ ID NO: 53, or SEQ ID NO: 55; and/or (b) a V$_L$ comprising an amino acid sequence selected from the group consisting of SEQ ID NO: 50, SEQ ID NO: 52, SEQ ID NO: 54, or SEQ ID NO: 56.

Preferred heavy and light chain combinations include:

(a) a heavy chain variable region comprising an amino acid sequence set forth in SEQ ID NO: 49, and a light chain variable region comprising an amino acid sequence set forth in SEQ ID NO: 50;

(b) a heavy chain variable region comprising an amino acid sequence set forth in SEQ ID NO: 51, and a light chain variable region comprising an amino acid sequence set forth in SEQ ID NO: 52;

(c) a heavy chain variable region comprising an amino acid sequence set forth in SEQ ID NO: 53, and a light chain variable region comprising an amino acid sequence set forth in SEQ ID NO: 54; or (d) a heavy chain variable region comprising an amino acid sequence set forth in SEQ ID NO: 55, and a light chain variable region comprising an amino acid sequence set forth in SEQ ID NO: 56.

In certain embodiments, a presently disclosed antibody or other antigen-binding protein comprises: (a) the $V_H$ of EXT010-01, EXT010-03, EXT010-04, EXT010-06, EXT010-07, EXT010-08, EXT010-10, EXT010-12, EXT010-13, EXT010-15, EXT010-17, EXT010-23, EXT010-24, EXT010-25, EXT010-26, EXT010-27, EXT010-28, EXT010-29, EXT010-30, EXT010-31, EXT010-32, EXT010-33, EXT010-34, EXT010-37, EXT010-40, EXT010-42, EXT010-44, EXT010-47, EXT010-48, EXT010-49, EXT010-55, EXT010-56, EXT010-59, or EXT010-60, as shown in Appendices A and C, and/or (b) the $V_L$ of EXT010-01, EXT010-03, EXT010-04, EXT010-06, EXT010-07, EXT010-08, EXT010-10, EXT010-12, EXT010-13, EXT010-15, EXT010-17, EXT010-23, EXT010-24, EXT010-25, EXT010-26, EXT010-27, EXT010-28, EXT010-29, EXT010-30, EXT010-31, EXT010-32, EXT010-33, EXT010-34, EXT010-37, EXT010-40, EXT010-42, EXT010-44, EXT010-47, EXT010-48, EXT010-49, EXT010-55, EXT010-56, EXT010-59, or EXT010-60, as shown in Appendices A and C.

For example, the antibody or other antigen-binding protein comprises (a) a $V_H$ comprising an amino acid sequence selected from the group consisting of SEQ ID NO: 57, SEQ ID NO: 59, or SEQ ID NO: 61; and/or (b) a $V_L$ comprising an amino acid sequence selected from the group consisting of SEQ ID NO: 58, SEQ ID NO: 60, or SEQ ID NO: 62.

Preferred heavy and light chain combinations include:

(a) a heavy chain variable region comprising an amino acid sequence set forth in SEQ ID NO: 57, and a light chain variable region comprising an amino acid sequence set forth in SEQ ID NO: 58;

(b) a heavy chain variable region comprising an amino acid sequence set forth in SEQ ID NO: 59, and a light chain variable region comprising an amino acid sequence set forth in SEQ ID NO: 60; or (c) a heavy chain variable region comprising an amino acid sequence set forth in SEQ ID NO: 61, and a light chain variable region comprising an amino acid sequence set forth in SEQ ID NO: 62.

In certain embodiments, the presently disclosed antibody or other antigen-binding protein comprises the heavy chain and light chain CDR1s, CDR2s and CDR3s of EXT009-01, EXT009-03, EXT009-04, EXT009-05, EXT009-07, EXT009-08, EXT009-09, EXT009-10, EXT009-12, EXT009-13, EXT009-14, EXT009-15, EXT009-17, EXT009-18, EXT009-19, EXT009-20, EXT009-21, EXT009-23, EXT009-25, EXT009-27, EXT009-29, EXT009-30, EXT009-31, EXT009-32, EXT009-33, EXT010-01, EXT010-03, EXT010-04, EXT010-06, EXT010-07, EXT010-08, EXT010-10, EXT010-12, EXT010-13, EXT010-15, EXT010-17, EXT010-23, EXT010-24, EXT010-25, EXT010-26, EXT010-27, EXT010-28, EXT010-29, EXT010-30, EXT010-31, EXT010-32, EXT010-33, EXT010-34, EXT010-37, EXT010-40, EXT010-42, EXT010-44, EXT010-47, EXT010-48, EXT010-49, EXT010-55, EXT010-56, EXT010-59, or EXT010-60, as shown in Tables 2 and 3, and Appendices B and D.

Given that each of EXT009-01, EXT009-03, EXT009-04, EXT009-05, EXT009-07, EXT009-08, EXT009-09, EXT009-10, EXT009-12, EXT009-13, EXT009-14, EXT009-15, EXT009-17, EXT009-18, EXT009-19, EXT009-20, EXT009-21, EXT009-23, EXT009-25, EXT009-27, EXT009-29, EXT009-30, EXT009-31, EXT009-32, and EXT009-33 can bind to $PRA^{300-309}$ in conjunction with HLA-A*0201 and that antigen-binding specificity is provided primarily by the CDR1, CDR2, and CDR3 regions, the $V_H$ CDR1, CDR2, and CDR3 sequences and $V_L$ CDR1, CDR2, and CDR3 sequences of each of EXT009-01, EXT009-03, EXT009-04, EXT009-05, EXT009-07, EXT009-08, EXT009-09, EXT009-10, EXT009-12, EXT009-13, EXT009-14, EXT009-15, EXT009-17, EXT009-18, EXT009-19, EXT009-20, EXT009-21, EXT009-23, EXT009-25, EXT009-27, EXT009-29, EXT009-30, EXT009-31, EXT009-32, and EXT009-33 can be "mixed and matched" (i.e., CDRs from different antibodies can be mixed and match, although each antibody must contain a $V_H$ CDR1, CDR2, and CDR3 and a $V_L$ CDR1, CDR2, and CDR3) to create other antibodies or other antigen-binding proteins that bind to $PRA^{300-309}$ in conjunction with HLA-A*0201.

Similarly, given that each of EXT010-01, EXT010-03, EXT010-04, EXT010-06, EXT010-07, EXT010-08, EXT010-10, EXT010-12, EXT010-13, EXT010-15, EXT010-17, EXT010-23, EXT010-24, EXT010-25, EXT010-26, EXT010-27, EXT010-28, EXT010-29, EXT010-30, EXT010-31, EXT010-32, EXT010-33, EXT010-34, EXT010-37, EXT010-40, EXT010-42, EXT010-44, EXT010-47, EXT010-48, EXT010-49, EXT010-55, EXT010-56, EXT010-59, and EXT010-60 can bind to $PRA^{435-443}$ in conjunction with HLA-A*0201 and that antigen-binding specificity is provided primarily by the CDR1, CDR2, and CDR3 regions, the $V_H$ CDR1, CDR2, and CDR3 sequences and $V_L$ CDR1, CDR2, and CDR3 sequences of each of EXT010-01, EXT010-03, EXT010-04, EXT010-06, EXT010-07, EXT010-08, EXT010-10, EXT010-12, EXT010-13, EXT010-15, EXT010-17, EXT010-23, EXT010-24, EXT010-25, EXT010-26, EXT010-27, EXT010-28, EXT010-29, EXT010-30, EXT010-31, EXT010-32, EXT010-33, EXT010-34, EXT010-37, EXT010-40, EXT010-42, EXT010-44, EXT010-47, EXT010-48, EXT010-49, EXT010-55, EXT010-56, EXT010-59, and EXT010-60 can be "mixed and matched" to create other antibodies or other antigen-binding proteins that bind to $PRA^{435-443}$ in conjunction with HLA-A*0201. Such "mixed and matched" antibodies can be tested using the binding assays described above.

When $V_H$ CDR sequences are mixed and matched, the CDR1, CDR2 and/or CDR3 sequence from a particular $V_H$ sequence is replaced with a structurally similar CDR sequence(s). Likewise, when $V_L$ CDR sequences are mixed and matched, the CDR1, CDR2 and/or CDR3 sequence from a particular $V_L$ sequence preferably is replaced with a structurally similar CDR sequence(s). It will be readily apparent to the ordinarily skilled artisan that novel $V_H$ and $V_L$ sequences can be created by substituting one or more $V_H$ and/or $V_L$ CDR region sequences with structurally similar sequences from the CDR sequences of the antibodies or antigen-binding portions thereof disclosed herein.

In certain embodiments, a presently disclosed antibody, or antigen-binding portion thereof comprises:

(a) the $V_H$ CDR1 of EXT009-01, EXT009-03, EXT009-04, EXT009-05, EXT009-07, EXT009-08, EXT009-09, EXT009-10, EXT009-12, EXT009-13, EXT009-14, EXT009-15, EXT009-17, EXT009-18, EXT009-19, EXT009-20, EXT009-21, EXT009-23, EXT009-25, EXT009-27, EXT009-29, EXT009-30, EXT009-31, EXT009-32, or EXT009-33, as shown in Table 2 and Appendix B;

(b) the V$_H$ CDR2 of EXT009-01, EXT009-03, EXT009-04, EXT009-05, EXT009-07, EXT009-08, EXT009-09, EXT009-10, EXT009-12, EXT009-13, EXT009-14, EXT009-15, EXT009-17, EXT009-18, EXT009-19, EXT009-20, EXT009-21, EXT009-23, EXT009-25, EXT009-27, EXT009-29, EXT009-30, EXT009-31, EXT009-32, or EXT009-33, as shown in Table 2 and Appendix B;

(c) the V$_H$ CDR3 of EXT009-01, EXT009-03, EXT009-04, EXT009-05, EXT009-07, EXT009-08, EXT009-09, EXT009-10, EXT009-12, EXT009-13, EXT009-14, EXT009-15, EXT009-17, EXT009-18, EXT009-19, EXT009-20, EXT009-21, EXT009-23, EXT009-25, EXT009-27, EXT009-29, EXT009-30, EXT009-31, EXT009-32, or EXT009-33, as shown in Table 2 and Appendix B;

(d) the V$_L$ CDR1 of EXT009-01, EXT009-03, EXT009-04, EXT009-05, EXT009-07, EXT009-08, EXT009-09, EXT009-10, EXT009-12, EXT009-13, EXT009-14, EXT009-15, EXT009-17, EXT009-18, EXT009-19, EXT009-20, EXT009-21, EXT009-23, EXT009-25, EXT009-27, EXT009-29, EXT009-30, EXT009-31, EXT009-32, or EXT009-33, as shown in Table 2 and Appendix B;

(e) the V$_L$ CDR2 of EXT009-01, EXT009-03, EXT009-04, EXT009-05, EXT009-07, EXT009-08, EXT009-09, EXT009-10, EXT009-12, EXT009-13, EXT009-14, EXT009-15, EXT009-17, EXT009-18, EXT009-19, EXT009-20, EXT009-21, EXT009-23, EXT009-25, EXT009-27, EXT009-29, EXT009-30, EXT009-31, EXT009-32, or EXT009-33, as shown in Table 2 and Appendix B; and (f) the V$_L$ CDR3 of EXT009-01, EXT009-03, EXT009-04, EXT009-05, EXT009-07, EXT009-08, EXT009-09, EXT009-10, EXT009-12, EXT009-13, EXT009-14, EXT009-15, EXT009-17, EXT009-18, EXT009-19, EXT009-20, EXT009-21, EXT009-23, EXT009-25, EXT009-27, EXT009-29, EXT009-30, EXT009-31, EXT009-32, or EXT009-33, as shown in Table 2 and Appendix B.

For example, a presently disclosed antibody, or antigen-binding portion thereof comprises:

(a) a heavy chain variable region CDR1 comprising an amino acid sequence selected from the group consisting of SEQ ID NOs: 7, 13, 19, and 25;

(b) a heavy chain variable region CDR2 comprising an amino acid sequence selected from the group consisting of SEQ ID NOs: 8, 14, 20, and 26;

(c) a heavy chain variable region CDR3 comprising an amino acid sequence selected from the group consisting of SEQ ID NOs: 9, 15, 21, and 27;

(d) a light chain variable region CDR1 comprising an amino acid sequence selected from the group consisting of SEQ ID NOs: 10, 16, 22, and 28;

(e) a light chain variable region CDR2 comprising an amino acid sequence selected from the group consisting of SEQ ID NOs: 11, 17, 23, and 29; and (f) a light chain variable region CDR3 comprising an amino acid sequence selected from the group consisting of SEQ ID NOs: 12, 18, 24, and 30.

In one embodiment, a presently disclosed antibody, or antigen-binding portion thereof comprises: a heavy chain variable region CDR1 comprising an amino acid sequence set forth in SEQ ID NO: 7; a heavy chain variable region CDR2 comprising an amino acid sequence set forth in SEQ ID NO: 8; a heavy chain variable region CDR3 comprising an amino acid sequence set forth in SEQ ID NO: 9; a light chain variable region CDR1 comprising an amino acid sequence set forth in SEQ ID NO: 10; a light chain variable region CDR2 comprising an amino acid sequence set forth in SEQ ID NO: 11; and a light chain variable region CDR3 comprising an amino acid sequence set forth in SEQ ID NO: 12. The antibody comprising this combination of CDR1, CDR2, and CDR3 is referred to as "Pr300#20" or "Pr#20".

In one embodiment, a presently disclosed antibody, or antigen-binding portion thereof comprises: a heavy chain variable region CDR1 comprising an amino acid sequence set forth in SEQ ID NO: 13; a heavy chain variable region CDR2 comprising an amino acid sequence set forth in SEQ ID NO: 14; a heavy chain variable region CDR3 comprising an amino acid sequence set forth in SEQ ID NO: 15; a light chain variable region CDR1 comprising an amino acid sequence set forth in SEQ ID NO: 16; a light chain variable region CDR2 comprising an amino acid sequence set forth in SEQ ID NO: 17; and a light chain variable region CDR3 comprising an amino acid sequence set forth in SEQ ID NO: 18. The antibody comprising this combination of CDR1, CDR2, and CDR3 is referred to as "Pr300#8".

In one embodiment, a presently disclosed antibody, or antigen-binding portion thereof comprises: a heavy chain variable region CDR1 comprising an amino acid sequence set forth in SEQ ID NO: 19; a heavy chain variable region CDR2 comprising an amino acid sequence set forth in SEQ ID NO: 20; a heavy chain variable region CDR3 comprising an amino acid sequence set forth in SEQ ID NO: 21; a light chain variable region CDR1 comprising an amino acid sequence set forth in SEQ ID NO: 22; a light chain variable region CDR2 comprising an amino acid sequence set forth in SEQ ID NO: 23; and a light chain variable region CDR3 comprising an amino acid sequence set forth in SEQ ID NO: 24. The antibody comprising this combination of CDR1, CDR2, and CDR3 is referred to as "Pr300#17".

In one embodiment, a presently disclosed antibody, or antigen-binding portion thereof comprises: a heavy chain variable region CDR1 comprising an amino acid sequence set forth in SEQ ID NO: 25; a heavy chain variable region CDR2 comprising an amino acid sequence set forth in SEQ ID NO: 26; a heavy chain variable region CDR3 comprising an amino acid sequence set forth in SEQ ID NO: 27; a light chain variable region CDR1 comprising an amino acid sequence set forth in SEQ ID NO: 28; a light chain variable region CDR2 comprising an amino acid sequence set forth in SEQ ID NO: 29; and a light chain variable region CDR3 comprising an amino acid sequence set forth in SEQ ID NO: 30. The antibody comprising this combination of CDR1, CDR2, and CDR3 is referred to as "Pr300#29".

In certain embodiments, a presently disclosed antibody, or antigen-binding portion thereof comprises:

(a) the V$_H$ CDR1 of EXT010-01, EXT010-03, EXT010-04, EXT010-06, EXT010-07, EXT010-08, EXT010-10, EXT010-12, EXT010-13, EXT010-15, EXT010-17, EXT010-23, EXT010-24, EXT010-25, EXT010-26, EXT010-27, EXT010-28, EXT010-29, EXT010-30, EXT010-31, EXT010-32, EXT010-33, EXT010-34, EXT010-37, EXT010-40, EXT010-42, EXT010-44, EXT010-47, EXT010-48, EXT010-49, EXT010-55, EXT010-56, EXT010-59, or EXT010-60, as shown in Table 3 and Appendix D;

(b) the V$_H$ CDR2 of EXT010-01, EXT010-03, EXT010-04, EXT010-06, EXT010-07, EXT010-08, EXT010-10, EXT010-12, EXT010-13, EXT010-15, EXT010-17, EXT010-23, EXT010-24, EXT010-25, EXT010-26, EXT010-27, EXT010-28, EXT010-29, EXT010-30, EXT010-31, EXT010-32, EXT010-33, EXT010-34, EXT010-37, EXT010-40, EXT010-42, EXT010-44, EXT010-47, EXT010-48, EXT010-49, EXT010-55, EXT010-56, EXT010-59, or EXT010-60, as shown in Table 3 and Appendix D;

(c) the V$_H$ CDR3 of EXT010-01, EXT010-03, EXT010-04, EXT010-06, EXT010-07, EXT010-08, EXT010-10, EXT010-12, EXT010-13, EXT010-15, EXT010-17, EXT010-23, EXT010-24, EXT010-25, EXT010-26, EXT010-27, EXT010-28, EXT010-29, EXT010-30, EXT010-31, EXT010-32, EXT010-33, EXT010-34, EXT010-37, EXT010-40, EXT010-42, EXT010-44, EXT010-47, EXT010-48, EXT010-49, EXT010-55, EXT010-56, EXT010-59, or EXT010-60, or EXT009-33, as shown in Table 3 and Appendix D;

(d) the V$_L$ CDR1 of EXT010-01, EXT010-03, EXT010-04, EXT010-06, EXT010-07, EXT010-08, EXT010-10, EXT010-12, EXT010-13, EXT010-15, EXT010-17, EXT010-23, EXT010-24, EXT010-25, EXT010-26, EXT010-27, EXT010-28, EXT010-29, EXT010-30, EXT010-31, EXT010-32, EXT010-33, EXT010-34, EXT010-37, EXT010-40, EXT010-42, EXT010-44, EXT010-47, EXT010-48, EXT010-49, EXT010-55, EXT010-56, EXT010-59, or EXT010-60, as shown in Table 3 and Appendix D;

(e) the V$_L$ CDR2 of EXT010-01, EXT010-03, EXT010-04, EXT010-06, EXT010-07, EXT010-08, EXT010-10, EXT010-12, EXT010-13, EXT010-15, EXT010-17, EXT010-23, EXT010-24, EXT010-25, EXT010-26, EXT010-27, EXT010-28, EXT010-29, EXT010-30, EXT010-31, EXT010-32, EXT010-33, EXT010-34, EXT010-37, EXT010-40, EXT010-42, EXT010-44, EXT010-47, EXT010-48, EXT010-49, EXT010-55, EXT010-56, EXT010-59, or EXT010-60, as shown in Table 3 and Appendix D; and (f) the V$_L$ CDR3 of EXT010-01, EXT010-03, EXT010-04, EXT010-06, EXT010-07, EXT010-08, EXT010-10, EXT010-12, EXT010-13, EXT010-15, EXT010-17, EXT010-23, EXT010-24, EXT010-25, EXT010-26, EXT010-27, EXT010-28, EXT010-29, EXT010-30, EXT010-31, EXT010-32, EXT010-33, EXT010-34, EXT010-37, EXT010-40, EXT010-42, EXT010-44, EXT010-47, EXT010-48, EXT010-49, EXT010-55, EXT010-56, EXT010-59, or EXT010-60, as shown in Table 3 and Appendix D.

For example, a presently disclosed antibody, or antigen-binding portion thereof comprises:

(a) a heavy chain variable region CDR1 comprising an amino acid sequence selected from the group consisting of SEQ ID NOs: 31, 37, and 43;

(b) a heavy chain variable region CDR2 comprising an amino acid sequence selected from the group consisting of SEQ ID NOs: 32, 38, and 44;

(c) a heavy chain variable region CDR3 comprising an amino acid sequence selected from the group consisting of SEQ ID NOs: 33, 39, and 45;

(d) a light chain variable region CDR1 comprising an amino acid sequence selected from the group consisting of SEQ ID NOs: 34, 40, and 46;

(e) a light chain variable region CDR2 comprising an amino acid sequence selected from the group consisting of SEQ ID NOs: 35, 41, and 47; and (f) a light chain variable region CDR3 comprising an amino acid sequence selected from the group consisting of SEQ ID NOs: 36, 42, and 48.

In one embodiment, a presently disclosed antibody, or antigen-binding portion thereof comprises: a heavy chain variable region CDR1 comprising an amino acid sequence set forth in SEQ ID NO: 31; a heavy chain variable region CDR2 comprising an amino acid sequence set forth in SEQ ID NO: 32; a heavy chain variable region CDR3 comprising an amino acid sequence set forth in SEQ ID NO: 33; a light chain variable region CDR1 comprising an amino acid sequence set forth in SEQ ID NO: 34; a light chain variable region CDR2 comprising an amino acid sequence set forth in SEQ ID NO: 35; and a light chain variable region CDR3 comprising an amino acid sequence set forth in SEQ ID NO: 36. The antibody comprising this combination of CDR1, CDR2, and CDR3 is referred to as "Pr4350#12".

In one embodiment, a presently disclosed antibody, or antigen-binding portion thereof comprises: a heavy chain variable region CDR1 comprising an amino acid sequence set forth in SEQ ID NO: 37; a heavy chain variable region CDR2 comprising an amino acid sequence set forth in SEQ ID NO: 38; a heavy chain variable region CDR3 comprising an amino acid sequence set forth in SEQ ID NO: 39; a light chain variable region CDR1 comprising an amino acid sequence set forth in SEQ ID NO: 40; a light chain variable region CDR2 comprising an amino acid sequence set forth in SEQ ID NO: 41; and a light chain variable region CDR3 comprising an amino acid sequence set forth in SEQ ID NO: 42. The antibody comprising this combination of CDR1, CDR2, and CDR3 is referred to as "Pr4350#37".

In one embodiment, a presently disclosed antibody, or antigen-binding portion thereof comprises: a heavy chain variable region CDR1 comprising an amino acid sequence set forth in SEQ ID NO: 43; a heavy chain variable region CDR2 comprising an amino acid sequence set forth in SEQ ID NO: 44; a heavy chain variable region CDR3 comprising an amino acid sequence set forth in SEQ ID NO: 45; a light chain variable region CDR1 comprising an amino acid sequence set forth in SEQ ID NO: 46; a light chain variable region CDR2 comprising an amino acid sequence set forth in SEQ ID NO: 47; and a light chain variable region CDR3 comprising an amino acid sequence set forth in SEQ ID NO: 48. The antibody comprising this combination of CDR1, CDR2, and CDR3 is referred to as "Pr4350#40".

The constant region/framework region of the presently disclosed antibodies can be altered, for example, by amino acid substitution, to modify the properties of the antibody (e.g., to increase or decrease one or more of: antigen binding affinity, Fc receptor binding, antibody carbohydrate, for example, glycosylation, fucosylation, etc, the number of cysteine residues, effector cell function, effector cell function, complement function or introduction of a conjugation site).

In certain embodiments, a presently disclosed antibody is a fully-human antibody. Fully-human mAbs are preferred for therapeutic use in humans because murine antibodies cause an immunogenicity reaction, known as the HAMA (human anti-mouse antibodies) response (Azinovic I, et al. Survival benefit associated with human anti-mouse antibody (HAMA) in patients with B-cell malignancies. Cancer Immunol Immunother 2006; 55(12):1451-8; Tjandra J J, et al. Development of human anti-murine antibody (HAMA) response in patients. Immunol Cell Biol 1990; 68(6):367-76), when administered to humans, causing serious side effects, including anaphylaxis and hypersensitivity reactions. This immunogenicity reaction is triggered by the human immune system recognizing the murine antibodies as foreign because of slightly different amino acid sequences from natural human antibodies. Humanization methods known in the art (Riechmann L, et al. Reshaping human antibodies for therapy. Nature 1988; 332 (6162): 332:323; Queen C, et al. A humanized antibody that binds to the interleukin 2 receptor. Proc Natl Acad Sci USA 1989; 86 (24): 10029-33) can be employed to reduce the immunogenicity of murine-derived antibodies (Gerd R, et al. Serological Analysis of Human Anti-Human Antibody Responses in Colon Cancer Patients Treated with Repeated Doses of Humanized Monoclonal Antibody A33. Cancer Res 2001; 61, 6851-6859).

The use of phage display libraries has made it possible to select large numbers of antibodies repertoires for unique and rare antibodies against very defined epitopes (for more details on phage display see McCafferty et al., Phage antibodies: filamentous phage displaying antibody variable domains. Nature, 348: 552-554.) The rapid identification of human Fab or scFvs highly specific for tumor antigen-derived peptide-MHC complex molecules has thus become possible. Immuno-toxins, generated by fusing TCR-like Fab specific for melanoma Ag MART-1 26-35/A2 or gp100 280-288/A2 to a truncated form of Pseudomonas endotoxin, have been shown to inhibit human melanoma growth both in vitro and in vivo (Klechevsky E, et al. Antitumor activity of immunotoxins with T-cell receptor-like specificity against human melanoma xenografts. Cancer Res 2008; 68 (15): 6360-6367). In addition, by engineering full-length monoclonal antibodies (mAbs) using the Fab fragments, it is possible to directly generate a therapeutic human mAbs, bypassing months of time-consuming work, normally needed for developing therapeutic mAbs, e.g., for treating cancers.

Homologous Antibodies

In certain embodiments, an antibody of the presently disclosed subject matter comprises heavy and light chain variable regions comprising amino acid sequences that are homologous to the amino acid sequences of the antibodies or antigen-binding portions thereof (e.g., scFvs) described herein (e.g., EXT009-01, EXT009-03, EXT009-04, EXT009-05, EXT009-07, EXT009-08, EXT009-09, EXT009-10, EXT009-12, EXT009-13, EXT009-14, EXT009-15, EXT009-17, EXT009-18, EXT009-19, EXT009-20, EXT009-21, EXT009-23, EXT009-25, EXT009-27, EXT009-29, EXT009-30, EXT009-31, EXT009-32, EXT009-33, EXT010-01, EXT010-03, EXT010-04, EXT010-06, EXT010-07, EXT010-08, EXT010-10, EXT010-12, EXT010-13, EXT010-15, EXT010-17, EXT010-23, EXT010-24, EXT010-25, EXT010-26, EXT010-27, EXT010-28, EXT010-29, EXT010-30, EXT010-31, EXT010-32, EXT010-33, EXT010-34, EXT010-37, EXT010-40, EXT010-42, EXT010-44, EXT010-47, EXT010-48, EXT010-49, EXT010-55, EXT010-56, EXT010-59, or EXT010-60), and wherein the antibodies or antigen-binding portions thereof retain the desired functional properties of the anti-PRAME antibodies or antigen-binding portions thereof of the presently disclosed subject matter.

For example, a presently disclosed antibody or antigen-binding portion thereof comprises a heavy chain variable region comprising an amino acid sequence that is at least 80% homologous to the $V_H$ sequence of EXT009-01, EXT009-03, EXT009-04, EXT009-05, EXT009-07, EXT009-08, EXT009-09, EXT009-10, EXT009-12, EXT009-13, EXT009-14, EXT009-15, EXT009-17, EXT009-18, EXT009-19, EXT009-20, EXT009-21, EXT009-23, EXT009-25, EXT009-27, EXT009-29, EXT009-30, EXT009-31, EXT009-32, EXT009-33, EXT010-01, EXT010-03, EXT010-04, EXT010-06, EXT010-07, EXT010-08, EXT010-10, EXT010-12, EXT010-13, EXT010-15, EXT010-17, EXT010-23, EXT010-24, EXT010-25, EXT010-26, EXT010-27, EXT010-28, EXT010-29, EXT010-30, EXT010-31, EXT010-32, EXT010-33, EXT010-34, EXT010-37, EXT010-40, EXT010-42, EXT010-44, EXT010-47, EXT010-48, EXT010-49, EXT010-55, EXT010-56, EXT010-59, or EXT010-60 (as shown in Appendices B and C), and a light chain variable region comprising an amino acid sequence that is at least 80% homologous to the $V_L$ sequence of EXT009-01, EXT009-03, EXT009-04, EXT009-05, EXT009-07, EXT009-08, EXT009-09, EXT009-10, EXT009-12, EXT009-13, EXT009-14, EXT009-15, EXT009-17, EXT009-18, EXT009-19, EXT009-20, EXT009-21, EXT009-23, EXT009-25, EXT009-27, EXT009-29, EXT009-30, EXT009-31, EXT009-32, EXT009-33, EXT010-01, EXT010-03, EXT010-04, EXT010-06, EXT010-07, EXT010-08, EXT010-10, EXT010-12, EXT010-13, EXT010-15, EXT010-17, EXT010-23, EXT010-24, EXT010-25, EXT010-26, EXT010-27, EXT010-28, EXT010-29, EXT010-30, EXT010-31, EXT010-32, EXT010-33, EXT010-34, EXT010-37, EXT010-40, EXT010-42, EXT010-44, EXT010-47, EXT010-48, EXT010-49, EXT010-55, EXT010-56, EXT010-59, or EXT010-60 (as shown in Appendices B and C), and the antibody or antigen-binding portion thereof binds to a PRAME peptide in conjunction with HLA-A*0201 with a $K_D$ of about $1\times10^{-7}$ M or less.

For example, a presently disclosed antibody or antigen-binding portion thereof comprises:

(a) a heavy chain variable region comprising an amino acid sequence that is at least 80% homologous to an amino acid sequence selected from the group consisting of SEQ ID NOs: 49, 51, 53, 55, 57, 59, and 61;

(b) a light chain variable region comprising an amino acid sequence that is at least 80% homologous to an amino acid sequence selected from the group consisting of SEQ ID NOs: 50, 52, 54, 56, 58, 60, and 62; and wherein the antibody or antigen-binding portion thereof binds to a PRAME peptide in conjunction with HLA-A*0201 with a $K_D$ of about $1\times10^{-7}$ M or less.

In certain embodiments, the $V_H$ and/or $V_L$ amino acid sequences can be 80%, 81%, 82%, 83%, 84%, 85%, 86%, 87%, 88%, 89%, 90%, 91%, 92%, 93%, 94%, 95%, 96%, 97%, 98%, 99%, or 100% homologous to the sequences set forth above. An antibody having $V_H$ and $V_L$ regions having high (i.e., 80% or greater) homology to the $V_H$ and $V_L$ regions of the sequences set forth above, can be obtained by mutagenesis (e.g., site-directed or PCR-mediated mutagenesis), followed by testing of the encoded altered antibody for retained function (i.e., the binding affinity) using the binding assays described herein.

As used herein, the percent homology between two amino acid sequences is equivalent to the percent identity between the two sequences. The percent identity between the two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent homology between two amino acid sequences can be determined using the algorithm of E. Meyers and W. Miller (Comput. Appl. Biosci., 4:11-17 (1988)) which has been incorporated into the ALIGN program (version 2.0), using a PAM120 weight residue table, a gap length penalty of 12 and a gap penalty of 4. In addition, the percent homology between two amino acid sequences can be determined using the Needleman and Wunsch (J. Mol. Biol. 48:444-453 (1970)) algorithm which has been incorporated into the GAP program in the GCG software package (available at www.gcg.com), using either a Blossum 62 matrix or a PAM250 matrix, and a gap weight of 16, 14, 12, 10, 8, 6, or 4 and a length weight of 1, 2, 3, 4, 5, or 6.

Additionally or alternatively, the protein sequences of the presently disclosed subject matter can further be used as a "query sequence" to perform a search against public databases to, for example, identify related sequences. Such searches can be performed using the XBLAST program (version 2.0) of Altschul, et al. (1990) J. Mol. Biol. 215: 403-10. BLAST protein searches can be performed with the XBLAST program, score=50, wordlength=3 to obtain amino acid sequences homologous to the antibody molecules of the invention. To obtain gapped alignments for comparison purposes, Gapped BLAST can be utilized as described in Altschul et al., (1997) Nucleic Acids Res. 25(17):3389-3402. When utilizing BLAST and Gapped BLAST programs, the default parameters of the respective programs (e.g., XBLAST and NBLAST) can be used.

Antibodies with Modifications

In certain embodiments, a presently disclosed antibody or antigen-binding portion thereof comprises a heavy chain variable region comprising CDR1, CDR2 and CDR3 sequences and a light chain variable region comprising CDR1, CDR2 and CDR3 sequences, wherein one or more of these CDR sequences comprise specified amino acid sequences based on the antibodies or antigen-binding portions thereof (e.g., scFvs) described herein (e.g., EXT009-01, EXT009-03, EXT009-04, EXT009-05, EXT009-07, EXT009-08, EXT009-09, EXT009-10, EXT009-12, EXT009-13, EXT009-14, EXT009-15, EXT009-17, EXT009-18, EXT009-19, EXT009-20, EXT009-21, EXT009-23, EXT009-25, EXT009-27, EXT009-29, EXT009-30, EXT009-31, EXT009-32, EXT009-33, EXT010-01, EXT010-03, EXT010-04, EXT010-06, EXT010-07, EXT010-08, EXT010-10, EXT010-12, EXT010-13, EXT010-15, EXT010-17, EXT010-23, EXT010-24, EXT010-25, EXT010-26, EXT010-27, EXT010-28, EXT010-29, EXT010-30, EXT010-31, EXT010-32, EXT010-33, EXT010-34, EXT010-37, EXT010-40, EXT010-42, EXT010-44, EXT010-47, EXT010-48, EXT010-49, EXT010-55, EXT010-56, EXT010-59, or EXT010-60, as shown in Tables 2 and 3 and Appendix D), or modifications thereof, and wherein the antibodies or antigen-binding portions thereof retain the desired functional properties of the anti-PRAME antibodies or antigen-binding portions thereof of the presently disclosed subject matter.

Modifications do not significantly affect or alter the binding characteristics of the antibody containing the amino acid sequence. Such modifications include amino acid substitutions, additions and deletions. Modifications can be introduced into the presently antibody or antigen-binding portion by standard techniques known in the art, such as site-directed mutagenesis and PCR-mediated mutagenesis.

The modifications can be conservative modifications, non-conservative modifications, or mixtures of conservative and non-conservative modifications. Conservative amino acid substitutions are ones in which the amino acid residue is replaced with an amino acid residue having a similar side chain. Families of amino acid residues having similar side chains have been defined in the art. Exemplary conservative amino acid substitutions are shown in Table 4. Amino acid substitutions may be introduced into an antibody of interest and the products screened for a desired activity, e.g., retained/improved antigen binding, decreased immunogenicity, or improved ADCC or CDC.

TABLE 4

| Original Residue | Exemplary conservative amino acid Substitutions |
| --- | --- |
| Ala (A) | Val; Leu; Ile |
| Arg (R) | Lys; Gln; Asn |
| Asn (N) | Gln; His; Asp, Lys; Arg |
| Asp (D) | Glu; Asn |
| Cys (C) | Ser; Ala |
| Gln (Q) | Asn; Glu |
| Glu (E) | Asp; Gln |
| Gly (G) | Ala |
| His (H) | Asn; Gln; Lys; Arg |
| Ile (I) | Leu; Val; Met; Ala; Phe |
| Leu (L) | Ile; Val; Met; Ala; Phe |
| Lys (K) | Arg; Gln; Asn |
| Met (M) | Leu; Phe; Ile |
| Phe (F) | Trp; Leu; Val; Ile; Ala; Tyr |
| Pro (P) | Ala |
| Ser (S) | Thr |
| Thr (T) | Val; Ser |
| Trp (W) | Tyr; Phe |
| Tyr (Y) | Trp; Phe; Thr; Ser |
| Val (V) | Ile; Leu; Met; Phe; Ala |

Amino acids may be grouped according to common side-chain properties:

hydrophobic: Norleucine, Met, Ala, Val, Leu, Ile;
neutral hydrophilic: Cys, Ser, Thr, Asn, Gln;
acidic: Asp, Glu;
basic: His, Lys, Arg;
residues that influence chain orientation: Gly, Pro;
aromatic: Trp, Tyr, Phe;

Thus, one or more amino acid residues within a CDR region can be replaced with other amino acid residues from the same group and the altered antibody can be tested for retained function using the functional assays described herein.

Non-conservative substitutions entail exchanging a member of one of these classes for another class.

In certain embodiments, no more than one, no more than two, no more than three, no more than four, no more than five residues within a specified sequence or a CDR region are altered.

Cross-Competing Antibodies

The presently disclosed subject matter provides antibodies or antigen-binding portions thereof that cross-compete for binding to a PRAME peptide/HLA complex (e.g., a PRAME peptide/HLA class I complex, a PRAME peptide/HLA-A2 complex, or a PRAME peptide/HLA-A*0201 complex) with any of the anti-PRAME antibodies or antigen-binding portions thereof (e.g., scFvs) of the presently disclosed subject matter (e.g., EXT009-01, EXT009-03, EXT009-04, EXT009-05, EXT009-07, EXT009-08, EXT009-09, EXT009-10, EXT009-12, EXT009-13, EXT009-14, EXT009-15, EXT009-17, EXT009-18, EXT009-19, EXT009-20, EXT009-21, EXT009-23, EXT009-25, EXT009-27, EXT009-29, EXT009-30, EXT009-31, EXT009-32, EXT009-33, EXT010-01, EXT010-03, EXT010-04, EXT010-06, EXT010-07, EXT010-08, EXT010-10, EXT010-12, EXT010-13, EXT010-15, EXT010-17, EXT010-23, EXT010-24, EXT010-25, EXT010-26, EXT010-27, EXT010-28, EXT010-29, EXT010-30, EXT010-31, EXT010-32, EXT010-33, EXT010-34, EXT010-37, EXT010-40, EXT010-42, EXT010-44, EXT010-47, EXT010-48, EXT010-49, EXT010-55, EXT010-56, EXT010-59, and EXT010-60). The cross-competing antibodies or antigen-binding portions thereof bind to the same epitope region, e.g., same epitope, adjacent epitope, or overlapping as any of the anti-PRAME antibodies or antigen-binding portions thereof described herein.

Such cross-competing antibodies can be identified based on their ability to cross-compete with any one of the presently disclosed anti-PRAME antibodies or antigen-binding portions thereof in standard PRAME binding assays. For example, Biacore analysis, ELISA assays or flow cytometry can be used to demonstrate cross-competition with the antibodies or antigen-binding portions thereof of the presently disclosed subject matter. The ability of a test antibody to inhibit the binding of, for example, any one of the presently disclosed anti-PRAME antibodies or antigen-binding portions thereof to a PRAME peptide/MHC (e.g., a PRAME/HLA complex more specifically, a PRAME/HLA class I complex, more specifically, a PRAME/HLA-A2 complex, and more specifically, a PRAME/HLA-A*0201 complex) demonstrates that the test antibody can compete with any one of the presently disclosed anti-PRAME antibodies or antigen-binding portions thereof for binding to such PRAME peptide/MHC complex.

Characterization of Antibody Binding to Antigen

Antibodies of the presently disclosed subject can be tested for binding to a PRAME peptide/HLA complex by, for example, standard ELISA. To determine the isotype of purified antibodies, isotype ELISAs can be performed using reagents specific for antibodies of a particular isotype. Anti-PRAME human IgGs can be further tested for reactivity with the PRAME peptide/MHC complex by Western blotting.

In certain embodiments, $K_D$ is measured by a radiolabeled antigen binding assay (RIA). In certain embodiments, an RIA is performed with the Fab version of an antibody of interest and its antigen. For example, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., J. Mol. Biol. 293:865-881 (1999)).

In certain embodiments, $K_D$ is measured using a BIA-CORE® surface plasmon resonance assay. For example, an assay using a BIACORE®-2000 or a BIACORE®-3000 (BIAcore, Inc., Piscataway, N.J.)

Immunoconjugates

The presently disclosed subject provides for an anti-PRAME antibody or an antigen-binding portion thereof conjugated to a therapeutic moiety, such as a cytotoxin, a drug (e.g., an immunosuppressant) or a radiotoxin. Such conjugates are referred to herein as "immunoconjugates". Immunoconjugates that include one or more cytotoxins are referred to as "immunotoxins." A cytotoxin or cytotoxic agent includes any agent that is detrimental to (e.g., kills) cells. Examples include toxins (such as ricin, diphtheria, gelonin), and drugs (such as cytochalasin B, gramicidin D, ethidium bromide, emetine, mitomycin, etoposide, tenoposide, colchicin, doxorubicin, daunorubicin, dihydroxy anthracin dione, mitoxantrone, mithramycin, 1-dehydrotestosterone, glucocorticoids, procaine, tetracaine, lidocaine, propranolol, and puromycin and analogs or homologs thereof).

Therapeutic agents also include, for example, calecheamicin, auristatin, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Other examples of therapeutic cytotoxins that can be conjugated to an anti-PRAME antibody or an antigen-binding portion thereof disclosed herein include duocarmycins, calicheamicins, maytansines and auristatins, and derivatives thereof. An example of a calicheamicin antibody conjugate is commercially available (Mylotarg™; Wyeth-Ayerst).

Cytotoxins can be conjugated to anti-PRAME antibody or an antigen-binding portion thereof disclosed herein using linker technology available in the art. Examples of linker types that have been used to conjugate a cytotoxin to an antibody include, but are not limited to, hydrazones, thioethers, esters, disulfides and peptide-containing linkers. A linker can be chosen that is, for example, susceptible to cleavage by low pH within the lysosomal compartment or susceptible to cleavage by proteases, such as proteases preferentially expressed in tumor tissue such as cathepsins (e.g., cathepsins B, C, D). For further discussion of types of cytotoxins, linkers and methods for conjugating therapeutic agents to antibodies, see also Saito, G. et al. (2003) Adv. Drug Deliv. Rev. 55:199-215; Trail, P. A. et al. (2003) Cancer Immunol. Immunother. 52:328-337; Payne, G. (2003) Cancer Cell 3:207-212; Allen, T. M. (2002) Nat. Rev. Cancer 2:750-763; Pastan, I. and Kreitman, R. J. (2002) Curr. Opin. Investig. Drugs 3:1089-1091; Senter, P. D. and Springer, C. J. (2001) Adv. Drug Deliv. Rev. 53:247-264.

Anti-PRAME antibodies of the presently disclosed subject matter also can be conjugated to a radioactive isotope to generate cytotoxic radiopharmaceuticals, also referred to as radioimmunoconjugates. Examples of radioactive isotopes that can be conjugated to antibodies for use diagnostically or therapeutically include, but are not limited to, $^{90}$Y, $^{131}$I, $^{225}$Ac, $^{213}$Bi, $^{223}$Ra, $^{177}$Lu, and $^{227}$Th. Method for preparing radioimmunconjugates are established in the art. Examples of radioimmunoconjugates are commercially available, including Zevalin™ (IDEC Pharmaceuticals) and Bexxar™ (Corixa Pharmaceuticals), and similar methods can be used to prepare radioimmunoconjugates using the antibodies of the invention.

The antibody conjugates of the presently disclosed subject matter can be used to modify a given biological response, and the drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, pseudomonas exotoxin, or diphtheria toxin; a protein such as tumor necrosis factor (TNF) or interferon-γ; or, biological response modifiers such as, for example, lymphokines, interleukin-1 ("IL-1"), interleukin-2

("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62:119-58 (1982).

Bispecific Molecules

The presently disclosed subject matter provides for bispecific molecules comprising an anti-PRAME antibody or an antigen-binding portion thereof disclosed herein. An antibody or an antigen-binding portion thereof of the presently disclosed subject matter, can be derivatized or linked to another functional molecule, e.g., another peptide or protein (e.g., another antibody or ligand for a receptor) to generate a bispecific molecule that binds to at least two different binding sites or target molecules. The antibody of the presently disclosed subject matter can in fact be derivatized or linked to more than one other functional molecule to generate multispecific molecules that bind to more than two different binding sites and/or target molecules; such multispecific molecules are also intended to be encompassed by the term "bispecific molecule" as used herein. To create a bispecific molecule, a presently disclosed anti-PRAME antibody or an antigen-binding portion thereof can be functionally linked (e.g., by chemical coupling, genetic fusion, noncovalent association or otherwise) to one or more other binding molecules, such as another antibody, antibody fragment, peptide or binding mimetic, such that a bispecific molecule results.

The presently disclosed subject matter provides bispecific molecules comprising at least one first binding specificity for a first target epitope or antigen and a second binding specificity for a second target epitope or antigen. The second target epitope or antigen can be different from the first epitope or antigen. In certain embodiments, the bispecific molecule is multispecific, the molecule can further include a third binding specificity. Where a first portion of a bispecific antibody binds to an antigen on a tumor cell for example and a second portion of a bispecific antibody recognizes an antigen on the surface of a human immune effector cell, the antibody is capable of recruiting the activity of that effector cell by specifically binding to the effector antigen on the human immune effector cell. In certain embodiments, bispecific antibodies, therefore, are able to form a link between effector cells, for example, T cells and tumor cells, thereby enhancing effector function.

The bispecific molecules of the presently disclosed subject matter can be prepared by conjugating the constituent binding specificities using methods known in the art. For example, each binding specificity of the bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-S-acetyl-thioacetate (SATA), 5,5'-dithiobis(2-nitrobenzoic acid) (DTNB), o-phenylenedimaleimide (oPDM), N-succinimidyl-3-(2-pyridyldithio)propionate (SPDP), and sulfosuccinimidyl 4-(N-maleimidomethyl) cyclohaxane-1-carboxylate (sulfo-SMCC) (see e.g., Karpovsky et al. (1984) J. Exp. Med. 160:1686; Liu, M A et al. (1985) Proc. Natl. Acad. Sci. USA 82:8648). Other methods include those described in Paulus (1985) Behring Ins. Mitt. No. 78, 118-132; Brennan et al. (1985) Science 229:81-83), and Glennie et al. (1987) J. Immunol. 139: 2367-2375). Preferred conjugating agents are SATA and sulfo-SMCC, both available from Pierce Chemical Co. (Rockford, Ill.).

When the binding specificities are antibodies, they can be conjugated via sulfhydryl bonding of the C-terminus hinge regions of the two heavy chains. In one non-limiting embodiment, the hinge region is modified to contain an odd number of sulfhydryl residues, preferably one, prior to conjugation.

Alternatively, both binding specificities can be encoded in the same vector and expressed and assembled in the same host cell. This method is particularly useful where the bispecific molecule is a mAb×mAb, mAb×Fab, Fab×F(ab')$_2$ or ligand×Fab fusion protein.

Binding of the bispecific molecules to their specific targets can be confirmed by, for example, enzyme-linked immunosorbent assay (ELISA), radioimmunoassay (RIA), FACS analysis, bioassay (e.g., growth inhibition), or Western Blot assay. Each of these assays generally detects the presence of protein-antibody complexes of particular interest by employing a labeled reagent (e.g., an antibody) specific for the complex of interest. Alternatively, the complexes can be detected using any of a variety of other immunoassays. For example, the antibody can be radioactively labeled and used in a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope can be detected by such means as the use of a γ counter or a scintillation counter or by autoradiography.

In certain embodiments, the bispecific antibodies recognize both PRAME/MHC complex and CD3 on immune T cells as described (Yan, et al., *J. Biol. Chem.* 2010; 285: 19637-19646; Rossi, et al., *Proc Natl Aca Sci USA* 2006; 103:6841-6) with a human IgG1 Fc. Bispecific antibodies recruit and target cytotoxic T cells to PRAME/MHC positive cancer cells, while maintaining Fc effector functions and long half life in vivo. Three mechanisms are involved in the specific killing of cancer cells mediated by bispecific antibodies: i) killing by activated T cells; ii) ADCC activity; iii) CDC activity. Other formats of bispecific antibodies can be constructed, such tandem scFv molecules (taFv), diabodies (Db), or single chain diabodies (scDb), and fusion protein with human serum albumin (Ryutaro, et al., *J Biol Chem* 2011; 286: 1812-1818; Anja, et al., *Blood* 2000; 95(6): 2098-2103; Weiner, et al., *J. Immunology* 1994; 152(5): 2385-2392; Dafne, et al., *J Biol Chem* 2007; 282: 12650-12660), but are devoid of Fc effector functions with distinct pharmacokinetic profiles.

Engineered and Modified Antibodies

An antibody of the presently disclosed subject matter further can be prepared using an antibody or an antigen-binding portion thereof having one or more of the $V_H$ and/or $V_L$ sequences disclosed herein as starting material to engineer a modified antibody, which modified antibody may have altered properties from the starting antibody. An antibody can be engineered by modifying one or more residues within one or both variable regions (i.e., $V_H$ and/or $V_L$), for example within one or more CDR regions and/or within one or more framework regions. Additionally or alternatively, an antibody can be engineered by modifying residues within the constant region(s), for example to alter the effector function(s) of the antibody.

One type of variable region engineering that can be performed is CDR grafting. Antibodies interact with target antigens predominantly through amino acid residues that are located in the six heavy and light chain CDRs. For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al. (1998) Nature 332:323-327; Jones, P. et al. (1986) Nature 321:522-525; Queen, C. et al. (1989) Proc. Natl. Acad. See. U.S.A. 86:10029-10033; U.S. Pat. No. 5,225,539 to Winter, and U.S. Pat. Nos. 5,530,101; 5,585,089; 5,693,762 and 6,180,370 to Queen et al.)

Framework sequences can be obtained from public DNA databases or published references that include germline antibody gene sequences. For example, germline DNA sequences for human heavy and light chain variable region genes can be found in the "VBase" human germline sequence database (available on the Internet), as well as in Kabat, E. A., et al. (1991) Sequences of Proteins of Immunological Interest, Fifth Edition, U.S. Department of Health and Human Services, NIH Publication No. 91-3242; Tomlinson, I. M., et al. (1992) "The Repertoire of Human Germline $V_H$ Sequences Reveals about Fifty Groups of $V_H$ Segments with Different Hypervariable Loops" J. Mol. Biol. 227:776-798; and Cox, J. P. L. et al. (1994) "A Directory of Human Germ-line $V_H$ Segments Reveals a Strong Bias in their Usage" Eur. J. Immunol. 24:827-836; the contents of each of which are expressly incorporated herein by reference. As another example, the germline DNA sequences for human heavy and light chain variable region genes can be found in the GenBank database.

The $V_H$ CDR1, CDR2, and CDR3 sequences, and the $V_L$ CDR1, CDR2, and CDR3 sequences, can be grafted onto framework regions that have the identical sequence as that found in the germline immunoglobulin gene from which the framework sequence derive, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370 to Queen et al).

Another type of variable region modification is to mutate amino acid residues within the $V_H$ and/or $V_L$ CDR1, CDR2 and/or CDR3 regions to thereby improve one or more binding properties (e.g., affinity) of the antibody of interest. Site-directed mutagenesis or PCR-mediated mutagenesis can be performed to introduce the mutation(s) and the effect on antibody binding, or other functional property of interest, can be evaluated in in vitro or in vivo assays. Preferably conservative modifications (as discussed above) are introduced. The mutations may be amino acid substitutions, additions or deletions. For example, no more than one, two, three, four or five residues within a CDR region are altered.

Accordingly, the presently disclosed subject matter provides for isolated anti-PRAME monoclonal antibodies or antigen-binding portions thereof comprising a heavy chain variable region comprising: (a) the $V_H$ CDR1 sequence of the antibodies and antigen-binding portions thereof (e.g., scFvs) disclosed herein (e.g., EXT009-01, EXT009-03, EXT009-04, EXT009-05, EXT009-07, EXT009-08, EXT009-09, EXT009-10, EXT009-12, EXT009-13, EXT009-14, EXT009-15, EXT009-17, EXT009-18, EXT009-19, EXT009-20, EXT009-21, EXT009-23, EXT009-25, EXT009-27, EXT009-29, EXT009-30, EXT009-31, EXT009-32, EXT009-33, EXT010-01, EXT010-03, EXT010-04, EXT010-06, EXT010-07, EXT010-08, EXT010-10, EXT010-12, EXT010-13, EXT010-15, EXT010-17, EXT010-23, EXT010-24, EXT010-25, EXT010-26, EXT010-27, EXT010-28, EXT010-29, EXT010-30, EXT010-31, EXT010-32, EXT010-33, EXT010-34, EXT010-37, EXT010-40, EXT010-42, EXT010-44, EXT010-47, EXT010-48, EXT010-49, EXT010-55, EXT010-56, EXT010-59, or EXT010-60), or an amino acid sequence having at least one (e.g., no more than one, no more than two, no more than three, no more than four or no more than five) amino acid modification (e.g., substitution, deletion and/or addition) as compared to the $V_H$ CDR1 sequence of any one of the antibodies or antigen-binding portions thereof disclosed herein; (b) the $V_H$ CDR2 sequence of any one of the antibodies or antigen-binding portions thereof disclosed herein, or an amino acid sequence having at least one (e.g., no more than one, no more than two, no more than three, no more than four or no more than five) amino acid modification (e.g., substitution, deletion and/or addition) as compared to the $V_H$ CDR2 of any one of the antibodies or antigen-binding portions thereof disclosed herein; (c) the $V_H$ CDR3 sequence of any one of the antibodies or antigen-binding portions thereof disclosed herein, or an amino acid sequence having at least one (e.g., no more than one, no more than two, no more than three, no more than four or no more than five) amino acid modification (e.g., substitution, deletion and/or addition) as compared to the $V_H$ CDR3 of any one of the antibodies or antigen-binding portions thereof disclosed herein; (d) the $V_L$ CDR1 sequence of any one of the antibodies or antigen-binding portions thereof disclosed herein, or an amino acid sequence having at least one (e.g., no more than one, no more than two, no more than three, no more than four or no more than five) amino acid modification (e.g., substitution, deletion and/or addition) as compared to the $V_L$ CDR1 of any one of the antibodies or antigen-binding portions thereof disclosed herein; (e) the $V_L$ CDR2 sequence of any one of the antibodies or antigen-binding portions thereof disclosed herein, or an amino acid sequence having at least one (e.g., no more than one, no more than two, no more than three, no more than four or no more than five) amino acid modification (e.g., substitution, deletion and/or addition) as compared to the $V_L$ CDR2 of any one of the antibodies or antigen-binding portions thereof disclosed herein; and (f) the $V_L$ CDR3 sequence of any one of the antibodies or antigen-binding portions thereof disclosed herein, or an amino acid sequence having at least one (e.g., no more than one, no more than two, no more than three, no more than four or no more than five) amino acid modification (e.g., substitution, deletion and/or addition) as compared to the $V_L$ CDR3 of any one of the antibodies or antigen-binding portions thereof disclosed herein.

For example, the presently disclosed subject matter provides for isolated anti-PRAME monoclonal antibodies or antigen-binding portions thereof comprising a heavy chain variable region comprising: (a) a $V_H$ CDR1 region comprising the amino acid sequence set forth in SEQ ID NO: 7, SEQ ID NO: 13, SEQ ID NO: 19, SEQ ID NO: 25, SEQ ID NO: 31, SEQ ID NO: 37, or SEQ ID NO: 43, or an amino acid sequence having at least one (e.g., no more than one, no more than two, no more than three, no more than four or no more than five) amino acid modification (e.g., substitution, deletion and/or addition) as compared to SEQ ID NO: 7, SEQ ID NO: 13, SEQ ID NO: 19, SEQ ID NO: 25, SEQ ID NO: 31, SEQ ID NO: 37, or SEQ ID NO: 43; (b) a $V_H$ CDR2 region comprising the amino acid sequence set forth in SEQ ID NO: 8, SEQ ID NO: 14, SEQ ID NO: 20, SEQ ID NO: 26, SEQ ID NO: 32, SEQ ID NO: 38, or SEQ ID NO: 44, or an amino acid sequence having at least one (e.g., no more than one, no more than two, no more than three, no more than four or no more than five) amino acid modification (e.g., substitution, deletion and/or addition) as compared to SEQ ID NO: 8, SEQ ID NO: 14, SEQ ID NO: 20, SEQ ID NO: 26, SEQ ID NO: 32, SEQ ID NO: 38, or SEQ ID NO: 44; (c) a $V_H$ CDR3 region comprising the amino acid sequence set forth in SEQ ID NO: 9, SEQ ID NO: 15, SEQ ID NO: 21, SEQ ID NO: 27, SEQ ID NO: 33, SEQ ID NO: 39, or SEQ ID NO: 45, or an amino acid sequence having at least one (e.g., no more than one, no more than two, no more than three, no more than four or no more than five) amino acid modification (e.g., substitution, deletion and/or addition) as compared to SEQ ID NO: 9, SEQ ID NO: 15, SEQ ID NO: 21, SEQ ID NO: 27, SEQ ID NO: 33, SEQ ID NO: 39, or SEQ ID NO: 45; (d) a $V_L$ CDR1 region comprising the amino acid sequence set forth in SEQ ID NO: 10, SEQ ID NO: 16, SEQ ID NO: 22, SEQ ID NO: 28, SEQ ID NO: 34, SEQ ID NO: 40, or SEQ ID NO: 46, or an amino acid sequence having at least one (e.g., no more than one, no more than two, no more than three, no more than four or no more than five) amino acid modification (e.g., substitution, deletion and/or addition) as compared to SEQ ID NO: 10, SEQ ID NO: 16, SEQ ID NO: 22, SEQ ID NO: 28, SEQ ID NO: 34, SEQ ID NO: 40, or SEQ ID NO: 46; (e) a $V_L$ CDR2 region comprising the amino acid sequence set forth in SEQ ID NO: 11, SEQ ID NO: 17, SEQ ID NO: 23, SEQ ID NO: 29, SEQ ID NO: 35, SEQ ID NO: 41, or SEQ ID NO: 47, or an amino acid sequence having at least one (e.g., no more than one, no more than two, no more than three, no more than four or no more than five) amino acid modification (e.g., substitution, deletion and/or addition) as compared to SEQ ID NO: 11, SEQ ID NO: 17, SEQ ID NO: 23, SEQ ID NO: 29, SEQ ID NO: 35, SEQ ID NO: 41, or SEQ ID NO: 47; and (f) a $V_L$ CDR3 region comprising the amino acid sequence set forth in SEQ ID NO: 12, SEQ ID NO: 18, SEQ ID NO: 24, SEQ ID NO: 30, SEQ ID NO: 36, SEQ ID NO: 42, or SEQ ID NO: 48, or an amino acid sequence having at least one (e.g., no more than one, no more than two, no more than three, no more than four or no more than five) amino acid modification (e.g., substitution, deletion and/or addition) as compared to SEQ ID NO: 12, SEQ ID NO: 18, SEQ ID NO: 24, SEQ ID NO: 30, SEQ ID NO: 36, SEQ ID NO: 42, or SEQ ID NO: 48.

Engineered antibodies of the presently disclosed subject matter include those in which modifications are made to framework residues within $V_H$ and/or $V_K$, e.g., to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived.

Another type of framework modification involves mutating one or more residues within the framework region, or even within one or more CDR regions, to remove T cell epitopes to thereby reduce the potential immunogenicity of the antibody. This approach is also referred to as "deimmunization" and is described in further detail in U.S. Patent Publication No. 20030153043 by Carr et al.

In addition or alternative to modifications made within the framework or CDR regions, anti-PRAME antibodies or antigen-binding portions thereof of the presently disclosed subject matter may be engineered to include modifications within the Fc region, typically to alter one or more functional properties of the antibody, such as serum half-life, complement fixation, Fc receptor binding, and/or antigen-dependent cellular cytotoxicity. Furthermore, a presently disclosed anti-PRAME antibody may be chemically modified (e.g., one or more chemical moieties can be attached to the antibody) or be modified to alter its glycosylation, again to alter one or more functional properties of the antibody. The hinge region of CH1 may be modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody. The Fc hinge region of an antibody may be mutated to decrease the biological half life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al. The antibody may be modified to increase its biological half life, e.g., the antibody may be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al. Furthermore, the Fc region may be altered by replacing at least one amino acid residue with a different amino acid residue to alter the effector function(s) of the antibody. The Fc region may be modified to increase the ability of the antibody to mediate antibody dependent cellular cytotoxicity (ADCC) and/or to increase the affinity of the antibody for an Fcγ receptor, e.g., as described in WO 00/42072 by Presta. In certain embodiments, a presently disclosed anti-PRAME antibody comprises an afucoslyated Fc region. Removal of the fucose residue from the N-glycans of the Fc portion of immunoglobulin G (IgG) can result in a dramatic enhancement of ADCC through improved affinity for Fcγ receptor IIIa (FcγRIIIa).

Additionally or alternatively, the glycosylation of an antibody may be modified. For example, an aglycoslated antibody can be made (i.e., the antibody lacks glycosylation). Glycosylation can be altered to, for example, increase the affinity of the antibody for antigen, see e.g., U.S. Pat. Nos. 5,714,350 and 6,350,861. Such carbohydrate modifications can be accomplished by, for example, altering one or more sites of glycosylation within the antibody sequence. For example, one or more amino acid substitution can be made that result in elimination of one or more variable region framework glycosylation sites to thereby eliminate glycosylation at that site.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery.

Another modification of the antibodies may be pegylation. An antibody can be pegylated to, for example, increase the biological (e.g., serum) half life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. The pegylation may be carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono ($C_1$-$C_{10}$) alkoxy- or aryloxy-polyethylene glycol or polyethylene glycol-maleimide. The antibody to be pegylated may be an aglycosylated antibody. Methods for pegylating proteins are known in the art and can be applied to the antibodies disclosed herein, see e.g., EP 0 154 316 and EP 0 401 384.

III. Methods of Preparation
I. Identification of Peptides with High Predictive Binding to MHC Molecules The presently disclosed subject matter provides for a method for the generation of antibodies that specifically bind to MHC-restricted peptides, which, when presented as part of a peptide/MHC complex are able to elicit a specific cytotoxic T-cell response. HLA class I molecules present endogenous derived peptides of about 8-12 amino acids in length to CD8$^+$ cytotoxic T lymphocytes. Peptides to be used in the presently disclosed method are generally about 6-22 amino acids in length, and in some embodiments, between about 9 and 20 amino acids (more specifically, between 8-11 amino acids, preferably 9 or 10 amino acids) and comprise an amino acid sequence derived from a protein of interest, for example, human PRAME protein (Genbank Accession No. NP_001278644 Version: NP_001278644.1, provided below) or an analog thereof.

Peptides suitable for use in generating antibodies in accordance with the presently disclosed method can be determined based on the presence of MHC molecule (e.g., HLA molecule, more specifically, HLA class I molecule, more specifically, HLA-A, more specifically, HLA-A2, and more specifically, HLA-A*0201) binding motifs and the cleavage sites for proteasomes and immune-proteasomes using computer prediction models known to those of skill in the art. For predicting MHC class I binding sites, such models include, but are not limited to, ProPred1 (described in more detail in Singh and Raghava, *Bioinformatics* 17(12): 1236-1237 2001), and SYFPEITHI (see Schuler et al. *Immunoinformatics Methods in Molecular Biology*, vol 409(1): 75-93 2007), Net MHC.

HLA-A*0201 is expressed in 39-46% of all caucasians and therefore, represents a suitable choice of MHC antigen for use in the present method. For preparation of one embodiment of a PRAME peptide antigen, amino acid sequences and predicted binding of putative PRAME epitopes to HLA-A*0201 molecules were identified using the predictive algorithm of the SYFPEITHI database (see Schuler (2007)).

Once appropriate peptides have been identified, peptide synthesis may be done in accordance with protocols well known to those of ordinary skill in the art. Because of their relatively small size, the peptides of the presently disclosed subject matter may be directly synthesized in solution or on a solid support in accordance with conventional peptide synthesis techniques. Various automatic synthesizers are commercially available and can be used in accordance with known protocols. The synthesis of peptides in solution phase has become a well-established procedure for large-scale production of synthetic peptides and as such is a suitable alternative method for preparing the peptides of the invention. (See e.g., Stewart et al., *Tetrahedron Letters* Vol. 39, pages 1517-1520 1998.)

Each of the peptides used in the protocols described herein was purchased and synthesized by Elim Biopharm, Inc. (Hayward, Calif.) using fluorenylmethoxycarbonyl chemistry and solid-phase synthesis and purified by high-pressure liquid chromatography. The quality of the peptides was assessed by high-performance liquid chromatography analysis, and the expected molecular weight was observed using matrix-assisted laser desorption mass spectrometry. Peptides were sterile and above 90% pure. The peptides were dissolved in DMSO and stored at −80° C.

Subsequent to peptide selection, binding activity of selected peptides is tested using the antigen-processing-deficient T2 cell line, which increases expression of HLA-A

[SEQ ID NO: 1]
```
  1  merrrlwgsi qsryismsvw tsprrlvela gqsllkdeal aiaalellpr elfpplfmaa 61  fdgrhsqtlk amvqawpftc lplgvlmkgq hlhletfkav ldgldvllaq evrprrwklq 121  vldlrknshq dfwtvwsgnr aslysfpepe aaqpmtkkrk vdglsteaeq pfipvevlvd 181  lflkegacde lfsyliekvk rkknvlrlcc kklkifampm qdikmilkmv qldsiedlev 241  tctwklptla kfspylgqmi nlrrlllshi hassyispek eeqyiaqfts qflslqclqa 301  lyvdslfflr grldqllrhv mnpletlsit ncrlsegdvm hlsqspsvsq lsvlslsgvm 361  ltdvspeplq allerasatl qdlvfdecgi tddqllallp slshcsqltt lsfygnsisi 421  salqsllqhl iglsnlthvl ypvplesyed ihgtlhlerl aylharlrel lcelgrpsmv 481  wlsanpcphc gdrtfydpep ilcpcfmpn
``` when stabilized by a peptide in the antigen-presenting groove. Briefly, T2 cells are pulsed with peptide for a time sufficient to induce HLA-A expression. HLA-A expression of T2 cells is then measured by immunostaining with a fluorescently labeled monoclonal antibody specific for HLA-A (for example, BB7.2) and flow cytometry. Fluorescence index (FI) is calculated as the mean fluorescence intensity (MFI) of HLA-A0201 on T2 cells as determined by fluorescence-activated cell-sorting analysis, using the formula FI=(MFI [T2 cells with peptide]/MFI [T2 cells without peptide]−1.

Fully human T-cell receptor (TCR)-like antibodies to PRAME were produced using the method disclosed herein. TCR-like anti-PRAME antibodies generated by phage display technology are specific for a PRAME peptide/HLA complex similar to that which induces HLA-restricted cytotoxic CD8 T-cells.

The PRAME protein sequence was screened using the SYFPEITHI algorithm and PRAME peptides (for example, $PRA^{100-108}$, $PRA^{142-151}$, $PRA^{300-309}$, $PRA^{425-433}$, and $PRA^{435-443}$) were identified that had predicted high-affinity binding to multiple HLA molecules that are highly expressed in the Caucasian population. $PRA^{100-108}$ spans PRAME amino acids 100-108, $PRA^{142-151}$ spans PRAME amino acids 142-151, $PRA^{300-309}$ spans PRAME amino acids 300-309, $PRA^{425-433}$, spans PRAME amino acids 425-433, and $PRA^{435-443}$ spans PRAME amino acids 435-443.

Once a suitable peptide has been identified, the target antigen to be used for phage display library screening, that is, a peptide/MHC complex (for example, PRAME/HLA complex, e.g., PRAME peptide/HLA-A*0201) is prepared by bringing the peptide and the histocompatibility antigen together in solution to form the complex.

2. Selecting A High Affinity scFv Against A PRAME Peptide

The next step is to the selection of phage that bind to the target antigen of interest with high affinity, from phage in a human phage display library that either does not bind or that binds with lower affinity. This is accomplished by iterative binding of phage to the antigen, which is bound to a solid support, for example, beads or mammalian cells followed by removal of non-bound phage and by elution of specifically bound phage. In certain embodiments, antigens are first biotinylated for immobilization to, for example, streptavidin-conjugated Dynabeads™ M-280. The phage library is incubated with the cells, beads or other solid support and non binding phage is removed by washing. Clones that bind are selected and tested.

Once selected, positive scFv clones are tested for their binding to HLA-A2/peptide complexes on live T2 cell surfaces by indirect flow cytometry. Briefly, phage clones are incubated with T2 cells that have been pulsed with a PRAME peptide, or an irrelevant peptide (control). The cells are washed and then with a mouse anti-M13 coat protein mAb. Cells are washed again and labeled with a FITC-goat (Fab)2 anti-mouse Ig prior to flow cytometry.

In other embodiments, the anti-PRAME antibodies may comprise one or more framework region amino acid substitutions designed to improve protein stability, antibody binding, expression levels or to introduce a site for conjugation of therapeutic agents. These scFv are then used to produce recombinant human monoclonal Igs in accordance with methods known to those of skill in the art.

Methods for reducing the proliferation of leukemia cells is also included, comprising contacting leukemia cells with a presently disclosed PRAME antibody. In a related aspect, the presently disclosed antibodies can be used for the prevention or treatment of leukemia. Administration of therapeutic antibodies is known in the art.

IV. Chimeric Antigen Receptors

Chimeric antigen receptors (CARs) are engineered receptors, which graft or confer a specificity of interest onto an immune effector cell. CARs can be used to graft the specificity of a monoclonal antibody onto a T cell; with transfer of their coding sequence facilitated by retroviral vectors.

There are three generations of CARs. "First generation" CARs are typically composed of an extracellular antigen binding domain (e.g., a scFv fused to a transmembrane domain, fused to cytoplasmic/intracellular domain of the T cell receptor chain. "First generation" CARs typically have the intracellular domain from the CD3ξ-chain, which is the primary transmitter of signals from endogenous TCRs. "First generation" CARs can provide de novo antigen recognition and cause activation of both $CD4^+$ and $CD8^+$ T cells through their CD3ζ-chain signaling domain in a single fusion molecule, independent of HLA-mediated antigen presentation. "Second generation" CARs add intracellular domains from various co-stimulatory molecules (e.g., CD28, 4-1BB, ICOS, OX40) to the cytoplasmic tail of the CAR to provide additional signals to the T cell. "Second generation" CARs comprise those that provide both co-stimulation (e.g., CD28 or 4-1BB) and activation (CD3ζ). Preclinical studies have indicated that "Second Generation" CARs can improve the anti-tumor activity of T cells. For example, robust efficacy of "Second Generation" CAR modified T cells was demonstrated in clinical trials targeting the CD19 molecule in patients with chronic lymphoblastic leukemia (CLL) and acute lymphoblastic leukemia (ALL). "Third generation" CARs comprise those that provide multiple co-stimulation (e.g., CD28 and 4-1BB) and activation (CD3ζ).

In accordance with the presently disclosed subject matter, the CARs comprise an extracellular antigen-binding domain, a transmembrane domain and an intracellular domain, where the extracellular antigen-binding domain binds to a PRAME peptide bound to an MHC molecule (e.g., a HLA molecule, more specifically, a HLA class I molecule). In certain embodiments, the extracellular antigen-binding domain is a scFv. In certain embodiments, the scFv is a human scFv. Non-limiting example of scFv include EXT009-01, EXT009-03, EXT009-04, EXT009-05, EXT009-07, EXT009-08, EXT009-09, EXT009-10, EXT009-12, EXT009-13, EXT009-14, EXT009-15, EXT009-17, EXT009-18, EXT009-19, EXT009-20, EXT009-21, EXT009-23, EXT009-25, EXT009-27, EXT009-29, EXT009-30, EXT009-31, EXT009-32, EXT009-33, EXT010-01, EXT010-03, EXT010-04, EXT010-06, EXT010-07, EXT010-08, EXT010-10, EXT010-12, EXT010-13, EXT010-15, EXT010-17, EXT010-23, EXT010-24, EXT010-25, EXT010-26, EXT010-27, EXT010-28, EXT010-29, EXT010-30, EXT010-31, EXT010-32, EXT010-33, EXT010-34, EXT010-37, EXT010-40, EXT010-42, EXT010-44, EXT010-47, EXT010-48, EXT010-49, EXT010-55, EXT010-56, EXT010-59, and EXT010-60.

In certain embodiments, the extracellular antigen-binding domain is a Fab, which is optionally crosslinked. In a certain embodiments, the extracellular binding domain is a $F(ab)_2$. In certain embodiments, any of the foregoing molecules may be comprised in a fusion protein with a heterologous sequence to form the extracellular antigen-binding domain.

In certain non-limiting embodiments, an extracellular antigen-binding domain of a presently disclosed CAR can comprise a linker connecting the heavy chain variable region and light chain variable region of the extracellular antigen-binding domain. As used herein, the term "linker" refers to a functional group (e.g., chemical or polypeptide) that covalently attaches two or more polypeptides or nucleic acids so that they are connected to one another. As used herein, a "peptide linker" refers to one or more amino acids used to couple two proteins together (e.g., to couple $V_H$ and $V_L$ domains). In one non-limiting example, the linker comprises amino acids having the sequence set forth in SEQ ID NO: 70, which is provided below. In one embodiment, the nucleotide sequence encoding the amino acid sequence of SEQ ID NO: 70 is set forth in SEQ ID NO: 71, which is provided below.

```
                                            (SEQ ID NO: 70)
GGGGSGGGGSGGGGS (SEQ ID NO: 71)
GGTGGTGGTGGTAGCGGCGGCGGCGGCTCTGGTGGTGGTGGATCC
```

In certain embodiments, the extracellular antigen-binding domain is a scFv, which comprises a $V_H$ comprising an amino acid sequence selected from the group consisting of SEQ ID NOS: 49, 51, 53, 55, 57, 59, and 61, and a $V_L$ comprising an amino acid sequence selected from the group consisting of SEQ ID NOs: 50, 52, 54, 56, 58, 60, and 62, and optionally a linker comprising the amino acid sequence set forth in SEQ ID NO: 70. In certain embodiments, the extracellular antigen-binding domain is a scFv comprising an amino acid sequence selected from the group consisting of SEQ ID NOS: 63, 64, 65, 66, 67, 68, and 69. In one non-limiting embodiment, the extracellular antigen-binding domain is a scFv comprising the amino acid sequence set forth in SEQ ID NO: 63, which comprise a $V_H$ comprising the amino acid sequence set forth in SEQ ID NO: 49, a $V_L$ comprising the amino acid sequence set forth in SEQ ID NO: 50, and a linker comprising the amino acid sequence set forth in SEQ ID NO: 70.

In addition, the extracellular antigen-binding domain can comprise a leader or a signal peptide that directs the nascent protein into the endoplasmic reticulum. Signal peptide or leader can be essential if the CAR is to be glycosylated and anchored in the cell membrane. The signal sequence or leader can be a peptide sequence (about 5, about 10, about 15, about 20, about 25, or about 30 amino acids long) present at the N-terminus of newly synthesized proteins that directs their entry to the secretory pathway. In non-limiting examples, the signal peptide is covalently joined to the 5' terminus of the extracellular antigen-binding domain.

In certain non-limiting embodiments, the transmembrane domain of the CAR comprises a hydrophobic alpha helix that spans at least a portion of the membrane. Different transmembrane domains result in different receptor stability. After antigen recognition, receptors cluster and a signal is transmitted to the cell. In accordance with the presently disclosed subject matter, the transmembrane domain of the CAR can comprise a CD8 polypeptide, a CD28 polypeptide, a CD3ζ polypeptide, a CD4 polypeptide, a 4-1BB polypeptide, an OX40 polypeptide, an ICOS polypeptide, a CTLA-4 polypeptide, a PD-1 polypeptide, a LAG-3 polypeptide, a 2B4 polypeptide, a BTLA polypeptide, a synthetic peptide (not based on a protein associated with the immune response), or a combination thereof.

In certain embodiments, the transmembrane domain of a presently disclosed CAR comprises a CD28 polypeptide.

In certain non-limiting embodiments, an intracellular domain of the CAR can comprise a CD3ζ polypeptide, which can activate or stimulate a cell (e.g., a cell of the lymphoid lineage, e.g., a T cell). CD3ζ comprises 3 ITAMs, and transmits an activation signal to the cell (e.g., a cell of the lymphoid lineage, e.g., a T cell) after antigen is bound. The CD3ζ polypeptide can have an amino acid sequence that is at least about 85%, about 90%, about 95%, about 96%, about 97%, about 98%, about 99% or about 100% homologous to the sequence having a NCBI Reference No: NP_932170 (SEQ ID No: 72), or fragments thereof, and/or may optionally comprise up to one or up to two or up to three conservative amino acid substitutions. In non-limiting embodiments, the CD3ζ polypeptide can have an amino acid sequence that is a consecutive portion of SEQ ID NO: 25 which is at least 20, or at least 30, or at least 40, or at least 50, and up to 164 amino acids in length. Alternatively or additionally, in non-limiting various embodiments, the CD3ζ polypeptide has an amino acid sequence of amino acids 1 to 164, 1 to 50, 50 to 100, 100 to 150, or 150 to 164 of SEQ ID NO: 72. In certain embodiments, the CD3ζ polypeptide has an amino acid sequence of amino acids 52 to 121 of SEQ ID NO: 72.

SEQ ID NO: 72 is provided below:

```
                                                    [SEQ ID NO: 72]
  1 MKWKALFTAA ILQAQLPITE AQSFGLLDPK LCYLLDGILF IYGVILTALF LRVKFSRSAD

61 APAYQQGQNQ LYNELNLGRR EEYDVLDKRR GRDPEMGGKP QRRKNPQEGL YNELQKDKMA

121 EAYSEIGMKG ERRRGKGHDG LYQGLSTATK DTYDALHMQA LPPR
```

In certain embodiments, the CD3ζ polypeptide has the amino acid sequence set forth in SEQ ID NO: 73, which is provided below.

```
                                                    [SEQ ID NO: 73]
RVKFSRSADAPAYQQGQNQLYNELNLGRREEYDVLDKRRGRDPEMGGKPR

RKNPQEGLYNELQKDKMAEAYSEIGMKGERRRGKGHDGLYQGLSTATKDT

YDALHMQALPPR
```

In certain non-limiting embodiments, an intracellular domain of the CAR further comprises at least one co-stimulatory signaling region comprising at least one co-stimulatory molecule, which can provide optimal lymphocyte activation. As used herein, "co-stimulatory molecules" refer to cell surface molecules other than antigen receptors or their ligands that are required for an efficient response of lymphocytes to antigen. The at least one co-stimulatory signaling region can include a CD28 polypeptide, a 4-1BB polypeptide, an OX40 polypeptide, an ICOS polypeptide, a PD-1 polypeptide, a CTLA-4 polypeptide, a LAG-3 polypeptide, a 2B4 polypeptide, a BTLA polypeptide, a synthetic peptide (not based on a protein associated with the immune response), or a combination thereof. The co-stimulatory molecule can bind to a co-stimulatory ligand, which is a protein expressed on cell surface that upon binding to its receptor produces a co-stimulatory response, i.e., an intracellular response that effects the stimulation provided when an antigen binds to its CAR molecule. In certain embodiments, the intracellular domain of the CAR comprises a co-stimulatory signaling region that comprises a CD28 polypeptide. In one non-limiting embodiment, the CAR comprises a CD28 transmembrane domain and a CD28 co-stimulatory signaling domain, where CD28 polypeptide comprised in the transmembrane domain and the co-stimulatory signaling region has the amino acid sequence set forth in SEQ ID NO: 74, which is provided below.

(SEQ ID NO: 74)
IEVMYPPPYLDNEKSNGTIIHVKGKHLCPSPLFPGPSKPFWVLVVVGGVL

ACYSLLVTVAFIIFWVRSKRSRLLHSDYMNMTPRRPGPTRKHYQPYAPPR

DFAAYRS

In addition, the presently disclosed subject matter provides immunoresponsive cells expressing a presently disclosed CAR. The immunoresponsive cells can be transduced with a presently disclosed CAR such that the cells express the CAR. The presently disclosed subject matter also provides methods of using such cells for the treatment of a tumor or PRAME-associated pathologic condition. The immunoresponsive cells of the presently disclosed subject matter can be cells of the lymphoid lineage. The lymphoid lineage, comprising B, T and natural killer (NK) cells, provides for the production of antibodies, regulation of the cellular immune system, detection of foreign agents in the blood, detection of cells foreign to the host, and the like. Non-limiting examples of immunoresponsive cells of the lymphoid lineage include T cells, Natural Killer (NK) cells, embryonic stem cells, and pluripotent stem cells (e.g., those from which lymphoid cells may be differentiated). T cells can be lymphocytes that mature in the thymus and are chiefly responsible for cell-mediated immunity. T cells are involved in the adaptive immune system. The T cells of the presently disclosed subject matter can be any type of T cells, including, but not limited to, T helper cells, cytotoxic T cells, memory T cells (including central memory T cells, stem-cell-like memory T cells (or stem-like memory T cells), and two types of effector memory T cells: e.g., $T_{EM}$ cells and $T_{EMRA}$ cells), Regulatory T cells (also known as suppressor T cells), Natural killer T cells, Mucosal associated invariant T cells, and γδ T cells. Cytotoxic T cells (CTL or killer T cells) are a subset of T lymphocytes capable of inducing the death of infected somatic or tumor cells. In certain embodiments, the CAR-expressing T cells express Foxp3 to achieve and maintain a T regulatory phenotype.

Natural killer (NK) cells can be lymphocytes that are part of cell-mediated immunity and act during the innate immune response. NK cells do not require prior activation in order to perform their cytotoxic effect on target cells.

Genetic modification of immunoresponsive cells (e.g., T cells, NK cells) can be accomplished by transducing a substantially homogeneous cell composition with a recombinant DNA or RNA construct. The vector can be a retroviral vector (e.g., gamma retroviral), which is employed for the introduction of the DNA or RNA construct into the host cell genome. For example, a polynucleotide encoding a presently disclosed CAR can be cloned into a retroviral vector and expression can be driven from its endogenous promoter, from the retroviral long terminal repeat, or from an alternative internal promoter.

Non-viral vectors or RNA may be used as well. Random chromosomal integration, or targeted integration (e.g., using a nuclease, transcription activator-like effector nucleases (TALENs), Zinc-finger nucleases (ZFNs), and/or clustered regularly interspaced short palindromic repeats (CRISPRs), or transgene expression (e.g., using a natural or chemically modified RNA) can be used.

For initial genetic modification of the cells to provide cells expressing a presently disclosed CAR, a retroviral vector is generally employed for transduction, however any other suitable viral vector or non-viral delivery system can be used. For subsequent genetic modification of the cells to provide cells comprising an antigen presenting complex comprising at least two co-stimulatory ligands, retroviral gene transfer (transduction) likewise proves effective. Combinations of retroviral vector and an appropriate packaging line are also suitable, where the capsid proteins will be functional for infecting human cells. Various amphotropic virus-producing cell lines are known, including, but not limited to, PA12 (Miller, et al. (1985) *Mol. Cell. Biol.* 5:431-437); PA317 (Miller, et al. (1986) *Mol. Cell. Biol.* 6:2895-2902); and CRIP (Danos, et al. (1988) *Proc. Natl. Acad. Sci.* USA 85:6460-6464). Non-amphotropic particles are suitable too, e.g., particles pseudotyped with VSVG, RD114 or GALV envelope and any other known in the art.

Possible methods of transduction also include direct co-culture of the cells with producer cells, e.g., by the method of Bregni, et al. (1992) *Blood* 80:1418-1422, or culturing with viral supernatant alone or concentrated vector stocks with or without appropriate growth factors and polycations, e.g., by the method of Xu, et al. (1994) *Exp. Hemat.* 22:223-230; and Hughes, et al. (1992) *J. Clin. Invest.* 89:1817.

Non-viral approaches can also be employed for the expression of a protein in cell. For example, a nucleic acid molecule can be introduced into a cell by administering the nucleic acid in the presence of lipofection (Feigner et al., Proc. Natl. Acad. Sci. U.S.A. 84:7413, 1987; Ono et al., Neuroscience Letters 17:259, 1990; Brigham et al., Am. J. Med. Sci. 298:278, 1989; Staubinger et al., Methods in Enzymology 101:512, 1983), asialoorosomucoid-polylysine conjugation (Wu et al., Journal of Biological Chemistry 263:14621, 1988; Wu et al., Journal of Biological Chemistry 264:16985, 1989), or by micro-injection under surgical conditions (Wolff et al., Science 247:1465, 1990). Other non-viral means for gene transfer include transfection in vitro using calcium phosphate, DEAE dextran, electroporation, and protoplast fusion. Liposomes can also be potentially beneficial for delivery of DNA into a cell. Transplantation of normal genes into the affected tissues of a subject can also be accomplished by transferring a normal nucleic acid into a cultivatable cell type ex vivo (e.g., an autologous or heterologous primary cell or progeny thereof), after which the cell (or its descendants) are injected into a targeted tissue or are injected systemically. Recombinant receptors can also be derived or obtained using transposases or targeted nucleases (e.g. Zinc finger nucleases, meganucleases, or TALE nucleases). Transient expression may be obtained by RNA electroporation.

cDNA expression for use in polynucleotide therapy methods can be directed from any suitable promoter (e.g., the human cytomegalovirus (CMV), simian virus 40 (SV40), or metallothionein promoters), and regulated by any appropriate mammalian regulatory element or intron (e.g., the elongation factor 1α enhancer/promoter/intron structure). For example, if desired, enhancers known to preferentially direct gene expression in specific cell types can be used to direct the expression of a nucleic acid. The enhancers used can include, without limitation, those that are characterized as tissue- or cell-specific enhancers. Alternatively, if a genomic clone is used as a therapeutic construct, regulation can be mediated by the cognate regulatory sequences or, if desired, by regulatory sequences derived from a heterologous source, including any of the promoters or regulatory elements described above.

The resulting cells can be grown under conditions similar to those for unmodified cells, whereby the modified cells can be expanded and used for a variety of purposes.

V. Pharmaceutical Compositions and Methods of Treatment

Antibodies and antigen binding proteins (e.g., CARs) of the presently disclosed subject matter can be administered for therapeutic treatments to a patient suffering from a tumor or PRAME-associated pathologic condition in an amount sufficient to prevent, inhibit, or reduce the progression of the tumor or pathologic condition. Progression includes, e.g., the growth, invasiveness, metastases and/or recurrence of the tumor or pathologic condition. Amounts effective for this use will depend upon the severity of the disease and the general state of the patient's own immune system. Dosing schedules will also vary with the disease state and status of the patient, and will typically range from a single bolus dosage or continuous infusion to multiple administrations per day (e.g., every 4-6 hours), or as indicated by the treating physician and the patient's condition.

The identification of medical conditions treatable by the antibodies and antigen binding proteins (e.g., CARs) of the presently disclosed subject matter is well within the ability and knowledge of one skilled in the art. For example, human individuals who are either suffering from a clinically significant leukemic disease or who are at risk of developing clinically significant symptoms are suitable for administration of a presently disclosed antibody or antigen binding protein. A clinician skilled in the art can readily determine, for example, by the use of clinical tests, physical examination and medical/family history, if an individual is a candidate for such treatment. Non-limiting examples of pathological conditions characterized by PRAME expression include chronic myelocytic leukemia (CML), acute lymphoblastic leukemia (ALL), acute myeloid/myelogenous leukemia (AML), myeloma, Non-Hodgkin lymphoma (also known as non-Hodgkin's lymphoma, NHL, or lymphoma), Chronic lymphocytic leukemia (CLL), mantle cell lymphoma, and multiple myeloma (MM). Additionally, solid tumors, in general and in particular, melanoma, ovarian cancer, head and neck cancer, breast cancer, renal cancer, lung cancer, gastrointestinal cancer, brain tumor, and neuroblastoma, are amenable to treatment using presently disclosed antibodies and antigen binding proteins (e.g., CARs).

In non-limiting certain embodiments, the presently disclosed subject matter provides a method of treating a medical condition by administering a presently disclosed PRAME antibody or antigen binding protein (e.g., a CAR) in combination with one or more other agents. For example, an embodiment of the presently disclosed subject matter provides a method of treating a medical condition by administering a presently disclosed antibody or antigen binding protein with an antineoplastic or antiangiogenic agent. The antibody antigen binding protein can be chemically or biosynthetically linked to one or more of the antineoplastic or antiangiogenic agents.

Any suitable method or route can be used to administer a presently disclosed antibody or antigen binding protein (e.g., a CAR), and optionally, to co-administer antineoplastic agents and/or antagonists of other receptors. Routes of administration include, for example, oral, intravenous, intraperitoneal, subcutaneous, or intramuscular administration. It should be emphasized, however, that the presently disclosed subject matter is not limited to any particular method or route of administration.

It is noted that a presently disclosed antibody or antigen binding protein (e.g., a CAR) can be administered as a conjugate, which binds specifically to the receptor and delivers a toxic, lethal payload following ligand-toxin internalization.

In certain embodiments, a presently disclosed antibody or antigen binding protein (e.g., a CAR) is administered together with one or more compound selected from the group consisting of compounds that are capable of killing a target cell, compounds that are capable of enhancing the killing effect by the effector cell, and compounds that are capable of upregulating the antigen targets on the cancer cell itself.

Non-limiting examples of compounds that are capable of killing a target cell include chemotherapeutic agents and cytotoxins, as disclosed herein. Non-limiting examples of compounds that are capable of enhancing the killing effect by the effector cell include antibodies (e.g., checkpoint blocking antibodies, and anti-CD47 antibodies), interferons (e.g., interferon-γ), cytokines (e.g., IL-2), and growth factors (e.g., GM-CSF). Non-limiting examples of compounds that are capable of upregulating the antigen targets on the cancer cell itself include tyrosine kinase inhibitors (e.g., MEK inhibitors), interferons (e.g., interferon-γ), Histone deacetylase inhibitors (HDAC inhibitors, e.g., vorinostat, romidepsin, chidamide, panobinostat, and belinostat), and methylation regulators (e.g., azacytidine, and decitabine).

It is understood that antibodies or antigen binding proteins (e.g., CARs) of the presently disclosed subject matter will be administered in the form of a composition additionally comprising a pharmaceutically acceptable carrier. Suitable pharmaceutically acceptable carriers include, for example, one or more of water, saline, phosphate buffered saline, dextrose, glycerol, ethanol and the like, as well as combinations thereof. Pharmaceutically acceptable carriers may further comprise minor amounts of auxiliary substances such as wetting or emulsifying agents, preservatives or buffers, which enhance the shelf life or effectiveness of the binding proteins. The compositions of the injection may, as is well known in the art, be formulated so as to provide quick, sustained or delayed release of the active ingredient after administration to the mammal.

Other aspects of the presently disclosed subject matter include without limitation, the use of antibodies and nucleic acids that encode them for treatment of PRAME associated disease, for diagnostic and prognostic applications as well as use as research tools for the detection of PRAME in cells and tissues. Pharmaceutical compositions comprising the disclosed antibodies and nucleic acids are encompassed by the presently disclosed subject matter. Vectors comprising the nucleic acids of the presently disclosed subject matter for antibody-based treatment by vectored immunotherapy are also contemplated by the presently disclosed subject matter. Vectors include expression vectors which enable the expression and secretion of antibodies, as well as vectors which are directed to cell surface expression of the antigen-binding proteins, such as chimeric antigen receptors.

Cells comprising the nucleic acids, for example cells that have been transfected with the vectors of the presently disclosed subject matter are also encompassed by the disclosure.

For use in diagnostic and research applications, kits are also provided that contain a presently disclosed anti- PRAME antibody or nucleic acids of the presently disclosed subject matter, assay reagents, buffers, and the like.

VI. Kits

The presently disclosed subject matter provides kits for the treatment or prevention of a PRAME-positive disease. In one embodiment, the kit comprises a therapeutic composition containing an effective amount of an antibody or antigen binding protein (e.g., a CAR) in unit dosage form. In some embodiments, the kit comprises a sterile container which contains a therapeutic or prophylactic vaccine; such containers can be boxes, ampules, bottles, vials, tubes, bags, pouches, blister-packs, or other suitable container forms known in the art. Such containers can be made of plastic, glass, laminated paper, metal foil, or other materials suitable for holding medicaments.

If desired, a presently disclosed antibody or antigen binding protein (e.g., a CAR) is provided together with instructions for administering the cell to a subject having or at risk of developing a PRAME-positive disease. The instructions will generally include information about the use of the composition for the treatment or prevention of a PRAME-positive disease. In other embodiments, the instructions include at least one of the following: description of the therapeutic agent; dosage schedule and administration for treatment or prevention of a PRAME-positive disease or symptoms thereof; precautions; warnings; indications; counter-indications; over-dosage information; adverse reactions; animal pharmacology; clinical studies; and/or references. The instructions may be printed directly on the container (when present), or as a label applied to the container, or as a separate sheet, pamphlet, card, or folder supplied in or with the container.

VII. Methods

1. Flow Cytometry Analysis.

For cell surface staining, cells were incubated with appropriate mAbs for 30 minutes on ice, washed, and incubated with secondary antibody reagents when necessary. Flow cytometry data were collected on a FACS Calibur (Becton Dickinson) or LSRFortessa (BD Biosciences) and analyzed with FlowJo V8.7.1 and 9.4.8 software.

2. Selection and Characterization of scFv Specific for FRAME Peptide/HLA-A0201 Complexes.

A human scFv antibody phage display library was used for the selection of mAb clones. In order to reduce the conformational change of MHC1 complex introduces by immobilizing onto plastic surfaces, a solution panning method was used in place of conventional plate panning. In brief, biotinylated antigens were first mixed with the human scFv phage library, then the antigen-scFv antibody complexes were pulled down by streptavidin-conjugated Dynabeads M-280 through a magnetic rack. Bound clones were then eluted and were used to infect *E. Coli* XL1-Blue. The scFv phage clones expressed in the bacteria were purified (Yasmina, et al., *Protein Science* 2008; 17(8): 1326-1335; Roberts et al., *Blood* 2002: 99 (10): 3748-3755). Panning was performed for 3-4 cycles to enrich scFv phage clones binding to HLA-A0201/PRAME complex specifically. Positive clones were determined by standard ELISA method against biotinylated single chain HLA-A0201/PRAME peptide complexes. Positive clones were further tested for their binding to HLA-A2/peptide complexes on live cell surfaces by flow cytometry, using a TAP-deficient, HLA-A0201+ cell line, T2. T2 cells were pulsed with peptides (50 ug/ml) in the serum-free RPMI1640 medium, in the presence of 20 μg/ml β2 M ON. The cells were washed, and the staining was performed in following steps.

The cells were first stained with purified scFv phage clones, and followed by staining with a mouse anti-M13 mAb, and finally the goat F(ab)2 anti-mouse Ig's conjugate to FITC. Each step of the staining was done between 30-60 minutes on ice and the cells were washed twice between each step of the staining.

3. Engineering Full Length mAb Using the Selected ScFv Fragments.

Full-length human IgG1 of the selected phage clones were produced in HEK293 and Chinese hamster ovary (CHO) cell lines, as described (Caron et al., *J Exp Med* 176:1191-1195. 1992). In brief, antibody variable regions were sub-cloned into mammalian expression vectors, with matching human lambda or kappa light chain constant region and human IgG1 constant region sequences. Molecular weight of the purified full length IgG antibodies were measured under both reducing and non-reducing conditions by electrophoresis.

4. Engineering Chimeric Antigen Receptors and Immune Effector Cells.

Nucleic acids that encode antibodies and antigen-binding proteins identified herein can be used engineer recombinant immune effector cells. Methods and vectors to generate genetically modified T-cells, for example, are known in the art (See Brentjens et al., *Safety and persistence of adoptively transferred autologous CD19-targeted T cells in patients with relapsed or chemotherapy refractory B-cell leukemias in Blood* 118(18):4817-4828, November 2011).

5. Characterization of the Full-Length Human IgG1 for the PRAME/A2 Complex.

Initially, specificities of the fully human IgG1 mAbs for the PRAME peptide/A2 complex were determined by staining T2 cells pulsed with or without a PRAME peptide (e.g., $PRA^{100-108}$, $PRA^{142-151}$, $PRA^{300-309}$, $PRA^{425-433}$, and $PRA^{435-443}$) or RHAMM-R3 control peptides, followed by secondary goat F(ab)2 anti-human IgG mAb conjugate to PE or FITC. The fluorescence intensity was measured by flow cytometry. The same method was used to determine the binding of the mAbs to fresh tumor cells and cell lines.

6. Radioimmunoassays.

PRAME antibody (e.g., Pr300-#20) was labeled with 125-I (PerkinElmer) using the chloramine-T method (38). 100 μg antibody was reacted with 1 mCi 125-I and 20 μg chloramine-T, quenched with 200 μg Na metabisulfite, then separated from free 125-I using a 10DG column (company) equilibrated with 2% bovine serum albumin in PBS. Specific activities of products were in the range of 7-8 mCi/mg.

Hematopoietic cell lines, adherent cell lines (harvested with a non-enzymatic cell stripper (name)), PBMCs from normal donors and AML patients were obtained as described. Cells were washed once with PBS and re-suspended in 2% human serum in PBS at $10^7$ cells/mL at 0°. Cells ($10^6$ tube in duplicate) were incubated with 125-I-labeled PRAME antibody(e.g., Pr300-#20) (1 μg/mL) for 45 minutes on ice, then washed extensively with 1% bovine serum albumin in PBS at 0°. To determine specific binding, a duplicate set of cells was assayed after pre-incubation in the presence of 50-fold excess unlabeled PRAME antibody (e.g., Pr300-#20) for 20 minutes on ice. Bound radioactivity was measured by a gamma counter, specific binding was determined, and the number of bound antibodies per cell was calculated from specific activity.

7. Antibody-Dependent Cellular Cytotoxicity (ADCC).

Target cells used for ADCC were T2 cells pulsed with or without PRAME peptide, and tumor cell lines without peptide pulsing. PRAME antibody(e.g., Pr300-#20) or its isotype control human IgG1 at various concentrations were incubated with target cells and fresh PBMCs at different effector: target (E:T) ratio for 16 hrs. The supernatant were harvested and the cytotoxicity was measured by LDH release assay using Cytotox 96 non-radioactive kit from Promega following their instruction. Cytotoxicity is also measured by standard 4 hours 51Cr-release assay.

8. Transduction and Selection of Luciferase/GFP Positive Cells.

BV173 cells were engineered to express high level of GFP-luciferase fusion protein, using lentiviral vectors containing a plasmid encoding the luc/GFP (39). Using single cell cloning, only the cells showing high level GFP expression were selected by flow cytometry analysis and were maintained and used for the animal study.

9. Therapeutic Trials of the Anti-PRAME Antibody in a Human Leukemia Xenograft NSG Model.

BV173 human leukemia cells and SET2 human AM cells were injected IV into NSG mice. On day 5, tumor engraftment was confirmed by firefly luciferase imaging in all mice that were to be treated; mice were then randomly divided into different treatment groups. Beginning on day 6, mice were treated with 50 µg anti-PRAME (e.g., Pr300-#20) twice weekly or control (no antibody) for two weeks. In animals that also received human effector cells with or without mAb, cells (CD34 and CD3-depleted healthy donor human PBMCs) were injected IV into mice ($10^7$ cells/mouse) 4 hr before the mAb injections. Tumor growth was assessed by luminescence imaging once to twice a week, and clinical activity was assessed daily.

10. Selection and Characterization of scFv Specific for PRAME Peptide/HLA-A0201 Complexes.

Selection of a PRAME-specific scFV is achieved using a 9-mer PRAME-derived peptide (e.g., $PRA^{100-108}$, $PRA^{425-433}$, or $PRA^{435-443}$) a 10-mer PRAME-derived peptide ($PRA^{142-151}$, or $PRA^{300-309}$). These peptides have been shown to be processed and presented by HLA-A0201 to induce cytotoxic $CD8^+$ T cells that are capable of killing PRAME-positive tumor cells.

Well established phage display libraries and screening methods known to those of skill in the art were used to select scFv fragments highly specific for a PRAME peptide/HLA-A2 complex. In one embodiment, a human scFv antibody phage display library ($7 \times 10^{10}$ clones) was used for the selection of mAb clones. In order to reduce the conformational change of MHC1 complex introduced by immobilizing onto plastic surfaces, a solution panning method was used in place of conventional plate panning. In brief, biotinylated antigens were first mixed with the human scFv phage library, then the antigen-scFv phage antibody complexes were pulled down by streptavidin-conjugated Dynabeads M-280 through a magnetic rack.

Bound clones were then eluted and were used to infect *E. Coli* XL1-Blue. The scFv phage clones expressed in the bacteria were purified (Yasmina, et al., *Protein Science* 2008; 17(8): 1326-1335 Roberts, et al., *Blood* 2002: 99 (10): 3748-3755). Panning was performed for 3-4 cycles to enrich scFv phage clones binding to HLA-A0201/PRAME complex specifically. Positive clones were determined by standard ELISA method against biotinylated single chain HLA-A0201/PRAME peptide complexes. Positive clones were further tested for their binding to HLA-A2/peptide complexes on live cell surfaces by flow cytometry, using a TAP-deficient, $HLA-A0201^+$ cell line, T2. T2 cells were pulsed with peptides (50 µg/ml) in serum-free RPMI1640 medium, in the presence of 20 µg/ml β2 M overnight. The cells were washed, and staining was performed as follows.

The cells were first stained with purified scFv phage clones, followed by staining with a mouse anti-M13 mAb, and finally, a goat $F(ab)_2$ anti-mouse Ig conjugated to FITC. Each step of the staining was done for 30-60 minutes on ice. The cells were washed twice between each staining step. The phage clone of anti-PRAME antibody was shown to bind to T2 cells pulsed with only $PRA^{300-309}$, but not to T2 cells alone, T2 cells pulsed with control EW peptide, or heteroclitic peptide PRAME.

Binding affinity of the full-length IgG1 of PRAME antibody to the peptide/HLA-A*0201 complex was tested by titration of anti-PRAME antibody (e.g., Pr300-#20) at indicated concentrations. T2 cells were pulsed with 50 µg/ml or 10 µg/ml, followed by secondary goat F(ab) anti-human IgG/PE.

The positive scFv clones were tested for their binding to HLA-A2/peptide complexes on live cell surfaces by indirect flow cytometry on: (i) a TAP deficient $HLA-A*0201^+$ T2 cells pulsed with PRAME peptide or irrelevant peptide; (ii) a PRAME+ $HLA-A*0201^+$ cell lines such as BV173, SET-2- and control $PRAME^-$ $HLA-A*0201^+$ cell line SUDHL-1, or $PRAME^+$ $HLA-A*0201^-$ cell line, HL-60, without pulsing with the peptide. The latter determine the recognition and binding affinity of the scFv to the naturally processed PRAME/A2 complex on tumor cells.

A total of 59 phage clones were screened for their ability to produce mAb specific for the PRAME peptide/A2 complex. The recognition of the PRAME peptide/A2 complex on live cells was measured by the binding of the phage scFv to T2 cells pulsed with the PRAME peptide and the other HLA-A2-binding peptides (50 µg/ml).

11. Engineering Full Length mAb Using the Selected ScFv Fragments.

Phage display technology allows for the rapid selection and production of antigen-specific scFv and Fab fragments, which are useful in and of themselves, or which can be further developed to provide complete antibodies, antigen-binding proteins or antigen-binding portions thereof. Complete mAbs with Fc domains have a number of advantages over the scFv and Fab antibodies. First, only full length Abs exert immunological function such as CDC and ADCC mediated via Fc domain. Second, bivalent mAbs offer stronger antigen-binding affinity than monomeric Fab Abs. Third, plasma half-life and renal clearance will be different with the Fab and bivalent mAb. The particular features and advantages of each can be matched to the planned effector strategy. Fourth, bivalent mAb may be internalized at different rates than scFv and Fab, altering immune function or carrier function. Alpha emitters, for example, do not need to be internalized to kill the targets, but many drugs and toxins will benefit from internalization of the immune complex. In one embodiment, therefore, once scFv clones specific for PRAME/HLA-A2 were obtained from phage display libraries, a full length IgG mAb using the scFv fragments was produced.

To produce recombinant human monoclonal IgG in Chinese hamster ovary (CHO) cells, a full length IgG mAb was engineered based on a method known to those of skill in the art (Tomomatsu et al., Production of human monoclonal antibodies against FceRla by a method combining in vitro immunization with phage display. Biosci Biotechnol Biochem 73(7): 1465-1469 2009). Briefly, antibody variable regions were sub-cloned into mammalian expression vectors matching Lambda or Kappa light chain constant sequences and IgG1 subclass Fc. Kinetic binding analysis (Yasmina et al., *Protein Science* 2008; 17(8): 1326-1335) confirmed specific binding of full length IgG to PRAME/HLA-A2, with a $K_D$ in nanomolar range.

Exemplary Embodiments

1. An isolated antibody, or an antigen-binding portion thereof, which binds to a PRAME peptide bound to a major histocompatibility complex (MHC) molecule.

2. The antibody or antigen-binding portion thereof of embodiment 1, wherein the MHC molecule is an HLA molecule.

3. The antibody or antigen-binding portion thereof of embodiment 2, wherein the HLA molecule is an HLA class I molecule.

4. The antibody or antigen-binding portion thereof of embodiment 3, wherein the HLA class I molecule is HLA-A.

5. The antibody or antigen-binding portion thereof of embodiment 4, wherein the HLA-A is HLA-A2.

6. The antibody or antigen-binding portion thereof of embodiment 5, wherein the HLA-A2 is HLA-A*0201.

7. The antibody or antigen-binding portion thereof of any one of the preceding embodiments, wherein the PRAME peptide is selected from the group consisting of $PRA^{100-108}$ (SEQ ID NO: 2), $PRA^{142-151}$ (SEQ ID NO: 3), $PRA^{300-309}$ (SEQ ID NO: 4), $PRA^{425-433}$ (SEQ ID NO: 5), and $PRA^{435-443}$ (SEQ ID NO: 6).

8. The antibody or antigen-binding portion thereof of any one of the preceding embodiments, wherein the PRAME peptide is $PRA^{300-309}$ (SEQ ID NO: 4).

9. The antibody or antigen-binding portion thereof of any one of the preceding embodiments, comprising a heavy chain variable region CDR3 sequence and a light chain variable region CDR3 sequence selected from the group consisting of:

(a) a heavy chain variable region CDR3 sequence comprising amino acid sequence set forth in SEQ ID NO: 9 or a modification thereof, and a light chain variable region CDR3 sequence comprising amino acid sequence set forth in SEQ ID NO: 12 or a modification thereof;

(b) a heavy chain variable region CDR3 sequence comprising an amino acid sequence set forth in SEQ ID NO: 15 or a modification thereof, and a light chain variable region CDR3 sequence comprising amino an acid sequence set forth in SEQ ID NO: 18 or a modification thereof;

(c) a heavy chain variable region CDR3 sequence comprising an amino acid sequence set forth in SEQ ID NO: 21 or a modification thereof, and a light chain variable region CDR3 sequence comprising an amino acid sequence set forth in SEQ ID NO: 24 or a modification thereof; and (d) a heavy chain variable region CDR3 sequence comprising an amino acid sequence set forth in SEQ ID NO: 27 or a modification thereof, and a light chain variable region CDR3 sequence comprising an amino acid sequence set forth in SEQ ID NO: 30 or a modification thereof.

10. The antibody or antigen-binding portion thereof of any one of the preceding embodiments, comprising a heavy chain variable region CDR2 sequence and a light chain variable region CDR2 sequence selected from the group consisting of:

(a) a heavy chain variable region CDR2 sequence comprising an amino acid sequence set forth in SEQ ID NO: 8 or a modification thereof, and a light chain variable region CDR2 sequence comprising an amino acid sequence set forth in SEQ ID NO: 11 or a modification thereof;

(b) a heavy chain variable region CDR2 sequence comprising an amino acid sequence set forth in SEQ ID NO: 14 or a modification thereof, and a light chain variable region CDR2 sequence comprising an amino acid sequence set forth in SEQ ID NO: 17 or a modification thereof;

(c) a heavy chain variable region CDR2 sequence comprising an amino acid sequence set forth in SEQ ID NO: 20 or a modification thereof, and a light chain variable region CDR2 sequence comprising an amino acid sequence set forth in SEQ ID NO: 23 or a modification thereof; and (d) a heavy chain variable region CDR2 sequence comprising an amino acid sequence set forth in SEQ ID NO: 26 or a modification thereof, and a light chain variable region CDR2 sequence comprising an amino acid sequence set forth in SEQ ID NO: 29 or a modification thereof.

11. The antibody or antigen-binding portion thereof of any one of the preceding embodiments, comprising a heavy chain variable region CDR1 sequence and a light chain variable region CDR1 sequence selected from the group consisting of:

(a) a heavy chain variable region CDR1 sequence comprising an amino acid sequence set forth in SEQ ID NO: 7 or a modification thereof, and a light chain variable region CDR1 sequence comprising an amino acid sequence set forth in SEQ ID NO: 10 or a modification thereof;

(b) a heavy chain variable region CDR1 sequence comprising an amino acid sequence set forth in SEQ ID NO: 13 or a modification thereof, and a light chain variable region CDR1 sequence comprising an amino acid sequence set forth in SEQ ID NO: 16 or a modification thereof;

(c) a heavy chain variable region CDR1 sequence comprising an amino acid sequence set forth in SEQ ID NO: 19 or a modification thereof, and a light chain variable region CDR1 sequence comprising an amino acid sequence set forth in SEQ ID NO: 22 or a modification thereof; and (d) a heavy chain variable region CDR1 sequence comprising an amino acid sequence set forth in SEQ ID NO: 25 or a modification thereof, and a light chain variable region CDR1 sequence comprising an amino acid sequence set forth in SEQ ID NO: 28 or a modification thereof.

12. The antibody or antigen-binding portion thereof of any one of the preceding embodiments, comprising:

(a) a heavy chain variable region CDR1 comprising an amino acid sequence set forth in SEQ ID NO: 7; a heavy chain variable region CDR2 comprising an amino acid sequence set forth in SEQ ID NO: 8; a heavy chain variable region CDR3 comprising an amino acid sequence set forth in SEQ ID NO: 9; a light chain variable region CDR1 comprising an amino acid sequence set forth in SEQ ID NO: 10; a light chain variable region CDR2 comprising an amino acid sequence set forth in SEQ ID NO: 11; and a light chain variable region CDR3 comprising an amino acid sequence set forth in SEQ ID NO: 12;

(b) a heavy chain variable region CDR1 comprising an amino acid sequence set forth in SEQ ID NO: 13; a heavy chain variable region CDR2 comprising an amino acid sequence set forth in SEQ ID NO: 14; a heavy chain variable region CDR3 comprising an amino acid sequence set forth in SEQ ID NO: 15; a light chain variable region CDR1 comprising an amino acid sequence set forth in SEQ ID NO: 16; a light chain variable region CDR2 comprising an amino acid sequence set forth in SEQ ID NO: 17; and a light chain variable region CDR3 comprising an amino acid sequence set forth in SEQ ID NO: 18;

(c) a heavy chain variable region CDR1 comprising an amino acid sequence set forth in SEQ ID NO: 19; a heavy chain variable region CDR2 comprising an amino acid sequence set forth in SEQ ID NO: 20; a heavy chain variable region CDR3 comprising an amino acid sequence set forth in SEQ ID NO: 21; a light chain variable region CDR1 comprising an amino acid sequence set forth in SEQ ID NO: 22; a light chain variable region CDR2 comprising an amino acid sequence set forth in SEQ ID NO: 23; and a light chain variable region CDR3 comprising an amino acid sequence set forth in SEQ ID NO: 24; or (d) a heavy chain variable region CDR1 comprising an amino acid sequence set forth in SEQ ID NO: 25; a heavy chain variable region CDR2 comprising an amino acid sequence set forth in SEQ ID NO: 26; a heavy chain variable region CDR3 comprising an amino acid sequence set forth in SEQ ID NO: 27; a light chain variable region CDR1 comprising an amino acid sequence set forth in SEQ ID NO: 28; a light chain variable region CDR2 comprising an amino acid sequence set forth in SEQ ID NO: 29; and a light chain variable region CDR3 comprising an amino acid sequence set forth in SEQ ID NO: 30.

13. The antibody or antigen-binding portion thereof of any one of the preceding embodiments, comprising: a heavy chain variable region CDR1 comprising an amino acid sequence set forth in SEQ ID NO: 7; a heavy chain variable region CDR2 comprising an amino acid sequence set forth in SEQ ID NO: 8; a heavy chain variable region CDR3 comprising an amino acid sequence set forth in SEQ ID NO: 9; a light chain variable region CDR1 comprising an amino acid sequence set forth in SEQ ID NO: 10; a light chain variable region CDR2 comprising an amino acid sequence set forth in SEQ ID NO: 11; and a light chain variable region CDR3 comprising an amino acid sequence set forth in SEQ ID NO: 12.

14. The antibody or antigen-binding portion thereof of any one of the preceding embodiments, comprising a heavy chain variable region that comprises an amino acid sequence that is at least 80% homologous to the sequence selected from the group consisting of SEQ ID NOS: 49, 51, 53, and 55.

15. The antibody or antigen-binding portion thereof of any one of the preceding embodiments, comprising a heavy chain variable region that comprises an amino acid sequence set forth in SEQ ID NO: 49, SEQ ID NO: 51, SEQ ID NO: 53, or SEQ ID NO: 55.

16. The antibody or antigen-binding portion thereof of any one of the preceding embodiments, comprising a light chain variable region that comprises an amino acid sequence that is at least 80% homologous to the sequence selected from the group consisting of SEQ ID NOS: 50, 52, 54, and 56.

17. The antibody or antigen-binding portion thereof of any one of the preceding embodiments, comprising a light chain variable region that comprises an amino acid sequence set forth in SEQ ID NO: 50, SEQ ID NO: 52, SEQ ID NO: 54, or SEQ ID NO: 56.

18. The antibody or antigen-binding portion thereof of any one of the preceding embodiments, comprising:

(a) a heavy chain variable region comprising an amino acid sequence set forth in SEQ ID NO: 49, and a light chain variable region that comprises an amino acid sequence set forth in SEQ ID NO: 50;

(b) a heavy chain variable region comprising an amino acid sequence set forth in SEQ ID NO: 51, and a light chain variable region that comprises an amino acid sequence set forth in SEQ ID NO: 52;

(c) a heavy chain variable region comprising an amino acid sequence set forth in SEQ ID NO: 53, and a light chain variable region that comprises an amino acid sequence set forth in SEQ ID NO: 54; or (d) a heavy chain variable region comprising an amino acid sequence set forth in SEQ ID NO: 55, and a light chain variable region that comprises an amino acid sequence set forth in SEQ ID NO: 56.

19. The antibody or antigen-binding portion thereof of any one of the preceding embodiments, comprising: a heavy chain variable region comprising an amino acid sequence set forth in SEQ ID NO: 49, and a light chain variable region that comprises an amino acid sequence set forth in SEQ ID NO: 50.

20. The antibody or antigen-binding portion thereof of any one of embodiments 1-7 and 9-19, wherein the PRAME peptide is PRA$^{435\text{-}443}$ (SEQ ID NO: 6).

21. The antibody or antigen-binding portion thereof of any one of embodiments 1-7 and 20, comprising a heavy chain variable region CDR3 sequence and a light chain variable region CDR3 sequence selected from the group consisting of:

(a) a heavy chain variable region CDR3 sequence comprising an amino acid sequence set forth in SEQ ID NO: 33 or a modification thereof, and a light chain variable region CDR3 sequence comprising an amino acid sequence set forth in SEQ ID NO: 36 or a modification thereof;

(b) a heavy chain variable region CDR3 sequence comprising an amino acid sequence set forth in SEQ ID NO: 39 or a modification thereof, and a light chain variable region CDR3 sequence comprising an amino acid sequence set forth in SEQ ID NO: 42 or a modification thereof; and (c) a heavy chain variable region CDR3 sequence comprising an amino acid sequence set forth in SEQ ID NO: 45 or a modification thereof, and a light chain variable region CDR3 sequence comprising an amino acid sequence set forth in SEQ ID NO: 48 or a modification thereof.

22. The antibody or antigen-binding portion thereof of any one of embodiments 1-7, 20 and 21, comprising a heavy chain variable region CDR2 sequence and a light chain variable region CDR2 sequence selected from the group consisting of:

(a) a heavy chain variable region CDR2 sequence comprising an amino acid sequence set forth in SEQ ID NO: 32 or a modification thereof, and a light chain variable region CDR2 sequence comprising an amino acid sequence set forth in SEQ ID NO: 35 or a modification thereof;

(b) a heavy chain variable region CDR2 sequence comprising an amino acid sequence set forth in SEQ ID NO: 38 or a modification thereof, and a light chain variable region CDR2 sequence comprising an amino acid sequence set forth in SEQ ID NO: 41 or a modification thereof; and (c) a heavy chain variable region CDR2 sequence comprising an amino acid sequence set forth in SEQ ID NO: 44 or a modification thereof, and a light chain variable region CDR2 sequence comprising an amino acid sequence set forth in SEQ ID NO: 47 or a modification thereof.

23. The antibody or antigen-binding portion thereof of any one of embodiments 1-7 and 20-22, comprising a heavy chain variable region CDR1 sequence and a light chain variable region CDR1 sequence selected from the group consisting of:

(a) a heavy chain variable region CDR1 sequence comprising an amino acid sequence set forth in SEQ ID NO: 31 or a modification thereof, and a light chain variable region CDR1 sequence comprising an amino acid sequence set forth in SEQ ID NO: 34 or a modification thereof;

(b) a heavy chain variable region CDR1 sequence comprising an amino acid sequence set forth in SEQ ID NO: 37 or a modification thereof, and a light chain variable region CDR1 sequence comprising an amino acid sequence set forth in SEQ ID NO: 40 or a modification thereof; and (c) a heavy chain variable region CDR1 sequence comprising an amino acid sequence set forth in SEQ ID NO: 43 or a modification thereof, and a light chain variable region CDR1 sequence comprising an amino acid sequence set forth in SEQ ID NO: 46 or a modification thereof.

24. The antibody or antigen-binding portion thereof of any one of embodiments 1-7 and 20-23, comprising:

(a) a heavy chain variable region CDR1 comprising an amino acid sequence set forth in SEQ ID NO: 31; a heavy chain variable region CDR2 comprising an amino acid sequence set forth in SEQ ID NO: 32; a heavy chain variable region CDR3 comprising an amino acid sequence set forth in SEQ ID NO: 33; a light chain variable region CDR1 comprising an amino acid sequence set forth in SEQ ID NO: 34; a light chain variable region CDR2 comprising an amino acid sequence set forth in SEQ ID NO: 35; and a light chain variable region CDR3 comprising an amino acid sequence set forth in SEQ ID NO: 36;

(b) a heavy chain variable region CDR1 comprising an amino acid sequence set forth in SEQ ID NO: 37; a heavy chain variable region CDR2 comprising an amino acid sequence set forth in SEQ ID NO: 38; a heavy chain variable region CDR3 comprising an amino acid sequence set forth in SEQ ID NO: 39; a light chain variable region CDR1 comprising an amino acid sequence set forth in SEQ ID NO: 40; a light chain variable region CDR2 comprising an amino acid sequence set forth in SEQ ID NO: 41; and a light chain variable region CDR3 comprising an amino acid sequence set forth in SEQ ID NO: 42; or (c) a heavy chain variable region CDR1 comprising an amino acid sequence set forth in SEQ ID NO: 43; a heavy chain variable region CDR2 comprising an amino acid sequence set forth in SEQ ID NO: 44; a heavy chain variable region CDR3 comprising an amino acid sequence set forth in SEQ ID NO: 45; a light chain variable region CDR1 comprising an amino acid sequence set forth in SEQ ID NO: 46; a light chain variable region CDR2 comprising an amino acid sequence set forth in SEQ ID NO: 47; and a light chain variable region CDR3 comprising an amino acid sequence set forth in SEQ ID NO: 48.

25. The antibody or antigen-binding portion thereof of any one of embodiments 1-7 and 20-24, comprising: a heavy chain variable region CDR1 comprising an amino acid sequence set forth in SEQ ID NO: 31; a heavy chain variable region CDR2 comprising an amino acid sequence set forth in SEQ ID NO: 32; a heavy chain variable region CDR3 comprising an amino acid sequence set forth in SEQ ID NO: 33; a light chain variable region CDR1 comprising an amino acid sequence set forth in SEQ ID NO: 34; a light chain variable region CDR2 comprising an amino acid sequence set forth in SEQ ID NO: 35; and a light chain variable region CDR3 comprising an amino acid sequence set forth in SEQ ID NO: 36.

26. The antibody or antigen-binding portion thereof of any one of embodiments 1-7 and 20-25, comprising a heavy chain variable region that comprises an amino acid sequence that is at least 80% homologous the sequence selected from the group consisting of SEQ ID NOS: 57, 59, and 61.

27. The antibody or antigen-binding portion thereof of any one of embodiments 1-7 and 20-26, comprising a heavy chain variable region that comprises an amino acid sequence set forth in SEQ ID NO: 57, SEQ ID NO: 59, or SEQ ID NO: 61.

28. The antibody or antigen-binding portion thereof of any one of embodiments 1-7 and 20-27, comprising a light chain variable region that comprises an amino acid sequence that is at least 80% homologous the sequence selected from the group consisting of SEQ ID NOS: 58, 60, and 62.

29. The antibody or antigen-binding portion thereof of any one of embodiments 1-7 and 20-28, comprising a light chain variable region that comprises an amino acid sequence set forth in SEQ ID NO: 58, SEQ ID NO: 60, or SEQ ID NO: 62.

30. The antibody or antigen-binding portion thereof of any one of embodiments 1-7 and 20-29, comprising:

(a) a heavy chain variable region comprising an amino acid sequence set forth in SEQ ID NO: 57, and a light chain variable region that comprising an amino acid sequence set forth in SEQ ID NO: 58;

(b) a heavy chain variable region comprising an amino acid sequence set forth in SEQ ID NO: 59, and a light chain variable region that comprising an amino acid sequence set forth in SEQ ID NO: 60; or (c) a heavy chain variable region comprising an amino acid sequence set forth in SEQ ID NO: 61, and a light chain variable region that comprising an amino acid sequence set forth in SEQ ID NO: 62.

31. The antibody or antigen-binding portion thereof of any one of embodiments 1-7 and 20-30, comprising: a heavy chain variable region comprising an amino acid sequence set forth in SEQ ID NO: 57, and a light chain variable region that comprising an amino acid sequence set forth in SEQ ID NO: 58.

32. The antibody or antigen-binding portion thereof of any one of embodiments 9-11 and 21-23, wherein the modification is selected from deletions, insertions, substitutions, and combinations thereof.

33. The antibody or antigen-binding portion thereof of any one of embodiments 9-11, 21-23 and 32, wherein the modification thereof consists of no more than 2, no more than 3, no more than 4, or no more than 5 modifications.

34. The antibody or antigen-binding portion thereof of any one of embodiments 1-33, which binds to the N-terminal of the PRAME peptide that is bound to the MHC molecule.

35. The antibody or antigen-binding portion thereof of any one of embodiments 1-33, which binds to the C-terminal of the PRAME peptide that is bound to the MHC molecule.

36. The antibody or antigen-binding portion thereof of any one of embodiments 1-35, which binds to the PRAME peptide that is bound to the MHC molecule with a binding affinity ($K_D$) of about $1 \times 10^{-7}$ M or less.

37. The antibody or antigen-binding portion thereof of embodiments 1-36, which binds to the PRAME peptide that is bound to the MHC molecule with a binding affinity ($K_D$) of about 2.4 nM.

38. An isolated antibody, or an antigen-binding portion thereof, which cross-competes for binding to a PRAME peptide bound to an MHC molecule with a reference antibody or antigen-binding portion comprising:

(a) a heavy chain variable region comprising an amino acid sequence set forth in SEQ ID NO: 49, and a light chain variable region that comprising an amino acid sequence set forth in SEQ ID NO: 50;

(b) a heavy chain variable region comprising an amino acid sequence set forth in SEQ ID NO: 51, and a light chain variable region that comprising an amino acid sequence set forth in SEQ ID NO: 52;

(c) a heavy chain variable region comprising an amino acid sequence set forth in SEQ ID NO: 53, and a light chain variable region that comprising an amino acid sequence set forth in SEQ ID NO: 54;

(d) a heavy chain variable region comprising an amino acid sequence set forth in SEQ ID NO: 55, and a light chain variable region that comprises an amino acid sequence set forth in SEQ ID NO: 56;

(e) a heavy chain variable region comprising an amino acid sequence set forth in SEQ ID NO: 57, and a light chain variable region that comprises an amino acid sequence set forth in SEQ ID NO: 58;

(f) a heavy chain variable region comprising an amino acid sequence set forth in SEQ ID NO: 59, and a light chain variable region that comprises an amino acid sequence set forth in SEQ ID NO: 60; or (g) a heavy chain variable region comprising an amino acid sequence set forth in SEQ ID NO: 61, and a light chain variable region that comprises an amino acid sequence set forth in SEQ ID NO: 62.

39. The antibody or antigen-binding portion thereof of embodiment 38, wherein the reference antibody or antigen-binding portion thereof comprises a heavy chain variable region comprising an amino acid sequence set forth in SEQ ID NO: 49, and a light chain variable region that comprising an amino acid sequence set forth in SEQ ID NO: 50.

40. The antibody or antigen-binding portion thereof of embodiment 38 or 39, wherein the MHC molecule is a HLA molecule.

41. The antibody or antigen-binding portion thereof of embodiment 40, wherein the HLA molecule is a HLA class I molecule.

42. The antibody or antigen-binding portion thereof of embodiment 41, wherein the HLA class I molecule is HLA-A.

43. The antibody or antigen-binding portion thereof of embodiment 42, wherein the HLA-A is HLA-A2.

44. The antibody or antigen-binding portion thereof of embodiment 43, wherein the HLA-A2 is HLA-A*0201.

45. The antibody or antigen-binding portion thereof of any one of embodiments 38-44, wherein the PRAME peptide is selected from the group consisting of $PRA^{100-108}$ (SEQ ID NO: 2), $PRA^{142-151}$ (SEQ ID NO: 3), $PRA^{300-309}$ (SEQ ID NO: 4), $PRA^{425-433}$ (SEQ ID NO: 5), and $PRA^{435-443}$ (SEQ ID NO: 6).

46. The antibody or antigen-binding portion thereof of any one of embodiments 38-45, wherein the PRAME peptide is $PRA^{300-309}$ (SEQ ID NO: 4).

47. The antibody or antigen-binding portion thereof of any one of embodiments 38-45, wherein the PRAME peptide is $PRA^{435-443}$ (SEQ ID NO: 6).

48. The antibody or antigen-binding portion thereof of any one of the preceding embodiments, wherein the antibody comprises a human variable region framework region.

49. The antibody or antigen-binding portion thereof of any one of the preceding embodiments, which is a fully human or an antigen-binding portion thereof.

50. The antibody or antigen-binding portion thereof of any one of embodiments 1-48, which is a chimeric antibody or an antigen-binding portion thereof.

51. The antibody or antigen-binding portion thereof of any one of embodiments 1-48, which is a humanized antibody or an antigen-binding portion thereof.

52. The antibody or antigen-binding portion thereof of any one of preceding embodiments, wherein the antigen-binding portion of the antibody is an Fab, Fab', F(ab')2, Fv or single chain Fv (scFv).

53. The antibody or antigen-binding portion thereof of any one of preceding embodiments, which is of an IgG1, IgG2, IgG3, or IgG4 isotype.

54. The antibody or antigen-binding portion thereof of any one of preceding embodiments, which is of an IgG1 isotype.

55. The antibody or antigen-binding portion thereof of any one of preceding embodiments, comprising one or more post-translational modifications.

56. The antibody or antigen-binding portion thereof of embodiment 55, wherein the one or more post-translational modifications comprise afucosylation.

57. The antibody or antigen-binding portion thereof of any one of preceding embodiments, comprising an afucosylated Fc region.

58. A composition comprising the antibody or antigen-binding portion thereof of any one of preceding embodiments, and a pharmaceutically acceptable carrier.

59. An immunoconjugate comprising the antibody or antigen-binding portion thereof of any one of embodiments 1-57, linked to a therapeutic agent.

60. The immunoconjugate of embodiment 59, wherein said therapeutic agent is a drug, cytotoxin, or a radioactive isotope.

61. A composition comprising the immunoconjugate of embodiment 59 or 60 and a pharmaceutically acceptable carrier.

62. A bispecific molecule comprising the antibody or antigen-binding portion thereof of anyone of embodiments 1-57, linked to a second functional moiety.

63. The bispecific molecule of embodiment 62, wherein the second functional moiety has a different binding specificity than said antibody or antigen binding portion thereof.

64. The bispecific molecule of embodiment 62 or 63, which recognizes CD3 and the PRAME peptide bound to the MHC molecule.

65. A composition comprising the bispecific molecule of any one of embodiments 62-64 and a pharmaceutically acceptable carrier.

66. An isolated nucleic acid that encodes an antibody or antigen-binding portion thereof of any one of embodiments 1-57.

67. An expression vector comprising the nucleic acid molecule of embodiment 66.

68. A host cell comprising the expression vector of embodiment 67.

69. A method for detecting PRAME in a whole cell or tissue, comprising:

(a) contacting a cell or tissue with an antibody or an antigen-binding portion thereof that binds to a PRAME peptide that is bound to an MHC molecule, wherein the antibody or antigen-binding portion thereof comprises a detectable label; and (b) determining the amount of the labeled antibody or antigen-binding portion thereof bound to the cell or tissue by measuring the amount of detectable label associated with the cell or tissue, wherein the amount of bound antibody or antigen-binding portion thereof indicates the amount of PRAME in the cell or tissue.

70. The method of embodiment 69, wherein the MHC molecule is a HLA molecule.

71. The method of embodiment 70, wherein the HLA molecule is a HLA class I molecule.

72. The method of embodiment 71, wherein the HLA class I molecule is HLA-A.

73. The method of embodiment 72, wherein the HLA-A is HLA-A2.

74. The method of embodiment 73, wherein the HLA-A2 is HLA-A*0201.

75. The method of any one of embodiments 69-75, wherein the PRAME peptide is selected from the group consisting of PRA$^{100\text{-}108}$ (SEQ ID NO: 2), PRA$^{142\text{-}151}$ (SEQ ID NO: 3), PRA$^{300\text{-}309}$ PRA$^{300}$-309 (SEQ ID NO: 4), PRA$^{425\text{-}433}$ (SEQ ID NO: 5), and PRA$^{435\text{-}443}$ (SEQ ID NO: 6).

76. The method of any one of embodiments 69-75, wherein the PRAME peptide is PRA$^{300\text{-}309}$ (SEQ ID NO: 4).

77. The method of any one of embodiments 69-75, wherein the PRAME peptide is PRA$^{435\text{-}443}$ (SEQ ID NO: 6).

78. The method of any one of embodiments 69-77, wherein the antibody or antigen-binding portion thereof is the antibody or antigen-binding portion thereof of any one of claims 1-57.

79. A chimeric antigen receptor (CAR) specific for a PRAME peptide bound to an MHC molecule.

80. The CAR of embodiment 79, wherein the MHC molecule is a HLA molecule.

81. The CAR of embodiment 80, wherein the HLA molecule is a HLA class I molecule.

82. The CAR of embodiment 81, wherein the HLA class I molecule is HLA-A.

83. The CAR of embodiment 82, wherein the HLA-A is HLA-A2.

84. The CAR of embodiment 83, wherein the HLA-A2 is HLA-A*0201.

85. The CAR of any one of embodiments 79-84, wherein the PRAME peptide is selected from the group consisting of PRA$^{100\text{-}108}$ (SEQ ID NO: 2), PRA$^{142\text{-}151}$ (SEQ ID NO: 3), PRA$^{300\text{-}309}$ (SEQ ID NO: 4), PRA$^{425\text{-}433}$ (SEQ ID NO: 5), and PRA$^{435\text{-}443}$ (SEQ ID NO: 6).

86. The CAR of any one of embodiments 79-85, wherein the PRAME peptide is PRA$^{300\text{-}309}$ (SEQ ID NO: 4).

87. The CAR of any one of embodiments 79-85, wherein the PRAME peptide is PRA$^{435\text{-}443}$ (SEQ ID NO: 6).

88. The CAR of any one of embodiments 79-87, wherein the CAR comprises an antigen-binding portion comprising a heavy chain variable region and a light chain variable region.

89. The CAR of embodiment 88, wherein the CAR comprises a linker between the heavy chain variable region and the light chain variable region.

90. The CAR of embodiment 89, wherein the linker comprises the amino acid sequence set forth in SEQ ID NO: 70.

91. The CAR of any one of embodiments 79-90, wherein the CAR comprises the antigen-binding portion of any one of claims 1-57.

92. The CAR of any one of embodiments 88-91, wherein the antigen-binding portion comprises a single-chain variable fragment (scFv).

93. The CAR of embodiment 92, wherein the scFv is a human scFv.

94. The CAR of embodiment 93, wherein the human scFv comprises the amino acid sequence selected from the group consisting of SEQ ID NOS: 63, 64, 65, 66, 67, 68, and 69.

95. The CAR of embodiment 93 or 94, wherein the human scFv comprises the amino acid sequence set forth in SEQ ID NO: 63.

96. The CAR of any one of embodiments 88-91, wherein the antigen-binding portion comprises a Fab, which is optionally crosslinked.

97. The CAR of any one of embodiments 88-91, wherein the antigen-binding portion comprises a F(ab)$_2$.

98. A method of treating a subject having a PRAME-positive disease, comprising administering an effective amount of the antibody or antigen-binding portion thereof of any one of embodiments 1-57 to the subject, thereby inducing death of a tumor cell in the subject.

99. A method of treating a subject having a PRAME-positive disease, comprising administering an effective amount of the CAR of any one of embodiments 79-97 to the subject, thereby inducing death of a tumor cell in the subject.

100. A method of treating a subject having a PRAME-positive disease, comprising administering an effective amount of the bispecific antibody of any one of embodiments 62-64 to the subject, thereby inducing death of a tumor cell in the subject.

101. The method of any one of embodiments 98-100, wherein the PRAME-positive disease is selected from the group consisting of breast cancer, ovarian cancer, melanoma, lung cancer, gastrointestinal cancer, brain tumor, head and neck cancer, renal cancer, myeloma, neuroblastoma, mantle cell lymphoma, chronic myelocytic leukemia, multiple myeloma, acute lymphoblastic leukemia (ALL), acute myeloid/myelogenous leukemia (AML), Non-Hodgkin lymphoma (NHL), and Chronic lymphocytic leukemia (CLL).

102. The method of any one of embodiments 98-101, wherein the subject is a human.

103. The method of any one of embodiments 98-102, further comprising administering one or more compound selected from the group consisting of compounds that are capable of killing the tumor cell, compounds that are capable of enhancing the killing effect by an effector cell, and compounds that are capable of upregulating the antigen targets on the tumor cell.

104. Use of the antibody or antigen-binding portion thereof of any one of embodiments 1-57 for the treatment of a PRAME-positive disease.

105. Use of the CAR of any one of embodiments 79-97 for the treatment of a PRAME-positive disease.

106. Use of the bispecific antibody of any one of embodiments 62-64 for the treatment of a PRAME-positive disease.

107. The use of any one of embodiments 104-106, wherein the PRAME-positive disease is selected from the group consisting of breast cancer, ovarian cancer, melanoma, lung cancer, gastrointestinal cancer, brain tumor, head and neck cancer, renal cancer, myeloma, neuroblastoma, mantle cell lymphoma, chronic myelocytic leukemia, multiple myeloma, acute lymphoblastic leukemia (ALL), acute myeloid/myelogenous leukemia (AML), Non-Hodgkin lymphoma (NHL), and Chronic lymphocytic leukemia (CLL).

108. The antibody or antigen-binding portion thereof of any one of embodiments 1-57 for use in treating a PRAME-positive disease in a subject.

109. The antibody or antigen-binding portion thereof of embodiment 108, wherein the PRAME-positive disease is selected from the group consisting of breast cancer, ovarian cancer, melanoma, lung cancer, gastrointestinal cancer, brain tumor, head and neck cancer, renal cancer, myeloma, neuroblastoma, mantle cell lymphoma, chronic myelocytic leukemia, multiple myeloma, acute lymphoblastic leukemia (ALL), acute myeloid/myelogenous leukemia (AML), Non-Hodgkin lymphoma (NHL), and Chronic lymphocytic leukemia (CLL).

110. The CAR of any one of embodiments 79-97 for use in treating a PRAME-positive disease in a subject.

111. The CAR of embodiment 110, wherein the PRAME-positive disease is selected from the group consisting of breast cancer, ovarian cancer, melanoma, lung cancer, gastrointestinal cancer, brain tumor, head and neck cancer, renal cancer, myeloma, neuroblastoma, mantle cell lymphoma, chronic myelocytic leukemia, multiple myeloma, acute lymphoblastic leukemia (ALL), acute myeloid/myelogenous leukemia (AML), Non-Hodgkin lymphoma (NHL), and Chronic lymphocytic leukemia (CLL).

112. The bispecific antibody of any one of embodiments 62-64 for use in treating a PRAME-positive disease in a subject.

113. The bispecific antibody of embodiment 112, wherein the PRAME-positive disease is selected from the group consisting of breast cancer, ovarian cancer, melanoma, lung cancer, gastrointestinal cancer, brain tumor, head and neck cancer, renal cancer, myeloma, neuroblastoma, mantle cell lymphoma, chronic myelocytic leukemia, multiple myeloma, acute lymphoblastic leukemia (ALL), acute myeloid/myelogenous leukemia (AML), Non-Hodgkin lymphoma (NHL), and Chronic lymphocytic leukemia (CLL).

114. A kit for treating a PRAME-positive disease, comprising the antibody or antigen-binding portion thereof of any one of embodiments 1-57.

115. A kit for treating a PRAME-positive disease, comprising the CAR of any one of embodiments 79-97.

116. A kit for treating a PRAME-positive disease, comprising the bispecific antibody of any one of embodiments 62-64.

117. The kit of any one of embodiments 114-116, wherein the kit further comprises written instructions for using the antibody or antigen-binding portion thereof, the CAR, or the bispecific antibody for treating a subject having a PRAME-positive disease.

118. The kit of any one of embodiments 114-117, wherein the PRAME-positive disease is selected from the group consisting of breast cancer, ovarian cancer, melanoma, lung cancer, gastrointestinal cancer, brain tumor, head and neck cancer, renal cancer, myeloma, neuroblastoma, mantle cell lymphoma, chronic myelocytic leukemia, multiple myeloma, acute lymphoblastic leukemia (ALL), acute myeloid/myelogenous leukemia (AML), Non-Hodgkin lymphoma (NHL), and Chronic lymphocytic leukemia (CLL).

EXAMPLES

The following examples are put forth so as to provide those of ordinary skill in the art with a complete disclosure and description of how to make and use the antibodies, bispecific antibodies, compositions comprising thereof, screening, and therapeutic methods of the presently disclosed subject matter, and are not intended to limit the scope of what the inventors regard as their presently disclosed subject matter. It is understood that various other embodiments may be practiced, given the general description provided above.

Example 1

Selection of ScFv Specific for PRAME Peptide/A2 Complex Using a Fully Human Phage Display Library Phage display against HLA-A*0201/PRAME peptide complex was performed for 3-4 panning rounds to enrich the scFv phage clones binding to HLA-A*0201/PRAME peptide complex specifically. Two PRAME peptides ($PRA^{300-309}$ and $PRA^{435-443}$) were used as they are restricted to expression in HLA-A*0201$^+$ tumor cells including, but not limited to, AML, ALL, CML, melanoma, breast and colon cancers, among others, and presented on the cell surface in sufficient quantities to reliably elicit a T cell-based cytolytic response against a native cancer cells. Individual scFv phage clones positive for the PRAME peptide/A2 complex were determined by ELISA and the clones that possessed unique DNA coding sequences were subjected to further characterization. To test if the ScFv bound to the PRAME p/A2 complex on live cells, the positive phage clones were tested for binding to a TAP deficient, HLA-A*0201-positive cell line, T2. T2 cells can only present the exogenous peptides and therefore have been widely used for detection of specific epitopes presented by HLA-A2 molecules. A total of 25 phage clones were screened on T2 cells and 4 clones showed good specific binding to T2 cells pulsed with only PRAME P300 peptide, a total of 34 phage clones were screened on T2 cells and 3 clones showed good specific binding to T2 cells pulsed with only PRAME P435 peptide, but not to T2 cells alone or pulsed with control RHAMM-3 peptide.

Example 2

Generation of Full-Length Human IgG1

Immunological function such as CDC and ADCC depend on the Fc domain of bivalent IgG. In addition, bivalent mAbs offer stronger antigen-binding avidity than monomeric scFv Abs. Therefore, 7 ScFv phage clones among 59 positive phage clones were selected to produce the full-length human monoclonal IgG1 in HEK293 and Chinese hamster ovary (CHO) cells. In brief, variable regions of the mAbs were sub-cloned into mammalian expression vectors with matching human lambda or kappa light chain constant region and human IgG1 constant region sequences. Purified full length IgG antibodies showed expected molecular weight under both reducing and non-reducing conditions. Seven clones were successfully engineered into human IgG1.

Example 3

PRAME Antibody Binding of Cancer Cells

The binding specificity of Pr300-#20 (also referred to "Pr#20"; comprising the heavy and light chain variable region sequences of EXT009-20 scFv) to PRAME+/HLA-A*02$^+$ cancer cells was tested. HLA-A2$^+$ AML cell lines AML-14 and SET-20, Ph$^{t+}$ ALL cell line BV173, and myeloma cell line U266 were stained with Pr#20 mAb conjugated to APC or an isotype control at 3 μg/ml and the binding was determined by flow cytometry. HLA-A2 negative cell line HL-60 was used as a negative control and no binding was detected, as shown in FIG. 1A. Therefore, Pr300#20 specifically bound to PRAME+/HLA-A*02$^+$ cancer cells. Other antibodies, e.g., Pr435#12 (comprising the heavy and light chain variable region sequences of EXT010-12) and Pr435#37 (comprising the heavy and light chain variable region sequences of EXT010-37) antibodies, also bound to multiple cancer cells, e.g., U266, and BV173 (data not shown).

Figure 1B:
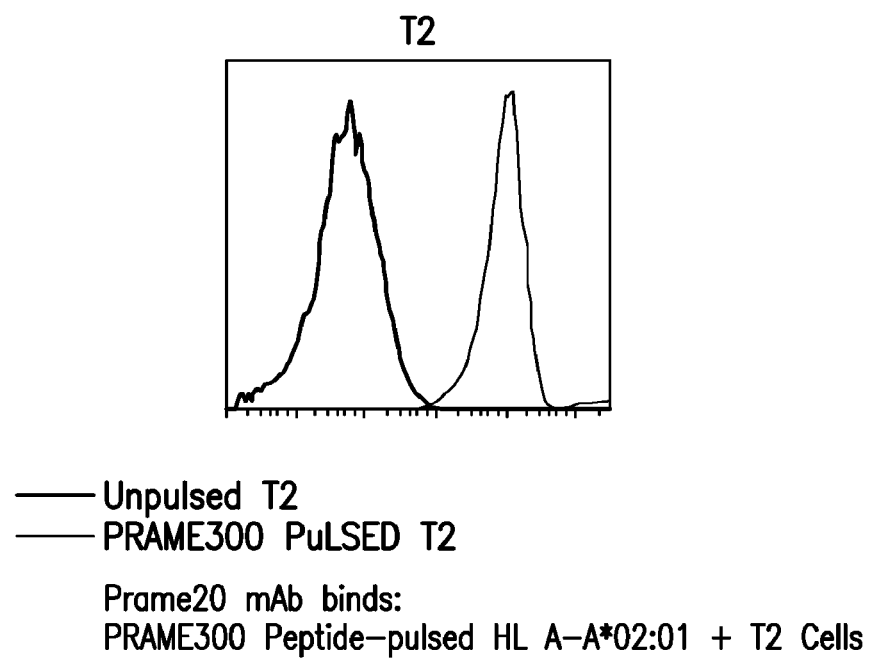
Figure 1C:
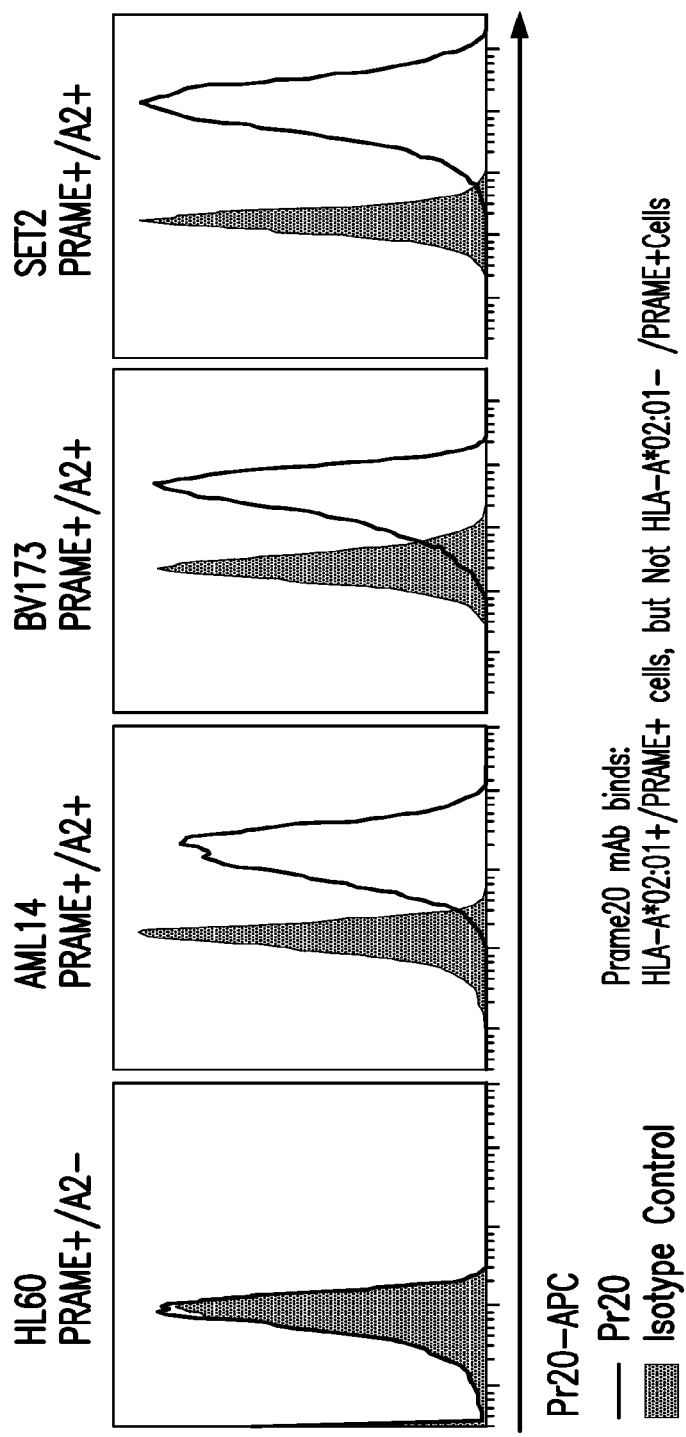

TAP-deficient T2 cells were pulsed overnight with 50 μg/mL PRAME300 peptide in serum-free media with 20 ug/mL B-2 microglobulin, as shown in FIG. 1B. Pr300#20 binding was measured using flow cytometry on unpulsed and pulsed T2 cells. Pr300#20 bound to PRAME$^+$/HLA-A*0201$^+$ leukemias AML14, BV173, and SET2 but not the PRAME+/HLA-A*0201$^-$ leukemia HL60, as shown in FIG. 1C.

Figure 1D:
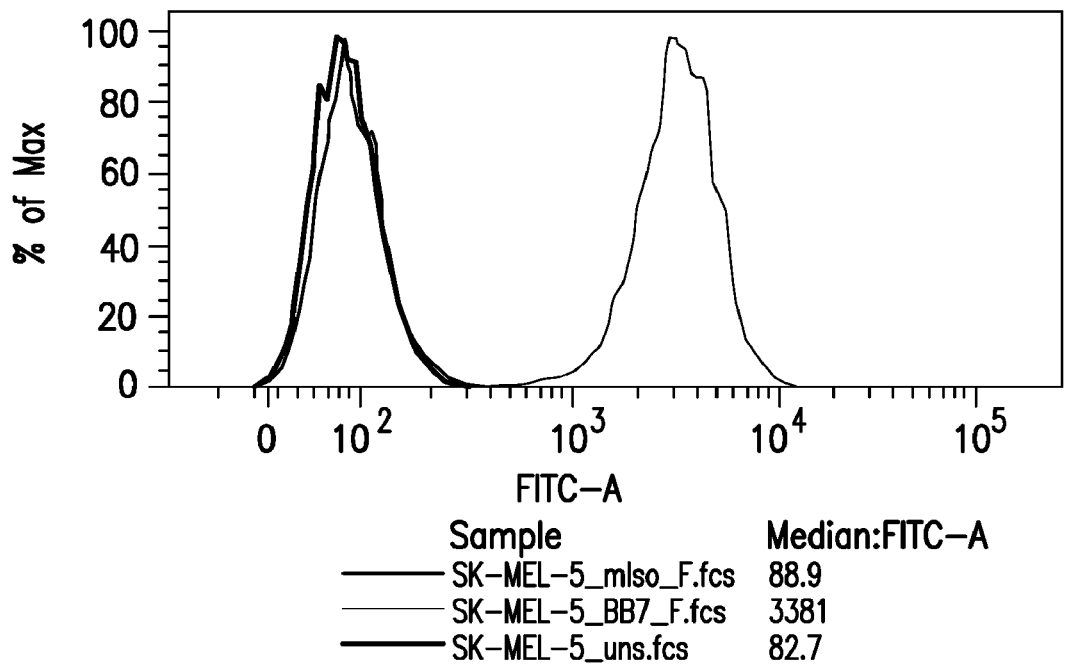
Figure 1D:
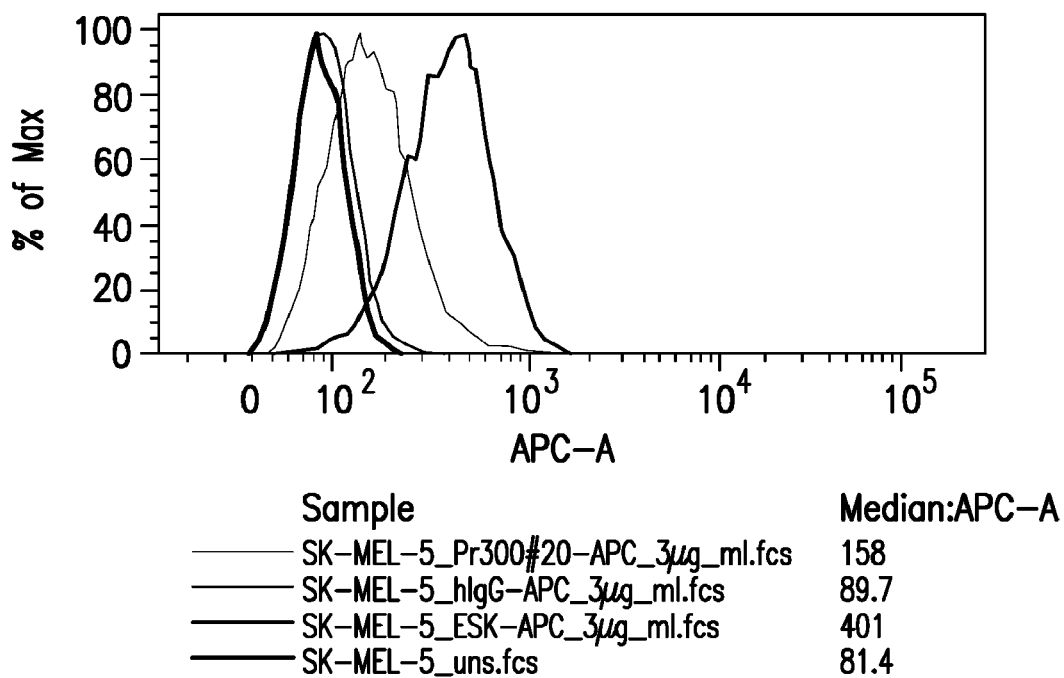

Binding of Pr300#20 to a HLA-A2+ melanoma cell line, SK-MEL-5 was determined by direct staining of the cells with the APC-conjugated mAb at 3 μg/ml (FIG. 1D, lower panel). The HLA-A2 expression was determined in parallel (FIG. 1D, upper panel). A TCR-like mAb specific for the PRAME/HLA-A2, ESK1, was used as a positive control.

Example 4

Engineering Antibodies to Enhance Their Cotytoxic Abilities

Figure 2:
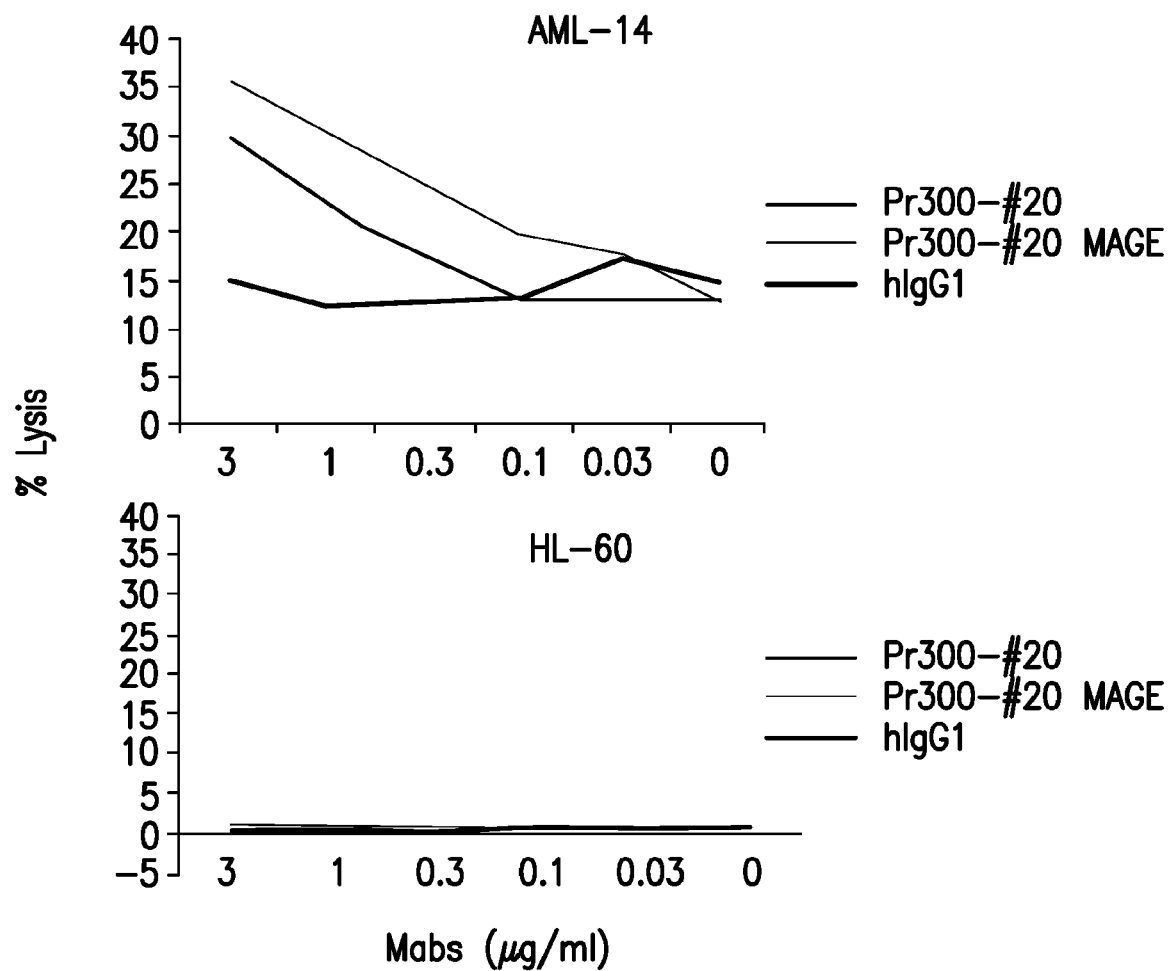
FIG. 2 represents ADCC activity of Pr300#20 and Pr300#20-Fc.

A modified afucosylated Fc functionality was added for one format to improve potency and a second format as a BiTE with an ScFv cross-reactive to CD3 was made, which displayed more potency. PRAME+ HLA-A2+ cell line AML-14 or control cell line HL-60 were incubated with PBMCs at an E:T ratio 50:1, in the presence or absence of serially diluted Pr#20, Pr#20-Fc enhanced (also referred to as "Pr300-#20-MAGE" or "Pr20M") or isotype control for 5 hours and the killing of the target cells was measured by 51Cr release. As shown in FIG. 2, Pr300#20-MAGE enhanced ADCC activity.

An early critical aspect in the development of therapeutic mAb targeting PRAME/HLA-A*0201 hinges on the relative expression density of the unique neo-epitope on the surface of cancer cells. It is determined which format is capable of killing cancer targets with such low densities, selectively in vitro and in vivo.

To test the in vitro anti-tumor activity of the PRAME-BiTE against human cancer cells. The dual binding of PRAME-BiTE to a panel of human cancer cells and T cells was first evaluated. PRAME-BiTEs were engineered using a scFv of the PRAME mAb at the N-terminal end and an anti-human CDR scFv of a mouse monoclonal antibody at the C-terminal end, with His-tag. The binding of the PRAME-BiTE to the tumor cell lines (and of the other arm to purified human CD3+ T cells, as well as human T cell line such as Jurkat,) was tested by flow cytometry. PRAME+/A02+ BV173, AML-14 versus HLA-A2 negative B lymphoma cell line Ramos or Jurkat T cells were stained with Pr#20-BiTE or control BiTE at concentrations of 10 or 1 µg/ml, followed by secondary mAb specific for His tag conjugated to FITC. As expected, Jurkat T cells bound both control and specific BiTE via the second arm.

Figure 3A:
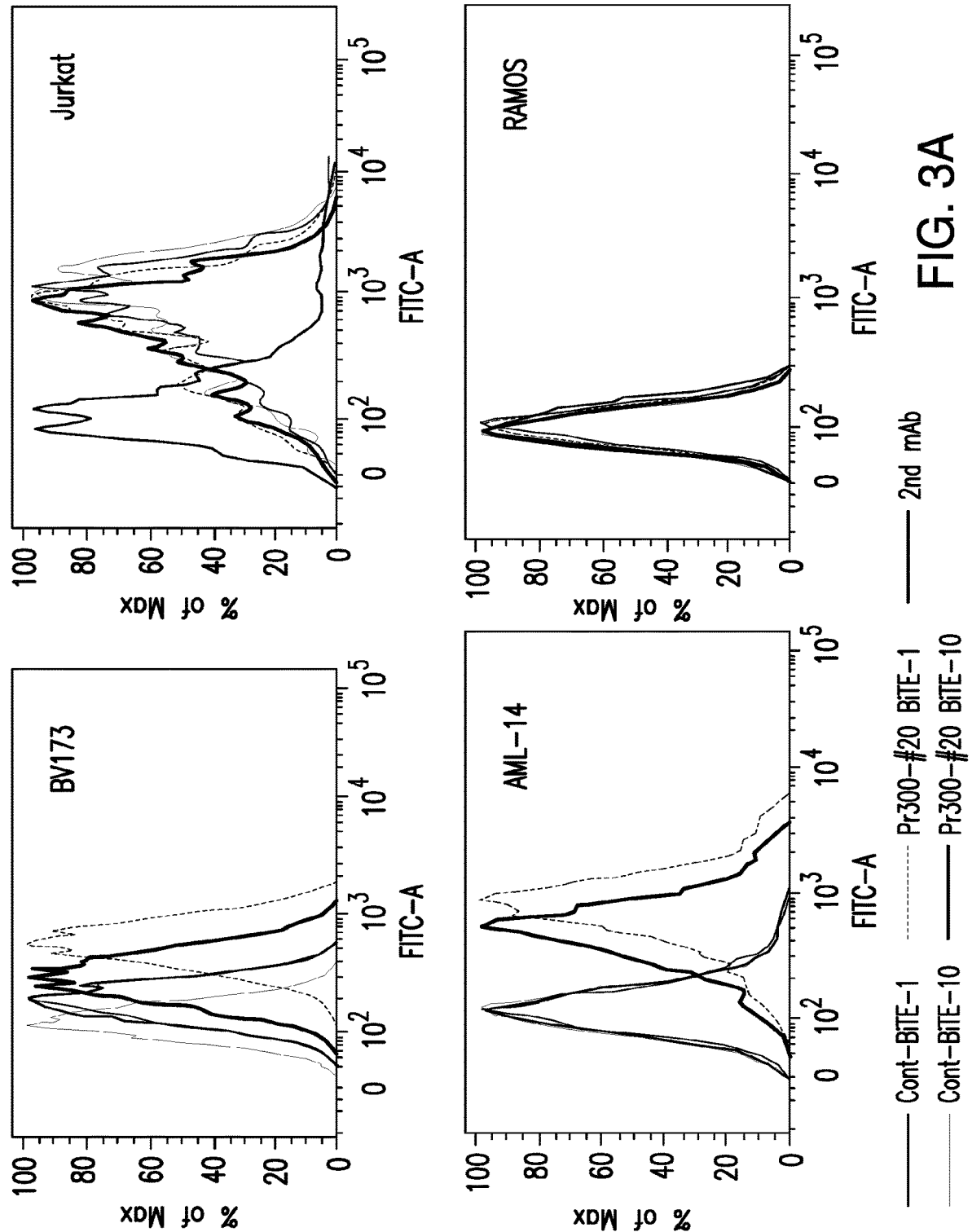
FIGS. 3A and 3B represent dual binding of Pr300#20-BiTE to tumor cells. (A) Binding of Pr300#20-BiTE to PRAME+/A02+ BV173, AML-14 and HLA-A2 negative B lymphoma cell line Ramos and Jurkat T cells. (B) Secondary mAb specific for His tag conjugated to FITC.
Figure 3B:
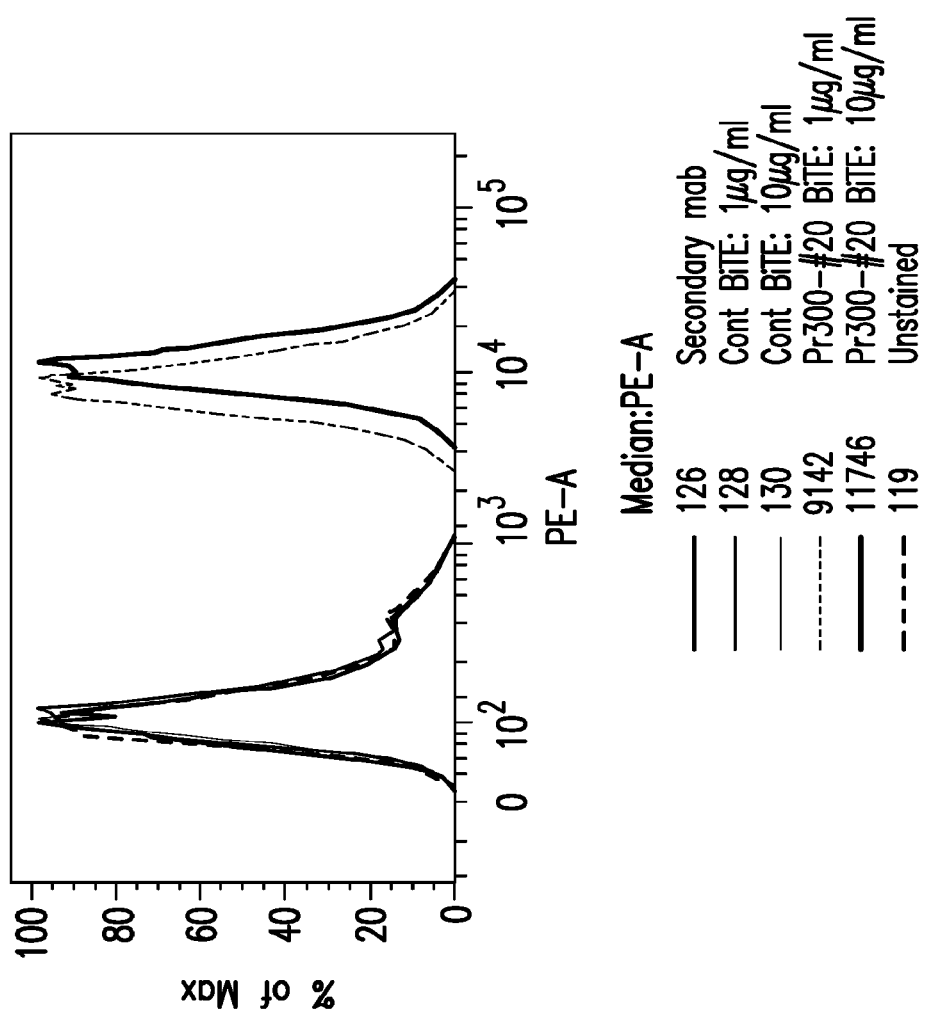

Further, the binding of the Pr300#20-BiTE against a primary ovarian cancer cells, derived from a HLA-A2+ patient was assessed. Cells were stained with Pr300#20-BiTE or control BiTE at 10 and 1 µg/ml for 30 minutes on ice, washed, and was followed by the staining with secondary mouse mAb against His-tag. As shown in FIGS. 3A and 3B, dual binding of the Pr300#20-BiTE to tumor cells and human T cells was detected.

Example 5

ADCC Activity of PRAME Antibody

Figure 4:
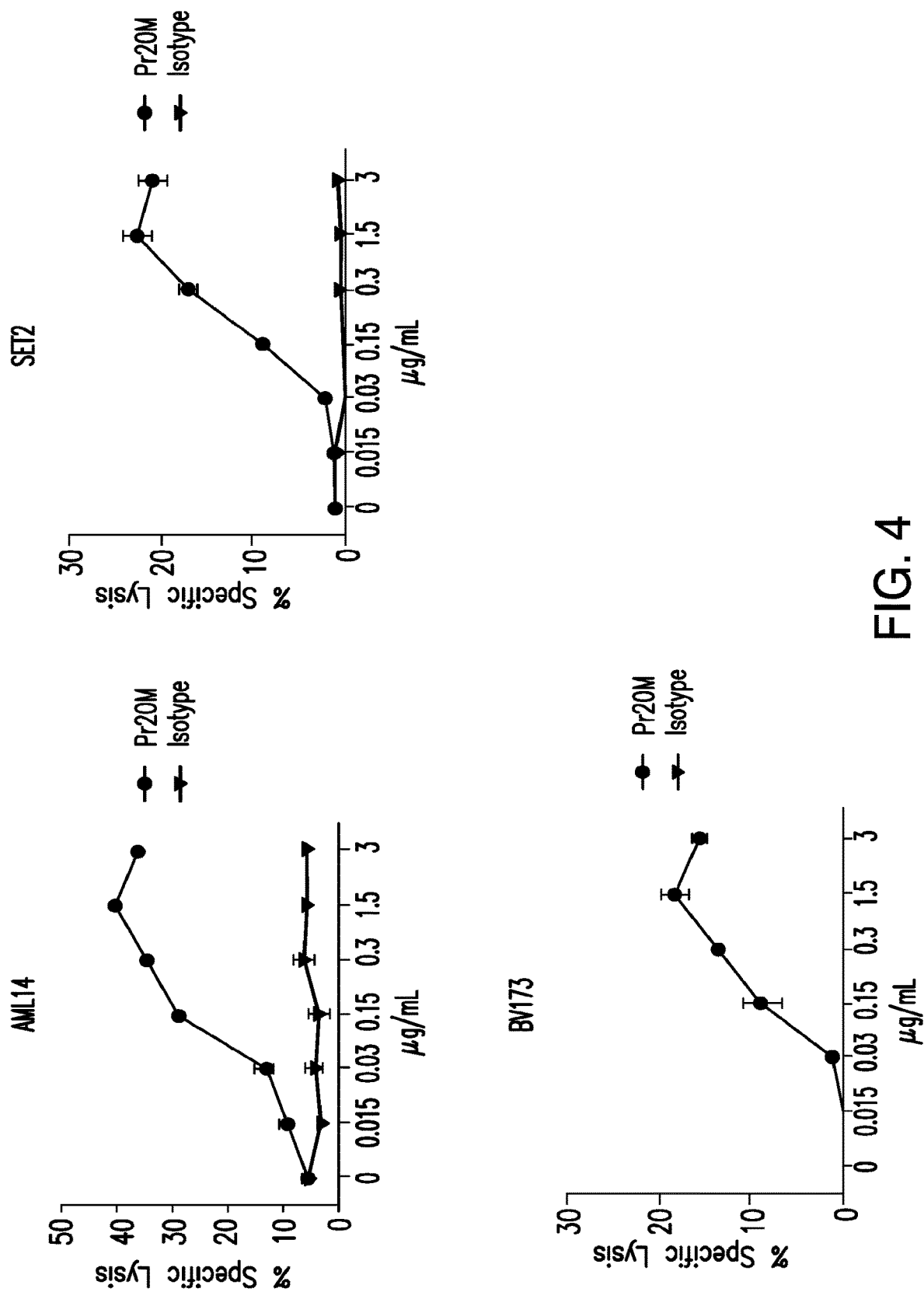
FIG. 4 represents ADCC activity of Pr300#20-MAGE.

Target PRAME+/HLA-A*0201+ cells were labeled by incubating for 1 hour at 37° C. with 100 uCi of $^{51}$Cr per $10 \times 10^5$ cells. Cells were washed and incubated at 37° C. for 6 hours with the indicated concentration of Pr300#20-MAGE (also referred to as "Pr20M") or isotype control and whole healthy human PBMC effectors. An effector:target ratio of 50:1 was used for all conditions. Percent specific lysis was determined from supernatant using the standard $^{51}$Cr release assay formula: [(experimental−spontaneous release)/(maximum load−spontaneous release)× 100]. As shown in FIG. 4, Pr300#20-MAGE mediated killing via ADCC with human PBMC in-vitro against three human PRAME+/HLA-A*02:01+ Leukemias: AML-14 and SET-2, which are AML; and BV173, which is Ph+ ALL. The EC50 was 2-3 nM; and $K_D$ was 3-4 nM.

Example 6

Figure 5A:
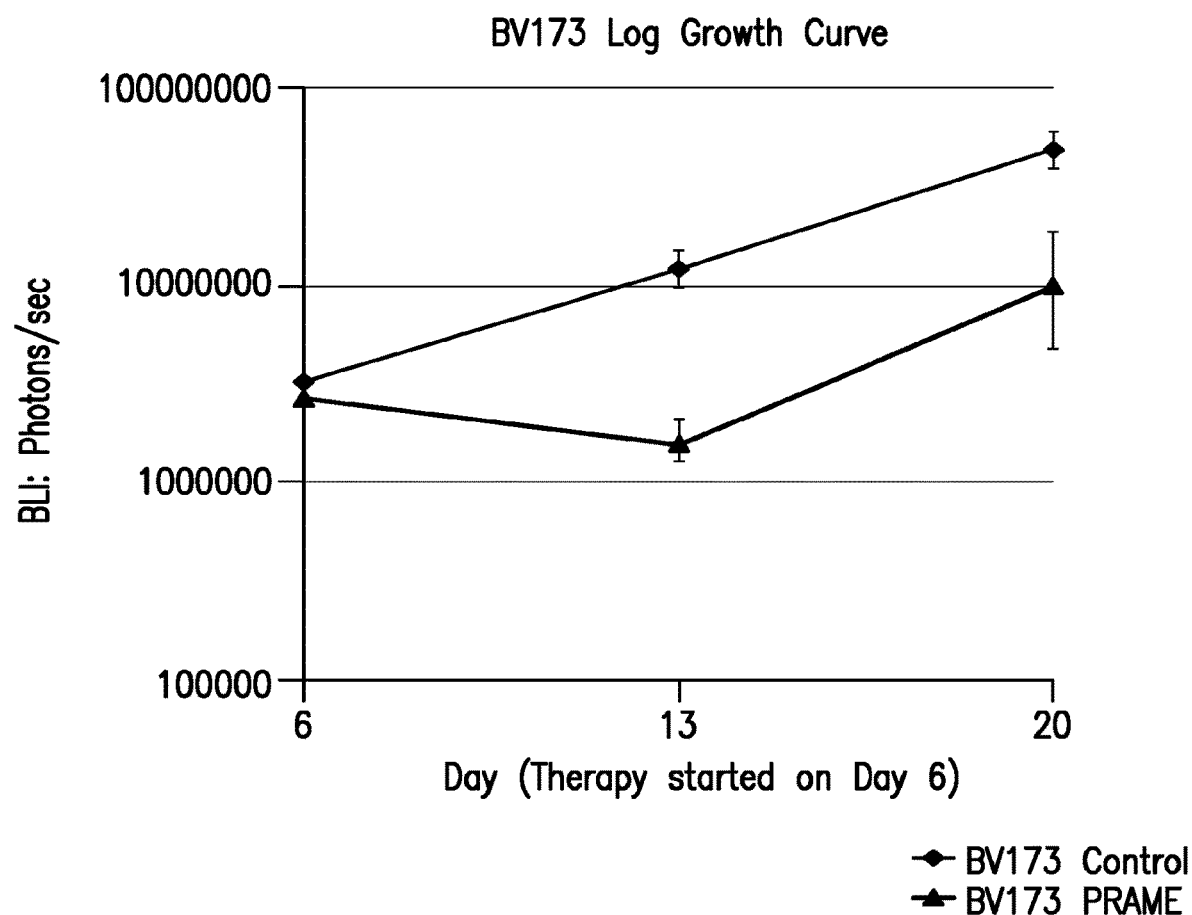
FIGS. 5A-5D represent in vivo anti-tumor activity of Pr300#20-MAGE. (A) BV173 log growth curve. (B) BV173 PRAME Images. (C) SET2 log growth curve. (D) SET2 PRAME images.
Figure 5B:
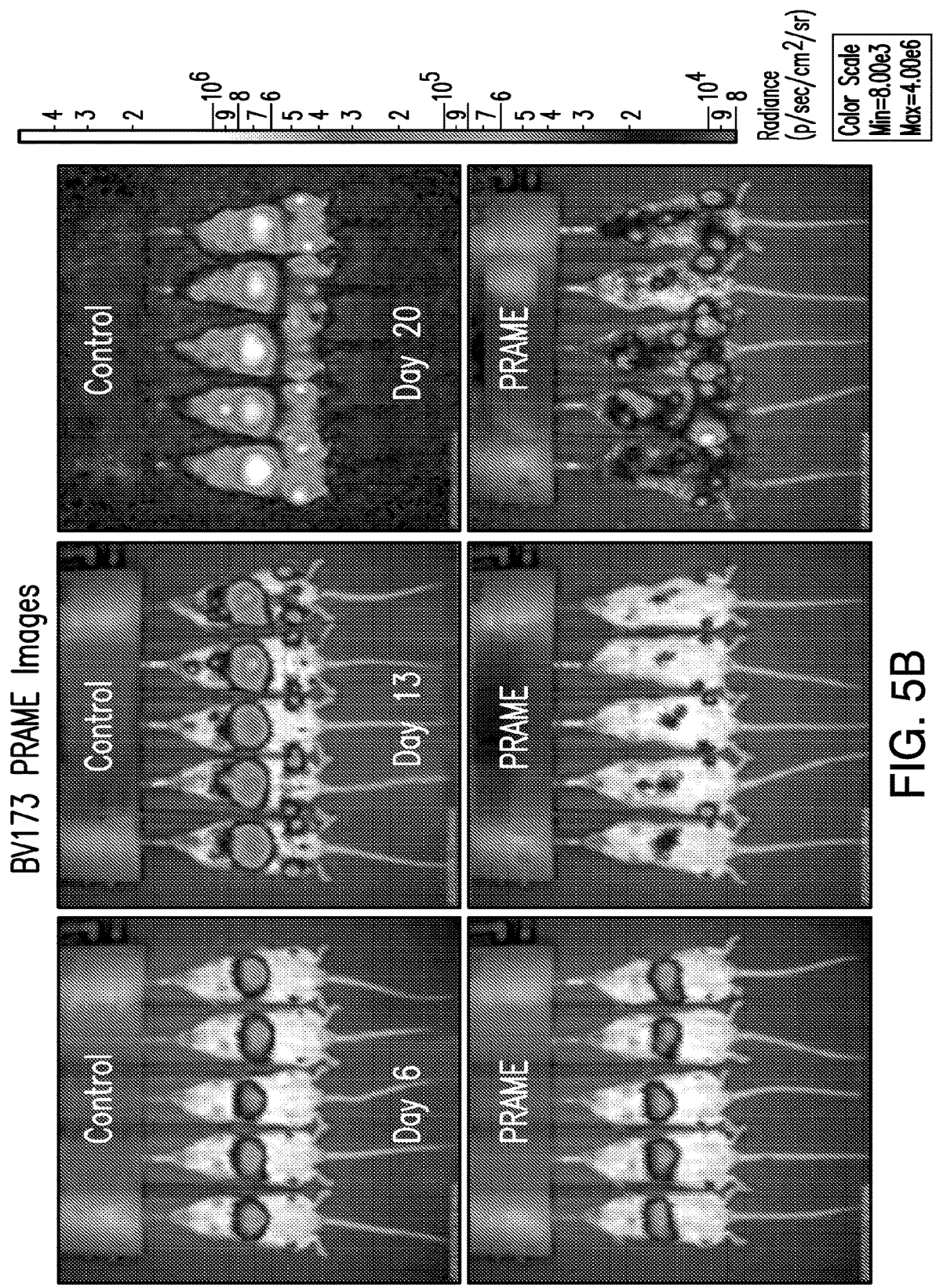
Figure 5C:
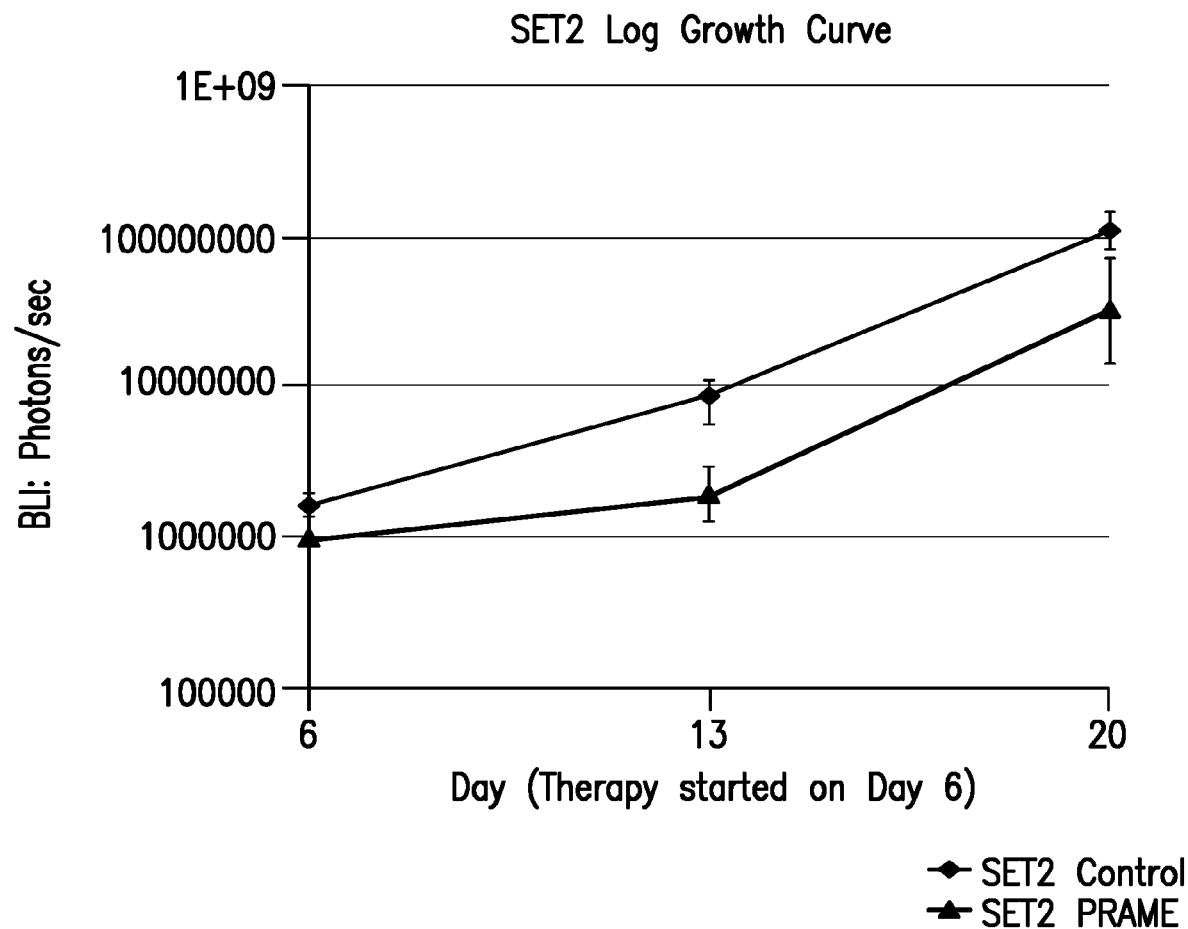
Figure 5D:
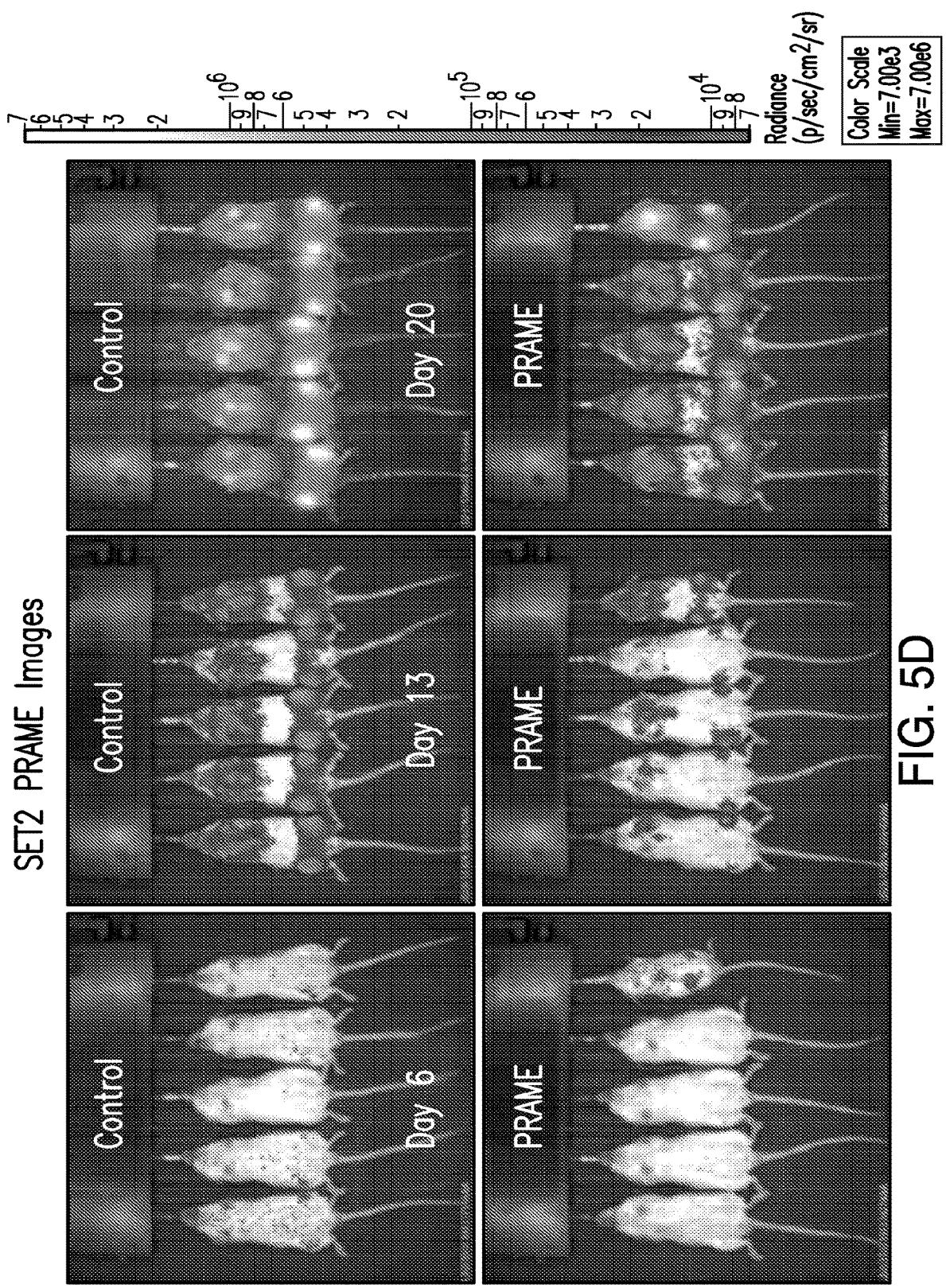

In Vivo Anti-Tumor Activity of PRAME Fc Enhanced mAb in Mouse Model of Human PRAME Cancer Cells NSG mice were injected intravenously with BV173 Ph+ human ALL (FIGS. 5A and 5B) or SET2 human AML (FIGS. 5C and 5C). Both leukemias' total burden in the mice were traced and quantitated with bioluminescence imaging (BLI) using luciferase in the cells. Mice were imaged on day 6 to confirm that all mice had engrafted the human cancers. Beginning on day 6, mice were treated with 50 micrograms of Pr300#20-MAGE twice weekly or control (no antibody) for 2 weeks. Quantitation of the growth by BLI is shown in FIGS. 5A and 5C. The raw images of the BLI are shown in FIGS. 5B and 5D. In both models, tumor growth was reduced by 56-8 fold by Pr300#20-MAGE antibody.

Example 7

PR#20 Binds to C-Terminal of $PRA^{300-309}$/MHC Complex

Peptides were synthesized to replace each non-anchor residue with alanine, as shown in FIG. 6A. Peptides were pulsed onto T2 cells overnight at 50 µg/mL in serum-free media with 20 µg/mL B-2 microglobulin. Pr#20 binding as well as peptide/HLA-A*02 stability, as measured by surface HLA-A*02 levels after pulsing, was quantified using flow cytometry. Alanine scan results are shown in FIGS. 6B-6D. Pr#20 mAb binding to T2 pulsed cells with peptides modified at positions is shown in x axis. "300" is native sequence positive control, as shown in FIG. 6A. Prame sequences used. As shown in FIG. 6B, reduced binding was seen after amino acids at positions 304-308 were changed. As shown in FIGS. 6C and 6D, changes at positions 304 and 305 reduced HLA-A02 binding. Positions 306-308 remained lower. Thus, Pr#20 mAb binds at the C-terminal end of $PRA^{300-309}$/MHC complex.

Figure 6E:
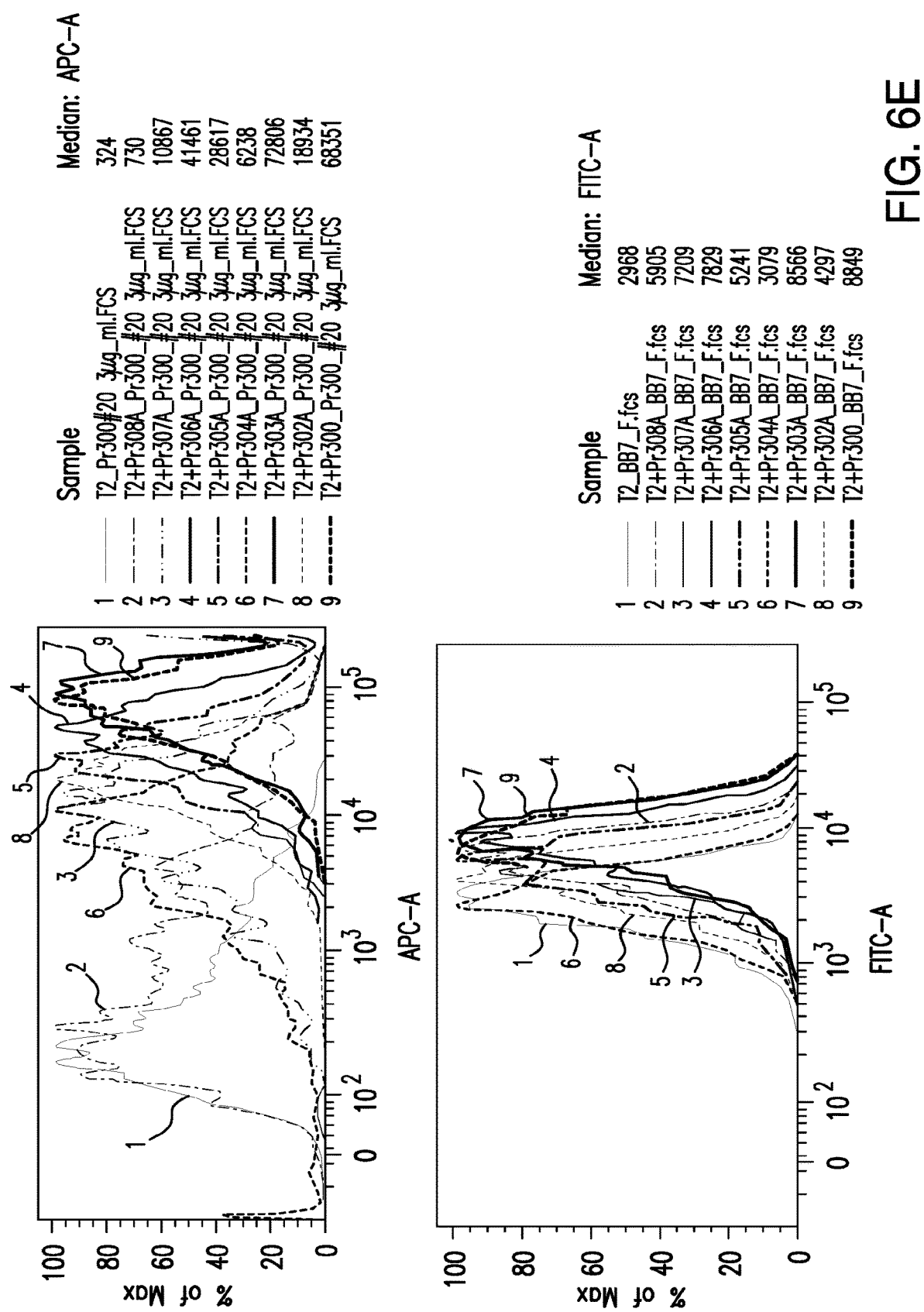
Figure 6F:
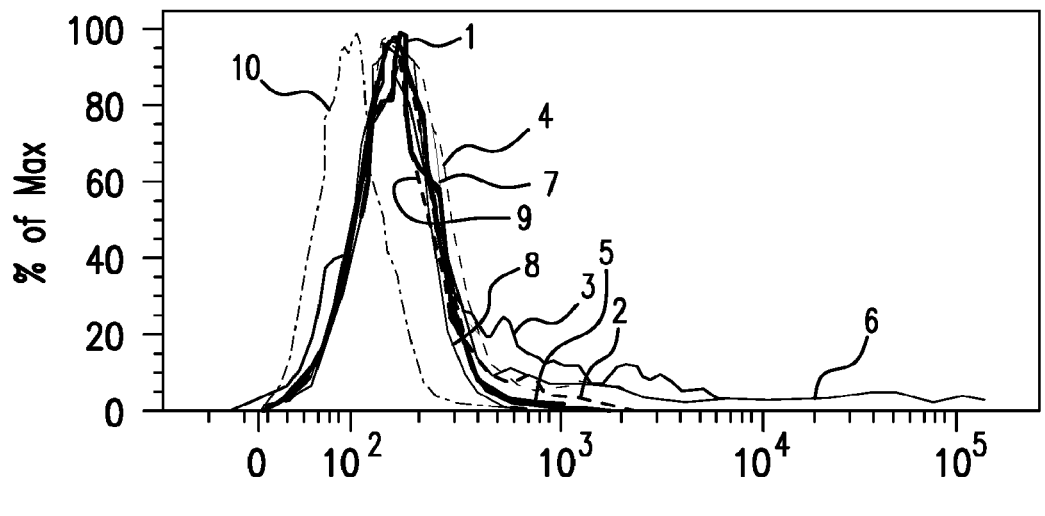

FIGS. 6E and 6F also show the binding of the Pr300#20 to T2 cells pulsed with Pr 300 or Pr 300 substituted with alanine. Pr#20 conjugated to APC did not bind to T2 cells alone (median fluorescence intensity MFI: 324), but bound strongly to the Pr300 peptide (MFI: 68351). Binding was not affected by the alanine substitution at position 4 (pr 303A peptide), but was partially reduced in the order of Pr306A, 305A, 302A, 307A, 304A and 308A (upper panel). To test if the HLA-A2 expression was correlated with the reduced binding of the Pr300 alanine peptides, anti-HLA-A2 mAb clone BB7 was used to stain the cells in parallel. HLA-A2 expression was significantly increased by pulsing with the pr300 peptide, compared with binding to T2 cells alone, as shown by MFI increasing from 2986 to 8849 (lower panel). The binding of the isotype control human IgG (hIgG) was negative for all the peptides tested as shown in FIG. 6F.

Example 8

Binding Position of PRAME Antibodies

Figure 7:
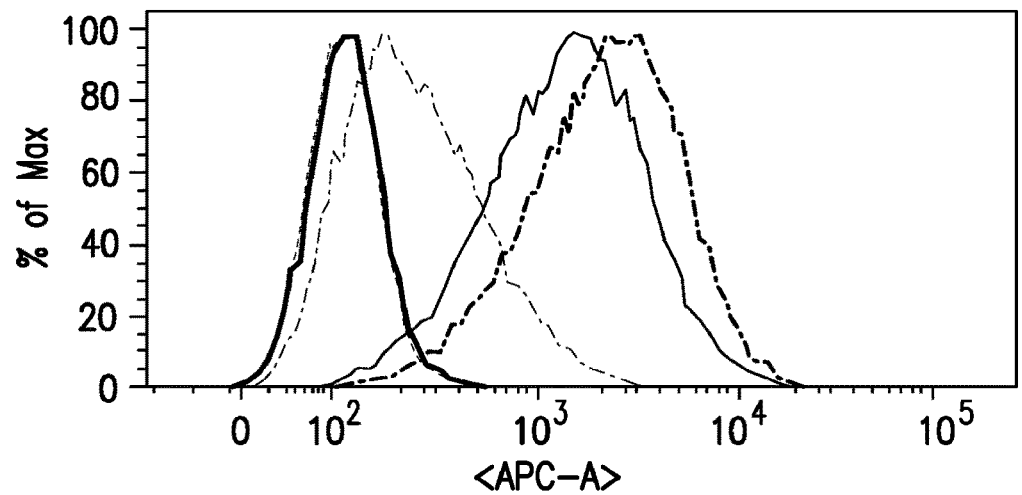
FIG. 7 represents binding specificity of the Pr300#20 and Pr300#29.
Figure 7:
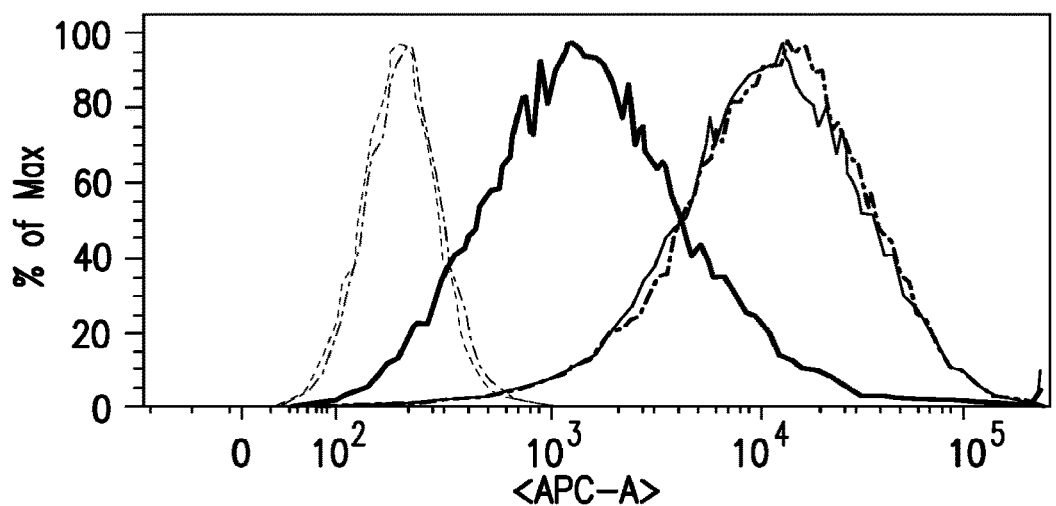
Figure 8:
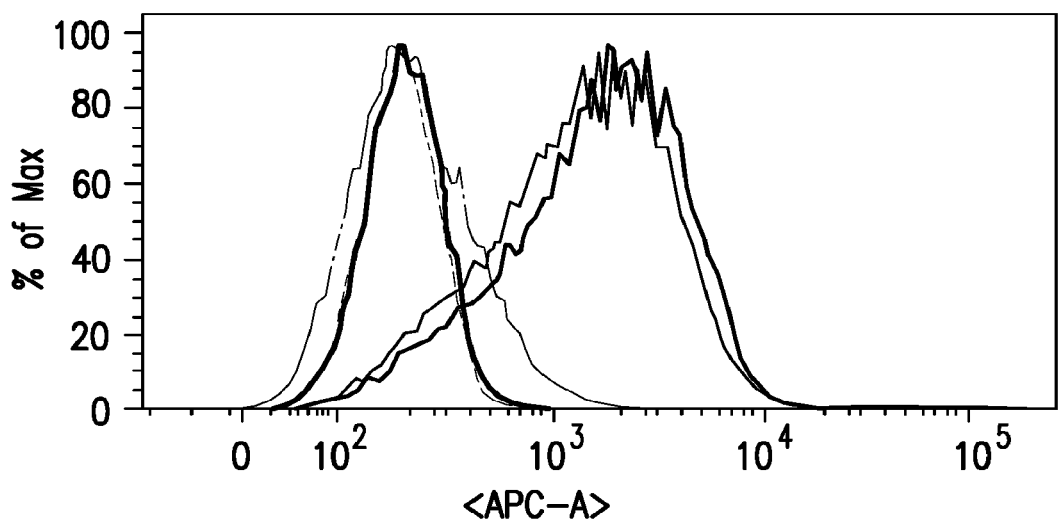
FIG. 8 represents binding specificity of the Pr300#20 and Pr300#29.
Figure 8:
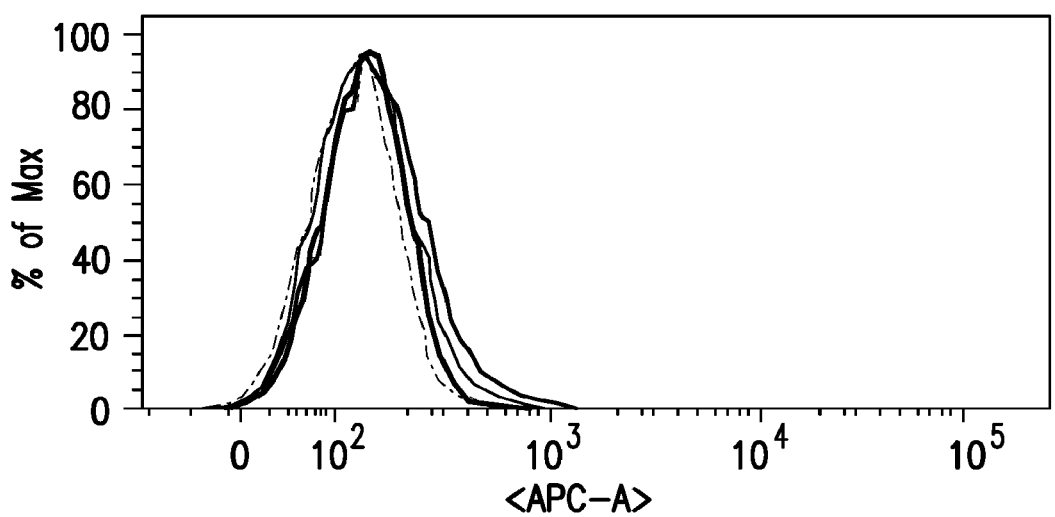

The binding specificity of the Pr300#20 mAb and Pr300#29 mAb (comprising the heavy and light chain variable region sequences of EXT009-29) was further determined by cold mAb blocking. Fifty-fold excessive amount cold mAbs Pr300#20 or Pr300#29 was added to the AML-14, SET-2, BV173 (all are positive for Pr300#20 mAb binding) or HL-60 cells (negative control cells) for 20 minutes on ice, and then the APC-conjugated Pr300#20mAb at 3 µg/ml was used to stain the cells. Interestingly, the Pr300#20 mAb binding was significantly (AML-14 FIG. 7 upper and SET-2 FIG. 7 lower) or almost completely (BV173; FIG. 8 upper) blocked by the cold mAb Pr300#20 but not by mAb Pr300#29. These results demonstrated the specificity of the mAb Pr300#20 and also suggested that the mAb Pr300#20 and Pr300#29 may recognize different positions of the PRA$^{300\text{-}309}$/HLA-A2 complex.

Figure 9A:
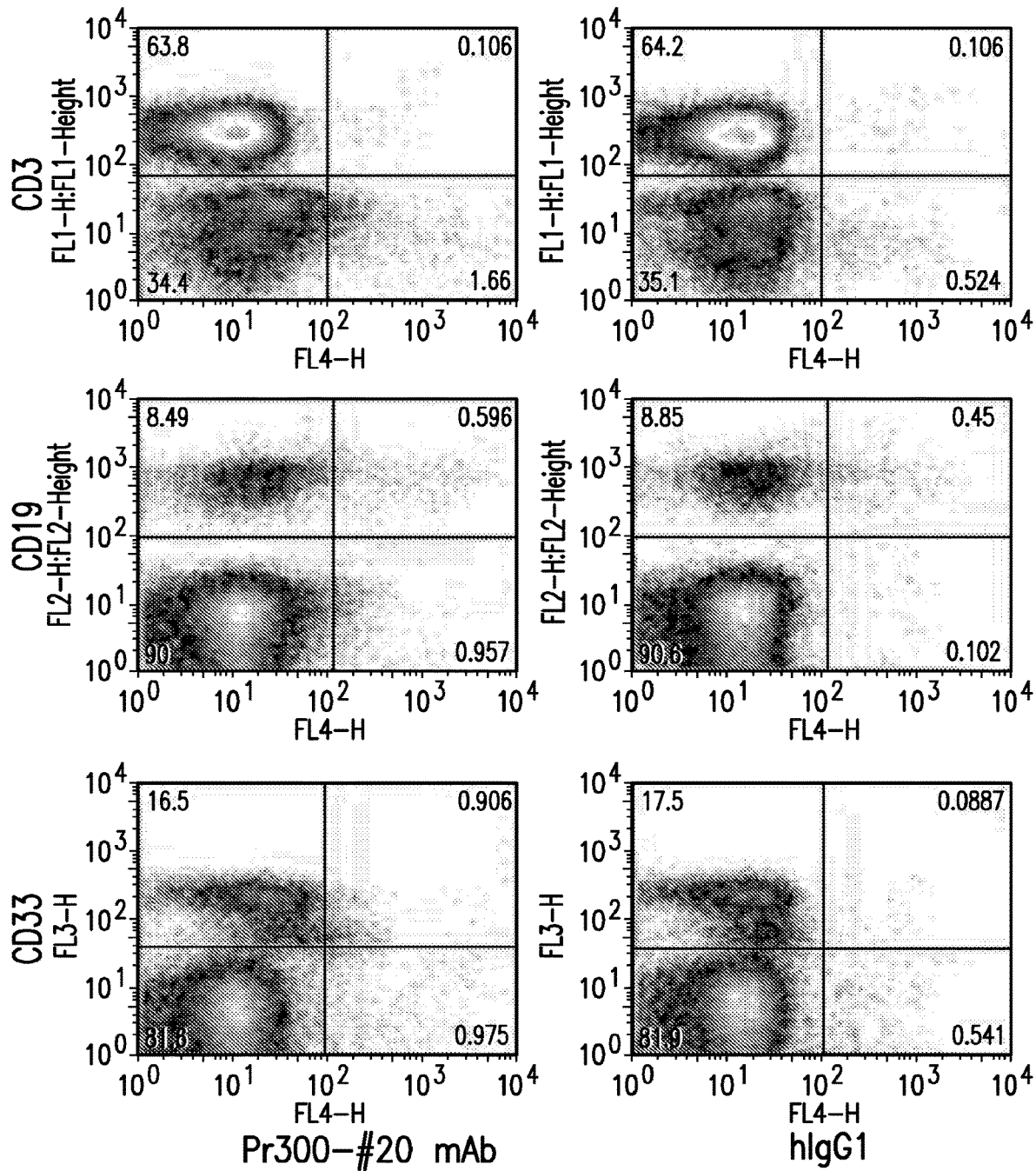
FIGS. 9A-9D represent binding of the Pr300#20 and Pr300#29 to normal PBMCs from multiple donors with various HLA-A haplotypes. (A) Binding of Pr300#20 to CD3−, CD19+ and CD33+ populations on HLA-A02+/A02+ donors. (B) Binding of Pr300#29 to CD3+, CD19+ and CD33+ populations on HLA-A02+/A02+ donors. (C) Binding of Pr300#20 to CD3+, CD19+ and CD33+ populations on HLA-A02−/A02− donors. (D) Binding of Pr300#29 to CD3+, CD19+ and CD33+ populations on HLA-A02−/A02− donors.
Figure 9B:
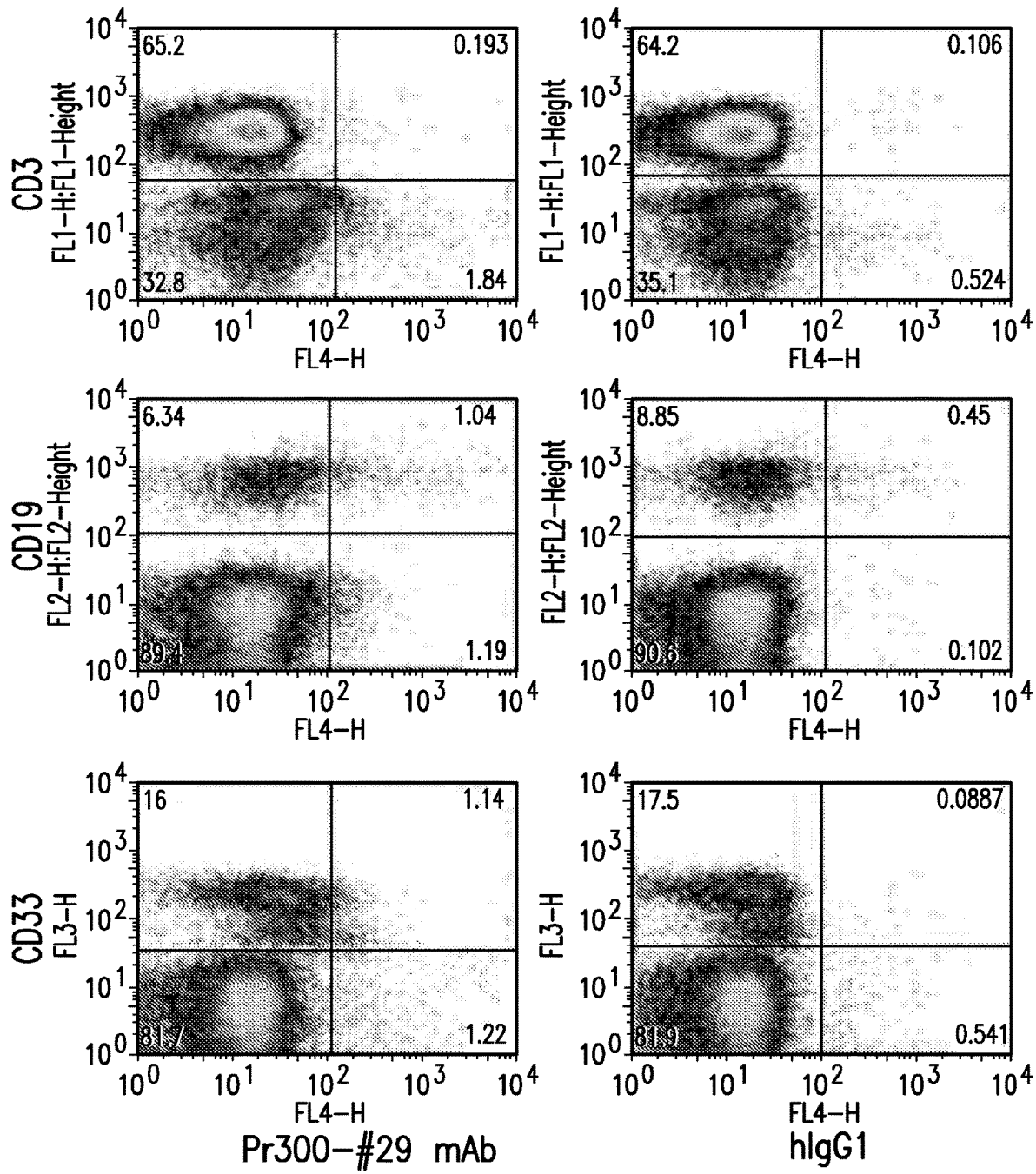
Figure 9C:
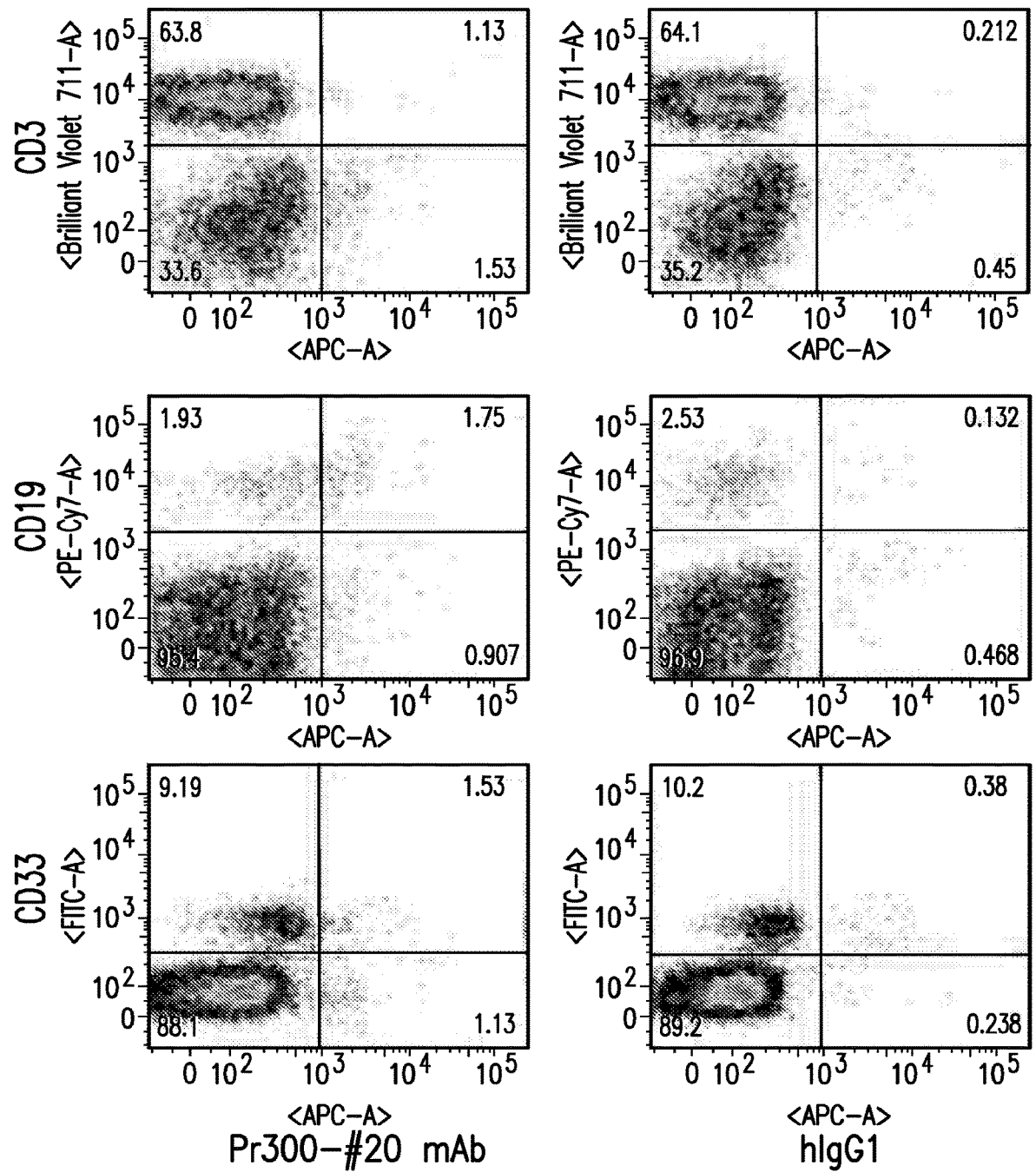
Figure 9D:
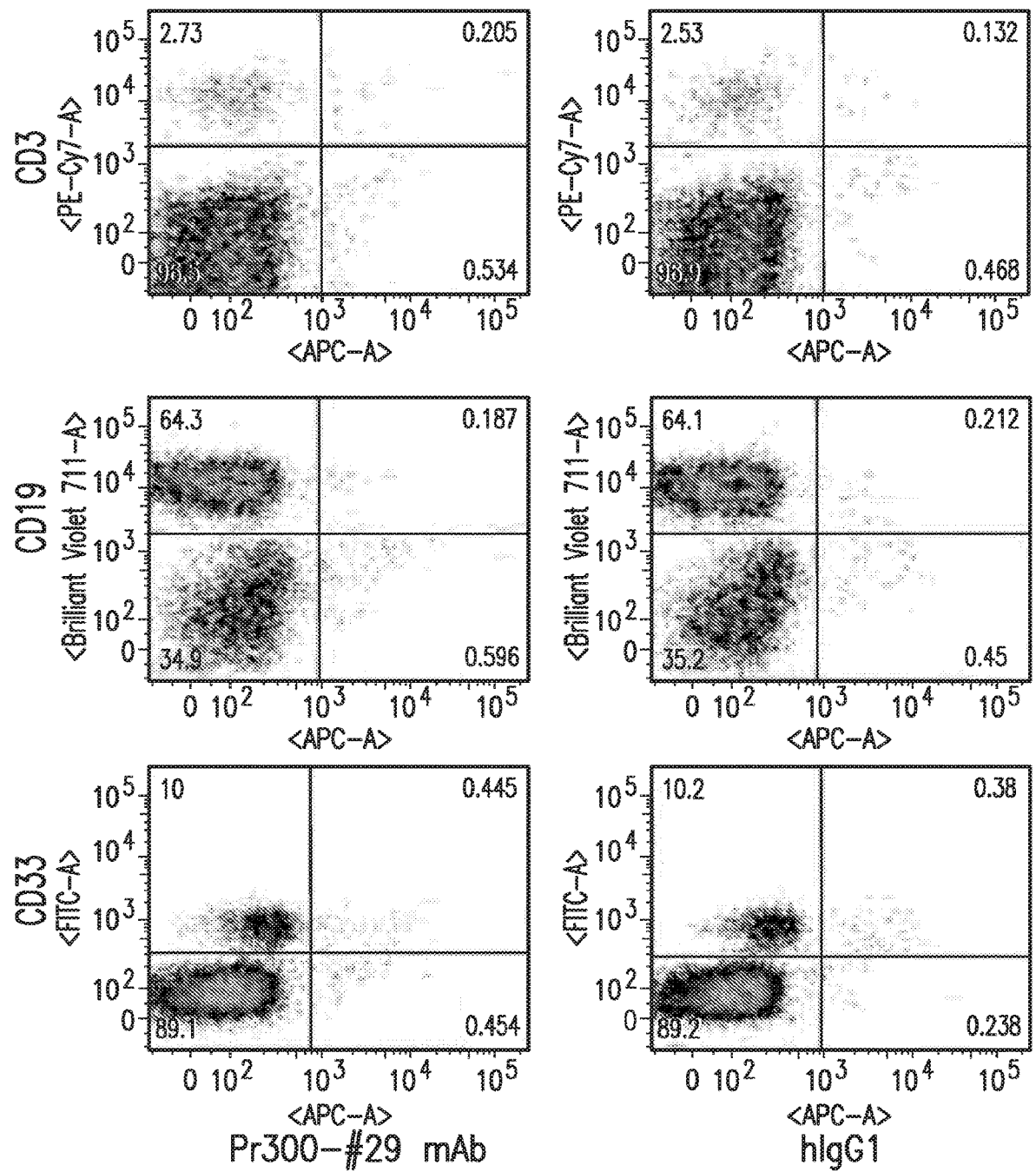

The binding of the Pr300#20 and Pr300#29 mAbs to normal PBMCs was tested on multiple donors with various HLA-A haplotypes. Representative data from HLA-A02$^{+/+}$ homozygous donor are shown in FIGS. 9A and 9B. Fc receptor (FcR) blocking reagent was first used to block a non-specific FcR binding, and followed by staining the PBMCs with APC conjugated Pr300#20 or Pr300#29, or control hIgG1 vs CD3, CD19 or CD33 conjugated with various fluorophores. Compared to the control mAb, no significant binding was seen by mAb Pr300#20 (FIG. 9A) on CD3$^+$, CD19$^+$ or CD33$^+$ populations; there was minimal binding of the CD19$^+$ and CD33$^+$ cells by mAb Pr300#29 in the HLA-A2$^+$ donor (FIG. 9B). Representative data from HLA-A02$^{-/-}$ donor are shown in FIGS. 9C and 9D. There was a minimal binding to the CD19$^+$ population by mAb Pr300#20 in the HLA-A2$^-$ donor (FIG. 9C). No significant binding of mAb Pr300#29 to CD3$^+$, CD19$^+$ or CD33$^+$ populations was seen (FIG. 9D).

Example 9

In Vivo Cytotoxicity of PRAME BiTE and CAR Targeting PRAME/MHC Complex in NSG Xenografts For BiTe therapeutics, in vitro-expanded human EBV-specific T cell effectors are used to avoid possible GVHD in mice. PRAME BiTE or control BiTE is given along with EBV-T cells with E: T ratio ranging from 1:1 to 5:1. The BiTEs are intravenously injected consecutively (iv) and EBV-T cells are intravenously injected into mice twice a week. Tumor growth is monitored by BLI twice a week. Experimental groups include: 1. Xenografted growth control. 2. EBV-specific T cells only control. 3. MPRAME-BiTE and T cells. 4. control-BiTE and T cells. Ten mice in each group. Similar groups are used to test the CAR targeting PRAME/MHC complex.

Example 10

Peptide Epitope Mapping for PRAME Phage Clones

Epitope mapping of four EXT009 antibodies against PRA$^{300\text{-}309}$ in conjunction with HLA-A*0201 (EXT009-8, EXT009-17, EXT009-20 and EXT009-29) was performed to determine the epitope binding. Briefly, mutant EXT009 peptides were generated with alanine substitutions and these were individually pulsed onto the surface of T2 cells. T2 cells were loaded with EXT009, EXT009-mut2 ("009-mut2"), EXT009-mut3 ("009-mut3"), EXT009-mut4 ("009-mut4"), EXT009-mut5 ("009-mut5"), EXT009-mut6 ("009-mut6"), EXT009-mut7 ("009-mut7"), EXT009-mut8 ("009-mut8"), EXT009-mut9 ("009-mut9") as well as EXT009-AAAA ("009-AAAA"), respectively. EXT009-AAAA was used as a control; 009-mut2 was for anchor position. Table 5 shows the sequences of the peptides.

TABLE 5

|  |  | SEQ ID NO |
|---|---|---|
| EXT009: | ALYVDSLFFL | 686 |
| 009-mut2: | A<u>A</u>YVDSLFFL | 687 |
| 009-mut3: | AL<u>A</u>VDSLFFL | 688 |
| 009-mut4: | ALY<u>A</u>DSLFFL | 689 |
| 009-mut5: | ALYV<u>A</u>SLFFL | 690 |
| 009-mut6: | ALYVD<u>A</u>LFFL | 691 |
| 009-mut7: | ALYVDS<u>A</u>FFL | 692 |
| 009-mut8: | ALYVDSL<u>A</u>FL | 693 |
| 009-mut9: | ALYVDSLF<u>A</u>L | 694 |
| 009-mut10: | ALYVDSLFF<u>A</u> | 695 |
| 009-AAAA: | ALY<u>AAAA</u>FFL | 696 |

Figure 10:
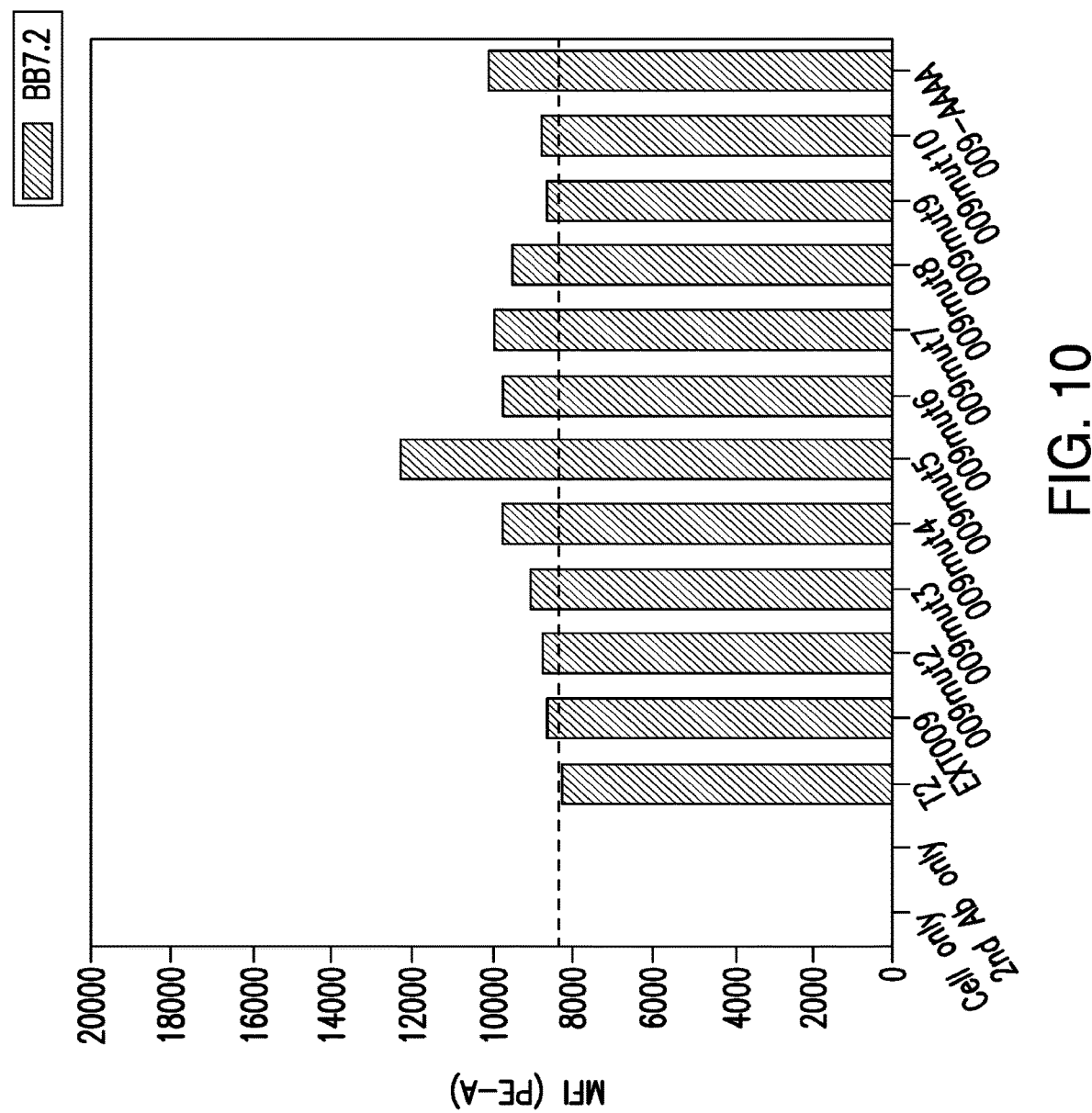
FIG. 10 represents results of T2 peptide loading quality controls (QC) detection by BB7.2 staining.
Figure 11A:
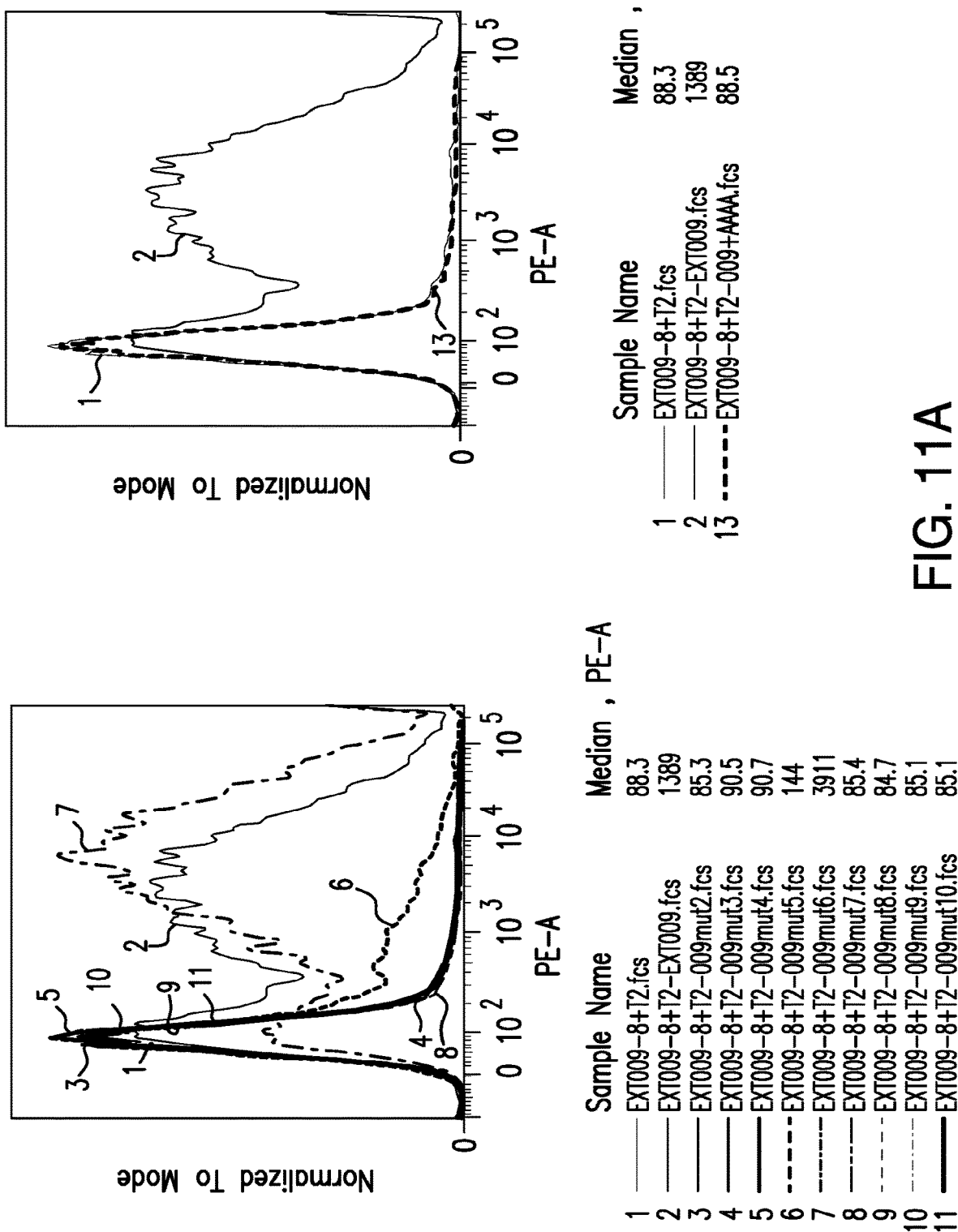
FIGS. 11A-11D represent histograms of EXT009-phage binding to T2 cells loaded with alanine mutants. (A) phage FACS histogram for EXT009-8 phage. No binding to 009-AAAA (positive 4-7). (B), phage FACS histogram for EXT009-17 phage. No binding to 009-AAAA (positive 4-7). (C) phage FACS histogram for EXT009-20 phage. No binding to 009-AAAA (positive 4-7). (D) phage FACS histogram for EXT009-29 phage. No binding to 009-AAAA (positive 4-7).
Figure 11B:
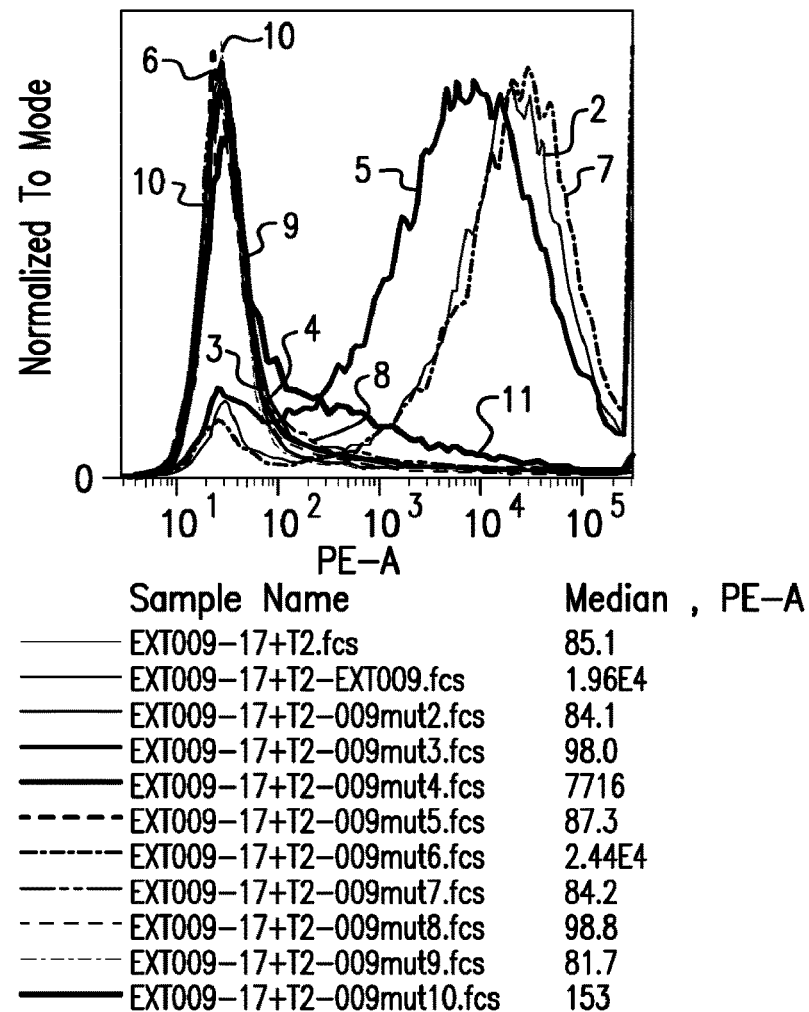
Figure 11B:
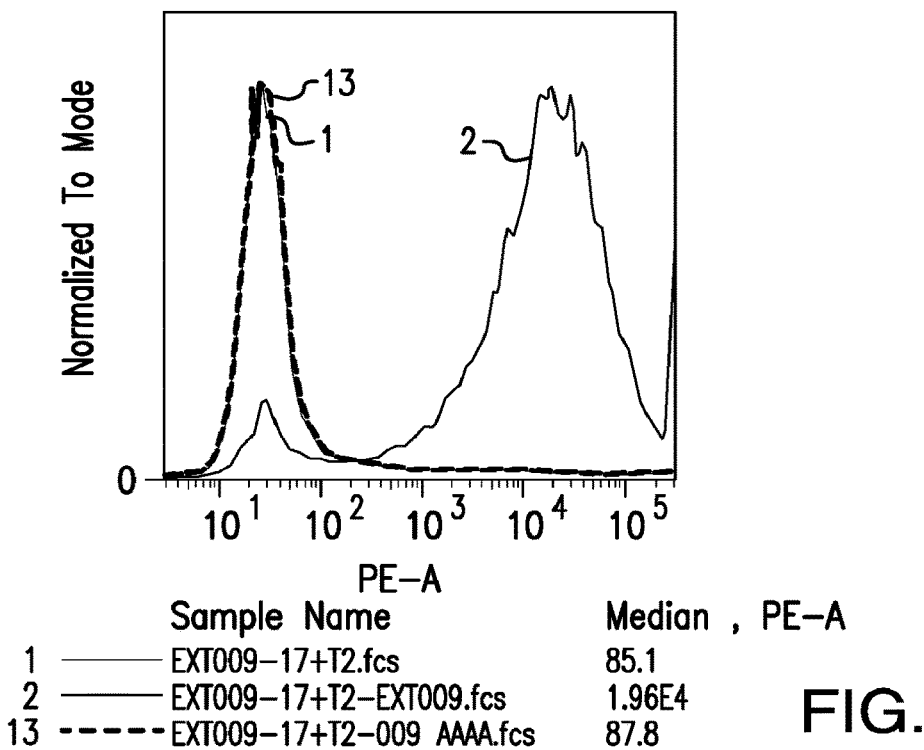
Figure 11C:
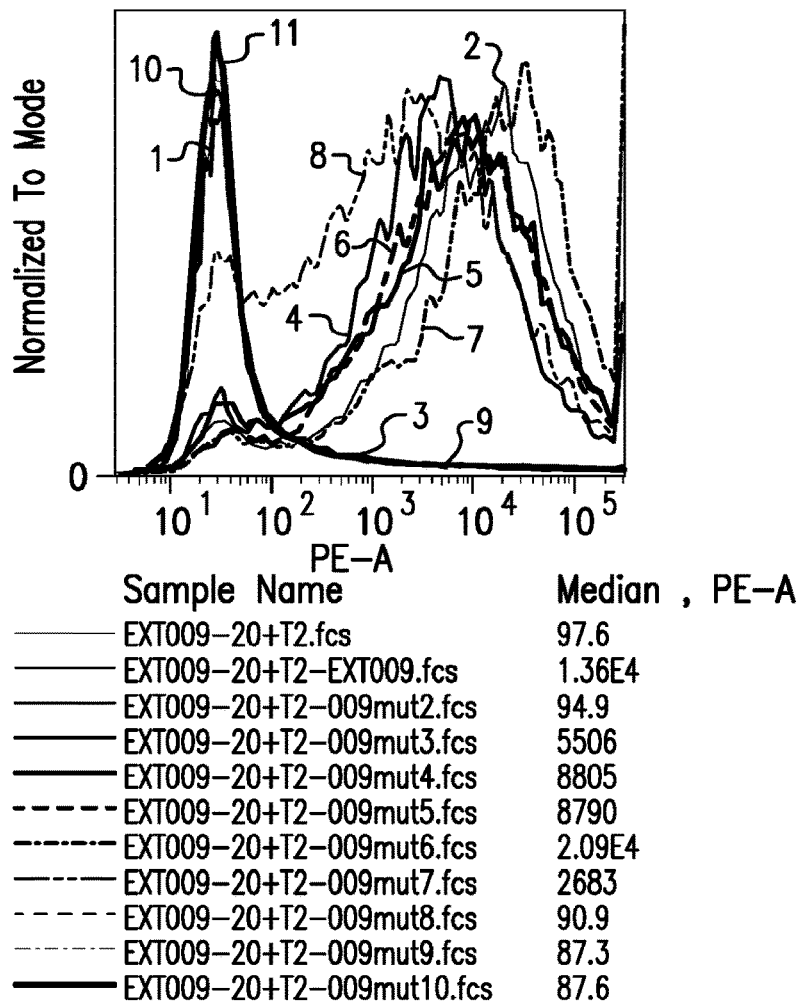
Figure 11C:
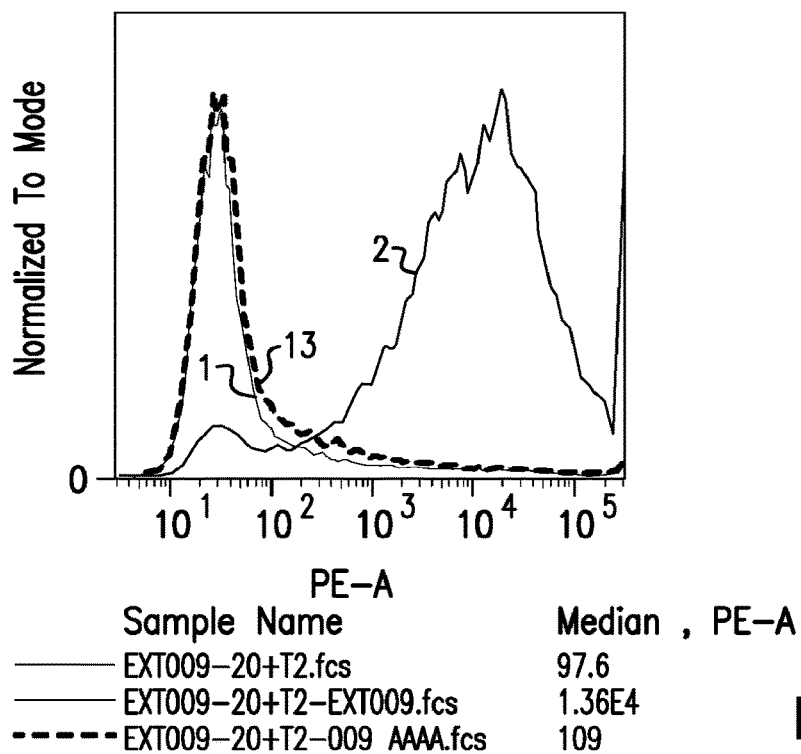
Figure 11D:
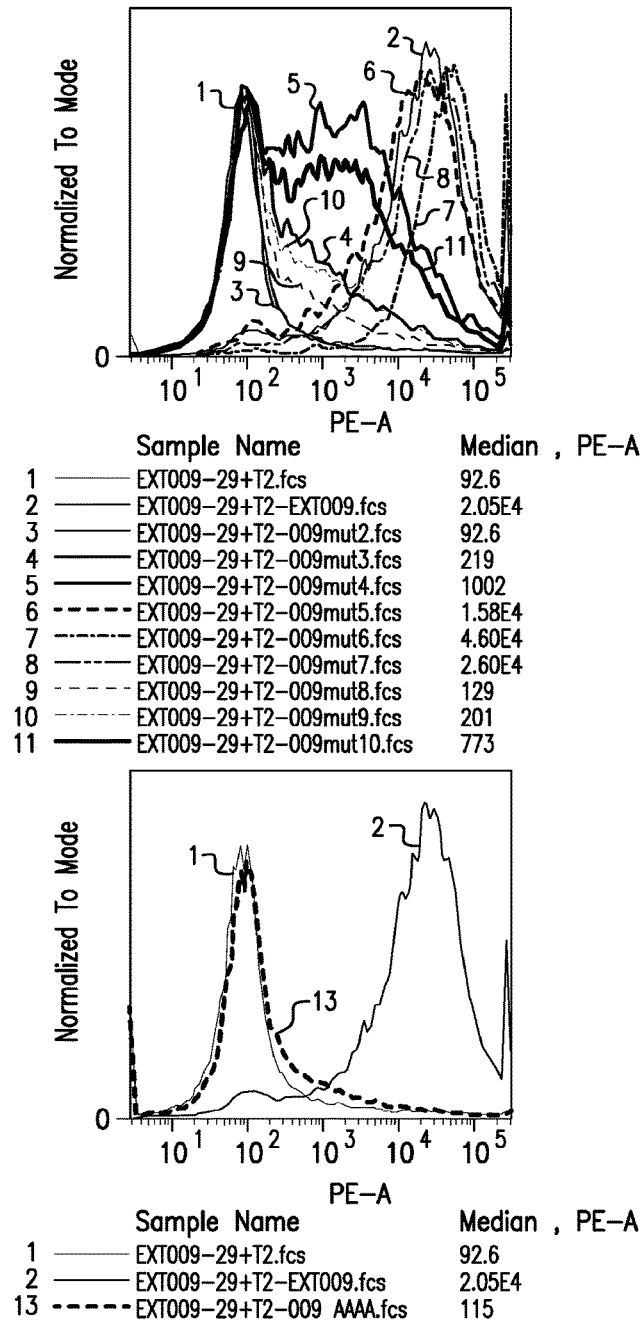

HLA-A expression of the T2 cells was measured by immunostaining with a fluorescently labeled mouse BB7.2 antibody (4 µg/ml), which is specific for HLA-A and flow cytometry. The results of T2 peptide loading quality controls (QC) detection by BB7.2 staining are shown in FIG. 10. As shown in FIG. 10, all loaded T2 cells showed higher MFI than T2 cell after BB7.2 staining. EXT009 only showed slightly higher MFI than T2 cell. See FIG. 10. 009mut3, mut4, mut5, mut6, mut7, mut8 as well as 009-AAAA showed higher MFI than EXT009.

Peptide-loaded T2 cells were stained with EXT009-phages (EXT009-8, EXT009-17, EXT009-20 and EXT009-29), followed by staining with a mouse anti-M13 mAb, and finally a FITC-goat (Fab)$_2$ anti-mouse Ig prior to flow cytometry. Binding was measured by flow cytometry. Fluorescence index (FI) was calculated as the mean fluorescence intensity (MFI) of HLA-A*0201 on T2 cells as determined by fluorescence-activated cell-sorting analysis, using the formula FI=(MFI [T2 cells with peptide]/MFI [T2 cells without peptide]−1. Table 6 summarizes the MFI values of EXT009-phage FACS staining towards T2 cells loaded with the panel of alanine mutants shown in Table 5. The histograms of the four EXT009-phage binding to T2 cells loaded with the panel of alanine mutants are shown in FIGS. 11A-11D.

009-8 and 009-17 showed sensitivity towards more positions than the other two clones. 009-20 only showed sensitivity to position 8, 9, and 10. Thus, the binding epitope is located at the C-terminal of the peptide. All 4 clones showed no binding towards 009-AAAA peptide loaded T2 cells.

TABLE 6

| Phage Clone | T2 | EXT 009 | 009-mut2 * | 009-mut3 | 009-mut4 | 009-mut5 | 009-mut6 | 009-mut7 | 009-mut8 | 009-mut9 | 009-mut10 | 009-AAAA (position 4-7) | Sensitive Position | Notes |
|---|---|---|---|---|---|---|---|---|---|---|---|---|---|---|
| EXT009-8 | 85.9 | 1359 | 83.3 | 88.2 | 87.6 | 138 | 3826 | 83.1 | 82.5 | 83.2 | 83.2 | 86.3 | 3, 4, 5, 7, 8, 9, 10 | Low MFI |
| EXT009-17 | 82.8 | 1.94E+04 | 82 | 95.5 | 7513 | 85.1 | 2.38E+04 | 82.1 | 96.1 | 79.7 | 146 | 85.7 | 3, 5, 7, 8, 9, 10 | High MFI |
| EXT009-20 | 95.1 | 1.32E+04 | 92.8 | 5310 | 8481 | 8444 | 2.01E+04 | 2555 | 88.9 | 85.6 | 85.7 | 106 | 8, 9, 10 | High MFI |
| EXT009-29 | 89.7 | 2.01E+04 | 90.6 | 207 | 954 | 1.52E+04 | 4.57E+04 | 2.56E+04 | 124 | 192 | 720 | 111 | 3, 4, 8, 9, 10 | High MFI |

APPENDIX A

EXT009-8
Lv(lamda)
DNA sequence
Cagtctgtcgtgacgcagccgcccgcagtgtctggggccctagggcagagggtcaccatctcctgcactgggaccacct ccaacatcggggcaggttttgatgtacactggtaccagcagcgtcccggagcagcccccaaactcctcatctccggtaaca cccatcggccctcaggggtccctgaccgcatctctggctccaagtctggcaccttagcctccctggccatcactgggctcca ggctgaggatgaggctgattattactgccagtcttatgacaggagcctgagtactatcctattcggcggagggaccaagctg accgtcctaggt [SEQ ID NO: 75]

AA sequence
QSVVTQPPAVSGALGQRVTISCTGTTSNIGAGFDVHWYQQRPGAAPKLLISGN

THRPSGVPDRISGSKSGTLASLAITGLQAEDEADYYCQSYDRSLSTILFGGGTK

LTVLG [SEQ ID NO: 52]

Hv
DNA sequence
Caggtccagctggtacagtctggggctgaggtgaagaagccggggtcctcggtgaaggtctcctgcaaggcttctggag gcactttcagcagtcatcctatcagctgggtgcgacaggcccccgggacaagggcttgagtggatgggaaggatcatccct atgcttgatataccaaacaacgcacagaagttccagggcagagtcacgattaccgcggacaaatccacggacactgccta cttggagctgagcagcctgacatctgaggacacggccgtgtattactgtgcgcgcggtctgtactactacgattactggggt caaggtactctggtgaccgtgtcctct [SEQ ID NO: 76]

AA sequence
QVQLVQSGAEVKKPGSSVKVSCKASGGTFSSHPISWVRQAPGQGLEWMGRII

PMLDIPNNAQKFQGRVTITADKSTDTAYLELSSLTSEDTAVYYCARGLYYYD

YWGQGTLVTVSS [SEQ ID NO: 51]

Full-length AA sequence
QSVVTQPPAVSGALGQRVTISCTGTTSNIGAGFDVHWYQQRPGAAPKLLISGN

THRPSGVPDRISGSKSGTLASLAITGLQAEDEADYYCQSYDRSLSTILFGGGTK

LTVLGSRGGGGSGGGGSGGGGSLEMAQVQLVQSGAEVKKPGSSVKVSCKAS

GGTFSSHPISWVRQAPGQGLEWMGRIIPMLDIPNNAQKFQGRVTITADKSTDT

AYLELSSLTSEDTAVYYCARGLYYYDYWGQGTLVTVSS [SEQ ID NO: 64]

Full-length DNA sequence
Cagtctgtcgtgacgcagccgcccgcagtgtctggggccctagggcagagggtcaccatctcctgcactgggaccacct ccaacatcggggcaggttttgatgtacactggtaccagcagcgtcccggagcagcccccaaactcctcatctccggtaaca cccatcggccctcaggggtccctgaccgcatctctggctccaagtctggcaccttagcctccctggccatcactgggctcca ggctgaggatgaggctgattattactgccagtcttatgacaggagcctgagtactatcctattcggcggagggaccaagctg

APPENDIX A accgtcctaggttctagaggtggtggtggtagcggcggcggcggctctggtggtggtggatccctcgagatggcccaggtccagctggt acagtctggggctgaggtgaagaagccggggtcctcggtgaaggtctcctgcaaggcttctggaggcactttcagcagtc atcctatcagctgggtgcgacaggcccgggacaagggcttgagtggatgggaaggatcatccctatgcttgatataccaa acaacgcacagaagttccagggcagagtcacgattaccgcggacaaatccacggacactgcctacttggagctgagcag cctgacatctgaggacacggccgtgtattactgtgcgcgcggtctgtactactacgattactggggtcaaggtactctggtga ccgtgtcctct [SEQ ID NO: 77]

EXT009-17
Lv(lamda)
DNA sequence
Cagtctgtgttgacgcagccgccctcagtgtctggggccccagggcagagggtcaccatctcctgcactgggagcagttc caacatcggggcaggttttgatgtacactggtaccagcagcttccaggaacagcccccaaactcctcatctttggtaacagc aatcggccctcaggagtccctgaccgattctctggctccaagtctggcacctcagcctccctggccatcactggcctccagg ctgaggatgaggctgactattactgccagtcctatgacagcagcctgagtggttatgtcttcggaagtgggaccaaggtcac cgtcctaggt [SEQ ID NO: 78]

AA sequence
QSVLTQPPSVSGAPGQRVTISCTGSSSNIGAGFDVHWYQQLPGTAPKLLIFGNS

NRPSGVPDRFSGSKSGTSASLAITGLQAEDEADYYCQSYDSSLSGYVFGSGTK

VTVLG [SEQ ID NO: 54]

Hv
DNA sequence
Gaggtgcagctggtggagtctggggctgaggtgaagaagcctgggtcctcggtgaaggtctcctgcaaggcttctggag gcaccttcagcagctatgctatcagctgggtgcgacaggcccctggacaagggcttgagtggatgggaaggatcatccct atctttggtatagcaaactacgcacagaagttccagggcagagtcacgattaccgcggacaaatccacgagcacagcctac atggagctgagcagcctgagatctgaggacacggccgtgtattactgtgcgcgctctatgtggtacatggattcttggggtc aaggtactctggtgaccgtgtcctct [SEQ ID NO: 79]

AA sequence
EVQLVESGAEVKKPGSSVKVSCKASGGTFSSYAISWVRQAPGQGLEWMGRII

PIFGIANYAQKFQGRVTITADKSTSTAYMELSSLRSEDTAVYYCARSMWYMD

SWGQGTLVTVSS [SEQ ID NO: 53]

Full-length AA sequence
QSVLTQPPSVSGAPGQRVTISCTGSSSNIGAGFDVHWYQQLPGTAPKLLIFGNS

NRPSGVPDRFSGSKSGTSASLAITGLQAEDEADYYCQSYDSSLSGYVFGSGTK

VTVLGSRGGGGSGGGGSGGGGSLEMAEVQLVESGAEVKKPGSSVKVSCKAS

GGTFSSYAISWVRQAPGQGLEWMGRIIPIFGIANYAQKFQGRVTITADKSTSTA

YMELSSLRSEDTAVYYCARSMWYMDSWGQGTLVTVSS [SEQ ID NO: 65]

Full-length DNA sequence
Cagtctgtgttgacgcagccgccctcagtgtctggggccccagggcagagggtcaccatctcctgcactgggagcagttc caacatcggggcaggttttgatgtacactggtaccagcagcttccaggaacagcccccaaactcctcatctttggtaacagc aatcggccctcaggagtccctgaccgattctctggctccaagtctggcacctcagcctccctggccatcactggcctccagg ctgaggatgaggctgactattactgccagtcctatgacagcagcctgagtggttatgtcttcggaagtgggaccaaggtcac cgtcctaggttctagaggtggtggtggtagcggcggcggcggctctggtggtggtggatccctcgagatggccgaggtgcagctggtgg agtctggggctgaggtgaagaagcctgggtcctcggtgaaggtctcctgcaaggcttctggaggcaccttcagcagctatg ctatcagctgggtgcgacaggcccctggacaagggcttgagtggatgggaaggatcatccctatctttggtatagcaaacta

APPENDIX A cgcacagaagttccagggcagagtcacgattaccgcggacaaatccacgagcacagcctacatggagctgagcagcctg agatctgaggacacggccgtgtattactgtgcgcgctctatgtggtacatggattcttggggtcaaggtactctggtgaccgt gtcctct [SEQ ID NO: 80]

EXT009-20
Lv(lamda)
DNA sequence
Caggctgtgctgactcagccaccctcagcgtctgggaccccgggcagagggtcaccatctcttgttctggaagcagctc caacatcggaagtaatactgtaaactggtaccagcagctcccaggaacggcccccaaactcctcatctatagtaataatcag cggccctcaggggtccctgaccgattctctggctccaagtctggcacctcagcctccctggccatcagtgggctccagtctg aggatgaggctgattattactgtgcagcatgggatgacagcctgaatggttcttatgtcttcggaactgggaccaaggtcacc gtcctaggt [SEQ ID NO: 81]

AA sequence
QAVLTQPPSASGTPGQRVTISCSGSSSNIGSNTVNWYQQLPGTAPKLLIYSNNQ

RPSGVPDRFSGSKSGTSASLAISGLQSEDEADYYCAAWDDSLNGSYVFGTGT

KVTVLG [SEQ ID NO: 50]

Hv
DNA sequence
Caggtgcagctggtgcaatctggagctgaggtgaggaagcctggggcctcagtgaaggtctcctgcaaggcttctggag gcaccttcagcagctatgctatcagctgggtgcgacaggcccctggacaagggcttgagtggatgggaaggatcatccct atccttggtatagcaaactacgcacagaagttccagggcagagtcacgattaccgcggacaaatccacgagcacagccta catggagctgagcagcctgagatctgaggacactgccgtgtattactgtgcgcgccattacggtcagtggtgggattactgg ggtcaaggtactctggtgaccgtctcctca [SEQ ID NO: 82]

AA sequence
QVQLVQSGAEVRKPGASVKVSCKASGGTFSSYAISWVRQAPGQGLEWMGRII

PILGIANYAQKFQGRVTITADKSTSTAYMELSSLRSEDTAVYYCARHYGQWW

DYWGQGTLVTVSS [SEQ ID NO: 49]

Full-length AA sequence
QAVLTQPPSASGTPGQRVTISCSGSSSNIGSNTVNWYQQLPGTAPKLLIYSNNQ

RPSGVPDRFSGSKSGTSASLAISGLQSEDEADYYCAAWDDSLNGSYVFGTGT

KVTVLGSRGGGGSGGGGSGGGGSLEMAQVQLVQSGAEVRKPGASVKVSCK

ASGGTFSSYAISWVRQAPGQGLEWMGRIIPILGIANYAQKFQGRVTITADKSTS

TAYMELSSLRSEDTAVYYCARHYGQWWDYWGQGTLVTVSS [SEQ ID NO: 63]

Full-length DNA sequence
Caggctgtgctgactcagccaccctcagcgtctgggaccccgggcagagggtcaccatctcttgttctggaagcagctc caacatcggaagtaatactgtaaactggtaccagcagctcccaggaacggcccccaaactcctcatctatagtaataatcag cggccctcaggggtccctgaccgattctctggctccaagtctggcacctcagcctccctggccatcagtgggctccagtctg aggatgaggctgattattactgtgcagcatgggatgacagcctgaatggttcttatgtcttcggaactgggaccaaggtcacc gtcctaggttctagaggtggtggtggtagcggcggcggcggctctggtggtggtggatccctcgagatggcccaggtgcagctggtgca atctggagctgaggtgaggaagcctggggcctcagtgaaggtctcctgcaaggcttctggaggcaccttcagcagctatgc tatcagctgggtgcgacaggcccctggacaagggcttgagtggatgggaaggatcatccctatccttggtatagcaaacta cgcacagaagttccagggcagagtcacgattaccgcggacaaatccacgagcacagcctacatggagctgagcagcctg agatctgaggacactgccgtgtattactgtgcgcgccattacggtcagtggtgggattactggggtcaaggtactctggtga ccgtctcctca [SEQ ID NO: 83]

APPENDIX A

EXT009-29
Lv(kappa)
DNA sequence
Gacatccagttgacccagtctccatcctccctgtctgcatctgtaggagacagagtcaccatcacttgccgggcaagtcaga gcattagcagctatttaaattggtatcagcagaaaccagggaaagcccctaagctcctgatctatgctgcatccagtttgcaa agtggggtcccatcaaggttcagtggcagtggatctgggacagatttcactctcaccatcagcagtctgcaacctgaagattt tgcaacttactactgtcaacagagttacagtacccctcgtacgttcggccaagggaccaaggtggaaatcaaacgt [SEQ ID NO: 84]

AA sequence
DIQLTQSPSSLSASVGDRVTITCRASQSISSYLNWYQQKPGKAPKLLIYAASSL

QSGVPSRFSGSGSGTDFTLTISSLQPEDFATYYCQQSYSTPRTFGQGTKVEIKR [SEQ ID NO: 56]

Hv
DNA sequence
Caggtgcagctggtgcagtctggagctgaggtgaagaagcctggggcctcagtgaaggtctcctgcaaggcttctggtta cacctttagcagctatggtatcagctgggtgcgacaggcccctggacaagggcttgagtggatgggatggatcagcccttta caatggtaacacaaactatgcgcagaacctccagggcagagtcaccatgaccacagacacatccacgaccacagcctac atggagctgaggagcctgacatctgacgacactgccgtgtattactgtgcgcgctactctggctactacgttgattactg gggtcaaggtactctggtgaccgtgtcctct [SEQ ID NO: 85]

AA sequence
QVQLVQSGAEVKKPGASVKVSCKASGYTFSSYGISWVRQAPGQGLEWMGWI

SPYNGNTNYAQNLQGRVTMTTDTSTTTAYMELRSLTSDDTAVYYCARYSGY

YYVDYWGQGTLVTVSS [SEQ ID NO: 55]

Full-length AA sequence
DIQLTQSPSSLSASVGDRVTITCRASQSISSYLNWYQQKPGKAPKLLIYAASSL

QSGVPSRFSGSGSGTDFTLTISSLQPEDFATYYCQQSYSTPRTFGQGTKVEIKRS

RGGGGSGGGGSGGGGSLEMAQVQLVQSGAEVKKPGASVKVSCKASGYTFSS

YGISWVRQAPGQGLEWMGWISPYNGNTNYAQNLQGRVTMTTDTSTTTAYM

ELRSLTSDDTAVYYCARYSGYYYVDYWGQGTLVTVSS [SEQ ID NO: 66]

Full-length DNA sequence
Gacatccagttgacccagtctccatcctccctgtctgcatctgtaggagacagagtcaccatcacttgccgggcaagtcaga gcattagcagctatttaaattggtatcagcagaaaccagggaaagcccctaagctcctgatctatgctgcatccagtttgcaa agtggggtcccatcaaggttcagtggcagtggatctgggacagatttcactctcaccatcagcagtctgcaacctgaagattt tgcaacttactactgtcaacagagttacagtacccctcgtacgttcggccaagggaccaaggtggaaatcaaacgttctagag gtggtggtggtagcggcggcggcggctctggtggtggtggatccctcgagatggcccaggtgcagctggtgcagtctggagctgagg tgaagaagcctggggcctcagtgaaggtctcctgcaaggcttctggttacacctttagcagctatggtatcagctgggtgcg acaggcccctggacaagggcttgagtggatgggatggatcagcccttacaatggtaacacaaactatgcgcagaacctcc agggcagagtcaccatgaccacagacacatccacgaccacagcctacatggagctgaggagcctgacatctgacgacac tgccgtgtattactgtgcgcgctactctggctactacgttgattactggggtcaaggtactctggtgaccgtgtcctct

[SEQ ID NO: 86]

EXT010-12
Lv(lamda)
DNA sequence
Aagcttctgcctgtgctgactcagccaccctcagtgtcagtggccccaggaaagacggccaggattacctgtgggggaaa caacattggaagtaaaagtgtgcactggtaccagcagaagccaggccaggcccctgtgctggtcatctattatgatagcga

APPENDIX A ccggccctcagggatccctgagcgattctctggctccaactctgggaacacggccaccctgaccatcagcagggtcgaag ccggggatgaggccgactattactgtcaggtgtgggatagtattactgatcattatgtcttcggaactgggaccaaggtcacc gtcctaggt [SEQ ID NO: 87]

AA sequence
KLLPVLTQPPSVSVAPGKTARITCGGNNIGSKSVHWYQQKPGQAPVLVIYYDS

DRPSGIPERFSGSNSGNTATLTISRVEAGDEADYYCQVWDSITDHYVFGTGTK

VTVLG [SEQ ID NO: 58]

Hv
DNA sequence
Gaggtgcagctggtggagtctgggggctgaggtgaagaagcctggggtcctcggtgaaggtctcctgcaaggcttctggag gcaccttcagcagctatgctatcagctgggtgcgacaggcccctggacaagggcttgagtggatgggaaggatcatccct atccttggtatagcaaactacgcacagaagttccagggcagagtcacgattaccgcggacaaatccacgagcacagccta catggagctgagcagcctgagatctgaggacactgccgtgtattactgtgcgcgccagggttacgtttggtctgaaatggatt tctggggtcaaggtactctggtgaccgtctcctca [SEQ ID NO: 88]

AA sequence
EVQLVESGAEVKKPGSSVKVSCKASGGTFSSYAISWVRQAPGQGLEWMGRII

PILGIANYAQKFQGRVTITADKSTSTAYMELSSLRSEDTAVYYCARQGYVWS

EMDFWGQGTLVTVSS [SEQ ID NO: 57]

Full-length AA sequence
KLLPVLTQPPSVSVAPGKTARITCGGNNIGSKSVHWYQQKPGQAPVLVIYYDS

DRPSGIPERFSGSNSGNTATLTISRVEAGDEADYYCQVWDSITDHYVFGTGTK

VTVLGSRGGGGSGGGGSGGGGSLEMAEVQLVESGAEVKKPGSSVKVSCKAS

GGTFSSYAISWVRQAPGQGLEWMGRIIPILGIANYAQKFQGRVTITADKSTST

AYMELSSLRSEDTAVYYCARQGYVWSEMDFWGQGTLVTVSS [SEQ ID NO: 67]

Full-length DNA sequence
Aagcttctgcctgtgctgactcagccaccctcagtgtcagtggccccaggaaagacggccaggattacctgtgggggaaa caacattggaagtaaaagtgtgcactggtaccagcagaagccaggccaggcccctgtgctggtcatctattatgatagcga ccggccctcagggatccctgagcgattctctggctccaactctgggaacacggccaccctgaccatcagcagggtcgaag ccggggatgaggccgactattactgtcaggtgtgggatagtattactgatcattatgtcttcggaactgggaccaaggtcacc gtcctaggttctagaggtggtggtggtagcggcggcggcggctctggtggtggtggatccctcgagatggccgaggtgcagctggtgga gtctgggggctgaggtgaagaagcctggggtcctcggtgaaggtctcctgcaaggcttctggaggcaccttcagcagctatgc tatcagctgggtgcgacaggcccctggacaagggcttgagtggatgggaaggatcatccctatccttggtatagcaaacta cgcacagaagttccagggcagagtcacgattaccgcggacaaatccacgagcacagcctacatggagctgagcagcctg agatctgaggacactgccgtgtattactgtgcgcgccagggttacgtttggtctgaaatggatttctggggtcaaggtactctg gtgaccgtctcctca [SEQ ID NO: 89]

EXT010-37
Lv(lamda)
DNA sequence
Aagcttctgcctgtgctgactcagccccactctgtgtcggagtctccggggaagacggtaaccatctcctgcaccggcagc agtggcagcattgccagcaactttgtgcagtggtaccagcagcgcccgggcagtgccccaccactgtaatctatgatgat aaccaaagaccctctggggtccctgatcggttctctgcctccatcgacagatcctccaattctgcctccctcaccatctctgga ctgaagactgacgacgaggctgactactactgtcagtcttatgatgaagcaatgtcatattcggcggagggaccaagctg accgtcctaggt [SEQ ID NO: 90]

APPENDIX A

AA sequence
KLLPVLTQPHSVSESPGKTVTISCTGSSGSIASNFVQWYQQRPGSAPTTVIYDD

NQRPSGVPDRFSASIDRSSNSASLTISGLKTDDEADYYCQSYDGSNVIFGGGTK

LTVLG [SEQ ID NO: 60]

Hv
DNA sequence
Gaggtgcagctggtggagtctggggctgaggtgaagaagcctggggcctcagtgaaggtttcctgcaaggcatctggat acaccttcaccagctactatatgcactgggtgcgacaggcccctggacaagggcttgagtggatgggaataatcaaccta gtggtggtagcacaagctacgcacagaagttccagggcagagtcaccatgaccagggacacgtccacgagcacagtcta catggagctgagcagcctgagatctgaggacacggccgtgtattactgtgcggcagggagctactactcgcttgatatctg gggccaagggacaatggtcaccgtctcttca [SEQ ID NO: 91]

AA sequence
EVQLVESGAEVKKPGASVKVSCKASGYTFTSYYMHWVRQAPGQGLEWMGII

NPSGGSTSYAQKFQGRVTMTRDTSTSTVYMELSSLRSEDTAVYYCAAGSYYS

LDIWGQGTMVTVSS [SEQ ID NO: 59]

Full-length AA sequence
KLLPVLTQPHSVSESPGKTVTISCTGSSGSIASNFVQWYQQRPGSAPTTVIYDD

NQRPSGVPDRFSASIDRSSNSASLTISGLKTDDEADYYCQSYDGSNVIFGGGTK

LTVLGSRGGGGSGGGGSGGGGSLEMAEVQLVESGAEVKKPGASVKVSCKAS

GYTFTSYYMHWVRQAPGQGLEWMGIINPSGGSTSYAQKFQGRVTMTRDTST

STVYMELSSLRSEDTAVYYCAAGSYYSLDIWGQGTMVTVSS [SEQ ID NO: 68]

Full-length DNA sequence
Aagcttctgcctgtgctgactcagcccccactctgtgtcggagtctccggggaagacggtaaccatctcctgcaccggcagc agtggcagcattgccagcaactttgtgcagtggtaccagcagcgcccgggcagtgcccccaccactgtaatctatgatgat aaccaaagaccctctggggtccctgatcggttctctgcctccatcgacagatcctccaattctgcctccctcaccatctctgga ctgaagactgacgacgaggctgactactactgtcagtcttatgatggaagcaatgtcatattcggcggagggaccaagctg accgtcctaggttctagaggtggtggtggtagcggcggcggcggctctggtggtggtggatcccctcgagatggccgaggtgcagctggt ggagtctggggctgaggtgaagaagcctggggcctcagtgaaggtttcctgcaaggcatctggatacaccttcaccagcta ctatatgcactgggtgcgacaggcccctggacaagggcttgagtggatgggaataatcaaccctagtggtggtagcacaa gctacgcacagaagttccagggcagagtcaccatgaccagggacacgtccacgagcacagtctacatggagctgagcag cctgagatctgaggacacggccgtgtattactgtgcggcagggagctactactcgcttgatatctggggccaagggacaat ggtcaccgtctcttca [SEQ ID NO: 92]

EXT010-40
Lv(lamda)
DNA sequence
Cagcctgtgctgactcagccaccctcagtgtcagtggccccaggagagacggccagtgtttcctgtggggggaacaactt tgggagtcagagtgtgcactggtaccagcagaagtcaggccaggccccttgttggtcatctattatgatcaggaccggccc tcagagatcccgcgcgattttctggctccaagtctgggaacacggccaccctgaccatcagcagggtcgaagccggggga tgaggccgactattactgtcaggtgtgggatacttatactgatcatgtggtcttcggcggagggaccaagctgaccgtcctag gt [SEQ ID NO: 93]

APPENDIX A

AA sequence
QPVLTQPPSVSVAPGETASVSCGGNNFGSQSVHWYQQKSGQAPLLVIYYDQD

RPSEIPARFSGSKSGNTATLTISRVEAGDEADYYCQVWDTYTDHVVFGGGTK

LTVLG [SEQ ID NO: 62]

Hv
DNA sequence
Gaggtccagctggtgcagtctggagctgaggtggagaagcctggggcctcagtgaaggtttcctgcaaggcatctggata caccttcagtagttattatatggactgggtgcgacaggcccctggacaagggcttgagtggatgggaagaatcaaccctact agtggtagcacaacctacgcacagaagttccagggcagggtcaccatgaccagggacacgtccacattcacggtttacat ggacctgagcagcctgagatctgaggacacggccgtatattactgtgcgcgctctggtggtggttacggtgattcttgggt caaggtactctggtgaccgtctcctca [SEQ ID NO: 94]

AA sequence
EVQLVQSGAEVEKPGASVKVSCKASGYTFSSYYMDWVRQAPGQGLEWMGR

INPTSGSTTYAQKFQGRVTMTRDTSTFTVYMDLSSLRSEDTAVYYCARSGGG

YGDSWGQGTLVTVSS [SEQ ID NO: 61]

Full-length AA sequence
QPVLTQPPSVSVAPGETASVSCGGNNFGSQSVHWYQQKSGQAPLLVIYYDQD

RPSEIPARFSGSKSGNTATLTISRVEAGDEADYYCQVWDTYTDHVVFGGGTK

LTVLGSRGGGGSGGGGSGGGGSLEMAEVQLVQSGAEVEKPGASVKVSCKAS

GYTFSSYYMDWVRQAPGQGLEWMGRINPTSGSTTYAQKFQGRVTMTRDTST

FTVYMDLSSLRSEDTAVYYCARSGGGYGDSWGQGTLVTVSS [SEQ ID NO: 69]

Full-length DNA sequence
Cagcctgtgctgactcagccaccctcagtgtcagtggccccaggagagacggccagtgtttcctgtgggggaacaacttt tgggagtcagagtgtgcactggtaccagcagaagtcaggccaggcccctttgttggtcatctattatgatcaggaccggccc tcagagatccctgcgcgattttctggctccaagtctgggaacacggccaccctgaccatcagcagggtcgaagccggggga tgaggccgactattactgtcaggtgtgggatacttatactgatcatgtggtcttcggcggagggaccaagctgaccgtcctag gttctagaggtggtggtggtagcggcggcggcggctctggtggtggtggatcccgagatggccgaggtccagctggtgcagtctgga gctgaggtggagaagcctggggcctcagtgaaggtttcctgcaaggcatctggatacaccttcagtagttattatatggactg ggtgcgacaggcccctggacaagggcttgagtggatgggaagaatcaaccctactagtggtagcacaacctacgcacag aagttccagggcagggtcaccatgaccagggacacgtccacattcacggtttacatggacctgagcagcctgagatctga ggacacggccgtatattactgtgcgcgctctggtggtggttacggtgattcttgggtcaaggtactctggtgaccgtctcctc a [SEQ ID NO: 95]

APPENDIX B

| clones | HCDR1 | HCDR2 | HCDR3 | LCDR1 | LCDR2 | LCDR3 |
|---|---|---|---|---|---|---|
| EXT009-01 | GGTFRTYG [SEQ ID NO: 96] | IIPMVGIA [SEQ ID NO: 117] | ARGFYSSDS [SEQ ID NO: 138] | SSNFGAGFD [SEQ ID NO: 159] | NNN [SEQ ID NO: 180] | QSYDVSLNGWV [SEQ ID NO: 191] |
| EXT009-03 | GYTFTSYG [SEQ ID NO: 97] | ISVYNGNT [SEQ ID NO: 118] | TRDPLLGAFDI [SEQ ID NO: 139] | SSNIGAGFD [SEQ ID NO: 160] | GNN [SEQ ID NO: 181] | QSYDSSLSGWV [SEQ ID NO: 192] |

APPENDIX B-continued

| clones | HCDR1 | HCDR2 | HCDR3 | LCDR1 | LCDR2 | LCDR3 |
|---|---|---|---|---|---|---|
| EXT009-04 | GYTFTSYY [SEQ ID NO: 98] | INPSGGST [SEQ ID NO: 119] | ARGYSYSDY [SEQ ID NO: 140] | SSNIGNDY [SEQ ID NO: 161] | DNN [SEQ ID NO: 182] | GTWDYSLTAYV [SEQ ID NO: 193] |
| EXT009-05 | GYTFTDYG [SEQ ID NO: 99] | IIPIFGIT [SEQ ID NO: 120] | ARGYYYADD [SEQ ID NO: 141] | SSNFGAGFD [SEQ ID NO: 162] | NNN [SEQ ID NO: 180] | QSYDVSLNGWV [SEQ ID NO: 194] |
| EXT009-07 | GGTFSSYA [SEQ ID NO: 100] | IIPILGIA [SEQ ID NO: 121] | ARSMGAWWDP [SEQ ID NO: 142] | SSNIGSNT [SEQ ID NO: 163] | SNN [SEQ ID NO: 183] | AAWDDSLNGFYV [SEQ ID NO: 195] |
| EXT009-09 | GYTFTNYY [SEQ ID NO: 101] | INPSVGST [SEQ ID NO: 122] | ARGQYGSQGKDS [SEQ ID NO: 143] | NSNIGNNY [SEQ ID NO: 164] | DNN [SEQ ID NO: 182] | ETWDISLNVGV [SEQ ID NO: 196] |
| EXT009-10 | GYTFTSYY [SEQ ID NO: 102] | INPSGGST [SEQ ID NO: 123] | ARGMSYYSSIDK [SEQ ID NO: 144] | SSNIGNDY [SEQ ID NO: 165] | END [SEQ ID NO: 184] | GTWDSSLNGGV [SEQ ID NO: 197] |
| EXT009-12 | GYTFTSYY [SEQ ID NO: 103] | INPSGGST [SEQ ID NO: 124] | ARGYYDSDR [SEQ ID NO: 145] | SSNIGNNY [SEQ ID NO: 166] | END [SEQ ID NO: 184] | GTWDNSLNGGV [SEQ ID NO: 198] |
| EXT009-13 | GYTFTSYG [SEQ ID NO: 104] | ISAYNGNT [SEQ ID NO: 125] | ARGYYYYDS [SEQ ID NO: 146] | SSNLGAGFD [SEQ ID NO: 167] | SDN [SEQ ID NO: 185] | QSYDSGLSGSV [SEQ ID NO: 199] |
| EXT009-14 | GNTFTSYY [SEQ ID NO: 105] | INPSGGST [SEQ ID NO: 126] | ARSGGYWSFDS [SEQ ID NO: 147] | QHITKY [SEQ ID NO: 168] | DAS [SEQ ID NO: 186] | QQYENLPLT [SEQ ID NO: 200] |
| EXT009-15 | GFYFSGFA [SEQ ID NO: 106] | VFNDGST [SEQ ID NO: 127] | ARQSPFYFDGPYDY [SEQ ID NO: 148] | TSNIGNNY [SEQ ID NO: 169] | DND [SEQ ID NO: 187] | GTWDSSLSAGV [SEQ ID NO: 201] |
| EXT009-18 | GYTFTSYY [SEQ ID NO: 107] | INPSGGST [SEQ ID NO: 128] | ARGYYGDTTGDN [SEQ ID NO: 149] | SSNIGNSY [SEQ ID NO: 170] | DNN [SEQ ID NO: 182] | GTWDTSLSSVWM [SEQ ID NO: 202] |
| EXT009-19 | GYTFTSYY [SEQ ID NO: 108] | INPSGGST [SEQ ID NO: 129] | ARGYGTSDS [SEQ ID NO: 150] | SSNIGNDY [SEQ ID NO: 171] | END [SEQ ID NO: 184] | GTWDSSLNGGV [SEQ ID NO: 203] |
| EXT009-21 | GGTFNDYS [SEQ ID NO: 109] | IIPVLDMT [SEQ ID NO: 130] | ARYYGDYSDP [SEQ ID NO: 151] | SSNIGSRT [SEQ ID NO: 172] | SNT [SEQ ID NO: 188] | AAWDDSLNGQV [SEQ ID NO: 204] |
| EXT009-23 | GFTFSSYS [SEQ ID NO: 110] | ISSGGNT [SEQ ID NO: 131] | AREGYMYVDH [SEQ ID NO: 152] | NSNIEHNY [SEQ ID NO: 173] | DND [SEQ ID NO: 187] | GTWDNTLSSFV [SEQ ID NO: 205] |
| EXT009-25 | GNSFSTYY [SEQ ID NO: 111] | INPTIGSR [SEQ ID NO: 132] | ARSVTWVLKDG [SEQ ID NO: 153] | QSISSY [SEQ ID NO: 174] | AAS [SEQ ID NO: 189] | QQSYSLPLT [SEQ ID NO: 206] |
| EXT009-27 | GYTFTSYY [SEQ ID NO: 112] | INPSGGST [SEQ ID NO: 133] | ARSSIGWLSYLDA [SEQ ID NO: 154] | QDIGNY [SEQ ID NO: 175] | DAS [SEQ ID NO: 186] | QKYNTAPG [SEQ ID NO: 207] |

APPENDIX B-continued

| clones | HCDR1 | HCDR2 | HCDR3 | LCDR1 | LCDR2 | LCDR3 |
|---|---|---|---|---|---|---|
| EXT009-30 | GGTFSSYA [SEQ ID NO: 113] | IIPIFGTA [SEQ ID NO: 134] | ARSSYGSYYGTYDY [SEQ ID NO: 155] | SSNIGAYD [SEQ ID NO: 176] | GNS [SEQ ID NO: 190] | QSYDSSLSVV [SEQ ID NO: 208] |
| EXT009-31 | GYTFTSYY [SEQ ID NO: 114] | INPTGGST [SEQ ID NO: 135] | ARGYSEGDV [SEQ ID NO: 156] | SSNIGNNY [SEQ ID NO: 177] | DNN [SEQ ID NO: 182] | ATWHSSLSPSYV [SEQ ID NO: 209] |
| EXT009-32 | GGTFSSYA [SEQ ID NO: 115] | IIPIFGTA [SEQ ID NO: 136] | ARYFGRYVDY [SEQ ID NO: 157] | SSNIGSNT [SEQ ID NO: 178] | SNN [SEQ ID NO: 183] | AAWDDSLNGHNYV [SEQ ID NO: 210] |
| EXT009-33 | GGTFNDYS [SEQ ID NO: 116] | IIPVLDMT [SEQ ID NO: 137] | ARQYGSFWDR [SEQ ID NO: 158] | SSNIGSNT [SEQ ID NO: 179] | SNN [SEQ ID NO: 183] | AAWDDSLNGYV [SEQ ID NO: 211] |

APPENDIX C

Linker
EXT009-01:
DNA Sequence:
CAGTCTGTCGTGACGCAGCCGCCCTCAGTGTCTGGGGCCCCAGGGCAGAGGGTCACCAT
CTCCTGTACTGGGAGCAGCTCCAACTTCGGGGCAGGTTTTGATGTACACTGGTACCAGC
AGCTTCCAGGAACAGCCCCCAAACTCCTCATCAATAATAACAACAATCGGCCCCCAGG
GGTCCCTGAGCGATTCTCTGGCTCCAAGTCTGGCACCTCAGCCTCCCTGGCCATCACTG
GGCTCCAGGCTGAGGATGAGGCTCAATATTACTGCCAGTCCTATGACGTCAGCCTGAAT
GGTTGGGTGTTCGGCGGAGGGACCAAGGTCACCGTCCTAGGTTCTAGAGGTGGTGGTGG
TAGCGGCGGCGGCGGCTCTGGTGGTGGTGGATCCCTCGAGATGGCCCAGGTGCAGCTG
GTGCAGTCCGGGGCTGAGGTGAAGAAGCCTGGGTCCTCGGTGAAGGTCTCCTGCAAGG
CTTCTGGAGGCACCTTCAGGACCTATGGTATCAACTGGGTGCGACAGGCCCCTGGACAA
GGGCTTGAGTGGATGGGAAGGATAATCCCTATGGTTGGTATAGCCAACTACGCACAGA
AGTTCCAGGGCAGAGTCACGATTACCGCGGACAAATCCACGAGCACAGCCTACATGGA
GCTGAACAGCCTGAGATCTGAGGACACGGCCGTGTATTACTGTGCGCGCGGTTTCTACT
CTTCTGATTCTTGGGGTCAAGGTACTCTGGTGACCGTCTCCTCA [SEQ ID NO: 212]
Amino Acid Sequence:
QSVVTQPPSVSGAPGQRVTISCTGSSSNFGAGFDVHWYQQLPGTAPKLLINNNNNRPPGVPE
RFSGSKSGTSASLAITGLQAEDEAQYYCQSYDVSLNGWVFGGGTKVTVLGSRGGGGSGGG
GSGGGGSLEMAQVQLVQSGAEVKKPGSSVKVSCKASGGTFRTYGINWVRQAPGQGLEWM
GRIIPMVGIANYAQKFQGRVTITADKSTSTAYMELNSLRSEDTAVYYCARGFYSSDSWGQG
TLVTVSS [SEQ ID NO: 213]
Light chain DNA Sequence:
CAGTCTGTCGTGACGCAGCCGCCCTCAGTGTCTGGGGCCCCAGGGCAGAGGGTCACCAT
CTCCTGTACTGGGAGCAGCTCCAACTTCGGGGCAGGTTTTGATGTACACTGGTACCAGC
AGCTTCCAGGAACAGCCCCCAAACTCCTCATCAATAATAACAACAATCGGCCCCCAGG

APPENDIX C

GGTCCCTGAGCGATTCTCTGGCTCCAAGTCTGGCACCTCAGCCTCCCTGGCCATCACTG

GGCTCCAGGCTGAGGATGAGGCTCAATATTACTGCCAGTCCTATGACGTCAGCCTGAAT

GGTTGGGTGTTCGGCGGAGGGACCAAGGTCACCGTCCTAGGT [SEQ ID NO: 214]

Light Chain Amino Acid Sequence:
QSVVTQPPSVSGAPGQRVTISCTGSSSNFGAGFDVHWYQQLPGTAPKLLINNNNRPPGVPE

RFSGSKSGTSASLAITGLQAEDEAQYYCQSYDVSLNGWVFGGGTKVTVLG [SEQ ID NO: 215]

Heavy Chain DNA Sequence:
CAGGTGCAGCTGGTGCAGTCCGGGGCTGAGGTGAAGAAGCCTGGGTCCTCGGTGAAGG

TCTCCTGCAAGGCTTCTGGAGGCACCTTCAGGACCTATGGTATCAACTGGGTGCGACAG

GCCCCTGGACAAGGGCTTGAGTGGATGGGAAGGATAATCCCTATGGTTGGTATAGCCA

ACTACGCACAGAAGTTCCAGGGCAGAGTCACGATTACCGCGGACAAATCCACGAGCAC

AGCCTACATGGAGCTGAACAGCCTGAGATCTGAGGACACGGCCGTGTATTACTGTGCGC

GCGGTTTCTACTCTTCTGATTCTTGGGGTCAAGGTACTCTGGTGACCGTCTCCTCA [SEQ ID NO: 216]

Heavy Chain Amino Acid Sequience:
QVQLVQSGAEVKKPGSSVKVSCKASGGTFRTYGINWVRQAPGQGLEWMGRIIPMVGIANY

AQKFQGRVTITADKSTSTAYMELNSLRSEDTAVYYCARGFYSSDSWGQGTLVTVSS [SEQ ID NO: 217]

EXT009-03:
DNA Sequence:
CAGTCTGTGTTGACGCAGCCGCCCTCAGTGTCTGGGGCCCCAGGGCAGAGGGTCACCAT

CTCCTGCACTGGGAGCAGCTCCAACATCGGGGCAGGTTTTGATGTACACTGGTACCAGC

AGCTTCCAGGAACAGCCCCCAAACTCCTCATCTATGGTAACAACAATCGACCCTCAGGG

GTCCCTGACCGATTCTCTGGCTCCAAGTCTGGCACCTCAGCCTCCCTGGCCATCACTGGG

CTCCAGGCTGAGGATGAGGCTGATTATTACTGCCAGTCCTATGACAGCAGCCTGAGTGG

TTGGGTGTTCGGCGGAGGGACCAAGCTGACCGTCCTAGGTTCTAGAGGTGGTGGTGGTA

GCGGCGGCGGCGGCTCTGGTGGTGGTGGATCCCTCGAGATGGCCCAGGTCCAGCTGGT

GCAGTCTGGAGCTGAGGTGAAGAAGCCTGGGGCCTCAGTGAAGGTCTCCTGCAAGACT

TCTGGTTACACCTTTACCAGCTACGGTATCAGCTGGGTGCGCCAGGCCCCTGGACAAGG

GCTTGAGTGGATGGGATGGATCAGCGTTTACAATGGTAACACAAATTATGCACAGAAAT

TCCAGGGCAGAGTCACCATGACCACAGACACATCCACGAGCACAGCCTACATGGAGCT

GAGGAGCCTGAGATCTGACGACACGGCCGTGTATTATTGTACGAGAGATCCCCTCCTGG

GGGCTTTTGATATCTGGGGCCAAGGGACAATGGTCACCGTCTCTTCA [SEQ ID NO: 218]

Amino Acid Sequence:
QSVLTQPPSVSGAPGQRVTISCTGSSSNIGAGFDVHWYQQLPGTAPKLLIYGNNNRPSGVPD

RFSGSKSGTSASLAITGLQAEDEADYYCQSYDSSLSGWVFGGGTKLTVLGSRGGGGSGGGG

SGGGGSLEMAQVQLVQSGAEVKKPGASVKVSCKTSGYTFTSYGISWVRQAPGQGLEWMG

WISVYNGNTNYAQKFQGRVTMTTDTSTSTAYMELRSLRSDDTAVYYCTRDPLLGAFDIWG

QGTMVTVSS [SEQ ID NO: 219]

Light Chain DNA Sequence:
CAGTCTGTGTTGACGCAGCCGCCCTCAGTGTCTGGGGCCCCAGGGCAGAGGGTCACCAT

CTCCTGCACTGGGAGCAGCTCCAACATCGGGGCAGGTTTTGATGTACACTGGTACCAGC

AGCTTCCAGGAACAGCCCCCAAACTCCTCATCTATGGTAACAACAATCGACCCTCAGGG

GTCCCTGACCGATTCTCTGGCTCCAAGTCTGGCACCTCAGCCTCCCTGGCCATCACTGGG

APPENDIX C

CTCCAGGCTGAGGATGAGGCTGATTATTACTGCCAGTCCTATGACAGCAGCCTGAGTGG

TTGGGTGTTCGGCGGAGGGACCAAGCTGACCGTCCTAGGT [SEQ ID NO: 220]

Light Chain Amino Acid Sequence:
QSVLTQPPSVSGAPGQRVTISCTGSSSNIGAGFDVHWYQQLPGTAPKLLIYGNNNRPSGVPD

RFSGSKSGTSASLAITGLQAEDEADYYCQSYDSSLSGWVFGGGTKLTVLG [SEQ ID NO: 221]

Heavy Chain DNA Sequence:
CAGGTCCAGCTGGTGCAGTCTGGAGCTGAGGTGAAGAAGCCTGGGGCCTCAGTGAAGG

TCTCCTGCAAGACTTCTGGTTACACCTTTACCAGCTACGGTATCAGCTGGGTGCGCCAG

GCCCCTGGACAAGGGCTTGAGTGGATGGGATGGATCAGCGTTTACAATGGTAACACAA

ATTATGCACAGAAATTCCAGGGCAGAGTCACCATGACCACAGACACATCCACGAGCAC

AGCCTACATGGAGCTGAGGAGCCTGAGATCTGACGACACGGCCGTGTATTATTGTACGA

GAGATCCCCTCCTGGGGGCTTTTGATATCTGGGGCCAAGGGACAATGGTCACCGTCTCT

TCA [SEQ ID NO: 222]

Heavy Chain Amino Acid Sequence:
QVQLVQSGAEVKKPGASVKVSCKTSGYTFTSYGISWVRQAPGQGLEWMGWISVYNGNTN

YAQKFQGRVTMTTDTSTSTAYMELRSLRSDDTAVYYCTRDPLLGAFDIWGQGTMVTVSS
[SEQ ID NO: 223]

EXT009-04:
DNA Sequence
CAGTCTGTGTTGACGCAGCCGCCCTCAGTGTCTGCGGCCCCCGGGCAGAGGGTCACCAT

CTCCTGCTCTGGAAGCAGCTCCAACATTGGAAATGATTATGTATCCTGGTACCAGCAAG

TCCCAGGAACAGCCCCCAAAGTCCTCATTTATGACAATAATAAGCGACCCTCAGGGATT

CCTGACCGATTCTCTGGCTCCAAGTCTGGCACGTCAGCCACCCTGGGCATCACCGGACT

CCAGACTGGGGACGAGGCCGATTATTACTGCGGAACATGGGATTACAGCCTGACTGCTT

ATGTCTTCGGAAGTGGGACCAAGCTGACCGTCCTAGGTTCTAGAGGTGGTGGTGGTAGC

GGCGGCGGCGGCTCTGGTGGTGGTGGATCCCTCGAGATGGCCCAGGTGCAGCTGGTGC

AGTCTGGGGCTGAGGTGAAGAAGCCTGGGGCCTCAGTGAAGGTTTCCTGCAAGGCATCT

GGATACACCTTCACCAGCTACTATATGCACTGGGTGCGACAGGCCCCTGGACAAGGGCT

TGAGTGGATGGGAATAATCAACCCTAGTGGTGGTAGCACAAGCTACGCACAGAAGTTC

CAGGGCAGAGTCACCATGACCAGGGACACGTCCACGAGCACAGTCTACATGGAGCTGA

GCAGCCTGAGATCTGAGGACACGGCCGTGTATTACTGTGCGCGCGGTTACTCTTACTCT

GATTACTGGGGTCAAGGTACTCTGGTGACCGTCTCCTCA [SEQ ID NO: 224]

Amino Acid Sequence:
QSVLTQPPSVSAAPGQRVTISCSGSSSNIGNDYVSWYQQVPGTAPKVLIYDNNKRPSGIPDRF

SGSKSGTSATLGITGLQTGDEADYYCGTWDYSLTAYVFGSGTKLTVLGSRGGGGSGGGGS

GGGGSLEMAQVQLVQSGAEVKKPGASVKVSCKASGYTFTSYYMHWVRQAPGQGLEWMG

IINPSGGSTSYAQKFQGRVTMTRDTSTSTVYMELSSLRSEDTAVYYCARGYSYSDYWGQGT

LVTVSS [SEQ ID NO: 225]

Light Chain DNA Sequence:
CAGTCTGTGTTGACGCAGCCGCCCTCAGTGTCTGCGGCCCCCGGGCAGAGGGTCACCAT

CTCCTGCTCTGGAAGCAGCTCCAACATTGGAAATGATTATGTATCCTGGTACCAGCAAG

TCCCAGGAACAGCCCCCAAAGTCCTCATTTATGACAATAATAAGCGACCCTCAGGGATT

APPENDIX C

CCTGACCGATTCTCTGGCTCCAAGTCTGGCACGTCAGCCACCCTGGGCATCACCGGACT

CCAGACTGGGGACGAGGCCGATTATTACTGCGGAACATGGATTACAGCCTGACTGCTT

ATGTCTTCGGAAGTGGGACCAAGCTGACCGTCCTAGGT [SEQ ID NO: 226]

Light Chain Amino Acid Sequence:
QSVLTQPPSVSAAPGQRVTISCSGSSSNIGNDYVSWYQQVPGTAPKVLIYDNNKRPSGIPDRF

SGSKSGTSATLGITGLQTGDEADYYCGTWDYSLTAYVFGSGTKLTVLG [SEQ ID NO: 227]

Heavy Chain DNA Sequence:
CAGGTGCAGCTGGTGCAGTCTGGGGCTGAGGTGAAGAAGCCTGGGGCCTCAGTGAAGG

TTTCCTGCAAGGCATCTGGATACACCTTCACCAGCTACTATATGCACTGGGTGCGACAG

GCCCCTGGACAAGGGCTTGAGTGGATGGGAATAATCAACCCTAGTGGTGGTAGCACAA

GCTACGCACAGAAGTTCCAGGGCAGAGTCACCATGACCAGGGACACGTCCACGAGCAC

AGTCTACATGGAGCTGAGCAGCCTGAGATCTGAGGACACGGCCGTGTATTACTGTGCGC

GCGGTTACTCTTACTCTGATTACTGGGGTCAAGGTACTCTGGTGACCGTCTCCTCA
[SEQ ID NO: 228]

Heavy Chain Amino Acid Sequence:
QVQLVQSGAEVKKPGASVKVSCKASGYTFTSYYMHWVRQAPGQGLEWMGIINPSGGSTSY

AQKFQGRVTMTRDTSTSTVYMELSSLRSEDTAVYYCARGYSYSDYWGQGTLVTVSS
[SEQ ID NO: 229]

EXT009-05:
DNA Sequence:
CAGTCTGTGTTGACGCAGCCGCCCTCAGTGTCTGGGGCCCCAGGGCAGAGGGTCACCAT

CTCCTGTACTGGGAGCAGCTCCAACTTCGGGGCAGGTTTTGATGTACACTGGTACCAGC

AGCTTCCAGGAACAGCCCCCAAACTCCTCATCAATAATAACAACAATCGGCCCCCAGG

GGTCCCTGAGCGATTCTCTGGCTCCAAGTCTGGCACCTCAGCCTCCCTGGCCATCACTG

GGCTCCAGGCTGAGGATGAGGCTCAATATTACTGCCAGTCCTATGACGTCAGCCTGAAT

GGTTGGGTGTTCGGCGGAGGGACCAAGCTGACCGTCCTAGGTTCTAGAGGTGGTGGTGG

TAGCGGCGGCGGCGGCTCTGGTGGTGGTGGATCCCTCGAGATGGCCCAGGTGCAGCTG

GTGCAGTCTGGGGCTGAGGTGAAGAAGCCTGGGGCCTCAGTGAAGGTCTCCTGCAAGG

CTTCTGGTTACACCTTTACCGACTATGGGATCACCTGGGTGCGACAGGCCCCTGGACAA

GGGCTTGAGTGGATGGGAAGGATCATCCCTATTTTTGGTATCACAAACTACGCACAGAA

GTTCCAGGGCAGAGTCACGGTGACCGCGGACAAACCCACGAGCACAGTCTTCATGGAG

CTGACCAGTCTTACACCTAAGGACACGGCCGTGTATTACTGTGCGCGCGGTTACTACTA

CGCTGATGACTGGGGTCAAGGTACTCTGGTGACCGTCTCCTCA [SEQ ID NO: 230]

Amino Acid Sequence:
QSVLTQPPSVSGAPGQRVTISCTGSSSNFGAGFDVHWYQQLPGTAPKLLINNNNNRPPGVPE

RFSGSKSGTSASLAITGLQAEDEAQYYCQSYDVSLNGWVFGGGTKLTVLGSRGGGGSGG

GSGGGGSLEMAQVQLVQSGAEVKKPGASVKVSCKASGYTFTDYGITWVRQAPGQGLEWM

GRIIPIFGITNYAQKFQGRVTVTADKPTSTVFMELTSLTPKDTAVYYCARGYYYADDWGQG

TLVTVSS [SEQ ID NO: 231]

Light Chain DNA Sequence:
CAGTCTGTGTTGACGCAGCCGCCCTCAGTGTCTGGGGCCCCAGGGCAGAGGGTCACCAT

CTCCTGTACTGGGAGCAGCTCCAACTTCGGGGCAGGTTTTGATGTACACTGGTACCAGC

AGCTTCCAGGAACAGCCCCCAAACTCCTCATCAATAATAACAACAATCGGCCCCCAGG

APPENDIX C

GGTCCCTGAGCGATTCTCTGGCTCCAAGTCTGGCACCTCAGCCTCCCTGGCCATCACTG

GGCTCCAGGCTGAGGATGAGGCTCAATATTACTGCCAGTCCTATGACGTCAGCCTGAAT

GGTTGGGTGTTCGGCGGAGGGACCAAGCTGACCGTCCTAGGT [SEQ ID NO: 232]

Light Chain Amino Acid Sequence:
QSVLTQPPSVSGAPGQRVTISCTGSSSNFGAGFDVHWYQQLPGTAPKLLINNNNNRPPGVPE

RFSGSKSGTSASLAITGLQAEDEAQYYCQSYDVSLNGWVFGGGTKLTVLG [SEQ ID NO: 233]

Heavy Chain DNA Sequence:
CAGGTGCAGCTGGTGCAGTCTGGGGCTGAGGTGAAGAAGCCTGGGGCCTCAGTGAAGG

TCTCCTGCAAGGCTTCTGGTTACACCTTTACCGACTATGGGATCACCTGGGTGCGACAG

GCCCCTGGACAAGGGCTTGAGTGGATGGGAAGGATCATCCCTATTTTTGGTATCACAAA

CTACGCACAGAAGTTCCAGGGCAGAGTCACGGTGACCGCGGACAAACCCACGAGCACA

GTCTTCATGGAGCTGACCAGTCTTACACCTAAGGACACGGCCGTGTATTACTGTGCGCG

CGGTTACTACTACGCTGATGACTGGGGTCAAGGTACTCTGGTGACCGTCTCCTCA
[SEQ ID NO: 234]

Heavy Chain Amino Acid Sequence:
QVQLVQSGAEVKKPGASVKVSCKASGYTFTDYGITWVRQAPGQGLEWMGRIIPIFGITNYA

QKFQGRVTVTADKPTSTVFMELTSLTPKDTAVYYCARGYYYADDWGQGTLVTVSS

[SEQ ID NO: 235]

EXT009-07:
DNA Sequence:
CAGTCTGTGTTGACTCAGCCACCCTCAGCGTCTGGGACCCCCGGGCAGAGGGTCACCAT

CTCTTGTTCTGGAAGCAGCTCCAACATCGGAAGTAATACTGTAAACTGGTACCAGCAGC

TCCCAGGAACGGCCCCCAAACTCCTCATCTATAGTAATAATCAGCGGCCCTCAGGGGTC

CCTGACCGATTCTCTGGCTCCAAGTCTGGCACCTCAGCCTCCCTGGCCATCAGTGGGCTC

CAGTCTGAGGATGAGGCTGATTATTACTGTGCAGCATGGGATGACAGCCTGAATGGCTT

TTATGTCTTCGGAACTGGGACCAAGCTGACCGTCCTAGGTTCTAGAGGTGGTGGTGGTA

GCGGCGGCGGCGGCTCTGGTGGTGGTGGATCCCTCGAGATGGCCCAGGTCCAGCTGGT

ACAGTCTGGGGCTGAGGTGAAGAAGCCTGGGTCCTCGGTGAAGGTCTCCTGCAAGGCTT

CTGGAGGCACCTTCAGCAGCTATGCTATCAGCTGGGTGCGACAGGCCCCTGGACAAGG

GCTTGAGTGGATGGGAAGGATCATCCCTATCCTTGGTATAGCAAACTACGCACAGAAGT

TCCAGGGCAGAGTCACGATTACCGCGGACAAATCCACGAGCACAGCCTACAACGAGCT

GAGCAGCCTGAGATCTGAGGACACGGCCGTGTATTACTGTGCGCGCTCTATGGGTGCTT

GGTGGGATCCGTGGGGTCAAGGTACTCTGGTGACCGTCTCCTCA [SEQ ID NO: 236]

Amino Acid Sequence:
QSVLTQPPSASGTPGQRVTISCSGSSSNIGSNTVNWYQQLPGTAPKLLIYSNNQRPSGVPDRF

SGSKSGTSASLAISGLQSEDEADYYCAAWDDSLNGFYVFGTGTKLTVLGSRGGGGSGGGGS

GGGGSLEMAQVQLVQSGAEVKKPGSSVKVSCKASGGTFSSYAISWVRQAPGQGLEWMGRI

IPILGIANYAQKFQGRVTITADKSTSTAYNELSSLRSEDTAVYYCARSMGAWWDPWGQGTL

VTVSS [SEQ ID NO: 237]

Light Chain DNA Sequence:
CAGTCTGTGTTGACTCAGCCACCCTCAGCGTCTGGGACCCCCGGGCAGAGGGTCACCAT

CTCTTGTTCTGGAAGCAGCTCCAACATCGGAAGTAATACTGTAAACTGGTACCAGCAGC

TCCCAGGAACGGCCCCCAAACTCCTCATCTATAGTAATAATCAGCGGCCCTCAGGGGTC

APPENDIX C

CCTGACCGATTCTCTGGCTCCAAGTCTGGCACCTCAGCCTCCCTGGCCATCAGTGGGCTC

CAGTCTGAGGATGAGGCTGATTATTACTGTGCAGCATGGGATGACAGCCTGAATGGCTT

TTATGTCTTCGGAACTGGGACCAAGCTGACCGTCCTAGGT [SEQ ID NO: 238]

Light Chain Amino Acid Sequence:
QSVLTQPPSASGTPGQRVTISCSGSSSNIGSNTVNWYQQLPGTAPKLLIYSNNQRPSGVPDRF

SGSKSGTSASLAISGLQSEDEADYYCAAWDDSLNGFYVFGTGTKLTVLG [SEQ ID NO: 239]

Heavy Chain DNA Sequence:
CAGGTCCAGCTGGTACAGTCTGGGGCTGAGGTGAAGAAGCCTGGGTCCTCGGTGAAGG

TCTCCTGCAAGGCTTCTGGAGGCACCTTCAGCAGCTATGCTATCAGCTGGGTGCGACAG

GCCCCTGGACAAGGGCTTGAGTGGATGGGAAGGATCATCCCTATCCTTGGTATAGCAAA

CTACGCACAGAAGTTCCAGGGCAGAGTCACGATTACCGCGGACAAATCCACGAGCACA

GCCTACAACGAGCTGAGCAGCCTGAGATCTGAGGACACGGCCGTGTATTACTGTGCGC

GCTCTATGGGTGCTTGGTGGGATCCGTGGGGTCAAGGTACTCTGGTGACCGTCTCCTCA

[SEQ ID NO: 240]

Heavy Chain Amino Acid Sequence:
QVQLVQSGAEVKKPGSSVKVSCKASGGTFSSYAISWVRQAPGQGLEWMGRIIPILGIANYA

QKFQGRVTITADKSTSTAYNELSSLRSEDTAVYYCARSMGAWWDPWGQGTLVTVSS (SEQ ID NO: 677)

EXT009-09:
DNA Sequence:
CAGTCTGTCGTGACGCAGCCGCCCTCAGTGTCTGCGGCCCCAGGACAGAAGGTCACCAT

CTCCTGCTCTGGAAGCAACTCCAACATTGGGAACAATTATGTCTCCTGGTACCAGCAAC

TCCCAGGAACAGCCCCCAAACTCCTCATCTATGACAATAATAAACGACCCTCAGGGATT

CCTGACCGATTCTCTGGCTCCAAGTCTGGCACGTCTGCCACCCTGGGCATCACCGGACT

CCAGACTGGCGACGAGGCCGATTATTACTGCGAAACATGGGATATCAGCCTGAATGTTG

GAGTGTTCGGCGGAGGGACCAAGCTGACCGTCCTAGGTTCTAGAGGTGGTGGTGGTAG

CGGCGGCGGCGGCTCTGGTGGTGGTGGATCCCTCGAGATGGCCGAGGTGCAGCTGGTG

GAGTCTGGGGGCTGAGGTGAAGAAGCCTGGGGCCTCAGTGAAGGTTTCCTGCAAGGCAT

CTGGATACACCTTCACCAACTACTATATACACTGGGTGCGACAGGCCCCTGGACAAGGG

CTTGAGTGGATGGGAATAATCAACCCTAGTGTTGGTAGCACAAGGTACGCACAGAAGTT

CCAGGGCAGAGTCACCATGACCAGGGACACGTCCACGAGCACACTGTACATGGAGTTG

AGCAGCCTGAGATCTGAGGACACGGCCGTATATTACTGTGCGCGCGGTCAGTACGGTTC

TCAGGGTAAAGATTCTTGGGGTCAAGGTACTCTGGTGACCGTCTCCTCA [SEQ ID NO: 241]

Amino Acid Sequence:
QSVVTQPPSVSAAPGQKVTISCSGSNSNIGNNYVSWYQQLPGTAPKLLIYDNNKRPSGIPDR

FSGSKSGTSATLGITGLQTGDEADYYCETWDISLNVGVFGGGTKLTVLGSRGGGGSGGGGS

GGGGSLEMAEVQLVESGAEVKKPGASVKVSCKASGYTFTNYYIHWVRQAPGQGLEWMGII

NPSVGSTRYAQKFQGRVTMTRDTSTSTLYMELSSLRSEDTAVYYCARGQYGSQGKDSWGQ

GTLVTVSS [SEQ ID NO: 242]

Light Chain DNA Sequence:
CAGTCTGTCGTGACGCAGCCGCCCTCAGTGTCTGCGGCCCCAGGACAGAAGGTCACCAT

CTCCTGCTCTGGAAGCAACTCCAACATTGGGAACAATTATGTCTCCTGGTACCAGCAAC

APPENDIX C
-continued

TCCCAGGAACAGCCCCCAAACTCCTCATCTATGACAATAATAAACGACCCTCAGGGATT

CCTGACCGATTCTCTGGCTCCAAGTCTGGCACGTCTGCCACCCTGGGCATCACCGGACT

CCAGACTGGCGACGAGGCCGATTATTACTGCGAAACATGGGATATCAGCCTGAATGTTG

GAGTGTTCGGCGGAGGGACCAAGCTGACCGTCCTAGGT [SEQ ID NO: 243]

Light Chain Amino Acid Sequence:
QSVVTQPPSVSAAPGQKVTISCSGSNSNIGNNYVSWYQQLPGTAPKLLIYDNNKRPSGIPDR

FSGSKSGTSATLGITGLQTGDEADYYCETWDISLNVGVFGGGTKLTVLG [SEQ ID NO: 244]

Heavy Chain DNA Sequence:
GAGGTGCAGCTGGTGGAGTCTGGGGCTGAGGTGAAGAAGCCTGGGGCCTCAGTGAAGG

TTTCCTGCAAGGCATCTGGATACACCTTCACCAACTACTATATACACTGGGTGCGACAG

GCCCCTGGACAAGGGCTTGAGTGGATGGGAATAATCAACCCTAGTGTTGGTAGCACAA

GGTACGCACAGAAGTTCCAGGGCAGAGTCACCATGACCAGGGACACGTCCACGAGCAC

ACTGTACATGGAGTTGAGCAGCCTGAGATCTGAGGACACGGCCGTATATTACTGTGCGC

GCGGTCAGTACGGTTCTCAGGGTAAAGATTCTTGGGGTCAAGGTACTCTGGTGACCGTC

TCCTCA [SEQ ID NO: 245]

Heavy Chain Amino Acid Sequence:
EVQLVESGAEVKKPGASVKVSCKASGYTFTNYYIHWVRQAPGQGLEWMGIINPSVGSTRY

AQKFQGRVTMTRDTSTSTLYMELSSLRSEDTAVYYCARGQYGSQGKDSWGQGTLVTVSS
[SEQ ID NO: 246]

EXT009-10:
DNA Sequence:
CAGTCTGTGTTGACGCAGCCGCCCTCAGTGTCTGCGGCCCCAGGACAGAAGGTCACCAT

CTCCTGCTCTGGAAGCAGCTCCAACATTGGGAATGATTATGTATCGTGGTACCAGCAAC

TCCCAGGAACAGCCCCCAAACTCCTCATTTATGAAAATGATCAGCGACCCTCAGGGATT

CCTGACCGATTCTCTGGCTCCAAGTCTGGCACGTCAGCCACCCTGGGCATCACCGGACT

CCAGACTGGGGACGAGGCCACTTATTACTGCGGAACTTGGGATAGCAGCCTGAATGGT

GGGGTGTTCGGCGGAGGGACCAAGGTCACCGTCCTAGGTTCTAGAGGTGGTGGTGGTA

GCGGCGGCGGCGGCTCTGGTGGTGGTGGATCCCTCGAGATGGCCGAGGTCCAGCTGGT

ACAGTCTGGGGCTGAGGTGAAGAAGCCTGGGGCCTCAGTGAAGGTTTCCTGCAAGGCA

TCTGGATACACCTTCACCAGCTACTATATGCACTGGGTGCGACAGGCCCCTGGACAAGG

GCTTGAGTGGATGGGAATAATCAACCCTAGTGGTGGTAGCACAAGCTACGCACAGAAG

TTCCAGGGCAGAGTCACCATGACCAGGGACACGTCCACGAGCACAGTCTACATGGAGC

TGAGCAGCCTGAGATCTGAGGACACGGCCGTGTATTACTGTGCGCGCGGTATGTCTTAC

TACTCTTCTATCGATAAATGGGGTCAAGGTACTCTGGTGACCGTCTCCTCA [SEQ ID NO: 247]

Amino Acid Sequence:
QSVLTQPPSVSAAPGQKVTISCSGSSSNIGNDYVSWYQQLPGTAPKLLIYENDQRPSGIPDRF

SGSKSGTSATLGITGLQTGDEATYYCGTWDSSLNGGVFGGGTKVTVLGSRGGGGSGGGGS

GGGGSLEMAEVQLVQSGAEVKKPGASVKVSCKASGYTFTSYYMHWVRQAPGQGLEWMG

IINPSGGSTSYAQKFQGRVTMTRDTSTSTVYMELSSLRSEDTAVYYCARGMSYYSSIDKWG

QGTLVTVSS [SEQ ID NO: 248]

APPENDIX C

Light Chain DNA Sequence:
CAGTCTGTGTTGACGCAGCCGCCCTCAGTGTCTGCGGCCCCAGGACAGAAGGTCACCAT

CTCCTGCTCTGGAAGCAGCTCCAACATTGGGAATGATTATGTATCGTGGTACCAGCAAC

TCCCAGGAACAGCCCCCAAACTCCTCATTTATGAAAATGATCAGCGACCCTCAGGGATT

CCTGACCGATTCTCTGGCTCCAAGTCTGGCACGTCAGCCACCCTGGGCATCACCGGACT

CCAGACTGGGGACGAGGCCACTTATTACTGCGGAACTTGGGATAGCAGCCTGAATGGT

GGGGTGTTCGGCGGAGGGACCAAGGTCACCGTCCTAGGT [SEQ ID NO: 249]

Light Chain Amino Acid Sequence:
QSVLTQPPSVSAAPGQKVTISCSGSSSNIGNDYVSWYQQLPGTAPKLLIYENDQRPSGIPDRF

SGSKSGTSATLGITGLQTGDEATYYCGTWDSSLNGGVFGGGTKVTVLG [SEQ ID NO: 250]

Heavy Chain DNA Sequence:
GAGGTCCAGCTGGTACAGTCTGGGGCTGAGGTGAAGAAGCCTGGGGCCTCAGTGAAGG

TTTCCTGCAAGGCATCTGGATACACCTTCACCAGCTACTATATGCACTGGGTGCGACAG

GCCCCTGGACAAGGGCTTGAGTGGATGGGAATAATCAACCCTAGTGGTGGTAGCACAA

GCTACGCACAGAAGTTCCAGGGCAGAGTCACCATGACCAGGGACACGTCCACGAGCAC

AGTCTACATGGAGCTGAGCAGCCTGAGATCTGAGGACACGGCCGTGTATTACTGTGCGC

GCGGTATGTCTTACTACTCTTCTATCGATAAATGGGGTCAAGGTACTCTGGTGACCGTCT

CCTCA [SEQ ID NO: 251]

Heavy Chain Amino Acid Sequence:
EVQLVQSGAEVKKPGASVKVSCKASGYTFTSYYMHWVRQAPGQGLEWMGIINPSGGSTSY

AQKFQGRVTMTRDTSTSTVYMELSSLRSEDTAVYYCARGMSYYSSIDKWGQGTLVTVSS

[SEQ ID NO: 252]

EXT009-12:
DNA Sequence:
CAGTCTGTCGTGACGCAGCCGCCCTCAGTGTCTGCGGCCCCAGGACAGAAGGTCACCAT

CTCCTGCTCTGGAAGCAGCTCCAACATTGGGAATAATTATGTATCCTGGTACCAGCAGC

TCCCAGGAACAGCCCCCAAACTCCTCATTTATGAAAATGATCAGCGACCCTCAGAGATT

CCTGACCGATTCTCTGGCTCCAAGTCTGGCACGTCAGCCACCCTGGGCATCACCGGACT

CCAGACTGGGGACGAGGCCACTTATTACTGCGGAACTTGGGATAACAGCCTGAATGGT

GGGGTGTTCGGCGGAGGGACCAAGCTGACCGTCCTAGGTTCTAGAGGTGGTGGTGGTA

GCGGCGGCGGCGGCTCTGGTGGTGGTGGATCCCTCGAGATGGCCCAGGTGCAGCTGGT

GCAGTCTGGGGCTGAGGTGAAGAAGCCTGGGGCCTCAGTGAAGGTTTCCTGCAAGGCA

TCTGGATACACCTTCACCAGCTACTATATGCACTGGGTGCGACAGGCCCCTGGACAAGG

GCTTGAGTGGATGGGAATAATCAACCCTAGTGGTGGTAGCACAAGCTACGCACAGAAG

TTCCAGGGCAGAGTCACCATGACCAGGGACACGTCCACGAGCACAGTCTACATGGAGC

TGAGCAGCCTGAGATCTGAGGACACTGCCGTGTATTACTGTGCGCGCGGTTACTACGAC

TCTGATCGTTGGGGTCAAGGTACTCTGGTGACCGTCTCCTCA [SEQ ID NO: 253]

Amino Acid Sequence:
QSVVTQPPSVSAAPGQKVTISCSGSSSNIGNNYVSWYQQLPGTAPKLLIYENDQRPSEIPDRF

SGSKSGTSATLGITGLQTGDEATYYCGTWDNSLNGGVFGGGTKLTVLGSRGGGGSGGGGS

APPENDIX C (continued)

GGGGSLEMAQVQLVQSGAEVKKPGASVKVSCKASGYTFTSYYMHWVRQAPGQGLEWMG

IINPSGGSTSYAQKFQGRVTMTRDTSTSTVYMELSSLRSEDTAVYYCARGYYDSDRWGQGT

LVTVSS [SEQ ID NO: 254]

Light Chain DNA Sequence:
CAGTCTGTCGTGACGCAGCCGCCCTCAGTGTCTGCGGCCCCAGGACAGAAGGTCACCAT

CTCCTGCTCTGGAAGCAGCTCCAACATTGGGAATAATTATGTATCCTGGTACCAGCAGC

TCCCAGGAACAGCCCCCAAACTCCTCATTTATGAAAATGATCAGCGACCCTCAGAGATT

CCTGACCGATTCTCTGGCTCCAAGTCTGGCACGTCAGCCACCCTGGGCATCACCGGACT

CCAGACTGGGGACGAGGCCACTTATTACTGCGGAACTTGGGATAACAGCCTGAATGGT

GGGGTGTTCGGCGGAGGGACCAAGCTGACCGTCCTAGGT [SEQ ID NO: 255]

Light Chain Amino Acid Sequence:
QSVVTQPPSVSAAPGQKVTISCSGSSSNIGNNYVSWYQQLPGTAPKLLIYENDQRPSEIPDRF

SGSKSGTSATLGITGLQTGDEATYYCGTWDNSLNGGVFGGGTKLTVLG [SEQ ID NO: 256]

Heavy Chain DNA Sequence:
CAGGTGCAGCTGGTGCAGTCTGGGGCTGAGGTGAAGAAGCCTGGGGCCTCAGTGAAGG

TTTCCTGCAAGGCATCTGGATACACCTTCACCAGCTACTATATGCACTGGGTGCGACAG

GCCCCTGGACAAGGGCTTGAGTGGATGGGAATAATCAACCCTAGTGGTGGTAGCACAA

GCTACGCACAGAAGTTCCAGGGCAGAGTCACCATGACCAGGGACACGTCCACGAGCAC

AGTCTACATGGAGCTGAGCAGCCTGAGATCTGAGGACACTGCCGTGTATTACTGTGCGC

GCGGTTACTACGACTCTGATCGTTGGGGTCAAGGTACTCTGGTGACCGTCTCCTCA

[SEQ ID NO: 257]

Heavy Chain Amino Acid Sequence:
QVQLVQSGAEVKKPGASVKVSCKASGYTFTSYYMHWVRQAPGQGLEWMGIINPSGGSTSY

AQKFQGRVTMTRDTSTSTVYMELSSLRSEDTAVYYCARGYYDSDRWGQGTLVTVSS

[SEQ ID NO: 258]

EXT009-13:
DNA Sequence:
CAGTCTGTGTTGACGCAGCCGCCCTCAGTGTCTGGGACTCCAGGGCAGAGGGTCACCAT

CTCCTGCACTGGGAGCAGCTCCAACCTCGGGGCAGGCTTTGATGTACACTGGTACCAGC

AGCTTCCAAGAACAGCCCCCAAACTCGTCATTTCTAGTGACAACAATCGGCCCTCAGGG

GTCCCTGACCGATTCTCTGCCTCTAAGTCTGGCACCTCGGCCTCCCTGGCCATCACTGGT

CTCCAGGCTGAGGATGAGGCTGATTATTACTGCCAGTCCTATGACAGCGGCCTGAGTGG

TTCGGTCTTCGGCGGAGGGACCAAGCTGACCGTCCTAGGTTCTAGAGGTGGTGGTGGTA

GCGGCGGCGGCGGCTCTGGTGGTGGTGGATCCCTCGAGATGGCCCAGGTGCAGCTGGT

GCAATCTGGAGCTGAGGTGAAGAAGCCTGGGGCCTCAGTGAAGGTCTCCTGCAAGGCT

TCTGGTTACACCTTTACCAGCTATGGTATCAGCTGGGTGCGACAGGCCCCTGGACAAGG

GCTTGAGTGGATGGGATGGATCAGCGCTTACAATGGTAACACAAACTATGCACAGAAG

CTCCAGGGCAGAGTCACCATGACCACAGACACATCCACGAGCACAGCCTACATGGAGC

TGAGGAGCCTGAGATCTGACGACACGGCCGTGTATTACTGTGCGCGCGGTTACTACTAC

TACGATTCTTGGGGTCAAGGTACTCTGGTGACCGTCTCCTCA [SEQ ID NO: 259]

APPENDIX C

Amino Acid Sequence:
QSVLTQPPSVSGTPGQRVTISCTGSSSNLGAGFDVHWYQQLPRTAPKLVISSDNNRPSGVPD

RFSASKSGTSASLAITGLQAEDEADYYCQSYDSGLSGSVFGGGTKLTVLGSRGGGGSGGGG

SGGGGSLEMAQVQLVQSGAEVKKPGASVKVSCKASGYTFTSYGISWVRQAPGQGLEWMG

WISAYNGNTNYAQKLQGRVTMTTDTSTSTAYMELRSLRSDDTAVYYCARGYYYYDSWGQ

GTLVTVSS [SEQ ID NO: 260]

Light Chain DNA Sequence:
CAGTCTGTGTTGACGCAGCCGCCCTCAGTGTCTGGGACTCCAGGGCAGAGGGTCACCAT

CTCCTGCACTGGGAGCAGCTCCAACCTCGGGGCAGGCTTTGATGTACACTGGTACCAGC

AGCTTCCAAGAACAGCCCCCAAACTCGTCATTTCTAGTGACAACAATCGGCCCTCAGGG

GTCCCTGACCGATTCTCTGCCTCTAAGTCTGGCACCTCGGCCTCCCTGGCCATCACTGGT

CTCCAGGCTGAGGATGAGGCTGATTATTACTGCCAGTCCTATGACAGCGGCCTGAGTGG

TTCGGTCTTCGGCGGAGGGACCAAGCTGACCGTCCTAGGT [SEQ ID NO: 261]

Light Chain Amino Acid Sequence:
QSVLTQPPSVSGTPGQRVTISCTGSSSNLGAGFDVHWYQQLPRTAPKLVISSDNNRPSGVPD

RFSASKSGTSASLAITGLQAEDEADYYCQSYDSGLSGSVFGGGTKLTVLG [SEQ ID NO: 262]

Heavy Chain DNA Sequence:
CAGGTGCAGCTGGTGCAATCTGGAGCTGAGGTGAAGAAGCCTGGGGCCTCAGTGAAGG

TCTCCTGCAAGGCTTCTGGTTACACCTTTACCAGCTATGGTATCAGCTGGGTGCGACAG

GCCCCTGGACAAGGGCTTGAGTGGATGGGATGGATCAGCGCTTACAATGGTAACACAA

ACTATGCACAGAAGCTCCAGGGCAGAGTCACCATGACCACAGACACATCCACGAGCAC

AGCCTACATGGAGCTGAGGAGCCTGAGATCTGACGACACGGCCGTGTATTACTGTGCGC

GCGGTTACTACTACTACGATTCTTGGGGTCAAGGTACTCTGGTGACCGTCTCCTCA

[SEQ ID NO: 263]

Heavy Chain Amino Acid Sequence:
QVQLVQSGAEVKKPGASVKVSCKASGYTFTSYGISWVRQAPGQGLEWMGWISAYNGNTN

YAQKLQGRVTMTTDTSTSTAYMELRSLRSDDTAVYYCARGYYYYDSWGQGTLVTVSS

[SEQ ID NO: 264]

EXT009-14:
DNA Sequence:
GACATCCAGTTGACCCAGTCTCCATCCTCCCTGTCTGCATCTGTCGGAGACAGCGTCAC

CATCACTTGCCAGGCGAGTCAGCACATTACCAAGTATTTAAATTGGTATCAGCAGAAAC

CAGGGAAAGCCCCTAAGCTCCTGATTTCCGATGCATCCGTTTTGGAAAAAGGGGTCCCA

TCTAGGTTCGGTGGAAGTGGATCTGGGACAGATTTTACTTTCACCATCAGCAGGCTGCA

GCCTGAAGACATTGCAACATATTACTGTCAACAGTATGAGAATCTCCCGCTCACTTTCG

GCGGAGGGACCAAGCTGGAGATCAAACGTTCTAGAGGTGGTGGTGGTAGCGGCGGCGG

CGGCTCTGGTGGTGGTGGATCCCTCGAGATGGCCCAGGTGCAGCTGGTGCAGTCTGGGG

CTGAGGTGAAGAAGCCTGGGGCCTCAGTGAGGCTTTCCTGCAAGGCGCCTGGAAACAC

CTTCACCAGCTACTATCTACATTGGGTGCGACAGGCCCCTGGACAAGGGCTTGAGTGGA

TGGGAATAATCAACCCTAGTGGTGGTTCCACAAACTACGCACAGAAGTTCCAGGGCAG

APPENDIX C

AGTCACCATGACCAGGGACACGTCCACGAGTACAGTCTACATGGAGATGAGCAGTCTG

AGATCTGACGACACTGCCGTGTATTACTGTGCGCGCTCTGGTGGTTACTGGTCTTTCGAT

TCTTGGGGTCAAGGTACTCTGGTGACCGTCTCCTCA [SEQ ID NO: 265]

Amino Acid Sequence:
DIQLTQSPSSLSASVGDSVTITCQASQHITKYLNWYQQKPGKAPKLLISDASVLEKGVPSRFG

GSGSGTDFTFTISRLQPEDIATYYCQQYENLPLTFGGGTKLEIKRSRGGGGSGGGGSGGGGS

LEMAQVQLVQSGAEVKKPGASVRLSCKAPGNTFTSYYLHWVRQAPGQGLEWMGIINPSGG

STNYAQKFQGRVTMTRDTSTSTVYMEMSSLRSDDTAVYYCARSGGYWSFDSWGQGTLVT

VSS [SEQ ID NO: 266]

Light Chain DNA Sequence:
GACATCCAGTTGACCCAGTCTCCATCCTCCCTGTCTGCATCTGTCGGAGACAGCGTCAC

CATCACTTGCCAGGCGAGTCAGCACATTACCAAGTATTTAAATTGGTATCAGCAGAAAC

CAGGGAAAGCCCCTAAGCTCCTGATTTCCGATGCATCCGTTTTGGAAAAAGGGGTCCCA
TCTAGGTTCGGTGGAAGTGGATCTGGGACAGATTTTACTTTCACCATCAGCAGGCTGCA

GCCTGAAGACATTGCAACATATTACTGTCAACAGTATGAGAATCTCCCGCTCACTTTCG

GCGGAGGGACCAAGCTGGAGATCAAACGT [SEQ ID NO: 267]

Light Chain Amino Acid Sequence:
DIQLTQSPSSLSASVGDSVTITCQASQHITKYLNWYQQKPGKAPKLLISDASVLEKGVPSRFG

GSGSGTDFTFTISRLQPEDIATYYCQQYENLPLTFGGGTKLEIKR [SEQ ID NO: 268]

Heavy Chain DNA Sequence:
CAGGTGCAGCTGGTGCAGTCTGGGGCTGAGGTGAAGAAGCCTGGGGCCTCAGTGAGGC

TTTCCTGCAAGGCGCCTGGAAACACCTTCACCAGCTACTATCTACATTGGGTGCGACAG

GCCCCTGGACAAGGGCTTGAGTGGATGGGAATAATCAACCCTAGTGGTGGTTCCACAA

ACTACGCACAGAAGTTCCAGGGCAGAGTCACCATGACCAGGGACACGTCCACGAGTAC

AGTCTACATGGAGATGAGCAGTCTGAGATCTGACGACACTGCCGTGTATTACTGTGCGC

GCTCTGGTGGTTACTGGTCTTTCGATTCTTGGGGTCAAGGTACTCTGGTGACCGTCTCCT

CA [SEQ ID NO: 269]

Heavy Chain Amino Acid Sequence:
QVQLVQSGAEVKKPGASVRLSCKAPGNTFTSYYLHWVRQAPGQGLEWMGIINPSGGSTNY

AQKFQGRVTMTRDTSTSTVYMEMSSLRSDDTAVYYCARSGGYWSFDSWGQGTLVTVSS

[SEQ ID NO: 270]

EXT009-15:
DNA Sequence:
CAGTCTGTGTTGACGCAGCCGCCCTCAGTGTCTGCGGCCCCAGGACAAAAGGTCACCAT

CTCCTGCTCTGGAAGCACCTCCAACATTGGAAATAATTATGTATCCTGGTACCAGCAAC

TCCCAGGAACAGCCCCCAAACTCGTCATTTATGACAATGATAATCGACCCTCAGGGATT

CCTGACCGATTCTCTGGCTCCAAGTCTGGCACGTCAGCCACCCTGGGCATCACCGGACT

CCACACTGGGGACGAGGCCGATTATTACTGCGGAACATGGGATAGCAGCCTGAGTGCT

GGGGTGTTCGGCGGAGGGACCAAGCTGACCGTCCTAGGTTCTAGAGGTGGTGGTGGTA

GCGGCGGCGGCGGCTCTGGTGGTGGTGGATCCCTCGAGATGGCCGAGGTGCAGCTGGT

GGAGTCTGGGGGAGGCTTAGTACAGCCGGGGGGGTCCCTGAGACTCTCCTGTGCAGCCT

CTGGATTCTACTTTAGCGGCTTTGCCATGAGCTGGGTCCGCCAGGCTCCAGGGAAGGGG

APPENDIX C

CTGGAGTGGCTCTCAGTTGTTTTTAACGATGGCAGTACCACATTCTATGCAGACTCCGTG

AAGGGCCGGTTCACCATGTCCAGAGATGATTCCAAGAACACAATTTCTCTGCAAATGAA

CAGCCTGAGAGCCGAAGACACGGCCGTATATTACTGTGCGCGCCAGTCTCCGTTCTACT

TCGACGGTCCGTACGATTACTGGGGTCAAGGTACTCTGGTGACCGTCTCCTCA [SEQ ID NO: 271]

Amino Acid Sequence:
QSVLTQPPSVSAAPGQKVTISCSGSTSNIGNNYVSWYQQLPGTAPKLVIYDNDNRPSGIPDRF

SGSKSGTSATLGITGLHTGDEADYYCGTWDSSLSAGVFGGGTKLTVLGSRGGGGSGGGGS

GGGGSLEMAEVQLVESGGGLVQPGGSLRLSCAASGFYFSGFAMSWVRQAPGKGLEWLSV

VFNDGSTTFYADSVKGRFTMSRDDSKNTISLQMNSLRAEDTAVYYCARQSPFYFDGPYDY

WGQGTLVTVSS [SEQ ID NO: 272]

Light Chain DNA Sequence:
CAGTCTGTGTTGACGCAGCCGCCCTCAGTGTCTGCGGCCCCAGGACAAAAGGTCACCAT

CTCCTGCTCTGGAAGCACCTCCAACATTGGAAATAATTATGTATCCTGGTACCAGCAAC

TCCCAGGAACAGCCCCCAAACTCGTCATTTATGACAATGATAATCGACCCTCAGGGATT

CCTGACCGATTCTCTGGCTCCAAGTCTGGCACGTCAGCCACCCTGGGCATCACCGGACT

CCACACTGGGGACGAGGCCGATTATTACTGCGGAACATGGGATAGCAGCCTGAGTGCT

GGGGTGTTCGGCGGAGGGACCAAGCTGACCGTCCTAGGT [SEQ ID NO: 273]

Light Chain Amino Acid Sequence:
QSVLTQPPSVSAAPGQKVTISCSGSTSNIGNNYVSWYQQLPGTAPKLVIYDNDNRPSGIPDRF

SGSKSGTSATLGITGLHTGDEADYYCGTWDSSLSAGVFGGGTKLTVLG [SEQ ID NO: 274]

Heavy Chain DNA Sequence:
GAGGTGCAGCTGGTGGAGTCTGGGGGAGGCTTAGTACAGCCGGGGGGTCCCTGAGAC

TCTCCTGTGCAGCCTCTGGATTCTACTTTAGCGGCTTTGCCATGAGCTGGGTCCGCCAGG

CTCCAGGGAAGGGGCTGGAGTGGCTCTCAGTTGTTTTTAACGATGGCAGTACCACATTC

TATGCAGACTCCGTGAAGGGCCGGTTCACCATGTCCAGAGATGATTCCAAGAACACAAT

TTCTCTGCAAATGAACAGCCTGAGAGCCGAAGACACGGCCGTATATTACTGTGCGCGCC

AGTCTCCGTTCTACTTCGACGGTCCGTACGATTACTGGGGTCAAGGTACTCTGGTGACC

GTCTCCTCA [SEQ ID NO: 275]

Heavy Chain Amino Acid Sequence:
EVQLVESGGGLVQPGGSLRLSCAASGFYFSGFAMSWVRQAPGKGLEWLSVVFNDGSTTFY

ADSVKGRFTMSRDDSKNTISLQMNSLRAEDTAVYYCARQSPFYFDGPYDYWGQGTLVTVSS

[SEQ ID NO: 276]

EXT009-18:
DNA Sequence:
CAGTCTGTGTTGACGCAGCCGCCCTCAGTGTCTGCGGCCCCAGGACAGAGGGTCACCAT

CTCCTGCTCTGGAACCAGTTCCAACATTGGGAACAGTTATGTCTCCTGGTACCAGCAGC

TCCCAGGAACAGCCCCCAAACTCCTCATTTTTGACAATAATAAGCGACCCTCAGGGGTT

CCTGACCGATTCTCTGGCTCCAAGTCTGGCACGTCAGCCACCCTGGGCATCACCGGACT

CCAGACTGGCGACGAGGCCACTTATTACTGCGGAACCTGGGATACCAGCCTGAGTTCTG

TCTGGATGTTCGGCGGAGGGACCAAGGTCACCGTCCTAGGTTCTAGAGGTGGTGGTGGT

AGCGGCGGCGGCGGCTCTGGTGGTGGTGGATCCCTCGAGATGGCCCAGGTGCAGCTGG

TGCAGTCTGGGGCTGAGGTGAAGAAGCCTGGGGCCTCAGTGAAGGTTTCCTGCAAGGC

-continued

APPENDIX C

ATCTGGATACACCTTCACCAGCTACTATATGCACTGGGTGCGACAGGCCCCTGGACAAG

GGCTTGAGTGGATGGGAATAATCAACCCTAGTGGTGGTAGCACAAGCTACGCACAGAA

GTTCCAGGGCAGAGTCACCATGACCAGGGACACGTCCACGAGCACAGTCTACATGGAG

CTGAGCAGCCTGAGATCTGAGGACACTGCCGTGTATTACTGTGCGCGCGGTTACTACGG

TGACACTACTGGTGATAACTGGGGTCAAGGTACTCTGGTGACCGTCTCCTCA [SEQ ID NO: 277]

Amino Acid Sequence:
QSVLTQPPSVSAAPGQRVTISCSGTSSNIGNSYVSWYQQLPGTAPKLLIFDNNKRPSGVPDRF

SGSKSGTSATLGITGLQTGDEATYYCGTWDTSLSSVWMFGGGTKVTVLGSRGGGGSGGGG

SGGGGSLEMAQVQLVQSGAEVKKPGASVKVSCKASGYTFTSYYMHWVRQAPGQGLEWM

GIINPSGGSTSYAQKFQGRVTMTRDTSTSTVYMELSSLRSEDTAVYYCARGYYGDTTGDNW

GQGTLVTVSS [SEQ ID NO: 278]

Light Chain DNA Sequence:
CAGTCTGTGTTGACGCAGCCGCCCTCAGTGTCTGCGGCCCCAGGACAGAGGGTCACCAT

CTCCTGCTCTGGAACCAGTTCCAACATTGGGAACAGTTATGTCTCCTGGTACCAGCAGC

TCCCAGGAACAGCCCCCAAACTCCTCATTTTTGACAATAATAAGCGACCCTCAGGGGTT

CCTGACCGATTCTCTGGCTCCAAGTCTGGCACGTCAGCCACCCTGGGCATCACCGGACT

CCAGACTGGCGACGAGGCCACTTATTACTGCGGAACCTGGGATACCAGCCTGAGTTCTG

TCTGGATGTTCGGCGGAGGGACCAAGGTCACCGTCCTAGGT [SEQ ID NO: 279]

Light Chain Amino Acid Sequence:
QSVLTQPPSVSAAPGQRVTISCSGTSSNIGNSYVSWYQQLPGTAPKLLIFDNNKRPSGVPDRF

SGSKSGTSATLGITGLQTGDEATYYCGTWDTSLSSVWMFGGGTKVTVLG [SEQ ID NO: 280]

Heavy Chain DNA Sequence:
CAGGTGCAGCTGGTGCAGTCTGGGGCTGAGGTGAAGAAGCCTGGGGCCTCAGTGAAGG

TTTCCTGCAAGGCATCTGGATACACCTTCACCAGCTACTATATGCACTGGGTGCGACAG

GCCCCTGGACAAGGGCTTGAGTGGATGGGAATAATCAACCCTAGTGGTGGTAGCACAA

GCTACGCACAGAAGTTCCAGGGCAGAGTCACCATGACCAGGGACACGTCCACGAGCAC

AGTCTACATGGAGCTGAGCAGCCTGAGATCTGAGGACACTGCCGTGTATTACTGTGCGC

GCGGTTACTACGGTGACACTACTGGTGATAACTGGGGTCAAGGTACTCTGGTGACCGTC

TCCTCA [SEQ ID NO: 281]

Heavy Chain Amino Acid Sequence:
QVQLVQSGAEVKKPGASVKVSCKASGYTFTSYYMHWVRQAPGQGLEWMGIINPSGGSTSY

AQKFQGRVTMTRDTSTSTVYMELSSLRSEDTAVYYCARGYYGDTTGDNWGQGTLVTVSS

[SEQ ID NO: 282]

EXT009-19:
DNA Sequence:
CAGTCTGTGTTGACGCAGCCGCCCTCAGTGTCTGCGGCCCCAGGACAGAAGGTCACCAT

CTCCTGCTCTGGAAGCAGCTCCAACATTGGGAATGATTATGTATCGTGGTACCAGCAAC

TCCCAGGAACAGCCCCCAAACTCCTCATTTATGAAAATGATCAGCGACCCTCAGGGATT

CCTGACCGATTCTCTGGCTCCAAGTCTGGCACGTCAGCCACCCTGGGCATCACCGGACT

CCAGACTGGGGACGAGGCCACTTATTACTGCGGAACTTGGGATAGCAGCCTGAATGGT

GGGGTGTTCGGCAGAGGGACCAAGCTGACCGTCCTAGGTTCTAGAGGTGGTGGTGGTA

GCGGCGGCGGCGGCTCTGGTGGTGGTGGATCCCTCGAGATGGCCCAGGTGCAGCTGGT

-continued

APPENDIX C

GCAGTCTGGGGCTGAGGTGAAGAAGCCTGGGGCCTCAGTGAAGGTCTCCTGCAAGGCA

TCTGGATACACCTTCACCAGCTACTATATGCACTGGGTGCGACAGGCCCCTGGACAAGG

GCTTGAGTGGATGGGAATAATCAACCCTAGTGGTGGTAGCACAAGCTACGCACAGAAG

TTCCAGGGCAGAGTCACCATGACCAGGGACACGTCCACGAGCACAGTCTACATGGAGC

TGAGCAGGCTGAGATCTGACGACACGGCCGTGTATTACTGTGCGCGCGGTTACGGTACT

TCTGATTCTTGGGGTCAAGGTACTCTGGTGACCGTCTCCTCA [SEQ ID NO: 283]

Amino Acid Sequence:
QSVLTQPPSVSAAPGQKVTISCSGSSSNIGNDYVSWYQQLPGTAPKLLIYENDQRPSGIPDRF

SGSKSGTSATLGITGLQTGDEATYYCGTWDSSLNGGVFGRGTKLTVLGSRGGGGSGGGGS

GGGGSLEMAQVQLVQSGAEVKKPGASVKVSCKASGYTFTSYYMHWVRQAPGQGLEWMG

IINPSGGSTSYAQKFQGRVTMTRDTSTSTVYMELSRLRSDDTAVYYCARGYGTSDSWGQGT

LVTVSS [SEQ ID NO: 284]

Light Chain DNA Sequence:
CAGTCTGTGTTGACGCAGCCGCCCTCAGTGTCTGCGGCCCCAGGACAGAAGGTCACCAT

CTCCTGCTCTGGAAGCAGCTCCAACATTGGGAATGATTATGTATCGTGGTACCAGCAAC

TCCCAGGAACAGCCCCCAAACTCCTCATTTATGAAAATGATCAGCGACCCTCAGGGATT

CCTGACCGATTCTCTGGCTCCAAGTCTGGCACGTCAGCCACCCTGGGCATCACCGGACT

CCAGACTGGGGACGAGGCCACTTATTACTGCGGAACTTGGGATAGCAGCCTGAATGGT

GGGGTGTTCGGCAGAGGGACCAAGCTGACCGTCCTAGGT [SEQ ID NO: 285]

Light Chain Amino Acid Sequence:
QSVLTQPPSVSAAPGQKVTISCSGSSSNIGNDYVSWYQQLPGTAPKLLIYENDQRPSGIPDRF

SGSKSGTSATLGITGLQTGDEATYYCGTWDSSLNGGVFGRGTKLTVLG [SEQ ID NO: 286]

Heavy Chain DNA Sequence:
CAGGTGCAGCTGGTGCAGTCTGGGGCTGAGGTGAAGAAGCCTGGGGCCTCAGTGAAGG

TCTCCTGCAAGGCATCTGGATACACCTTCACCAGCTACTATATGCACTGGGTGCGACAG

GCCCCTGGACAAGGGCTTGAGTGGATGGGAATAATCAACCCTAGTGGTGGTAGCACAA

GCTACGCACAGAAGTTCCAGGGCAGAGTCACCATGACCAGGGACACGTCCACGAGCAC

AGTCTACATGGAGCTGAGCAGGCTGAGATCTGACGACACGGCCGTGTATTACTGTGCGC

GCGGTTACGGTACTTCTGATTCTTGGGGTCAAGGTACTCTGGTGACCGTCTCCTCA

[SEQ ID NO: 287]

Heavy Chain Amino Acid Sequence:
QVQLVQSGAEVKKPGASVKVSCKASGYTFTSYYMHWVRQAPGQGLEWMGIINPSGGSTSY

AQKFQGRVTMTRDTSTSTVYMELSRLRSDDTAVYYCARGYGTSDSWGQGTLVTVSS

[SEQ ID NO: 288]

EXT009-21:
DNA Sequence:
CAGTCTGTGTTGACGCAGCCGCCCTCAGCGTCTGAGACCCCCGGGCAGAGGGTCACCAT

CTCTTGTTCTGGAAGCAGCTCCAACATCGGAAGTAGGACTGTAAACTGGTACCAGCAGC

TCCCAGGAACGGCCCCCAAACTCCTCATCTATAGTAATACTCAGCGGCCCTCAGGGGTC

CCTGACCGATTCTCTGGCTCCAAGTCTGGCACCTCAGCCTCCCTGGCCATCAGTGGGCTC

CAGTCTGAGGATGAGGCTGATTACTACTGTGCAGCATGGGATGACAGTCTGAATGGTCA

GGTCTTCGGAACTGGGACCAAGGTCACCGTCCTAGGTTCTAGAGGTGGTGGTGGTAGCG

APPENDIX C

GCGGCGGCGGCTCTGGTGGTGGTGGATCCCTCGAGATGGCCGAGGTCCAGCTGGTGCA

GTCTGGGGCTGAGGTGAAGAAGCCTGGGTCCTCGGTGAAGGTCTCCTGCAAGGCTTCTG

GAGGCACCTTCAACGACTATAGTGTCAGCTGGGTGCGACAGTCCCCTGGACAAGGGCTT

GAGTGGATGGGAAGGATCATCCCCGTCCTTGATATGACAACCGTCGCACAGAAATTCCA

GGGCAGAGTCACAATTAACGCGGACAAATCGACGAGCACAGTGAACATGGAGCTGAGC

AGCCTCAGATCTGATGACACGGCCGTGTATTACTGTGCGCGCTACTACGGTGACTACTC

TGATCCGTGGGGTCAAGGTACTCTGGTGACCGTCTCCTCA [SEQ ID NO: 289]

Amino Acid Sequence:
QSVLTQPPSASETPGQRVTISCSGSSSNIGSRTVNWYQQLPGTAPKLLIYSNTQRPSGVPDRFS

GSKSGTSASLAISGLQSEDEADYYCAAWDDSLNGQVFGTGTKVTVLGSRGGGGSGGGGSG

GGGSLEMAEVQLVQSGAEVKKPGSSVKVSCKASGGTFNDYSVSWVRQSPGQGLEWMGRII

PVLDMTTVAQKFQGRVTINADKSTSTVNMELSSLRSDDTAVYYCARYYGDYSDPWGQGTL

VTVSS [SEQ ID NO: 290]

Light Chain DNA Sequence:
CAGTCTGTGTTGACGCAGCCGCCCTCAGCGTCTGAGACCCCCGGGCAGAGGGTCACCAT

CTCTTGTTCTGGAAGCAGCTCCAACATCGGAAGTAGGACTGTAAACTGGTACCAGCAGC

TCCCAGGAACGGCCCCCAAACTCCTCATCTATAGTAATACTCAGCGGCCCTCAGGGGTC

CCTGACCGATTCTCTGGCTCCAAGTCTGGCACCTCAGCCTCCCTGGCCATCAGTGGGCTC

CAGTCTGAGGATGAGGCTGATTACTACTGTGCAGCATGGGATGACAGTCTGAATGGTCA

GGTCTTCGGAACTGGGACCAAGGTCACCGTCCTAGGT [SEQ ID NO: 291]

Light Chain Amino Acid Sequence:
QSVLTQPPSASETPGQRVTISCSGSSSNIGSRTVNWYQQLPGTAPKLLIYSNTQRPSGVPDRFS

GSKSGTSASLAISGLQSEDEADYYCAAWDDSLNGQVFGTGTKVTVLG [SEQ ID NO: 292]

Heavy Chain DNA Sequence
GAGGTCCAGCTGGTGCAGTCTGGGGCTGAGGTGAAGAAGCCTGGGTCCTCGGTGAAGG

TCTCCTGCAAGGCTTCTGGAGGCACCTTCAACGACTATAGTGTCAGCTGGGTGCGACAG

TCCCCTGGACAAGGGCTTGAGTGGATGGGAAGGATCATCCCCGTCCTTGATATGACAAC

CGTCGCACAGAAATTCCAGGGCAGAGTCACAATTAACGCGGACAAATCGACGAGCACA

GTGAACATGGAGCTGAGCAGCCTCAGATCTGATGACACGGCCGTGTATTACTGTGCGCG

CTACTACGGTGACTACTCTGATCCGTGGGGTCAAGGTACTCTGGTGACCGTCTCCTCA

[SEQ ID NO: 293]

Heavy Chain Amino Acid Sequence:
EVQLVQSGAEVKKPGSSVKVSCKASGGTFNDYSVSWVRQSPGQGLEWMGRIIPVLDMTTV

AQKFQGRVTINADKSTSTVNMELSSLRSDDTAVYYCARYYGDYSDPWGQGTLVTVSS

[SEQ ID NO: 294]

EXT009-23:
DNA Sequence:
CAGTCTGTGTTGACTCAGCCGCCCTCAGTGTCTGCGGCCCCAGGACAGAAGGTCACCAT

CTCCTGCTCGGGCAGCAACTCGAACATTGAACATAATTATGTCTCCTGGTATCAGCAAT

TCCCAGGAACAGCCCCCAAACTCCTCATTTATGACAATGATAAGCGACCCTCAGGGATT

CCTGACCGATTCTCTGGCTCCAAGTCTGGCACGTCAGCCACCCTGGGCATCACCGGACT

CCAGACTGGGGACGAGGCCGAATATTACTGCGGAACATGGGATAACACCCTGAGTTCTT

APPENDIX C

TTGTCTTCGGAAGTGGGACCAAGGTCACCGTCCTAGGTTCTAGAGGTGGTGGTGGTAGC

GGCGGCGGCGGCTCTGGTGGTGGTGGATCCCTCGAGATGGCCCAGGTGCAGCTGGTGC

AGTCTGGGGGAGGCGTGGTCCAGCCTGGGAGGTCCCTGAGACTCTCCTGTGCAGCCTCT

GGATTCACCTTCAGTAGCTATAGCATGAACTGGGTCCGCCAGGCTCCAGGGAAGGGGCT

GGAGTGGGTCTCAGTTATTTCTAGCGGTGGTAACACATACTACGCAGACTCCGTGAAGG

GCCGATTCACCATCTCCAGAGACAATTCCAAGAACACGCTGTATCTTCAAATGAACAGC

CTGAGAGCCGGGGACACTGCCGTGTATTACTGTGCGCGCGAAGGTTACATGTACGTTGA

TCATTGGGGTCAAGGTACTCTGGTGACCGTCTCCTCA [SEQ ID NO: 295]

Amino Acid Sequence:
QSVLTQPPSVSAAPGQKVTISCSGSNSNIEHNYVSWYQQFPGTAPKLLIYDNDKRPSGIPDRF

SGSKSGTSATLGITGLQTGDEAEYYCGTWDNTLSSFVFGSGTKVTVLGSRGGGGSGGGGSG

GGGSLEMAQVQLVQSGGGVVQPGRSLRLSCAASGFTFSSYSMNWVRQAPGKGLEWVSVIS

SGGNTYYADSVKGRFTISRDNSKNTLYLQMNSLRAGDTAVYYCAREGYMYVDHWGQGTL

VTVSS [SEQ ID NO: 296]

Light Chain DNA Sequence:
CAGTCTGTGTTGACTCAGCCGCCCTCAGTGTCTGCGGCCCCAGGACAGAAGGTCACCAT

CTCCTGCTCGGGCAGCAACTCGAACATTGAACATAATTATGTCTCCTGGTATCAGCAAT

TCCCAGGAACAGCCCCCAAACTCCTCATTTATGACAATGATAAGCGACCCTCAGGGATT

CCTGACCGATTCTCTGGCTCCAAGTCTGGCACGTCAGCCACCCTGGGCATCACCGGACT

CCAGACTGGGGACGAGGCCGAATATTACTGCGGAACATGGGATAACACCCTGAGTTCTT

TTGTCTTCGGAAGTGGGACCAAGGTCACCGTCCTAGGT [SEQ ID NO: 297]

Light Chain Amino Acid Sequence:
QSVLTQPPSVSAAPGQKVTISCSGSNSNIEHNYVSWYQQFPGTAPKLLIYDNDKRPSGIPDRF

SGSKSGTSATLGITGLQTGDEAEYYCGTWDNTLSSFVFGSGTKVTVLG [SEQ ID NO: 298]

Heavy Chain DNA Sequence:
CAGGTGCAGCTGGTGCAGTCTGGGGGAGGCGTGGTCCAGCCTGGGAGGTCCCTGAGAC

TCTCCTGTGCAGCCTCTGGATTCACCTTCAGTAGCTATAGCATGAACTGGGTCCGCCAG

GCTCCAGGGAAGGGGCTGGAGTGGGTCTCAGTTATTTCTAGCGGTGGTAACACATACTA

CGCAGACTCCGTGAAGGGCCGATTCACCATCTCCAGAGACAATTCCAAGAACACGCTGT

ATCTTCAAATGAACAGCCTGAGAGCCGGGGACACTGCCGTGTATTACTGTGCGCGCGAA

GGTTACATGTACGTTGATCATTGGGGTCAAGGTACTCTGGTGACCGTCTCCTCA [SEQ ID NO: 299]

Heavy Chain Amino Acid Sequence:
QVQLVQSGGGVVQPGRSLRLSCAASGFTFSSYSMNWVRQAPGKGLEWVSVISSGGNTYYA

DSVKGRFTISRDNSKNTLYLQMNSLRAGDTAVYYCAREGYMYVDHWGQGTLVTVSS [SEQ ID NO: 300]

EXT009-25:
DNA Sequence:
GACATCCAGTTGACCCAGTCTCCATCCTCCCTGTCTGCATCTGTAGGAGACAGAGTCAC

CATCACTTGCCGGGCAAGTCAGAGCATTAGCAGCTATTTAAATTGGTATCAGCAGAAAC

CAGGGAAAGCCCCTAAGCTCCTGATCTATGCTGCATCCAGTTTGCAAAGTGGGGTCCCA

TCAAGGTTCAGTGGCAGTGGATCTGGGACAGATTTCACTCTCGCCATCAGCAGTCTGCA

ACCTGAAGATTTTGCAACTTACTTCTGTCAACAGAGTTACAGTCTTCCGCTCACTTTCGG

CGGAGGGACCAAGCTGGAGATCAAACGTTCTAGAGGTGGTGGTGGTAGCGGCGGCGGC

-continued

APPENDIX C

GGCTCTGGTGGTGGTGGATCCCTCGAGATGGCCCAGGTGCAGCTGGTGCAGTCTGGGGC

TGAGGTGAAGAAGCCTGGGGCCTCAGTGAGGGTCTCCTGCAAGGCATCTGGGAACAGC

TTCAGCACCTATTATATCCACTGGGTGCGACAGGCCCCTGGACAAGGACTTGAGTGGAT

GGGAATAATCAACCCTACTATTGGTAGCAGAGTCTATGCACCGAAGTTCCAGGGCAGA

GTCACCATGACCAGGGACACGTCCACGAGCACAGTCTACATGGAACTGAGCAGCCTGA

CATCTGAGGACACTGCCGTGTATTACTGTGCGCGCTCTGTTACTTGGGTTCTGAAAGATG

GTTGGGGTCAAGGTACTCTGGTGACCGTCTCCTCA [SEQ ID NO: 301]

Amino Acid Sequence:
DIQLTQSPSSLSASVGDRVTITCRASQSISSYLNWYQQKPGKAPKLLIYAASSLQSGVPSRFS

GSGSGTDFTLAISSLQPEDFATYFCQQSYSLPLTFGGGTKLEIKRSRGGGGSGGGGSGGGGSL

EMAQVQLVQSGAEVKKPGASVRVSCKASGNSFSTYYIHWVRQAPGQGLEWMGIINPTIGSR

VYAPKFQGRVTMTRDTSTSTVYMELSSLTSEDTAVYYCARSVTWVLKDGWGQGTLVTVSS

[SEQ ID NO: 302]

Light Chain DNA Sequence:
GACATCCAGTTGACCCAGTCTCCATCCTCCCTGTCTGCATCTGTAGGAGACAGAGTCAC

CATCACTTGCCGGGCAAGTCAGAGCATTAGCAGCTATTTAAATTGGTATCAGCAGAAAC

CAGGGAAAGCCCCTAAGCTCCTGATCTATGCTGCATCCAGTTTGCAAAGTGGGGTCCCA

TCAAGGTTCAGTGGCAGTGGATCTGGGACAGATTTCACTCTCGCCATCAGCAGTCTGCA

ACCTGAAGATTTTGCAACTTACTTCTGTCAACAGAGTTACAGTCTTCCGCTCACTTTCGG

CGGAGGGACCAAGCTGGAGATCAAACGT [SEQ ID NO: 303]

Light Chain Amino Acid Sequence:
DIQLTQSPSSLSASVGDRVTITCRASQSISSYLNWYQQKPGKAPKLLIYAASSLQSGVPSRFS

GSGSGTDFTLAISSLQPEDFATYFCQQSYSLPLTFGGGTKLEIKR [SEQ ID NO: 304]

Heavy Chain DNA Sequence:
CAGGTGCAGCTGGTGCAGTCTGGGGCTGAGGTGAAGAAGCCTGGGGCCTCAGTGAGGG

TCTCCTGCAAGGCATCTGGGAACAGCTTCAGCACCTATTATATCCACTGGGTGCGACAG

GCCCCTGGACAAGGACTTGAGTGGATGGGAATAATCAACCCTACTATTGGTAGCAGAGT

CTATGCACCGAAGTTCCAGGGCAGAGTCACCATGACCAGGGACACGTCCACGAGCACA

GTCTACATGGAACTGAGCAGCCTGACATCTGAGGACACTGCCGTGTATTACTGTGCGCG

CTCTGTTACTTGGGTTCTGAAAGATGGTTGGGGTCAAGGTACTCTGGTGACCGTCTCCTCA

[SEQ ID NO: 305]

Heavy Chain Amino Acid Sequence:
QVQLVQSGAEVKKPGASVRVSCKASGNSFSTYYIEWVRQAPGQGLEWMGIINPTIGSRVYA

PKFQGRVTMTRDTSTSTVYMELSSLTSEDTAVYYCARSVTWVLKDGWGQGTLVTVSS [SEQ ID NO: 306]

EXT009-27:
DNA Sequence:
GACATCCAGTTGACCCAGTCTCCATCCTCCCTGTCTGCATCTGTTGGAGACAGAGTCAC

CATCACTTGCCGGGCGAGTCAGGACATTGGCAATTATGTAGCCTGGTATCAGCAGAAAG

TAGGGAAAGTTCCTAACCTCCTGATCTATGATGCATCCACTTTGCAATCAGGAGTCCCA

TCTCGGTTCAGCGGCAGTGGATCTCGGACAGAGTTCACTCTCACCATCAGCAGTCTGCA

GCCTGAAGATGTTGCAACTTATTACTGTCAAAAGTATAACACTGCCCCTGGGTTCGGCC

AAGGGACCAAGGTGGAAATCAAACGTTCTAGAGGTGGTGGTGGTAGCGGCGGCGGCGG

-continued

APPENDIX C

CTCTGGTGGTGGTGGATCCCTCGAGATGGCCCAGATGCAGCTGGTGCAGTCTGGGGCTG

AGGTGAAGAAGCCTGGGGCCTCAGTGAAGGTTTCCTGCAAGGCATCTGGATACACCTTC

ACCAGCTACTATATGCACTGGGTGCGACAGGCCCCTGGACAAGGGCTTGAGTGGATGG

GAATAATCAACCCTAGTGGTGGTAGCACAAGCTACGCACAGAAGTTCCAGGGCAGAGT

CACCATGACCAGGGACACGTCCACGAGCACAGTCTACATGGAGCTGAGCAGCCTGAGA

TCTGAGGACACGGCCGTGTATTACTGTGCGCGCTCTTCTATCGGTTGGCTGTCTTACCTG

GATGCTTGGGGTCAAGGTACTCTGGTGACCGTCTCCTCA [SEQ ID NO: 307]

Amino Acid Sequence:
DIQLTQSPSSLSASVGDRVTITCRASQDIGNYVAWYQQKVGKVPNLLIYDASTLQSGVPSRF

SGSGSRTEFTLTISSLQPEDVATYYCQKYNTAPGFGQGTKVEIKRSRGGGGSGGGGSGGGGS

LEMAQMQLVQSGAEVKKPGASVKVSCKASGYTFTSYYMHWVRQAPGQGLEWMGIINPSG

GSTSYAQKFQGRVTMTRDTSTSTVYMELSSLRSEDTAVYYCARSSIGWLSYLDAWGQGTL

VTVSS [SEQ ID NO: 308]

Light Chain DNA Sequence:
GACATCCAGTTGACCCAGTCTCCATCCTCCCTGTCTGCATCTGTTGGAGACAGAGTCAC

CATCACTTGCCGGGCGAGTCAGGACATTGGCAATTATGTAGCCTGGTATCAGCAGAAAG

TAGGGAAAGTTCCTAACCTCCTGATCTATGATGCATCCACTTTGCAATCAGGAGTCCCA

TCTCGGTTCAGCGGCAGTGGATCTCGGACAGAGTTCACTCTCACCATCAGCAGTCTGCA

GCCTGAAGATGTTGCAACTTATTACTGTCAAAAGTATAACACTGCCCCTGGGTTCGGCC

AAGGGACCAAGGTGGAAATCAAACGT [SEQ ID NO: 309]

Light Chain Amino Acid Sequence:
DIQLTQSPSSLSASVGDRVTITCRASQDIGNYVAWYQQKVGKVPNLLIYDASTLQSGVPSRF

SGSGSRTEFTLTISSLQPEDVATYYCQKYNTAPGFGQGTKVEIKR [SEQ ID NO: 310]

Heavy Chain DNA Sequence:
CAGATGCAGCTGGTGCAGTCTGGGGCTGAGGTGAAGAAGCCTGGGGCCTCAGTGAAGG

TTTCCTGCAAGGCATCTGGATACACCTTCACCAGCTACTATATGCACTGGGTGCGACAG

GCCCCTGGACAAGGGCTTGAGTGGATGGGAATAATCAACCCTAGTGGTGGTAGCACAA

GCTACGCACAGAAGTTCCAGGGCAGAGTCACCATGACCAGGGACACGTCCACGAGCAC

AGTCTACATGGAGCTGAGCAGCCTGAGATCTGAGGACACGGCCGTGTATTACTGTGCGC

GCTCTTCTATCGGTTGGCTGTCTTACCTGGATGCTTGGGGTCAAGGTACTCTGGTGACCG

TCTCCTCA [SEQ ID NO: 311]

Heavy Chain Amino Acid Sequence:
QMQLVQSGAEVKKPGASVKVSCKASGYTFTSYYMHWVRQAPGQGLEWMGIINPSGGSTS

YAQKFQGRVTMTRDTSTSTVYMELSSLRSEDTAVYYCARSSIGWLSYLDAWGQGTLVTVSS

[SEQ ID NO: 312]

EXT009-30:
DNA Sequence:
CAGTCTGTCGTGACGCAGCCGCCCTCAGTGTCTGGGGCCCCAGGGCAGAGGGTCACCAT

CTCCTGCACTGGGAGCAGCTCCAACATCGGGGCAGGTTATGATGTACACTGGTACCAGC

AGCTTCCAGGAACAGCCCCCAAACTCCTCATCTATGGTAACAGCAATCGGCCCTCAGGG

GTCCCTGACCGATTCTCTGGCTCCAAGTCTGGCACCTCAGCCTCCTGGCCATCACTGGG

CTCCAGGCTGAGGATGAGGCTGATTATTACTGCCAGTCCTATGACAGCAGCCTGAGTGT

APPENDIX C

GGTATTCGGCGGAGGGACCAAGCTGACCGTCCTAGGTTCTAGAGGTGGTGGTGGTAGC

GGCGGCGGCGGCTCTGGTGGTGGTGGATCCCTCGAGATGGCCCAGGTGCAGCTGGTGC

AGTCTGGGGCTGAGGTGAAGAAGCCTGGGGCCTCAGTGAAGGTCTCCTGCACGGCTTCT

GGAGGCACCTTCAGCAGCTATGCTATCAGCTGGGTGCGACAGGCCCCTGGACAAGGGC

TTGAGTGGATGGGAGGGATCATCCCTATCTTTGGTACAGCAAACTACGCACAGAAGTTC

CAGGGCAGAGTCACGATTACCGCGGACAAATCCACGAGCACAGCCTACATGGAGCTGA

GCAGCCTGAGATCTGAGGACACTGCCGTGTATTACTGTGCGCGCTCTTCTTACGGTTCTT

ACTACGGTACTTACGATTACTGGGGTCAAGGTACTCTGGTGACCGTCTCCTCA [SEQ ID NO: 313]

Amino Acid Sequence:
QSVVTQPPSVSGAPGQRVTISCTGSSSNIGAGYDVHWYQQLPGTAPKLLIYGNSNRPSGVPD

RFSGSKSGTSASLAITGLQAEDEADYYCQSYDSSLSVVFGGGTKLTVLGSRGGGGSGGGGS

GGGGSLEMAQVQLVQSGAEVKKPGASVKVSCTASGGTFSSYAISWVRQAPGQGLEWMGG

IIPIFGTANYAQKFQGRVTITADKSTSTAYMELSSLRSEDTAVYYCARSSYGSYYGTYDYWG

QGTLVTVSS [SEQ ID NO: 314]

Light Chain DNA Sequence:
CAGTCTGTCGTGACGCAGCCGCCCTCAGTGTCTGGGGCCCCAGGGCAGAGGGTCACCAT

CTCCTGCACTGGGAGCAGCTCCAACATCGGGGCAGGTTATGATGTACACTGGTACCAGC

AGCTTCCAGGAACAGCCCCCAAACTCCTCATCTATGGTAACAGCAATCGGCCCTCAGGG

GTCCCTGACCGATTCTCTGGCTCCAAGTCTGGCACCTCAGCCTCCCTGGCCATCACTGGG

CTCCAGGCTGAGGATGAGGCTGATTATTACTGCCAGTCCTATGACAGCAGCCTGAGTGT

GGTATTCGGCGGAGGGACCAAGCTGACCGTCCTAGGT [SEQ ID NO: 315]

Light Chain Amino Acid Sequence:
QSVVTQPPSVSGAPGQRVTISCTGSSSNIGAGYDVHWYQQLPGTAPKLLIYGNSNRPSGVPD

RFSGSKSGTSASLAITGLQAEDEADYYCQSYDSSLSVVFGGGTKLTVLG [SEQ ID NO: 316]

Heavy Chain DNA Sequence:
CAGGTGCAGCTGGTGCAGTCTGGGGCTGAGGTGAAGAAGCCTGGGGCCTCAGTGAAGG

TCTCCTGCACGGCTTCTGGAGGCACCTTCAGCAGCTATGCTATCAGCTGGGTGCGACAG

GCCCCTGGACAAGGGCTTGAGTGGATGGGAGGGATCATCCCTATCTTTGGTACAGCAAA

CTACGCACAGAAGTTCCAGGGCAGAGTCACGATTACCGCGGACAAATCCACGAGCACA

GCCTACATGGAGCTGAGCAGCCTGAGATCTGAGGACACTGCCGTGTATTACTGTGCGCG

CTCTTCTTACGGTTCTTACTACGGTACTTACGATTACTGGGGTCAAGGTACTCTGGTGAC

CGTCTCCTCA [SEQ ID NO: 317]

Heavy Chain Amino Acid Sequence:
QVQLVQSGAEVKKPGASVKVSCTASGGTFSSYAISWVRQAPGQGLEWMGGIIPIFGTANYA

QKFQGRVTITADKSTSTAYMELSSLRSEDTAVYYCARSSYGSYYGTYDYWGQGTLVTVSS

[SEQ ID NO: 318]

EXT009-31:
DNA Sequence:
CAGTCTGTGTTGACGCAGCCGCCCTCAGTGTCTGCGGCCCCAGGACAGAAGGTCACCAT

CTCCTGCTCTGGAAGCAGCTCCAACATTGGGAATAATTATGTATCCTGGTACCAGCAAC

TCCCAGGAACAGCCCCCAAACTCCTCATTTATGACAATAATAAGCGACCCTCAGGGATT

CCTGACCGATTCTCTGGCTCCAAGTCTGGCACGTCAGCCACCCTGGGCATCACCGGACT

APPENDIX C

CCAGACTGGGGACGAGGCCGATTATTACTGCGCAACATGGCATAGCAGCCTGAGTCCCT

CTTATGTCTTCGGAACTGGGACCAAGGTCACCGTCCTAGGTTCTAGAGGTGGTGGTGGT

AGCGGCGGCGGCGGCTCTGGTGGTGGTGGATCCCTCGAGATGGCCCAGGTGCAGCTGG

TGCAGTCTGGGGCTGAGGTCAAGAAGCCTGGGGCCTCAGTGAAGGTTTCCTGCAAGGC

ATCTGGATACACTTTCACCAGCTACTATATGCACTGGGTGCGACAGGCCCCTGGACAAG

GGCTTGAGTGGTTGGGAATAATCAACCCTACTGGTGGTAGCACATTCTACGCACAGAAG

TTTCAGGGCAGAGTCACCATGACCAGAGACACGTCCACGAGCACAGTCTACATGCAGC

TGCGCAACCTGAGATCTGAGGACACTGCCGTGTATTACTGTGCGCGCGGTTACTCTGAA

GGTGATGTTTGGGGTCAAGGTACTCTGGTGACCGTCTCCTCA [SEQ ID NO: 319]

Amino Acid Sequence:
QSVLTQPPSVSAAPGQKVTISCSGSSSNIGNNYVSWYQQLPGTAPKLLIYDNNKRPSGIPDRF

SGSKSGTSATLGITGLQTGDEADYYCATWHSSLSPSYVFGTGTKVTVLGSRGGGGSGGGGS

GGGGSLEMAQVQLVQSGAEVKKPGASVKVSCKASGYTFTSYYMHWVRQAPGQGLEWLGI

INPTGGSTFYAQKFQGRVTMTRDTSTSTVYMQLRNLRSEDTAVYYCARGYSEGDVWGQGT

LVTVSS [SEQ ID NO: 320]

Light Chain DNA Sequence:
CAGTCTGTGTTGACGCAGCCGCCCTCAGTGTCTGCGGCCCCAGGACAGAAGGTCACCAT

CTCCTGCTCTGGAAGCAGCTCCAACATTGGGAATAATTATGTATCCTGGTACCAGCAAC

TCCCAGGAACAGCCCCCAAACTCCTCATTTATGACAATAATAAGCGACCCTCAGGGATT

CCTGACCGATTCTCTGGCTCCAAGTCTGGCACGTCAGCCACCCTGGGCATCACCGGACT

CCAGACTGGGGACGAGGCCGATTATTACTGCGCAACATGGCATAGCAGCCTGAGTCCCT

CTTATGTCTTCGGAACTGGGACCAAGGTCACCGTCCTAGGT [SEQ ID NO: 321]

Light Chain Amino Acid Sequence:
QSVLTQPPSVSAAPGQKVTISCSGSSSNIGNNYVSWYQQLPGTAPKLLIYDNNKRPSGIPDRF

SGSKSGTSATLGITGLQTGDEADYYCATWHSSLSPSYVFGTGTKVTVLG [SEQ ID NO: 322]

Heavy Chain DNA Sequence:
CAGGTGCAGCTGGTGCAGTCTGGGGCTGAGGTCAAGAAGCCTGGGGCCTCAGTGAAGG

TTTCCTGCAAGGCATCTGGATACACTTTCACCAGCTACTATATGCACTGGGTGCGACAG

GCCCCTGGACAAGGGCTTGAGTGGTTGGGAATAATCAACCCTACTGGTGGTAGCACATT

CTACGCACAGAAGTTTCAGGGCAGAGTCACCATGACCAGAGACACGTCCACGAGCACA

GTCTACATGCAGCTGCGCAACCTGAGATCTGAGGACACTGCCGTGTATTACTGTGCGCG

CGGTTACTCTGAAGGTGATGTTTGGGGTCAAGGTACTCTGGTGACCGTCTCCTCA [SEQ ID NO: 323]

Heavy Chain Amino Acid Sequence:
QVQLVQSGAEVKKPGASVKVSCKASGYTFTSYYMHWVRQAPGQGLEWLGIINPTGGSTFY

AQKFQGRVTMTRDTSTSTVYMQLRNLRSEDTAVYYCARGYSEGDVWGQGTLVTVSS [SEQ ID NO: 324]

EXT009-32:
DNA Sequence:
CAGTCTGTGGTGACTCAGCCACCCTCAGCGTCTGGGACCCCCGGGCAGAGGGTCACCAT

CTCTTGTTCTGGAAGCAGCTCCAACATCGGAAGTAATACTGTAAACTGGTACCAGCAGC

TCCCAGGAACGGCCCCCAAACTCCTCATCTATAGTAATAATCAGCGGCCCTCAGGGGTC

CCTGACCGATTCTCTGGCTCCAAGTCTGGCACCTCAGCCTCCCTGGCCATCAGTGGGCTC

CAGTCTGAGGATGAGGCTGATTATTACTGTGCAGCATGGGATGACAGCCTGAATGGTCA

APPENDIX C

TAATTATGTCTTCGGAACTGGGACCAAGGTCACCGTCCTAGGTTCTAGAGGTGGTGGTG

GTAGCGGCGGCGGCGGCTCTGGTGGTGGTGGATCCCTCGAGATGGCCCAGGTGCAGCT

GGTGCAGTCTGGGGCTGAGGTGAAGAAGCCTGGGTCCTCGGTGAAGGTCTCCTGCAAG

GCTTCTGGAGGCACCTTCAGCAGCTATGCTATCAGCTGGGTGCGACAGGCCCCTGGACA

AGGGCTTGAGTGGATGGGAGGGATCATCCCTATCTTTGGTACAGCAAACTACGCACAGA

AGTTCCAGGGCAGAGTCACGATTACCGCGGACAAATCCACGAGCACAGCCTACATGGA

GCTGAGCAGCCTGAGATCTGAGGACACGGCCGTGTATTACTGTGCGCGCTACTTCGGTC

GTTACGTTGATTACTGGGGTCAAGGTACTCTGGTGACCGTCTCCTCA [SEQ ID NO: 325]

Amino Acid Sequence:
QSVVTQPPSASGTPGQRVTISCSGSSSNIGSNTVNWYQQLPGTAPKLLIYSNNQRPSGVPDRF

SGSKSGTSASLAISGLQSEDEADYYCAAWDDSLNGHNYVFGTGTKVTVLGSRGGGGSGGG

GSGGGGSLEMAQVQLVQSGAEVKKPGSSVKVSCKASGGTFSSYAISWVRQAPGQGLEWM

GGIIPIFGTANYAQKFQGRVTITADKSTSTAYMELSSLRSEDTAVYYCARYFGRYVDYWGQ

GTLVTVSS [SEQ ID NO: 326]

Light Chain DNA Sequence:
CAGTCTGTGGTGACTCAGCCACCCTCAGCGTCTGGGACCCCCGGGCAGAGGGTCACCAT

CTCTTGTTCTGGAAGCAGCTCCAACATCGGAAGTAATACTGTAAACTGGTACCAGCAGC

TCCCAGGAACGGCCCCCAAACTCCTCATCTATAGTAATAATCAGCGGCCCTCAGGGGTC

CCTGACCGATTCTCTGGCTCCAAGTCTGGCACCTCAGCCTCCCTGGCCATCAGTGGGCTC

CAGTCTGAGGATGAGGCTGATTATTACTGTGCAGCATGGGATGACAGCCTGAATGGTCA

TAATTATGTCTTCGGAACTGGGACCAAGGTCACCGTCCTAGGT [SEQ ID NO: 327]

Light Chain AMINO ACID Sequence:
QSVVTQPPSASGTPGQRVTISCSGSSSNIGSNTVNWYQQLPGTAPKLLIYSNNQRPSGVPDRF

SGSKSGTSASLAISGLQSEDEADYYCAAWDDSLNGHNYVFGTGTKVTVLG [SEQ ID NO: 328]

Heavy Chain DNA Sequence:
CAGGTGCAGCTGGTGCAGTCTGGGGCTGAGGTGAAGAAGCCTGGGTCCTCGGTGAAGG

TCTCCTGCAAGGCTTCTGGAGGCACCTTCAGCAGCTATGCTATCAGCTGGGTGCGACAG

GCCCCTGGACAAGGGCTTGAGTGGATGGGAGGGATCATCCCTATCTTTGGTACAGCAAA

CTACGCACAGAAGTTCCAGGGCAGAGTCACGATTACCGCGGACAAATCCACGAGCACA

GCCTACATGGAGCTGAGCAGCCTGAGATCTGAGGACACGGCCGTGTATTACTGTGCGCG

CTACTTCGGTCGTTACGTTGATTACTGGGGTCAAGGTACTCTGGTGACCGTCTCCTCA

[SEQ ID NO: 329]

Heavy Chain Amino Acid Sequence:
QVQLVQSGAEVKKPGSSVKVSCKASGGTFSSYAISWVRQAPGQGLEWMGGIIPIFGTANYA

QKFQGRVTITADKSTSTAYMELSSLRSEDTAVYYCARYFGRYVDYWGQGTLVTVSS

[SEQ ID NO: 330]

EXT009-33:
DNA Sequence:
TCCTATGTGCTGACTCAGCCACCCTCAGCGTCTGGGACCCCCGGGCAGAGGGTCACCAT

CTCTTGTTCTGGAAGCAGCTCCAACATCGGAAGTAATACTGTAAACTGGTACCAGCAGC

TCCCAGGAACGGCCCCCAAACTCCTCATCTATAGTAATAATCAGCGGCCCTCAGGGGTC

CCTGACCGATTCTCTGGCTCCAAGTCTGGCACCTCAGCCTCCCTGGCCATCAGTGGGCTC

APPENDIX C

CAGTCTGAGGATGAGGCTGATTATTACTGTGCAGCATGGGATGACAGCCTGAATGGTTA

TGTCTTCGGAACTGGGACCAAGGTCACCGTCCTAGGTTCTAGAGGTGGTGGTGGTAGCG

GCGGCGGCGGCTCTGGTGGTGGTGGATCCCTCGAGATGGCCGAGGTCCAGCTGGTGCA

GTCTGGGGCTGAGGTGAAGAAGCCTGGGTCCTCGGTGAAGGTCTCCTGCAAGGCTTCTG

GAGGCACCTTCAACGACTATAGTGTCAGCTGGGTGCGACAGTCCCCTGGACAAGGGCTT

GAGTGGATGGGAAGGATCATCCCCGTCCTTGATATGACAACCGTCGCACAGAAATTCCA

GGGCAGAGTCACAATTAACGCGGACAAATCGACGAGCACAGTGAACATGGAGCTGAGC

AGCCTCAGATCTGATGACACGGCCGTGTATTACTGTGCGCGCCAGTACGGTTCTTTCTG

GGATCGTTGGGGTCAAGGTACTCTGGTGACCGTCTCCTCA [SEQ ID NO: 331]

Amino Acid Sequence:
SYVLTQPPSASGTPGQRVTISCSGSSSNIGSNTVNWYQQLPGTAPKLLIYSNNQRPSGVPDRF

SGSKSGTSASLAISGLQSEDEADYYCAAWDDSLNGYVFGTGTKVTVLGSRGGGGSGGGGS

GGGGSLEMAEVQLVQSGAEVKKPGSSVKVSCKASGGTFNDYSVSWVRQSPGQGLEWMGR

IIPVLDMTTVAQKFQGRVTINADKSTSTVNMELSSLRSDDTAVYYCARQYGSFWDRWGQG

TLVTVSS [SEQ ID NO: 332]

Light Chain DNA Sequence:
TCCTATGTGCTGACTCAGCCACCCTCAGCGTCTGGGACCCCCGGGCAGAGGGTCACCAT

CTCTTGTTCTGGAAGCAGCTCCAACATCGGAAGTAATACTGTAAACTGGTACCAGCAGC

TCCCAGGAACGGCCCCCAAACTCCTCATCTATAGTAATAATCAGCGGCCCTCAGGGGTC

CCTGACCGATTCTCTGGCTCCAAGTCTGGCACCTCAGCCTCCCTGGCCATCAGTGGGCTC

CAGTCTGAGGATGAGGCTGATTATTACTGTGCAGCATGGGATGACAGCCTGAATGGTTA

TGTCTTCGGAACTGGGACCAAGGTCACCGTCCTAGGT [SEQ ID NO: 333]

Light Chain Amino Acid Sequence:
SYVLTQPPSASGTPGQRVTISCSGSSSNIGSNTVNWYQQLPGTAPKLLIYSNNQRPSGVPDRF

SGSKSGTSASLAISGLQSEDEADYYCAAWDDSLNGYVFGTGTKVTVLG [SEQ ID NO: 334]

Heavy Chain DNA Sequence:
GAGGTCCAGCTGGTGCAGTCTGGGGCTGAGGTGAAGAAGCCTGGGTCCTCGGTGAAGG

TCTCCTGCAAGGCTTCTGGAGGCACCTTCAACGACTATAGTGTCAGCTGGGTGCGACAG

TCCCCTGGACAAGGGCTTGAGTGGATGGGAAGGATCATCCCCGTCCTTGATATGACAAC

CGTCGCACAGAAATTCCAGGGCAGAGTCACAATTAACGCGGACAAATCGACGAGCACA

GTGAACATGGAGCTGAGCAGCCTCAGATCTGATGACACGGCCGTGTATTACTGTGCGCG

CCAGTACGGTTCTTTCTGGGATCGTTGGGGTCAAGGTACTCTGGTGACCGTCTCCTCA

[SEQ ID NO: 335]

Heavy Chain Amino Acid Sequence:
EVQLVQSGAEVKKPGSSVKVSCKASGGTFNDYSVSWVRQSPGQGLEWMGRIIPVLDMTTV

AQKFQGRVTINADKSTSTVNMELSSLRSDDTAVYYCARQYGSFWDRWGQGTLVTVSS

[SEQ ID NO: 336]

linker
EXT010-01
DNA sequence:
CAGTCTGTGTTGACGCAGCCGCCCTCAGTGTCTGGGGCCCTAGGGCAGAGGGTGACCAT

CTCCTGCACTGGGGGCCGCTCCAACATCGGGGCAGCCTTTGATGTGCACTGGTACCAGA

AACTTCCAGGGAGAGCCCCCACAGTCGTCATCTCTGGTGACAATAGGCGACCCTCAGGG

-continued

APPENDIX C

GTCCCTGACCGATTCTCTGCCTCCAAGTCTGGCGTCTCAGCCTCACTGGCCATCACTGGG

CTCCAGGCTGCGGATGAGGCTGATTACTACTGCCAATCCTATGACACCAGTCTGAATGT

GTTGTTCGGCGGCGGGACCAAGCTGACCGTCCTAGGTTCTAGAGGTGGTGGTGGTAGCG

GCGGCGGCGGCTCTGGTGGTGGTGGATCCCTCGAGATGGCCGAGGTGCAGCTGGTGGA

GTCTGGGGCTGAGGTGAAGAAGCCTGGGGCCTCAGTGAAGGTTTCCTGCAAGGCATCTG

GATACACCTTCACCAGCTACTATATGCACTGGGTGCGACAGGCCCCTGGACAAGGGCTT

GAGTGGATGGGAATAATCAACCCTAGTGGTGGTAGCACAAGCTACGCACAGAAGTTCC

AGGGCAGAGTCACCATGACCAGGGACACGTCCACGAGCACAGTCTACATGGAGCTGAG

CAGCCTGAGATCTGAGGACACGGCCGTGTATTACTGTGCGGCAGGGAGCTACTACTCGC

TTGATATCTGGGGCCAAGGGACAATGGTCACCGTCTCTTCA [SEQ ID NO: 337]
Amino Acid sequence:
QSVLTQPPSVSGALGQRVTISCTGGRSNIGAAFDVHWYQKLPGRAPTVVISGDNRRPSGVPD

RFSASKSGVSASLAITGLQAADEADYYCQSYDTSLNVLFGGGTKLTVLGSRGGGGSGGGGS

GGGGSLEMAEVQLVESGAEVKKPGASVKVSCKASGYTFTSYYMHWVRQAPGQGLEWMGI

INPSGGSTSYAQKFQGRVTMTRDTSTSTVYMELSSLRSEDTAVYYCAAGSYYSLDIWGQGT

MVTVSS [SEQ ID NO: 338]

Light Chain DNA sequence:
CAGTCTGTGTTGACGCAGCCGCCCTCAGTGTCTGGGGCCCTAGGGCAGAGGGTGACCAT

CTCCTGCACTGGGGGCCGCTCCAACATCGGGGCAGCCTTTGATGTGCACTGGTACCAGA

AACTTCCAGGGAGAGCCCCCACAGTCGTCATCTCTGGTGACAATAGGCGACCCTCAGGG

GTCCCTGACCGATTCTCTGCCTCCAAGTCTGGCGTCTCAGCCTCACTGGCCATCACTGGG

CTCCAGGCTGCGGATGAGGCTGATTACTACTGCCAATCCTATGACACCAGTCTGAATGT

GTTGTTCGGCGGCGGGACCAAGCTGACCGTCCTAGGT [SEQ ID NO: 339]

Light Chain Amino Acid sequence:
QSVLTQPPSVSGALGQRVTISCTGGRSNIGAAFDVHWYQKLPGRAPTVVISGDNRRPSGVPD

RFSASKSGVSASLAITGLQAADEADYYCQSYDTSLNVLFGGGTKLTVLG [SEQ ID NO: 340]

Heavy Chain DNA sequence:
GAGGTGCAGCTGGTGGAGTCTGGGGCTGAGGTGAAGAAGCCTGGGGCCTCAGTGAAGG

TTTCCTGCAAGGCATCTGGATACACCTTCACCAGCTACTATATGCACTGGGTGCGACAG

GCCCCTGGACAAGGGCTTGAGTGGATGGGAATAATCAACCCTAGTGGTGGTAGCACAA

GCTACGCACAGAAGTTCCAGGGCAGAGTCACCATGACCAGGGACACGTCCACGAGCAC

AGTCTACATGGAGCTGAGCAGCCTGAGATCTGAGGACACGGCCGTGTATTACTGTGCGG

CAGGGAGCTACTACTCGCTTGATATCTGGGGCCAAGGGACAATGGTCACCGTCTCTTCA

[SEQ ID NO: 341]

Heavy Chain Amino Acid sequence:
EVQLVESGAEVKKPGASVKVSCKASGYTFTSYYMHWVRQAPGQGLEWMGIINPSGGSTSY

AQKFQGRVTMTRDTSTSTVYMELSSLRSEDTAVYYCAAGSYYSLDIWGQGTMVTVSS

[SEQ ID NO: 342]

EXT010-03
DNA sequence:
CAGTCTGTGTTGACTCAGCCACCCTCAGTGTCAGTGGCCCCAGGAAAGACGGCCAGCAT

TACCTGTGGGGGAAACAACATTGAAAGTAAAAGTGTGCACTGGTACCAGCAGAAGCCA

APPENDIX C

GGCCAGGCCCCTGTACTGGTCATCTATTTTGATAGCGACCGGCCCTCAGGGATCCCTGA

GCGATTCTCTGGCTCCAACTCTGGGAACACGGCCACCCTGACCATCAGCAGGGTCGAAG

CCGGGGATGAGGCCGACTATTACTGTCAGGTGTGGGATAGTAGTAGTGATCATTATGTC

TTCGGAACTGGGACCAAGGTCACCGTCCTAGGTTCTAGAGGTGGTGGTGGTAGCGGCGG

CGGCGGCTCTGGTGGTGGTGGATCCCTCGAGATGGCCGAGGTCCAGCTGGTGCAGTCTG

GGGCTGAGGTGAAGAAGCCTGGGGCCTCAGTGAAGGTTTCCTGCAAGGCATCTGGATA

CACCTTCACCAGCTACTATATGCACTGGGTGCGACAGGCCCCTGGACAAGGGCTTGAGT

GGATGGGAATAATCAACCCTAGTGGTGGTAGCACAAGCTACGCACAGAAGTTCCAGGG

CAGAGTCACCATGACCAGGGACACGTCCACGAGCACAGTCTACATGGAGCTGAGCAGC

CTGAGATCTGAGGACACGGCCGTGTATTACTGTGCGAGTGGGAGCCGATATGCTTTTGA

TATCTGGGGCCAAGGGACAATGGTCACCGTCTCTTCA [SEQ ID NO: 343]

Amino Acid sequence:
QSVLTQPPSVSVAPGKTASITCGGNNIESKSVHWYQQKPGQAPVLVIYFDSDRPSGIPERFSG

SNSGNTATLTISRVEAGDEADYYCQVWDSSSDHYVFGTGTKVTVLGSRGGGGSGGGGSGG

GGSLEMAEVQLVQSGAEVKKPGASVKVSCKASGYTFTSYYMHWVRQAPGQGLEWMGIIN

PSGGSTSYAQKFQGRVTMTRDTSTSTVYMELSSLRSEDTAVYYCASGSRYAFDIWGQGTM

VTVSS [SEQ ID NO: 344]

Light Chain DNA sequence:
CAGTCTGTGTTGACTCAGCCACCCTCAGTGTCAGTGGCCCCAGGAAAGACGGCCAGCAT

TACCTGTGGGGGAAACAACATTGAAAGTAAAAGTGTGCACTGGTACCAGCAGAAGCCA

GGCCAGGCCCCTGTACTGGTCATCTATTTTGATAGCGACCGGCCCTCAGGGATCCCTGA

GCGATTCTCTGGCTCCAACTCTGGGAACACGGCCACCCTGACCATCAGCAGGGTCGAAG

CCGGGGATGAGGCCGACTATTACTGTCAGGTGTGGGATAGTAGTAGTGATCATTATGTC

TTCGGAACTGGGACCAAGGTCACCGTCCTAGGT [SEQ ID NO: 345]

Light Chain Amino Acid sequence:
QSVLTQPPSVSVAPGKTASITCGGNNIESKSVHWYQQKPGQAPVLVIYFDSDRPSGIPERFSG

SNSGNTATLTISRVEAGDEADYYCQVWDSSSDHYVFGTGTKVTVLG [SEQ ID NO: 346]

Heavy Chain DNA sequence:
GAGGTCCAGCTGGTGCAGTCTGGGGCTGAGGTGAAGAAGCCTGGGGCCTCAGTGAAGG

TTTCCTGCAAGGCATCTGGATACACCTTCACCAGCTACTATATGCACTGGGTGCGACAG

GCCCCTGGACAAGGGCTTGAGTGGATGGGAATAATCAACCCTAGTGGTGGTAGCACAA

GCTACGCACAGAAGTTCCAGGGCAGAGTCACCATGACCAGGGACACGTCCACGAGCAC

APPENDIX C

AGTCTACATGGAGCTGAGCAGCCTGAGATCTGAGGACACGGCCGTGTATTACTGTGCGA

GTGGGAGCCGATATGCTTTTGATATCTGGGGCCAAGGGACAATGGTCACCGTCTCTTCA

[SEQ ID NO: 347]

Heavy Chain Amino Acid sequence:
EVQLVQSGAEVKKPGASVKVSCKASGYTFTSYYMHWVRQAPGQGLEWMGIINPSGGSTSY

AQKFQGRVTMTRDTSTSTVYMELSSLRSEDTAVYYCASGSRYAFDIWGQGTMVTVSS

[SEQ ID NO: 348]

EXT010-04
DNA sequence:
CAGGCTGTGCTGACTCAGCCACCCTCAGTGTCAGTGGCCCCAGGAAAGACGGCCAGGA

TTACCTGTGGGGGAAACAACATTGGAAGTAAAAGTGTGCACTGGTACCAGCAGAAGCC

AGGCCAGGCCCCTGTGCTGGTCATCTATTATGATAGCGACCGGCCCTCAGGGATCCCTG

AGCGATTCTCTGGCTCCAACTCTGGGAACACGGCCACCCTGACCATCAGCAGGGTCGAA

GCCGGGGATGAGGCCGACTATTACTGTCAGGTGTGGGATAGTAGTAGTGATCATCCGGT

GTTCGGCGGAGGGACCAAGCTGACCGTCCTAGGTTCTAGAGGTGGTGGTGGTAGCGGC

GGCGGCGGCTCTGGTGGTGGTGGATCCCTCGAGATGGCCGAGGTGCAGCTGGTGGAGT

CTGGGGCTGAGGTGAAGAAGCCTGGGGCCTCAGTGAAGGTTTCCTGCAAGGCATCTGG

ATACACCTTCACCAGCTACTATATGCACTGGGTGCGACAGGCCCCTGGACAAGGGCTTG

AGTGGATGGGAATAATCAACCCTAGTGGTGGTAGCACAAGCTACGCACAGAAGTTCCA

GGGCAGAGTCACCATGACCAGGGACACGTCCACGAGCACAGTCTACATGGAGCTGAGC

AGCCTGAGATCTGAGGACACGGCCGTGTATTACTGTGCGAGGGCTATTACTGCCCTTGA

TGCTTTTGATATCTGGGGCCAAGGGACAATGGTCACCGTCTCTTCA [SEQ ID NO: 349]

Amino Acid sequence:
QAVLTQPPSVSVAPGKTARITCGGNNIGSKSVHWYQQKPGQAPVLVIYYDSDRPSGIPERFS

GSNSGNTATLTISRVEAGDEADYYCQVWDSSSDHPVFGGGTKLTVLGSRGGGGSGGGGSG

GGGSLEMAEVQLVESGAEVKKPGASVKVSCKASGYTFTSYYMHWVRQAPGQGLEWMGII

NPSGGSTSYAQKFQGRVTMTRDTSTSTVYMELSSLRSEDTAVYYCARAITALDAFDIWGQG

TMVTVSS [SEQ ID NO: 350]

Light Chain DNA sequence:
CAGGCTGTGCTGACTCAGCCACCCTCAGTGTCAGTGGCCCCAGGAAAGACGGCCAGGA

TTACCTGTGGGGGAAACAACATTGGAAGTAAAAGTGTGCACTGGTACCAGCAGAAGCC

AGGCCAGGCCCCTGTGCTGGTCATCTATTATGATAGCGACCGGCCCTCAGGGATCCCTG

AGCGATTCTCTGGCTCCAACTCTGGGAACACGGCCACCCTGACCATCAGCAGGGTCGAA

GCCGGGGATGAGGCCGACTATTACTGTCAGGTGTGGGATAGTAGTAGTGATCATCCGGT

GTTCGGCGGAGGGACCAAGCTGACCGTCCTAGGT [SEQ ID NO: 351]

Light Chain Amino Acid sequence:
QAVLTQPPSVSVAPGKTARITCGGNNIGSKSVHWYQQKPGQAPVLVIYYDSDRPSGIPERFS

GSNSGNTATLTISRVEAGDEADYYCQVWDSSSDHPVFGGGTKLTVLG [SEQ ID NO: 352]

Heavy Chain DNA sequence:
GAGGTGCAGCTGGTGGAGTCTGGGGCTGAGGTGAAGAAGCCTGGGGCCTCAGTGAAGG

TTTCCTGCAAGGCATCTGGATACACCTTCACCAGCTACTATATGCACTGGGTGCGACAG

GCCCCTGGACAAGGGCTTGAGTGGATGGGAATAATCAACCCTAGTGGTGGTAGCACAA

APPENDIX C

GCTACGCACAGAAGTTCCAGGGCAGAGTCACCATGACCAGGGACACGTCCACGAGCAC

AGTCTACATGGAGCTGAGCAGCCTGAGATCTGAGGACACGGCCGTGTATTACTGTGCGA

GGGCTATTACTGCCCTTGATGCTTTTGATATCTGGGGCCAAGGGACAATGGTCACCGTC

TCTTCA [SEQ ID NO: 353]

Heavy Chain Amino Acid sequence:
EVQLVESGAEVKKPGASVKVSCKASGYTFTSYYMHWVRQAPGQGLEWMGIINPSGGSTSY

AQKFQGRVTMTRDTSTSTVYMELSSLRSEDTAVYYCARAITALDAFDIWGQGTMVTVSS
[SEQ ID NO: 354]

EXT010-06
DNA sequence:
CTGCCTGTGCTGACTCAGCCACCCTCGGTGTCAGTGGCCCCAGGACAGACGGCCAGGAT

TACCTGTGGGGGAAACAACATTGGAAGTAAAAGTGTGCACTGGTACCAGCAGAAGCCA

GGCCAGGCCCCTGTGCTGGTCGTCTATGATGATAGCGACCGGCCCTCAGGGATCCCTGA

GCGATTCTCTGGCTCCAACTCTGGGAACACGGCCACCCTGACCATCAGCAGGGTCGAAG

CCGGGGATGAGGCCGACTATTACTGTCAGGTGTGGGATAGTAGTAGTGATCATGGGGTA

TTCGGCGGAGGGACCAAGCTGACCGTCCTAGGTTCTAGAGGTGGTGGTGGTAGCGGCG

GCGGCGGCTCTGGTGGTGGTGGATCCCTCGAGATGGCCCAGGTCCAGCTGGTACAGTCT

GGGGCTGAGGTGAAGAAGCCTGGGGCCTCAGTGAAGGTTTCCTGCAAGGCATCTGAAT

ACACCCTCACCACCTATTATATGCACTGGGTGCGACAGGCCCCTGGACAAGGGCTTGAG

TGGATGGGAATAATCAATCCTGGTAGTGGTAGCACAAGTTACGCACAGAAGTTCCAGG

GCAGACTCACCATGACCAGCGACACGTCCACGAGCACAGTCTACATGGAGCTGAGCAG

CCTGAGATCTGAGGACACGGCCATGTATTACTGTGCTAGAGCGTTTGGTTACGGGGACT

ACTTCTACGGTATGGACGTCTGGGGCCAAGGGACCACGGTCACCGTCTCCTCA

[SEQ ID NO: 355]

Amino Acid sequence:
LPVLTQPPSVSVAPGQTARITCGGNNIGSKSVHWYQQKPGQAPVLVVYDDSDRPSGIPERFS

GSNSGNTATLTISRVEAGDEADYYCQVWDSSSDHGVFGGGTKLTVLGSRGGGGSGGGGSG

GGGSLEMAQVQLVQSGAEVKKPGASVKVSCKASEYTLTTYYMHWVRQAPGQGLEWMGII

NPGSGSTSYAQKFQGRLTMTSDTSTSTVYMELSSLRSEDTAMYYCARAFGYGDYFYGMDV

WGQGTTVTVSS [SEQ ID NO: 356]

Light Chain DNA sequence:
CTGCCTGTGCTGACTCAGCCACCCTCGGTGTCAGTGGCCCCAGGACAGACGGCCAGGAT

TACCTGTGGGGGAAACAACATTGGAAGTAAAAGTGTGCACTGGTACCAGCAGAAGCCA

GGCCAGGCCCCTGTGCTGGTCGTCTATGATGATAGCGACCGGCCCTCAGGGATCCCTGA

GCGATTCTCTGGCTCCAACTCTGGGAACACGGCCACCCTGACCATCAGCAGGGTCGAAG

CCGGGGATGAGGCCGACTATTACTGTCAGGTGTGGGATAGTAGTAGTGATCATGGGGTA

TTCGGCGGAGGGACCAAGCTGACCGTCCTAGGT [SEQ ID NO: 357]

Light Chain Amino Acid sequence:
LPVLTQPPSVSVAPGQTARITCGGNNIGSKSVHWYQQKPGQAPVLVVYDDSDRPSGIPERFS

GSNSGNTATLTISRVEAGDEADYYCQVWDSSSDHGVFGGGTKLTVLG [SEQ ID NO: 358]

APPENDIX C

Heavy Chain DNA sequence:
CAGGTCCAGCTGGTACAGTCTGGGGCTGAGGTGAAGAAGCCTGGGGCCTCAGTGAAGG

TTTCCTGCAAGGCATCTGAATACACCCTCACCACCTATTATATGCACTGGGTGCGACAG

GCCCCTGGACAAGGGCTTGAGTGGATGGGAATAATCAATCCTGGTAGTGGTAGCACAA

GTTACGCACAGAAGTTCCAGGGCAGACTCACCATGACCAGCGACACGTCCACGAGCAC

AGTCTACATGGAGCTGAGCAGCCTGAGATCTGAGGACACGGCCATGTATTACTGTGCTA

GAGCGTTTGGTTACGGGGACTACTTCTACGGTATGGACGTCTGGGGCCAAGGGACCACG

GTCACCGTCTCCTCA [SEQ ID NO: 359]

Heavy Chain Amino Acid sequence:
QVQLVQSGAEVKKPGASVKVSCKASEYTLTTYYMHWVRQAPGQGLEWMGIINPGSGSTSY

AQKFQGRLTMTSDTSTSTVYMELSSLRSEDTAMYYCARAFGYGDYFYGMDVWGQGTTVT

VSS [SEQ ID NO: 360]

EXT010-07
DNA sequence:
CAGGCTGTGCTGACTCAGCCGCCCTCAGTGTCTGGGGCCCCAGGGCAGAGGGTCACCAT

CTCCTGCACTGGGAGCAGCTCCAACATCGGGGCAGGTCATGATGTACATTGGTATCACC

AACTTCCAGGAACAGCCCCCAAACTCCTCATCTATAGTAATGGCAATCGGCCCTCAGGG

ATCCCTGACCGATTCTCTGGCTCCAAGTCTGGCACCTCAGCCTCCCTGGCCATCACTGGG

CTCCAGGCTGAGGATGAGGGTGATTATTATTGCCAGTCCTATGACAGCAGCCTGAGTGG

TGATGTGGTCTTCGGCGGAGGGACCAAGGTCACCGTCCTAGGTTCTAGAGGTGGTGGTG

GTAGCGGCGGCGGCGGCTCTGGTGGTGGTGGATCCCTCGAGATGGCCGAGGTGCAGCT

GGTGGAGTCTGGGGGAGGCTTGGTCCAGCCTGGGGGGTCCCTGAGACTCTCCTGTGCAG

CCTCTGGATTCAGGTTCAGTGGCTATAGCATGAACTGGGTCCGCCAGGCTCCAGGGAAG

GGGCTGGAGTGGGTTTCATACATTAGAAGTAGTAGTGATCTTATAACCTACGCAGACTC

TGTGAAGGGCCGATTCACCATCTCCAGAGACAATGCCAAGAACTCACTGTATCTGCAGA

TGAACAGCCTGAGAGACGAGGACACGGCTGTCTATTATTGTGCGAGAGATATGGGCAG

CACCTGGTACCGAGGTGCTTTTGATTTTTGGGGCCAAGGGACAATGGTCACCGTCTCTTCA

[SEQ ID NO: 361]

Amino Acid sequence:
QAVLTQPPSVSGAPGQRVTISCTGSSSNIGAGHDVHWYHQLPGTAPKLLIYSNGNRPSGIPD

RFSGSKSGTSASLAITGLQAEDEGDYYCQSYDSSLSGDVVFGGGTKVTVLGSRGGGGSGGG

GSGGGGSLEMAEVQLVESGGGLVQPGGSLRLSCAASGFRFSGYSMNWVRQAPGKGLEWV

SYIRSSSDLITYADSVKGRFTISRDNAKNSLYLQMNSLRDEDTAVYYCARDMGSTWYRGAF

DFWGQGTMVTVSS [SEQ ID NO: 362]

Light Chain DNA sequence:
CAGGCTGTGCTGACTCAGCCGCCCTCAGTGTCTGGGGCCCCAGGGCAGAGGGTCACCAT

CTCCTGCACTGGGAGCAGCTCCAACATCGGGGCAGGTCATGATGTACATTGGTATCACC

AACTTCCAGGAACAGCCCCCAAACTCCTCATCTATAGTAATGGCAATCGGCCCTCAGGG

ATCCCTGACCGATTCTCTGGCTCCAAGTCTGGCACCTCAGCCTCCCTGGCCATCACTGGG

CTCCAGGCTGAGGATGAGGGTGATTATTATTGCCAGTCCTATGACAGCAGCCTGAGTGG

TGATGTGGTCTTCGGCGGAGGGACCAAGGTCACCGTCCTAGGT [SEQ ID NO: 363]

APPENDIX C

Light Chain Amino Acid sequence:
QAVLTQPPSVSGAPGQRVTISCTGSSSNIGAGHDVHWYHQLPGTAPKLLIYSNGNRPSGIPD

RFSGSKSGTSASLAITGLQAEDEGDYYCQSYDSSLSGDVVFGGGTKVTVLG [SEQ ID NO: 364]

Heavy Chain DNA sequence:
GAGGTGCAGCTGGTGGAGTCTGGGGGAGGCTTGGTCCAGCCTGGGGGGTCCCTGAGAC

TCTCCTGTGCAGCCTCTGGATTCAGGTTCAGTGGCTATAGCATGAACTGGGTCCGCCAG

GCTCCAGGGAAGGGGCTGGAGTGGGTTTCATACATTAGAAGTAGTAGTGATCTTATAAC

CTACGCAGACTCTGTGAAGGGCCGATTCACCATCTCCAGAGACAATGCCAAGAACTCAC

TGTATCTGCAGATGAACAGCCTGAGAGACGAGGACACGGCTGTCTATTATTGTGCGAGA

GATATGGGCAGCACCTGGTACCGAGGTGCTTTTGATTTTTGGGGCCAAGGGACAATGGT

CACCGTCTCTTCA [SEQ ID NO: 365]

Heavy Chain Amino Acid sequence:
EVQLVESGGGLVQPGGSLRLSCAASGFRFSGYSMNWVRQAPGKGLEWVSYIRSSSDLITYA

DSVKGRFTISRDNAKNSLYLQMNSLRDEDTAVYYCARDMGSTWYRGAFDFWGQGTMVT

VSS [SEQ ID NO: 366]

EXT010-08
DNA sequence:
CTGCCTGTGCTGACTCAGCCACCCTCAGTGTCAGTGGCCCCAGGAGAGACGGCCAGCAT

TACCTGTGGGGGAAACAATATTGGACGTCAAAGTGTGCACTGGTACCAGCAGAAGCCA

GGCCAGGCCCCTTTGTTAGTCATCTATTATGATGCCGACCGGCCCTCTGGGATCCCTGA

GCGATTCTCTGGCTCCAACTCTGGGAACACGGCCACCCTGACCCTCAGCAGGGTCGAAG

CCGGGGATGAGGCCGACTATTATTGTCAGGTGTGGGATAGTAGTAGTGATCATTATGTC

TTCGGAACTGGGACCAAGGTCACCGTCCTAGGTTCTAGAGGTGGTGGTGGTAGCGGCGG

CGGCGGCTCTGGTGGTGGTGGATCCCTCGAGATGGCCGAGGTCCAGCTGGTGCAGTCTG

GGGCTGAGGTGAAGAAGCCTGGGGCCTCAGTGAAGGTTTCCTGCAAGGCATCTGGATA

CACCTTCACCAGCTACTATATACACTGGGTGCGACAGGCCCCTGGACAAGGGCTTGAGT

GGATGGGAGTAATCAACCCTAGTGGTGGTAGCACAAGCTACGCACAGAAGTTCCAGGG

CAGAGTCACCATGACCAGGGACACGTCCACGAGCACAGTCTACATGGAGCTCAGCAGC

CTGAGATCTGAGGACACGGCCGTATATTACTGTGCGCGCTCTCCGGGTGGTGGTTACGG

TCAGGATGGTTGGGGTCAAGGTACTCTGGTGACCGTCTCCTCA [SEQ ID NO: 367]

Amino Acid sequence:
LPVLTQPPSVSVAPGETASITCGGNNIGRQSVHWYQQKPGQAPLLVIYYDADRPSGIPERFSG

SNSGNTATLTLSRVEAGDEADYYCQVWDSSSDHYVFGTGTKVTVLGSRGGGGSGGGGSG

GGGSLEMAEVQLVQSGAEVKKPGASVKVSCKASGYTFTSYYIHWVRQAPGQGLEWMGVI

NPSGGSTSYAQKFQGRVTMTRDTSTSTVYMELSSLRSEDTAVYYCARSPGGGYGQDWGQ

GTLVTVSS [SEQ ID NO: 368]

Light Chain DNA sequence:
CTGCCTGTGCTGACTCAGCCACCCTCAGTGTCAGTGGCCCCAGGAGAGACGGCCAGCAT

TACCTGTGGGGGAAACAATATTGGACGTCAAAGTGTGCACTGGTACCAGCAGAAGCCA

GGCCAGGCCCCTTTGTTAGTCATCTATTATGATGCCGACCGGCCCTCTGGGATCCCTGA

-continued

APPENDIX C

GCGATTCTCTGGCTCCAACTCTGGGAACACGGCCACCCTGACCCTCAGCAGGGTCGAAG

CCGGGGATGAGGCCGACTATTATTGTCAGGTGTGGGATAGTAGTAGTGATCATTATGTC

TTCGGAACTGGGACCAAGGTCACCGTCCTAGGT [SEQ ID NO: 369]

Light Chain Amino Acid sequence:
LPVLTQPPSVSVAPGETASITCGGNNIGRQSVHWYQQKPGQAPLLVIYYDADRPSGIPERFSG

SNSGNTATLTLSRVEAGDEADYYCQVWDSSSDHYVFGTGTKVTVLG [SEQ ID NO: 370]

Heavy Chain DNA sequence:
GAGGTCCAGCTGGTGCAGTCTGGGGCTGAGGTGAAGAAGCCTGGGGCCTCAGTGAAGG

TTTCCTGCAAGGCATCTGGATACACCTTCACCAGCTACTATATACACTGGGTGCGACAG

GCCCCTGGACAAGGGCTTGAGTGGATGGGAGTAATCAACCCTAGTGGTGGTAGCACAA

GCTACGCACAGAAGTTCCAGGGCAGAGTCACCATGACCAGGGACACGTCCACGAGCAC

AGTCTACATGGAGCTCAGCAGCCTGAGATCTGAGGACACGGCCGTATATTACTGTGCGC

GCTCTCCGGGTGGTGGTTACGGTCAGGATGGTTGGGGTCAAGGTACTCTGGTGACCGTC

TCCTCA [SEQ ID NO: 371]

Heavy Chain Amino Acid sequence:
EVQLVQSGAEVKKPGASVKVSCKASGYTFTSYYIHWVRQAPGQGLEWMGVINPSGGSTSY

AQKFQGRVTMTRDTSTSTVYMELSSLRSEDTAVYYCARSPGGGYGQDGWGQGTLVTVSS

[SEQ ID NO: 372]

EXT010-10
DNA sequence:
GATGTTGTGATGACTCAGTCTCCATCCTCCCTGTCTGCATCTGTAGGAGACAGAGTCACC

ATCACTTGCCGGGCAAGTCAGAGCATTAGCAGCTATTTAAATTGGTATCAGCAGAAACC

AGGGAAAGCCCCTAAGCTCCTGATCTATGCTGCATCCAGTTTGCAAAGTGGGGTCCCAT

CAAGGTTCAGTGGCAGTGGATCTGGGACAGATTTCACTCTCACCATCAGCAGTCTGCAA

CCTGAAGATTTTGCAACTTACTACTGTCAACAGAGTTACAGTACCCCCTTCACCTTCGGC

CAAGGGACACGACTGGAGATTAAACGTTCTAGAGGTGGTGGTGGTAGCGGCGGCGGCG

GCTCTGGTGGTGGTGGATCCCTCGAGATGGCCCAGGTGCAGCTGGTGCAATCTGGGGCT

GAGGTGAAGGAGCCTGGAGCCTCAGTTAAGGTTTCCTGCAAGGCGTCTGGATACACCTT

CAGCAGCTTCTATATGCACTGGGTGCGACAGGCCCCTGGACAAGGGCTTGAGTGGATGG

GAATAATCGACCCTAATTCTGGTTTCACAAGCTACGCACAGAACTTCCAGGCCAGACTC

ACCATGACCAGGGACCCGTCCACTAACACAGTCTACATGGAACTCAGCAACCTGAGAT

CTGACGACACTGCCGTGTATTACTGTGCGCGCTACATCTACTACATGGGTTACGATGAA

TGGGGTCAAGGTACTCTGGTGACCGTCTCCTCA [SEQ ID NO: 373]

Amino Acid sequence:
DVVMTQSPSSLSASVGDRVTITCRASQSISSYLNWYQQKPGKAPKLLIYAASSLQSGVPSRFS

GSGSGTDFTLTISSLQPEDFATYYCQQSYSTPFTFGQGTRLEIKRSRGGGGSGGGGSGGGGSL

EMAQVQLVQSGAEVKEPGASVKVSCKASGYTFSSFYMHWVRQAPGQGLEWMGIIDPNSGF

TSYAQNFQARLTMTRDPSTNTVYMELSNLRSDDTAVYYCARYIYYMGYDEWGQGTLVTV

SS [SEQ ID NO: 374]

Light Chain DNA sequence:
GATGTTGTGATGACTCAGTCTCCATCCTCCCTGTCTGCATCTGTAGGAGACAGAGTCACC

ATCACTTGCCGGGCAAGTCAGAGCATTAGCAGCTATTTAAATTGGTATCAGCAGAAACC

APPENDIX C

AGGGAAAGCCCCTAAGCTCCTGATCTATGCTGCATCCAGTTTGCAAAGTGGGGTCCCAT

CAAGGTTCAGTGGCAGTGGATCTGGGACAGATTTCACTCTCACCATCAGCAGTCTGCAA

CCTGAAGATTTTGCAACTTACTACTGTCAACAGAGTTACAGTACCCCCTTCACCTTCGGC

CAAGGGACACGACTGGAGATTAAACGT [SEQ ID NO: 375]

Light Chain Amino Acid sequence:
DVVMTQSPSSLSASVGDRVTITCRASQSISSYLNWYQQKPGKAPKLLIYAASSLQSGVPSRFS

GSGSGTDFTLTISSLQPEDFATYYCQQSYSTPFTFGQGTRLEIKR [SEQ ID NO: 376]

Heavy Chain DNA sequence:
CAGGTGCAGCTGGTGCAATCTGGGGCTGAGGTGAAGGAGCCTGGAGCCTCAGTTAAGG

TTTCCTGCAAGGCGTCTGGATACACCTTCAGCAGCTTCTATATGCACTGGGTGCGACAG

GCCCCTGGACAAGGGCTTGAGTGGATGGGAATAATCGACCCTAATTCTGGTTTCACAAG

CTACGCACAGAACTTCCAGGCCAGACTCACCATGACCAGGGACCCGTCCACTAACACA

GTCTACATGGAACTCAGCAACCTGAGATCTGACGACACTGCCGTGTATTACTGTGCGCG

CTACATCTACTACATGGGTTACGATGAATGGGGTCAAGGTACTCTGGTGACCGTCTCCT

CA [SEQ ID NO: 377]

Heavy Chain Amino Acid sequence:
QVQLVQSGAEVKEPGASVKVSCKASGYTFSSFYMHWVRQAPGQGLEWMGIIDPNSGFTSY

AQNFQARLTMTRDPSTNTVYMELSNLRSDDTAVYYCARYIYYMGYDEWGQGTLVTVSS

[SEQ ID NO: 378]

EXT010-13
DNA sequence:
CAGGCTGTGCTGACTCAGCCACCCTCAGTGTCAGTGGCCCCAGGAAAGACGGCCCGGA

TCACCTGTGGTGGAGACAACATTGAAACTAAAAGTGTGCACTGGTACCAGCAGAGGCC

AGGCCAGGCCCCTGTACTGGTCATCTATTATGATAACGACCGGCCCTCAGGGATCCCTG

AGCGGTTCTCTGGCTCCAACTCTGGGGACACGCCCACCCTGACCATCAGCAGGGTCGAA

GCCGGGGACGAGGCCGACTATTACTGTCAGGTGTGGGATAAAAGTAATGATCACATGG

TGTTTGGCGGAGGGACCAAGCTGACCGTCCTAGGTTCTAGAGGTGGTGGTGGTAGCGGC

GGCGGCGGCTCTGGTGGTGGTGGATCCCTCGAGATGGCCGAAGTGCAGCTGGTGCAGTC

TGGGGCTGAGGTGAAGAAGCCTGGGGCCTCAGTGAAGATTTCCTGCAAGGCATCTGGA

TACACCTTCACCAGCTACTATATGCACTGGGTGCGACAGGCCCCTGGACAAGGGCTTGA

GTGGATGGGAATAATCAACCCTAGTGGTGGTTACACAAGCTACGCACAGAAGTTCCAG

GGCAGAGTCACCATGACCAGGGACACGTCCACGAGCACAGTCTACATGGAGCTGAGCA

GCCTGAGATCTGAGGACACCGCCATGTATTACTGTGCGCGCGGTATGCTGACTTACCTG

GATTCTTGGGGTCAAGGTACTCTGGTGACCGTCTCCTCA [SEQ ID NO: 379]

Amino Acid sequence:
QAVLTQPPSVSVAPGKTARITCGGDNIETKSVHWYQQRPGQAPVLVIYYDNDRPSGIPERFS

GSNSGDTPTLTISRVEAGDEADYYCQVWDKSNDHMVFGGGTKLTVLGSRGGGGSGGGGS

GGGGSLEMAEVQLVQSGAEVKKPGASVKISCKASGYTFTSYYMHWVRQAPGQGLEWMGI

INPSGGYTSYAQKFQGRVTMTRDTSTSTVYMELSSLRSEDTAMYYCARGMLTYLDSWGQG

TLVTVSS [SEQ ID NO: 380]

APPENDIX C

Light Chain DNA sequence:
CAGGCTGTGCTGACTCAGCCACCCTCAGTGTCAGTGGCCCCAGGAAAGACGGCCCGGA

TCACCTGTGGTGGAGACAACATTGAAACTAAAAGTGTGCACTGGTACCAGCAGAGGCC

AGGCCAGGCCCCTGTACTGGTCATCTATTATGATAACGACCGGCCCTCAGGGATCCCTG

AGCGGTTCTCTGGCTCCAACTCTGGGGACACGCCCACCCTGACCATCAGCAGGGTCGAA

GCCGGGGACGAGGCCGACTATTACTGTCAGGTGTGGGATAAAAGTAATGATCACATGG

TGTTTGGCGGAGGGACCAAGCTGACCGTCCTAGGT [SEQ ID NO: 381]

Light Chain Amino Acid sequence:
QAVLTQPPSVSVAPGKTARITCGGDNIETKSVHWYQQRPGQAPVLVIYYDNDRPSGIPERFS

GSNSGDTPTLTISRVEAGDEADYYCQVWDKSNDHMVFGGGTKLTVLG [SEQ ID NO: 382]

Heavy Chain DNA sequence:
GAAGTGCAGCTGGTGCAGTCTGGGGCTGAGGTGAAGAAGCCTGGGGCCTCAGTGAAGA

TTTCCTGCAAGGCATCTGGATACACCTTCACCAGCTACTATATGCACTGGGTGCGACAG

GCCCCTGGACAAGGGCTTGAGTGGATGGGAATAATCAACCCTAGTGGTGGTTACACAA

GCTACGCACAGAAGTTCCAGGGCAGAGTCACCATGACCAGGGACACGTCCACGAGCAC

AGTCTACATGGAGCTGAGCAGCCTGAGATCTGAGGACACCGCCATGTATTACTGTGCGC

GCGGTATGCTGACTTACCTGGATTCTTGGGGTCAAGGTACTCTGGTGACCGTCTCCTCA

[SEQ ID NO: 383]

Heavy Chain Amino Acid sequence:
EVQLVQSGAEVKKPGASVKISCKASGYTFTSYYMHWVRQAPGQGLEWMGIINPSGGYTSY

AQKFQGRVTMTRDTSTSTVYMELSSLRSEDTAMYYCARGMLTYLDSWGQGTLVTVSS

[SEQ ID NO: 384]

EXT010-15
DNA sequence:
CAATCTGCCCTGACTCAGCCTCCCTCCGCGTCCGGGTCTCCTGGACAGTCAGTCACCATC

TCCTGCACTGGAGCCAGCAGTCACGTTGGTGCTTACAGCTATGTCTCCTGGTACCAACA

GCACCCAGGCAAAGCCCCCAAACTCATAATTTATGACGTCAATAAGCGGCCCTCAGGG

GTCCCTGATCGCTTCTCTGGCTCCAAGTCTGGCAACACGGCCTCCCTGACCGTCTCTGGG

CTCCAGGCTGAGGATGAGGCTGATTATTACTGCAGCTCATATGCAAGCAGCAACAATTA

TGTGCTTTTCGGCGGAGGGACCAAGCTGACCGTCCTAGGTTCTAGAGGTGGTGGTGGTA

GCGGCGGCGGCGGCTCTGGTGGTGGTGGATCCCTCGAGATGGCCCAGGTGCAGCTGGT

GCAGTCTGGGGCTGAGGTGAAGAAGCCTGGGGCCTCAGTGAAGGTCTCCTGCAAGGCT

TCTGGATACACCTTCAGCAGCTTCTATATGCACTGGGTGCGACAGGCCCCTGGACAAGG

GCTTGAGTGGATGGGAATAATCGACCCTAATTCTGGTTTCACAAGCTACGCACAGAACT

TCCAGGCCAGACTCACCATGACCAGGGACCCGTCCACTAACACAGTCTACATGGAACTC

AGCAACCTGAGATCTGACGACACGGCCGTGTATTACTGTGCGCGCTACATCTACGCTTC

TGGTATCGATACTTGGGGTCAAGGTACTCTGGTGACCGTCTCCTCA [SEQ ID NO: 385]

Amino Acid sequence:
QSALTQPPSASGSPGQSVTISCTGASSHVGAYSYVSWYQQHPGKAPKLIIYDVNKRPSGVPD

RFSGSKSGNTASLTVSGLQAEDEADYYCSSYASSNNYVLFGGGTKLTVLGSRGGGGSGGG

APPENDIX C

GSGGGGSLEMAQVQLVQSGAEVKKPGASVKVSCKASGYTFSSFYMHWVRQAPGQGLEW

MGIIDPNSGFTSYAQNFQARLTMTRDPSTNTVYMELSNLRSDDTAVYYCARYIYASGIDTW

GQGTLVTVSS [SEQ ID NO: 386]

Light Chain DNA sequence:
CAATCTGCCCTGACTCAGCCTCCCTCCGCGTCCGGGTCTCCTGGACAGTCAGTCACCATC

TCCTGCACTGGAGCCAGCAGTCACGTTGGTGCTTACAGCTATGTCTCCTGGTACCAACA

GCACCCAGGCAAAGCCCCCAAACTCATAATTTATGACGTCAATAAGCGGCCCTCAGGG

GTCCCTGATCGCTTCTCTGGCTCCAAGTCTGGCAACACGGCCTCCCTGACCGTCTCTGGG

CTCCAGGCTGAGGATGAGGCTGATTATTACTGCAGCTCATATGCAAGCAGCAACAATTA

TGTGCTTTTCGGCGGAGGGACCAAGCTGACCGTCCTAGGT [SEQ ID NO: 387]

Light Chain Amino Acid sequence:
QSALTQPPSASGSPGQSVTISCTGASSHVGAYSYVSWYQQHPGKAPKLIIYDVNKRPSGVPD

RFSGSKSGNTASLTVSGLQAEDEADYYCSSYASSNNYVLFGGGTKLTVLG [SEQ ID NO: 388]

Heavy Chain DNA sequence:
CAGGTGCAGCTGGTGCAGTCTGGGGCTGAGGTGAAGAAGCCTGGGGCCTCAGTGAAGG

TCTCCTGCAAGGCTTCTGGATACACCTTCAGCAGCTTCTATATGCACTGGGTGCGACAG

GCCCCTGGACAAGGGCTTGAGTGGATGGGAATAATCGACCCTAATTCTGGTTTCACAAG

CTACGCACAGAACTTCCAGGCCAGACTCACCATGACCAGGGACCCGTCCACTAACACA

GTCTACATGGAACTCAGCAACCTGAGATCTGACGACACGGCCGTGTATTACTGTGCGCG

CTACATCTACGCTTCTGGTATCGATACTTGGGGTCAAGGTACTCTGGTGACCGTCTCCTCA

[SEQ ID NO: 389]

Heavy Chain Amino Acid sequence:
QVQLVQSGAEVKKPGASVKVSCKASGYTFSSFYMHWVRQAPGQGLEWMGIIDPNSGFTSY

AQNFQARLTMTRDPSTNTVYMELSNLRSDDTAVYYCARYIYASGIDTWGQGTLVTVSS

[SEQ ID NO: 390]

EXT010-17
DNA sequence:
GACATCCAGTTGACCCAGTCTCCATCCTCCCTGTCTGCATCTGTAGGAGACAGAGTCAC

CATCACTTGTCGGGCAAGTCAGAGCATTAGCAGCTATTTAAATTGGTATCAGCAGAAAC

CAGGGAAAGCCCCTAAGCTCCTGATCTATGCTGCATCCAGTTTGCAAAGTGGGGTCCCA

TCAAGGTTCAGTGGCAGTGGATCTGGGACAGATTTCACTCTCACCATCAGCAGTCTGCA

ACCTGAAGATTTTGCAACTTACTACTGTCAACAGAGTTACAGTACCCCGCTCACTTTCGG

CGGAGGGACCAAGGTGGAGATCAAACGTTCTAGAGGTGGTGGTGGTAGCGGCGGCGGC

GGCTCTGGTGGTGGTGGATCCCTCGAGATGGCCCAGGTGCAGCTGGTGCAGTCTGGGGC

TGAGGTGAAGAAGCCTGGGGCCTCAGTGAAGGTTTCCTGCAAGGCATCTGGATACACCT

TCACCAGCTACTATATGCACTGGGTGCGACAGGCCCCTGGACAAGGGCTTGAGTGGATG

GGAATAATCAACCCTAGTGGTGGTAGCACAAGCTACGCACAGAAGTTCCAGGGCAGAG

TCACCATGACCAGGGACACGTCCACGAGCACAGTCTACATGGAGCTGAGCAGCCTGAG

ATCTGACGACACGGCCGTGTATTACTGTGCGCGCTCTTACTACTCTGTTGGTACTCAGTG

GCTGGATTCTTGGGGTCAAGGTACTCTGGTGACCGTCTCCTCA [SEQ ID NO: 391]

APPENDIX C

Amino Acid sequence:
DIQLTQSPSSLSASVGDRVTITCRASQSISSYLNWYQQKPGKAPKLLIYAASSLQSGVPSRFS

GSGSGTDFTLTISSLQPEDFATYYCQQSYSTPLTFGGGTKVEIKRSRGGGGSGGGGSGGGGS

LEMAQVQLVQSGAEVKKPGASVKVSCKASGYTFTSYYMHWVRQAPGQGLEWMGIINPSG

GSTSYAQKFQGRVTMTRDTSTSTVYMELSSLRSDDTAVYYCARSYYSVGTQWLDSWGQG

TLVTVSS [SEQ ID NO: 392]

Light Chain DNA sequence:
GACATCCAGTTGACCCAGTCTCCATCCTCCCTGTCTGCATCTGTAGGAGACAGAGTCAC

CATCACTTGTCGGGCAAGTCAGAGCATTAGCAGCTATTTAAATTGGTATCAGCAGAAAC

CAGGGAAAGCCCCTAAGCTCCTGATCTATGCTGCATCCAGTTTGCAAAGTGGGGTCCCA

TCAAGGTTCAGTGGCAGTGGATCTGGGACAGATTTCACTCTCACCATCAGCAGTCTGCA

ACCTGAAGATTTTGCAACTTACTACTGTCAACAGAGTTACAGTACCCCGCTCACTTTCGG

CGGAGGGACCAAGGTGGAGATCAAACGT [SEQ ID NO: 393]

Light Chain Amino Acid sequence:
DIQLTQSPSSLSASVGDRVTITCRASQSISSYLNWYQQKPGKAPKLLIYAASSLQSGVPSRFS

GSGSGTDFTLTISSLQPEDFATYYCQQSYSTPLTFGGGTKVEIKR [SEQ ID NO: 394]

Heavy Chain DNA sequence:
CAGGTGCAGCTGGTGCAGTCTGGGGCTGAGGTGAAGAAGCCTGGGGCCTCAGTGAAGG

TTTCCTGCAAGGCATCTGGATACACCTTCACCAGCTACTATATGCACTGGGTGCGACAG

GCCCCTGGACAAGGGCTTGAGTGGATGGGAATAATCAACCCTAGTGGTGGTAGCACAA

GCTACGCACAGAAGTTCCAGGGCAGAGTCACCATGACCAGGGACACGTCCACGAGCAC

AGTCTACATGGAGCTGAGCAGCCTGAGATCTGACGACACGGCCGTGTATTACTGTGCGC

GCTCTTACTACTCTGTTGGTACTCAGTGGCTGGATTCTTGGGGTCAAGGTACTCTGGTGA

CCGTCTCCTCA [SEQ ID NO: 395]

Heavy Chain Amino Acid sequence:
QVQLVQSGAEVKKPGASVKVSCKASGYTFTSYYMHWVRQAPGQGLEWMGIINPSGGSTSY

AQKFQGRVTMTRDTSTSTVYMELSSLRSDDTAVYYCARSYYSVGTQWLDSWGQGTLVTV

SS [SEQ ID NO: 396]

EXT010-23
DNA sequence:
TCCTATGAGCTGACTCAGCCACCCTCGATGTCAGTGGCCCCAGGACAGACGGCCAGGAT

TACCTGTGGGGGAAACAACGTTGGCAGAAAAAGTGTGCACTGGTACCAGCAGAAGCCA

GGCCAGGCCCCTGTGCTGGTCGTCTATGATGATAGCGTCCGGCCCTCAGGGATCCCTGA

GCGATTCTCTGGCTCCAACTCTGGGAACACGGCCACCCTGACCATCAGCAGGGTCGAAG

CCGGGGATGAGGCCGACTATTTCTGTCAGGTGTGGGATAATTTTCGTGATCAGGTGTTC

GGCGGAGGGACCAAGCTGACCGTCCTAGGTTCTAGAGGTGGTGGTGGTAGCGGCGGCG

GCGGCTCTGGTGGTGGTGGATCCCTCGAGATGGCCGAGGTGCAGCTGGTGGAGTCTGGG

GCTGAGGTGAAGAAGCCTGGGGCCTCAGTGAAGGTTTCCTGCAAGGCATCTGGATACA

CCTTCACCAGCTACTATATGCACTGGGTGCGACAGGCCCCTGGACAAGGGCTTGAGTGG

ATGGGAATAATCAACCCTAGTGGTGGTAGCACAAGCTACGCACAGAAGTTCCAGGGCA

-continued

APPENDIX C

GAGTCACCATGACCAGGGACACGTCCACGAGCACAGTCTACATGGCGCTGAGCAGCCT

GAGATCTGAGGACACGGCCGTATATTACTGTGCGCGCGGTGTTTCTTTCATGTCTGCTAT

GGATTCTTGGGGTCAAGGTACTCTGGTGACCGTCTCCTCA [SEQ ID NO: 397]

Amino Acid sequence:
SYELTQPPSMSVAPGQTARITCGGNNVGRKSVHWYQQKPGQAPVLVVYDDSVRPSGIPERF

SGSNSGNTATLTISRVEAGDEADYFCQVWDNFRDQVFGGGTKLTVLGSRGGGGSGGGGSG

GGGSLEMAEVQLVESGAEVKKPGASVKVSCKASGYTFTSYYMHWVRQAPGQGLEWMGII

NPSGGSTSYAQKFQGRVTMTRDTSTSTVYMALSSLRSEDTAVYYCARGVSFMSAMDSWG

QGTLVTVSS [SEQ ID NO: 398]

Light Chain DNA sequence:
TCCTATGAGCTGACTCAGCCACCCTCGATGTCAGTGGCCCCAGGACAGACGGCCAGGAT

TACCTGTGGGGGAAACAACGTTGGCAGAAAAAGTGTGCACTGGTACCAGCAGAAGCCA

GGCCAGGCCCCTGTGCTGGTCGTCTATGATGATAGCGTCCGGCCCTCAGGGATCCCTGA

GCGATTCTCTGGCTCCAACTCTGGGAACACGGCCACCCTGACCATCAGCAGGGTCGAAG

CCGGGGATGAGGCCGACTATTTCTGTCAGGTGTGGGATAATTTTCGTGATCAGGTGTTC

GGCGGAGGGACCAAGCTGACCGTCCTAGGT [SEQ ID NO: 399]

Light Chain Amino Acid sequence:
SYELTQPPSMSVAPGQTARITCGGNNVGRKSVHWYQQKPGQAPVLVVYDDSVRPSGIPERF

SGSNSGNTATLTISRVEAGDEADYFCQVWDNFRDQVFGGGTKLTVLG [SEQ ID NO: 400]

Heavy Chain DNA sequence:
GAGGTGCAGCTGGTGGAGTCTGGGGCTGAGGTGAAGAAGCCTGGGGCCTCAGTGAAGG

TTTCCTGCAAGGCATCTGGATACACCTTCACCAGCTACTATATGCACTGGGTGCGACAG

GCCCCTGGACAAGGGCTTGAGTGGATGGGAATAATCAACCCTAGTGGTGGTAGCACAA

GCTACGCACAGAAGTTCCAGGGCAGAGTCACCATGACCAGGGACACGTCCACGAGCAC

AGTCTACATGGCGCTGAGCAGCCTGAGATCTGAGGACACGGCCGTATATTACTGTGCGC

GCGGTGTTTCTTTCATGTCTGCTATGGATTCTTGGGGTCAAGGTACTCTGGTGACCGTCT

CCTCA [SEQ ID NO: 401]

Heavy Chain Amino Acid sequence:
EVQLVESGAEVKKPGASVKVSCKASGYTFTSYYMHWVRQAPGQGLEWMGIINPSGGSTSY

AQKFQGRVTMTRDTSTSTVYMALSSLRSEDTAVYYCARGVSFMSAMDSWGQGTLVTVSS

[SEQ ID NO: 402]

EXT010-24
DNA sequence:
GACATCCAGTTGACCCAGTCTCCTTCCACCCTGGCTGCATCTGTCGGAGAAAGAGTCAC

CATCACTTGCCGGGCCAGTCAGAATATTGGTAACTGGTTGGCCTGGTATCAGCAGAAAC

CAGGGAAAGCCCCTAAGGTCCTGATGTTTCAGGCATCTAATTTAGAAGCTGGGGTCCCA

TCAAGGTTCAGCGGCAGTGGATTTGGGACAGAATTCACTCTTACCATCAGCAGCCTGCA

GCCTGATGATTTTGCAACTTATTACTGTCAACAGTATTATGGTACCCCTCTCACTTTCGG

CGGAGGGACCAAGGTGGAGATCAAACGTTCTAGAGGTGGTGGTGGTAGCGGCGGCGGC

GGCTCTGGTGGTGGTGGATCCCTCGAGATGGCCGAGGTCCAGCTGGTGCAGTCTGGGGC

TGAGGTGAAGAAGCCTGGGGCCTCAGTGAAGGTCTCCTGCAAGGCTTCTGGATACACCT

TCACCGGCTACTATATGCACTGGGTGCGACAGGCCCCTGGACAAGGGCTTGAGTGGATG

-continued

APENDIX C

```
GGACGGATCAACCCTAACAGTGGTGGCACAAACTATGCACAGAAGTTTCAGGGCAGGG

TCACCATGACCAGGGACACGTCCATCAGCACAGCCTACATGGAGCTGAGCAGGCTGAG

ATCTGACGACACGGCCGTGTATTACTGTGCGCGCGACTGGTCTTCTTACGACTCTGTTAT

GGATTCTTGGGGTCAAGGTACTCTGGTGACCGTCTCCTCA [SEQ ID NO: 403]
```
Amino Acid sequence:
DIQLTQSPSTLAASVGERVTITCRASQNIGNWLAWYQQKPGKAPKVLMFQASNLEAGVPSR

FSGSGFGTEFTLTISSLQPDDFATYYCQQYYGTPLTFGGGTKVEIKRSRGGGGSGGGGSGGG

GSLEMAEVQLVQSGAEVKKPGASVKVSCKASGYTFTGYYMHWVRQAPGQGLEWMGRIN

PNSGGTNYAQKFQGRVTMTRDTSISTAYMELSRLRSDDTAVYYCARDWSSYDSVMDSWG

QGTLVTVSS [SEQ ID NO: 404]

Light Chain DNA sequence:
```
GACATCCAGTTGACCCAGTCTCCTTCCACCCTGGCTGCATCTGTCGGAGAAAGAGTCAC

CATCACTTGCCGGGCCAGTCAGAATATTGGTAACTGGTTGGCCTGGTATCAGCAGAAAC

CAGGGAAAGCCCCTAAGGTCCTGATGTTTCAGGCATCTAATTTAGAAGCTGGGGTCCCA

TCAAGGTTCAGCGGCAGTGGATTTGGGACAGAATTCACTCTTACCATCAGCAGCCTGCA

GCCTGATGATTTTGCAACTTATTACTGTCAACAGTATTATGGTACCCCTCTCACTTTCGG

CGGAGGGACCAAGGTGGAGATCAAACGT [SEQ ID NO: 405]
```
Light Chain Amino Acid sequence:
DIQLTQSPSTLAASVGERVTITCRASQNIGNWLAWYQQKPGKAPKVLMFQASNLEAGVPSR

FSGSGFGTEFTLTISSLQPDDFATYYCQQYYGTPLTFGGGTKVEIKR [SEQ ID NO: 406]

Heavy Chain DNA sequence:
```
GAGGTCCAGCTGGTGCAGTCTGGGGCTGAGGTGAAGAAGCCTGGGGCCTCAGTGAAGG

TCTCCTGCAAGGCTTCTGGATACACCTTCACCGGCTACTATATGCACTGGGTGCGACAG

GCCCCTGGACAAGGGCTTGAGTGGATGGGACGGATCAACCCTAACAGTGGTGGCACAA

ACTATGCACAGAAGTTTCAGGGCAGGGTCACCATGACCAGGGACACGTCCATCAGCAC

AGCCTACATGGAGCTGAGCAGGCTGAGATCTGACGACACGGCCGTGTATTACTGTGCGC

GCGACTGGTCTTCTTACGACTCTGTTATGGATTCTTGGGGTCAAGGTACTCTGGTGACCG

TCTCCTCA [SEQ ID NO: 407]
```
Heavy Chain Amino Acid sequence:
EVQLVQSGAEVKKPGASVKVSCKASGYTFTGYYMHWVRQAPGQGLEWMGRINPNSGGTN

YAQKFQGRVTMTRDTSISTAYMELSRLRSDDTAVYYCARDWSSYDSVMDSWGQGTLVTV

SS [SEQ ID NO: 408]

EXT010-25
DNA sequence:
```
TCTTCTGAGCTGACTCAGGACCCTGCTGTGTCTGTGGCCTTGGGACAGACAGTCAGGAT

CACATGCCAGGGAGACAGCCTCAGAGACTTTTATGCAACCTGGTACCAGCAGAAGCCA

GGACAGGCCCCTGTACTTGTCATCTATGGTGAAAATTACCGGCCCTCAGGGATCCCAGA

CCGGTTCTCTGGCTCCAGGTCAGGAAATACAGCTTCCTTGACCATCAGTGGGCTCAGG

CGGAGGATGAGGCTGACTATTACTGTAAGTCCCGCGACAGCAATGTTTACCATTGGGTA

TTCGGCGGCGGGACCAAGCTGACCGTCCTAGGTTCTAGAGGTGGTGGTGGTAGCGGCG

GCGGCGGCTCTGGTGGTGGTGGATCCCTCGAGATGGCCCAGGTCCAGCTGGTGCAGTCT

GGAGCTGAGGTGAAGAAGCCTGGGGCCTCAGTGAAGGTCTCCTGCAAGGCTTCTGGTTA
```

APPENDIX C

```
CACCTTTACCAGCTACGGTATCAGCTGGGTGCGACAGGCCCCTGGACAAGGGCTTGAGT

GGATGGGATGGATCAGCGCTTACAATGGTAACACAAACTATGCACAGAAGCTCCAGGG

CAGAGTCACCATGACCACAGACACATCCACGAGCACAGCCTACATGGAGCTGAGGAGC

CTGAGATCTGACGACACGGCCGTGTATTACTGTGCGCGCTGGGTTGGTATGGAAGAAGA

AGATCATTGGGGTCAAGGTACTCTGGTGACCGTCTCCTCA [SEQ ID NO: 409]
```

Amino Acid sequence:
SSELTQDPAVSVALGQTVRITCQGDSLRDFYATWYQQKPGQAPVLVIYGENYRPSGIPDRFS
GSRSGNTASLTISGAQAEDEADYYCKSRDSNVYHWVFGGGTKLTVLGSRGGGGSGGGGSG
GGGSLEMAQVQLVQSGAEVKKPGASVKVSCKASGYTFTSYGISWVRQAPGQGLEWMGWI
SAYNGNTNYAQKLQGRVTMTTDTSTSTAYMELRSLRSDDTAVYYCARWVGMEEEDHWG
QGTLVTVSS [SEQ ID NO: 410]

Light Chain DNA sequence:
```
TCTTCTGAGCTGACTCAGGACCCTGCTGTGTCTGTGGCCTTGGGACAGACAGTCAGGAT

CACATGCCAGGGAGACAGCCTCAGAGACTTTTATGCAACCTGGTACCAGCAGAAGCCA

GGACAGGCCCCTGTACTTGTCATCTATGGTGAAAATTACCGGCCCTCAGGGATCCCAGA

CCGGTTCTCTGGCTCCAGGTCAGGAAATACAGCTTCCTTGACCATCAGTGGGCTCAGG

CGGAGGATGAGGCTGACTATTACTGTAAGTCCCGCGACAGCAATGTTTACCATTGGGTA

TTCGGCGGCGGGACCAAGCTGACCGTCCTAGGT [SEQ ID NO: 411]
```

Light Chain Amino Acid sequence:
SSELTQDPAVSVALGQTVRITCQGDSLRDFYATWYQQKPGQAPVLVIYGENYRPSGIPDRFS
GSRSGNTASLTISGAQAEDEADYYCKSRDSNVYHWVFGGGTKLTVLG [SEQ ID NO: 412]

Heavy Chain DNA sequence:
```
CAGGTCCAGCTGGTGCAGTCTGGAGCTGAGGTGAAGAAGCCTGGGGCCTCAGTGAAGG

TCTCCTGCAAGGCTTCTGGTTACACCTTTACCAGCTACGGTATCAGCTGGGTGCGACAG

GCCCCTGGACAAGGGCTTGAGTGGATGGGATGGATCAGCGCTTACAATGGTAACACAA

ACTATGCACAGAAGCTCCAGGGCAGAGTCACCATGACCACAGACACATCCACGAGCAC

AGCCTACATGGAGCTGAGGAGCCTGAGATCTGACGACACGGCCGTGTATTACTGTGCGC

GCTGGGTTGGTATGGAAGAAGAAGATCATTGGGGTCAAGGTACTCTGGTGACCGTCTCC

TCA [SEQ ID NO: 413]
```

Heavy Chain Amino Acid sequence:
QVQLVQSGAEVKKPGASVKVSCKASGYTFTSYGISWVRQAPGQGLEWMGWISAYNGNTN
YAQKLQGRVTMTTDTSTSTAYMELRSLRSDDTAVYYCARWVGMEEEDHWQGTLVTVSS
[SEQ ID NO: 414]

EXT010-26
DNA sequence:
```
CAGTCTGTCGTGACGCAGCCGCCCTCAGTGTCTGGGGCCCCAGGGCAGAGGGTCACCAT

GTCCTGCACTGGGAGCAGCTCCAACATCGGGGCAGGTCATGATGTACACTGGTACCAAC

AATTTCCAGAGACAGCCCCCAAACTCCTCATCTCTGGTAACGGCGATCGGCCCTCTGGG

GTCCCTGACCGCTTCTCTGGCTCCAAGTCTGGCACCTCAGCCTCCCTGGCCATCGCTGGA

CTCCAGGCTGAGGATGAGGCTGATTATTACTGCCAGTCCTATGACAGCAGCCTGAGTGG

TTATGTCTTCGGCAGTGGGACCAAGGTCACCGTCCTAGGTTCTAGAGGTGGTGGTGGTA

GCGGCGGCGGCGGCTCTGGTGGTGGTGGATCCCTCGAGATGGCCGAGGTGCAGCTGGT
```

-continued

APPENDIX C

GGAGACTGGGGCTGAGGTGAAGAAGCCTGGGGCCTCCGTGAAGATTTCCTGCAAGGCA

TCTGGATACACCTTCAGTAGTTACTATCTACATTGGCTGCGACAGGCCCCTGGACAAGG

GCCTCAGTGGATGGGAGTAATCAACCCGAGCGGTGGTTACACAAGCTACGCACAGAGA

TTCCAGGGCAGAGTCACCATGACCAGGGACACGTCCACAGAAACAATCTACATGGAGC

TGAGCAGCCTGACGTCTGATGACACGGCCGTATATTACTGTGCGCGCTCTGTTACTCATT

CTTCTTCTGCTTTCGATTACTGGGGTCAAGGTACTCTGGTGACCGTCTCCTCA [SEQ ID NO: 415]

Amino Acid sequence:
QSVVTQPPSVSGAPGQRVTMSCTGSSSNIGAGHDVHWYQQFPETAPKLLISGNGDRPSGVP

DRFSGSKSGTSASLAIAGLQAEDEADYYCQSYDSSLSGYVFGSGTKVTVLGSRGGGGSGGG

GSGGGGSLEMAEVQLVETGAEVKKPGASVKISCKASGYTFSSYYLHWLRQAPGQGPQWM

GVINPSGGYTSYAQRFQGRVTMTRDTSTETIYMELSSLTSDDTAVYYCARSVTHSSSAFDY

WGQGTLVTVSS [SEQ ID NO: 416]

Light Chain DNA sequence:
CAGTCTGTCGTGACGCAGCCGCCCTCAGTGTCTGGGGCCCCAGGGCAGAGGGTCACCAT

GTCCTGCACTGGGAGCAGCTCCAACATCGGGGCAGGTCATGATGTACACTGGTACCAAC

AATTTCCAGAGACAGCCCCCAAACTCCTCATCTCTGGTAACGGCGATCGGCCCTCTGGG

GTCCCTGACCGCTTCTCTGGCTCCAAGTCTGGCACCTCAGCCTCCCTGGCCATCGCTGGA

CTCCAGGCTGAGGATGAGGCTGATTATTACTGCCAGTCCTATGACAGCAGCCTGAGTGG

TTATGTCTTCGGCAGTGGGACCAAGGTCACCGTCCTAGGT [SEQ ID NO: 417]

Light Chain Amino Acid sequence:
QSVVTQPPSVSGAPGQRVTMSCTGSSSNIGAGHDVHWYQQFPETAPKLLISGNGDRPSGVP

DRFSGSKSGTSASLAIAGLQAEDEADYYCQSYDSSLSGYVFGSGTKVTVLG [SEQ ID NO: 418]

Heavy Chain DNA sequence:
GAGGTGCAGCTGGTGGAGACTGGGGCTGAGGTGAAGAAGCCTGGGGCCTCCGTGAAGA

TTTCCTGCAAGGCATCTGGATACACCTTCAGTAGTTACTATCTACATTGGCTGCGACAGG

CCCCTGGACAAGGGCCTCAGTGGATGGGAGTAATCAACCCGAGCGGTGGTTACACAAG

CTACGCACAGAGATTCCAGGGCAGAGTCACCATGACCAGGGACACGTCCACAGAAACA

ATCTACATGGAGCTGAGCAGCCTGACGTCTGATGACACGGCCGTATATTACTGTGCGCG

CTCTGTTACTCATTCTTCTTCTGCTTTCGATTACTGGGGTCAAGGTACTCTGGTGACCGTC

TCCTCA [SEQ ID NO: 419]

Heavy Chain Amino Acid sequence:
EVQLVETGAEVKKPGASVKISCKASGYTFSSYYLHWLRQAPGQGPQWMGVINPSGGYTSY

AQRFQGRVTMTRDTSTETIYMELSSLTSDDTAVYYCARSVTHSSSAFDYWGQGTLVTVSS

[SEQ ID NO: 420]

EXT010-27
DNA sequence:
CAGTCTGTGTTGACTCAGCCACCCTCAGTGTCAGTGGCCCCAGGACAGACGGCCAGGAT

TACCTGTGGGGGAAACAACATTGGAACTAAAACTGTTCACTGGTACCAGCAGAAGTCA

GGCCAGGCCCCTGTGCTGGTCATCTATTATGATATCGACCGGCCCTCAGGGATCCCTGA

GCGGTTCTCTGGCTCCACCTCTGGAAATACGGCCACCCTGACCATCAGCAGGGTCGAAG

CCGGGGATGAGGCCGACTATCACTGTCAGGTGTGGGATAGTGGCAGTTATCAGGGGGT

GTTCGGCGGAGGGACCAAGCTGACCGTCCTAGGTTCTAGAGGTGGTGGTGGTAGCGGC

APPENDIX C

GGCGGCGGCTCTGGTGGTGGTGGATCCCTCGAGATGGCCCAGATGCAGCTGGTGCAGTC

TGGGGCTGAGGTGAAGAAGCCTGGGGCCTCAGTGAAGGTTTCCTGCAAGGCATCTGGA

TACACCTTCACCAGCTACTATATGCACTGGGTGCGACAGGCCCCTGGACAAGGGCTTGA

GTGGATGGGAATAATCAACCCTAGTGGTGGTAGCACAAGCTACGCACAGAAGTTCCAG

GGCAGAGTCACCATGACCAGGGACACGTCCACGAGCACAGTCTACATGGAGCTGAGCA

GCCTGAGATCTGAGGACACTGCCGTGTATTACTGTGCGCGCGGTCAGTCTGGTGTTGTTT

ACGATTGGGGTCAAGGTACTCTGGTGACCGTCTCCTCA [SEQ ID NO: 421]

Amino Acid sequence:
QSVLTQPPSVSVAPGQTARITCGGNNIGTKTVHWYQQKSGQAPVLVIYYDIDRPSGIPERFS

GSTSGNTATLTISRVEAGDEADYHCQVWDSGSYQGVFGGGTKLTVLGSRGGGGSGGGGSG

GGGSLEMAQMQLVQSGAEVKKPGASVKVSCKASGYTFTSYYMHWVRQAPGQGLEWMGII

NPSGGSTSYAQKFQGRVTMTRDTSTSTVYMELSSLRSEDTAVYYCARGQSGVVYDWGQGT

LVTVSS [SEQ ID NO: 422]

Light Chain DNA sequence:
CAGTCTGTGTTGACTCAGCCACCCTCAGTGTCAGTGGCCCCAGGACAGACGGCCAGGAT

TACCTGTGGGGGAAACAACATTGGAACTAAAACTGTTCACTGGTACCAGCAGAAGTCA

GGCCAGGCCCCTGTGCTGGTCATCTATTATGATATCGACCGGCCCTCAGGGATCCCTGA

GCGGTTCTCTGGCTCCACCTCTGGAAATACGGCCACCCTGACCATCAGCAGGGTCGAAG

CCGGGGATGAGGCCGACTATCACTGTCAGGTGTGGGATAGTGGCAGTTATCAGGGGGT

GTTCGGCGGAGGGACCAAGCTGACCGTCCTAGGT [SEQ ID NO: 423]

Light Chain Amino Acid sequence:
QSVLTQPPSVSVAPGQTARITCGGNNIGTKTVHWYQQKSGQAPVLVIYYDIDRPSGIPERFS

GSTSGNTATLTISRVEAGDEADYHCQVWDSGSYQGVFGGGTKLTVLG [SEQ ID NO: 424]

Heavy Chain DNA sequence:
CAGATGCAGCTGGTGCAGTCTGGGGCTGAGGTGAAGAAGCCTGGGGCCTCAGTGAAGG

TTTCCTGCAAGGCATCTGGATACACCTTCACCAGCTACTATATGCACTGGGTGCGACAG

GCCCCTGGACAAGGGCTTGAGTGGATGGGAATAATCAACCCTAGTGGTGGTAGCACAA

GCTACGCACAGAAGTTCCAGGGCAGAGTCACCATGACCAGGGACACGTCCACGAGCAC

AGTCTACATGGAGCTGAGCAGCCTGAGATCTGAGGACACTGCCGTGTATTACTGTGCGC

GCGGTCAGTCTGGTGTTGTTTACGATTGGGGTCAAGGTACTCTGGTGACCGTCTCCTCA

[SEQ ID NO: 425]

Heavy Chain Amino Acid sequence:
QMQLVQSGAEVKKPGASVKVSCKASGYTFTSYYMHWVRQAPGQGLEWMGIINPSGGSTS

YAQKFQGRVTMTRDTSTSTVYMELSSLRSEDTAVYYCARGQSGVVYDWGQGTLVTVSS

[SEQ ID NO: 426]

EXT010-28
DNA sequence:
GAAATTGTGTTGACACAGTCTCCAGGCACCCTGTCTTTGTCTCCAGGGGAAAGAGCATC

CCTCTCCTGCAGGGCCAGTCAGAGTATTACCGACAACTTCTTAGCCTGGTACCAGCAGA

AACCTGGCCAGGCTCCCAGGCTCCTCTTCTATGGGGCATCCTACAGGGCCAATGGCATC

CCAGACAGGTTCAGTGGCAGTGGGTCTGGGACAGACTTCACTCTCACCATCAGCAGACT

GGAGCCTGAAGATTTTGCCGTGTATTACTGTCACCAGTATGGCAGCTCACCTCCGGGCA

APPENDIX C

CTTTCGGCCCTGGGACCAAAGTGGATATCAAACGTTCTAGAGGTGGTGGTGGTAGCGGC

GGCGGCGGCTCTGGTGGTGGTGGATCCCTCGAGATGGCCGAGGTCCAGCTGGTACAGTC

TGGGGCTGAGGTGAAGAAGCCTGGGGCCTCAGTGAAGCTTTCCTGCAAGGCATCTGGAT

ACACCTTCACCAGTTACTACATGCACTGGGTGCGACAGGCCCCTGGACAAGGGCTTGAG

TGGATGGGAATAATTAACCCTACTGGTGGTTACACAACCTACGCACAGAAGTTCCAGGA

CAGAGTCGCCATTACCAGGGACACGTCCATGAGCACAGTCTACATGGAGCTGAGCAAC

CTGAGATCTGAAGACACGGCCGTGTATTACTGTGCGCGCGGTACTACTTACATGTGGTC

TGGTTACGATTCTTGGGGTCAAGGTACTCTGGTGACCGTCTCCTCA [SEQ ID NO: 427]

Amino Acid sequence:
MKYLLPTAAAGLLLLAAQPAMAELEIVLTQSPGTLSLSPGERASLSCRASQSITDNFLAWYQ

QKPGQAPRLLFYGASYRANGIPDRFSGSGSGTDFTLTISRLEPEDFAVYYCHQYGSSPPGTFG

PGTKVDIKRSRGGGGSGGGGSGGGGSLEMAEVQLVQSGAEVKKPGASVKLSCKASGYTFT

SYYMHWVRQAPGQGLEWMGIINPTGGYTTYAQKFQDRVAITRDTSMSTVYMELSNLRSED

TAVYYCARGTTYMWSGYDSWGQGTLVTVSS [SEQ ID NO: 428]

Light Chain DNA sequence:
GAAATTGTGTTGACACAGTCTCCAGGCACCCTGTCTTTGTCTCCAGGGGAAAGAGCATC

CCTCTCCTGCAGGGCCAGTCAGAGTATTACCGACAACTTCTTAGCCTGGTACCAGCAGA

AACCTGGCCAGGCTCCCAGGCTCCTCTTCTATGGGGCATCCTACAGGGCCAATGGCATC

CCAGACAGGTTCAGTGGCAGTGGGTCTGGGACAGACTTCACTCTCACCATCAGCAGACT

GGAGCCTGAAGATTTTGCCGTGTATTACTGTCACCAGTATGGCAGCTCACCTCCGGGCA

CTTTCGGCCCTGGGACCAAAGTGGATATCAAACGT [SEQ ID NO: 429]

Light Chain Amino Acid sequence:
EIVLTQSPGTLSLSPGERASLSCRASQSITDNFLAWYQQKPGQAPRLLFYGASYRANGIPDRF

SGSGSGTDFTLTISRLEPEDFAVYYCHQYGSSPPGTFGPGTKVDIKR [SEQ ID NO: 430]

Heavy Chain DNA sequence:
GAGGTCCAGCTGGTACAGTCTGGGGCTGAGGTGAAGAAGCCTGGGGCCTCAGTGAAGC

TTTCCTGCAAGGCATCTGGATACACCTTCACCAGTTACTACATGCACTGGGTGCGACAG

GCCCCTGGACAAGGGCTTGAGTGGATGGGAATAATTAACCCTACTGGTGGTTACACAAC

CTACGCACAGAAGTTCCAGGACAGAGTCGCCATTACCAGGGACACGTCCATGAGCACA

GTCTACATGGAGCTGAGCAACCTGAGATCTGAAGACACGGCCGTGTATTACTGTGCGCG

CGGTACTACTTACATGTGGTCTGGTTACGATTCTTGGGGTCAAGGTACTCTGGTGACCGT

CTCCTCA [SEQ ID NO: 431]

Heavy Chain Amino Acid sequence:
EVQLVQSGAEVKKPGASVKLSCKASGYTFTSYYMHWVRQAPGQGLEWMGIINPTGGYTTY

AQKFQDRVAITRDTSMSTVYMELSNLRSEDTAVYYCARGTTYMWSGYDSWGQGTLVTVSS

[SEQ ID NO: 432]

EXT010-29
DNA sequence:
CAGGCTGTGCTGACTCAGCCTGCCTCCGTGTCTGGGTCTCCTGGACAGTCGATCACCGT

CTCCTGCACTGGAACCAGCAGTGACGTTGGTGGTTATAACTATGTCTCCTGGTACCAAC

AGCACCCAGGCAAAGCCCCCAAACTCATGATTTATGATGTCAGTCAGCGGCCCTCAGGG

GTTTCTCATCGCTTCTCTGGCTCCAAGTCTGGCAACACGGCCTCCCTGACCATCTCTGGG

APPENDIX C

```
CTCCAGGCTGAGGACGAGGCTGATTATTACTGCAGTTCATATACAAGCACCAGTGTTTA

TGTCTTCGGAACTGGGACCAAGGTCACCGTCCTAGGTTCTAGAGGTGGTGGTGGTAGCG

GCGGCGGCGGCTCTGGTGGTGGTGGATCCCTCGAGATGGCCCAGGTGCAGCTGGTGCA

GTCTGGACCTGAGGTGAAGAAGCCTGGGGCCTCAGTGAAGGTTTCCTGCAAGGCATCTG

GATACACCTTCACCAGTTACTATATGCACTGGGTGCGACAGGCCCCTGGACAAGGGCTT

GAGTGGATGGGAATAATCAACCCTAGTGGTGGTAGCACAACCTACGCACAGAAGTTCC

AGGGCAGAGTCACCATGACCAGGGACACGTCCACGAGCACAGTCTACATGGAGCTGAG

CAGCCTGAGATCTGAGGACACTGCCGTGTATTACTGTGCGCGCTCTGTTATGCATTACTA

CGACTTCTTCGATGGTTGGGGTCAAGGTACTCTGGTGACCGTCTCCTCA [SEQ ID NO: 433]
```

Amino Acid sequence:
QAVLTQPASVSGSPGQSITVSCTGTSSDVGGYNYVSWYQQHPGKAPKLMIYDVSQRPSGVS

HRFSGSKSGNTASLTISGLQAEDEADYYCSSYTSTSVYVFGTGTKVTVLGSRGGGGSGGGG

SGGGGSLEMAQVQLVQSGPEVKKPGASVKVSCKASGYTFTSYYMHWVRQAPGQGLEWM

GIINPSGGSTTYAQKFQGRVTMTRDTSTSTVYMELSSLRSEDTAVYYCARSVMHYYDFFDG

WGQGTLVTVSS [SEQ ID NO: 434]

Light Chain DNA sequence:
```
CAGGCTGTGCTGACTCAGCCTGCCTCCGTGTCTGGGTCTCCTGGACAGTCGATCACCGT

CTCCTGCACTGGAACCAGCAGTGACGTTGGTGGTTATAACTATGTCTCCTGGTACCAAC

AGCACCCAGGCAAAGCCCCCAAACTCATGATTTATGATGTCAGTCAGCGGCCCTCAGGG

GTTTCTCATCGCTTCTCTGGCTCCAAGTCTGGCAACACGGCCTCCCTGACCATCTCTGGG

CTCCAGGCTGAGGACGAGGCTGATTATTACTGCAGTTCATATACAAGCACCAGTGTTTA

TGTCTTCGGAACTGGGACCAAGGTCACCGTCCTAGGT [SEQ ID NO: 435]
```

Light Chain Amino Acid sequence:
QAVLTQPASVSGSPGQSITVSCTGTSSDVGGYNYVSWYQQHPGKAPKLMIYDVSQRPSGVS

HRFSGSKSGNTASLTISGLQAEDEADYYCSSYTSTSVYVFGTGTKVTVLG [SEQ ID NO: 436]

Heavy Chain DNA sequence:
```
CAGGTGCAGCTGGTGCAGTCTGGACCTGAGGTGAAGAAGCCTGGGGCCTCAGTGAAGG

TTTCCTGCAAGGCATCTGGATACACCTTCACCAGTTACTATATGCACTGGGTGCGACAG

GCCCCTGGACAAGGGCTTGAGTGGATGGGAATAATCAACCCTAGTGGTGGTAGCACAA

CCTACGCACAGAAGTTCCAGGGCAGAGTCACCATGACCAGGGACACGTCCACGAGCAC

AGTCTACATGGAGCTGAGCAGCCTGAGATCTGAGGACACTGCCGTGTATTACTGTGCGC

GCTCTGTTATGCATTACTACGACTTCTTCGATGGTTGGGGTCAAGGTACTCTGGTGACCG

TCTCCTCA [SEQ ID NO: 437]
```

Heavy Chain Amino Acid sequence:
QVQLVQSGPEVKKPGASVKVSCKASGYTFTSYYMHWVRQAPGQGLEWMGIINPSGGSTTY

AQKFQGRVTMTRDTSTSTVYMELSSLRSEDTAVYYCARSVMHYYDFFDGWGQGTLVTVSS

[SEQ ID NO: 438]

EXT010-30
DNA sequence:
```
CAATCTGcCCTGACTCAGCCTGCCTCCGTGTCTGGGTCTCCTGGACAGTCGATCACCATC

TCCTGCAGTGGAACCAGCAGTGACGTTGGTGCATATAACTATGTCTCCTGGTACCAACA

ACACCCAGGCAAAGCCCCCAAACTCATGATCTATGATGTCACTAAGCGGCCCTCAGGG
```

-continued

APPENDIX C

GTTTCTCATCGCTTCTCTGGCTCCAAGTCTGGCAACACGGCCTCCCTGACCATCTCTGGG

CTCCAGGCTGAGGACGAGGCTGATTATTACTGCAGCTCGTTTACAGCCATCGGCACTTG

GGTGTTCGGCGGAGGGACCAAGCTGACCGTCCTAGGTTCTAGAGGTGGTGGTGGTAGC

GGCGGCGGCGGCTCTGGTGGTGGTGGATCCCTCGAGATGGCCCAGGTCCAGCTGGTGC

AGTCTGGGGCTGAGGTGGAGAAGCCTGGGGCCTCAGTGAAAGTTTCCTGCAAGGCATCT

GGATACACCTTCACCAGCTCCTATCTGCACTGGGTGCGACAGGCCCCTGGACAAGGACT

TGAGTGGATGGGAATAATCAACCCTACTGCTGGTAGCACAAGCTACGCACAGAAGTTCC

AGGACAGAGTCACCATGACCAGGGACACGTCGACGAGCACAGTCTACATGGAGCTGAG

CAgGCTGAGATCTGACGACACGGCCGTGTATTACTGTGCGCGCGGTTACTCTTTCGCTGG

TTACTACGATTGGTGGGGTCAAGGTACTCTGGTGACCGTCTCCTCA [SEQ ID NO: 439]

Amino Acid sequence:
QSALTQPASVSGSPGQSITISCSGTSSDVGAYNYVSWYQQHPGKAPKLMIYDVTKRPSGVSH

RFSGSKSGNTASLTISGLQAEDEADYYCSSFTAIGTWVFGGGTKLTVLGSRGGGGSGGGGS

GGGGSLEMAQVQLVQSGAEVEKPGASVKVSCKASGYTFTSSYLHWVRQAPGQGLEWMGII

NPTAGSTSYAQKFQDRVTMTRDTSTSTVYMELSRLRSDDTAVYYCARGYSFAGYYDWWG

QGTLVTVSS [SEQ ID NO: 440]

Light Chain DNA sequence:
CAATCTGcCCTGACTCAGCCTGCCTCCGTGTCTGGGTCTCCTGGACAGTCGATCACCATC

TCCTGCAGTGGAACCAGCAGTGACGTTGGTGCATATAACTATGTCTCCTGGTACCAACA

ACACCCAGGCAAAGCCCCCAAAACTCATGATCTATGATGTCACTAAGCGGCCCTCAGGG

GTTTCTCATCGCTTCTCTGGCTCCAAGTCTGGCAACACGGCCTCCCTGACCATCTCTGGG

CTCCAGGCTGAGGACGAGGCTGATTATTACTGCAGCTCGTTTACAGCCATCGGCACTTG

GGTGTTCGGCGGAGGGACCAAGCTGACCGTCCTAGGT [SEQ ID NO: 441]

Light Chain Amino Acid sequence:
QSALTQPASVSGSPGQSITISCSGTSSDVGAYNYVSWYQQHPGKAPKLMIYDVTKRPSGVSH

RFSGSKSGNTASLTISGLQAEDEADYYCSSFTAIGTWVFGGGTKLTVLG [SEQ ID NO: 442]

Heavy Chain DNA sequence:
CAGGTCCAGCTGGTGCAGTCTGGGGCTGAGGTGGAGAAGCCTGGGGCCTCAGTGAAAG

TTTCCTGCAAGGCATCTGGATACACCTTCACCAGCTCCTATCTGCACTGGGTGCGACAG

GCCCCTGGACAAGGACTTGAGTGGATGGGAATAATCAACCCTACTGCTGGTAGCACAA

GCTACGCACAGAAGTTCCAGGACAGAGTCACCATGACCAGGGACACGTCGACGAGCAC

AGTCTACATGGAGCTGAGCAgGCTGAGATCTGACGACACGGCCGTGTATTACTGTGCGC

GCGGTTACTCTTTCGCTGGTTACTACGATTGGTGGGGTCAAGGTACTCTGGTGACCGTCT

CCTCA [SEQ ID NO: 443]

Heavy Chain Amino Acid sequence:
QVQLVQSGAEVEKPGASVKVSCKASGYTFTSSYLHWVRQAPGQGLEWMGIINPTAGSTSY

AQKFQDRVTMTRDTSTSTVYMELSRLRSDDTAVYYCARGYSFAGYYDWWGQGTLVTVSS

[SEQ ID NO: 444]

EXT010-31
DNA sequence:
CAGTCTGTGTTGACGCAGCCGCCCTCAGTGTCTGGGGCCCCAGGGCAGAGGGTCACCAT

CTCCTGCACTGGGAGCAGCTCCAACATCGGGGCAGGTTATGATGTACACTGGTACCAAC

APPENDIX C

AACTTCCGGGAAGAGCCCCCAAAGTCCTCATCTATGGTAACAACAATCGGCCCTCGGGG

GTCCCTGACCGATTCTCTGGCTCCAAGTCTGGCACCTCAGCCTCCCTGGCCATCACTGGT

CTCCGGGTTGAGGATGAGGCTGATTATTACTGCCAGTCCTATGACAACAACCTGAGTGG

GGTATTCGGCGGAGGGACCAAGCTGACCGTCCTAGGTTCTAGAGGTGGTGGTGGTAGC

GGCGGCGGCGGCTCTGGTGGTGGTGGATCCCTCGAGATGGCCCAGATGCAGCTGGTGC

AGTCTGGGGCTGAGGTGAAGAAGCCTGGGGCCTCACTGAAGGTTTCCTGCAAGGCATCT

GGATACACCTTCACCAGTTACTATATGCACTGGGTGCGACAGGCCCCTGGGCAAGGGCT

TGAGTGGATGGGAATAATCAACCCTACTGGTGGTAGCACAAGCTACGCACAGAAGTTC

CAGGGCAGAGTCACCATGACCAGGGACACGTCCACGAGCACAGTCTACATGGAGCTGA

GCAGCCTGAGATCTGAGGACACGGCCGTGTATTACTGTGCGCGCTCTATCACTTACTGG

TCTGCTTACGATTACTGGGGTCAAGGTACTCTGGTGACCGTCTCCTCA [SEQ ID NO: 445]

Amino Acid sequence:
QSVLTQPPSVSGAPGQRVTISCTGSSSNIGAGYDVHWYQQLPGRAPKVLIYGNNNRPSGVPD

RFSGSKSGTSASLAITGLRVEDEADYYCQSYDNNLSGVFGGGTKLTVLGSRGGGGSGGGGS

GGGGSLEMAQMQLVQSGAEVKKPGASLKVSCKASGYTFTSYYMHWVRQAPGQGLEWMG

IINPTGGSTSYAQKFQGRVTMTRDTSTSTVYMELSSLRSEDTAVYYCARSITYWSAYDYWG

QGTLVTVSS [SEQ ID NO: 446]

Light Chain DNA sequence:
CAGTCTGTGTTGACGCAGCCGCCCTCAGTGTCTGGGGCCCCAGGGCAGAGGGTCACCAT

CTCCTGCACTGGGAGCAGCTCCAACATCGGGGCAGGTTATGATGTACACTGGTACCAAC

AACTTCCGGGAAGAGCCCCCAAAGTCCTCATCTATGGTAACAACAATCGGCCCTCGGGG

GTCCCTGACCGATTCTCTGGCTCCAAGTCTGGCACCTCAGCCTCCCTGGCCATCACTGGT

CTCCGGGTTGAGGATGAGGCTGATTATTACTGCCAGTCCTATGACAACAACCTGAGTGG

GGTATTCGGCGGAGGGACCAAGCTGACCGTCCTAGGT [SEQ ID NO: 447]

Light Chain Amino Acid sequence:
QSVLTQPPSVSGAPGQRVTISCTGSSSNIGAGYDVHWYQQLPGRAPKVLIYGNNNRPSGVPD

RFSGSKSGTSASLAITGLRVEDEADYYCQSYDNNLSGVFGGGTKLTVLG [SEQ ID NO: 448]

Heavy Chain DNA sequence:
CAGATGCAGCTGGTGCAGTCTGGGGCTGAGGTGAAGAAGCCTGGGGCCTCACTGAAGG

TTTCCTGCAAGGCATCTGGATACACCTTCACCAGTTACTATATGCACTGGGTGCGACAG

GCCCCTGGGCAAGGGCTTGAGTGGATGGGAATAATCAACCCTACTGGTGGTAGCACAA

GCTACGCACAGAAGTTCCAGGGCAGAGTCACCATGACCAGGGACACGTCCACGAGCAC

AGTCTACATGGAGCTGAGCAGCCTGAGATCTGAGGACACGGCCGTGTATTACTGTGCGC

GCTCTATCACTTACTGGTCTGCTTACGATTACTGGGGTCAAGGTACTCTGGTGACCGTCT

CCTCA [SEQ ID NO: 449]

APPENDIX C

Heavy Chain Amino Acid sequence:
QMQLVQSGAEVKKPGASLKVSCKASGYTFTSYYMHWVRQAPGQGLEWMGIINPTGGSTS

YAQKFQGRVTMTRDTSTSTVYMELSSLRSEDTAVYYCARSITYWSAYDYWGQGTLVTVSS

[SEQ ID NO: 450]

EXT010-32
DNA sequence:
CAGTCTGTGTTGACGCAGCCGCCCTCAGTGTCTGCGGCCCCAGGACAGAAGGTCACCAT

CTCCTGCTCTGGAAGCAGCTCCAACATTGGGAATAATTATGTATCCTGGTACCAGCAGC

TCCCAGGAACAGCCCCCAAACTCCTCATTTATGACAATAATAAGCGACCCTCAGGGATT

CCTGACCGATTCTCTGGCTCCAAGTCTGGCACGTCAGCCACCCTGGGCATCACCGGACT

CCAGACTGGGGACGAGGCCGATTATTACTGCGGCATATGGGATAGCAGCCTGAGTGCT

GGCTCTTATGTCTTCGGAAATGGGACCAAGGTCACCGTCCTAGGTTCTAGAGGTGGTGG

TGGTAGCGGCGGCGGCGGCTCTGGTGGTGGTGGATCCCTCGAGATGGCCCAGATGCAG

CTGGTGCAGTCTGGGGCTGAGGTGAAGAAGCCTGGGGCCTCAGTGAAGGTTTCCTGCAA

GGCGTCTGGATACACCTTCACCAGCTACTATATACACTGGGTGCGACAGGCCCCTGGAC

AAGGGCTTGAGTGGATGGGAATGATCAATCCTACTGCTGGTACCACAAACTACACACA

GAACTTTCAGGACAGAGTCACCATGACCAGGGACACGTCCACGACCACAGTCTTCATG

GAGCTGACCAGCCTGAGATCTGAGGACACGGCCGTGTATTACTGTGCGCGCTACGTTTT

CGGTTCTGGTCAGGATTCTTGGGGTCAAGGTACTCTGGTGACCGTCTCCTCA

[SEQ ID NO: 451]

Amino Acid sequence:
QSVLTQPPSVSAAPGQKVTISCSGSSSNIGNNYVSWYQQLPGTAPKLLIYDNNKRPSGIPDRF

SGSKSGTSATLGITGLQTGDEADYYCGIWDSSLSAGSYVFGNGTKVTVLGSRGGGGSGGGG

SGGGGSLEMAQMQLVQSGAEVKKPGASVKVSCKASGYTFTSYYIHWVRQAPGQGLEWM

GMINPTAGTTNYTQNFQDRVTMTRDTSTTTVFMELTSLRSEDTAVYYCARYVFGSGQDSW

GQGTLVTVSS [SEQ ID NO: 452]

Light Chain DNA sequence:
CAGTCTGTGTTGACGCAGCCGCCCTCAGTGTCTGCGGCCCCAGGACAGAAGGTCACCAT

CTCCTGCTCTGGAAGCAGCTCCAACATTGGGAATAATTATGTATCCTGGTACCAGCAGC

TCCCAGGAACAGCCCCCAAACTCCTCATTTATGACAATAATAAGCGACCCTCAGGGATT

CCTGACCGATTCTCTGGCTCCAAGTCTGGCACGTCAGCCACCCTGGGCATCACCGGACT

CCAGACTGGGGACGAGGCCGATTATTACTGCGGCATATGGGATAGCAGCCTGAGTGCT

GGCTCTTATGTCTTCGGAAATGGGACCAAGGTCACCGTCCTAGGT [SEQ ID NO: 453]

Light Chain Amino Acid sequence:
QSVLTQPPSVSAAPGQKVTISCSGSSSNIGNNYVSWYQQLPGTAPKLLIYDNNKRPSGIPDRF

SGSKSGTSATLGITGLQTGDEADYYCGIWDSSLSAGSYVFGNGTKVTVLG

[SEQ ID NO: 454]

Heavy Chain DNA sequence:
CAGATGCAGCTGGTGCAGTCTGGGGCTGAGGTGAAGAAGCCTGGGGCCTCAGTGAAGG

TTTCCTGCAAGGCGTCTGGATACACCTTCACCAGCTACTATATACACTGGGTGCGACAG

GCCCCTGGACAAGGGCTTGAGTGGATGGGAATGATCAATCCTACTGCTGGTACCACAAA

CTACACACAGAACTTTCAGGACAGAGTCACCATGACCAGGGACACGTCCACGACCACA

APPENDIX C

GTCTTCATGGAGCTGACCAGCCTGAGATCTGAGGACACGGCCGTGTATTACTGTGCGCG

CTACGTTTTCGGTTCTGGTCAGGATTCTTGGGGTCAAGGTACTCTGGTGACCGTCTCCTCA

[SEQ ID NO: 455]

Heavy Chain Amino Acid sequence:
QMQLVQSGAEVKKPGASVKVSCKASGYTFTSYYIHWVRQAPGQGLEWMGMINPTAGTTN

YTQNFQDRVTMTRDTSTTTVFMELTSLRSEDTAVYYCARYVFGSGQDSWGQGTLVTVSS

[SEQ ID NO: 456]

EXT010-33
DNA sequence:
CAGTCTGTGTTGACTCAGCCACCCTCGGTGTCAGTGGCCCCAGGAAAGACGGCCAGGAT

TACCTGTGGGGGAAACAACATTGGAAGTAAAAGTGTGCACTGGTACCAGCAGAAGCCA

GGCCAGGCCCCTGTGCTGGTCGTCTATGATGATAGCGACCGGCCCTCAGGGATCCCTGA

GCGATTCTCTGGCTCCAACTCTGGGAACACGGCCACCCTGACCATCAGCAGGGTCGAAG

CCGGGGATGAGGCCGACTATTACTGTCAGGTGTGGGATAGTAGTAGTGATCATGTGGTA

TTCGGCGGAGGGACCAAGCTGACCGTCCTAGGTTCTAGAGGTGGTGGTGGTAGCGGCG

GCGGCGGCTCTGGTGGTGGTGGATCCCTCGAGATGGCCGAGGTGCAGCTGGTGGAGTCT

GGGGCTGAGGTGAAGAAGCCTGGGGCCTCAGTGAAAGTTTTCTGCAAGGCATCTGGAT

ACGCCTTCACCAGCTACTATATTCACTGGGTGCGACAGGCCCCTGGACAAGGTCTTGAG

TGGATGGGAGTAATCAACCCTACTGGTGGTTACACAACCTACGCACAGAAGTTCCAGGG

CAGAGTCACCATGACCAGTGACACGTCCACGAACACAGTCTACATGGAACTGAGCAGC

CTGAGATCTGAGGACACGGCCGTGTATTACTGTGCGCGCGGTGTTTACGGTTCTCTGGA

TTCTTGGGGTCAAGGTACTCTGGTGACCGTCTCCTCA [SEQ ID NO: 457]

Amino Acid sequence:
QSVLTQPPSVSVAPGKTARITCGGNNIGSKSVHWYQQKPGQAPVLVVYDDSDRPSGIPERFS

GSNSGNTATLTISRVEAGDEADYYCQVWDSSSDHVVFGGGTKLTVLGSRGGGGSGGGGSG

GGGSLEMAEVQLVESGAEVKKPGASVKVFCKASGYAFTSYYIHWVRQAPGQGLEWMGVI

NPTGGYTTYAQKFQGRVTMTSDTSTNTVYMELSSLRSEDTAVYYCARGVYGSLDSWGQG

TLVTVSS [SEQ ID NO: 458]

Light Chain DNA sequence:
CAGTCTGTGTTGACTCAGCCACCCTCGGTGTCAGTGGCCCCAGGAAAGACGGCCAGGAT

TACCTGTGGGGGAAACAACATTGGAAGTAAAAGTGTGCACTGGTACCAGCAGAAGCCA

GGCCAGGCCCCTGTGCTGGTCGTCTATGATGATAGCGACCGGCCCTCAGGGATCCCTGA

GCGATTCTCTGGCTCCAACTCTGGGAACACGGCCACCCTGACCATCAGCAGGGTCGAAG

CCGGGGATGAGGCCGACTATTACTGTCAGGTGTGGGATAGTAGTAGTGATCATGTGGTA

TTCGGCGGAGGGACCAAGCTGACCGTCCTAGGT [SEQ ID NO: 459]

Light Chain Amino Acid sequence:
QSVLTQPPSVSVAPGKTARITCGGNNIGSKSVHWYQQKPGQAPVLVVYDDSDRPSGIPERFS

GSNSGNTATLTISRVEAGDEADYYCQVWDSSSDHVVFGGGTKLTVLG [SEQ ID NO: 460]

Heavy Chain DNA sequence:
GAGGTGCAGCTGGTGGAGTCTGGGGCTGAGGTGAAGAAGCCTGGGGCCTCAGTGAAAG

TTTTCTGCAAGGCATCTGGATACGCCTTCACCAGCTACTATATTCACTGGGTGCGACAG

GCCCCTGGACAAGGTCTTGAGTGGATGGGAGTAATCAACCCTACTGGTGGTTACACAAC

-continued

APPENDIX C

CTACGCACAGAAGTTCCAGGGCAGAGTCACCATGACCAGTGACACGTCCACGAACACA

GTCTACATGGAACTGAGCAGCCTGAGATCTGAGGACACGGCCGTGTATTACTGTGCGCG

CGGTGTTTACGGTTCTCTGGATTCTTGGGGTCAAGGTACTCTGGTGACCGTCTCCTCA

[SEQ ID NO: 461]

Heavy Chain Amino Acid sequence:
EVQLVESGAEVKKPGASVKVFCKASGYAFTSYYIHWVRQAPGQGLEWMGVINPTGGYTTY

AQKFQGRVTMTSDTSTNTVYMELSSLRSEDTAVYYCARGVYGSLDSWGQGTLVTVSS

[SEQ ID NO: 462]

EXT010-34
DNA sequence:
CAGGCTGTGCTGACTCAGCCACCCTCGGTGTCAGTGGCCCCAGGAAAGACGGCCAGGA

TTACCTGTGCGGGAAACAAAATTGAAAGTAAAAGTGTGCATTGGTACCAGAAGAAGCC

AGGCCAGGCCCCTGTGTTGGTCGTCTATGATGATAGTGACCGGCCCTCAGGGATCCCTG

AGCGATTCTCTGGCTCCAACTCTGGGAACACGGCCACCCTGACCATCAGCGGGGTCGAA

GCCGGGGATGAGGCCGACTATTACTGTCAGGTGTGGGATAGTAGTAATGATGTCCAGGT

GTTCGGCGGAGGGACCAAGCTGACCGTCCTAGGTTCTAGAGGTGGTGGTGGTAGCGGC

GGCGGCGGCTCTGGTGGTGGTGGATCCCTCGAGATGGCCCAGGTCCAGCTGGTGCAGTC

TGGGGCTGAGGTGAAGAAGCCTGGGGCCTCAGTGCAGGTTTCCTGCAGGGCATCTGGAT

ACACAATCACCTCCTACTATATGCACTGGGTGCGACAGGCCCCTGGACAAGGGCTTGAG

TGGATGGGAGTAATCAACCCTAATGCTGGCAGCACAAGATACGCACAGAAATTCCAGG

GCAGAGTCACCATGAGCACTGACACGTCCACGAGCACAGTCTACATGGCGCTGAGTAG

TCTGAGATCTGACGACACGGCCGTGTATTACTGTGCGCGCCAGTCTTCTGGTCGTGACG

GTTTCGATTCTTGGGGTCAAGGTACTCTGGTGACCGTCTCCTCA [SEQ ID NO: 463]

Amino Acid sequence:
QAVLTQPPSVSVAPGKTARITCAGNKIESKSVHWYQKKPGQAPVLVVYDDSDRPSGIPERFS

GSNSGNTATLTISGVEAGDEADYYCQVWDSSNDVQVFGGGTKLTVLGSRGGGGSGGGGSG

GGGSLEMAQVQLVQSGAEVKKPGASVQVSCRASGYTITSYYMHWVRQAPGQGLEWMGVI

NPNAGSTRYAQKFQGRVTMSDTSTSTVYMALSSLRSDDTAVYYCARQSSGRDGFDSWGQ

GTLVTVSS [SEQ ID NO: 464]

Light Chain DNA sequence:
CAGGCTGTGCTGACTCAGCCACCCTCGGTGTCAGTGGCCCCAGGAAAGACGGCCAGGA

TTACCTGTGCGGGAAACAAAATTGAAAGTAAAAGTGTGCATTGGTACCAGAAGAAGCC

AGGCCAGGCCCCTGTGTTGGTCGTCTATGATGATAGTGACCGGCCCTCAGGGATCCCTG

AGCGATTCTCTGGCTCCAACTCTGGGAACACGGCCACCCTGACCATCAGCGGGGTCGAA

GCCGGGGATGAGGCCGACTATTACTGTCAGGTGTGGGATAGTAGTAATGATGTCCAGGT

GTTCGGCGGAGGGACCAAGCTGACCGTCCTAGGT [SEQ ID NO: 465]

Light Chain Amino Acid sequence:
QAVLTQPPSVSVAPGKTARITCAGNKIESKSVHWYQKKPGQAPVLVVYDDSDRPSGIPERFS

GSNSGNTATLTISGVEAGDEADYYCQVWDSSNDVQVFGGGTKLTVLG [SEQ ID NO: 466]

Heavy Chain DNA sequence:
CAGGTCCAGCTGGTGCAGTCTGGGGCTGAGGTGAAGAAGCCTGGGGCCTCAGTGCAGG

TTTCCTGCAGGGCATCTGGATACACAATCACCTCCTACTATATGCACTGGGTGCGACAG

APPENDIX C

GCCCCTGGACAAGGGCTTGAGTGGATGGGAGTAATCAACCCTAATGCTGGCAGCACAA

GATACGCACAGAAATTCCAGGGCAGAGTCACCATGAGCACTGACACGTCCACGAGCAC

AGTCTACATGGCGCTGAGTAGTCTGAGATCTGACGACACGGCCGTGTATTACTGTGCGC

GCCAGTCTTCTGGTCGTGACGGTTTCGATTCTTGGGGTCAAGGTACTCTGGTGACCGTCT

CCTCA [SEQ ID NO: 467]

Heavy Chain Amino Acid sequence:
QVQLVQSGAEVKKPGASVQVSCRASGYTITSYYMHWVRQAPGQGLEWMGVINPNAGSTR

YAQKFQGRVTMSTDTSTSTVYMALSSLRSDDTAVYYCARQSSGRDGFDSWGQGTLVTVSS
[SEQ ID NO: 468]

EXT010-42
DNA sequence:
TCCTATGTGCTGACTCAGCCACCCTCAGTGTCAGTGGCCCCAGGAAAGACGGCCAGGAT

TACCTGTGGGGGAAACAACATTGGAAGTAAAAGTGTGCACTGGTACCAGCAGAAGCCA

GGCCAGGCCCCTGTGCTGGTCATCTATTATGATAGCGACCGGCCCTCAGGGATCCCTGA

GCGATTCTCTGGCTCCAACTCTGGGAACACGGCCACCCTGACCATCAGCAGGGTCGAAG

CCGGGGATGAGGCCGACTATTACTGTCAGGTGTGGGATAGTAGTAGTGATCTTCCTTAT

GTCTTCGGAACTGGGACCAAGGTCACCGTCCTAGGTTCTAGAGGTGGTGGTGGTAGCGG

CGGCGGCGGCTCTGGTGGTGGTGGATCCCTCGAGATGGCCCAGATGCGGCTGGTGCAGT

CTGGGGCTGAGGTGAAGAAGCCTGGGGCCTCAGTGAAGGTTTCCTGCAAGGCATCTGG

ATACACCTTCACCAGCTACTATATGCACTGGGTGCGACAGGCCCCTGGACAAGGGCTTG

AGTGGATGGGAATAATCAACCCTACTAGTGGTACCACAAGCTTCGCACAGAAGTTCCAG

GGCAGAGTCACCATGACCAGGGACACGTCCACGAGCACAGTCTACATGGAGCTGAGCA

GCCTGAGATCTGAGGACACTGCCGTGTATTACTGTGCGCGCTCTCCGTCTTTCTACTACG

ATGGTTGGGGTCAAGGTACTCTGGTGACCGTCTCCTCA [SEQ ID NO: 469]

Amino Acid sequence:
SYVLTQPPSVSVAPGKTARITCGGNNIGSKSVHWYQQKPGQAPVLVIYYDSDRPSGIPERFS

GSNSGNTATLTISRVEAGDEADYYCQVWDSSSDLPYVFGTGTKVTVLGSRGGGGSGGGGS

GGGGSLEMAQMRLVQSGAEVKKPGASVKVSCKASGYTFTSYYMHWVRQAPGQGLEWMG

IINPTSGTTSFAQKFQGRVTMTRDTSTSTVYMELSSLRSEDTAVYYCARSPSFYYDGWGQGT

LVTVSS [SEQ ID NO: 470]

Light Chain DNA sequence:
TCCTATGTGCTGACTCAGCCACCCTCAGTGTCAGTGGCCCCAGGAAAGACGGCCAGGAT

TACCTGTGGGGGAAACAACATTGGAAGTAAAAGTGTGCACTGGTACCAGCAGAAGCCA

GGCCAGGCCCCTGTGCTGGTCATCTATTATGATAGCGACCGGCCCTCAGGGATCCCTGA

GCGATTCTCTGGCTCCAACTCTGGGAACACGGCCACCCTGACCATCAGCAGGGTCGAAG

CCGGGGATGAGGCCGACTATTACTGTCAGGTGTGGGATAGTAGTAGTGATCTTCCTTAT

GTCTTCGGAACTGGGACCAAGGTCACCGTCCTAGGT [SEQ ID NO: 471]

Light Chain Amino Acid sequence:
SYVLTQPPSVSVAPGKTARITCGGNNIGSKSVHWYQQKPGQAPVLVIYYDSDRPSGIPERFS

GSNSGNTATLTISRVEAGDEADYYCQVWDSSSDLPYVFGTGTKVTVLG [SEQ ID NO: 472]

-continued

APPENDIX C

Heavy Chain DNA sequence:
CAGATGCGGCTGGTGCAGTCTGGGGCTGAGGTGAAGAAGCCTGGGGCCTCAGTGAAGG

TTTCCTGCAAGGCATCTGGATACACCTTCACCAGCTACTATATGCACTGGGTGCGACAG

GCCCCTGGACAAGGGCTTGAGTGGATGGGAATAATCAACCCTACTAGTGGTACCACAA

GCTTCGCACAGAAGTTCCAGGGCAGAGTCACCATGACCAGGGACACGTCCACGAGCAC

AGTCTACATGGAGCTGAGCAGCCTGAGATCTGAGGACACTGCCGTGTATTACTGTGCGC

GCTCTCCGTCTTTCTACTACGATGGTTGGGGTCAAGGTACTCTGGTGACCGTCTCCTCA

[SEQ ID NO: 473]

Heavy Chain Amino Acid sequence:
QMRLVQSGAEVKKPGASVKVSCKASGYTFTSYYMHWVRQAPGQGLEWMGIINPTSGTTSF

AQKFQGRVTMTRDTSTSTVYMELSSLRSEDTAVYYCARSPSFYYDGWGQGTLVTVSS

[SEQ ID NO: 474]

EXT010-44
DNA sequence:
CAGTCTGTGTTGACGCAGCCGCCCTCAGTGTCTGGGGCCCCAGGGCAGAGGGTCACCAT

CTCCTGCACTGGGAGCAGCTCCAACATCGGGGCAGGTTATGATGTACACTGGTACCAGC

AGCTTCCAGGAACAGCCCCCAAACTCCTCATCCAGGGTAACAGCAATCGGCCCTCAGG

GGTCCCTGATCGATTCTCTGGCTCCAAGTCTGGCGCCTCAGCCTCCCTGGCCATCACTGG

GCTCCAGGCTGAGGATGAGGCTGATTATTACTGCCAGTCCTATGACGACAGGTTGAGTG

GCTCTTATGTCTTTGGAACTGGGACCAAGGTCACCGTCCTAGGTTCTAGAGGTGGTGGT

GGTAGCGGCGGCGGCGGCTCTGGTGGTGGTGGATCCCTCGAGATGGCCCAGGTGCAGC

TGGTGCAGTCTGGGGCTGAGGTGAAGAGGCCTGGGGCCTCAGTGAAGGTTTCCTGCAA

GGCATCTGGATACAGCTTCACCAACTACTATATGCACTGGGTGCGACAGGCCCCTGGAC

ACGGGCTTGAGTGGATGGGTTTAATCACCCCTACTAATGGTGGCGCCAACTACGCACAG

AAGTTCCGGGGAAGAGTCTCCTTGACCAGGGACACGTCCACGGACACAGTCTACATGG

AGTTGAGCAGCCTGACTTCTGAGGACACGGCCGTGTATTACTGTGCGCGCCAGTGGTCT

TACACTTCTTTCTCTCTGTCTGGTTACATCTCTTACGATTCTTGGGGTCAAGGTACTCTGG

TGACCGTCTCCTCA [SEQ ID NO: 475]

Amino Acid sequence:
QSVLTQPPSVSGAPGQRVTISCTGSSSNIGAGYDVHWYQQLPGTAPKLLIQGNSNRPSGVPD

RFSGSKSGASASLAITGLQAEDEADYYCQSYDDRLSGSYVFGTGTKVTVLGSRGGGGSGGG

GSGGGGSLEMAQVQLVQSGAEVKRPGASVKVSCKASGYSFTNYYMHWVRQAPGHGLEW

MGLITPTNGGANYAQKFRGRVSLTRDTSTDTVYMELSSLTSEDTAVYYCARQWSYTSFSLS

GYISYDSWGQGTLVTVSS [SEQ ID NO: 476]

Light Chain DNA sequence:
CAGTCTGTGTTGACGCAGCCGCCCTCAGTGTCTGGGGCCCCAGGGCAGAGGGTCACCAT

CTCCTGCACTGGGAGCAGCTCCAACATCGGGGCAGGTTATGATGTACACTGGTACCAGC

AGCTTCCAGGAACAGCCCCCAAACTCCTCATCCAGGGTAACAGCAATCGGCCCTCAGG

GGTCCCTGATCGATTCTCTGGCTCCAAGTCTGGCGCCTCAGCCTCCCTGGCCATCACTGG

GCTCCAGGCTGAGGATGAGGCTGATTATTACTGCCAGTCCTATGACGACAGGTTGAGTG

GCTCTTATGTCTTTGGAACTGGGACCAAGGTCACCGTCCTAGGT [SEQ ID NO: 477]

APPENDIX C

Light Chain Amino Acid sequence:
QSVLTQPPSVSGAPGQRVTISCTGSSSNIGAGYDVHWYQQLPGTAPKLLIQGNSNRPSGVPD

RFSGSKSGASASLAITGLQAEDEADYYCQSYDDRLSGSYVFGTGTKVTVLG [SEQ ID NO: 478]

Heavy Chain DNA sequence:
CAGGTGCAGCTGGTGCAGTCTGGGGCTGAGGTGAAGAGGCCTGGGGCCTCAGTGAAGG

TTTCCTGCAAGGCATCTGGATACAGCTTCACCAACTACTATATGCACTGGGTGCGACAG

GCCCCTGGACACGGGCTTGAGTGGATGGGTTTAATCACCCCTACTAATGGTGGCGCCAA

CTACGCACAGAAGTTCCGGGGAAGAGTCTCCTTGACCAGGGACACGTCCACGGACACA

GTCTACATGGAGTTGAGCAGCCTGACTTCTGAGGACACGGCCGTGTATTACTGTGCGCG

CCAGTGGTCTTACACTTCTTTCTCTGTCTGGTTACATCTCTTACGATTCTTGGGGTCAA

GGTACTCTGGTGACCGTCTCCTCA [SEQ ID NO: 479]

Heavy Chain Amino Acid sequence:
QVQLVQSGAEVKRPGASVKVSCKASGYSFTNYYMHWVRQAPGHGLEWMGLITPTNGGAN

YAQKFRGRVSLTRDTSTDTVYMELSSLTSEDTAVYYCARQWSYTSFSLSGYISYDSWGQGT

LVTVSS [SEQ ID NO: 480]

EXT010-47
DNA sequence:
TCCTATGTGCTGACTCAGCCACCCTCAGTGTCAGTGGCCCCAGGAAAGACGGCCAGGAT

TACCTGTGGGGGAAACAACATTGGAAGTAAAAGTGTGCACTGGTACCAGCAGAAGCCA

GGCCAGGCCCCTGTGCTGGTCATCTATTATGATAGCGACCGGCCCTCAGGGATCCCTGA

GCGATTCTCTGGCTCCAACTCTGGGAACACGGCCACCCTGACCATCAGCAGGGTCGAAG

CCGGGGATGAGGCCGACTATTACTGTCAGGTGTGGGATAGTAGTAGTGATCAAGGGGT

GTTCGGCGGAGGGACCAAGCTGACCGTCCTAGGTTCTAGAGGTGGTGGTGGTAGCGGC

GGCGGCGGCTCTGGTGGTGGTGGATCCCTCGAGATGGCCGAGGTGCAGCTGGTGCAGTC

TGGGGGAGGCTTGGTACAGCCTAGGGGGTCCCTGAGACTCTCCTGTGCAGGCTCTGGAT

TCACCTTCAGTAGCTATGCTATGCACTGGGTTCGCCAGGCTCCAGGCAAGGGGCTGGAG

TGGGTGGCAGTTATATCATATGATGGAAGCAATAAATACTACGCAGACTCCGTGAAGG

GCCGATTCACCATCTCCAGAGACAATTCCAAGAACACGCTGTATCTGCAAATGAACAGC

CTGAGAGCTGAGGACACGGCCGTGTATTACTGTGCGCGCAACGGTTACTGGTACTGGGG

TTCTGGTGAACATGGTTCTTGGTACGATTCTTGGGGTCAAGGTACTCTGGTGACCGTCTC

CTCA [SEQ ID NO: 481]

Amino Acid sequence:
SYVLTQPPSVSVAPGKTARITCGGNNIGSKSVHWYQQKPGQAPVLVIYYDSDRPSGIPERFS

GSNSGNTATLTISRVEAGDEADYYCQVWDSSSDQGVFGGGTKLTVLGSRGGGGSGGGGSG

GGGSLEMAEVQLVQSGGGLVQPRGSLRLSCAGSGFTFSSYAMHWVRQAPGKGLEWVAVIS

YDGSNKYYADSVKGRFTISRDNSKNTLYLQMNSLRAEDTAVYYCARNGYWYWGSEHGS

WYDSWGQGTLVTVSS [SEQ ID NO: 482]

Light Chain DNA sequence:
TCCTATGTGCTGACTCAGCCACCCTCAGTGTCAGTGGCCCCAGGAAAGACGGCCAGGAT

TACCTGTGGGGGAAACAACATTGGAAGTAAAAGTGTGCACTGGTACCAGCAGAAGCCA

GGCCAGGCCCCTGTGCTGGTCATCTATTATGATAGCGACCGGCCCTCAGGGATCCCTGA

GCGATTCTCTGGCTCCAACTCTGGGAACACGGCCACCCTGACCATCAGCAGGGTCGAAG

APPENDIX C

CCGGGGATGAGGCCGACTATTACTGTCAGGTGTGGGATAGTAGTAGTGATCAAGGGGT

GTTCGGCGGAGGGACCAAGCTGACCGTCCTAGGT [SEQ ID NO: 483]

Light Chain Amino Acid sequence:
SYVLTQPPSVSVAPGKTARITCGGNNIGSKSVHWYQQKPGQAPVLVIYYDSDRPSGIPERFS

GSNSGNTATLTISRVEAGDEADYYCQVWDSSSDQGVFGGGTKLTVLG [SEQ ID NO: 484]

Heavy Chain DNA sequence:
GAGGTGCAGCTGGTGCAGTCTGGGGGAGGCTTGGTACAGCCTAGGGGGTCCCTGAGAC

TCTCCTGTGCAGGCTCTGGATTCACCTTCAGTAGCTATGCTATGCACTGGGTTCGCCAGG

CTCCAGGCAAGGGGCTGGAGTGGGTGGCAGTTATATCATATGATGGAAGCAATAAATA

CTACGCAGACTCCGTGAAGGGCCGATTCACCATCTCCAGAGACAATTCCAAGAACACG

CTGTATCTGCAAATGAACAGCCTGAGAGCTGAGGACACGGCCGTGTATTACTGTGCGCG

CAACGGTTACTGGTACTGGGGTTCTGGTAACATGGTTCTTGGTACGATTCTTGGGGTC

AAGGTACTCTGGTGACCGTCTCCTCA [SEQ ID NO: 485]

Heavy Chain Amino Acid sequence:
EVQLVQSGGGLVQPRGSLRLSCAGSGFTFSSYAMHWVRQAPGKGLEWVAVISYDGSNKYY

ADSVKGRFTISRDNSKNTLYLQMNSLRAEDTAVYYCARNGYWYWGSEHGSWYDSWGQ

GTLVTVSS [SEQ ID NO: 486]

EXT010-48
DNA sequence:
TCCTATGTGCTGACTCAGCCACTCTCAGTGTCAGTGGCCCCAGGAACGCCGGCCAGGAT

TACCTGTGAGGGAAACAACATTGGAAGTAATAGCGTGCACTGGTACCAGCAGAAGGCA

GGCCAGGCCCCTGTGTTGGTCATCTATTATGATAGCGACCGGCCCTCAGGGATCCCTGA

GCGATTCTCTGGCTCCACCTCTGGGAACACGGCCACCCTGACCATCAGCAGGGTCGAAG

GCGGGGATGAGGCCGACTATTTCTGTCAGGTGTGGGATAGTGCTATAAATCATGTGGTC

TTCGGCGGAGGGACCAAGCTGACCGTCCTAGGTTCTAGAGGTGGTGGTGGTAGCGGCG

GCGGCGGCTCTGGTGGTGGTGGATCCCTCGAGATGGCCCAGGTGCAGCTGGTGCAGTCT

GGGGCTGAGGAGAAGAAGCCTGGGACCTCAGTGAGGGTTTCCTGCAAGGCATCTGGAT

ACACCTTCACCAGTTACTATATGCACTGGGTGCGACAGGCCCCTGGACAAGGGCTTGAG

TGGATGGGAATAATCAACCCTAGTGGTGGTAGCACAAGCTACGCACAGAAGTTCCAGG

GCAGAGTCACCATGACCAGGGACACGTCCACGAGCACAGTCTACATGGAGCTGAGCAG

CCTGAGATCTGAGGACACTGCCGTGTATTACTGTGCGCGCGGTATGCCGGACGTTGTTG

ATGACTGGGGTCAAGGTACTCTGGTGACCGTCTCCTCA [SEQ ID NO: 487]

Amino Acid sequence:
SYVLTQPLSVSVAPGTPARITCEGNNIGSNSVHWYQQKAGQAPVLVIYYDSDRPSGIPERFS

GSTSGNTATLTISRVEGGDEADYFCQVWDSAINHVVFGGGTKLTVLGSRGGGGSGGGGSG

GGGSLEMAQVQLVQSGAEEKKPGTSVRVSCKASGYTFTSYYMHWVRQAPGQGLEWMGII

NPSGGSTSYAQKFQGRVTMTRDTSTSTVYMELSSLRSEDTAVYYCARGMPDVVDDWGQG

TLVTVSS [SEQ ID NO: 488]

Light Chain DNA sequence:
TCCTATGTGCTGACTCAGCCACTCTCAGTGTCAGTGGCCCCAGGAACGCCGGCCAGGAT

TACCTGTGAGGGAAACAACATTGGAAGTAATAGCGTGCACTGGTACCAGCAGAAGGCA

GGCCAGGCCCCTGTGTTGGTCATCTATTATGATAGCGACCGGCCCTCAGGGATCCCTGA

-continued

APPENDIX C

GCGATTCTCTGGCTCCACCTCTGGGAACACGGCCACCCTGACCATCAGCAGGGTCGAAG

GCGGGGATGAGGCCGACTATTTCTGTCAGGTGTGGGATAGTGCTATAAATCATGTGGTC

TTCGGCGGAGGGACCAAGCTGACCGTCCTAGGT [SEQ ID NO: 489]

Light Chain Amino Acid sequence:
SYVLTQPLSVSVAPGTPARITCEGNNIGSNSVHWYQQKAGQAPVLVIYYDSDRPSGIPERFS

GSTSGNTATLTISRVEGGDEADYFCQVWDSAINHVVFGGGTKLTVLG [SEQ ID NO: 490]

Heavy Chain DNA sequence:
CAGGTGCAGCTGGTGCAGTCTGGGGCTGAGGAGAAGAAGCCTGGGACCTCAGTGAGGG

TTTCCTGCAAGGCATCTGGATACACCTTCACCAGTTACTATATGCACTGGGTGCGACAG

GCCCCTGGACAAGGGCTTGAGTGGATGGGAATAATCAACCCTAGTGGTGGTAGCACAA

GCTACGCACAGAAGTTCCAGGGCAGAGTCACCATGACCAGGGACACGTCCACGAGCAC

AGTCTACATGGAGCTGAGCAGCCTGAGATCTGAGGACACTGCCGTGTATTACTGTGCGC

GCGGTATGCCGGACGTTGTTGATGACTGGGGTCAAGGTACTCTGGTGACCGTCTCCTCA

[SEQ ID NO: 491]

Heavy Chain Amino Acid sequence:
QVQLVQSGAEEKKPGTSVRVSCKASGYTFTSYYMHWVRQAPGQGLEWMGIINPSGGSTSY

AQKFQGRVTMTRDTSTSTVYMELSSLRSEDTAVYYCARGMPDVVDDWGQGTLVTVSS

[SEQ ID NO: 492]

EXT010-49
DNA sequence:
CAGGCTGTGCTGACTCAGCCACCCTCAGTGTCAGTGGCCCCAGGAAAGACGGCCAGGA

TTACCTGTGGGGGAAACAACATTGGAAGTAAAAGTGTGCACTGGTACCAGCAGAAGCC

AGGCCAGGCCCCTGTGCTGGTCATCTATTATGATAGCGACCGGCCCTCAGGGATCCCTG

AGCGATTCTCTGGCTCCAACTCTGGGAACACGGCCACCCTGACCATCAGCAGGGTCGAA

GCCGGGGATGAGGCCGACTATTACTGTCAGGTGTGGGATAGTAGTAGTGATCATTGGGT

GTTCGGCGGAGGGACCAAGCTGACCGTCCTAGGTTCTAGAGGTGGTGGTGGTAGCGGC

GGCGGCGGCTCTGGTGGTGGTGGATCCCTCGAGATGGCCGAGGTCCAGCTGGTGCAGTC

TGGGGCTGAGGTGAAGAAGCCTGGGGCCTCAGTGAAGGTTTCCTGCAAGGCATCTGGA

TACACCTTCACCAGCTACTATATGCACTGGGTGCGACAGGCCCCTGGACAAGGGCTTGA

GTGGATGGGAGTAATCAACCCTAGTGGTGGTTACACAAGCTACGCACAGAAGTTCCAG

GGCAGAGTCACCATGACCAGGGACACGTCCACGAGCACAGTCTACATGGAGCTGAGCA

GCCTGAGATCTGAGGACACGGCCGTGTATTACTGTGCGCGCTCTTCTTCTGGTGGTAAC

GGTGCTGATTCTTGGGGTCAAGGTACTCTGGTGACCGTCTCCTCA [SEQ ID NO: 493]

Amino Acid sequence:
QAVLTQPPSVSVAPGKTARITCGGNNIGSKSVHWYQQKPGQAPVLVIYYDSDRPSGIPERFS

GSNSGNTATLTISRVEAGDEADYYCQVWDSSSDHWVFGGGTKLTVLGSRGGGGSGGGGSG

GGGSLEMAEVQLVQSGAEVKKPGASVKVSCKASGYTFTSYYMHWVRQAPGQGLEWMGV

INPSGGYTSYAQKFQGRVTMTRDTSTSTVYMELSSLRSEDTAVYYCARSSSGGNGADSWG

QGTLVTVSS [SEQ ID NO: 494]

Light Chain DNA sequence:
CAGGCTGTGCTGACTCAGCCACCCTCAGTGTCAGTGGCCCCAGGAAAGACGGCCAGGA

TTACCTGTGGGGGAAACAACATTGGAAGTAAAAGTGTGCACTGGTACCAGCAGAAGCC

-continued

APPENDIX C

AGGCCAGGCCCCTGTGCTGGTCATCTATTATGATAGCGACCGGCCCTCAGGGATCCCTG

AGCGATTCTCTGGCTCCAACTCTGGGAACACGGCCACCCTGACCATCAGCAGGGTCGAA

GCCGGGGATGAGGCCGACTATTACTGTCAGGTGTGGGATAGTAGTAGTGATCATTGGGT

GTTCGGCGGAGGGACCAAGCTGACCGTCCTAGGT [SEQ ID NO: 495]

Light Chain Amino Acid sequence:
QAVLTQPPSVSVAPGKTARITCGGNNIGSKSVHWYQQKPGQAPVLVIYYDSDRPSGIPERFS

GSNSGNTATLTISRVEAGDEADYYCQVWDSSSDHWVFGGGTKLTVLG [SEQ ID NO: 496]

Heavy Chain DNA sequence:
GAGGTCCAGCTGGTGCAGTCTGGGGCTGAGGTGAAGAAGCCTGGGGCCTCAGTGAAGG

TTTCCTGCAAGGCATCTGGATACACCTTCACCAGCTACTATATGCACTGGGTGCGACAG

GCCCCTGGACAAGGGCTTGAGTGGATGGGAGTAATCAACCCTAGTGGTGGTTACACAA

GCTACGCACAGAAGTTCCAGGGCAGAGTCACCATGACCAGGGACACGTCCACGAGCAC

AGTCTACATGGAGCTGAGCAGCCTGAGATCTGAGGACACGGCCGTGTATTACTGTGCGC

GCTCTTCTTCTGGTGGTAACGGTGCTGATTCTTGGGGTCAAGGTACTCTGGTGACCGTCT

CCTCA [SEQ ID NO: 497]

Heavy Chain Amino Acid sequence:
EVQLVQSGAEVKKPGASVKVSCKASGYTFTSYYMHWVRQAPGQGLEWMGVINPSGGYTS

YAQKFQGRVTMTRDTSTSTVYMELSSLRSEDTAVYYCARSSSGGNGADSWGQGTLVTVSS

[SEQ ID NO: 498]

EXT010-55
DNA sequence:
CAGTCTGTGTTGACTCAGCCACCCTCAACGTCTGGGACCCCCGGGCAGAGGGTCACCAT

CTCTTGTTCTGGAAGCAGCTCCAACATCGGAAGAAATACTGCAAACTGGTACCAGCAGC

TCCCAGGAACGGCCCCCAAACTCCTCATCTATAGTAATAATCACCGGCCCTCAGGGGTC

CCTGACCGATTCTCTGGCTCCAAGTCTGGCACCTCAGCCTCCCTGGCCATCAGTGGGCTC

CAGTCTGAGGATGAGGCTGATTATTACTGTGCAGCATGGGATGACAGCCTGAATGGTCC

GGTGTTCGGCGGAGGGACCAAGCTGACCGTCCTAGGTTCTAGAGGTGGTGGTGGTAGC

GGCGGCGGCGGCTCTGGTGGTGGTGGATCCCTCGAGATGGCCGAGGTCCAGCTGGTGC

AGTCTGGAGCTGAGGTGAAGAAGCCTGGGGCCTCAGTGAAGGTCTCCTGCAAGGCTTCT

GGTTACACCTTTACCAGCTATGGTATCAGCTGGGTGCGACAGGCCCCTGGACAAGGGCT

TGAGTGGATGGGATGGATCAGCGCTTACAATGGTAACACAAACTATGCACAGAAGCTC

CAGGGCAGAGTCACCATGACCACAGACACATCCACGAGCACAGCCTACATGGAGCTGA

GGAGCCTGAGATCTGACGACACTGCCGTGTATTACTGTGCGCGCTCTTACTACGCTGCT

GACTGGTGGTGGCATGCTACTATGATGGATATGTGGGGTCAAGGTACTCTGGTGACCGT

CTCCTCA [SEQ ID NO: 499]

Amino Acid sequence:
QSVLTQPPSTSGTPGQRVTISCSGSSSNIGRNTANWYQQLPGTAPKLLIYSNNHRPSGVPDRF

SGSKSGTSASLAISGLQSEDEADYYCAAWDDSLNGPVFGGGTKLTVLGSRGGGGSGGGGS

GGGGSLEMAEVQLVQSGAEVKKPGASVKVSCKASGYTFTSYGISWVRQAPGQGLEWMGW

ISAYNGNTNYAQKLQGRVTMTTDTSTSTAYMELRSLRSDDTAVYYCARSYYAADWWWH

ATMMDMWGQGTLVTVSS [SEQ ID NO: 500]

APPENDIX C

Light Chain DNA sequence:
CAGTCTGTGTTGACTCAGCCACCCTCAACGTCTGGGACCCCCGGGCAGAGGGTCACCAT

CTCTTGTTCTGGAAGCAGCTCCAACATCGGAAGAAATACTGCAAACTGGTACCAGCAGC

TCCCAGGAACGGCCCCCAAACTCCTCATCTATAGTAATAATCACCGGCCCTCAGGGGTC

CCTGACCGATTCTCTGGCTCCAAGTCTGGCACCTCAGCCTCCCTGGCCATCAGTGGGCTC

CAGTCTGAGGATGAGGCTGATTATTACTGTGCAGCATGGGATGACAGCCTGAATGGTCC

GGTGTTCGGCGGAGGGACCAAGCTGACCGTCCTAGGT [SEQ ID NO: 501]

Light Chain Amino Acid sequence:
QSVLTQPPSTSGTPGQRVTISCSGSSSNIGRNTANWYQQLPGTAPKLLIYSNNHRPSGVPDRF

SGSKSGTSASLAISGLQSEDEADYYCAAWDDSLNGPVFGGGTKLTVLG [SEQ ID NO: 502]

Heavy Chain DNA sequence:
GAGGTCCAGCTGGTGCAGTCTGGAGCTGAGGTGAAGAAGCCTGGGGCCTCAGTGAAGG

TCTCCTGCAAGGCTTCTGGTTACACCTTTACCAGCTATGGTATCAGCTGGGTGCGACAG

GCCCCTGGACAAGGGCTTGAGTGGATGGGATGGATCAGCGCTTACAATGGTAACACAA

ACTATGCACAGAAGCTCCAGGGCAGAGTCACCATGACCACAGACACATCCACGAGCAC

AGCCTACATGGAGCTGAGGAGCCTGAGATCTGACGACACTGCCGTGTATTACTGTGCGC

GCTCTTACTACGCTGCTGACTGGTGGTGGCATGCTACTATGATGGATATGTGGGGTCAA

GGTACTCTGGTGACCGTCTCCTCA [SEQ ID NO: 503]

Heavy Chain Amino Acid sequence:
EVQLVQSGAEVKKPGASVKVSCKASGYTFTSYGISWVRQAPGQGLEWMGWISAYNGNTN

YAQKLQGRVTMTTDTSTSTAYMELRSLRSDDTAVYYCARSYYAADWWWHATMMDMWG

QGTLVTVSS [SEQ ID NO: 504]

EXT010-56
DNA sequence:
GACATCCAGATGACCCAGTCTCCATCCTCCCTGTCTGCATCTGTAGGAGACAGAGTCAC

CATCACTTGCCGGGCGAGTCAGGGCATTGGCAATTATTTAGCCTGGTATCAGCAGAAAC

CAGGGAAAGTTCCTAAGCTCCTGATCTATTCTGTATCCACTCTGCAATCAGGGGTCCCAT

CTCGGTTCAGCGGCAGTGGATCTGGGACAGATTTCGCTCTCACCATCAGCAGCCTGCAG

CCTGATGATTTTGCAACTTATTACTGTCAAAAGTATAACAGTGCCCCGGGGACTTTCGG

CCCTGGGACCAAAGTGGATATCAAACGTTCTAGAGGTGGTGGTGGTAGCGGCGGCGGC

GGCTCTGGTGGTGGTGGATCCCTCGAGATGGCCCAGGTCCAGCTGGTGCAGTCTGGGGC

TGAGGTGAAGAAGCCTGGGGCCTCAGTGAAGGTCTCCTGCAAGACTTCTGGATACACCT

TCACCACCTATGATTTCAACTGGGTGCGACAGGCCGCTGGACAAGGGCTTGAGTGGATG

GGATGGATGAACCCTAACAGTGGTAACACAGGCTATGCAAAGAAGTTCCAGGGCAGAG

TCACCATGACCAGGGACACCTCCATAAACACAGCCTACATGGAGCTGAGCAGCCTGAC

ATCTGAAGACACGGCCGTGTATTACTGTGCGCGCGGTTACGGTGTTTTCCATTACGATTC

TTGGGGTCAAGGTACTCTGGTGACCGTCTCCTCA [SEQ ID NO: 505]

Amino Acid sequence:
LPVLTQPPSVSVAPGKTARITCGGNNIGSKSVHWYQQKPGQAPVLVIYYDSRPSGIPERFS

GSNSGNTATLTISRVEAGDEADYYCQVWDSSSDHYVFGTGTKVTVLGSRGGGSGGGGSG

-continued

APPENDIX C

GGGSLEMAQMQLVQSGAEVKKPGASVKVSCKASGYTFTSYYMHWVRQAPGQGLEWMGII

NPSGGSTSYAQKFQGRVTMTRDTSTSTVYMELSSLRSEDTAVYYCARSGSYGDSDSWGQG

TLVTVSS [SEQ ID NO: 506]

Light Chain DNA sequence:
CTGCCTGTGCTGACTCAGCCACCCTCAGTGTCAGTGGCCCCAGGAAAGACGGCCAGGAT

TACCTGTGGGGGAAACAACATTGGAAGTAAAAGTGTGCACTGGTACCAGCAGAAGCCA

GGCCAGGCCCCTGTGCTGGTCATCTATTATGATAGCGACCGGCCCTCAGGGATCCCTGA

GCGATTCTCTGGCTCCAACTCTGGGAACACGGCCACCCTGACCATCAGCAGGGTCGAAG

CCGGGGATGAGGCCGACTATTACTGTCAGGTGTGGGATAGTAGTAGTGATCATTATGTC

TTCGGAACTGGGACCAAGGTCACCGTCCTAGGT [SEQ ID NO: 507]

Light Chain Amino Acid sequence:
LPVLTQPPSVSVAPGKTARITCGGNNIGSKSVHWYQQKPGQAPVLVIYYDSDRPSGIPERFS

GSNSGNTATLTISRVEAGDEADYYCQVWDSSSDHYVFGTGTKVTVLG [SEQ ID NO: 508]

Heavy Chain DNA sequence:
CAGATGCAGCTGGTGCAGTCTGGGGCTGAGGTGAAGAAGCCTGGGGCCTCAGTGAAGG

TTTCCTGCAAGGCATCTGGATACACCTTCACCAGCTACTATATGCACTGGGTGCGACAG

GCCCCTGGACAAGGGCTTGAGTGGATGGGAATAATCAACCCTAGTGGTGGTAGCACAA

GCTACGCACAGAAGTTCCAGGGCAGAGTCACCATGACCAGGGACACGTCCACGAGCAC

AGTCTACATGGAGCTGAGCAGCCTGAGATCTGAGGACACTGCCGTGTATTACTGTGCGC

GCTCTGGTTCTTACGGTGACTCTGATTCTTGGGGTCAAGGTACTCTGGTGACCGTCTCCT

CA [SEQ ID NO: 509]

Heavy Chain Amino Acid sequence:
QMQLVQSGAEVKKPGASVKVSCKASGYTFTSYYMHWVRQAPGQGLEWMGIINPSGGSTS

YAQKFQGRVTMTRDTSTSTVYMELSSLRSEDTAVYYCARSGSYGDSDSWGQGTLVTVSS

[SEQ ID NO: 510]

EXT010-59
DNA sequence:
CAGCCTGTGCTGACTCAGCCACCCTCGGTGTCAGTGGCCCCAAGACAGACGGCCAGGAT

TACCTGTGGGGGAGACAACGTTGGAAGTAAAAGTGTGCACTGGTACCAGCAGAAGCCA

GGTCAGGCCCCTGTACTGGTCGTCTATGATGATAGCGACCGGCCCTCAGGGATCCCTGA

GCGATTCTCTGGCTCCAACTCTGGGAACACAGCCACTCTGACCATCAGCGGGACCCAGG

CTATGGATGAGGCTGACTATTACTGTCAGGCGTGGGACAGCAGCACTGTGGTATTCGGC

GGAGGGACCAAGCTGACCGTCCTAGGTTCTAGAGGTGGTGGTGGTAGCGGCGGCGGCG

GCTCTGGTGGTGGTGGATCCCTCGAGATGGCCCAGCTGCAGCTGCAGGAGTCGGGCCCA

GGACTGGTGAAGCCTTCGGAGACCCTGTCCCTCACCTGCACTGTCTCTGGTGCCTCCATC

AGCAGTACTTATTACTACTGGAGCTGGATCCGGCAGTCCCCAGGGAAGGGACTGGAGT

GGATTGGGTATATCGGTTACAGTGGGATCACCAACTACAACCCCTCCCTCCAGAGTCGA

GTCACCATATCAGTAGACACGTCCAAGAACCAGTTCTCCCTGAAGCTGACCTCTGTGAC

CGCCGCAGACACGGCCGTGTATTACTGTGCGCGCGGTTCTTGGTGGTACTCTTACTACG

ATCATTGGGGTCAAGGTACTCTGGTGACCGTCTCCTCA [SEQ ID NO: 511]

APPENDIX C

Amino Acid sequence:
QPVLTQPPSVSVAPRQTARITCGGDNVGSKSVHWYQQKPGQAPVLVVYDDSDRPSGIPERF

SGSNSGNTATLTISGTQAMDEADYYCQAWDSSTVVFGGGTKLTVLGSRGGGGSGGGGSGG

GGSLEMAQLQLQESGPGLVKPSETLSLTCTVSGASISSTYYYWSWIRQSPGKGLEWIGYIGY

SGITNYNPSLQSRVTISVDTSKNQFSLKLTSVTAADTAVYYCARGSWWYSYYDHWGQGTL

VTVSS [SEQ ID NO: 512]

Light Chain DNA sequence:
CAGCCTGTGCTGACTCAGCCACCCTCGGTGTCAGTGGCCCCAAGACAGACGGCCAGGAT

TACCTGTGGGGGAGACAACGTTGGAAGTAAAAGTGTGCACTGGTACCAGCAGAAGCCA

GGTCAGGCCCCTGTACTGGTCGTCTATGATGATAGCGACCGGCCCTCAGGGATCCCTGA

GCGATTCTCTGGCTCCAACTCTGGGAACACAGCCACTCTGACCATCAGCGGGACCCAGG

CTATGGATGAGGCTGACTATTACTGTCAGGCGTGGGACAGCAGCACTGTGGTATTCGGC

GGAGGGACCAAGCTGACCGTCCTAGGT [SEQ ID NO: 513]

Light Chain Amino Acid sequence:
QPVLTQPPSVSVAPRQTARITCGGDNVGSKSVHWYQQKPGQAPVLVVYDDSDRPSGIPERF

SGSNSGNTATLTISGTQAMDEADYYCQAWDSSTVVFGGGTKLTVLG [SEQ ID NO: 514]

Heavy Chain DNA sequence:
CAGCTGCAGCTGCAGGAGTCGGGCCCAGGACTGGTGAAGCCTTCGGAGACCCTGTCCCT

CACCTGCACTGTCTCTGGTGCCTCCATCAGCAGTACTTATTACTACTGGAGCTGGATCCG

GCAGTCCCCAGGGAAGGGACTGGAGTGGATTGGGTATATCGGTTACAGTGGGATCACC

AACTACAACCCCTCCCTCCAGAGTCGAGTCACCATATCAGTAGACACGTCCAAGAACCA

GTTCTCCCTGAAGCTGACCTCTGTGACCGCCGCAGACACGGCCGTGTATTACTGTGCGC

GCGGTTCTTGGTGGTACTCTTACTACGATCATTGGGGTCAAGGTACTCTGGTGACCGTCT

CCTCA [SEQ ID NO: 515]

Heavy Chain Amino Acid sequence:
QLQLQESGPGLVKPSETLSLTCTVSGASISSTYYYWSWIRQSPGKGLEWIGYIGYSGITNYNP

SLQSRVTISVDTSKNQFSLKLTSVTAADTAVYYCARGSWWYSYYDHWGQGTLVTVSS

[SEQ ID NO: 516]

EXT010-60
DNA sequence:
GACATCCAGATGACCCAGTCTCCATCCTCCCTGTCTGCATCTGTAGGAGACAGAGTCAC

CATCACTTGCCGGGCGAGTCAGGGCATTGGCAATTATTTAGCCTGGTATCAGCAGAAAC

CAGGGAAAGTTCCTAAGCTCCTGATCTATTCTGTATCCACTCTGCAATCAGGGGTCCCAT

CTCGGTTCAGCGGCAGTGGATCTGGGACAGATTTCGCTCTCACCATCAGCAGCCTGCAG

CCTGATGATTTTGCAACTTATTACTGTCAAAAGTATAACAGTGCCCCGGGGACTTTCGG

CCCTGGGACCAAAGTGGATATCAAACGTTCTAGAGGTGGTGGTGGTAGCGGCGGCGGC

GGCTCTGGTGGTGGTGGATCCCTCGAGATGGCCCAGGTCCAGCTGGTGCAGTCTGGGGC

TGAGGTGAAGAAGCCTGGGGCCTCAGTGAAGGTCTCCTGCAAGACTTCTGGATACACCT

TCACCACCTATGATTTCAACTGGGTGCGACAGGCCGCTGGACAAGGGCTTGAGTGGATG

GGATGGATGAACCCTAACAGTGGTAACACAGGCTATGCAAAGAAGTTCCAGGGCAGAG

TCACCATGACCAGGGACACCTCCATAAACACAGCCTACATGGAGCTGAGCAGCCTGAC

ATCTGAAGACACGGCCGTGTATTACTGTGCGCGCGGTTACGGTGTTTTCCATTACGATTC

APPENDIX C

TTGGGGTCAAGGTACTCTGGTGACCGTCTCCTCA [SEQ ID NO: 517]

Amino Acid sequence:
DIQMTQSPSSLSASVGDRVTITCRASQGIGNYLAWYQQKPGKVPKLLIYSVSTLQSGVPSRFS

GSGSGTDFALTISSLQPDDFATYYCQKYNSAPGTFGPGTKVDIKRSRGGGGSGGGGSGGGG

SLEMAQVQLVQSGAEVKKPGASVKVSCKTSGYTFTTYDFNWVRQAAGQGLEWMGWMNP

NSGNTGYAKKFQGRVTMTRDTSINTAYMELSSLTSEDTAVYYCARGYGVFHYDSWGQGT

LVTVSS [SEQ ID NO: 518]

Light Chain DNA sequence:
GACATCCAGATGACCCAGTCTCCATCCTCCCTGTCTGCATCTGTAGGAGACAGAGTCAC

CATCACTTGCCGGGCGAGTCAGGGCATTGGCAATTATTTAGCCTGGTATCAGCAGAAAC

CAGGGAAAGTTCCTAAGCTCCTGATCTATTCTGTATCCACTCTGCAATCAGGGGTCCCAT

CTCGGTTCAGCGGCAGTGGATCTGGGACAGATTTCGCTCTCACCATCAGCAGCCTGCAG

CCTGATGATTTTGCAACTTATTACTGTCAAAAGTATAACAGTGCCCCGGGGACTTTCGG

CCCTGGGACCAAAGTGGATATCAAACGT [SEQ ID NO: 519]

Light Chain Amino Acid sequence:
DIQMTQSPSSLSASVGDRVTITCRASQGIGNYLAWYQQKPGKVPKLLIYSVSTLQSGVPSRFS

GSGSGTDFALTISSLQPDDFATYYCQKYNSAPGTFGPGTKVDIKR [SEQ ID NO: 520]

Heavy Chain DNA sequence:
CAGGTCCAGCTGGTGCAGTCTGGGGCTGAGGTGAAGAAGCCTGGGGCCTCAGTGAAGG

TCTCCTGCAAGACTTCTGGATACACCTTCACCACCTATGATTTCAACTGGGTGCGACAG

GCCGCTGGACAAGGGCTTGAGTGGATGGGATGGATGAACCCTAACAGTGGTAACACAG

GCTATGCAAAGAAGTTCCAGGGCAGAGTCACCATGACCAGGGACACCTCCATAAACAC

AGCCTACATGGAGCTGAGCAGCCTGACATCTGAAGACACGGCCGTGTATTACTGTGCGC

GCGGTTACGGTGTTTTCCATTACGATTCTTGGGGTCAAGGTACTCTGGTGACCGTCTCCT

CA [SEQ ID NO: 521]

Heavy Chain Amino Acid sequence:
QVQLVQSGAEVKKPGASVKVSCKTSGYTFTTYDFNWVRQAAGQGLEWMGWMNPNSGNT

GYAKKFQGRVTMTRDTSINTAYMELSSLTSEDTAVYYCARGYGVFHYDSWGQGTLVTVSS

[SEQ ID NO: 522]

APPENDIX D

| clones | HCDR1 | HCDR2 | HCDR3 | LCDR1 | LCDR2 | LCDR3 |
|---|---|---|---|---|---|---|
| EXT010-01 | GYTFTSYY [SEQ ID NO: 523] | INPSGGST [SEQ ID NO: 539] | AAGSYYSLDI [SEQ ID NO: 561] | RSNIGAAFD [SEQ ID NO: 592] | GDN [SEQ ID NO: 622] | QSYDTSLNVL [SEQ ID NO: 646] |
| EXT010-03 | GYTFTSYY [SEQ ID NO: 523] | INPSGGST [SEQ ID NO: 539] | ASGSRYAFDI [SEQ ID NO: 562] | NIESKS [SEQ ID NO: 593] | FDS [SEQ ID NO: 623] | QVWDSSSDHYV [SEQ ID NO: 647] |
| EXT010-04 | GYTFTSYY [SEQ ID NO: 523] | INPSGGST [SEQ ID NO: 539] | ARAITALDAFDI [SEQ ID NO: 563] | NIGSKS [SEQ ID NO: 594] | YDS [SEQ ID NO: 624] | QVWDSSSDHPV [SEQ ID NO: 648] |
| EXT010-06 | EYTLTTYY [SEQ ID NO: 524] | INPSGSGT [SEQ ID NO: 540] | ARAFGYGDYFYGMDV [SEQ ID NO: 564] | NIGSKS [SEQ ID NO: 595] | DDS [SEQ ID NO: 625] | QVWDSSSDHGV [SEQ ID NO: 649] |

APPENDIX D-continued

| clones | HCDR1 | HCDR2 | HCDR3 | LCDR1 | LCDR2 | LCDR3 |
|---|---|---|---|---|---|---|
| EXT010-07 | GFRFSGYS [SEQ ID NO: 525] | IRSSSDLI [SEQ ID NO: 541] | ARDMGSTW YRGAFDF [SEQ ID NO: 565] | SSNIGAGH D [SEQ ID NO: 596] | SNG [SEQ ID NO: 626] | QSYDSSLSG DVV [SEQ ID NO: 650] |
| EXT010-08 | GYTFTSYY [SEQ ID NO: 523] | INPSGGST [SEQ ID NO: 539] | ARSPGGGYG QDG [SEQ ID NO: 566] | NIGRQS [SEQ ID NO: 597] | YDA [SEQ ID NO: 627] | QVWDSSSD HYV [SEQ ID NO: 651] |
| EXT010-10 | GYTFSSFY [SEQ ID NO: 526] | IDPNSGFT [SEQ ID NO: 542] | ARYIYYMG YDE [SEQ ID NO: 567] | QSISSY [SEQ ID NO: 598] | AAS [SEQ ID NO: 628] | QQSYSTPFT [SEQ ID NO: 652] |
| EXT010-13 | GYTFTSYY [SEQ ID NO: 523] | INPSGGYT [SEQ ID NO: 543] | ARGMLTYL DS [SEQ ID NO: 568] | NIETKS [SEQ ID NO: 599] | YDN [SEQ ID NO: 629] | QVWDKSND HMV [SEQ ID NO: 653] |
| EXT010-15 | GYTFSSFY [SEQ ID NO: 527] | IDPNSGFT [SEQ ID NO: 544] | ARYIYASGI DT [SEQ ID NO: 569] | SSHVGAYS Y [SEQ ID NO: 600] | DVN [SEQ ID NO: 630] | SSYASSNNY VL [SEQ ID NO: 654] |
| EXT010-17 | GYTFTSYY [SEQ ID NO: 523] | INPSGGST [SEQ ID NO: 539] | ARSYYSVGT QWLDS [SEQ ID NO: 570] | QSISSY [SEQ ID NO: 598] | AAS [SEQ ID NO: 628] | QQSYSTPLT [SEQ ID NO: 655] |
| EXT010-23 | GYTFTSYY [SEQ ID NO: 523] | INPSGGST [SEQ ID NO: 539] | ARSVSFMSA MDS [SEQ ID NO: 571] | NVGRKS [SEQ ID NO: 601] | DDS [SEQ ID NO: 625] | QVWDNFRD QV [SEQ ID NO: 656] |
| EXT010-24 | GYTFTGYY [SEQ ID NO: 528] | INPNSGGT [SEQ ID NO: 545] | ARDWSSYDS VMDS [SEQ ID NO: 572] | QNIGNW [SEQ ID NO: 602] | QAS [SEQ ID NO: 631] | QQYYGTPL T [SEQ ID NO: 657] |
| EXT010-25 | GYTFTSYG [SEQ ID NO: 529] | ISAYNGNT [SEQ ID NO: 546] | ARWVGMEE EDH [SEQ ID NO: 573] | SLRDFY [SEQ ID NO: 603] | GEN [SEQ ID NO: 632] | KSRDSNVY HWV [SEQ ID NO: 658] |
| EXT010-26 | GYTFSSYY [SEQ ID NO: 530] | INPSGGYT [SEQ ID NO: 547] | ARSVTHSSS AFDY [SEQ ID NO: 574] | SSNIGAGH D [SEQ ID NO: 604] | GNG [SEQ ID NO: 633] | QSYDSSLSG YV [SEQ ID NO: 659] |
| EXT010-27 | GYTFTSYY [SEQ ID NO: 523] | INPSGGST [SEQ ID NO: 539] | ARGQSGVV YD [SEQ ID NO: 575] | NIGTKT [SEQ ID NO: 605] | YDI [SEQ ID NO: 634] | QVWDSGSY QGV [SEQ ID NO: 660] |
| EXT010-28 | GYTFTSYY [SEQ ID NO: 523] | INPTGGYT [SEQ ID NO: 548] | ARGTTYMW SGYDS [SEQ ID NO: 576] | QSITDNF [SEQ ID NO: 606] | GAS [SEQ ID NO: 635] | HQYGSSPPG T [SEQ ID NO: 661] |
| EXT010-29 | GYTFTSYY [SEQ ID NO: 523] | INPSGGST [SEQ ID NO: 539] | ARSVMHYY DFFDG [SEQ ID NO: 577] | SSDVGGY NY [SEQ ID NO: 607] | DVS [SEQ ID NO: 636] | SSYTSTSVY V [SEQ ID NO: 662] |
| EXT010-30 | GYTFTSSY [SEQ ID NO: 531] | INPTAGST [SEQ ID NO: 549] | ARGYSFAGY YDW [SEQ ID NO: 578] | SSDVGAY NY [SEQ ID NO: 608] | DVT [SEQ ID NO: 637] | SSFTAIGTW V [SEQ ID NO: 663] |
| EXT010-31 | GYTFTSYY [SEQ ID NO: 523] | INPTGGST [SEQ ID NO: 550] | ARSITYWSA YDY [SEQ ID NO: 579] | SSNIGAGY D [SEQ ID NO: 609] | GNN [SEQ ID NO: 638] | QSYDNNLS GV [SEQ ID NO: 664] |
| EXT010-32 | GYTFTSYY [SEQ ID NO: 523] | INPTAGTT [SEQ ID NO: 551] | ARYVFGSGQ DS [SEQ ID NO: 580] | SSNIGNNY [SEQ ID NO: 610] | DNN [SEQ ID NO: 639] | GIWDSSLSA GSYV [SEQ ID NO: 665] |
| EXT010-33 | GYAFTSYY [SEQ ID NO: 532] | INPTGGYT [SEQ ID NO: 552] | ARGVYGSLD S [SEQ ID NO: 581] | NIGSKS [SEQ ID NO: 611] | DDS [SEQ ID NO: 625] | QVWDSSSD HVV [SEQ ID NO: 666] |
| EXT010-34 | GYTITSYY [SEQ ID NO: 533] | INPNAGST [SEQ ID NO: 553] | ARQSSGRDG FDS [SEQ ID NO: 582] | KIESKS [SEQ ID NO: 612] | DDS [SEQ ID NO: 625] | QVWDSSND VQV [SEQ ID NO: 667] |
| EXT010-42 | GYTFTSYY [SEQ ID NO: 523] | INPTSGTT [SEQ ID NO: 554] | ARSPSFYYD G [SEQ ID NO: 583] | NIGSKS [SEQ ID NO: 613] | YDS [SEQ ID NO: 640] | QVWDSSSD LPYV [SEQ ID NO: 668] |

APPENDIX D-continued

| clones | HCDR1 | HCDR2 | HCDR3 | LCDR1 | LCDR2 | LCDR3 |
|---|---|---|---|---|---|---|
| EXT010-44 | GYSFTNYY [SEQ ID NO: 534] | ITPTNGGA [SEQ ID NO: 555] | ARQWSYTSF SLSGYISYDS [SEQ ID NO: 584] | SSNIGAGY D [SEQ ID NO: 614] | GNS [SEQ ID NO: 641] | QSYDDRLS GSYV [SEQ ID NO: 669] |
| EXT010-47 | GFTFSSYA [SEQ ID NO: 535] | ISYDGSNK [SEQ ID NO: 556] | ARNGYWYW GSGEHGSW YDS [SEQ ID NO: 585] | NIGSKS [SEQ ID NO: 615] | YDS [SEQ ID NO: 642] | QVWDSSSD QGV [SEQ ID NO: 670] |
| EXT010-48 | GYTFTSYY [SEQ ID NO: 523] | INPSGGST [SEQ ID NO: 539] | ARGMPDVV DD [SEQ ID NO: 586] | NIGSNS [SEQ ID NO: 616] | YDS [SEQ ID NO: 642] | QVWDSAIN HVV [SEQ ID NO: 671] |
| EXT010-49 | GYTFTSYY [SEQ ID NO: 523] | INPSGGYT [SEQ ID NO: 557] | ARSSSGGNG ADS [SEQ ID NO: 587] | NIGSKS [SEQ ID NO: 617] | YDS [SEQ ID NO: 642] | QVWDSSSD HWV [SEQ ID NO: 672] |
| EXT010-55 | GYTFTSYG [SEQ ID NO: 536] | ISAYNGNT [SEQ ID NO: 558] | ARSYYAAD WWWHATM MDM [SEQ ID NO: 588] | SSNIGRNT [SEQ ID NO: 618] | SNN [SEQ ID NO: 643] | AAWDDSLN GPV [SEQ ID NO: 673] |
| EXT010-56 | GYTFTSYY [SEQ ID NO: 523] | INRSGGST [SEQ ID NO: 539] | ARSGSYGDS DS [SEQ ID NO: 589] | NIGSKS [SEQ ID NO: 619] | YDS [SEQ ID NO: 644] | QVWDSSSD HYV [SEQ ID NO: 674] |
| EXT010-59 | GASISSTYY Y [SEQ ID NO: 537] | IGYSGIT [SEQ ID NO: 559] | ARGSWWYS YYDH [SEQ ID NO: 590] | NVGSKS [SEQ ID NO: 620] | DDS [SEQ ID NO: 625] | QAWDSSTV V [SEQ ID NO: 675] |
| EXT010-60 | GYTFTTYD [SEQ ID NO: 538] | MNPNSGNT [SEQ ID NO: 560] | ARGYGVFH YDS [SEQ ID NO: 591] | QGIGNY [SEQ ID NO: 621] | SVS [SEQ ID NO: 645] | QKYNSAPG T [SEQ ID NO: 676] |

REFERENCES

1. Wadelin F, Fulton J, McEwan P A, Spriggs K A, Emsley J, Heery D M. Leucine-rich repeat protein PRAME: expression, potential functions and clinical implications for leukaemia. Mol Cancer. 2010; 9:226. PMCID: 2936344.

2. van Baren N, Chambost H, Ferrant A, Michaux L, Ikeda H, Millard I, et al. PRAME, a gene encoding an antigen recognized on a human melanoma by cytolytic T cells, is expressed in acute leukemia cells. Br J Haematol. 1998; 102(5):1376-9.

3. Oehler V G, Guthrie K A, Cummings C L, Sabo K, Wood B L, Gooley T, et al. The preferentially expressed antigen in melanoma (PRAME) inhibits myeloid differentiation in normal hematopoietic and leukemic progenitor cells. Blood. 2009; 114(15):3299-308. PMCID: 2759652.

4. Qin Y, Zhu H, Jiang B, Li J, Lu X, Li L, et al. Expression patterns of WT1 and PRAME in acute myeloid leukemia patients and their usefulness for monitoring minimal residual disease. Leuk Res. 2009; 33(3):384-90.

5. Segal N H, Blachere N E, Guevara-Patino J A, Gallardo H F, Shiu H Y, Viale A, et al. Identification of cancer-testis genes expressed by melanoma and soft tissue sarcoma using bioinformatics. Cancer Immun. 2005; 5:2.

6. Proto-Siqueira R, Figueiredo-Pontes L L, Panepucci R A, Garcia A B, Rizzatti E G, Nascimento F M, et al. PRAME is a membrane and cytoplasmic protein aberrantly expressed in chronic lymphocytic leukemia and mantle cell lymphoma. Leuk Res. 2006; 30(11):1333-9.

7. Proto-Siqueira R, Falcao R P, de Souza C A, Ismael S J, Zago M A. The expression of PRAME in chronic lymphoproliferative disorders. Leuk Res. 2003; 27(5):393-6.

8. Neumann F, Sturm C, Hulsmeyer M, Dauth N, Guillaume P, Luescher I F, et al. Fab antibodies capable of blocking T cells by competitive binding have the identical specificity but a higher affinity to the MHC-peptide-complex than the T cell receptor. Immunol Lett. 2009; 125(2):86-92.

9. Greiner J, Ringhoffer M, Simikopinko O, Szmaragowska A, Huebsch S, Maurer U, et al. Simultaneous expression of different immunogenic antigens in acute myeloid leukemia. Exp Hematol. 2000; 28(12):1413-22.

10. Vulcani-Freitas T M, Saba-Silva N, Cappellano A, Cavalheiro S, Toledo S R. PRAME gene expression profile in medulloblastoma. Arq Neuropsiquiatr. 2011; 69(1):9-12.

11. Sergeeva A, Alatrash G, He H, Ruisaard K, Lu S, Wygant J, et al. An anti-PR1/HLA-A2 T-cell receptor-like antibody mediates complement-dependent cytotoxicity against acute myeloid leukemia progenitor cells. Blood. 2011; 117(16):4262-72.

12. Luetkens T, Schafhausen P, Uhlich F, Stasche T, Akbulak R, Bartels B M, et al. Expression, epigenetic regulation, and humoral immunogenicity of cancer-testis antigens in chronic myeloid leukemia. Leuk Res. 2010; 34(12):1647-55.

13. Gerber J M, Qin L, Kowalski J, Smith B D, Griffin C A, Vala M S, et al. Characterization of chronic myeloid leukemia stem cells. Am J Hematol. 2011; 86(1):31-7. PMCID: 3010878.

14. Quintarelli C, Dotti G, Hasan S T, De Angelis B, Hoyos V, Errichiello S, et al. High-avidity cytotoxic T lymphocytes specific for a new PRAME-derived peptide can target leukemic and leukemic-precursor cells. Blood. 2011; 117(12):3353-62.

15. Epping M T, Wang L, Edel M J, Carlee L, Hernandez M, Bernards R. The human tumor antigen PRAME is a dominant repressor of retinoic acid receptor signaling. Cell. 2005; 122(6):835-47.

16. Sakashita A, Kizaki M, Pakkala S, Schiller G, Tsuruoka N, Tomosaki R, et al. 9-cis-retinoic acid: effects on normal and leukemic hematopoiesis in vitro. Blood. 1993; 81(4):1009-16.

17. Roman-Gomez J, Jimenez-Velasco A, Agirre X, Castillejo J A, Navarro G, Jose-Eneriz E S, et al. Epigenetic regulation of PRAME gene in chronic myeloid leukemia. Leuk Res. 2007; 31(11):1521-8.

18. Quintarelli C, Dotti G, De Angelis B, Hoyos V, Mims M, Luciano L, et al. Cytotoxic T lymphocytes directed to the preferentially expressed antigen of melanoma (PRAME) target chronic myeloid leukemia. Blood. 2008; 112(5):1876-85.

19. Griffioen M, Kessler J H, Borghi M, van Soest R A, van der Minne C, Nouta J, et al. Detection and functional analysis of CD8+ T cells specific for PRAME: a target for T-cell therapy. Clin Cancer Res. 2006; 12(10):3130-6.

20. Kessler J H, Beekman N J, Bres-Vloemans S A, Verdijk P, van Veelen P A, Kloosterman-Joosten A M, et al. Efficient identification of novel HLA-A(*)0201-presented cytotoxic T lymphocyte epitopes in the widely expressed tumor antigen PRAME by proteasome-mediated digestion analysis. J Exp Med. 2001; 193(1):73-88. PMCID: 2195886.

21. Li L, Giannopoulos K, Reinhardt P, Tabarkiewicz J, Schmitt A, Greiner J, et al. Immunotherapy for patients with acute myeloid leukemia using autologous dendritic cells generated from leukemic blasts. Int J Oncol. 2006; 28(4): 855-61.

22. Ikeda H, Lethe B, Lehmann F, van Baren N, Baurain J F, de Smet C, et al. Characterization of an antigen that is recognized on a melanoma showing partial HLA loss by CTL expressing an NK inhibitory receptor. Immunity. 1997; 6(2):199-208.

23. Matsushita M, Yamazaki R, Ikeda H, Kawakami Y. Preferentially expressed antigen of melanoma (PRAME) in the development of diagnostic and therapeutic methods for hematological malignancies. Leuk Lymphoma. 2003; 44(3): 439-44.

24. Doolan P, Clynes M, Kennedy S, Mehta J P, Crown J, O'Driscoll L. Prevalence and prognostic and predictive relevance of PRAME in breast cancer. Breast Cancer Res Treat. 2008; 109(2):359-65.

25. Rezvani K, Yong A S, Tawab A, Jafarpour B, Eniafe R, Mielke S, et al. Ex vivo characterization of polyclonal memory CD8+ T-cell responses to PRAME-specific peptides in patients with acute lymphoblastic leukemia and acute and chronic myeloid leukemia. Blood. 2009; 113(10): 2245-55. PMCID: 2652370.

26. Klechevsky E, Gallegos M, Denkberg G, Palucka K, Banchereau J, Cohen C, et al. Antitumor activity of immunotoxins with T-cell receptor-like specificity against human melanoma xenografts. Cancer Res. 2008; 68(15):6360-7. PMCID: 2728007.

27. Epel M, Carmi I, Soueid-Baumgarten S, Oh S K, Bera T, Pastan I, et al. Targeting TARP, a novel breast and prostate tumor-associated antigen, with T cell receptor-like human recombinant antibodies. Eur J Immunol. 2008; 38(6):1706-20. PMCID: 2682370.

28. Wittman V P, Woodburn D, Nguyen T, Neethling F A, Wright S, Weidanz J A. Antibody targeting to a class I MHC-peptide epitope promotes tumor cell death. J Immunol. 2006; 177(6):4187-95.

29. Verma B, Jain R, Caseltine S, Rennels A, Bhattacharya R, Markiewski M M, et al. TCR mimic monoclonal antibodies induce apoptosis of tumor cells via immune effector-independent mechanisms. J Immunol. 2011; 186(5): 3265-76.

30. Saito Y, Uchida N, Tanaka S, Suzuki N, Tomizawa-Murasawa M, Sone A, et al. Induction of cell cycle entry eliminates human leukemia stem cells in a mouse model of AML. Nat Biotechnol. 2010; 28(3):275-80.

31. Sutherland M K, Yu C, Lewis T S, Miyamoto J B, Morris-Tilden C A, Jonas M, et al. Anti-leukemic activity of lintuzumab (SGN-33) in preclinical models of acute myeloid leukemia. MAbs. 2009; 1(5):481-90. PMCID: 2759498.

32. Zarrinkar P P, Gunawardane R N, Cramer M D, Gardner M F, Brigham D, Belli B, et al. AC220 is a uniquely potent and selective inhibitor of FLT3 for the treatment of acute myeloid leukemia (AML). Blood. 2009; 114(14): 2984-92. PMCID: 2756206.

33. Doronina S O, Toki B E, Torgov M Y, Mendelsohn B A, Cerveny C G, Chace D F, et al. Development of potent monoclonal antibody auristatin conjugates for cancer therapy. Nat Biotechnol. 2003; 21(7):778-84.

All patents, publications and other references cited herein are incorporated by reference in their entireties into the presently disclosed subject matter.

What is claimed is:

1. A monoclonal antibody or an antigen-binding portion thereof, which binds to a PRAME peptide bound to a major histocompatibility complex (MHC) molecule, wherein the antibody or antigen-binding portion thereof each comprises: a heavy chain variable region comprising a CDR1 comprising the amino acid sequence set forth in SEQ ID NO: 7, a CDR2 comprising the amino acid sequence set forth in SEQ ID NO: 8, and a CDR3 comprising the amino acid sequence set forth in SEQ ID NO: 9; and a light chain variable region comprising a CDR1 comprising the amino acid sequence set forth in SEQ ID NO: 10, a CDR2 comprising the amino acid sequence set forth in SEQ ID NO: 11, and a CDR3 comprising the amino acid sequence set forth in SEQ ID NO: 12.

2. The antibody or antigen-binding portion thereof of claim 1, wherein the heavy chain variable region comprises an amino acid sequence that is at least 80% homologous to or identical to the amino acid sequence set forth in SEQ ID NO: 49; and/or the light chain variable region comprises an amino acid sequence that is at least 80% homologous to or identical to the amino acid sequence set forth in SEQ ID NO: 50.

3. The antibody or antigen-binding portion thereof of claim 2, wherein the heavy chain variable region comprises the amino acid sequence set forth in SEQ ID NO: 49; or the light chain variable region comprises the amino acid sequence set forth in SEQ ID NO: 50.

4. The antibody or antigen-binding portion thereof of claim 1, wherein the heavy chain variable region comprises the amino acid sequence set forth in SEQ ID NO: 49, and the light chain variable region comprises the amino acid sequence set forth in SEQ ID NO: 50.

5. The antibody or antigen-binding portion thereof of claim 1, wherein the antigen-binding portion is a Fab, a Fab', a F(ab')$_2$, a variable fragment (Fv), or a single chain variable fragment (scFv).

6. An immunoconjugate comprising the antibody or antigen-binding portion thereof of claim 1, linked to a therapeutic agent.

7. A bispecific molecule comprising the antibody or antigen-binding portion thereof of claim 1, linked to a second functional moiety.

8. A composition comprising the antibody or antigen-binding portion thereof of claim 1 and a pharmaceutically acceptable carrier.

9. A composition comprising the immunoconjugate of claim 6 and a pharmaceutically acceptable carrier.

10. A composition comprising the bispecific molecule of claim 7 and a pharmaceutically acceptable carrier.

11. A monoclonal antibody or an antigen-binding portion thereof, which binds to a PRAME peptide bound to a major histocompatibility complex (MHC) molecule, wherein the antibody or antigen-binding portion thereof each comprises: (a) a heavy chain variable region comprising a CDR1 comprising the amino acid sequence set forth in SEQ ID NO: 13, a CDR2 comprising the amino acid sequence set forth in SEQ ID NO: 14, and a CDR3 comprising the amino acid sequence set forth in SEQ ID NO: 15; and (b) a light chain variable region comprising a CDR1 comprising the amino acid sequence set forth in SEQ ID NO: 16, a CDR2 comprising the amino acid sequence set forth in SEQ ID NO: 17, and a CDR3 comprising the amino acid sequence set forth in SEQ ID NO: 18.

12. The antibody or antigen-binding portion thereof of claim 11, wherein the heavy chain variable region comprises an amino acid sequence that is at least 80% homologous to or identical to the amino acid sequence set forth in SEQ ID NO: 51; and/or the light chain variable region comprises an amino acid sequence that is at least 80% homologous to or identical to the amino acid sequence set forth in SEQ ID NO: 52.

13. The antibody or antigen-binding portion thereof of claim 11, wherein the heavy chain variable region comprises the amino acid sequence set forth in SEQ ID NO: 51, and the light chain variable region comprises the amino acid sequence set forth in SEQ ID NO: 52.

14. The antibody or antigen-binding portion thereof of claim 11, wherein the antigen-binding portion is a Fab, a Fab', a F(ab')$_2$, a variable fragment (Fv), or a single chain variable fragment (scFv).

15. An immunoconjugate comprising the antibody or antigen-binding portion thereof of claim 11, linked to a therapeutic agent.

16. A bispecific molecule comprising the antibody or antigen-binding portion thereof of claim 11, linked to a second functional moiety.

17. A monoclonal antibody or an antigen-binding portion thereof, which binds to a PRAME peptide bound to a major histocompatibility complex (MHC) molecule, wherein the antibody or antigen-binding portion thereof each comprises: (a) a heavy chain variable region comprising a CDR1 comprising the amino acid sequence set forth in SEQ ID NO: 19, a CDR2 comprising the amino acid sequence set forth in SEQ ID NO: 20, and a CDR3 comprising the amino acid sequence set forth in SEQ ID NO: 21; and (b) a light chain variable region comprising a CDR1 comprising the amino acid sequence set forth in SEQ ID NO: 22, a CDR2 comprising the amino acid sequence set forth in SEQ ID NO: 23, and a CDR3 comprising the amino acid sequence set forth in SEQ ID NO: 24.

18. The antibody or antigen-binding portion thereof of claim 17, wherein the heavy chain variable region comprises an amino acid sequence that is at least 80% homologous to or identical to the amino acid sequence set forth in SEQ ID NO: 53; and/or the light chain variable region comprises an amino acid sequence that is at least 80% homologous to or identical to the amino acid sequence set forth in SEQ ID NO: 54.

19. The antibody or antigen-binding portion thereof of claim 17, wherein the heavy chain variable region comprises the amino acid sequence set forth in SEQ ID NO: 53, and the light chain variable region comprises the amino acid sequence set forth in SEQ ID NO: 54.

20. The antibody or antigen-binding portion thereof of claim 17, wherein the antigen-binding portion is a Fab, a Fab', a F(ab')$_2$, a variable fragment (Fv), or a single chain variable fragment (scFv).

21. An immunoconjugate comprising the antibody or antigen-binding portion thereof of claim 17, linked to a therapeutic agent.

22. A bispecific molecule comprising the antibody or antigen-binding portion thereof of claim 17, linked to a second functional moiety.

23. A monoclonal antibody or an antigen-binding portion thereof, which binds to a PRAME peptide bound to a major histocompatibility complex (MHC) molecule, wherein the antibody or antigen-binding portion thereof each comprises: (a) a heavy chain variable region comprising a CDR1 comprising the amino acid sequence set forth in SEQ ID NO: 25, a CDR2 comprising the amino acid sequence set forth in SEQ ID NO: 26, and a CDR3 comprising the amino acid sequence set forth in SEQ ID NO: 27; and (b) a light chain variable region comprising a CDR1 comprising the amino acid sequence set forth in SEQ ID NO: 28, a CDR2 comprising the amino acid sequence set forth in SEQ ID NO: 29, and a CDR3 comprising the amino acid sequence set forth in SEQ ID NO: 30.

24. The antibody or antigen-binding portion thereof of claim 23, wherein the heavy chain variable region comprises an amino acid sequence that is at least 80% homologous to or identical to the amino acid sequence set forth in SEQ ID NO: 55; and/or the light chain variable region comprises an amino acid sequence that is at least 80% homologous to or identical to the amino acid sequence set forth in SEQ ID NO: 56.

25. The antibody or antigen-binding portion thereof of claim 23, wherein the heavy chain variable region comprises the amino acid sequence set forth in SEQ ID NO: 55, and the light chain variable region comprises the amino acid sequence set forth in SEQ ID NO: 56.

26. The antibody or antigen-binding portion thereof of claim 23, wherein the antigen-binding portion is a Fab, a Fab', a F(ab')$_2$, a variable fragment (Fv), or a single chain variable fragment (scFv).

27. An immunoconjugate comprising the antibody or antigen-binding portion thereof of claim 23, linked to a therapeutic agent.

28. A bispecific molecule comprising the antibody or antigen-binding portion thereof of claim 23, linked to a second functional moiety.

29. A monoclonal antibody or an antigen-binding portion thereof, which binds to a PRAME peptide bound to a major histocompatibility complex (MHC) molecule, wherein the antibody or antigen-binding portion thereof each comprises: (a) a heavy chain variable region comprising a CDR1 comprising the amino acid sequence set forth in SEQ ID NO: 31, a CDR2 comprising the amino acid sequence set forth in SEQ ID NO: 32, and a CDR3 comprising the amino acid sequence set forth in SEQ ID NO: 33; and (b) a light chain variable region comprising a CDR1 comprising the amino acid sequence set forth in SEQ ID NO: 34, a CDR2 comprising the amino acid sequence set forth in SEQ ID NO: 35, and a CDR3 comprising the amino acid sequence set forth in SEQ ID NO: 36.

30. The antibody or antigen-binding portion thereof of claim 29, wherein the heavy chain variable region comprises an amino acid sequence that is at least 80% homologous to or identical to the amino acid sequence set forth in SEQ ID NO: 57; and/or the light chain variable region comprises an amino acid sequence that is at least 80% homologous to or identical to the amino acid sequence set forth in SEQ ID NO: 58.

31. The antibody or antigen-binding portion thereof of claim 29, wherein the heavy chain variable region comprises the amino acid sequence set forth in SEQ ID NO: 57, and the light chain variable region comprises the amino acid sequence set forth in SEQ ID NO: 58.

32. The antibody or antigen-binding portion thereof of claim 29, wherein the antigen-binding portion is a Fab, a Fab', a F(ab')$_2$, a variable fragment (Fv), or a single chain variable fragment (scFv).

33. An immunoconjugate comprising the antibody or antigen-binding portion thereof of claim 29, linked to a therapeutic agent.

34. A bispecific molecule comprising the antibody or antigen-binding portion thereof of claim 29, linked to a second functional moiety.

35. A monoclonal antibody or an antigen-binding portion thereof, which binds to a PRAME peptide bound to a major histocompatibility complex (MHC) molecule, wherein the antibody or antigen-binding portion thereof each comprises: (a) a heavy chain variable region comprising a CDR1 comprising the amino acid sequence set forth in SEQ ID NO: 37, a CDR2 comprising the amino acid sequence set forth in SEQ ID NO: 38, and a CDR3 comprising the amino acid sequence set forth in SEQ ID NO: 39; and (b) a light chain variable region comprising a CDR1 comprising the amino acid sequence set forth in SEQ ID NO: 40, a CDR2 comprising the amino acid sequence set forth in SEQ ID NO: 41, and a CDR3 comprising the amino acid sequence set forth in SEQ ID NO: 42.

36. The antibody or antigen-binding portion thereof of claim 35, wherein the heavy chain variable region comprises an amino acid sequence that is at least 80% homologous to or identical to the amino acid sequence set forth in SEQ ID NO: 59; and/or light chain variable region comprises an amino acid sequence that is at least 80% homologous to or identical to the amino acid sequence set forth in SEQ ID NO: 60.

37. The antibody or antigen-binding portion thereof of claim 35, wherein the heavy chain variable region comprises the amino acid sequence set forth in SEQ ID NO: 59, and the light chain variable region comprises the amino acid sequence set forth in SEQ ID NO: 60.

38. The antibody or antigen-binding portion thereof of claim 35, wherein the antigen-binding portion is a Fab, a Fab', a F(ab')$_2$, a variable fragment (Fv), or a single chain variable fragment (scFv).

39. An immunoconjugate comprising the antibody or antigen-binding portion thereof of claim 35, linked to a therapeutic agent.

40. A bispecific molecule comprising the antibody or antigen-binding portion thereof of claim 35, linked to a second functional moiety.

41. A monoclonal antibody or an antigen-binding portion thereof, which binds to a PRAME peptide bound to a major histocompatibility complex (MHC) molecule, wherein the antibody or antigen-binding portion thereof each comprises: (a) a heavy chain variable region comprising a CDR1 comprising the amino acid sequence set forth in SEQ ID NO: 43, a CDR2 comprising the amino acid sequence set forth in SEQ ID NO: 44, and a CDR3 comprising the amino acid sequence set forth in SEQ ID NO: 45; and (b) a light chain variable region comprising a CDR1 comprising the amino acid sequence set forth in SEQ ID NO: 46, a CDR2 comprising the amino acid sequence set forth in SEQ ID NO: 47, and a CDR3 comprising the amino acid sequence set forth in SEQ ID NO: 48.

42. The antibody or antigen-binding portion thereof of claim 41, wherein the heavy chain variable region comprises an amino acid sequence that is at least 80% homologous to or identical to the amino acid sequence set forth in SEQ ID NO: 61; and/or the light chain variable region comprises an amino acid sequence that is at least 80% homologous to or identical to the amino acid sequence set forth in SEQ ID NO: 62.

43. The antibody or antigen-binding portion thereof of claim 41, wherein the heavy chain variable region comprises the amino acid sequence set forth in SEQ ID NO: 61, and the light chain variable region comprises the amino acid sequence set forth in SEQ ID NO: 62.

44. The antibody or antigen-binding portion thereof of claim 41, wherein the antigen-binding portion is a Fab, a Fab', a F(ab')$_2$, a variable fragment (Fv), or a single chain variable fragment (scFv).

45. An immunoconjugate comprising the antibody or antigen-binding portion thereof of claim 41, linked to a therapeutic agent.

46. A bispecific molecule comprising the antibody or antigen-binding portion thereof of claim 41, linked to a second functional moiety.

* * * * *

SEQUENCE LISTING

```
<160> NUMBER OF SEQ ID NOS: 696

<210> SEQ ID NO 1
<211> LENGTH: 509
<212> TYPE: PRT
<213> ORGANISM: Homo sapiens

<400> SEQUENCE: 1

Met Glu Arg Arg Arg Leu Trp Gly Ser Ile Gln Ser Arg Tyr Ile Ser
1               5                   10                  15

Met Ser Val Trp Thr Ser Pro Arg Arg Leu Val Glu Leu Ala Gly Gln
            20                  25                  30

Ser Leu Leu Lys Asp Glu Ala Leu Ala Ile Ala Ala Leu Glu Leu Leu
        35                  40                  45

Pro Arg Glu Leu Phe Pro Pro Leu Phe Met Ala Ala Phe Asp Gly Arg
    50                  55                  60
```

```
His Ser Gln Thr Leu Lys Ala Met Val Gln Ala Trp Pro Phe Thr Cys
 65                  70                  75                  80

Leu Pro Leu Gly Val Leu Met Lys Gly Gln His Leu His Leu Glu Thr
                 85                  90                  95

Phe Lys Ala Val Leu Asp Gly Leu Asp Val Leu Leu Ala Gln Glu Val
                100                 105                 110

Arg Pro Arg Arg Trp Lys Leu Gln Val Leu Asp Leu Arg Lys Asn Ser
            115                 120                 125

His Gln Asp Phe Trp Thr Val Trp Ser Gly Asn Arg Ala Ser Leu Tyr
            130                 135                 140

Ser Phe Pro Glu Pro Glu Ala Ala Gln Pro Met Thr Lys Lys Arg Lys
145                 150                 155                 160

Val Asp Gly Leu Ser Thr Glu Ala Glu Gln Pro Phe Ile Pro Val Glu
                165                 170                 175

Val Leu Val Asp Leu Phe Leu Lys Glu Gly Ala Cys Asp Glu Leu Phe
                180                 185                 190

Ser Tyr Leu Ile Glu Lys Val Lys Arg Lys Lys Asn Val Leu Arg Leu
            195                 200                 205

Cys Cys Lys Lys Leu Lys Ile Phe Ala Met Pro Met Gln Asp Ile Lys
210                 215                 220

Met Ile Leu Lys Met Val Gln Leu Asp Ser Ile Glu Asp Leu Glu Val
225                 230                 235                 240

Thr Cys Thr Trp Lys Leu Pro Thr Leu Ala Lys Phe Ser Pro Tyr Leu
                245                 250                 255

Gly Gln Met Ile Asn Leu Arg Arg Leu Leu Ser His Ile His Ala
            260                 265                 270

Ser Ser Tyr Ile Ser Pro Glu Lys Glu Glu Gln Tyr Ile Ala Gln Phe
            275                 280                 285

Thr Ser Gln Phe Leu Ser Leu Gln Cys Leu Gln Ala Leu Tyr Val Asp
            290                 295                 300

Ser Leu Phe Phe Leu Arg Gly Arg Leu Asp Gln Leu Leu Arg His Val
305                 310                 315                 320

Met Asn Pro Leu Glu Thr Leu Ser Ile Thr Asn Cys Arg Leu Ser Glu
                325                 330                 335

Gly Asp Val Met His Leu Ser Gln Ser Pro Ser Val Ser Gln Leu Ser
                340                 345                 350

Val Leu Ser Leu Ser Gly Val Met Leu Thr Asp Val Ser Pro Glu Pro
                355                 360                 365

Leu Gln Ala Leu Leu Glu Arg Ala Ser Ala Thr Leu Gln Asp Leu Val
            370                 375                 380

Phe Asp Glu Cys Gly Ile Thr Asp Asp Gln Leu Leu Ala Leu Leu Pro
385                 390                 395                 400

Ser Leu Ser His Cys Ser Gln Leu Thr Thr Leu Ser Phe Tyr Gly Asn
                405                 410                 415

Ser Ile Ser Ile Ser Ala Leu Gln Ser Leu Leu Gln His Leu Ile Gly
            420                 425                 430

Leu Ser Asn Leu Thr His Val Leu Tyr Pro Val Pro Leu Glu Ser Tyr
            435                 440                 445

Glu Asp Ile His Gly Thr Leu His Leu Glu Arg Leu Ala Tyr Leu His
            450                 455                 460

Ala Arg Leu Arg Glu Leu Leu Cys Glu Leu Gly Arg Pro Ser Met Val
465                 470                 475                 480
```

```
Trp Leu Ser Ala Asn Pro Cys Pro His Cys Gly Asp Arg Thr Phe Tyr
                485                 490                 495

Asp Pro Glu Pro Ile Leu Cys Pro Cys Phe Met Pro Asn
            500                 505
```

<210> SEQ ID NO 2
<211> LENGTH: 9
<212> TYPE: PRT
<213> ORGANISM: Artificial Sequence
<220> FEATURE:
<223> OTHER INFORMATION: Synthetic

<400> SEQUENCE: 2

```
Val Leu Asp Gly Leu Asp Val Leu Leu
1               5
```

<210> SEQ ID NO 3
<211> LENGTH: 10
<212> TYPE: PRT
<213> ORGANISM: Artificial Sequence
<220> FEATURE:
<223> OTHER INFORMATION: Synthetic

<400> SEQUENCE: 3

```
Ser Leu Tyr Ser Phe Pro Glu Pro Glu Ala
1               5                   10
```

<210> SEQ ID NO 4
<211> LENGTH: 10
<212> TYPE: PRT
<213> ORGANISM: Artificial Sequence
<220> FEATURE:
<223> OTHER INFORMATION: Synthetic

<400> SEQUENCE: 4

```
Ala Leu Tyr Val Asp Ser Leu Phe Phe Leu
1               5                   10
```

<210> SEQ ID NO 5
<211> LENGTH: 9
<212> TYPE: PRT
<213> ORGANISM: Artificial Sequence
<220> FEATURE:
<223> OTHER INFORMATION: Synthetic

<400> SEQUENCE: 5

```
Ser Leu Leu Gln His Leu Ile Gly Leu
1               5
```

<210> SEQ ID NO 6
<211> LENGTH: 9
<212> TYPE: PRT
<213> ORGANISM: Artificial Sequence
<220> FEATURE:
<223> OTHER INFORMATION: Synthetic

<400> SEQUENCE: 6

```
Asn Leu Thr His Val Leu Tyr Pro Val
1               5
```

<210> SEQ ID NO 7
<211> LENGTH: 8
<212> TYPE: PRT
<213> ORGANISM: Artificial Sequence
<220> FEATURE:
<223> OTHER INFORMATION: Synthetic

```
<400> SEQUENCE: 7

Gly Gly Thr Phe Ser Ser Tyr Ala
1               5

<210> SEQ ID NO 8
<211> LENGTH: 8
<212> TYPE: PRT
<213> ORGANISM: Artificial Sequence
<220> FEATURE:
<223> OTHER INFORMATION: Synthetic

<400> SEQUENCE: 8

Ile Ile Pro Ile Leu Gly Ile Ala
1               5

<210> SEQ ID NO 9
<211> LENGTH: 10
<212> TYPE: PRT
<213> ORGANISM: Artificial Sequence
<220> FEATURE:
<223> OTHER INFORMATION: Synthetic

<400> SEQUENCE: 9

Ala Arg His Tyr Gly Gln Trp Trp Asp Tyr
1               5                   10

<210> SEQ ID NO 10
<211> LENGTH: 8
<212> TYPE: PRT
<213> ORGANISM: Artificial Sequence
<220> FEATURE:
<223> OTHER INFORMATION: Synthetic

<400> SEQUENCE: 10

Ser Ser Asn Ile Gly Ser Asn Thr
1               5

<210> SEQ ID NO 11
<211> LENGTH: 3
<212> TYPE: PRT
<213> ORGANISM: Artificial Sequence
<220> FEATURE:
<223> OTHER INFORMATION: Synthetic

<400> SEQUENCE: 11

Ser Asn Asn
1

<210> SEQ ID NO 12
<211> LENGTH: 12
<212> TYPE: PRT
<213> ORGANISM: Artificial Sequence
<220> FEATURE:
<223> OTHER INFORMATION: Synthetic

<400> SEQUENCE: 12

Ala Ala Trp Asp Asp Ser Leu Asn Gly Ser Tyr Val
1               5                   10

<210> SEQ ID NO 13
<211> LENGTH: 8
<212> TYPE: PRT
<213> ORGANISM: Artificial Sequence
<220> FEATURE:
<223> OTHER INFORMATION: Synthetic

<400> SEQUENCE: 13
```

```
Gly Gly Thr Phe Ser Ser His Pro
1               5

<210> SEQ ID NO 14
<211> LENGTH: 8
<212> TYPE: PRT
<213> ORGANISM: Artificial Sequence
<220> FEATURE:
<223> OTHER INFORMATION: Synthetic

<400> SEQUENCE: 14

Ile Ile Pro Met Leu Asp Ile Pro
1               5

<210> SEQ ID NO 15
<211> LENGTH: 9
<212> TYPE: PRT
<213> ORGANISM: Artificial Sequence
<220> FEATURE:
<223> OTHER INFORMATION: Synthetic

<400> SEQUENCE: 15

Ala Arg Gly Leu Tyr Tyr Tyr Asp Tyr
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic

<400> SEQUENCE: 16

Thr Ser Asn Ile Gly Ala Gly Phe Asp
1               5

<210> SEQ ID NO 17
<211> LENGTH: 3
<212> TYPE: PRT
<213> ORGANISM: Artificial Sequence
<220> FEATURE:
<223> OTHER INFORMATION: Synthetic

<400> SEQUENCE: 17

Gly Asn Thr
1

<210> SEQ ID NO 18
<211> LENGTH: 11
<212> TYPE: PRT
<213> ORGANISM: Artificial Sequence
<220> FEATURE:
<223> OTHER INFORMATION: Synthetic

<400> SEQUENCE: 18

Gln Ser Tyr Asp Arg Ser Leu Ser Thr Ile Leu
1               5                   10

<210> SEQ ID NO 19
<211> LENGTH: 8
<212> TYPE: PRT
<213> ORGANISM: Artificial Sequence
<220> FEATURE:
<223> OTHER INFORMATION: Synthetic

<400> SEQUENCE: 19
```

```
Gly Gly Thr Phe Ser Ser Tyr Ala
1               5

<210> SEQ ID NO 20
<211> LENGTH: 8
<212> TYPE: PRT
<213> ORGANISM: Artificial Sequence
<220> FEATURE:
<223> OTHER INFORMATION: Synthetic

<400> SEQUENCE: 20

Ile Ile Pro Ile Phe Gly Ile Ala
1               5

<210> SEQ ID NO 21
<211> LENGTH: 9
<212> TYPE: PRT
<213> ORGANISM: Artificial Sequence
<220> FEATURE:
<223> OTHER INFORMATION: Synthetic

<400> SEQUENCE: 21

Ala Arg Ser Met Trp Tyr Met Asp Ser
1               5

<210> SEQ ID NO 22
<211> LENGTH: 9
<212> TYPE: PRT
<213> ORGANISM: Artificial Sequence
<220> FEATURE:
<223> OTHER INFORMATION: Synthetic

<400> SEQUENCE: 22

Ser Ser Asn Ile Gly Ala Gly Phe Asp
1               5

<210> SEQ ID NO 23
<211> LENGTH: 3
<212> TYPE: PRT
<213> ORGANISM: Artificial Sequence
<220> FEATURE:
<223> OTHER INFORMATION: Synthetic

<400> SEQUENCE: 23

Gly Asn Ser
1

<210> SEQ ID NO 24
<211> LENGTH: 11
<212> TYPE: PRT
<213> ORGANISM: Artificial Sequence
<220> FEATURE:
<223> OTHER INFORMATION: Synthetic

<400> SEQUENCE: 24

Gln Ser Tyr Asp Ser Ser Leu Ser Gly Tyr Val
1               5                   10

<210> SEQ ID NO 25
<211> LENGTH: 8
<212> TYPE: PRT
<213> ORGANISM: Artificial Sequence
<220> FEATURE:
<223> OTHER INFORMATION: Synthetic

<400> SEQUENCE: 25

Gly Tyr Thr Phe Ser Ser Tyr Gly
```

```
1               5

<210> SEQ ID NO 26
<211> LENGTH: 8
<212> TYPE: PRT
<213> ORGANISM: Artificial Sequence
<220> FEATURE:
<223> OTHER INFORMATION: Synthetic

<400> SEQUENCE: 26

Ile Ser Pro Tyr Asn Gly Asn Thr
1               5

<210> SEQ ID NO 27
<211> LENGTH: 11
<212> TYPE: PRT
<213> ORGANISM: Artificial Sequence
<220> FEATURE:
<223> OTHER INFORMATION: Synthetic

<400> SEQUENCE: 27

Ala Arg Tyr Ser Gly Tyr Tyr Tyr Val Asp Tyr
1               5                   10

<210> SEQ ID NO 28
<211> LENGTH: 6
<212> TYPE: PRT
<213> ORGANISM: Artificial Sequence
<220> FEATURE:
<223> OTHER INFORMATION: Synthetic

<400> SEQUENCE: 28

Gln Ser Ile Ser Ser Tyr
1               5

<210> SEQ ID NO 29
<211> LENGTH: 3
<212> TYPE: PRT
<213> ORGANISM: Artificial Sequence
<220> FEATURE:
<223> OTHER INFORMATION: Synthetic

<400> SEQUENCE: 29

Ala Ala Ser
1

<210> SEQ ID NO 30
<211> LENGTH: 9
<212> TYPE: PRT
<213> ORGANISM: Artificial Sequence
<220> FEATURE:
<223> OTHER INFORMATION: Synthetic

<400> SEQUENCE: 30

Gln Gln Ser Tyr Ser Thr Pro Arg Thr
1               5

<210> SEQ ID NO 31
<211> LENGTH: 8
<212> TYPE: PRT
<213> ORGANISM: Artificial Sequence
<220> FEATURE:
<223> OTHER INFORMATION: Synthetic

<400> SEQUENCE: 31

Gly Gly Thr Phe Ser Ser Tyr Ala
1               5
```

```
<210> SEQ ID NO 32
<211> LENGTH: 8
<212> TYPE: PRT
<213> ORGANISM: Artificial Sequence
<220> FEATURE:
<223> OTHER INFORMATION: Synthetic

<400> SEQUENCE: 32

Ile Ile Pro Ile Leu Gly Ile Ala
1               5

<210> SEQ ID NO 33
<211> LENGTH: 12
<212> TYPE: PRT
<213> ORGANISM: Artificial Sequence
<220> FEATURE:
<223> OTHER INFORMATION: Synthetic

<400> SEQUENCE: 33

Ala Arg Gln Gly Tyr Val Trp Ser Glu Met Asp Phe
1               5                   10

<210> SEQ ID NO 34
<211> LENGTH: 6
<212> TYPE: PRT
<213> ORGANISM: Artificial Sequence
<220> FEATURE:
<223> OTHER INFORMATION: Synthetic

<400> SEQUENCE: 34

Asn Ile Gly Ser Lys Ser
1               5

<210> SEQ ID NO 35
<211> LENGTH: 3
<212> TYPE: PRT
<213> ORGANISM: Artificial Sequence
<220> FEATURE:
<223> OTHER INFORMATION: Synthetic

<400> SEQUENCE: 35

Tyr Asp Ser
1

<210> SEQ ID NO 36
<211> LENGTH: 11
<212> TYPE: PRT
<213> ORGANISM: Artificial Sequence
<220> FEATURE:
<223> OTHER INFORMATION: Synthetic

<400> SEQUENCE: 36

Gln Val Trp Asp Ser Ile Thr Asp His Tyr Val
1               5                   10

<210> SEQ ID NO 37
<211> LENGTH: 8
<212> TYPE: PRT
<213> ORGANISM: Artificial Sequence
<220> FEATURE:
<223> OTHER INFORMATION: Synthetic

<400> SEQUENCE: 37

Gly Tyr Thr Phe Thr Ser Tyr Tyr
1               5
```

```
<210> SEQ ID NO 38
<211> LENGTH: 8
<212> TYPE: PRT
<213> ORGANISM: Artificial Sequence
<220> FEATURE:
<223> OTHER INFORMATION: Synthetic

<400> SEQUENCE: 38

Ile Asn Pro Ser Gly Gly Ser Thr
1               5

<210> SEQ ID NO 39
<211> LENGTH: 10
<212> TYPE: PRT
<213> ORGANISM: Artificial Sequence
<220> FEATURE:
<223> OTHER INFORMATION: Synthetic

<400> SEQUENCE: 39

Ala Ala Gly Ser Tyr Tyr Ser Leu Asp Ile
1               5                   10

<210> SEQ ID NO 40
<211> LENGTH: 8
<212> TYPE: PRT
<213> ORGANISM: Artificial Sequence
<220> FEATURE:
<223> OTHER INFORMATION: Synthetic

<400> SEQUENCE: 40

Ser Gly Ser Ile Ala Ser Asn Phe
1               5

<210> SEQ ID NO 41
<211> LENGTH: 3
<212> TYPE: PRT
<213> ORGANISM: Artificial Sequence
<220> FEATURE:
<223> OTHER INFORMATION: Synthetic

<400> SEQUENCE: 41

Asp Asp Asn
1

<210> SEQ ID NO 42
<211> LENGTH: 9
<212> TYPE: PRT
<213> ORGANISM: Artificial Sequence
<220> FEATURE:
<223> OTHER INFORMATION: Synthetic

<400> SEQUENCE: 42

Gln Ser Tyr Asp Gly Ser Asn Val Ile
1               5

<210> SEQ ID NO 43
<211> LENGTH: 8
<212> TYPE: PRT
<213> ORGANISM: Artificial Sequence
<220> FEATURE:
<223> OTHER INFORMATION: Synthetic

<400> SEQUENCE: 43

Gly Tyr Thr Phe Ser Ser Tyr Tyr
1               5

<210> SEQ ID NO 44
<211> LENGTH: 8
<212> TYPE: PRT
<213> ORGANISM: Artificial Sequence
<220> FEATURE:
<223> OTHER INFORMATION: Synthetic
```

```
<213> ORGANISM: Artificial Sequence
<220> FEATURE:
<223> OTHER INFORMATION: Synthetic

<400> SEQUENCE: 46

Asn Phe Gly Ser Gln Ser
1               5

<210> SEQ ID NO 47
<211> LENGTH: 3
<212> TYPE: PRT
<213> ORGANISM: Artificial Sequence
<220> FEATURE:
<223> OTHER INFORMATION: Synthetic

<400> SEQUENCE: 47

Tyr Asp Gln
1

<210> SEQ ID NO 48
<211> LENGTH: 11
<212> TYPE: PRT
<213> ORGANISM: Artificial Sequence
<220> FEATURE:
<223> OTHER INFORMATION: Synthetic

<400> SEQUENCE: 48

Gln Val Trp Asp Thr Tyr Thr Asp His Val Val
1               5                   10

<210> SEQ ID NO 49
<211> LENGTH: 117
<212> TYPE: PRT
<213> ORGANISM: Artificial Sequence
<220> FEATURE:
<223> OTHER INFORMATION: Synthetic

<400> SEQUENCE: 49

Gln Val Gln Leu Val Gln Ser Gly Ala Glu Val Arg Lys Pro Gly Ala
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg His Tyr Gly Gln Trp Trp Asp Tyr Trp Gly Gln Gly Thr Leu
            100                 105                 110

Val Thr Val Ser Ser
        115

<210> SEQ ID NO 50
<211> LENGTH: 112
<212> TYPE: PRT
<213> ORGANISM: Artificial Sequence
<220> FEATURE:
<223> OTHER INFORMATION: Synthetic

<400> SEQUENCE: 50
```

```
Gln Ala Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Ser Tyr Val Phe Gly Thr Gly Thr Lys Val Thr Val Leu Gly
            100                 105                 110
```

<210> SEQ ID NO 51
<211> LENGTH: 116
<212> TYPE: PRT
<213> ORGANISM: Artificial Sequence
<220> FEATURE:
<223> OTHER INFORMATION: Synthetic

<400> SEQUENCE: 51

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser His
            20                  25                  30

Pro Ile Ser Trp Val Arg Gln Ala Pro Gly Gln Gly Leu Glu Trp Met
        35                  40                  45

Gly Arg Ile Ile Pro Met Leu Asp Ile Pro Asn Asn Ala Gln Lys Phe
    50                  55                  60

Gln Gly Arg Val Thr Ile Thr Ala Asp Lys Ser Thr Asp Thr Ala Tyr
65                  70                  75                  80

Leu Glu Leu Ser Ser Leu Thr Ser Glu Asp Thr Ala Val Tyr Tyr Cys
                85                  90                  95

Ala Arg Gly Leu Tyr Tyr Tyr Asp Tyr Trp Gly Gln Gly Thr Leu Val
            100                 105                 110

Thr Val Ser Ser
        115
```

<210> SEQ ID NO 52
<211> LENGTH: 112
<212> TYPE: PRT
<213> ORGANISM: Artificial Sequence
<220> FEATURE:
<223> OTHER INFORMATION: Synthetic

<400> SEQUENCE: 52

```
Gln Ser Val Val Thr Gln Pro Pro Ala Val Ser Gly Ala Leu Gly Gln
1               5                   10                  15

Arg Val Thr Ile Ser Cys Thr Gly Thr Thr Ser Asn Ile Gly Ala Gly
            20                  25                  30

Phe Asp Val His Trp Tyr Gln Gln Arg Pro Gly Ala Ala Pro Lys Leu
        35                  40                  45

Leu Ile Ser Gly Asn Thr His Arg Pro Ser Gly Val Pro Asp Arg Ile
    50                  55                  60

Ser Gly Ser Lys Ser Gly Thr Leu Ala Ser Leu Ala Ile Thr Gly Leu
65                  70                  75                  80
```

Gln Ala Glu Asp Glu Ala Asp Tyr Tyr Cys Gln Ser Tyr Asp Arg Ser
                85                  90                  95

Leu Ser Thr Ile Leu Phe Gly Gly Gly Thr Lys Leu Thr Val Leu Gly
            100                 105                 110

<210> SEQ ID NO 53
<211> LENGTH: 116
<212> TYPE: PRT
<213> ORGANISM: Artificial Sequence
<220> FEATURE:
<223> OTHER INFORMATION: Synthetic

<400> SEQUENCE: 53

Glu Val Gln Leu Val Glu Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Phe Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Met Trp Tyr Met Asp Ser Trp Gly Gln Gly Thr Leu Val
            100                 105                 110

Thr Val Ser Ser
        115

<210> SEQ ID NO 54
<211> LENGTH: 112
<212> TYPE: PRT
<213> ORGANISM: Artificial Sequence
<220> FEATURE:
<223> OTHER INFORMATION: Synthetic

<400> SEQUENCE: 54

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Phe Asp Val His Trp Tyr Gln Gln Leu Pro Gly Thr Ala Pro Lys Leu
        35                  40                  45

Leu Ile Phe Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Tyr Val Phe Gly Ser Gly Thr Lys Val Thr Val Leu Gly
            100                 105                 110

<210> SEQ ID NO 55
<211> LENGTH: 118
<212> TYPE: PRT
<213> ORGANISM: Artificial Sequence
<220> FEATURE:
<223> OTHER INFORMATION: Synthetic

<400> SEQUENCE: 55

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Ser Ser Tyr
            20                  25                  30
Gly Ile Ser Trp Val Arg Gln Ala Pro Gly Gln Gly Leu Glu Trp Met
        35                  40                  45
Gly Trp Ile Ser Pro Tyr Asn Gly Asn Thr Asn Tyr Ala Gln Asn Leu
    50                  55                  60
Gln Gly Arg Val Thr Met Thr Thr Asp Thr Ser Thr Thr Thr Ala Tyr
65                  70                  75                  80
Met Glu Leu Arg Ser Leu Thr Ser Asp Asp Thr Ala Val Tyr Tyr Cys
                85                  90                  95
Ala Arg Tyr Ser Gly Tyr Tyr Val Asp Tyr Trp Gly Gln Gly Thr
            100                 105                 110
Leu Val Thr Val Ser Ser
            115
```

<210> SEQ ID NO 56
<211> LENGTH: 108
<212> TYPE: PRT
<213> ORGANISM: Artificial Sequence
<220> FEATURE:
<223> OTHER INFORMATION: Synthetic

<400> SEQUENCE: 56

```
Asp Ile Gln Leu Thr Gln Ser Pro Ser Ser Leu Ser Ala Ser Val Gly
1               5                   10                  15
Asp Arg Val Thr Ile Thr Cys Arg Ala Ser Gln Ser Ile Ser Ser Tyr
            20                  25                  30
Leu Asn Trp Tyr Gln Gln Lys Pro Gly Lys Ala Pro Lys Leu Leu Ile
        35                  40                  45
Tyr Ala Ala Ser Ser Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Ser Tyr Ser Thr Pro Arg
                85                  90                  95
Thr Phe Gly Gln Gly Thr Lys Val Glu Ile Lys Arg
            100                 105
```

<210> SEQ ID NO 57
<211> LENGTH: 119
<212> TYPE: PRT
<213> ORGANISM: Artificial Sequence
<220> FEATURE:
<223> OTHER INFORMATION: Synthetic

<400> SEQUENCE: 57

```
Glu Val Gln Leu Val Glu Ser Gly Ala Glu Val Lys Lys Pro Gly Ser
1               5                   10                  15
Ser Val Lys Val Ser Cys Lys Ala Ser Gly Gly Thr Phe Ser Ser Tyr
            20                  25                  30
Ala Ile Ser Trp Val Arg Gln Ala Pro Gly Gln Gly Leu Glu Trp Met
        35                  40                  45
Gly Arg Ile Ile Pro Ile Leu Gly Ile Ala Asn Tyr Ala Gln Lys Phe
    50                  55                  60
```

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gln Gly Tyr Val Trp Ser Glu Met Asp Phe Trp Gly Gln Gly
            100                 105                 110

Thr Leu Val Thr Val Ser Ser
            115

<210> SEQ ID NO 58
<211> LENGTH: 111
<212> TYPE: PRT
<213> ORGANISM: Artificial Sequence
<220> FEATURE:
<223> OTHER INFORMATION: Synthetic

<400> SEQUENCE: 58

Lys Leu Leu Pro Val Leu Thr Gln Pro Pro Ser Val Ser Val Ala Pro
1               5                   10                  15

Gly Lys Thr Ala Arg Ile Thr Cys Gly Gly Asn Asn Ile Gly Ser Lys
            20                  25                  30

Ser Val His Trp Tyr Gln Gln Lys Pro Gly Gln Ala Pro Val Leu Val
        35                  40                  45

Ile Tyr Tyr Asp Ser Asp Arg Pro Ser Gly Ile Pro Glu Arg Phe Ser
    50                  55                  60

Gly Ser Asn Ser Gly Asn Thr Ala Thr Leu Thr Ile Ser Arg Val Glu
65                  70                  75                  80

Ala Gly Asp Glu Ala Asp Tyr Tyr Cys Gln Val Trp Asp Ser Ile Thr
                85                  90                  95

Asp His Tyr Val Phe Gly Thr Gly Thr Lys Val Thr Val Leu Gly
            100                 105                 110

<210> SEQ ID NO 59
<211> LENGTH: 117
<212> TYPE: PRT
<213> ORGANISM: Artificial Sequence
<220> FEATURE:
<223> OTHER INFORMATION: Synthetic

<400> SEQUENCE: 59

Glu Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Ala Gly Ser Tyr Tyr Ser Leu Asp Ile Trp Gly Gln Gly Thr Met
            100                 105                 110

Val Thr Val Ser Ser
            115

<210> SEQ ID NO 60
<211> LENGTH: 113
<212> TYPE: PRT
<213> ORGANISM: Artificial Sequence
<220> FEATURE:
<223> OTHER INFORMATION: Synthetic

<400> SEQUENCE: 60

Lys Leu Leu Pro Val Leu Thr Gln Pro His Ser Val Ser Glu Ser Pro
1               5                   10                  15

Gly Lys Thr Val Thr Ile Ser Cys Thr Gly Ser Ser Gly Ser Ile Ala
            20                  25                  30

Ser Asn Phe Val Gln Trp Tyr Gln Gln Arg Pro Gly Ser Ala Pro Thr
        35                  40                  45

Thr Val Ile Tyr Asp Asp Asn Gln Arg Pro Ser Gly Val Pro Asp Arg
    50                  55                  60

Phe Ser Ala Ser Ile Asp Arg Ser Ser Asn Ser Ala Ser Leu Thr Ile
65                  70                  75                  80

Ser Gly Leu Lys Thr Asp Asp Glu Ala Asp Tyr Tyr Cys Gln Ser Tyr
                85                  90                  95

Asp Gly Ser Asn Val Ile Phe Gly Gly Gly Thr Lys Leu Thr Val Leu
            100                 105                 110

Gly

<210> SEQ ID NO 61
<211> LENGTH: 117
<212> TYPE: PRT
<213> ORGANISM: Artificial Sequence
<220> FEATURE:
<223> OTHER INFORMATION: Synthetic

<400> SEQUENCE: 61

Glu Val Gln Leu Val Gln Ser Gly Ala Glu Val Lys Pro Gly Ala
1               5                   10                  15

Ser Val Lys Val Ser Cys Lys Ala Ser Gly Tyr Thr Phe Ser Ser Tyr
            20                  25                  30

Tyr Met Asp Trp Val Arg Gln Ala Pro Gly Gln Gly Leu Glu Trp Met
        35                  40                  45

Gly Arg Ile Asn Pro Thr Ser Gly Ser Thr Thr Tyr Ala Gln Lys Phe
    50                  55                  60

Gln Gly Arg Val Thr Met Thr Arg Asp Thr Ser Thr Phe Thr Val Tyr
65                  70                  75                  80

Met Asp Leu Ser Ser Leu Arg Ser Glu Asp Thr Ala Val Tyr Tyr Cys
                85                  90                  95

Ala Arg Ser Gly Gly Gly Tyr Gly Asp Ser Trp Gly Gln Gly Thr Leu
            100                 105                 110

Val Thr Val Ser Ser
        115

<210> SEQ ID NO 62
<211> LENGTH: 109
<212> TYPE: PRT
<213> ORGANISM: Artificial Sequence
<220> FEATURE:
<223> OTHER INFORMATION: Synthetic

<400> SEQUENCE: 62

Gln Pro Val Leu Thr Gln Pro Pro Ser Val Ser Val Ala Pro Gly Glu
1               5                   10                  15

```
Thr Ala Ser Val Ser Cys Gly Gly Asn Asn Phe Gly Ser Gln Ser Val
             20                  25                  30

His Trp Tyr Gln Gln Lys Ser Gly Gln Ala Pro Leu Leu Val Ile Tyr
         35                  40                  45

Tyr Asp Gln Asp Arg Pro Ser Glu Ile Pro Ala Arg Phe Ser Gly Ser
 50                  55                  60

Lys Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Thr Tyr Thr Asp His
                 85                  90                  95

Val Val Phe Gly Gly Gly Thr Lys Leu Thr Val Leu Gly
                100                 105
```

<210> SEQ ID NO 63
<211> LENGTH: 250
<212> TYPE: PRT
<213> ORGANISM: Artificial Sequence
<220> FEATURE:
<223> OTHER INFORMATION: Synthetic

<400> SEQUENCE: 63

```
Gln Ala Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
             20                  25                  30

Thr Val Asn Trp Tyr Gln Gln Leu Pro Gly Thr Ala Pro Lys Leu Leu
         35                  40                  45

Ile Tyr Ser Asn Asn Gln Arg Pro Ser Gly Val Pro Asp Arg Phe Ser
 50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Asp Ser Leu
                 85                  90                  95

Asn Gly Ser Tyr Val Phe Gly Thr Gly Thr Lys Val Thr Val Leu Gly
                100                 105                 110

Ser Arg Gly Gly Gly Gly Ser Gly Gly Gly Ser Gly Gly Gly Gly
             115                 120                 125

Ser Leu Glu Met Ala Gln Val Gln Leu Val Gln Ser Gly Ala Glu Val
130                 135                 140

Arg Lys Pro Gly Ala Ser Val Lys Val Ser Cys Lys Ala Ser Gly Gly
145                 150                 155                 160

Thr Phe Ser Ser Tyr Ala Ile Ser Trp Val Arg Gln Ala Pro Gly Gln
                165                 170                 175

Gly Leu Glu Trp Met Gly Arg Ile Ile Pro Ile Leu Gly Ile Ala Asn
                180                 185                 190

Tyr Ala Gln Lys Phe Gln Gly Arg Val Thr Ile Thr Ala Asp Lys Ser
            195                 200                 205

Thr Ser Thr Ala Tyr Met Glu Leu Ser Ser Leu Arg Ser Glu Asp Thr
        210                 215                 220

Ala Val Tyr Tyr Cys Ala Arg His Tyr Gly Gln Trp Trp Asp Tyr Trp
225                 230                 235                 240

Gly Gln Gly Thr Leu Val Thr Val Ser Ser
                245                 250
```

<210> SEQ ID NO 64
<211> LENGTH: 249

```
<212> TYPE: PRT
<213> ORGANISM: Artificial Sequence
<220> FEATURE:
<223> OTHER INFORMATION: Synthetic

<400> SEQUENCE: 64

Gln Ser Val Val Thr Gln Pro Pro Ala Val Ser Gly Ala Leu Gly Gln
1               5                   10                  15

Arg Val Thr Ile Ser Cys Thr Gly Thr Ser Asn Ile Gly Ala Gly
            20                  25                  30

Phe Asp Val His Trp Tyr Gln Gln Arg Pro Gly Ala Ala Pro Lys Leu
            35                  40                  45

Leu Ile Ser Gly Asn Thr His Arg Pro Ser Gly Val Pro Asp Arg Ile
    50                  55                  60

Ser Gly Ser Lys Ser Gly Thr Leu Ala Ser Leu Ala Ile Thr Gly Leu
65                  70                  75                  80

Gln Ala Glu Asp Glu Ala Asp Tyr Tyr Cys Gln Ser Tyr Asp Arg Ser
                85                  90                  95

Leu Ser Thr Ile Leu Phe Gly Gly Gly Thr Lys Leu Thr Val Leu Gly
            100                 105                 110

Ser Arg Gly Gly Gly Gly Ser Gly Gly Gly Ser Gly Gly Gly Gly
            115                 120                 125

Ser Leu Glu Met Ala Gln Val Gln Leu Val Gln Ser Gly Ala Glu Val
130                 135                 140

Lys Lys Pro Gly Ser Ser Val Lys Val Ser Cys Lys Ala Ser Gly Gly
145                 150                 155                 160

Thr Phe Ser Ser His Pro Ile Ser Trp Val Arg Gln Ala Pro Gly Gln
                165                 170                 175

Gly Leu Glu Trp Met Gly Arg Ile Ile Pro Met Leu Asp Ile Pro Asn
            180                 185                 190

Asn Ala Gln Lys Phe Gln Gly Arg Val Thr Ile Thr Ala Asp Lys Ser
            195                 200                 205

Thr Asp Thr Ala Tyr Leu Glu Leu Ser Ser Leu Thr Ser Glu Asp Thr
210                 215                 220

Ala Val Tyr Tyr Cys Ala Arg Gly Leu Tyr Tyr Tyr Asp Tyr Trp Gly
225                 230                 235                 240

Gln Gly Thr Leu Val Thr Val Ser Ser
                245

<210> SEQ ID NO 65
<211> LENGTH: 249
<212> TYPE: PRT
<213> ORGANISM: Artificial Sequence
<220> FEATURE:
<223> OTHER INFORMATION: Synthetic

<400> SEQUENCE: 65

Gln Ser Val Leu Thr Gln Pro Pro Ser Val Ser Gly Ala Pro Gly Gln
1               5                   10                  15

Arg Val Thr Ile Ser Cys Thr Gly Ser Ser Asn Ile Gly Ala Gly
            20                  25                  30

Phe Asp Val His Trp Tyr Gln Gln Leu Pro Gly Thr Ala Pro Lys Leu
            35                  40                  45

Leu Ile Phe Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80
```

Gln Ala Glu Asp Glu Ala Asp Tyr Tyr Cys Gln Ser Tyr Asp Ser Ser
                85                  90                  95

Leu Ser Gly Tyr Val Phe Gly Ser Gly Thr Lys Val Thr Val Leu Gly
            100                 105                 110

Ser Arg Gly Gly Gly Gly Ser Gly Gly Gly Ser Gly Gly Gly Gly
        115                 120                 125

Ser Leu Glu Met Ala Glu Val Gln Leu Val Glu Ser Gly Ala Glu Val
130                 135                 140

Lys Lys Pro Gly Ser Ser Val Lys Val Ser Cys Lys Ala Ser Gly Gly
145                 150                 155                 160

Thr Phe Ser Ser Tyr Ala Ile Ser Trp Val Arg Gln Ala Pro Gly Gln
                165                 170                 175

Gly Leu Glu Trp Met Gly Arg Ile Ile Pro Ile Phe Gly Ile Ala Asn
            180                 185                 190

Tyr Ala Gln Lys Phe Gln Gly Arg Val Thr Ile Thr Ala Asp Lys Ser
        195                 200                 205

Thr Ser Thr Ala Tyr Met Glu Leu Ser Ser Leu Arg Ser Glu Asp Thr
210                 215                 220

Ala Val Tyr Tyr Cys Ala Arg Ser Met Trp Tyr Met Asp Ser Trp Gly
225                 230                 235                 240

Gln Gly Thr Leu Val Thr Val Ser Ser
                245

<210> SEQ ID NO 66
<211> LENGTH: 247
<212> TYPE: PRT
<213> ORGANISM: Artificial Sequence
<220> FEATURE:
<223> OTHER INFORMATION: Synthetic

<400> SEQUENCE: 66

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Arg
                85                  90                  95

Thr Phe Gly Gln Gly Thr Lys Val Glu Ile Lys Arg Ser Arg Gly Gly
            100                 105                 110

Gly Gly Ser Gly Gly Gly Gly Ser Gly Gly Gly Gly Ser Leu Glu Met
        115                 120                 125

Ala Gln Val Gln Leu Val Gln Ser Gly Ala Glu Val Lys Lys Pro Gly
    130                 135                 140

Ala Ser Val Lys Val Ser Cys Lys Ala Ser Gly Tyr Thr Phe Ser Ser
145                 150                 155                 160

Tyr Gly Ile Ser Trp Val Arg Gln Ala Pro Gly Gln Gly Leu Glu Trp
                165                 170                 175

Met Gly Trp Ile Ser Pro Tyr Asn Gly Asn Thr Asn Tyr Ala Gln Asn
            180                 185                 190

Leu Gln Gly Arg Val Thr Met Thr Thr Asp Thr Ser Thr Thr Thr Ala
            195                 200                 205

Tyr Met Glu Leu Arg Ser Leu Thr Ser Asp Asp Thr Ala Val Tyr Tyr
        210                 215                 220

Cys Ala Arg Tyr Ser Gly Tyr Tyr Tyr Val Asp Tyr Trp Gly Gln Gly
225                 230                 235                 240

Thr Leu Val Thr Val Ser Ser
            245

<210> SEQ ID NO 67
<211> LENGTH: 251
<212> TYPE: PRT
<213> ORGANISM: Artificial Sequence
<220> FEATURE:
<223> OTHER INFORMATION: Synthetic

<400> SEQUENCE: 67

Lys Leu Leu Pro Val Leu Thr Gln Pro Pro Ser Val Ser Val Ala Pro
1               5                   10                  15

Gly Lys Thr Ala Arg Ile Thr Cys Gly Gly Asn Asn Ile Gly Ser Lys
            20                  25                  30

Ser Val His Trp Tyr Gln Gln Lys Pro Gly Gln Ala Pro Val Leu Val
        35                  40                  45

Ile Tyr Tyr Asp Ser Asp Arg Pro Ser Gly Ile Pro Glu Arg Phe Ser
50                  55                  60

Gly Ser Asn Ser Gly Asn Thr Ala Thr Leu Thr Ile Ser Arg Val Glu
65                  70                  75                  80

Ala Gly Asp Glu Ala Asp Tyr Tyr Cys Gln Val Trp Asp Ser Ile Thr
                85                  90                  95

Asp His Tyr Val Phe Gly Thr Gly Thr Lys Val Thr Val Leu Gly Ser
            100                 105                 110

Arg Gly Gly Gly Gly Ser Gly Gly Gly Gly Ser Gly Gly Gly Gly Ser
        115                 120                 125

Leu Glu Met Ala Glu Val Gln Leu Val Glu Ser Gly Ala Glu Val Lys
    130                 135                 140

Lys Pro Gly Ser Ser Val Lys Val Ser Cys Lys Ala Ser Gly Gly Thr
145                 150                 155                 160

Phe Ser Ser Tyr Ala Ile Ser Trp Val Arg Gln Ala Pro Gly Gln Gly
                165                 170                 175

Leu Glu Trp Met Gly Arg Ile Ile Pro Ile Leu Gly Ile Ala Asn Tyr
            180                 185                 190

Ala Gln Lys Phe Gln Gly Arg Val Thr Ile Thr Ala Asp Lys Ser Thr
        195                 200                 205

Ser Thr Ala Tyr Met Glu Leu Ser Ser Leu Arg Ser Glu Asp Thr Ala
    210                 215                 220

Val Tyr Tyr Cys Ala Arg Gln Gly Tyr Val Trp Ser Glu Met Asp Phe
225                 230                 235                 240

Trp Gly Gln Gly Thr Leu Val Thr Val Ser Ser
                245                 250

<210> SEQ ID NO 68
<211> LENGTH: 251
<212> TYPE: PRT
<213> ORGANISM: Artificial Sequence
<220> FEATURE:
<223> OTHER INFORMATION: Synthetic -continued

```
<400> SEQUENCE: 68

Lys Leu Leu Pro Val Leu Thr Gln Pro His Ser Val Ser Glu Ser Pro
1               5                   10                  15

Gly Lys Thr Val Thr Ile Ser Cys Thr Gly Ser Ser Gly Ser Ile Ala
            20                  25                  30

Ser Asn Phe Val Gln Trp Tyr Gln Gln Arg Pro Gly Ser Ala Pro Thr
        35                  40                  45

Thr Val Ile Tyr Asp Asp Asn Gln Arg Pro Ser Gly Val Pro Asp Arg
    50                  55                  60

Phe Ser Ala Ser Ile Asp Arg Ser Ser Asn Ser Ala Ser Leu Thr Ile
65                  70                  75                  80

Ser Gly Leu Lys Thr Asp Asp Glu Ala Asp Tyr Tyr Cys Gln Ser Tyr
                85                  90                  95

Asp Gly Ser Asn Val Ile Phe Gly Gly Gly Thr Lys Leu Thr Val Leu
            100                 105                 110

Gly Ser Arg Gly Gly Gly Gly Ser Gly Gly Gly Ser Gly Gly Gly
        115                 120                 125

Gly Ser Leu Glu Met Ala Glu Val Gln Leu Val Glu Ser Gly Ala Glu
    130                 135                 140

Val Lys Lys Pro Gly Ala Ser Val Lys Val Ser Cys Lys Ala Ser Gly
145                 150                 155                 160

Tyr Thr Phe Thr Ser Tyr Tyr Met His Trp Val Arg Gln Ala Pro Gly
                165                 170                 175

Gln Gly Leu Glu Trp Met Gly Ile Ile Asn Pro Ser Gly Gly Ser Thr
            180                 185                 190

Ser Tyr Ala Gln Lys Phe Gln Gly Arg Val Thr Met Thr Arg Asp Thr
        195                 200                 205

Ser Thr Ser Thr Val Tyr Met Glu Leu Ser Ser Leu Arg Ser Glu Asp
    210                 215                 220

Thr Ala Val Tyr Tyr Cys Ala Ala Gly Ser Tyr Tyr Ser Leu Asp Ile
225                 230                 235                 240

Trp Gly Gln Gly Thr Met Val Thr Val Ser Ser
                245                 250

<210> SEQ ID NO 69
<211> LENGTH: 247
<212> TYPE: PRT
<213> ORGANISM: Artificial Sequence
<220> FEATURE:
<223> OTHER INFORMATION: Synthetic

<400> SEQUENCE: 69

Gln Pro Val Leu Thr Gln Pro Ser Val Ser Val Ala Pro Gly Glu
1               5                   10                  15

Thr Ala Ser Val Ser Cys Gly Gly Asn Asn Phe Gly Ser Gln Ser Val
            20                  25                  30

His Trp Tyr Gln Gln Lys Ser Gly Gln Ala Pro Leu Leu Val Ile Tyr
        35                  40                  45

Tyr Asp Gln Asp Arg Pro Ser Glu Ile Pro Ala Arg Phe Ser Gly Ser
    50                  55                  60

Lys Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Thr Tyr Thr Asp His
                85                  90                  95

Val Val Phe Gly Gly Gly Thr Lys Leu Thr Val Leu Gly Ser Arg Gly
```

```
                    100                 105                 110
Gly Gly Gly Ser Gly Gly Gly Ser Gly Gly Gly Ser Leu Glu
            115                 120                 125
Met Ala Glu Val Gln Leu Val Gln Ser Gly Ala Glu Val Lys Pro
            130                 135                 140
Gly Ala Ser Val Lys Val Ser Cys Lys Ala Ser Gly Tyr Thr Phe Ser
145                 150                 155                 160
Ser Tyr Tyr Met Asp Trp Val Arg Gln Ala Pro Gly Gln Gly Leu Glu
                165                 170                 175
Trp Met Gly Arg Ile Asn Pro Thr Ser Gly Ser Thr Thr Tyr Ala Gln
            180                 185                 190
Lys Phe Gln Gly Arg Val Thr Met Thr Arg Asp Thr Ser Thr Ser Thr Phe Thr
            195                 200                 205
Val Tyr Met Asp Leu Ser Ser Leu Arg Ser Glu Asp Thr Ala Val Tyr
            210                 215                 220
Tyr Cys Ala Arg Ser Gly Gly Tyr Gly Asp Ser Trp Gly Gln Gly
225                 230                 235                 240
Thr Leu Val Thr Val Ser Ser
                245

<210> SEQ ID NO 70
<211> LENGTH: 15
<212> TYPE: PRT
<213> ORGANISM: Artificial Sequence
<220> FEATURE:
<223> OTHER INFORMATION: Synthetic

<400> SEQUENCE: 70

Gly Gly Gly Gly Ser Gly Gly Gly Gly Ser Gly Gly Gly Gly Ser
1               5                   10                  15

<210> SEQ ID NO 71
<211> LENGTH: 45
<212> TYPE: PRT
<213> ORGANISM: Artificial Sequence
<220> FEATURE:
<223> OTHER INFORMATION: Synthetic

<400> SEQUENCE: 71

Gly Gly Thr Gly Gly Thr Gly Gly Thr Gly Gly Thr Ala Gly Cys Gly
1               5                   10                  15
Gly Cys Gly Gly Cys Gly Gly Cys Gly Gly Cys Thr Cys Thr Gly Gly
            20                  25                  30
Thr Gly Gly Thr Gly Gly Thr Gly Gly Ala Thr Cys Cys
            35                  40                  45

<210> SEQ ID NO 72
<211> LENGTH: 164
<212> TYPE: PRT
<213> ORGANISM: Artificial Sequence
<220> FEATURE:
<223> OTHER INFORMATION: Synthetic

<400> SEQUENCE: 72

Met Lys Trp Lys Ala Leu Phe Thr Ala Ala Ile Leu Gln Ala Gln Leu
1               5                   10                  15
Pro Ile Thr Glu Ala Gln Ser Phe Gly Leu Leu Asp Pro Lys Leu Cys
            20                  25                  30
Tyr Leu Leu Asp Gly Ile Leu Phe Ile Tyr Gly Val Ile Leu Thr Ala
            35                  40                  45
```

Leu Phe Leu Arg Val Lys Phe Ser Arg Ser Ala Asp Ala Pro Ala Tyr
            50                  55                  60

Gln Gln Gly Gln Asn Gln Leu Tyr Asn Glu Leu Asn Leu Gly Arg Arg
 65                  70                  75                  80

Glu Glu Tyr Asp Val Leu Asp Lys Arg Gly Arg Asp Pro Glu Met
                 85                  90                  95

Gly Gly Lys Pro Gln Arg Arg Lys Asn Pro Gln Glu Gly Leu Tyr Asn
            100                 105                 110

Glu Leu Gln Lys Asp Lys Met Ala Glu Ala Tyr Ser Glu Ile Gly Met
            115                 120                 125

Lys Gly Glu Arg Arg Arg Gly Lys Gly His Asp Gly Leu Tyr Gln Gly
            130                 135                 140

Leu Ser Thr Ala Thr Lys Asp Thr Tyr Asp Ala Leu His Met Gln Ala
145                 150                 155                 160

Leu Pro Pro Arg

<210> SEQ ID NO 73
<211> LENGTH: 112
<212> TYPE: PRT
<213> ORGANISM: Artificial Sequence
<220> FEATURE:
<223> OTHER INFORMATION: Synthetic

<400> SEQUENCE: 73

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
                20                  25                  30

Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
        50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 74
<211> LENGTH: 107
<212> TYPE: PRT
<213> ORGANISM: Artificial Sequence
<220> FEATURE:
<223> OTHER INFORMATION: Synthetic

<400> SEQUENCE: 74

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
                20                  25                  30

Phe Pro Gly Pro Ser Lys Pro Phe Trp Val Leu Val Val Val Gly Gly
            35                  40                  45

Val Leu Ala Cys Tyr Ser Leu Leu Val Thr Val Ala Phe Ile Ile Phe
        50                  55                  60

Trp Val Arg Ser Lys Arg Ser Arg Leu Leu His Ser Asp Tyr Met Asn
65                  70                  75                  80

Met Thr Pro Arg Arg Pro Gly Pro Thr Arg Lys His Tyr Gln Pro Tyr
            85                  90                  95

Ala Pro Pro Arg Asp Phe Ala Ala Tyr Arg Ser
            100                 105

<210> SEQ ID NO 75
<211> LENGTH: 336
<212> TYPE: DNA
<213> ORGANISM: Artificial Sequence
<220> FEATURE:
<223> OTHER INFORMATION: Synthetic

<400> SEQUENCE: 75
cagtctgtcg tgacgcagcc gcccgcagtg tctggggccc tagggcagag ggtcaccatc    60
tcctgcactg ggaccacctc aacatcggg gcaggttttg atgtacactg gtaccagcag   120
cgtcccggag cagcccccaa actcctcatc tccggtaaca cccatcggcc ctcaggggtc   180
cctgaccgca tctctggctc caagtctggc accttagcct ccctggccat cactgggctc   240
caggctgagg atgaggctga ttattactgc cagtcttatg acaggagcct gagtactatc   300
ctattcggcg agggaccaa gctgaccgtc ctaggt                              336

<210> SEQ ID NO 76
<211> LENGTH: 348
<212> TYPE: DNA
<213> ORGANISM: Artificial Sequence
<220> FEATURE:
<223> OTHER INFORMATION: Synthetic

<400> SEQUENCE: 76
caggtccagc tggtacagtc tggggctgag gtgaagaagc cggggtcctc ggtgaaggtc    60
tcctgcaagg cttctggagg cactttcagc agtcatccta tcagctgggt gcgacaggcc   120
ccgggacaag gcttgagtg gatgggaagg atcatcccta tgcttgatat accaaacaac   180
gcacagaagt tccagggcag agtcacgatt accgcggaca atccacgga cactgcctac   240 ttggagctga gcagcctgac atctgaggac acggccgtgt attactgtgc gcgcggtctg   300
tactactacg attactgggg tcaaggtact ctggtgaccg tgtcctct                348

<210> SEQ ID NO 77
<211> LENGTH: 747
<212> TYPE: DNA
<213> ORGANISM: Artificial Sequence
<220> FEATURE:
<223> OTHER INFORMATION: Synthetic

<400> SEQUENCE: 77
cagtctgtcg tgacgcagcc gcccgcagtg tctggggccc tagggcagag ggtcaccatc    60
tcctgcactg ggaccacctc aacatcggg gcaggttttg atgtacactg gtaccagcag   120
cgtcccggag cagcccccaa actcctcatc tccggtaaca cccatcggcc ctcaggggtc   180
cctgaccgca tctctggctc caagtctggc accttagcct ccctggccat cactgggctc   240
caggctgagg atgaggctga ttattactgc cagtcttatg acaggagcct gagtactatc   300
ctattcggcg agggaccaa gctgaccgtc ctaggttcta gaggtggtgg tggtagcggc   360
ggcggcggct ctggtggtgg tggatccctc gagatggccc aggtccagct ggtacagtct   420
ggggctgagg tgaagaagcc ggggtcctcg gtgaaggtct cctgcaaggc ttctggaggc   480
actttcagca gtcatcctat cagctgggtg cgacaggccc cgggacaagg cttgagtgg   540

| | |
|---|---|
| atgggaagga tcatccctat gcttgatata ccaaacaacg cacagaagtt ccagggcaga | 600 |
| gtcacgatta ccgcggacaa atccacggac actgcctact tggagctgag cagcctgaca | 660 |
| tctgaggaca cggccgtgta ttactgtgcg cgcggtctgt actactacga ttactggggt | 720 |
| caaggtactc tggtgaccgt gtcctct | 747 |

<210> SEQ ID NO 78
<211> LENGTH: 336
<212> TYPE: DNA
<213> ORGANISM: Artificial Sequence
<220> FEATURE:
<223> OTHER INFORMATION: Synthetic

<400> SEQUENCE: 78

| | |
|---|---|
| cagtctgtgt tgacgcagcc gccctcagtg tctggggccc cagggcagag ggtcaccatc | 60 |
| tcctgcactg ggagcagttc aacatcgggg gcaggttttg atgtacactg gtaccagcag | 120 |
| cttccaggaa cagcccccaa actcctcatc tttggtaaca gcaatcggcc ctcaggagtc | 180 |
| cctgaccgat tctctggctc caagtctggc acctcagcct ccctggccat cactggcctc | 240 |
| caggctgagg atgaggctga ctattactgc cagtcctatg acagcagcct gagtggttat | 300 |
| gtcttcggaa gtgggaccaa ggtcaccgtc ctaggt | 336 |

<210> SEQ ID NO 79
<211> LENGTH: 348
<212> TYPE: DNA
<213> ORGANISM: Artificial Sequence
<220> FEATURE:
<223> OTHER INFORMATION: Synthetic

<400> SEQUENCE: 79

| | |
|---|---|
| gaggtgcagc tggtggagtc tgggggctgag gtgaagaagc ctgggtcctc ggtgaaggtc | 60 |
| tcctgcaagg cttctggagg caccttcagc agctatgcta tcagctgggt gcgacaggcc | 120 |
| cctggacaag gcttgagtg gatgggaagg atcatcccta tctttggtat agcaaactac | 180 |
| gcacagaagt tccagggcag agtcacgatt accgcggaca atccacgag cacagcctac | 240 |
| atggagctga gcagcctgag atctgaggac acggccgtgt attactgtgc gcgctctatg | 300 |
| tggtacatgg attcttgggg tcaaggtact ctggtgaccg tgtcctct | 348 |

<210> SEQ ID NO 80
<211> LENGTH: 747
<212> TYPE: DNA
<213> ORGANISM: Artificial Sequence
<220> FEATURE:
<223> OTHER INFORMATION: Synthetic

<400> SEQUENCE: 80

| | |
|---|---|
| cagtctgtgt tgacgcagcc gccctcagtg tctggggccc cagggcagag ggtcaccatc | 60 |
| tcctgcactg ggagcagttc aacatcgggg gcaggttttg atgtacactg gtaccagcag | 120 |
| cttccaggaa cagcccccaa actcctcatc tttggtaaca gcaatcggcc ctcaggagtc | 180 |
| cctgaccgat tctctggctc caagtctggc acctcagcct ccctggccat cactggcctc | 240 |
| caggctgagg atgaggctga ctattactgc cagtcctatg acagcagcct gagtggttat | 300 |
| gtcttcggaa gtgggaccaa ggtcaccgtc ctaggttcta gaggtggtgg tggtagcggc | 360 |
| ggcggcggct ctggtggtgg tggatccctc gagatggccg aggtgcagct ggtggagtct | 420 |
| gggggctgag tgaagaagcc tgggtcctcg gtgaaggtct cctgcaaggc ttctggaggc | 480 |
| accttcagca gctatgctat cagctgggtg cgacaggccc ctggacaagg cttgagtgg | 540 |

```
atgggaagga tcatccctat ctttggtata gcaaactacg cacagaagtt ccagggcaga    600
gtcacgatta ccgcggacaa atccacgagc acagcctaca tggagctgag cagcctgaga    660
tctgaggaca cggccgtgta ttactgtgcg cgctctatgt ggtacatgga ttcttggggt    720
caaggtactc tggtgaccgt gtcctct                                        747
```

<210> SEQ ID NO 81
<211> LENGTH: 336
<212> TYPE: DNA
<213> ORGANISM: Artificial Sequence
<220> FEATURE:
<223> OTHER INFORMATION: Synthetic

<400> SEQUENCE: 81

```
caggctgtgc tgactcagcc accctcagcg tctgggaccc ccgggcagag ggtcaccatc     60
tcttgttctg gaagcagctc caacatcgga agtaatactg taaactggta ccagcagctc    120
ccaggaacgg cccccaaact cctcatctat agtaataatc agcggccctc aggggtccct    180
gaccgattct ctggctccaa gtctggcacc tcagcctccc tggccatcag tgggctccag    240
tctgaggatg aggctgatta ttactgtgca gcatgggatg acagcctgaa tggttcttat    300
gtcttcggaa ctgggaccaa ggtcaccgtc ctaggt                              336
```

<210> SEQ ID NO 82
<211> LENGTH: 351
<212> TYPE: DNA
<213> ORGANISM: Artificial Sequence
<220> FEATURE:
<223> OTHER INFORMATION: Synthetic

<400> SEQUENCE: 82

```
caggtgcagc tggtgcaatc tggagctgag gtgaggaagc ctggggcctc agtgaaggtc     60
tcctgcaagg cttctggagg caccttcagc agctatgcta tcagctgggt gcgacaggcc    120
cctggacaag gcttgagtg gatgggaagg atcatccctat ccttggtat agcaaactac    180 gcacagaagt tccagggcag agtcacgatt accgcggaca atccacgag cacagcctac    240 atggagctga gcagcctgag atctgaggac actgccgtgt attactgtgc gcgccattac    300
ggtcagtggt gggattactg gggtcaaggt actctggtga ccgtctcctc a             351
```

<210> SEQ ID NO 83
<211> LENGTH: 750
<212> TYPE: DNA
<213> ORGANISM: Artificial Sequence
<220> FEATURE:
<223> OTHER INFORMATION: Synthetic

<400> SEQUENCE: 83

```
caggctgtgc tgactcagcc accctcagcg tctgggaccc ccgggcagag ggtcaccatc     60
tcttgttctg gaagcagctc caacatcgga agtaatactg taaactggta ccagcagctc    120
ccaggaacgg cccccaaact cctcatctat agtaataatc agcggccctc aggggtccct    180
gaccgattct ctggctccaa gtctggcacc tcagcctccc tggccatcag tgggctccag    240
tctgaggatg aggctgatta ttactgtgca gcatgggatg acagcctgaa tggttcttat    300
gtcttcggaa ctgggaccaa ggtcaccgtc ctaggttcta gaggtggtgg tggtagcggc    360
ggcggcggct ctggtggtgg tggatccctc gagatggccc aggtgcagct ggtgcaatct    420
ggagctgagg tgaggaagcc tggggcctca gtgaaggtct cctgcaaggc ttctggaggc    480
```

```
accttcagca gctatgctat cagctgggtg cgacaggccc ctggacaagg gcttgagtgg      540
atgggaagga tcatccctat ccttggtata gcaaactacg cacagaagtt ccagggcaga      600
gtcacgatta ccgcggacaa atccacgagc acagcctaca tggagctgag cagcctgaga      660
tctgaggaca ctgccgtgta ttactgtgcg cgccattacg gtcagtggtg ggattactgg      720
ggtcaaggta ctctggtgac cgtctcctca                                       750
```

```
<210> SEQ ID NO 84
<211> LENGTH: 324
<212> TYPE: DNA
<213> ORGANISM: Artificial Sequence
<220> FEATURE:
<223> OTHER INFORMATION: Synthetic

<400> SEQUENCE: 84
gacatccagt tgacccagtc tccatcctcc ctgtctgcat ctgtaggaga cagagtcacc       60
atcacttgcc gggcaagtca gagcattagc agctatttaa attggtatca gcagaaacca      120
gggaaagccc ctaagctcct gatctatgct gcatccagtt tgcaaagtgg ggtcccatca      180
aggttcagtg gcagtggatc tgggacagat ttcactctca ccatcagcag tctgcaacct      240
gaagattttg caacttacta ctgtcaacag agttacagta cccctcgtac gttcggccaa      300
gggaccaagg tggaaatcaa acgt                                             324
```

```
<210> SEQ ID NO 85
<211> LENGTH: 354
<212> TYPE: DNA
<213> ORGANISM: Artificial Sequence
<220> FEATURE:
<223> OTHER INFORMATION: Synthetic

<400> SEQUENCE: 85
caggtgcagc tggtgcagtc tggagctgag gtgaagaagc ctggggcctc agtgaaggtc       60
tcctgcaagg cttctggtta cacctttagc agctatggta tcagctgggt gcgacaggcc      120
cctggacaag gcttgagtg gatgggatgg atcagccctt acaatggtaa cacaaactat      180
gcgcagaacc tccagggcag agtcaccatg accacagaca catccacgac cacagcctac      240
atggagctga ggagcctgac atctgacgac actgccgtgt attactgtgc gcgctactct      300
ggctactact acgttgatta ctgggggtcaa ggtactctgg tgaccgtgtc ctct           354
```

```
<210> SEQ ID NO 86
<211> LENGTH: 741
<212> TYPE: DNA
<213> ORGANISM: Artificial Sequence
<220> FEATURE:
<223> OTHER INFORMATION: Synthetic

<400> SEQUENCE: 86
gacatccagt tgacccagtc tccatcctcc ctgtctgcat ctgtaggaga cagagtcacc       60
atcacttgcc gggcaagtca gagcattagc agctatttaa attggtatca gcagaaacca      120
gggaaagccc ctaagctcct gatctatgct gcatccagtt tgcaaagtgg ggtcccatca      180
aggttcagtg gcagtggatc tgggacagat ttcactctca ccatcagcag tctgcaacct      240
gaagattttg caacttacta ctgtcaacag agttacagta cccctcgtac gttcggccaa      300
gggaccaagg tggaaatcaa acgttctaga ggtggtggtg gtagcggcgg cggcggctct      360
ggtggtggtg gatcctcga gatggcccag gtgcagctgg tgcagtctgg agctgaggtg      420
aagaagcctg gggcctcagt gaaggtctcc tgcaaggctt ctggttacac ctttagcagc      480
```

```
tatggtatca gctgggtgcg acaggcccct ggacaagggc ttgagtggat gggatggatc    540
agcccttaca atggtaacac aaactatgcg cagaacctcc agggcagagt caccatgacc    600
acagacacat ccacgaccac agcctacatg gagctgagga gcctgacatc tgacgacact    660
gccgtgtatt actgtgcgcg ctactctggc tactactacg ttgattactg gggtcaaggt    720
actctggtga ccgtgtcctc t                                              741
```

<210> SEQ ID NO 87
<211> LENGTH: 333
<212> TYPE: DNA
<213> ORGANISM: Artificial Sequence
<220> FEATURE:
<223> OTHER INFORMATION: Synthetic

<400> SEQUENCE: 87

```
aagcttctgc ctgtgctgac tcagccaccc tcagtgtcag tggccccagg aaagacggcc    60
aggattacct gtgggggaaa caacattgga agtaaaagtg tgcactggta ccagcagaag   120
ccaggccagg cccctgtgct ggtcatctat tatgatagcg accggccctc agggatccct   180
gagcgattct ctggctccaa ctctgggaac acggccaccc tgaccatcag cagggtcgaa   240
gccggggatg aggccgacta ttactgtcag gtgtgggata gtattactga tcattatgtc   300
ttcggaactg ggaccaaggt caccgtccta ggt                                333
```

<210> SEQ ID NO 88
<211> LENGTH: 357
<212> TYPE: DNA
<213> ORGANISM: Artificial Sequence
<220> FEATURE:
<223> OTHER INFORMATION: Synthetic

<400> SEQUENCE: 88

```
gaggtgcagc tggtggagtc tgggggtgag gtgaagaagc ctgggtcctc ggtgaaggtc    60
tcctgcaagg cttctggagg caccttcagc agctatgcta tcagctgggt gcgacaggcc   120
cctggacaag gcttgagtg gatgggaagg atcatcccta tccttggtat agcaaactac   180
gcacagaagt tccagggcag agtcacgatt accgcggaca aatccacgag cacagcctac   240
atggagctga gcagcctgag atctgaggac actgccgtgt attactgtgc gcgccagggt   300
tacgtttggt ctgaaatgga tttctggggt caaggtactc tggtgaccgt ctcctca      357
```

<210> SEQ ID NO 89
<211> LENGTH: 753
<212> TYPE: DNA
<213> ORGANISM: Artificial Sequence
<220> FEATURE:
<223> OTHER INFORMATION: Synthetic

<400> SEQUENCE: 89

```
aagcttctgc ctgtgctgac tcagccaccc tcagtgtcag tggccccagg aaagacggcc    60
aggattacct gtgggggaaa caacattgga agtaaaagtg tgcactggta ccagcagaag   120
ccaggccagg cccctgtgct ggtcatctat tatgatagcg accggccctc agggatccct   180
gagcgattct ctggctccaa ctctgggaac acggccaccc tgaccatcag cagggtcgaa   240
gccggggatg aggccgacta ttactgtcag gtgtgggata gtattactga tcattatgtc   300
ttcggaactg ggaccaaggt caccgtccta ggttctagag gtggtggtgg tagcggcggc   360
ggcggctctg gtggtggtgg atccctcgag atggccgagg tgcagctggt ggagtctggg   420
```

| | |
|---|---|
| gctgaggtga agaagcctgg gtcctcggtg aaggtctcct gcaaggcttc tggaggcacc | 480 |
| ttcagcagct atgctatcag ctgggtgcga caggcccctg gacaagggct tgagtggatg | 540 |
| ggaaggatca tccctatcct tggtatagca aactacgcac agaagttcca gggcagagtc | 600 |
| acgattaccg cggacaaatc cacgagcaca gcctacatgg agctgagcag cctgagatct | 660 |
| gaggacactg ccgtgtatta ctgtgcgcgc cagggttacg tttggtctga aatggatttc | 720 |
| tggggtcaag gtactctggt gaccgtctcc tca | 753 |

<210> SEQ ID NO 90
<211> LENGTH: 339
<212> TYPE: DNA
<213> ORGANISM: Artificial Sequence
<220> FEATURE:
<223> OTHER INFORMATION: Synthetic

<400> SEQUENCE: 90

| | |
|---|---|
| aagcttctgc ctgtgctgac tcagccccac tctgtgtcgg agtctccggg gaagacggta | 60 |
| accatctcct gcaccggcag cagtggcagc attgccagca ctttgtgca gtggtaccag | 120 |
| cagcgcccgg gcagtgcccc caccactgta atctatgatg ataaccaaag accctctggg | 180 |
| gtccctgatc ggttctctgc ctccatcgac agatcctcca attctgcctc cctcaccatc | 240 |
| tctggactga agactgacga cgaggctgac tactactgtc agtcttatga tggaagcaat | 300 |
| gtcatattcg gcggagggac caagctgacc gtcctaggt | 339 |

<210> SEQ ID NO 91
<211> LENGTH: 351
<212> TYPE: DNA
<213> ORGANISM: Artificial Sequence
<220> FEATURE:
<223> OTHER INFORMATION: Synthetic

<400> SEQUENCE: 91

| | |
|---|---|
| gaggtgcagc tggtggagtc tgggggctgag gtgaagaagc ctggggcctc agtgaaggtt | 60 |
| tcctgcaagg catctggata caccttcacc agctactata tgcactgggt gcgacaggcc | 120 |
| cctggacaag gcttgagtg gatgggaata atcaacccta gtggtggtag cacaagctac | 180 |
| gcacagaagt tccagggcag agtcaccatg accagggaca cgtccacgag cacagtctac | 240 |
| atggagctga gcagcctgag atctgaggac acggccgtgt attactgtgc ggcagggagc | 300 |
| tactactcgc ttgatatctg gggccaaggg acaatggtca ccgtctcttc a | 351 |

<210> SEQ ID NO 92
<211> LENGTH: 753
<212> TYPE: DNA
<213> ORGANISM: Artificial Sequence
<220> FEATURE:
<223> OTHER INFORMATION: Synthetic

<400> SEQUENCE: 92

| | |
|---|---|
| aagcttctgc ctgtgctgac tcagccccac tctgtgtcgg agtctccggg gaagacggta | 60 |
| accatctcct gcaccggcag cagtggcagc attgccagca ctttgtgca gtggtaccag | 120 |
| cagcgcccgg gcagtgcccc caccactgta atctatgatg ataaccaaag accctctggg | 180 |
| gtccctgatc ggttctctgc ctccatcgac agatcctcca attctgcctc cctcaccatc | 240 |
| tctggactga agactgacga cgaggctgac tactactgtc agtcttatga tggaagcaat | 300 |
| gtcatattcg gcggagggac caagctgacc gtcctaggtt ctagaggtgg tggtggtagc | 360 |
| ggcggcggcg gctctggtgg tggtggatcc ctcgagatgg ccgaggtgca gctggtggag | 420 |

```
tctggggctg aggtgaagaa gcctggggcc tcagtgaagg tttcctgcaa ggcatctgga      480
tacaccttca ccagctacta tatgcactgg gtgcgacagg cccctggaca agggcttgag      540
tggatgggaa taatcaaccc tagtggtggt agcacaagct acgcacagaa gttccagggc      600
agagtcacca tgaccaggga cacgtccacg agcacagtct acatggagct gagcagcctg      660
agatctgagg acacggccgt gtattactgt gcggcaggga gctactactc gcttgatatc      720
tggggccaag ggacaatggt caccgtctct tca                                   753

<210> SEQ ID NO 93
<211> LENGTH: 327
<212> TYPE: DNA
<213> ORGANISM: Artificial Sequence
<220> FEATURE:
<223> OTHER INFORMATION: Synthetic

<400> SEQUENCE: 93
cagcctgtgc tgactcagcc accctcagtg tcagtggccc caggagagac ggccagtgtt       60
tcctgtgggg ggaacaactt gggagtcag agtgtgcact ggtaccagca gaagtcaggc      120
caggcccctt tgttggtcat ctattatgat caggaccggc cctcagagat ccctgcgcga      180
ttttctggct ccaagtctgg gaacacggcc accctgacca tcagcagggt cgaagccggg      240
gatgaggccg actattactg tcaggtgtgg gatacttata ctgatcatgt ggtcttcggc      300
ggagggacca gctgaccgt cctaggt                                           327

<210> SEQ ID NO 94
<211> LENGTH: 351
<212> TYPE: DNA
<213> ORGANISM: Artificial Sequence
<220> FEATURE:
<223> OTHER INFORMATION: Synthetic

<400> SEQUENCE: 94
gaggtccagc tggtgcagtc tggagctgag gtggagaagc ctggggcctc agtgaaggtt       60
tcctgcaagg catctggata caccttcagt agttattata tggactgggt gcgacaggcc      120
cctggacaag ggcttgagtg gatgggaaga atcaaccctc tagtggtag cacaacctac       180 gcacagaagt tccagggcag ggtcaccatg accagggaca cgtccacatt cacggtttac      240
atggacctga gcagcctgag atctgaggac acggccgtat attactgtgc gcgctctggt      300
ggtggttacg gtgattcttg gggtcaaggt actctggtga ccgtctcctc a               351

<210> SEQ ID NO 95
<211> LENGTH: 741
<212> TYPE: DNA
<213> ORGANISM: Artificial Sequence
<220> FEATURE:
<223> OTHER INFORMATION: Synthetic

<400> SEQUENCE: 95
cagcctgtgc tgactcagcc accctcagtg tcagtggccc caggagagac ggccagtgtt       60
tcctgtgggg ggaacaactt gggagtcag agtgtgcact ggtaccagca gaagtcaggc      120
caggcccctt tgttggtcat ctattatgat caggaccggc cctcagagat ccctgcgcga      180
ttttctggct ccaagtctgg gaacacggcc accctgacca tcagcagggt cgaagccggg      240
gatgaggccg actattactg tcaggtgtgg gatacttata ctgatcatgt ggtcttcggc      300
ggagggacca gctgaccgt cctaggttct agaggtggtg gtggtagcgg cggcggcggc      360
```

```
tctggtggtg gtggatccct cgagatggcc gaggtccagc tggtgcagtc tggagctgag    420
gtggagaagc ctggggcctc agtgaaggtt tcctgcaagg catctggata caccttcagt    480
agttattata tggactgggt gcgacaggcc cctggacaag gcttgagtg gatgggaaga     540 atcaaccta ctagtggtag cacaacctac gcacagaagt tccagggcag ggtcaccatg     600
accagggaca cgtccacatt cacggtttac atggacctga gcagcctgag atctgaggac    660
acggccgtat attactgtgc gcgctctggt ggtggttacg gtgattcttg gggtcaaggt    720
actctggtga ccgtctcctc a                                              741
```

<210> SEQ ID NO 96
<211> LENGTH: 8
<212> TYPE: PRT
<213> ORGANISM: Artificial Sequence
<220> FEATURE:
<223> OTHER INFORMATION: Synthetic

<400> SEQUENCE: 96

Gly Gly Thr Phe Arg Thr Tyr Gly
1               5

<210> SEQ ID NO 97
<211> LENGTH: 8
<212> TYPE: PRT
<213> ORGANISM: Artificial Sequence
<220> FEATURE:
<223> OTHER INFORMATION: Synthetic

<400> SEQUENCE: 97

Gly Tyr Thr Phe Thr Ser Tyr Gly
1               5

<210> SEQ ID NO 98
<211> LENGTH: 8
<212> TYPE: PRT
<213> ORGANISM: Artificial Sequence
<220> FEATURE:
<223> OTHER INFORMATION: Synthetic

<400> SEQUENCE: 98

Gly Tyr Thr Phe Thr Ser Tyr Tyr
1               5

<210> SEQ ID NO 99
<211> LENGTH: 8
<212> TYPE: PRT
<213> ORGANISM: Artificial Sequence
<220> FEATURE:
<223> OTHER INFORMATION: Synthetic

<400> SEQUENCE: 99

Gly Tyr Thr Phe Thr Asp Tyr Gly
1               5

<210> SEQ ID NO 100
<211> LENGTH: 8
<212> TYPE: PRT
<213> ORGANISM: Artificial Sequence
<220> FEATURE:
<223> OTHER INFORMATION: Synthetic

<400> SEQUENCE: 100

Gly Gly Thr Phe Ser Ser Tyr Ala
1               5

```
<210> SEQ ID NO 101
<211> LENGTH: 8
<212> TYPE: PRT
<213> ORGANISM: Artificial Sequence
<220> FEATURE:
<223> OTHER INFORMATION: Synthetic

<400> SEQUENCE: 101

Gly Tyr Thr Phe Thr Asn Tyr Tyr
1               5

<210> SEQ ID NO 102
<211> LENGTH: 8
<212> TYPE: PRT
<213> ORGANISM: Artificial Sequence
<220> FEATURE:
<223> OTHER INFORMATION: Synthetic

<400> SEQUENCE: 102

Gly Tyr Thr Phe Thr Ser Tyr Tyr
1               5

<210> SEQ ID NO 103
<211> LENGTH: 8
<212> TYPE: PRT
<213> ORGANISM: Artificial Sequence
<220> FEATURE:
<223> OTHER INFORMATION: Synthetic

<400> SEQUENCE: 103

Gly Tyr Thr Phe Thr Ser Tyr Tyr
1               5

<210> SEQ ID NO 104
<211> LENGTH: 8
<212> TYPE: PRT
<213> ORGANISM: Artificial Sequence
<220> FEATURE:
<223> OTHER INFORMATION: Synthetic

<400> SEQUENCE: 104

Gly Tyr Thr Phe Thr Ser Tyr Gly
1               5

<210> SEQ ID NO 105
<211> LENGTH: 8
<212> TYPE: PRT
<213> ORGANISM: Artificial Sequence
<220> FEATURE:
<223> OTHER INFORMATION: Synthetic

<400> SEQUENCE: 105

Gly Asn Thr Phe Thr Ser Tyr Tyr
1               5

<210> SEQ ID NO 106
<211> LENGTH: 8
<212> TYPE: PRT
<213> ORGANISM: Artificial Sequence
<220> FEATURE:
<223> OTHER INFORMATION: Synthetic

<400> SEQUENCE: 106

Gly Phe Tyr Phe Ser Gly Phe Ala
1               5
```

```
<210> SEQ ID NO 107
<211> LENGTH: 8
<212> TYPE: PRT
<213> ORGANISM: Artificial Sequence
<220> FEATURE:
<223> OTHER INFORMATION: Synthetic

<400> SEQUENCE: 107

Gly Tyr Thr Phe Thr Ser Tyr Tyr
1               5

<210> SEQ ID NO 108
<211> LENGTH: 8
<212> TYPE: PRT
<213> ORGANISM: Artificial Sequence
<220> FEATURE:
<223> OTHER INFORMATION: Synthetic

<400> SEQUENCE: 108

Gly Tyr Thr Phe Thr Ser Tyr Tyr
1               5

<210> SEQ ID NO 109
<211> LENGTH: 8
<212> TYPE: PRT
<213> ORGANISM: Artificial Sequence
<220> FEATURE:
<223> OTHER INFORMATION: Synthetic

<400> SEQUENCE: 109

Gly Gly Thr Phe Asn Asp Tyr Ser
1               5

<210> SEQ ID NO 110
<211> LENGTH: 8
<212> TYPE: PRT
<213> ORGANISM: Artificial Sequence
<220> FEATURE:
<223> OTHER INFORMATION: Synthetic

<400> SEQUENCE: 110

Gly Phe Thr Phe Ser Ser Tyr Ser
1               5

<210> SEQ ID NO 111
<211> LENGTH: 8
<212> TYPE: PRT
<213> ORGANISM: Artificial Sequence
<220> FEATURE:
<223> OTHER INFORMATION: Synthetic

<400> SEQUENCE: 111

Gly Asn Ser Phe Ser Thr Tyr Tyr
1               5

<210> SEQ ID NO 112
<211> LENGTH: 8
<212> TYPE: PRT
<213> ORGANISM: Artificial Sequence
<220> FEATURE:
<223> OTHER INFORMATION: Synthetic

<400> SEQUENCE: 112

Gly Tyr Thr Phe Thr Ser Tyr Tyr
1               5

<210> SEQ ID NO 113
```

```
<211> LENGTH: 8
<212> TYPE: PRT
<213> ORGANISM: Artificial Sequence
<220> FEATURE:
<223> OTHER INFORMATION: Synthetic

<400> SEQUENCE: 113

Gly Gly Thr Phe Ser Ser Tyr Ala
1               5

<210> SEQ ID NO 114
<211> LENGTH: 8
<212> TYPE: PRT
<213> ORGANISM: Artificial Sequence
<220> FEATURE:
<223> OTHER INFORMATION: Synthetic

<400> SEQUENCE: 114

Gly Tyr Thr Phe Thr Ser Tyr Tyr
1               5

<210> SEQ ID NO 115
<211> LENGTH: 8
<212> TYPE: PRT
<213> ORGANISM: Artificial Sequence
<220> FEATURE:
<223> OTHER INFORMATION: Synthetic

<400> SEQUENCE: 115

Gly Gly Thr Phe Ser Ser Tyr Ala
1               5

<210> SEQ ID NO 116
<211> LENGTH: 8
<212> TYPE: PRT
<213> ORGANISM: Artificial Sequence
<220> FEATURE:
<223> OTHER INFORMATION: Synthetic

<400> SEQUENCE: 116

Gly Gly Thr Phe Asn Asp Tyr Ser
1               5

<210> SEQ ID NO 117
<211> LENGTH: 8
<212> TYPE: PRT
<213> ORGANISM: Artificial Sequence
<220> FEATURE:
<223> OTHER INFORMATION: Synthetic

<400> SEQUENCE: 117

Ile Ile Pro Met Val Gly Ile Ala
1               5

<210> SEQ ID NO 118
<211> LENGTH: 8
<212> TYPE: PRT
<213> ORGANISM: Artificial Sequence
<220> FEATURE:
<223> OTHER INFORMATION: Synthetic

<400> SEQUENCE: 118

Ile Ser Val Tyr Asn Gly Asn Thr
1               5

<210> SEQ ID NO 119
<211> LENGTH: 8
```

```
<212> TYPE: PRT
<213> ORGANISM: Artificial Sequence
<220> FEATURE:
<223> OTHER INFORMATION: Synthetic

<400> SEQUENCE: 119

Ile Asn Pro Ser Gly Gly Ser Thr
1               5

<210> SEQ ID NO 120
<211> LENGTH: 8
<212> TYPE: PRT
<213> ORGANISM: Artificial Sequence
<220> FEATURE:
<223> OTHER INFORMATION: Synthetic

<400> SEQUENCE: 120

Ile Ile Pro Ile Phe Gly Ile Thr
1               5

<210> SEQ ID NO 121
<211> LENGTH: 8
<212> TYPE: PRT
<213> ORGANISM: Artificial Sequence
<220> FEATURE:
<223> OTHER INFORMATION: Synthetic

<400> SEQUENCE: 121

Ile Ile Pro Ile Leu Gly Ile Ala
1               5

<210> SEQ ID NO 122
<211> LENGTH: 8
<212> TYPE: PRT
<213> ORGANISM: Artificial Sequence
<220> FEATURE:
<223> OTHER INFORMATION: Synthetic

<400> SEQUENCE: 122

Ile Asn Pro Ser Val Gly Ser Thr
1               5

<210> SEQ ID NO 123
<211> LENGTH: 8
<212> TYPE: PRT
<213> ORGANISM: Artificial Sequence
<220> FEATURE:
<223> OTHER INFORMATION: Synthetic

<400> SEQUENCE: 123

Ile Asn Pro Ser Gly Gly Ser Thr
1               5

<210> SEQ ID NO 124
<211> LENGTH: 8
<212> TYPE: PRT
<213> ORGANISM: Artificial Sequence
<220> FEATURE:
<223> OTHER INFORMATION: Synthetic

<400> SEQUENCE: 124

Ile Asn Pro Ser Gly Gly Ser Thr
1               5

<210> SEQ ID NO 125
<211> LENGTH: 8
<212> TYPE: PRT
```

```
<213> ORGANISM: Artificial Sequence
<220> FEATURE:
<223> OTHER INFORMATION: Synthetic

<400> SEQUENCE: 125

Ile Ser Ala Tyr Asn Gly Asn Thr
1               5

<210> SEQ ID NO 126
<211> LENGTH: 8
<212> TYPE: PRT
<213> ORGANISM: Artificial Sequence
<220> FEATURE:
<223> OTHER INFORMATION: Synthetic

<400> SEQUENCE: 126

Ile Asn Pro Ser Gly Gly Ser Thr
1               5

<210> SEQ ID NO 127
<211> LENGTH: 8
<212> TYPE: PRT
<213> ORGANISM: Artificial Sequence
<220> FEATURE:
<223> OTHER INFORMATION: Synthetic

<400> SEQUENCE: 127

Val Phe Asn Asp Gly Ser Thr Thr
1               5

<210> SEQ ID NO 128
<211> LENGTH: 8
<212> TYPE: PRT
<213> ORGANISM: Artificial Sequence
<220> FEATURE:
<223> OTHER INFORMATION: Synthetic

<400> SEQUENCE: 128

Ile Asn Pro Ser Gly Gly Ser Thr
1               5

<210> SEQ ID NO 129
<211> LENGTH: 8
<212> TYPE: PRT
<213> ORGANISM: Artificial Sequence
<220> FEATURE:
<223> OTHER INFORMATION: Synthetic

<400> SEQUENCE: 129

Ile Asn Pro Ser Gly Gly Ser Thr
1               5

<210> SEQ ID NO 130
<211> LENGTH: 8
<212> TYPE: PRT
<213> ORGANISM: Artificial Sequence
<220> FEATURE:
<223> OTHER INFORMATION: Synthetic

<400> SEQUENCE: 130

Ile Ile Pro Val Leu Asp Met Thr
1               5

<210> SEQ ID NO 131
<211> LENGTH: 7
<212> TYPE: PRT
<213> ORGANISM: Artificial Sequence
```

```
<220> FEATURE:
<223> OTHER INFORMATION: Synthetic

<400> SEQUENCE: 131

Ile Ser Ser Gly Gly Asn Thr
1               5

<210> SEQ ID NO 132
<211> LENGTH: 8
<212> TYPE: PRT
<213> ORGANISM: Artificial Sequence
<220> FEATURE:
<223> OTHER INFORMATION: Synthetic

<400> SEQUENCE: 132

Ile Asn Pro Thr Ile Gly Ser Arg
1               5

<210> SEQ ID NO 133
<211> LENGTH: 8
<212> TYPE: PRT
<213> ORGANISM: Artificial Sequence
<220> FEATURE:
<223> OTHER INFORMATION: Synthetic

<400> SEQUENCE: 133

Ile Asn Pro Ser Gly Gly Ser Thr
1               5

<210> SEQ ID NO 134
<211> LENGTH: 8
<212> TYPE: PRT
<213> ORGANISM: Artificial Sequence
<220> FEATURE:
<223> OTHER INFORMATION: Synthetic

<400> SEQUENCE: 134

Ile Ile Pro Ile Phe Gly Thr Ala
1               5

<210> SEQ ID NO 135
<211> LENGTH: 8
<212> TYPE: PRT
<213> ORGANISM: Artificial Sequence
<220> FEATURE:
<223> OTHER INFORMATION: Synthetic

<400> SEQUENCE: 135

Ile Asn Pro Thr Gly Gly Ser Thr
1               5

<210> SEQ ID NO 136
<211> LENGTH: 8
<212> TYPE: PRT
<213> ORGANISM: Artificial Sequence
<220> FEATURE:
<223> OTHER INFORMATION: Synthetic

<400> SEQUENCE: 136

Ile Ile Pro Ile Phe Gly Thr Ala
1               5

<210> SEQ ID NO 137
<211> LENGTH: 8
<212> TYPE: PRT
<213> ORGANISM: Artificial Sequence
<220> FEATURE:
```

<223> OTHER INFORMATION: Synthetic

<400> SEQUENCE: 137

Ile Ile Pro Val Leu Asp Met Thr
1               5

<210> SEQ ID NO 138
<211> LENGTH: 9
<212> TYPE: PRT
<213> ORGANISM: Artificial Sequence
<220> FEATURE:
<223> OTHER INFORMATION: Synthetic

<400> SEQUENCE: 138

Ala Arg Gly Phe Tyr Ser Ser Asp Ser
1               5

<210> SEQ ID NO 139
<211> LENGTH: 11
<212> TYPE: PRT
<213> ORGANISM: Artificial Sequence
<220> FEATURE:
<223> OTHER INFORMATION: Synthetic

<400> SEQUENCE: 139

Thr Arg Asp Pro Leu Leu Gly Ala Phe Asp Ile
1               5                   10

<210> SEQ ID NO 140
<211> LENGTH: 9
<212> TYPE: PRT
<213> ORGANISM: Artificial Sequence
<220> FEATURE:
<223> OTHER INFORMATION: Synthetic

<400> SEQUENCE: 140

Ala Arg Gly Tyr Ser Tyr Ser Asp Tyr
1               5

<210> SEQ ID NO 141
<211> LENGTH: 9
<212> TYPE: PRT
<213> ORGANISM: Artificial Sequence
<220> FEATURE:
<223> OTHER INFORMATION: Synthetic

<400> SEQUENCE: 141

Ala Arg Gly Tyr Tyr Tyr Ala Asp Asp
1               5

<210> SEQ ID NO 142
<211> LENGTH: 10
<212> TYPE: PRT
<213> ORGANISM: Artificial Sequence
<220> FEATURE:
<223> OTHER INFORMATION: Synthetic

<400> SEQUENCE: 142

Ala Arg Ser Met Gly Ala Trp Trp Asp Pro
1               5                   10

<210> SEQ ID NO 143
<211> LENGTH: 12
<212> TYPE: PRT
<213> ORGANISM: Artificial Sequence
<220> FEATURE:
<223> OTHER INFORMATION: Synthetic

<400> SEQUENCE: 143

Ala Arg Gly Gln Tyr Gly Ser Gln Gly Lys Asp Ser
1               5                   10

<210> SEQ ID NO 144
<211> LENGTH: 12
<212> TYPE: PRT
<213> ORGANISM: Artificial Sequence
<220> FEATURE:
<223> OTHER INFORMATION: Synthetic

<400> SEQUENCE: 144

Ala Arg Gly Met Ser Tyr Tyr Ser Ser Ile Asp Lys
1               5                   10

<210> SEQ ID NO 145
<211> LENGTH: 9
<212> TYPE: PRT
<213> ORGANISM: Artificial Sequence
<220> FEATURE:
<223> OTHER INFORMATION: Synthetic

<400> SEQUENCE: 145

Ala Arg Gly Tyr Tyr Asp Ser Asp Arg
1               5

<210> SEQ ID NO 146
<211> LENGTH: 9
<212> TYPE: PRT
<213> ORGANISM: Artificial Sequence
<220> FEATURE:
<223> OTHER INFORMATION: Synthetic

<400> SEQUENCE: 146

Ala Arg Gly Tyr Tyr Tyr Tyr Asp Ser
1               5

<210> SEQ ID NO 147
<211> LENGTH: 11
<212> TYPE: PRT
<213> ORGANISM: Artificial Sequence
<220> FEATURE:
<223> OTHER INFORMATION: Synthetic

<400> SEQUENCE: 147

Ala Arg Ser Gly Gly Tyr Trp Ser Phe Asp Ser
1               5                   10

<210> SEQ ID NO 148
<211> LENGTH: 14
<212> TYPE: PRT
<213> ORGANISM: Artificial Sequence
<220> FEATURE:
<223> OTHER INFORMATION: Synthetic

<400> SEQUENCE: 148

Ala Arg Gln Ser Pro Phe Tyr Phe Asp Gly Pro Tyr Asp Tyr
1               5                   10

<210> SEQ ID NO 149
<211> LENGTH: 12
<212> TYPE: PRT
<213> ORGANISM: Artificial Sequence
<220> FEATURE:
<223> OTHER INFORMATION: Synthetic

```
<400> SEQUENCE: 149

Ala Arg Gly Tyr Tyr Gly Asp Thr Thr Gly Asp Asn
1               5                   10

<210> SEQ ID NO 150
<211> LENGTH: 9
<212> TYPE: PRT
<213> ORGANISM: Artificial Sequence
<220> FEATURE:
<223> OTHER INFORMATION: Synthetic

<400> SEQUENCE: 150

Ala Arg Gly Tyr Gly Thr Ser Asp Ser
1               5

<210> SEQ ID NO 151
<211> LENGTH: 10
<212> TYPE: PRT
<213> ORGANISM: Artificial Sequence
<220> FEATURE:
<223> OTHER INFORMATION: Synthetic

<400> SEQUENCE: 151

Ala Arg Tyr Tyr Gly Asp Tyr Ser Asp Pro
1               5                   10

<210> SEQ ID NO 152
<211> LENGTH: 10
<212> TYPE: PRT
<213> ORGANISM: Artificial Sequence
<220> FEATURE:
<223> OTHER INFORMATION: Synthetic

<400> SEQUENCE: 152

Ala Arg Glu Gly Tyr Met Tyr Val Asp His
1               5                   10

<210> SEQ ID NO 153
<211> LENGTH: 11
<212> TYPE: PRT
<213> ORGANISM: Artificial Sequence
<220> FEATURE:
<223> OTHER INFORMATION: Synthetic

<400> SEQUENCE: 153

Ala Arg Ser Val Thr Trp Val Leu Lys Asp Gly
1               5                   10

<210> SEQ ID NO 154
<211> LENGTH: 13
<212> TYPE: PRT
<213> ORGANISM: Artificial Sequence
<220> FEATURE:
<223> OTHER INFORMATION: Synthetic

<400> SEQUENCE: 154

Ala Arg Ser Ser Ile Gly Trp Leu Ser Tyr Leu Asp Ala
1               5                   10

<210> SEQ ID NO 155
<211> LENGTH: 14
<212> TYPE: PRT
<213> ORGANISM: Artificial Sequence
<220> FEATURE:
<223> OTHER INFORMATION: Synthetic

<400> SEQUENCE: 155
```

Ala Arg Ser Ser Tyr Gly Ser Tyr Tyr Gly Thr Tyr Asp Tyr
1               5                   10

<210> SEQ ID NO 156
<211> LENGTH: 9
<212> TYPE: PRT
<213> ORGANISM: Artificial Sequence
<220> FEATURE:
<223> OTHER INFORMATION: Synthetic

<400> SEQUENCE: 156

Ala Arg Gly Tyr Ser Glu Gly Asp Val
1               5

<210> SEQ ID NO 157
<211> LENGTH: 10
<212> TYPE: PRT
<213> ORGANISM: Artificial Sequence
<220> FEATURE:
<223> OTHER INFORMATION: Synthetic

<400> SEQUENCE: 157

Ala Arg Tyr Phe Gly Arg Tyr Val Asp Tyr
1               5                   10

<210> SEQ ID NO 158
<211> LENGTH: 10
<212> TYPE: PRT
<213> ORGANISM: Artificial Sequence
<220> FEATURE:
<223> OTHER INFORMATION: Synthetic

<400> SEQUENCE: 158

Ala Arg Gln Tyr Gly Ser Phe Trp Asp Arg
1               5                   10

<210> SEQ ID NO 159
<211> LENGTH: 9
<212> TYPE: PRT
<213> ORGANISM: Artificial Sequence
<220> FEATURE:
<223> OTHER INFORMATION: Synthetic

<400> SEQUENCE: 159

Ser Ser Asn Phe Gly Ala Gly Phe Asp
1               5

<210> SEQ ID NO 160
<211> LENGTH: 9
<212> TYPE: PRT
<213> ORGANISM: Artificial Sequence
<220> FEATURE:
<223> OTHER INFORMATION: Synthetic

<400> SEQUENCE: 160

Ser Ser Asn Ile Gly Ala Gly Phe Asp
1               5

<210> SEQ ID NO 161
<211> LENGTH: 8
<212> TYPE: PRT
<213> ORGANISM: Artificial Sequence
<220> FEATURE:
<223> OTHER INFORMATION: Synthetic

<400> SEQUENCE: 161

```
Ser Ser Asn Ile Gly Asn Asp Tyr
1               5

<210> SEQ ID NO 162
<211> LENGTH: 9
<212> TYPE: PRT
<213> ORGANISM: Artificial Sequence
<220> FEATURE:
<223> OTHER INFORMATION: Synthetic

<400> SEQUENCE: 162

Ser Ser Asn Phe Gly Ala Gly Phe Asp
1               5

<210> SEQ ID NO 163
<211> LENGTH: 8
<212> TYPE: PRT
<213> ORGANISM: Artificial Sequence
<220> FEATURE:
<223> OTHER INFORMATION: Synthetic

<400> SEQUENCE: 163

Ser Ser Asn Ile Gly Ser Asn Thr
1               5

<210> SEQ ID NO 164
<211> LENGTH: 8
<212> TYPE: PRT
<213> ORGANISM: Artificial Sequence
<220> FEATURE:
<223> OTHER INFORMATION: Synthetic

<400> SEQUENCE: 164

Asn Ser Asn Ile Gly Asn Asn Tyr
1               5

<210> SEQ ID NO 165
<211> LENGTH: 8
<212> TYPE: PRT
<213> ORGANISM: Artificial Sequence
<220> FEATURE:
<223> OTHER INFORMATION: Synthetic

<400> SEQUENCE: 165

Ser Ser Asn Ile Gly Asn Asp Tyr
1               5

<210> SEQ ID NO 166
<211> LENGTH: 8
<212> TYPE: PRT
<213> ORGANISM: Artificial Sequence
<220> FEATURE:
<223> OTHER INFORMATION: Synthetic

<400> SEQUENCE: 166

Ser Ser Asn Ile Gly Asn Asn Tyr
1               5

<210> SEQ ID NO 167
<211> LENGTH: 9
<212> TYPE: PRT
<213> ORGANISM: Artificial Sequence
<220> FEATURE:
<223> OTHER INFORMATION: Synthetic

<400> SEQUENCE: 167

Ser Ser Asn Leu Gly Ala Gly Phe Asp
```

```
1               5

<210> SEQ ID NO 168
<211> LENGTH: 6
<212> TYPE: PRT
<213> ORGANISM: Artificial Sequence
<220> FEATURE:
<223> OTHER INFORMATION: Synthetic

<400> SEQUENCE: 168

Gln His Ile Thr Lys Tyr
1               5

<210> SEQ ID NO 169
<211> LENGTH: 8
<212> TYPE: PRT
<213> ORGANISM: Artificial Sequence
<220> FEATURE:
<223> OTHER INFORMATION: Synthetic

<400> SEQUENCE: 169

Thr Ser Asn Ile Gly Asn Asn Tyr
1               5

<210> SEQ ID NO 170
<211> LENGTH: 8
<212> TYPE: PRT
<213> ORGANISM: Artificial Sequence
<220> FEATURE:
<223> OTHER INFORMATION: Synthetic

<400> SEQUENCE: 170

Ser Ser Asn Ile Gly Asn Ser Tyr
1               5

<210> SEQ ID NO 171
<211> LENGTH: 8
<212> TYPE: PRT
<213> ORGANISM: Artificial Sequence
<220> FEATURE:
<223> OTHER INFORMATION: Synthetic

<400> SEQUENCE: 171

Ser Ser Asn Ile Gly Asn Asp Tyr
1               5

<210> SEQ ID NO 172
<211> LENGTH: 8
<212> TYPE: PRT
<213> ORGANISM: Artificial Sequence
<220> FEATURE:
<223> OTHER INFORMATION: Synthetic

<400> SEQUENCE: 172

Ser Ser Asn Ile Gly Ser Arg Thr
1               5

<210> SEQ ID NO 173
<211> LENGTH: 8
<212> TYPE: PRT
<213> ORGANISM: Artificial Sequence
<220> FEATURE:
<223> OTHER INFORMATION: Synthetic

<400> SEQUENCE: 173

Asn Ser Asn Ile Glu His Asn Tyr
1               5
```

```
<210> SEQ ID NO 174
<211> LENGTH: 6
<212> TYPE: PRT
<213> ORGANISM: Artificial Sequence
<220> FEATURE:
<223> OTHER INFORMATION: Synthetic

<400> SEQUENCE: 174

Gln Ser Ile Ser Ser Tyr
1               5

<210> SEQ ID NO 175
<211> LENGTH: 6
<212> TYPE: PRT
<213> ORGANISM: Artificial Sequence
<220> FEATURE:
<223> OTHER INFORMATION: Synthetic

<400> SEQUENCE: 175

Gln Asp Ile Gly Asn Tyr
1               5

<210> SEQ ID NO 176
<211> LENGTH: 9
<212> TYPE: PRT
<213> ORGANISM: Artificial Sequence
<220> FEATURE:
<223> OTHER INFORMATION: Synthetic

<400> SEQUENCE: 176

Ser Ser Asn Ile Gly Ala Gly Tyr Asp
1               5

<210> SEQ ID NO 177
<211> LENGTH: 8
<212> TYPE: PRT
<213> ORGANISM: Artificial Sequence
<220> FEATURE:
<223> OTHER INFORMATION: Synthetic

<400> SEQUENCE: 177

Ser Ser Asn Ile Gly Asn Asn Tyr
1               5

<210> SEQ ID NO 178
<211> LENGTH: 8
<212> TYPE: PRT
<213> ORGANISM: Artificial Sequence
<220> FEATURE:
<223> OTHER INFORMATION: Synthetic

<400> SEQUENCE: 178

Ser Ser Asn Ile Gly Ser Asn Thr
1               5

<210> SEQ ID NO 179
<211> LENGTH: 8
<212> TYPE: PRT
<213> ORGANISM: Artificial Sequence
<220> FEATURE:
<223> OTHER INFORMATION: Synthetic

<400> SEQUENCE: 179

Ser Ser Asn Ile Gly Ser Asn Thr
1               5
```

<210> SEQ ID NO 180
<211> LENGTH: 3
<212> TYPE: PRT
<213> ORGANISM: Artificial Sequence
<220> FEATURE:
<223> OTHER INFORMATION: Synthetic

<400> SEQUENCE: 180

Asn Asn Asn
1

<210> SEQ ID NO 181
<211> LENGTH: 3
<212> TYPE: PRT
<213> ORGANISM: Artificial Sequence
<220> FEATURE:
<223> OTHER INFORMATION: Synthetic

<400> SEQUENCE: 181

Gly Asn Asn
1

<210> SEQ ID NO 182
<211> LENGTH: 3
<212> TYPE: PRT
<213> ORGANISM: Artificial Sequence
<220> FEATURE:
<223> OTHER INFORMATION: Synthetic

<400> SEQUENCE: 182

Asp Asn Asn
1

<210> SEQ ID NO 183
<211> LENGTH: 3
<212> TYPE: PRT
<213> ORGANISM: Artificial Sequence
<220> FEATURE:
<223> OTHER INFORMATION: Synthetic

<400> SEQUENCE: 183

Ser Asn Asn
1

<210> SEQ ID NO 184
<211> LENGTH: 3
<212> TYPE: PRT
<213> ORGANISM: Artificial Sequence
<220> FEATURE:
<223> OTHER INFORMATION: Synthetic

<400> SEQUENCE: 184

Glu Asn Asp
1

<210> SEQ ID NO 185
<211> LENGTH: 3
<212> TYPE: PRT
<213> ORGANISM: Artificial Sequence
<220> FEATURE:
<223> OTHER INFORMATION: Synthetic

<400> SEQUENCE: 185

Ser Asp Asn
1

```
<210> SEQ ID NO 186
<211> LENGTH: 3
<212> TYPE: PRT
<213> ORGANISM: Artificial Sequence
<220> FEATURE:
<223> OTHER INFORMATION: Synthetic

<400> SEQUENCE: 186

Asp Ala Ser
1

<210> SEQ ID NO 187
<211> LENGTH: 3
<212> TYPE: PRT
<213> ORGANISM: Artificial Sequence
<220> FEATURE:
<223> OTHER INFORMATION: Synthetic

<400> SEQUENCE: 187

Asp Asn Asp
1

<210> SEQ ID NO 188
<211> LENGTH: 3
<212> TYPE: PRT
<213> ORGANISM: Artificial Sequence
<220> FEATURE:
<223> OTHER INFORMATION: Synthetic

<400> SEQUENCE: 188

Ser Asn Thr
1

<210> SEQ ID NO 189
<211> LENGTH: 3
<212> TYPE: PRT
<213> ORGANISM: Artificial Sequence
<220> FEATURE:
<223> OTHER INFORMATION: Synthetic

<400> SEQUENCE: 189

Ala Ala Ser
1

<210> SEQ ID NO 190
<211> LENGTH: 3
<212> TYPE: PRT
<213> ORGANISM: Artificial Sequence
<220> FEATURE:
<223> OTHER INFORMATION: Synthetic

<400> SEQUENCE: 190

Gly Asn Ser
1

<210> SEQ ID NO 191
<211> LENGTH: 11
<212> TYPE: PRT
<213> ORGANISM: Artificial Sequence
<220> FEATURE:
<223> OTHER INFORMATION: Synthetic

<400> SEQUENCE: 191

Gln Ser Tyr Asp Val Ser Leu Asn Gly Trp Val
1               5                   10

<210> SEQ ID NO 192
```

```
<211> LENGTH: 11
<212> TYPE: PRT
<213> ORGANISM: Artificial Sequence
<220> FEATURE:
<223> OTHER INFORMATION: Synthetic

<400> SEQUENCE: 192

Gln Ser Tyr Asp Ser Ser Leu Ser Gly Trp Val
1               5                   10

<210> SEQ ID NO 193
<211> LENGTH: 11
<212> TYPE: PRT
<213> ORGANISM: Artificial Sequence
<220> FEATURE:
<223> OTHER INFORMATION: Synthetic

<400> SEQUENCE: 193

Gly Thr Trp Asp Tyr Ser Leu Thr Ala Tyr Val
1               5                   10

<210> SEQ ID NO 194
<211> LENGTH: 11
<212> TYPE: PRT
<213> ORGANISM: Artificial Sequence
<220> FEATURE:
<223> OTHER INFORMATION: Synthetic

<400> SEQUENCE: 194

Gln Ser Tyr Asp Val Ser Leu Asn Gly Trp Val
1               5                   10

<210> SEQ ID NO 195
<211> LENGTH: 12
<212> TYPE: PRT
<213> ORGANISM: Artificial Sequence
<220> FEATURE:
<223> OTHER INFORMATION: Synthetic

<400> SEQUENCE: 195

Ala Ala Trp Asp Asp Ser Leu Asn Gly Phe Tyr Val
1               5                   10

<210> SEQ ID NO 196
<211> LENGTH: 11
<212> TYPE: PRT
<213> ORGANISM: Artificial Sequence
<220> FEATURE:
<223> OTHER INFORMATION: Synthetic

<400> SEQUENCE: 196

Glu Thr Trp Asp Ile Ser Leu Asn Val Gly Val
1               5                   10

<210> SEQ ID NO 197
<211> LENGTH: 11
<212> TYPE: PRT
<213> ORGANISM: Artificial Sequence
<220> FEATURE:
<223> OTHER INFORMATION: Synthetic

<400> SEQUENCE: 197

Gly Thr Trp Asp Ser Ser Leu Asn Gly Gly Val
1               5                   10

<210> SEQ ID NO 198
<211> LENGTH: 11
```

```
<212> TYPE: PRT
<213> ORGANISM: Artificial Sequence
<220> FEATURE:
<223> OTHER INFORMATION: Synthetic

<400> SEQUENCE: 198

Gly Thr Trp Asp Asn Ser Leu Asn Gly Gly Val
1               5                   10

<210> SEQ ID NO 199
<211> LENGTH: 11
<212> TYPE: PRT
<213> ORGANISM: Artificial Sequence
<220> FEATURE:
<223> OTHER INFORMATION: Synthetic

<400> SEQUENCE: 199

Gln Ser Tyr Asp Ser Gly Leu Ser Gly Ser Val
1               5                   10

<210> SEQ ID NO 200
<211> LENGTH: 9
<212> TYPE: PRT
<213> ORGANISM: Artificial Sequence
<220> FEATURE:
<223> OTHER INFORMATION: Synthetic

<400> SEQUENCE: 200

Gln Gln Tyr Glu Asn Leu Pro Leu Thr
1               5

<210> SEQ ID NO 201
<211> LENGTH: 11
<212> TYPE: PRT
<213> ORGANISM: Artificial Sequence
<220> FEATURE:
<223> OTHER INFORMATION: Synthetic

<400> SEQUENCE: 201

Gly Thr Trp Asp Ser Ser Leu Ser Ala Gly Val
1               5                   10

<210> SEQ ID NO 202
<211> LENGTH: 12
<212> TYPE: PRT
<213> ORGANISM: Artificial Sequence
<220> FEATURE:
<223> OTHER INFORMATION: Synthetic

<400> SEQUENCE: 202

Gly Thr Trp Asp Thr Ser Leu Ser Ser Val Trp Met
1               5                   10

<210> SEQ ID NO 203
<211> LENGTH: 11
<212> TYPE: PRT
<213> ORGANISM: Artificial Sequence
<220> FEATURE:
<223> OTHER INFORMATION: Synthetic

<400> SEQUENCE: 203

Gly Thr Trp Asp Ser Ser Leu Asn Gly Gly Val
1               5                   10

<210> SEQ ID NO 204
<211> LENGTH: 11
<212> TYPE: PRT
```

```
<213> ORGANISM: Artificial Sequence
<220> FEATURE:
<223> OTHER INFORMATION: Synthetic

<400> SEQUENCE: 204

Ala Ala Trp Asp Asp Ser Leu Asn Gly Gln Val
1               5                   10

<210> SEQ ID NO 205
<211> LENGTH: 11
<212> TYPE: PRT
<213> ORGANISM: Artificial Sequence
<220> FEATURE:
<223> OTHER INFORMATION: Synthetic

<400> SEQUENCE: 205

Gly Thr Trp Asp Asn Thr Leu Ser Ser Phe Val
1               5                   10

<210> SEQ ID NO 206
<211> LENGTH: 9
<212> TYPE: PRT
<213> ORGANISM: Artificial Sequence
<220> FEATURE:
<223> OTHER INFORMATION: Synthetic

<400> SEQUENCE: 206

Gln Gln Ser Tyr Ser Leu Pro Leu Thr
1               5

<210> SEQ ID NO 207
<211> LENGTH: 8
<212> TYPE: PRT
<213> ORGANISM: Artificial Sequence
<220> FEATURE:
<223> OTHER INFORMATION: Synthetic

<400> SEQUENCE: 207

Gln Lys Tyr Asn Thr Ala Pro Gly
1               5

<210> SEQ ID NO 208
<211> LENGTH: 10
<212> TYPE: PRT
<213> ORGANISM: Artificial Sequence
<220> FEATURE:
<223> OTHER INFORMATION: Synthetic

<400> SEQUENCE: 208

Gln Ser Tyr Asp Ser Ser Leu Ser Val Val
1               5                   10

<210> SEQ ID NO 209
<211> LENGTH: 12
<212> TYPE: PRT
<213> ORGANISM: Artificial Sequence
<220> FEATURE:
<223> OTHER INFORMATION: Synthetic

<400> SEQUENCE: 209

Ala Thr Trp His Ser Ser Leu Ser Pro Ser Tyr Val
1               5                   10

<210> SEQ ID NO 210
<211> LENGTH: 13
<212> TYPE: PRT
<213> ORGANISM: Artificial Sequence
```

<220> FEATURE:
<223> OTHER INFORMATION: Synthetic

<400> SEQUENCE: 210

Ala Ala Trp Asp Asp Ser Leu Asn Gly His Asn Tyr Val
1               5                   10

<210> SEQ ID NO 211
<211> LENGTH: 11
<212> TYPE: PRT
<213> ORGANISM: Artificial Sequence
<220> FEATURE:
<223> OTHER INFORMATION: Synthetic

<400> SEQUENCE: 211

Ala Ala Trp Asp Asp Ser Leu Asn Gly Tyr Val
1               5                   10

<210> SEQ ID NO 212
<211> LENGTH: 747
<212> TYPE: DNA
<213> ORGANISM: Artificial Sequence
<220> FEATURE:
<223> OTHER INFORMATION: Synthetic

<400> SEQUENCE: 212

```
cagtctgtcg tgacgcagcc gccctcagtg tctggggccc cagggcagag ggtcaccatc      60
tcctgtactg ggagcagctc caacttcggg gcaggttttg atgtacactg gtaccagcag     120
cttccaggaa cagccccaa actcctcatc aataataaca caatcggcc ccaggggtc        180
cctgagcgat tctctggctc caagtctggc acctcagcct ccctggccat cactgggctc     240
caggctgagg atgaggctca atattactgc cagtcctatg acgtcagcct gaatggttgg     300
gtgttcggcg gagggaccaa ggtcaccgtc ctaggttcta gaggtggtgg tggtagcggc     360
ggcggcggct ctggtggtgg tggatccctc gagatggccc aggtgcagct ggtgcagtcc     420
ggggctgagg tgaagaagcc tgggtcctcg gtgaaggtct cctgcaaggc ttctggaggc     480
accttcagga cctatggtat caactgggtg cgacaggccc ctggacaagg gcttgagtgg     540
atgggaagga taatccctat ggttggtata gccaactacg cacagaagtt ccagggcaga     600
gtcacgatta ccgcggacaa atccacgagc acagcctaca tggagctgaa cagcctgaga     660
tctgaggaca cggccgtgta ttactgtgcg cgcggtttct actcttctga ttcttggggt     720
caaggtactc tggtgaccgt ctcctca                                         747
```

<210> SEQ ID NO 213
<211> LENGTH: 249
<212> TYPE: PRT
<213> ORGANISM: Artificial Sequence
<220> FEATURE:
<223> OTHER INFORMATION: Synthetic

<400> SEQUENCE: 213

Gln Ser Val Val Thr Gln Pro Pro Ser Val Ser Gly Ala Pro Gly Gln
1               5                   10                  15

Arg Val Thr Ile Ser Cys Thr Gly Ser Ser Ser Asn Phe Gly Ala Gly
            20                  25                  30

Phe Asp Val His Trp Tyr Gln Gln Leu Pro Gly Thr Ala Pro Lys Leu
        35                  40                  45

Leu Ile Asn Asn Asn Asn Arg Pro Pro Gly Val Pro Glu Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Gln Tyr Tyr Cys Gln Ser Tyr Asp Val Ser
                85                  90                  95

Leu Asn Gly Trp Val Phe Gly Gly Gly Thr Lys Val Thr Val Leu Gly
            100                 105                 110

Ser Arg Gly Gly Gly Gly Ser Gly Gly Gly Ser Gly Gly Gly Gly
        115                 120                 125

Ser Leu Glu Met Ala Gln Val Gln Leu Val Gln Ser Gly Ala Glu Val
    130                 135                 140

Lys Lys Pro Gly Ser Ser Val Lys Val Ser Cys Lys Ala Ser Gly Gly
145                 150                 155                 160

Thr Phe Arg Thr Tyr Gly Ile Asn Trp Val Arg Gln Ala Pro Gly Gln
            165                 170                 175

Gly Leu Glu Trp Met Gly Arg Ile Ile Pro Met Val Gly Ile Ala Asn
            180                 185                 190

Tyr Ala Gln Lys Phe Gln Gly Arg Val Thr Ile Thr Ala Asp Lys Ser
            195                 200                 205

Thr Ser Thr Ala Tyr Met Glu Leu Asn Ser Leu Arg Ser Glu Asp Thr
    210                 215                 220

Ala Val Tyr Tyr Cys Ala Arg Gly Phe Tyr Ser Ser Asp Ser Trp Gly
225                 230                 235                 240

Gln Gly Thr Leu Val Thr Val Ser Ser
                245

<210> SEQ ID NO 214
<211> LENGTH: 336
<212> TYPE: DNA
<213> ORGANISM: Artificial Sequence
<220> FEATURE:
<223> OTHER INFORMATION: Synthetic

<400> SEQUENCE: 214
cagtctgtcg tgacgcagcc gccctcagtg tctggggccc cagggcagag ggtcaccatc    60
tcctgtactg ggagcagctc caacttcggg gcaggttttg atgtacactg gtaccagcag   120
cttccaggaa cagcccccaa actcctcatc aataataaca caatcggcc cccaggggtc    180 cctgagcgat tctctggctc caagtctggc acctcagcct ccctggccat cactgggctc   240
caggctgagg atgaggctca atattactgc cagtcctatg acgtcagcct gaatggttgg   300
gtgttcggcg agggaccaa ggtcaccgtc ctaggt                              336

<210> SEQ ID NO 215
<211> LENGTH: 112
<212> TYPE: PRT
<213> ORGANISM: Artificial Sequence
<220> FEATURE:
<223> OTHER INFORMATION: Synthetic

<400> SEQUENCE: 215

Gln Ser Val Val Thr Gln Pro Pro Ser Val Ser Gly Ala Pro Gly Gln
1                   5                   10                  15

Arg Val Thr Ile Ser Cys Thr Gly Ser Ser Ser Asn Phe Gly Ala Gly
            20                  25                  30

Phe Asp Val His Trp Tyr Gln Gln Leu Pro Gly Thr Ala Pro Lys Leu
        35                  40                  45

Leu Ile Asn Asn Asn Asn Asn Arg Pro Pro Gly Val Pro Glu Arg Phe
    50                  55                  60

```
Ser Gly Ser Lys Ser Gly Thr Ser Ala Ser Leu Ala Ile Thr Gly Leu
 65                  70                  75                  80

Gln Ala Glu Asp Glu Ala Gln Tyr Tyr Cys Gln Ser Tyr Asp Val Ser
                 85                  90                  95

Leu Asn Gly Trp Val Phe Gly Gly Gly Thr Lys Val Thr Val Leu Gly
            100                 105                 110

<210> SEQ ID NO 216
<211> LENGTH: 348
<212> TYPE: DNA
<213> ORGANISM: Artificial Sequence
<220> FEATURE:
<223> OTHER INFORMATION: Synthetic

<400> SEQUENCE: 216
caggtgcagc tggtgcagtc cggggctgag gtgaagaagc ctgggtcctc ggtgaaggtc      60
tcctgcaagg cttctggagg caccttcagg acctatggta tcaactgggt gcgacaggcc     120
cctggacaag ggcttgagtg gatgggaagg ataatcccta tggttggtat agccaactac     180
gcacagaagt tccagggcag agtcacgatt accgcggaca aatccacgag cacagcctac     240
atggagctga acagcctgag atctgaggac acggccgtgt attactgtgc gcgcggtttc     300
tactcttctg attcttgggg tcaaggtact ctggtgaccg tctcctca                  348

<210> SEQ ID NO 217
<211> LENGTH: 116
<212> TYPE: PRT
<213> ORGANISM: Artificial Sequence
<220> FEATURE:
<223> OTHER INFORMATION: Synthetic

<400> SEQUENCE: 217

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Arg Thr Tyr
            20                  25                  30

Gly Ile Asn Trp Val Arg Gln Ala Pro Gly Gln Gly Leu Glu Trp Met
        35                  40                  45

Gly Arg Ile Ile Pro Met Val Gly Ile Ala Asn Tyr Ala Gln Lys Phe
    50                  55                  60

Gln Gly Arg Val Thr Ile Thr Ala Asp Lys Ser Thr Ser Thr Ala Tyr
 65                  70                  75                  80

Met Glu Leu Asn Ser Leu Arg Ser Glu Asp Thr Ala Val Tyr Tyr Cys
                 85                  90                  95

Ala Arg Gly Phe Tyr Ser Ser Asp Ser Trp Gly Gln Gly Thr Leu Val
            100                 105                 110

Thr Val Ser Ser
        115

<210> SEQ ID NO 218
<211> LENGTH: 753
<212> TYPE: DNA
<213> ORGANISM: Artificial Sequence
<220> FEATURE:
<223> OTHER INFORMATION: Synthetic

<400> SEQUENCE: 218
cagtctgtgt tgacgcagcc gccctcagtg tctggggccc cagggcagag ggtcaccatc      60
tcctgcactg ggagcagctc caacatcggg gcaggttttg atgtacactg gtaccagcag     120
```

```
cttccaggaa cagcccccaa actcctcatc tatggtaaca acaatcgacc ctcagggtc      180 cctgaccgat tctctggctc caagtctggc acctcagcct ccctggccat cactgggctc     240
caggctgagg atgaggctga ttattactgc cagtcctatg acagcagcct gagtggttgg     300
gtgttcggcg agggaccaa gctgaccgtc ctaggttcta gaggtggtgg tggtagcggc      360
ggcggcggct ctggtggtgg tggatccctc gagatggccc aggtccagct ggtgcagtct     420
ggagctgagg tgaagaagcc tggggcctca gtgaaggtct cctgcaagac ttctggttac     480
acctttacca gctacggtat cagctgggtg cgccaggccc ctggacaagg gcttgagtgg     540
atgggatgga tcagcgttta caatggtaac acaaattatg cacagaaatt ccagggcaga     600
gtcaccatga ccacagacac atccacgagc acagcctaca tggagctgag gagcctgaga     660
tctgacgaca cggccgtgta ttattgtacg agagatcccc tcctgggggc ttttgatatc     720
tggggccaag ggacaatggt caccgtctct tca                                  753
```

<210> SEQ ID NO 219
<211> LENGTH: 251
<212> TYPE: PRT
<213> ORGANISM: Artificial Sequence
<220> FEATURE:
<223> OTHER INFORMATION: Synthetic

<400> SEQUENCE: 219

```
Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Phe Asp Val His Trp Tyr Gln Gln Leu Pro Gly Thr Ala Pro Lys Leu
        35                  40                  45

Leu Ile Tyr Gly Asn Asn Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Trp Val Phe Gly Gly Thr Lys Leu Thr Val Leu Gly
            100                 105                 110

Ser Arg Gly Gly Gly Ser Gly Gly Gly Ser Gly Gly Gly Gly
            115                 120                 125

Ser Leu Glu Met Ala Gln Val Gln Leu Val Gln Ser Gly Ala Glu Val
    130                 135                 140

Lys Lys Pro Gly Ala Ser Val Lys Val Ser Cys Lys Thr Ser Gly Tyr
145                 150                 155                 160

Thr Phe Thr Ser Tyr Gly Ile Ser Trp Val Arg Gln Ala Pro Gly Gln
                165                 170                 175

Gly Leu Glu Trp Met Gly Trp Ile Ser Val Tyr Asn Gly Asn Thr Asn
            180                 185                 190

Tyr Ala Gln Lys Phe Gln Gly Arg Val Thr Met Thr Thr Asp Thr Ser
        195                 200                 205

Thr Ser Thr Ala Tyr Met Glu Leu Arg Ser Leu Arg Ser Asp Asp Thr
    210                 215                 220

Ala Val Tyr Tyr Cys Thr Arg Asp Pro Leu Leu Gly Ala Phe Asp Ile
225                 230                 235                 240

Trp Gly Gln Gly Thr Met Val Thr Val Ser Ser
                245                 250
```

<210> SEQ ID NO 220
<211> LENGTH: 336
<212> TYPE: DNA
<213> ORGANISM: Artificial Sequence
<220> FEATURE:
<223> OTHER INFORMATION: Synthetic

<400> SEQUENCE: 220

```
cagtctgtgt tgacgcagcc gccctcagtg tctggggccc cagggcagag ggtcaccatc      60
tcctgcactg ggagcagctc caacatcggg gcaggttttg atgtacactg gtaccagcag     120
cttccaggaa cagcccccaa actcctcatc tatggtaaca acaatcgacc ctcagggggtc    180
cctgaccgat tctctggctc caagtctggc acctcagcct ccctggccat cactgggctc     240
caggctgagg atgaggctga ttattactgc cagtcctatg acagcagcct gagtggttgg     300
gtgttcggcg gagggaccaa gctgaccgtc ctaggt                                336
```

<210> SEQ ID NO 221
<211> LENGTH: 112
<212> TYPE: PRT
<213> ORGANISM: Artificial Sequence
<220> FEATURE:
<223> OTHER INFORMATION: Synthetic

<400> SEQUENCE: 221

```
Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Phe Asp Val His Trp Tyr Gln Gln Leu Pro Gly Thr Ala Pro Lys Leu
        35                  40                  45

Leu Ile Tyr Gly Asn Asn Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Trp Val Phe Gly Gly Gly Thr Lys Leu Thr Val Leu Gly
            100                 105                 110
```

<210> SEQ ID NO 222
<211> LENGTH: 354
<212> TYPE: DNA
<213> ORGANISM: Artificial Sequence
<220> FEATURE:
<223> OTHER INFORMATION: Synthetic

<400> SEQUENCE: 222

```
caggtccagc tggtgcagtc tggagctgag gtgaagaagc ctggggcctc agtgaaggtc      60
tcctgcaaga cttctggtta cacctttacc agctacggta tcagctgggt gcgccaggcc     120
cctggacaag gcttgagtg gatgggatgg atcagcgttt acaatggtaa cacaaattat     180
gcacagaaat tccagggcag agtcaccatg accacagaca catccacgag cacagcctac     240
atggagctga ggagcctgag atctgacgac acggccgtgt attattgtac gagagatccc     300
ctcctggggg cttttgatat ctggggccaa gggacaatgg tcaccgtctc ttca           354
```

<210> SEQ ID NO 223

<211> LENGTH: 118
<212> TYPE: PRT
<213> ORGANISM: Artificial Sequence
<220> FEATURE:
<223> OTHER INFORMATION: Synthetic

<400> SEQUENCE: 223

Gln Val Gln Leu Val Gln Ser Gly Ala Glu Val Lys Lys Pro Gly Ala
1               5                   10                  15

Ser Val Lys Val Ser Cys Lys Thr Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Val Tyr Asn Gly Asn Thr Asn Tyr Ala Gln Lys Phe
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Thr Arg Asp Pro Leu Leu Gly Ala Phe Asp Ile Trp Gly Gln Gly Thr
            100                 105                 110

Met Val Thr Val Ser Ser
        115

<210> SEQ ID NO 224
<211> LENGTH: 744
<212> TYPE: DNA
<213> ORGANISM: Artificial Sequence
<220> FEATURE:
<223> OTHER INFORMATION: Synthetic

<400> SEQUENCE: 224
cagtctgtgt tgacgcagcc gccctcagtg tctgcggccc ccgggcagag ggtcaccatc      60
tcctgctctg gaagcagctc caacattgga aatgattatg tatcctgta  ccagcaagtc     120
ccaggaacag ccccccaaagt cctcatttat gacaataata agcgaccctc agggattcct    180
gaccgattct ctggctccaa gtctggcacg tcagccaccc tgggcatcac cggactccag    240
actggggacg aggccgatta ttactgcgga acatgggatt acagcctgac tgcttatgtc    300
ttcggaagtg ggaccaagct gaccgtccta ggttctagag gtggtggtgg tagcggcggc    360
ggcggctctg gtggtggtgg atccctcgag atggcccagg tgcagctggt gcagtctggg    420
gctgaggtga agaagcctgg ggcctcagtg aaggtttcct gcaaggcatc tggatacacc    480
ttcaccagct actatatgca ctgggtgcga caggcccctg acaagggct  tgagtggatg    540
ggaataatca accctagtgg tggtagcaca agctacgcac agaagttcca gggcagagtc    600
accatgacca gggacacgtc cacgagcaca gtctacatgg agctgagcag cctgagatct    660
gaggacacgg ccgtgtatta ctgtgcgcgc ggttactctt actctgatta ctggggtcaa    720
ggtactctgg tgaccgtctc ctca                                            744

<210> SEQ ID NO 225
<211> LENGTH: 248
<212> TYPE: PRT
<213> ORGANISM: Artificial Sequence
<220> FEATURE:
<223> OTHER INFORMATION: Synthetic

<400> SEQUENCE: 225

Gln Ser Val Leu Thr Gln Pro Pro Ser Val Ser Ala Ala Pro Gly Gln

```
            1               5                  10                 15
         Arg Val Thr Ile Ser Cys Ser Gly Ser Ser Asn Ile Gly Asn Asp
                         20                  25                 30

Tyr Val Ser Trp Tyr Gln Gln Val Pro Gly Thr Ala Pro Lys Val Leu
                         35                  40                 45

Ile Tyr Asp Asn Asn Lys Arg Pro Ser Gly Ile Pro Asp Arg Phe Ser
                         50                  55                 60

Gly Ser Lys Ser Gly Thr Ser Ala Thr Leu Gly Ile Thr Gly Leu Gln
         65                  70                  75                 80

Thr Gly Asp Glu Ala Asp Tyr Tyr Cys Gly Thr Trp Asp Tyr Ser Leu
                              85                  90                 95

Thr Ala Tyr Val Phe Gly Ser Gly Thr Lys Leu Thr Val Leu Gly Ser
                         100                 105                110

Arg Gly Gly Gly Ser Gly Gly Gly Ser Gly Gly Gly Ser
                         115                 120                125

Leu Glu Met Ala Gln Val Gln Leu Val Gln Ser Gly Ala Glu Val Lys
         130                 135                 140

Lys Pro Gly Ala Ser Val Lys Val Ser Cys Lys Ala Ser Gly Tyr Thr
         145                 150                 155                160

Phe Thr Ser Tyr Tyr Met His Trp Val Arg Gln Ala Pro Gly Gln Gly
                         165                 170                175

Leu Glu Trp Met Gly Ile Ile Asn Pro Ser Gly Gly Ser Thr Ser Tyr
                         180                 185                190

Ala Gln Lys Phe Gln Gly Arg Val Thr Met Thr Arg Asp Thr Ser Thr
                         195                 200                 205

Ser Thr Val Tyr Met Glu Leu Ser Ser Leu Arg Ser Glu Asp Thr Ala
                 210                 215                 220

Val Tyr Tyr Cys Ala Arg Gly Tyr Ser Tyr Ser Asp Tyr Trp Gly Gln
         225                 230                 235                240

Gly Thr Leu Val Thr Val Ser Ser
                         245

<210> SEQ ID NO 226
<211> LENGTH: 333
<212> TYPE: DNA
<213> ORGANISM: Artificial Sequence
<220> FEATURE:
<223> OTHER INFORMATION: Synthetic

<400> SEQUENCE: 226
cagtctgtgt tgacgcagcc gccctcagtg tctgcggccc ccgggcagag ggtcaccatc      60
tcctgctctg gaagcagctc caacattgga aatgattatg tatcctggta ccagcaagtc     120
ccaggaacag cccccaaagt cctcatttat gacaataata gcgaccctca gggattcct      180 gaccgattct ctggctccaa gtctggcacg tcagccaccc tgggcatcac cggactccag     240
actggggacg aggccgatta ttactgcgga acatgggatt acagcctgac tgcttatgtc     300
ttcggaagtg ggaccaagct gaccgtccta ggt                                  333

<210> SEQ ID NO 227
<211> LENGTH: 111
<212> TYPE: PRT
<213> ORGANISM: Artificial Sequence
<220> FEATURE:
<223> OTHER INFORMATION: Synthetic

<400> SEQUENCE: 227
```

Gln Ser Val Leu Thr Gln Pro Pro Ser Val Ser Ala Ala Pro Gly Gln
1               5                   10                  15

Arg Val Thr Ile Ser Cys Ser Gly Ser Ser Asn Ile Gly Asn Asp
            20                  25                  30

Tyr Val Ser Trp Tyr Gln Gln Val Pro Gly Thr Ala Pro Lys Val Leu
            35                  40                  45

Ile Tyr Asp Asn Asn Lys Arg Pro Ser Gly Ile Pro Asp Arg Phe Ser
        50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Tyr Ser Leu
                85                  90                  95

Thr Ala Tyr Val Phe Gly Ser Gly Thr Lys Leu Thr Val Leu Gly
            100                 105                 110

<210> SEQ ID NO 228
<211> LENGTH: 348
<212> TYPE: DNA
<213> ORGANISM: Artificial Sequence
<220> FEATURE:
<223> OTHER INFORMATION: Synthetic

<400> SEQUENCE: 228
caggtgcagc tggtgcagtc tggggctgag gtgaagaagc ctggggcctc agtgaaggtt      60
tcctgcaagg catctggata caccttcacc agctactata tgcactgggt gcgacaggcc     120
cctggacaag gcttgagtg gatgggaata atcaacccta gtggtggtag cacaagctac     180
gcacagaagt tccagggcag agtcaccatg accagggaca cgtccacgag cacagtctac     240
atggagctga gcagcctgag atctgaggac acggccgtgt attactgtgc gcgcggttac     300
tcttactctg attactgggg tcaaggtact ctggtgaccg tctcctca                  348

<210> SEQ ID NO 229
<211> LENGTH: 116
<212> TYPE: PRT
<213> ORGANISM: Artificial Sequence
<220> FEATURE:
<223> OTHER INFORMATION: Synthetic

<400> SEQUENCE: 229

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Tyr Ser Tyr Ser Asp Tyr Trp Gly Gln Gly Thr Leu Val
            100                 105                 110

Thr Val Ser Ser
        115

<210> SEQ ID NO 230

<211> LENGTH: 747
<212> TYPE: DNA
<213> ORGANISM: Artificial Sequence
<220> FEATURE:
<223> OTHER INFORMATION: Synthetic

<400> SEQUENCE: 230

```
cagtctgtgt tgacgcagcc gccctcagtg tctggggccc cagggcagag ggtcaccatc      60
tcctgtactg ggagcagctc caacttcggg gcaggttttg atgtacactg gtaccagcag     120
cttccaggaa cagcccccaa actcctcatc aataataaca caatcggcc cccagggggtc    180
cctgagcgat tctctggctc caagtctggc acctcagcct ccctggccat cactgggctc     240
caggctgagg atgaggctca atattactgc cagtcctatg acgtcagcct gaatggttgg     300
gtgttcggcg agggaccaa gctgaccgtc ctaggttcta gaggtggtgg tggtagcggc      360
ggcggcggct ctggtggtgg tggatccctc gagatggccc aggtgcagct ggtgcagtct     420
ggggctgagg tgaagaagcc tggggcctca gtgaaggtct cctgcaaggc ttctggttac     480
acctttaccg actatgggat cacctgggtg cgacaggccc ctggacaagg gcttgagtgg     540
atgggaagga tcatccctat ttttggtatc acaaactacg cacagaagtt ccagggcaga     600
gtcacggtga ccgcggacaa acccacgagc acagtcttca tggagctgac cagtcttaca     660
cctaaggaca cggccgtgta ttactgtgcg cgcggttact actacgctga tgactggggt     720
caaggtactc tggtgaccgt ctcctca                                         747
```

<210> SEQ ID NO 231
<211> LENGTH: 249
<212> TYPE: PRT
<213> ORGANISM: Artificial Sequence
<220> FEATURE:
<223> OTHER INFORMATION: Synthetic

<400> SEQUENCE: 231

```
Gln Ser Val Leu Thr Gln Pro Pro Ser Val Ser Gly Ala Pro Gly Gln
1               5                   10                  15

Arg Val Thr Ile Ser Cys Thr Gly Ser Ser Asn Phe Gly Ala Gly
            20                  25                  30

Phe Asp Val His Trp Tyr Gln Gln Leu Pro Gly Thr Ala Pro Lys Leu
        35                  40                  45

Leu Ile Asn Asn Asn Asn Arg Pro Pro Gly Val Pro Glu Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Gln Tyr Tyr Cys Gln Ser Tyr Asp Val Ser
                85                  90                  95

Leu Asn Gly Trp Val Phe Gly Gly Gly Thr Lys Leu Thr Val Leu Gly
            100                 105                 110

Ser Arg Gly Gly Gly Gly Ser Gly Gly Gly Gly Ser Gly Gly Gly Gly
        115                 120                 125

Ser Leu Glu Met Ala Gln Val Gln Leu Val Gln Ser Gly Ala Glu Val
130                 135                 140

Lys Lys Pro Gly Ala Ser Val Lys Val Ser Cys Lys Ala Ser Gly Tyr
145                 150                 155                 160

Thr Phe Thr Asp Tyr Gly Ile Thr Trp Val Arg Gln Ala Pro Gly Gln
                165                 170                 175

Gly Leu Glu Trp Met Gly Arg Ile Ile Pro Ile Phe Gly Ile Thr Asn
            180                 185                 190
```

Tyr Ala Gln Lys Phe Gln Gly Arg Val Thr Val Thr Ala Asp Lys Pro
         195                 200                 205

Thr Ser Thr Val Phe Met Glu Leu Thr Ser Leu Thr Pro Lys Asp Thr
        210                 215                 220

Ala Val Tyr Tyr Cys Ala Arg Gly Tyr Tyr Ala Asp Asp Trp Gly
225                 230                 235                 240

Gln Gly Thr Leu Val Thr Val Ser Ser
                245

<210> SEQ ID NO 232
<211> LENGTH: 336
<212> TYPE: DNA
<213> ORGANISM: Artificial Sequence
<220> FEATURE:
<223> OTHER INFORMATION: Synthetic

<400> SEQUENCE: 232
cagtctgtgt tgacgcagcc gccctcagtg tctggggccc cagggcagag ggtcaccatc      60
tcctgtactg ggagcagctc aacttcgggg gcaggttttg atgtacactg gtaccagcag     120
cttccaggaa cagcccccaa actcctcatc aataataaca caatcggccc ccagggggtc     180
cctgagcgat tctctggctc caagtctggc acctcagcct ccctggccat cactgggctc     240
caggctgagg atgaggctca atattactgc cagtcctatg acgtcagcct gaatggttgg     300
gtgttcggcg gagggaccaa gctgaccgtc ctaggt                               336

<210> SEQ ID NO 233
<211> LENGTH: 112
<212> TYPE: PRT
<213> ORGANISM: Artificial Sequence
<220> FEATURE:
<223> OTHER INFORMATION: Synthetic

<400> SEQUENCE: 233

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Phe Gly Ala Gly
            20                  25                  30

Phe Asp Val His Trp Tyr Gln Gln Leu Pro Gly Thr Ala Pro Lys Leu
        35                  40                  45

Leu Ile Asn Asn Asn Asn Arg Pro Pro Gly Val Pro Glu Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Gln Tyr Tyr Cys Gln Ser Tyr Asp Val Ser
                85                  90                  95

Leu Asn Gly Trp Val Phe Gly Gly Gly Thr Lys Leu Thr Val Leu Gly
            100                 105                 110

<210> SEQ ID NO 234
<211> LENGTH: 348
<212> TYPE: DNA
<213> ORGANISM: Artificial Sequence
<220> FEATURE:
<223> OTHER INFORMATION: Synthetic

<400> SEQUENCE: 234
caggtgcagc tggtgcagtc tggggctgag gtgaagaagc ctggggcctc agtgaaggtc      60
tcctgcaagg cttctggtta cacctttacc gactatggga tcacctgggt gcgacaggcc    120

```
cctggacaag ggcttgagtg gatgggaagg atcatccta ttttggtat cacaaactac    180 gcacagaagt tccagggcag agtcacggtg accgcggaca acccacgag cacagtcttc    240 atggagctga ccagtcttac acctaaggac acggccgtgt attactgtgc gcgcggttac    300
tactacgctg atgactgggg tcaaggtact ctggtgaccg tctcctca               348
```

```
<210> SEQ ID NO 235
<211> LENGTH: 116
<212> TYPE: PRT
<213> ORGANISM: Artificial Sequence
<220> FEATURE:
<223> OTHER INFORMATION: Synthetic

<400> SEQUENCE: 235
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Gly Ile Thr Trp Val Arg Gln Ala Pro Gly Gln Gly Leu Glu Trp Met
        35                  40                  45

Gly Arg Ile Ile Pro Ile Phe Gly Ile Thr Asn Tyr Ala Gln Lys Phe
    50                  55                  60

Gln Gly Arg Val Thr Val Thr Ala Asp Lys Pro Thr Ser Thr Val Phe
65                  70                  75                  80

Met Glu Leu Thr Ser Leu Thr Pro Lys Asp Thr Ala Val Tyr Tyr Cys
                85                  90                  95

Ala Arg Gly Tyr Tyr Tyr Ala Asp Asp Trp Gly Gln Gly Thr Leu Val
            100                 105                 110

Thr Val Ser Ser
        115

```
<210> SEQ ID NO 236
<211> LENGTH: 750
<212> TYPE: DNA
<213> ORGANISM: Artificial Sequence
<220> FEATURE:
<223> OTHER INFORMATION: Synthetic

<400> SEQUENCE: 236
cagtctgtgt tgactcagcc accctcagcg tctgggaccc ccgggcagag ggtcaccatc     60
tcttgttctg gaagcagctc caacatcgga agtaatactg taaactggta ccagcagctc    120
ccaggaacgg cccccaaact cctcatctat agtaataatc agcggccctc aggggtccct    180
gaccgattct ctggctccaa gtctggcacc tcagcctccc tggccatcag tgggctccag    240
tctgaggatg aggctgatta ttactgtgca gcatgggatg acagcctgaa tggcttttat    300
gtcttcggaa ctgggaccaa gctgaccgtc ctaggttcta gaggtggtgg tggtagcggc    360
ggcggcggct ctggtggtgg tggatccctc gagatggccc aggtccagct ggtacagtct    420
ggggctgagg tgaagaagcc tgggtcctcg gtgaaggtct cctgcaaggc ttctggaggc    480
accttcagca gctatgctat cagctgggtg cgacaggccc ctggacaagg gcttgagtgg    540
atgggaagga tcatccctat ccttggtata gcaaactacg cacagaagtt ccagggcaga    600
gtcacgatta ccgcggacaa atccacgagc acagcctaca cgagctgagc agcctgaga    660 tctgaggaca cggccgtgta ttactgtgcg cgctctatgg gtgcttggtg ggatccgtgg    720
ggtcaaggta ctctggtgac cgtctcctca                                    750
```

<210> SEQ ID NO 237
<211> LENGTH: 250
<212> TYPE: PRT
<213> ORGANISM: Artificial Sequence
<220> FEATURE:
<223> OTHER INFORMATION: Synthetic

<400> SEQUENCE: 237

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Phe Tyr Val Phe Gly Thr Gly Thr Lys Leu Thr Val Leu Gly
            100                 105                 110

Ser Arg Gly Gly Gly Gly Ser Gly Gly Gly Ser Gly Gly Gly Gly
        115                 120                 125

Ser Leu Glu Met Ala Gln Val Gln Leu Val Gln Ser Gly Ala Glu Val
130                 135                 140

Lys Lys Pro Gly Ser Ser Val Lys Val Ser Cys Lys Ala Ser Gly Gly
145                 150                 155                 160

Thr Phe Ser Ser Tyr Ala Ile Ser Trp Val Arg Gln Ala Pro Gly Gln
                165                 170                 175

Gly Leu Glu Trp Met Gly Arg Ile Ile Pro Ile Leu Gly Ile Ala Asn
            180                 185                 190

Tyr Ala Gln Lys Phe Gln Gly Arg Val Thr Ile Thr Ala Asp Lys Ser
        195                 200                 205

Thr Ser Thr Ala Tyr Asn Glu Leu Ser Ser Leu Arg Ser Glu Asp Thr
    210                 215                 220

Ala Val Tyr Tyr Cys Ala Arg Ser Met Gly Ala Trp Trp Asp Pro Trp
225                 230                 235                 240

Gly Gln Gly Thr Leu Val Thr Val Ser Ser
                245                 250
```

<210> SEQ ID NO 238
<211> LENGTH: 336
<212> TYPE: DNA
<213> ORGANISM: Artificial Sequence
<220> FEATURE:
<223> OTHER INFORMATION: Synthetic

<400> SEQUENCE: 238

```
cagtctgtgt tgactcagcc accctcagcg tctgggaccc ccgggcagag ggtcaccatc    60
tcttgttctg gaagcagctc aacatcgga agtaatactg taaactggta ccagcagctc   120
ccaggaacgg cccccaaact cctcatctat agtaataatc agcggccctc agggtccct   180 gaccgattct ctggctccaa gtctggcacc tcagcctccc tggccatcag tgggctccag   240
tctgaggatg aggctgatta ttactgtgca gcatgggatg acagcctgaa tggcttttat   300
gtcttcggaa ctgggaccaa gctgaccgtc ctaggt                             336
```

<210> SEQ ID NO 239
<211> LENGTH: 112
<212> TYPE: PRT
<213> ORGANISM: Artificial Sequence
<220> FEATURE:
<223> OTHER INFORMATION: Synthetic

<400> SEQUENCE: 239

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
                20                  25                  30

Thr Val Asn Trp Tyr Gln Gln Leu Pro Gly Thr Ala Pro Lys Leu Leu
            35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Phe Tyr Val Phe Gly Thr Gly Thr Lys Leu Thr Val Leu Gly
            100                 105                 110
```

<210> SEQ ID NO 240
<211> LENGTH: 351
<212> TYPE: DNA
<213> ORGANISM: Artificial Sequence
<220> FEATURE:
<223> OTHER INFORMATION: Synthetic

<400> SEQUENCE: 240

| | | | | | |
|---|---|---|---|---|---|
| caggtccagc | tggtacagtc | tggggctgag | gtgaagaagc | ctgggtcctc | ggtgaaggtc | 60 |
| tcctgcaagg | cttctggagg | caccttcagc | agctatgcta | tcagctgggt | gcgacaggcc | 120 |
| cctggacaag | ggcttgagtg | gatgggaagg | atcatcccta | tccttggtat | agcaaactac | 180 |
| gcacagaagt | tccagggcag | agtcacgatt | accgcggaca | aatccacgag | cacagcctac | 240 |
| atggagctga | gcagcctgag | atctgaggac | acggccgtgt | attactgtgc | gcgctctatg | 300 |
| ggtgcttggt | gggatccgtg | gggtcaaggt | actctggtga | ccgtctcctc | a | 351 |

<210> SEQ ID NO 241
<211> LENGTH: 753
<212> TYPE: DNA
<213> ORGANISM: Artificial Sequence
<220> FEATURE:
<223> OTHER INFORMATION: Synthetic

<400> SEQUENCE: 241

| | | | | | |
|---|---|---|---|---|---|
| cagtctgtcg | tgacgcagcc | gccctcagtg | tctgcggccc | caggacagaa | ggtcaccatc | 60 |
| tcctgctctg | gaagcaactc | caacattggg | aacaattatg | tctcctggta | ccagcaactc | 120 |
| ccaggaacag | cccccaaact | cctcatctat | gacaataata | aacgaccctc | aggggattcct | 180 |
| gaccgattct | ctggctccaa | gtctggcacg | tctgccaccc | tgggcatcac | cggactccag | 240 |
| actggcgacg | aggccgatta | ttactgcgaa | acatgggata | tcagcctgaa | tgttggagtg | 300 |
| ttcggcggag | ggaccaagct | gaccgtccta | ggttctagag | gtggtggtgg | tagcggcggc | 360 |
| ggcggctctg | gtggtggtgg | atccctcgag | atggccgagg | tgcagctggt | ggagtctggg | 420 |
| gctgaggtga | agaagcctgg | ggcctcagtg | aaggtttcct | gcaaggcatc | tggatacacc | 480 |

```
ttcaccaact actatataca ctgggtgcga caggcccctg gacaagggct tgagtggatg    540
ggaataatca accctagtgt tggtagcaca aggtacgcac agaagttcca gggcagagtc    600
accatgacca gggacacgtc cacgagcaca ctgtacatgg agttgagcag cctgagatct    660
gaggacacgg ccgtatatta ctgtgcgcgc ggtcagtacg gttctcaggg taaagattct    720
tggggtcaag gtactctggt gaccgtctcc tca                                 753
```

<210> SEQ ID NO 242
<211> LENGTH: 251
<212> TYPE: PRT
<213> ORGANISM: Artificial Sequence
<220> FEATURE:
<223> OTHER INFORMATION: Synthetic

<400> SEQUENCE: 242

```
Gln Ser Val Val Thr Gln Pro Pro Ser Val Ser Ala Ala Pro Gly Gln
1               5                   10                  15

Lys Val Thr Ile Ser Cys Ser Gly Ser Asn Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Glu Thr Trp Asp Ile Ser Leu
                85                  90                  95

Asn Val Gly Val Phe Gly Gly Gly Thr Lys Leu Thr Val Leu Gly Ser
            100                 105                 110

Arg Gly Gly Gly Ser Gly Gly Gly Gly Ser Gly Gly Gly Gly Ser
        115                 120                 125

Leu Glu Met Ala Glu Val Gln Leu Val Glu Ser Gly Ala Glu Val Lys
    130                 135                 140

Lys Pro Gly Ala Ser Val Lys Val Ser Cys Lys Ala Ser Gly Tyr Thr
145                 150                 155                 160

Phe Thr Asn Tyr Tyr Ile His Trp Val Arg Gln Ala Pro Gly Gln Gly
                165                 170                 175

Leu Glu Trp Met Gly Ile Ile Asn Pro Ser Val Gly Ser Thr Arg Tyr
            180                 185                 190

Ala Gln Lys Phe Gln Gly Arg Val Thr Met Thr Arg Asp Thr Ser Thr
        195                 200                 205

Ser Thr Leu Tyr Met Glu Leu Ser Ser Leu Arg Ser Glu Asp Thr Ala
    210                 215                 220

Val Tyr Tyr Cys Ala Arg Gly Gln Tyr Gly Ser Gln Gly Lys Asp Ser
225                 230                 235                 240

Trp Gly Gln Gly Thr Leu Val Thr Val Ser Ser
                245                 250
```

<210> SEQ ID NO 243
<211> LENGTH: 333
<212> TYPE: DNA
<213> ORGANISM: Artificial Sequence
<220> FEATURE:
<223> OTHER INFORMATION: Synthetic

<400> SEQUENCE: 243

```
cagtctgtcg tgacgcagcc gccctcagtg tctgcggccc caggacagaa ggtcaccatc    60
tcctgctctg gaagcaactc caacattggg aacaattatg tctcctggta ccagcaactc   120
ccaggaacag cccccaaact cctcatctat gacaataata acgaccctc agggattcct    180 gaccgattct ctggctccaa gtctggcacg tctgccaccc tgggcatcac cggactccag   240
actggcgacg aggccgatta ttactgcgaa acatgggata tcagcctgaa tgttggagtg   300
ttcggcggag ggaccaagct gaccgtccta ggt                                333
```

<210> SEQ ID NO 244
<211> LENGTH: 111
<212> TYPE: PRT
<213> ORGANISM: Artificial Sequence
<220> FEATURE:
<223> OTHER INFORMATION: Synthetic

<400> SEQUENCE: 244

```
Gln Ser Val Val Thr Gln Pro Pro Ser Val Ser Ala Ala Pro Gly Gln
1               5                   10                  15

Lys Val Thr Ile Ser Cys Ser Gly Ser Asn Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Glu Thr Trp Asp Ile Ser Leu
                85                  90                  95

Asn Val Gly Val Phe Gly Gly Gly Thr Lys Leu Thr Val Leu Gly
            100                 105                 110
```

<210> SEQ ID NO 245
<211> LENGTH: 357
<212> TYPE: DNA
<213> ORGANISM: Artificial Sequence
<220> FEATURE:
<223> OTHER INFORMATION: Synthetic

<400> SEQUENCE: 245

```
gaggtgcagc tggtggagtc tggggctgag gtgaagaagc ctggggcctc agtgaaggtt    60
tcctgcaagg catctggata caccttcacc aactactata tacactgggt gcgacaggcc   120
cctggacaag gcttgagtg gatgggaata atcaaccctg tgttggtag cacaaggtac    180 gcacagaagt tccagggcag agtcaccatg accagggaca cgtccacgag cacactgtac   240
atggagttga gcagcctgag atctgaggac acggccgtat attactgtgc gcgcggtcag   300
tacggttctc agggtaaaga ttcttggggt caaggtactc tggtgaccgt ctcctca      357
```

<210> SEQ ID NO 246
<211> LENGTH: 119
<212> TYPE: PRT
<213> ORGANISM: Artificial Sequence
<220> FEATURE:
<223> OTHER INFORMATION: Synthetic

<400> SEQUENCE: 246

```
Glu Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Asn Tyr
```

20                  25                  30

Tyr Ile His Trp Val Arg Gln Ala Pro Gly Gln Gly Leu Glu Trp Met
            35                  40                  45

Gly Ile Ile Asn Pro Ser Val Gly Ser Thr Arg Tyr Ala Gln Lys Phe
    50                  55                  60

Gln Gly Arg Val Thr Met Thr Arg Asp Thr Ser Thr Ser Thr Leu Tyr
65                  70                  75                  80

Met Glu Leu Ser Ser Leu Arg Ser Glu Asp Thr Ala Val Tyr Tyr Cys
                85                  90                  95

Ala Arg Gly Gln Tyr Gly Ser Gln Gly Lys Asp Ser Trp Gly Gln Gly
                100                 105                 110

Thr Leu Val Thr Val Ser Ser
        115

<210> SEQ ID NO 247
<211> LENGTH: 753
<212> TYPE: DNA
<213> ORGANISM: Artificial Sequence
<220> FEATURE:
<223> OTHER INFORMATION: Synthetic

<400> SEQUENCE: 247
cagtctgtgt tgacgcagcc gccctcagtg tctgcggccc caggacagaa ggtcaccatc      60
tcctgctctg gaagcagctc caacattggg aatgattatg tatcgtggta ccagcaactc     120
ccaggaacag ccccccaaact cctcatttat gaaaatgatc agcgaccctc agggattcct    180
gaccgattct ctggctccaa gtctggcacg tcagccaccc tgggcatcac cggactccag     240
actggggacg aggccactta ttactgcgga acttgggata gcagcctgaa tggtggggtg     300
ttcggcggag ggaccaaggt caccgtccta ggttctagag gtggtggtgg tagcggcggc     360
ggcggctctg gtggtggtgg atccctcgag atggccgagg tccagctggt acagtctggg     420
gctgaggtga agaagcctgg ggcctcagtg aaggtttcct gcaaggcatc tggatacacc     480
ttcaccagct actatatgca ctgggtgcga caggcccctg gacaagggct tgagtggatg     540
ggaataatca accctagtgg tggtagcaca agctacgcac agaagttcca gggcagagtc     600
accatgacca gggacacgtc cacgagcaca gtctacatgg agctgagcag cctgagatct     660
gaggacacgg ccgtgtatta ctgtgcgcgc ggtatgtctt actactcttc tatcgataaa     720
tggggtcaag gtactctggt gaccgtctcc tca                                  753

<210> SEQ ID NO 248
<211> LENGTH: 251
<212> TYPE: PRT
<213> ORGANISM: Artificial Sequence
<220> FEATURE:
<223> OTHER INFORMATION: Synthetic

<400> SEQUENCE: 248

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asp
            20                  25                  30

Tyr Val Ser Trp Tyr Gln Gln Leu Pro Gly Thr Ala Pro Lys Leu Leu
        35                  40                  45

Ile Tyr Glu Asn Asp Gln Arg Pro Ser Gly Ile Pro Asp Arg Phe Ser
    50                  55                  60

Gly Ser Lys Ser Gly Thr Ser Ala Thr Leu Gly Ile Thr Gly Leu Gln

Thr Gly Asp Glu Ala Thr Tyr Tyr Cys Gly Thr Trp Asp Ser Ser Leu
65                  70                  75                  80

Asn Gly Gly Val Phe Gly Gly Gly Thr Lys Val Thr Val Leu Gly Ser
            85                  90                  95

Arg Gly Gly Gly Ser Gly Gly Gly Ser Gly Gly Gly Ser
                100                 105                 110

Leu Glu Met Ala Glu Val Gln Leu Val Gln Ser Gly Ala Glu Val Lys
    115                 120                 125

Lys Pro Gly Ala Ser Val Lys Val Ser Cys Lys Ala Ser Gly Tyr Thr
130                 135                 140

Phe Thr Ser Tyr Tyr Met His Trp Val Arg Gln Ala Pro Gly Gln Gly
145                 150                 155                 160

Leu Glu Trp Met Gly Ile Ile Asn Pro Ser Gly Gly Ser Thr Ser Tyr
            165                 170                 175

Ala Gln Lys Phe Gln Gly Arg Val Thr Met Thr Arg Asp Thr Ser Thr
        180                 185                 190

Ser Thr Val Tyr Met Glu Leu Ser Ser Leu Arg Ser Glu Asp Thr Ala
    195                 200                 205

Val Tyr Tyr Cys Ala Arg Gly Met Ser Tyr Tyr Ser Ser Ile Asp Lys
210                 215                 220

Trp Gly Gln Gly Thr Leu Val Thr Val Ser Ser
225                 230                 235                 240

<210> SEQ ID NO 249
<211> LENGTH: 333
<212> TYPE: DNA
<213> ORGANISM: Artificial Sequence
<220> FEATURE:
<223> OTHER INFORMATION: Synthetic

<400> SEQUENCE: 249
cagtctgtgt tgacgcagcc gccctcagtg tctgcggccc caggacagaa ggtcaccatc      60
tcctgctctg gaagcagctc caacattggg aatgattatg tatcgtggta ccagcaactc     120
ccaggaacag cccccaaact cctcatttat gaaaatgatc agcgaccctc agggattcct     180
gaccgattct ctggctccaa gtctggcacg tcagccaccc tgggcatcac cggactccag     240
actggggacg aggccactta ttactgcgga acttgggata gcagcctgaa tggtggggtg     300
ttcggcggag ggaccaaggt caccgtccta ggt                                  333

<210> SEQ ID NO 250
<211> LENGTH: 111
<212> TYPE: PRT
<213> ORGANISM: Artificial Sequence
<220> FEATURE:
<223> OTHER INFORMATION: Synthetic

<400> SEQUENCE: 250

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asp
            20                  25                  30

Tyr Val Ser Trp Tyr Gln Gln Leu Pro Gly Thr Ala Pro Lys Leu Leu
        35                  40                  45

Ile Tyr Glu Asn Asp Gln Arg Pro Ser Gly Ile Pro Asp Arg Phe Ser
    50                  55                  60

```
Gly Ser Lys Ser Gly Thr Ser Ala Thr Leu Gly Ile Thr Gly Leu Gln
 65                  70                  75                  80

Thr Gly Asp Glu Ala Thr Tyr Tyr Cys Gly Thr Trp Asp Ser Ser Leu
                 85                  90                  95

Asn Gly Gly Val Phe Gly Gly Gly Thr Lys Val Thr Val Leu Gly
            100                 105                 110

<210> SEQ ID NO 251
<211> LENGTH: 357
<212> TYPE: DNA
<213> ORGANISM: Artificial Sequence
<220> FEATURE:
<223> OTHER INFORMATION: Synthetic

<400> SEQUENCE: 251
gaggtccagc tggtacagtc tggggctgag gtgaagaagc ctggggcctc agtgaaggtt      60
tcctgcaagg catctggata caccttcacc agctactata tgcactgggt gcgacaggcc    120
cctggacaag gcttgagtg gatgggaata atcaaccct gtggtggtag cacaagctac     180
gcacagaagt tccagggcag agtcaccatg accagggaca cgtccacgag cacagtctac    240
atggagctga gcagcctgag atctgaggac acggccgtgt attactgtgc gcgcggtatg    300
tcttactact cttctatcga taaatggggt caaggtactc tggtgaccgt ctcctca       357

<210> SEQ ID NO 252
<211> LENGTH: 119
<212> TYPE: PRT
<213> ORGANISM: Artificial Sequence
<220> FEATURE:
<223> OTHER INFORMATION: Synthetic

<400> SEQUENCE: 252

Glu Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Ser Tyr
                 20                  25                  30

Tyr Met His Trp Val Arg Gln Ala Pro Gly Gln Gly Leu Glu Trp Met
             35                  40                  45

Gly Ile Ile Asn Pro Ser Gly Gly Ser Thr Ser Tyr Ala Gln Lys Phe
         50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Gly Met Ser Tyr Tyr Ser Ser Ile Asp Lys Trp Gly Gln Gly
            100                 105                 110

Thr Leu Val Thr Val Ser Ser
        115

<210> SEQ ID NO 253
<211> LENGTH: 744
<212> TYPE: DNA
<213> ORGANISM: Artificial Sequence
<220> FEATURE:
<223> OTHER INFORMATION: Synthetic

<400> SEQUENCE: 253
cagtctgtcg tgacgcagcc gccctcagtg tctgcggccc caggacagaa ggtcaccatc      60
tcctgctctg gaagcagctc caacattggg aataattatg tatcctggta ccagcagctc    120
```

```
ccaggaacag ccccccaaact cctcatttat gaaaatgatc agcgaccctc agagattcct      180
gaccgattct ctggctccaa gtctggcacg tcagccaccc tgggcatcac cggactccag      240
actggggacg aggccactta ttactgcgga acttgggata cagcctgaa tggtggggtg       300 ttcggcggag ggaccaagct gaccgtccta ggttctagag gtggtggtgg tagcggcggc      360
ggcggctctg gtggtggtgg atccctcgag atggcccagg tgcagctggt gcagtctggg      420
gctgaggtga agaagcctgg ggcctcagtg aaggtttcct gcaaggcatc tggatacacc      480
ttcaccagct actatatgca ctgggtgcga caggcccctg acaagggct tgagtggatg       540 ggaataatca accctagtgg tggtagcaca agctacgcac agaagttcca gggcagagtc      600
accatgacca gggacacgtc cacgagcaca gtctacatgg agctgagcag cctgagatct      660
gaggacactg ccgtgtatta ctgtgcgcgc ggttactacg actctgatcg ttggggtcaa      720
ggtactctgg tgaccgtctc ctca                                             744
```

<210> SEQ ID NO 254
<211> LENGTH: 248
<212> TYPE: PRT
<213> ORGANISM: Artificial Sequence
<220> FEATURE:
<223> OTHER INFORMATION: Synthetic

<400> SEQUENCE: 254

```
Gln Ser Val Val Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Glu Asn Asp Gln Arg Pro Ser Glu Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Thr Tyr Tyr Cys Gly Thr Trp Asp Asn Ser Leu
                85                  90                  95

Asn Gly Gly Val Phe Gly Gly Gly Thr Lys Leu Thr Val Leu Gly Ser
            100                 105                 110

Arg Gly Gly Gly Ser Gly Gly Gly Ser Gly Gly Gly Ser
        115                 120                 125

Leu Glu Met Ala Gln Val Gln Leu Val Gln Ser Gly Ala Glu Val Lys
    130                 135                 140

Lys Pro Gly Ala Ser Val Lys Val Ser Cys Lys Ala Ser Gly Tyr Thr
145                 150                 155                 160

Phe Thr Ser Tyr Tyr Met His Trp Val Arg Gln Ala Pro Gly Gln Gly
                165                 170                 175

Leu Glu Trp Met Gly Ile Ile Asn Pro Ser Gly Gly Ser Thr Ser Tyr
            180                 185                 190

Ala Gln Lys Phe Gln Gly Arg Val Thr Met Thr Arg Asp Thr Ser Thr
        195                 200                 205

Ser Thr Val Tyr Met Glu Leu Ser Ser Leu Arg Ser Glu Asp Thr Ala
    210                 215                 220

Val Tyr Tyr Cys Ala Arg Gly Tyr Tyr Asp Ser Asp Arg Trp Gly Gln
225                 230                 235                 240

Gly Thr Leu Val Thr Val Ser Ser
                245
```

<210> SEQ ID NO 255
<211> LENGTH: 333
<212> TYPE: DNA
<213> ORGANISM: Artificial Sequence
<220> FEATURE:
<223> OTHER INFORMATION: Synthetic

<400> SEQUENCE: 255

```
cagtctgtcg tgacgcagcc gccctcagtg tctgcggccc caggacagaa ggtcaccatc      60
tcctgctctg gaagcagctc caacattggg aataattatg tatcctggta ccagcagctc     120
ccaggaacag cccccaaact cctcatttat gaaaatgatc agcgaccctc agagattcct     180
gaccgattct ctggctccaa gtctggcacg tcagccaccc tgggcatcac cggactccag     240
actgggacg aggccactta ttactgcgga acttgggata cagcctgaa tggtggggtg       300
ttcggcggag ggaccaagct gaccgtccta ggt                                  333
```

<210> SEQ ID NO 256
<211> LENGTH: 111
<212> TYPE: PRT
<213> ORGANISM: Artificial Sequence
<220> FEATURE:
<223> OTHER INFORMATION: Synthetic

<400> SEQUENCE: 256

```
Gln Ser Val Val Thr Gln Pro Pro Ser Val Ser Ala Ala Pro Gly Gln
1               5                   10                  15
Lys Val Thr Ile Ser Cys Ser Gly Ser Ser Ser Asn Ile Gly Asn Asn
            20                  25                  30
Tyr Val Ser Trp Tyr Gln Gln Leu Pro Gly Thr Ala Pro Lys Leu Leu
        35                  40                  45
Ile Tyr Glu Asn Asp Gln Arg Pro Ser Glu Ile Pro Asp Arg Phe Ser
    50                  55                  60
Gly Ser Lys Ser Gly Thr Ser Ala Thr Leu Gly Ile Thr Gly Leu Gln
65                  70                  75                  80
Thr Gly Asp Glu Ala Thr Tyr Tyr Cys Gly Thr Trp Asp Asn Ser Leu
                85                  90                  95
Asn Gly Gly Val Phe Gly Gly Gly Thr Lys Leu Thr Val Leu Gly
            100                 105                 110
```

<210> SEQ ID NO 257
<211> LENGTH: 348
<212> TYPE: DNA
<213> ORGANISM: Artificial Sequence
<220> FEATURE:
<223> OTHER INFORMATION: Synthetic

<400> SEQUENCE: 257

```
caggtgcagc tggtgcagtc tggggctgag gtgaagaagc ctggggcctc agtgaaggtt      60
tcctgcaagg catctggata caccttcacc agctactata tgcactgggt gcgacaggcc     120
cctggacaag gcttgagtg gatgggaata atcaacccta gtggtggtag cacaagctac      180
gcacagaagt tccagggcag agtcaccatg accaggaca cgtccacgag cacagtctac      240
atggagctga gcagcctgag atctgaggac actgccgtgt attactgtgc gcgcggttac     300
tacgactctg atcgttgggg tcaaggtact ctggtgaccg tctcctca                  348
```

<210> SEQ ID NO 258
<211> LENGTH: 116

```
<212> TYPE: PRT
<213> ORGANISM: Artificial Sequence
<220> FEATURE:
<223> OTHER INFORMATION: Synthetic

<400> SEQUENCE: 258

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Tyr Tyr Asp Ser Asp Arg Trp Gly Gln Gly Thr Leu Val
            100                 105                 110

Thr Val Ser Ser
        115

<210> SEQ ID NO 259
<211> LENGTH: 747
<212> TYPE: DNA
<213> ORGANISM: Artificial Sequence
<220> FEATURE:
<223> OTHER INFORMATION: Synthetic

<400> SEQUENCE: 259
cagtctgtgt tgacgcagcc gccctcagtg tctgggactc cagggcagag ggtcaccatc      60
tcctgcactg ggagcagctc caacctcggg gcaggctttg atgtacactg gtaccagcag     120
cttccaagaa cagcccccaa actcgtcatt tctagtgaca caatcggcc ctcagggggtc     180
cctgaccgat tctctgcctc taagtctggc acctcggcct ccctggccat cactggtctc     240
caggctgagg atgaggctga ttattactgc cagtcctatg acagcggcct gagtggttcg     300
gtcttcggcg agggaccaa gctgaccgtc ctaggttcta gaggtggtgg tggtagcggc     360
ggcggcggct ctggtggtgg tggatccctc gagatggccc aggtgcagct ggtgcaatct     420
ggagctgagg tgaagaagcc tggggcctca gtgaaggtct cctgcaaggc ttctggttac     480
acctttacca gctatggtat cagctgggtg cgacaggccc ctggacaagg gcttgagtgg     540
atgggatgga tcagcgctta caatggtaac acaaactatg cacagaagct ccagggcaga     600
gtcaccatga ccacagacac atccacgagc acagcctaca tggagctgag gagcctgaga     660
tctgacgaca cggccgtgta ttactgtgcg cgcggttact actactacga ttcttggggt     720
caaggtactc tggtgaccgt ctcctca                                          747

<210> SEQ ID NO 260
<211> LENGTH: 249
<212> TYPE: PRT
<213> ORGANISM: Artificial Sequence
<220> FEATURE:
<223> OTHER INFORMATION: Synthetic

<400> SEQUENCE: 260

Gln Ser Val Leu Thr Gln Pro Pro Ser Val Ser Gly Thr Pro Gly Gln
1               5                   10                  15
```

Arg Val Thr Ile Ser Cys Thr Gly Ser Ser Asn Leu Gly Ala Gly
        20                  25                  30

Phe Asp Val His Trp Tyr Gln Gln Leu Pro Arg Thr Ala Pro Lys Leu
            35                  40                  45

Val Ile Ser Ser Asp Asn Asn Arg Pro Ser Gly Val Pro Asp Arg Phe
50                  55                  60

Ser Ala Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Gly
                85                  90                  95

Leu Ser Gly Ser Val Phe Gly Gly Gly Thr Lys Leu Thr Val Leu Gly
            100                 105                 110

Ser Arg Gly Gly Gly Gly Ser Gly Gly Gly Gly Ser Gly Gly Gly Gly
            115                 120                 125

Ser Leu Glu Met Ala Gln Val Gln Leu Val Gln Ser Gly Ala Glu Val
130                 135                 140

Lys Lys Pro Gly Ala Ser Val Lys Val Ser Cys Lys Ala Ser Gly Tyr
145                 150                 155                 160

Thr Phe Thr Ser Tyr Gly Ile Ser Trp Val Arg Gln Ala Pro Gly Gln
                165                 170                 175

Gly Leu Glu Trp Met Gly Trp Ile Ser Ala Tyr Asn Gly Asn Thr Asn
            180                 185                 190

Tyr Ala Gln Lys Leu Gln Gly Arg Val Thr Met Thr Thr Asp Thr Ser
            195                 200                 205

Thr Ser Thr Ala Tyr Met Glu Leu Arg Ser Leu Arg Ser Asp Asp Thr
210                 215                 220

Ala Val Tyr Tyr Cys Ala Arg Gly Tyr Tyr Tyr Asp Ser Trp Gly
225                 230                 235                 240

Gln Gly Thr Leu Val Thr Val Ser Ser
                245

<210> SEQ ID NO 261
<211> LENGTH: 336
<212> TYPE: DNA
<213> ORGANISM: Artificial Sequence
<220> FEATURE:
<223> OTHER INFORMATION: Synthetic

<400> SEQUENCE: 261
cagtctgtgt tgacgcagcc gccctcagtg tctgggactc cagggcagag ggtcaccatc    60
tcctgcactg ggagcagctc caacctcggg gcaggctttg atgtacactg gtaccagcag   120
cttccaagaa cagcccccaa actcgtcatt tctagtgaca caatcggccc tcagggggtc   180
cctgaccgat tctctgcctc taagtctggc acctcggcct ccctggccat cactggtctc   240
caggctgagg atgaggctga ttattactgc cagtcctatg acagcggcct gagtggttcg   300
gtcttcggcg agggaccaa gctgaccgtc ctaggt                              336

<210> SEQ ID NO 262
<211> LENGTH: 112
<212> TYPE: PRT
<213> ORGANISM: Artificial Sequence
<220> FEATURE:
<223> OTHER INFORMATION: Synthetic

<400> SEQUENCE: 262

Gln Ser Val Leu Thr Gln Pro Pro Ser Val Ser Gly Thr Pro Gly Gln

```
            1               5                  10                 15
Arg Val Thr Ile Ser Cys Thr Gly Ser Ser Ser Asn Leu Gly Ala Gly
                20                  25                  30

Phe Asp Val His Trp Tyr Gln Gln Leu Pro Arg Thr Ala Pro Lys Leu
                35                  40                  45

Val Ile Ser Ser Asp Asn Asn Arg Pro Ser Gly Val Pro Asp Arg Phe
        50                  55                  60

Ser Ala Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Gly
                    85                  90                  95

Leu Ser Gly Ser Val Phe Gly Gly Gly Thr Lys Leu Thr Val Leu Gly
                100                 105                 110
```

<210> SEQ ID NO 263
<211> LENGTH: 348
<212> TYPE: DNA
<213> ORGANISM: Artificial Sequence
<220> FEATURE:
<223> OTHER INFORMATION: Synthetic

<400> SEQUENCE: 263

```
caggtgcagc tggtgcaatc tggagctgag gtgaagaagc ctggggcctc agtgaaggtc    60
tcctgcaagg cttctggtta cacctttacc agctatggta tcagctgggt gcgacaggcc   120
cctggacaag gcttgagtg atgggatgg atcagcgctt acaatggtaa cacaaactat    180
gcacagaagc tccagggcag agtcaccatg accacagaca catccacgag cacagcctac   240
atggagctga ggagcctgag atctgacgac acggccgtgt attactgtgc gcgcggttac   300
tactactacg attcttgggg tcaaggtact ctggtgaccg tctcctca               348
```

<210> SEQ ID NO 264
<211> LENGTH: 116
<212> TYPE: PRT
<213> ORGANISM: Artificial Sequence
<220> FEATURE:
<223> OTHER INFORMATION: Synthetic

<400> SEQUENCE: 264

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Tyr Tyr Tyr Tyr Asp Ser Trp Gly Gln Gly Thr Leu Val
                100                 105                 110

Thr Val Ser Ser
            115
```

<210> SEQ ID NO 265
<211> LENGTH: 741

```
<212> TYPE: DNA
<213> ORGANISM: Artificial Sequence
<220> FEATURE:
<223> OTHER INFORMATION: Synthetic

<400> SEQUENCE: 265
gacatccagt tgacccagtc tccatcctcc ctgtctgcat ctgtcggaga cagcgtcacc      60
atcacttgcc aggcgagtca gcacattacc aagtatttaa attggtatca gcagaaacca     120
gggaaagccc ctaagctcct gatttccgat gcatccgttt tggaaaaagg ggtcccatct     180
aggttcggtg aagtggatc tgggacagat tttactttca ccatcagcag gctgcagcct     240
gaagacattg caacatatta ctgtcaacag tatgagaatc tcccgctcac tttcggcgga    300
gggaccaagc tggagatcaa acgttctaga ggtggtggtg gtagcggcgg cggcggctct    360
ggtggtggtg gatccctcga gatggcccag gtgcagctgg tgcagtctgg ggctgaggtg    420
aagaagcctg ggcctcagt gaggctttcc tgcaaggcgc ctggaaacac cttcaccagc    480
tactatctac attgggtgcg acaggcccct ggacaagggc ttgagtggat gggaataatc    540
aaccctagtg gtggttccac aaactacgca cagaagttcc agggcagagt caccatgacc    600
agggacacgt ccacgagtac agtctacatg gagatgagca gtctgagatc tgacgacact    660
gccgtgtatt actgtgcgcg ctctggtggt tactggtctt tcgattcttg ggtcaaggt    720
actctggtga ccgtctcctc a                                               741

<210> SEQ ID NO 266
<211> LENGTH: 247
<212> TYPE: PRT
<213> ORGANISM: Artificial Sequence
<220> FEATURE:
<223> OTHER INFORMATION: Synthetic

<400> SEQUENCE: 266

Asp Ile Gln Leu Thr Gln Ser Pro Ser Leu Ser Ala Ser Val Gly
1               5                   10                  15

Asp Ser Val Thr Ile Thr Cys Gln Ala Ser Gln His Ile Thr Lys Tyr
            20                  25                  30

Leu Asn Trp Tyr Gln Gln Lys Pro Gly Lys Ala Pro Lys Leu Leu Ile
        35                  40                  45

Ser Asp Ala Ser Val Leu Glu Lys Gly Val Pro Ser Arg Phe Gly Gly
    50                  55                  60

Ser Gly Ser Gly Thr Asp Phe Thr Phe Thr Ile Ser Arg Leu Gln Pro
65                  70                  75                  80

Glu Asp Ile Ala Thr Tyr Tyr Cys Gln Gln Tyr Glu Asn Leu Pro Leu
                85                  90                  95

Thr Phe Gly Gly Gly Thr Lys Leu Glu Ile Lys Arg Ser Arg Gly Gly
            100                 105                 110

Gly Gly Ser Gly Gly Gly Gly Ser Gly Gly Gly Ser Leu Glu Met
        115                 120                 125

Ala Gln Val Gln Leu Val Gln Ser Gly Ala Glu Val Lys Lys Pro Gly
    130                 135                 140

Ala Ser Val Arg Leu Ser Cys Lys Ala Pro Gly Asn Thr Phe Thr Ser
145                 150                 155                 160

Tyr Tyr Leu His Trp Val Arg Gln Ala Pro Gly Gln Gly Leu Glu Trp
                165                 170                 175

Met Gly Ile Ile Asn Pro Ser Gly Gly Ser Thr Asn Tyr Ala Gln Lys
            180                 185                 190
```

```
Phe Gln Gly Arg Val Thr Met Thr Arg Asp Thr Ser Thr Ser Thr Val
            195                 200                 205
Tyr Met Glu Met Ser Ser Leu Arg Ser Asp Thr Ala Val Tyr Tyr
        210                 215                 220
Cys Ala Arg Ser Gly Gly Tyr Trp Ser Phe Asp Ser Trp Gln Gly
225                 230                 235                 240
Thr Leu Val Thr Val Ser Ser
                245

<210> SEQ ID NO 267
<211> LENGTH: 324
<212> TYPE: DNA
<213> ORGANISM: Artificial Sequence
<220> FEATURE:
<223> OTHER INFORMATION: Synthetic

<400> SEQUENCE: 267
gacatccagt tgacccagtc tccatcctcc ctgtctgcat ctgtcggaga cagcgtcacc      60
atcacttgcc aggcgagtca gcacattacc aagtatttaa attggtatca gcagaaacca    120
gggaaagccc ctaagctcct gatttccgat gcatccgttt tggaaaaagg ggtcccatct    180
aggttcggtg aagtggatc tgggacagat tttactttca ccatcagcag gctgcagcct     240
gaagacattg caacatatta ctgtcaacag tatgagaatc tcccgctcac tttcggcgga    300
gggaccaagc tggagatcaa acgt                                           324

<210> SEQ ID NO 268
<211> LENGTH: 108
<212> TYPE: PRT
<213> ORGANISM: Artificial Sequence
<220> FEATURE:
<223> OTHER INFORMATION: Synthetic

<400> SEQUENCE: 268

Asp Ile Gln Leu Thr Gln Ser Pro Ser Ser Leu Ser Ala Ser Val Gly
1               5                   10                  15
Asp Ser Val Thr Ile Thr Cys Gln Ala Ser Gln His Ile Thr Lys Tyr
            20                  25                  30
Leu Asn Trp Tyr Gln Gln Lys Pro Gly Lys Ala Pro Lys Leu Leu Ile
        35                  40                  45
Ser Asp Ala Ser Val Leu Glu Lys Gly Val Pro Ser Arg Phe Gly Gly
    50                  55                  60
Ser Gly Ser Gly Thr Asp Phe Thr Phe Thr Ile Ser Arg Leu Gln Pro
65                  70                  75                  80
Glu Asp Ile Ala Thr Tyr Tyr Cys Gln Gln Tyr Glu Asn Leu Pro Leu
                85                  90                  95
Thr Phe Gly Gly Gly Thr Lys Leu Glu Ile Lys Arg
            100                 105

<210> SEQ ID NO 269
<211> LENGTH: 354
<212> TYPE: DNA
<213> ORGANISM: Artificial Sequence
<220> FEATURE:
<223> OTHER INFORMATION: Synthetic

<400> SEQUENCE: 269
caggtgcagc tggtgcagtc tggggctgag gtgaagaagc ctggggcctc agtgaggctt      60
tcctgcaagg cgcctggaaa caccttcacc agctactata cattgggt gcgacaggcc      120
```

```
cctggacaag ggcttgagtg gatgggaata atcaaccta gtggtggttc cacaaactac    180
gcacagaagt tccagggcag agtcaccatg accagggaca cgtccacgag tacagtctac    240
atggagatga gcagtctgag atctgacgac actgccgtgt attactgtgc gcgctctggt    300
ggttactggt ctttcgattc ttggggtcaa ggtactctgg tgaccgtctc ctca           354
```

<210> SEQ ID NO 270
<211> LENGTH: 118
<212> TYPE: PRT
<213> ORGANISM: Artificial Sequence
<220> FEATURE:
<223> OTHER INFORMATION: Synthetic

<400> SEQUENCE: 270

```
Gln Val Gln Leu Val Gln Ser Gly Ala Glu Val Lys Lys Pro Gly Ala
1               5                   10                  15

Ser Val Arg Leu Ser Cys Lys Ala Pro Gly Asn Thr Phe Thr Ser Tyr
            20                  25                  30

Tyr Leu His Trp Val Arg Gln Ala Pro Gly Gln Gly Leu Glu Trp Met
        35                  40                  45

Gly Ile Ile Asn Pro Ser Gly Gly Ser Thr Asn Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Met Ser Ser Leu Arg Ser Asp Asp Thr Ala Val Tyr Tyr Cys
                85                  90                  95

Ala Arg Ser Gly Gly Tyr Trp Ser Phe Asp Ser Trp Gly Gln Gly Thr
            100                 105                 110

Leu Val Thr Val Ser Ser
        115
```

<210> SEQ ID NO 271
<211> LENGTH: 759
<212> TYPE: DNA
<213> ORGANISM: Artificial Sequence
<220> FEATURE:
<223> OTHER INFORMATION: Synthetic

<400> SEQUENCE: 271

```
cagtctgtgt tgacgcagcc gccctcagtg tctgcggccc caggacaaaa ggtcaccatc     60
tcctgctctg gaagcacctc caacattgga aataattatg tatcctggta ccagcaactc    120
ccaggaacag cccccaaact cgtcatttat gacaatgata tcgaccctc agggattcct     180 gaccgattct ctggctccaa gtctggcacg tcagccaccc tgggcatcac cggactccac    240 actgggacg aggccgatta ttactgcgga acatgggata gcagcctgag tgctggggtg    300
ttcggcggag ggaccaagct gaccgtccta ggttctagag tggtggtgg tagcggcggc    360 ggcggctctg gtggtggtgg atccctcgag atggccgagg tgcagctggt ggagtctggg    420
ggaggcttag tacagccggg ggggtccctg agactctcct gtgcagcctc tggattctac    480
tttagcggct tgccatgag ctgggtccgc caggctccag ggaaggggct ggagtggctc     540
tcagttgttt ttaacgatgg cagtaccaca ttctatgcag actccgtgaa gggccggttc    600
accatgtcca gagatgattc caagaacaca atttctctgc aaatgaacag cctgagagcc    660
gaagacacgg ccgtatatta ctgtgcgcgc cagtctccgt tctacttcga cggtccgtac    720
gattactggg gtcaaggtac tctggtgacc gtctcctca                            759
```

```
<210> SEQ ID NO 272
<211> LENGTH: 253
<212> TYPE: PRT
<213> ORGANISM: Artificial Sequence
<220> FEATURE:
<223> OTHER INFORMATION: Synthetic

<400> SEQUENCE: 272

Gln Ser Val Leu Thr Gln Pro Pro Ser Val Ser Ala Ala Pro Gly Gln
1               5                   10                  15

Lys Val Thr Ile Ser Cys Ser Gly Ser Thr Ser Asn Ile Gly Asn Asn
            20                  25                  30

Tyr Val Ser Trp Tyr Gln Gln Leu Pro Gly Thr Ala Pro Lys Leu Val
        35                  40                  45

Ile Tyr Asp Asn Asp Asn Arg Pro Ser Gly Ile Pro Asp Arg Phe Ser
    50                  55                  60

Gly Ser Lys Ser Gly Thr Ser Ala Thr Leu Gly Ile Thr Gly Leu His
65                  70                  75                  80

Thr Gly Asp Glu Ala Asp Tyr Tyr Cys Gly Thr Trp Asp Ser Ser Leu
                85                  90                  95

Ser Ala Gly Val Phe Gly Gly Gly Thr Lys Leu Thr Val Leu Gly Ser
            100                 105                 110

Arg Gly Gly Gly Gly Ser Gly Gly Gly Ser Gly Gly Gly Gly Ser
        115                 120                 125

Leu Glu Met Ala Glu Val Gln Leu Val Glu Ser Gly Gly Gly Leu Val
    130                 135                 140

Gln Pro Gly Gly Ser Leu Arg Leu Ser Cys Ala Ala Ser Gly Phe Tyr
145                 150                 155                 160

Phe Ser Gly Phe Ala Met Ser Trp Val Arg Gln Ala Pro Gly Lys Gly
                165                 170                 175

Leu Glu Trp Leu Ser Val Val Phe Asn Asp Gly Ser Thr Thr Phe Tyr
            180                 185                 190

Ala Asp Ser Val Lys Gly Arg Phe Thr Met Ser Arg Asp Asp Ser Lys
        195                 200                 205

Asn Thr Ile Ser Leu Gln Met Asn Ser Leu Arg Ala Glu Asp Thr Ala
    210                 215                 220

Val Tyr Tyr Cys Ala Arg Gln Ser Pro Phe Tyr Phe Asp Gly Pro Tyr
225                 230                 235                 240

Asp Tyr Trp Gly Gln Gly Thr Leu Val Thr Val Ser Ser
                245                 250

<210> SEQ ID NO 273
<211> LENGTH: 333
<212> TYPE: DNA
<213> ORGANISM: Artificial Sequence
<220> FEATURE:
<223> OTHER INFORMATION: Synthetic

<400> SEQUENCE: 273
cagtctgtgt tgacgcagcc gccctcagtg tctgcggccc caggacaaaa ggtcaccatc      60
tcctgctctg gaagcacctc caacattgga ataattatg tatcctggta ccagcaactc     120
ccaggaacag cccccaaact cgtcatttat gacaatgata atcgaccctc agggattcct     180
gaccgattct ctggctccaa gtctggcacg tcagccaccc tgggcatcac cggactccac     240
actggggacg aggccgatta ttactgcgga catgggata gcagcctgag tgctggggtg     300
ttcggcggag ggaccaagct gaccgtccta ggt                                  333
```

<210> SEQ ID NO 274
<211> LENGTH: 111
<212> TYPE: PRT
<213> ORGANISM: Artificial Sequence
<220> FEATURE:
<223> OTHER INFORMATION: Synthetic

<400> SEQUENCE: 274

```
Gln Ser Val Leu Thr Gln Pro Pro Ser Val Ala Ala Pro Gly Gln
1               5                   10                  15

Lys Val Thr Ile Ser Cys Ser Gly Ser Thr Ser Asn Ile Gly Asn Asn
            20                  25                  30

Tyr Val Ser Trp Tyr Gln Leu Pro Gly Thr Ala Pro Lys Leu Val
            35                  40                  45

Ile Tyr Asp Asn Asp Asn Arg Pro Ser Gly Ile Pro Asp Arg Phe Ser
50                  55                  60

Gly Ser Lys Ser Gly Thr Ser Ala Thr Leu Gly Ile Thr Gly Leu His
65                  70                  75                  80

Thr Gly Asp Glu Ala Asp Tyr Tyr Cys Gly Thr Trp Asp Ser Ser Leu
                85                  90                  95

Ser Ala Gly Val Phe Gly Gly Gly Thr Lys Leu Thr Val Leu Gly
            100                 105                 110
```

<210> SEQ ID NO 275
<211> LENGTH: 363
<212> TYPE: DNA
<213> ORGANISM: Artificial Sequence
<220> FEATURE:
<223> OTHER INFORMATION: Synthetic

<400> SEQUENCE: 275

```
gaggtgcagc tggtggagtc tgggggaggc ttagtacagc cggggggggtc cctgagactc      60 tcctgtgcag cctctggatt ctactttagc ggctttgcca tgagctgggt ccgccaggct     120
ccagggaagg ggctggagtg gctctcagtt gtttttaacg atggcagtac cacattctat     180
gcagactccg tgaagggccg gttcaccatg tccagagatg attccaagaa cacaatttct     240
ctgcaaatga acagcctgag agccgaagac acggccgtat attactgtgc gcgccagtct     300
ccgttctact cgacggtcc gtacgattac tggggtcaag gtactctggt gaccgtctcc     360
tca                                                                   363
```

<210> SEQ ID NO 276
<211> LENGTH: 121
<212> TYPE: PRT
<213> ORGANISM: Artificial Sequence
<220> FEATURE:
<223> OTHER INFORMATION: Synthetic

<400> SEQUENCE: 276

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Tyr Phe Ser Gly Phe
            20                  25                  30

Ala Met Ser Trp Val Arg Gln Ala Pro Gly Lys Gly Leu Glu Trp Leu
            35                  40                  45

Ser Val Val Phe Asn Asp Gly Ser Thr Thr Phe Tyr Ala Asp Ser Val
50                  55                  60

Lys Gly Arg Phe Thr Met Ser Arg Asp Asp Ser Lys Asn Thr Ile Ser
65                  70                  75                  80
```

Leu Gln Met Asn Ser Leu Arg Ala Glu Asp Thr Ala Val Tyr Tyr Cys
                85                  90                  95

Ala Arg Gln Ser Pro Phe Tyr Phe Asp Gly Pro Tyr Asp Tyr Trp Gly
            100                 105                 110

Gln Gly Thr Leu Val Thr Val Ser Ser
        115                 120

<210> SEQ ID NO 277
<211> LENGTH: 756
<212> TYPE: DNA
<213> ORGANISM: Artificial Sequence
<220> FEATURE:
<223> OTHER INFORMATION: Synthetic

<400> SEQUENCE: 277

```
cagtctgtgt tgacgcagcc gccctcagtg tctgcggccc caggacagag ggtcaccatc      60
tcctgctctg gaaccagttc caacattggg aacagttatg tctcctggta ccagcagctc     120
ccaggaacag cccccaaact cctcattttt gacaataata agcgaccctc aggggttcct     180
gaccgattct ctggctccaa gtctggcacg tcagccaccc tgggcatcac cggactccag     240
actggcgaca aggccactta ttactgcgga acctgggata ccagcctgag ttctgtctgg     300
atgttcggcg agggaccaa ggtcaccgtc ctaggttcta gaggtggtgg tggtagcggc     360
ggcggcggct ctggtggtgg tggatccctc gagatggccc aggtgcagct ggtgcagtct     420
ggggctgagg tgaagaagcc tggggcctca gtgaaggttt cctgcaaggc atctggatac     480
accttcacca gctactatat gcactgggtg cgacaggccc ctggacaagg gcttgagtgg     540
atgggaataa tcaaccctag tggtggtagc acaagctacg cacagaagtt ccagggcaga     600
gtcaccatga ccagggacac gtccacgagc acagtctaca tggagctgag cagcctgaga     660
tctgaggaca ctgccgtgta ttactgtgcg cgcggttact acggtgacac tactggtgat     720
aactggggtc aaggtactct ggtgaccgtc tcctca                                756
```

<210> SEQ ID NO 278
<211> LENGTH: 252
<212> TYPE: PRT
<213> ORGANISM: Artificial Sequence
<220> FEATURE:
<223> OTHER INFORMATION: Synthetic

<400> SEQUENCE: 278

Gln Ser Val Leu Thr Gln Pro Pro Ser Val Ser Ala Ala Pro Gly Gln
1               5                   10                  15

Arg Val Thr Ile Ser Cys Ser Gly Thr Ser Ser Asn Ile Gly Asn Ser
            20                  25                  30

Tyr Val Ser Trp Tyr Gln Gln Leu Pro Gly Thr Ala Pro Lys Leu Leu
        35                  40                  45

Ile Phe Asp Asn Asn Lys Arg Pro Ser Gly Val Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Thr Tyr Tyr Cys Gly Thr Trp Asp Thr Ser Leu
                85                  90                  95

Ser Ser Val Trp Met Phe Gly Gly Gly Thr Lys Val Thr Val Leu Gly
            100                 105                 110

Ser Arg Gly Gly Gly Gly Ser Gly Gly Gly Gly Ser Gly Gly Gly Gly
        115                 120                 125

Ser Leu Glu Met Ala Gln Val Gln Leu Val Gln Ser Gly Ala Glu Val
    130                 135                 140

Lys Lys Pro Gly Ala Ser Val Lys Val Ser Cys Lys Ala Ser Gly Tyr
145                 150                 155                 160

Thr Phe Thr Ser Tyr Tyr Met His Trp Val Arg Gln Ala Pro Gly Gln
                165                 170                 175

Gly Leu Glu Trp Met Gly Ile Ile Asn Pro Ser Gly Gly Ser Thr Ser
            180                 185                 190

Tyr Ala Gln Lys Phe Gln Gly Arg Val Thr Met Thr Arg Asp Thr Ser
        195                 200                 205

Thr Ser Thr Val Tyr Met Glu Leu Ser Ser Leu Arg Ser Glu Asp Thr
    210                 215                 220

Ala Val Tyr Tyr Cys Ala Arg Gly Tyr Tyr Gly Asp Thr Thr Gly Asp
225                 230                 235                 240

Asn Trp Gly Gln Gly Thr Leu Val Thr Val Ser Ser
                245                 250

<210> SEQ ID NO 279
<211> LENGTH: 336
<212> TYPE: DNA
<213> ORGANISM: Artificial Sequence
<220> FEATURE:
<223> OTHER INFORMATION: Synthetic

<400> SEQUENCE: 279
cagtctgtgt tgacgcagcc gccctcagtg tctgcggccc caggacagag ggtcaccatc      60
tcctgctctg gaaccagttc caacattggg aacagttatg tctcctggta ccagcagctc     120
ccaggaacag cccccaaact cctcattttt gacaataata gcgaccctca gggggttcct     180
gaccgattct ctggctccaa gtctggcacg tcagccaccc tgggcatcac cggactccag     240
actggcgacg aggccactta ttactgcgga acctgggata ccagcctgag ttctgtctgg     300
atgttcggcg agggaccaa ggtcaccgtc ctaggt                                336

<210> SEQ ID NO 280
<211> LENGTH: 112
<212> TYPE: PRT
<213> ORGANISM: Artificial Sequence
<220> FEATURE:
<223> OTHER INFORMATION: Synthetic

<400> SEQUENCE: 280

Gln Ser Val Leu Thr Gln Pro Pro Ser Val Ser Ala Ala Pro Gly Gln
1               5                   10                  15

Arg Val Thr Ile Ser Cys Ser Gly Thr Ser Ser Asn Ile Gly Asn Ser
            20                  25                  30

Tyr Val Ser Trp Tyr Gln Gln Leu Pro Gly Thr Ala Pro Lys Leu Leu
        35                  40                  45

Ile Phe Asp Asn Asn Lys Arg Pro Ser Gly Val Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Thr Tyr Tyr Cys Gly Thr Trp Asp Thr Ser Leu
                85                  90                  95

Ser Ser Val Trp Met Phe Gly Gly Gly Thr Lys Val Thr Val Leu Gly
            100                 105                 110

-continued

<210> SEQ ID NO 281
<211> LENGTH: 357
<212> TYPE: DNA
<213> ORGANISM: Artificial Sequence
<220> FEATURE:
<223> OTHER INFORMATION: Synthetic

<400> SEQUENCE: 281

| caggtgcagc | tggtgcagtc | tggggctgag | gtgaagaagc | ctggggcctc | agtgaaggtt | 60 |
| tcctgcaagg | catctggata | caccttcacc | agctactata | tgcactgggt | gcgacaggcc | 120 |
| cctggacaag | ggcttgagtg | gatgggaata | atcaacccta | gtggtggtag | cacaagctac | 180 |
| gcacagaagt | tccagggcag | agtcaccatg | accagggaca | cgtccacgag | cacagtctac | 240 |
| atggagctga | gcagcctgag | atctgaggac | actgccgtgt | attactgtgc | gcgcggttac | 300 |
| tacggtgaca | ctactggtga | taactggggt | caaggtactc | tggtgaccgt | ctcctca | 357 |

<210> SEQ ID NO 282
<211> LENGTH: 119
<212> TYPE: PRT
<213> ORGANISM: Artificial Sequence
<220> FEATURE:
<223> OTHER INFORMATION: Synthetic

<400> SEQUENCE: 282

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Tyr Tyr Gly Asp Thr Thr Gly Asp Asn Trp Gly Gln Gly
            100                 105                 110

Thr Leu Val Thr Val Ser Ser
        115

<210> SEQ ID NO 283
<211> LENGTH: 744
<212> TYPE: DNA
<213> ORGANISM: Artificial Sequence
<220> FEATURE:
<223> OTHER INFORMATION: Synthetic

<400> SEQUENCE: 283

| cagtctgtgt | tgacgcagcc | gccctcagtg | tctgcggccc | caggacagaa | ggtcaccatc | 60 |
| tcctgctctg | gaagcagctc | caacattggg | aatgattatg | tatcgtggta | ccagcaactc | 120 |
| ccaggaacag | cccccaaact | cctcatttat | gaaaatgatc | agcgaccctc | agggattcct | 180 |
| gaccgattct | ctggctccaa | gtctggcacg | tcagccaccc | tgggcatcac | cggactccag | 240 |
| actggggacg | aggccactta | ttactgcgga | acttgggata | gcagcctgaa | tggtggggtg | 300 |
| ttcggcagag | ggaccaagct | gaccgtccta | ggttctagag | gtggtggtgg | tagcggcggc | 360 |
| ggcggctctg | gtggtggtgg | atccctcgag | atggcccagg | tgcagctggt | gcagtctggg | 420 |

```
gctgaggtga agaagcctgg ggcctcagtg aaggtctcct gcaaggcatc tggatacacc    480
ttcaccagct actatatgca ctgggtgcga caggcccctg gacaagggct tgagtggatg    540
ggaataatca accctagtgg tggtagcaca agctacgcac agaagttcca gggcagagtc    600
accatgacca gggacacgtc cacgagcaca gtctacatgg agctgagcag gctgagatct    660
gacgacacgg ccgtgtatta ctgtgcgcgc ggttacggta cttctgattc ttggggtcaa    720
ggtactctgg tgaccgtctc ctca                                           744
```

<210> SEQ ID NO 284
<211> LENGTH: 248
<212> TYPE: PRT
<213> ORGANISM: Artificial Sequence
<220> FEATURE:
<223> OTHER INFORMATION: Synthetic

<400> SEQUENCE: 284

```
Gln Ser Val Leu Thr Gln Pro Pro Ser Val Ala Ala Pro Gly Gln
1               5                   10                  15

Lys Val Thr Ile Ser Cys Ser Gly Ser Ser Asn Ile Gly Asn Asp
            20                  25                  30

Tyr Val Ser Trp Tyr Gln Gln Leu Pro Gly Thr Ala Pro Lys Leu Leu
        35                  40                  45

Ile Tyr Glu Asn Asp Gln Arg Pro Ser Gly Ile Pro Asp Arg Phe Ser
50                  55                  60

Gly Ser Lys Ser Gly Thr Ser Ala Thr Leu Gly Ile Thr Gly Leu Gln
65                  70                  75                  80

Thr Gly Asp Glu Ala Thr Tyr Tyr Cys Gly Thr Trp Asp Ser Ser Leu
                85                  90                  95

Asn Gly Gly Val Phe Gly Arg Gly Thr Lys Leu Thr Val Leu Gly Ser
            100                 105                 110

Arg Gly Gly Gly Gly Ser Gly Gly Gly Ser Gly Gly Gly Gly Ser
            115                 120                 125

Leu Glu Met Ala Gln Val Gln Leu Val Gln Ser Gly Ala Glu Val Lys
130                 135                 140

Lys Pro Gly Ala Ser Val Lys Val Ser Cys Lys Ala Ser Gly Tyr Thr
145                 150                 155                 160

Phe Thr Ser Tyr Tyr Met His Trp Val Arg Gln Ala Pro Gly Gln Gly
                165                 170                 175

Leu Glu Trp Met Gly Ile Ile Asn Pro Ser Gly Gly Ser Thr Ser Tyr
            180                 185                 190

Ala Gln Lys Phe Gln Gly Arg Val Thr Met Thr Arg Asp Thr Ser Thr
        195                 200                 205

Ser Thr Val Tyr Met Glu Leu Ser Arg Leu Arg Ser Asp Asp Thr Ala
    210                 215                 220

Val Tyr Tyr Cys Ala Arg Gly Tyr Gly Thr Ser Asp Ser Trp Gly Gln
225                 230                 235                 240

Gly Thr Leu Val Thr Val Ser Ser
                245
```

<210> SEQ ID NO 285
<211> LENGTH: 333
<212> TYPE: DNA
<213> ORGANISM: Artificial Sequence
<220> FEATURE:
<223> OTHER INFORMATION: Synthetic

<400> SEQUENCE: 285

```
cagtctgtgt tgacgcagcc gccctcagtg tctgcggccc caggacagaa ggtcaccatc        60
tcctgctctg gaagcagctc caacattggg aatgattatg tatcgtggta ccagcaactc       120
ccaggaacag ccccaaact cctcatttat gaaaatgatc agcgaccctc aggattcct        180
```
(note: line 120 as shown)

```
ccaggaacag ccccaaact cctcatttat gaaaatgatc agcgaccctc aggattcct        180 gaccgattct ctggctccaa gtctggcacg tcagccaccc tgggcatcac cggactccag       240
actggggacg aggccactta ttactgcgga acttgggata gcagcctgaa tggtggggtg       300
ttcggcagag ggaccaagct gaccgtccta ggt                                     333
```

<210> SEQ ID NO 286
<211> LENGTH: 111
<212> TYPE: PRT
<213> ORGANISM: Artificial Sequence
<220> FEATURE:
<223> OTHER INFORMATION: Synthetic

<400> SEQUENCE: 286

Gln Ser Val Leu Thr Gln Pro Pro Ser Val Ala Ala Pro Gly Gln
1               5                   10                  15

Lys Val Thr Ile Ser Cys Ser Gly Ser Ser Asn Ile Gly Asn Asp
            20                  25                  30

Tyr Val Ser Trp Tyr Gln Gln Leu Pro Gly Thr Ala Pro Lys Leu Leu
        35                  40                  45

Ile Tyr Glu Asn Asp Gln Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Thr Tyr Tyr Cys Gly Thr Trp Asp Ser Ser Leu
                85                  90                  95

Asn Gly Gly Val Phe Gly Arg Gly Thr Lys Leu Thr Val Leu Gly
            100                 105                 110

<210> SEQ ID NO 287
<211> LENGTH: 348
<212> TYPE: DNA
<213> ORGANISM: Artificial Sequence
<220> FEATURE:
<223> OTHER INFORMATION: Synthetic

<400> SEQUENCE: 287

```
caggtgcagc tggtgcagtc tggggctgag gtgaagaagc ctggggcctc agtgaaggtc        60
tcctgcaagg catctggata caccttcacc agctactata tgcactgggt gcgacaggcc       120
cctggacaag gcttgagtg gatgggaata atcaaccta gtggtggtag cacaagctac        180
gcacagaagt tccagggcag agtcaccatg accagggaca cgtccacgag cacagtctac       240
atggagctga gcaggctgag atctgacgac acggccgtgt attactgtgc gcgcggttac       300
ggtacttctg attcttgggg tcaaggtact ctggtgaccg tctcctca                    348
```

<210> SEQ ID NO 288
<211> LENGTH: 116
<212> TYPE: PRT
<213> ORGANISM: Artificial Sequence
<220> FEATURE:
<223> OTHER INFORMATION: Synthetic

<400> SEQUENCE: 288

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Arg Leu Arg Ser Asp Asp Thr Ala Val Tyr Tyr Cys
                85                  90                  95

Ala Arg Gly Tyr Gly Thr Ser Asp Ser Trp Gly Gln Gly Thr Leu Val
            100                 105                 110

Thr Val Ser Ser
        115

<210> SEQ ID NO 289
<211> LENGTH: 747
<212> TYPE: DNA
<213> ORGANISM: Artificial Sequence
<220> FEATURE:
<223> OTHER INFORMATION: Synthetic

<400> SEQUENCE: 289
cagtctgtgt tgacgcagcc gccctcagcg tctgagaccc ccggggcagag ggtcaccatc    60 tcttgttctg gaagcagctc caacatcgga agtaggactg taaactggta ccagcagctc   120
ccaggaacgg ccccccaaact cctcatctat agtaatactc agcggccctc agggtccct   180 gaccgattct ctggctccaa gtctggcacc tcagcctccc tggccatcag tgggctccag   240
tctgaggatg aggctgatta ctactgtgca gcatgggatg acagtctgaa tggtcaggtc   300
ttcggaactg ggaccaaggt caccgtccta ggttctagag gtggtggtgg tagcggcggc   360
ggcggctctg gtggtggtgg atccctcgag atggccgagg tccagctggt gcagtctggg   420
gctgaggtga agaagcctgg gtcctcggtg aaggtctcct gcaaggcttc tggaggcacc   480
ttcaacgact atagtgtcag ctgggtgcga cagtccccctg acaagggcct gagtggatg   540 ggaaggatca tccccgtcct tgatatgaca accgtcgcac agaaattcca gggcagagtc   600
acaattaacg cggacaaatc gacgagcaca gtgaacatgg agctgagcag cctcagatct   660
gatgacacgg ccgtgtatta ctgtgcgcgc tactacggtg actactctga tccgtggggt   720
caaggtactc tggtgaccgt ctcctca                                        747

<210> SEQ ID NO 290
<211> LENGTH: 249
<212> TYPE: PRT
<213> ORGANISM: Artificial Sequence
<220> FEATURE:
<223> OTHER INFORMATION: Synthetic

<400> SEQUENCE: 290

Gln Ser Val Leu Thr Gln Pro Pro Ser Ala Ser Glu Thr Pro Gly Gln
1               5                   10                  15

Arg Val Thr Ile Ser Cys Ser Gly Ser Ser Ser Asn Ile Gly Ser Arg
            20                  25                  30

Thr Val Asn Trp Tyr Gln Gln Leu Pro Gly Thr Ala Pro Lys Leu Leu
        35                  40                  45

Ile Tyr Ser Asn Thr Gln Arg Pro Ser Gly Val Pro Asp Arg Phe Ser
    50                  55                  60

```
Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Asp Ser Leu
                 85                  90                  95

Asn Gly Gln Val Phe Gly Thr Gly Thr Lys Val Thr Val Leu Gly Ser
            100                 105                 110

Arg Gly Gly Gly Gly Ser Gly Gly Gly Ser Gly Gly Gly Gly Ser
        115                 120                 125

Leu Glu Met Ala Glu Val Gln Leu Val Gln Ser Gly Ala Glu Val Lys
    130                 135                 140

Lys Pro Gly Ser Ser Val Lys Val Ser Cys Lys Ala Ser Gly Gly Thr
145                 150                 155                 160

Phe Asn Asp Tyr Ser Val Ser Trp Val Arg Gln Ser Pro Gly Gln Gly
                165                 170                 175

Leu Glu Trp Met Gly Arg Ile Ile Pro Val Leu Asp Met Thr Thr Val
            180                 185                 190

Ala Gln Lys Phe Gln Gly Arg Val Thr Ile Asn Ala Asp Lys Ser Thr
        195                 200                 205

Ser Thr Val Asn Met Glu Leu Ser Ser Leu Arg Ser Asp Asp Thr Ala
210                 215                 220

Val Tyr Tyr Cys Ala Arg Tyr Tyr Gly Asp Tyr Ser Asp Pro Trp Gly
225                 230                 235                 240

Gln Gly Thr Leu Val Thr Val Ser Ser
                245
```

<210> SEQ ID NO 291
<211> LENGTH: 333
<212> TYPE: DNA
<213> ORGANISM: Artificial Sequence
<220> FEATURE:
<223> OTHER INFORMATION: Synthetic

<400> SEQUENCE: 291

```
cagtctgtgt tgacgcagcc gccctcagcg tctgagaccc ccgggcagag ggtcaccatc    60
tcttgttctg gaagcagctc caacatcgga agtaggactg taaactggta ccagcagctc   120
ccaggaacgg cccccaaact cctcatctat agtaatactc agcggccctc aggggtccct   180
gaccgattct ctggctccaa gtctggcacc tcagcctccc tggccatcag tgggctccag   240
tctgaggatg aggctgatta ctactgtgca gcatgggatg acagtctgaa tggtcaggtc   300
ttcggaactg ggaccaaggt caccgtccta ggt                                333
```

<210> SEQ ID NO 292
<211> LENGTH: 111
<212> TYPE: PRT
<213> ORGANISM: Artificial Sequence
<220> FEATURE:
<223> OTHER INFORMATION: Synthetic

<400> SEQUENCE: 292

```
Gln Ser Val Leu Thr Gln Pro Pro Ser Ala Ser Glu Thr Pro Gly Gln
  1               5                  10                  15

Arg Val Thr Ile Ser Cys Ser Gly Ser Ser Ser Asn Ile Gly Ser Arg
             20                  25                  30

Thr Val Asn Trp Tyr Gln Gln Leu Pro Gly Thr Ala Pro Lys Leu Leu
         35                  40                  45

Ile Tyr Ser Asn Thr Gln Arg Pro Ser Gly Val Pro Asp Arg Phe Ser
 50                  55                  60
```

```
Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Gln Val Phe Gly Thr Gly Thr Lys Val Thr Val Leu Gly
            100                 105                 110

<210> SEQ ID NO 293
<211> LENGTH: 351
<212> TYPE: DNA
<213> ORGANISM: Artificial Sequence
<220> FEATURE:
<223> OTHER INFORMATION: Synthetic

<400> SEQUENCE: 293
gaggtccagc tggtgcagtc tggggctgag gtgaagaagc ctgggtcctc ggtgaaggtc      60
tcctgcaagg cttctggagg caccttcaac gactatagtg tcagctgggt gcgacagtcc     120
cctggacaag ggcttgagtg gatgggaagg atcatcccg tccttgatat gacaaccgtc      180
gcacagaaat tccagggcag agtcacaatt aacgcggaca atcgacgag cacagtgaac      240 atggagctga gcagcctcag atctgatgac acggccgtgt attactgtgc gcgctactac     300
ggtgactact ctgatccgtg gggtcaaggt actctggtga ccgtctcctc a              351

<210> SEQ ID NO 294
<211> LENGTH: 117
<212> TYPE: PRT
<213> ORGANISM: Artificial Sequence
<220> FEATURE:
<223> OTHER INFORMATION: Synthetic

<400> SEQUENCE: 294

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Asp Tyr
            20                  25                  30

Ser Val Ser Trp Val Arg Gln Ser Pro Gly Gln Gly Leu Glu Trp Met
        35                  40                  45

Gly Arg Ile Ile Pro Val Leu Asp Met Thr Thr Val Ala Gln Lys Phe
    50                  55                  60

Gln Gly Arg Val Thr Ile Asn Ala Asp Lys Ser Thr Ser Thr Val Asn
65                  70                  75                  80

Met Glu Leu Ser Ser Leu Arg Ser Asp Asp Thr Ala Val Tyr Tyr Cys
                85                  90                  95

Ala Arg Tyr Tyr Gly Asp Tyr Ser Asp Pro Trp Gly Gln Gly Thr Leu
            100                 105                 110

Val Thr Val Ser Ser
        115

<210> SEQ ID NO 295
<211> LENGTH: 744
<212> TYPE: DNA
<213> ORGANISM: Artificial Sequence
<220> FEATURE:
<223> OTHER INFORMATION: Synthetic

<400> SEQUENCE: 295
cagtctgtgt tgactcagcc gccctcagtg tctgcggccc caggacagaa ggtcaccatc      60
tcctgctcgg gcagcaactc gaacattgaa cataattatg tctcctggta tcagcaattc     120
```

```
ccaggaacag cccccaaact cctcatttat gacaatgata agcgaccctc agggattcct    180
gaccgattct ctggctccaa gtctggcacg tcagccaccc tgggcatcac cggactccag    240
actggggacg aggccgaata ttactgcgga acatgggata cacccctgag ttcttttgtc    300
ttcggaagtg ggaccaaggt caccgtccta ggttctagag gtggtggtgg tagcggcggc    360
ggcggctctg gtggtggtgg atccctcgag atggcccagg tgcagctggt gcagtctggg    420
ggaggcgtgg tccagcctgg gaggtccctg agactctcct gtgcagcctc tggattcacc    480
ttcagtagct atagcatgaa ctgggtccgc caggctccag ggaaggggct ggagtgggtc    540
tcagttattt ctagcggtgg taacacatac tacgcagact ccgtgaaggg ccgattcacc    600
atctccagag acaattccaa gaacacgctg tatcttcaaa tgaacagcct gagagccggg    660
gacactgccg tgtattactg tgcgcgcgaa ggttacatgt acgttgatca ttggggtcaa    720
ggtactctgg tgaccgtctc ctca    744
```

<210> SEQ ID NO 296
<211> LENGTH: 248
<212> TYPE: PRT
<213> ORGANISM: Artificial Sequence
<220> FEATURE:
<223> OTHER INFORMATION: Synthetic

<400> SEQUENCE: 296

```
Gln Ser Val Leu Thr Gln Pro Pro Ser Val Ser Ala Ala Pro Gly Gln
1               5                   10                  15

Lys Val Thr Ile Ser Cys Ser Gly Ser Asn Ser Asn Ile Glu His Asn
            20                  25                  30

Tyr Val Ser Trp Tyr Gln Gln Phe Pro Gly Thr Ala Pro Lys Leu Leu
        35                  40                  45

Ile Tyr Asp Asn Asp Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Glu Tyr Tyr Cys Gly Thr Trp Asp Asn Thr Leu
                85                  90                  95

Ser Ser Phe Val Phe Gly Ser Gly Thr Lys Val Thr Val Leu Gly Ser
            100                 105                 110

Arg Gly Gly Gly Gly Ser Gly Gly Gly Gly Ser Gly Gly Gly Gly Ser
        115                 120                 125

Leu Glu Met Ala Gln Val Gln Leu Val Gln Ser Gly Gly Gly Val Val
    130                 135                 140

Gln Pro Gly Arg Ser Leu Arg Leu Ser Cys Ala Ala Ser Gly Phe Thr
145                 150                 155                 160

Phe Ser Ser Tyr Ser Met Asn Trp Val Arg Gln Ala Pro Gly Lys Gly
                165                 170                 175

Leu Glu Trp Val Ser Val Ile Ser Ser Gly Gly Asn Thr Tyr Tyr Ala
            180                 185                 190

Asp Ser Val Lys Gly Arg Phe Thr Ile Ser Arg Asp Asn Ser Lys Asn
        195                 200                 205

Thr Leu Tyr Leu Gln Met Asn Ser Leu Arg Ala Gly Asp Thr Ala Val
    210                 215                 220

Tyr Tyr Cys Ala Arg Glu Gly Tyr Met Tyr Val Asp His Trp Gly Gln
225                 230                 235                 240

Gly Thr Leu Val Thr Val Ser Ser
                245
```

<210> SEQ ID NO 297
<211> LENGTH: 333
<212> TYPE: DNA
<213> ORGANISM: Artificial Sequence
<220> FEATURE:
<223> OTHER INFORMATION: Synthetic

<400> SEQUENCE: 297

```
cagtctgtgt tgactcagcc gccctcagtg tctgcggccc caggacagaa ggtcaccatc      60
tcctgctcgg gcagcaactc gaacattgaa cataattatg tctcctggta tcagcaattc     120
ccaggaacag cccccaaact cctcatttat gacaatgata agcgaccctc agggattcct     180
gaccgattct ctggctccaa gtctggcacg tcagccaccc tgggcatcac cggactccag     240
actggggacg aggccgaata ttactgcgga acatgggata cacccctgag ttcttttgtc     300
ttcggaagtg ggaccaaggt caccgtccta ggt                                   333
```

<210> SEQ ID NO 298
<211> LENGTH: 111
<212> TYPE: PRT
<213> ORGANISM: Artificial Sequence
<220> FEATURE:
<223> OTHER INFORMATION: Synthetic

<400> SEQUENCE: 298

Gln Ser Val Leu Thr Gln Pro Pro Ser Val Ser Ala Ala Pro Gly Gln
1               5                   10                  15
Lys Val Thr Ile Ser Cys Ser Gly Ser Asn Ser Asn Ile Glu His Asn
            20                  25                  30
Tyr Val Ser Trp Tyr Gln Gln Phe Pro Gly Thr Ala Pro Lys Leu Leu
        35                  40                  45
Ile Tyr Asp Asn Asp Lys Arg Pro Ser Gly Ile Pro Asp Arg Phe Ser
    50                  55                  60
Gly Ser Lys Ser Gly Thr Ser Ala Thr Leu Gly Ile Thr Gly Leu Gln
65                  70                  75                  80
Thr Gly Asp Glu Ala Glu Tyr Tyr Cys Gly Thr Trp Asp Asn Thr Leu
                85                  90                  95
Ser Ser Phe Val Phe Gly Ser Gly Thr Lys Val Thr Val Leu Gly
            100                 105                 110

<210> SEQ ID NO 299
<211> LENGTH: 348
<212> TYPE: DNA
<213> ORGANISM: Artificial Sequence
<220> FEATURE:
<223> OTHER INFORMATION: Synthetic

<400> SEQUENCE: 299

```
caggtgcagc tggtgcagtc tggggggaggc gtggtccagc ctgggaggtc cctgagactc      60
tcctgtgcag cctctggatt caccttcagt agctatagca tgaactgggt ccgccaggct     120
ccagggaagg ggctggagtg ggtctcagtt atttctagcg gtggtaacac atactacgca     180
gactccgtga aggccgatt caccatctcc agagacaatt ccaagaacac gctgtatctt     240
caaatgaaca gcctgagagc cggggacact gccgtgtatt actgtgcgcg cgaaggttac     300
atgtacgttg atcattgggg tcaaggtact ctggtgaccg tctcctca                   348
```

<210> SEQ ID NO 300

<211> LENGTH: 116
<212> TYPE: PRT
<213> ORGANISM: Artificial Sequence
<220> FEATURE:
<223> OTHER INFORMATION: Synthetic

<400> SEQUENCE: 300

```
Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Val Ile Ser Ser Gly Gly Asn Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Gly Asp Thr Ala Val Tyr Tyr Cys Ala
                85                  90                  95

Arg Glu Gly Tyr Met Tyr Val Asp His Trp Gly Gln Gly Thr Leu Val
            100                 105                 110

Thr Val Ser Ser
        115
```

<210> SEQ ID NO 301
<211> LENGTH: 741
<212> TYPE: DNA
<213> ORGANISM: Artificial Sequence
<220> FEATURE:
<223> OTHER INFORMATION: Synthetic

<400> SEQUENCE: 301

| | | | | | |
|---|---|---|---|---|---|
| gacatccagt | tgacccagtc | tccatcctcc | ctgtctgcat | ctgtaggaga | cagagtcacc | 60 |
| atcacttgcc | gggcaagtca | gagcattagc | agctatttaa | attggtatca | gcagaaacca | 120 |
| gggaaagccc | ctaagctcct | gatctatgct | gcatccagtt | tgcaaagtgg | ggtcccatca | 180 |
| aggttcagtg | gcagtggatc | tgggacagat | ttcactctcg | ccatcagcag | tctgcaacct | 240 |
| gaagattttg | caacttactt | ctgtcaacag | agttacagtt | ttccgctcac | tttcggcgga | 300 |
| gggaccaagc | tggagatcaa | acgttctaga | ggtggtggtg | gtagcggcgg | cggcggctct | 360 |
| ggtggtggtg | gatccctcga | gatggcccag | gtgcagctgg | tgcagtctgg | ggctgaggtg | 420 |
| aagaagcctg | ggcctcagt | gagggtctcc | tgcaaggcat | ctgggaacag | cttcagcacc | 480 |
| tattatatcc | actgggtgcg | acaggcccct | ggacaaggac | ttgagtggat | gggaataatc | 540 |
| aaccctacta | ttggtagcag | agtctatgca | ccgaagttcc | agggcagagt | caccatgacc | 600 |
| agggacacgt | ccacgagcac | agtctacatg | gaactgagca | gcctgacatc | tgaggacact | 660 |
| gccgtgtatt | actgtgcgcg | ctctgttact | tgggttctga | agatggttg | gggtcaaggt | 720 |
| actctggtga | ccgtctcctc | a | | | | 741 |

<210> SEQ ID NO 302
<211> LENGTH: 247
<212> TYPE: PRT
<213> ORGANISM: Artificial Sequence
<220> FEATURE:
<223> OTHER INFORMATION: Synthetic

<400> SEQUENCE: 302

Asp Ile Gln Leu Thr Gln Ser Pro Ser Ser Leu Ser Ala Ser Val Gly

```
                1               5                   10                  15
Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
                35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Ala Ile Ser Ser Leu Gln Pro
65                  70                  75                  80

Glu Asp Phe Ala Thr Tyr Phe Cys Gln Gln Ser Tyr Ser Leu Pro Leu
                85                  90                  95

Thr Phe Gly Gly Gly Thr Lys Leu Glu Ile Lys Arg Ser Arg Gly Gly
                100                 105                 110

Gly Gly Ser Gly Gly Gly Ser Gly Gly Gly Ser Leu Glu Met
                115                 120                 125

Ala Gln Val Gln Leu Val Gln Ser Gly Ala Glu Val Lys Lys Pro Gly
            130                 135                 140

Ala Ser Val Arg Val Ser Cys Lys Ala Ser Gly Asn Ser Phe Ser Thr
145                 150                 155                 160

Tyr Tyr Ile His Trp Val Arg Gln Ala Pro Gly Gln Gly Leu Glu Trp
                165                 170                 175

Met Gly Ile Ile Asn Pro Thr Ile Gly Ser Arg Val Tyr Ala Pro Lys
                180                 185                 190

Phe Gln Gly Arg Val Thr Met Thr Arg Asp Thr Ser Thr Ser Thr Val
            195                 200                 205

Tyr Met Glu Leu Ser Ser Leu Thr Ser Glu Asp Thr Ala Val Tyr Tyr
        210                 215                 220

Cys Ala Arg Ser Val Thr Trp Val Leu Lys Asp Gly Trp Gly Gln Gly
225                 230                 235                 240

Thr Leu Val Thr Val Ser Ser
                245
```

<210> SEQ ID NO 303
<211> LENGTH: 324
<212> TYPE: DNA
<213> ORGANISM: Artificial Sequence
<220> FEATURE:
<223> OTHER INFORMATION: Synthetic

<400> SEQUENCE: 303

```
gacatccagt tgacccagtc tccatcctcc ctgtctgcat ctgtaggaga cagagtcacc      60
atcacttgcc gggcaagtca gagcattagc agctatttaa attggtatca gcagaaacca     120
gggaaagccc ctaagctcct gatctatgct gcatccagtt tgcaaagtgg ggtcccatca     180
aggttcagtg gcagtggatc tgggacagat ttcactctcg ccatcagcag tctgcaacct     240
gaagattttg caacttactt ctgtcaacag agttacagtc ttccgctcac tttcggcgga     300
gggaccaagc tggagatcaa acgt                                            324
```

<210> SEQ ID NO 304
<211> LENGTH: 108
<212> TYPE: PRT
<213> ORGANISM: Artificial Sequence
<220> FEATURE:
<223> OTHER INFORMATION: Synthetic

<400> SEQUENCE: 304

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Ala Ile Ser Ser Leu Gln Pro
65                  70                  75                  80

Glu Asp Phe Ala Thr Tyr Phe Cys Gln Gln Ser Tyr Ser Leu Pro Leu
                85                  90                  95

Thr Phe Gly Gly Gly Thr Lys Leu Glu Ile Lys Arg
            100                 105
```

<210> SEQ ID NO 305
<211> LENGTH: 354
<212> TYPE: DNA
<213> ORGANISM: Artificial Sequence
<220> FEATURE:
<223> OTHER INFORMATION: Synthetic

<400> SEQUENCE: 305

```
caggtgcagc tggtgcagtc tggggctgag gtgaagaagc ctggggcctc agtgagggtc      60
tcctgcaagg catctgggaa cagcttcagc acctattata tccactgggt gcgacaggcc     120
cctggacaag gacttgagtg gatgggaata atcaaccctt ctattggtag cagagtctat     180
gcaccgaagt tccagggcag agtcaccatg accagggaca cgtccacgag cacagtctac     240
atggaactga gcagcctgac atctgaggac actgccgtgt attactgtgc gcgctctgtt     300
acttgggttc tgaaagatgg ttggggtcaa ggtactctgg tgaccgtctc ctca           354
```

<210> SEQ ID NO 306
<211> LENGTH: 118
<212> TYPE: PRT
<213> ORGANISM: Artificial Sequence
<220> FEATURE:
<223> OTHER INFORMATION: Synthetic

<400> SEQUENCE: 306

```
Gln Val Gln Leu Val Gln Ser Gly Ala Glu Val Lys Lys Pro Gly Ala
1               5                   10                  15

Ser Val Arg Val Ser Cys Lys Ala Ser Gly Asn Ser Phe Ser Thr Tyr
            20                  25                  30

Tyr Ile His Trp Val Arg Gln Ala Pro Gly Gln Gly Leu Glu Trp Met
        35                  40                  45

Gly Ile Ile Asn Pro Thr Ile Gly Ser Arg Val Tyr Ala Pro Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Thr Ser Glu Asp Thr Ala Val Tyr Tyr Cys
                85                  90                  95

Ala Arg Ser Val Thr Trp Val Leu Lys Asp Gly Trp Gly Gln Gly Thr
            100                 105                 110

Leu Val Thr Val Ser Ser
        115
```

<210> SEQ ID NO 307

<211> LENGTH: 744
<212> TYPE: DNA
<213> ORGANISM: Artificial Sequence
<220> FEATURE:
<223> OTHER INFORMATION: Synthetic

<400> SEQUENCE: 307

```
gacatccagt tgacccagtc tccatcctcc ctgtctgcat ctgttggaga cagagtcacc      60
atcacttgcc gggcgagtca ggacattggc aattatgtag cctggtatca gcagaaagta     120
gggaaagttc ctaacctcct gatctatgat gcatccactt tgcaatcagg agtcccatct     180
cggttcagcg gcagtggatc tcggacagag ttcactctca ccatcagcag tctgcagcct     240
gaagatgttg caacttatta ctgtcaaaag tataacactg cccctgggtt cggccaaggg     300
accaaggtgg aaatcaaacg ttctagaggt ggtggtggta gcggcggcgg cggctctggt     360
ggtggtggat ccctcgagat ggcccagatg cagctggtgc agtctggggc tgaggtgaag     420
aagcctgggg cctcagtgaa ggtttcctgc aaggcatctg gatacacctt caccagctac     480
tatatgcact gggtgcgaca ggcccctgga caagggcttg agtggatggg aataatcaac     540
cctagtggtg gtagcacaag ctacgcacag aagttccagg gcagagtcac catgaccagg     600
gacacgtcca cgagcacagt ctacatggag ctgagcagcc tgagatctga ggacacggcc     660
gtgtattact gtgcgcgctc ttctatcggt tggctgtctt acctggatgc ttggggtcaa     720
ggtactctgg tgaccgtctc ctca                                            744
```

<210> SEQ ID NO 308
<211> LENGTH: 248
<212> TYPE: PRT
<213> ORGANISM: Artificial Sequence
<220> FEATURE:
<223> OTHER INFORMATION: Synthetic

<400> SEQUENCE: 308

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Asp Ile Gly Asn Tyr
            20                  25                  30

Val Ala Trp Tyr Gln Gln Lys Val Gly Lys Val Pro Asn Leu Leu Ile
        35                  40                  45

Tyr Asp Ala Ser Thr Leu Gln Ser Gly Val Pro Ser Arg Phe Ser Gly
    50                  55                  60

Ser Gly Ser Arg Thr Glu Phe Thr Leu Thr Ile Ser Ser Leu Gln Pro
65                  70                  75                  80

Glu Asp Val Ala Thr Tyr Tyr Cys Gln Lys Tyr Asn Thr Ala Pro Gly
                85                  90                  95

Phe Gly Gln Gly Thr Lys Val Glu Ile Lys Arg Ser Arg Gly Gly Gly
            100                 105                 110

Gly Ser Gly Gly Gly Gly Ser Gly Gly Gly Gly Ser Leu Glu Met Ala
        115                 120                 125

Gln Met Gln Leu Val Gln Ser Gly Ala Glu Val Lys Lys Pro Gly Ala
    130                 135                 140

Ser Val Lys Val Ser Cys Lys Ala Ser Gly Tyr Thr Phe Thr Ser Tyr
145                 150                 155                 160

Tyr Met His Trp Val Arg Gln Ala Pro Gly Gln Gly Leu Glu Trp Met
                165                 170                 175

Gly Ile Ile Asn Pro Ser Gly Gly Ser Thr Ser Tyr Ala Gln Lys Phe
            180                 185                 190
```

Gln Gly Arg Val Thr Met Thr Arg Asp Thr Ser Thr Ser Thr Val Tyr
        195                 200                 205

Met Glu Leu Ser Ser Leu Arg Ser Glu Asp Thr Ala Val Tyr Tyr Cys
        210                 215                 220

Ala Arg Ser Ser Ile Gly Trp Leu Ser Tyr Leu Asp Ala Trp Gly Gln
225                 230                 235                 240

Gly Thr Leu Val Thr Val Ser Ser
                245

<210> SEQ ID NO 309
<211> LENGTH: 321
<212> TYPE: DNA
<213> ORGANISM: Artificial Sequence
<220> FEATURE:
<223> OTHER INFORMATION: Synthetic

<400> SEQUENCE: 309
gacatccagt tgacccagtc tccatcctcc ctgtctgcat ctgttggaga cagagtcacc      60
atcacttgcc gggcgagtca ggacattggc aattatgtag cctggtatca gcagaaagta     120
gggaaagttc ctaacctcct gatctatgat gcatccactt tgcaatcagg agtcccatct     180
cggttcagcg gcagtggatc tcggacagag ttcactctca ccatcagcag tctgcagcct     240
gaagatgttg caacttatta ctgtcaaaag tataacactg ccctgggtt cggccaaggg      300 accaaggtgg aaatcaaacg t                                               321

<210> SEQ ID NO 310
<211> LENGTH: 107
<212> TYPE: PRT
<213> ORGANISM: Artificial Sequence
<220> FEATURE:
<223> OTHER INFORMATION: Synthetic

<400> SEQUENCE: 310

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Asp Ile Gly Asn Tyr
            20                  25                  30

Val Ala Trp Tyr Gln Gln Lys Val Gly Lys Val Pro Asn Leu Leu Ile
        35                  40                  45

Tyr Asp Ala Ser Thr Leu Gln Ser Gly Val Pro Ser Arg Phe Ser Gly
    50                  55                  60

Ser Gly Ser Arg Thr Glu Phe Thr Leu Thr Ile Ser Ser Leu Gln Pro
65                  70                  75                  80

Glu Asp Val Ala Thr Tyr Tyr Cys Gln Lys Tyr Asn Thr Ala Pro Gly
                85                  90                  95

Phe Gly Gln Gly Thr Lys Val Glu Ile Lys Arg
            100                 105

<210> SEQ ID NO 311
<211> LENGTH: 360
<212> TYPE: DNA
<213> ORGANISM: Artificial Sequence
<220> FEATURE:
<223> OTHER INFORMATION: Synthetic

<400> SEQUENCE: 311
cagatgcagc tggtgcagtc tggggctgag gtgaagaagc ctggggcctc agtgaaggtt      60
tcctgcaagg catctggata caccttcacc agctactata tgcactgggt gcgacaggcc     120

```
cctggacaag ggcttgagtg gatgggaata tcaaccccta gtggtggtag cacaagctac    180
gcacagaagt tccagggcag agtcaccatg accagggaca cgtccacgag cacagtctac    240
atggagctga gcagcctgag atctgaggac acggccgtgt attactgtgc gcgctcttct    300
atcggttggc tgtcttacct ggatgcttgg ggtcaaggta ctctggtgac cgtctcctca    360
```

<210> SEQ ID NO 312
<211> LENGTH: 120
<212> TYPE: PRT
<213> ORGANISM: Artificial Sequence
<220> FEATURE:
<223> OTHER INFORMATION: Synthetic

<400> SEQUENCE: 312

```
Gln Met Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Ser Ile Gly Trp Leu Ser Tyr Leu Asp Ala Trp Gly Gln
            100                 105                 110

Gly Thr Leu Val Thr Val Ser Ser
        115                 120
```

<210> SEQ ID NO 313
<211> LENGTH: 759
<212> TYPE: DNA
<213> ORGANISM: Artificial Sequence
<220> FEATURE:
<223> OTHER INFORMATION: Synthetic

<400> SEQUENCE: 313

```
cagtctgtcg tgacgcagcc gccctcagtg tctggggccc cagggcagag ggtcaccatc    60
tcctgcactg ggagcagctc caacatcggg gcaggttatg atgtacactg gtaccagcag    120
cttccaggaa cagccccca actcctcatc tatggtaaca gcaatcggcc ctcaggggtc    180
cctgaccgat tctctggctc caagtctggc acctcagcct ccctggccat cactgggctc    240
caggctgagg atgaggctga ttattactgc cagtcctatg acagcagcct gagtgtggta    300
ttcggcggag ggaccaagct gaccgtccta ggttctagag tggtggtgg tagcggcggc    360 ggcggctctg gtggtggtgg atccctcgag atggcccagg tgcagctggt gcagtctggg    420
gctgaggtga agaagcctgg ggcctcagtg aaggtctcct gcacggcttc tggaggcacc    480
ttcagcagct atgctatcag ctgggtgcga caggcccctg gacaagggct tgagtggatg    540
ggagggatca tccctatctt tggtacagca aactacgcac agaagttcca gggcagagtc    600
acgattaccg cggacaaatc cacgagcaca gcctacatgg agctgagcag cctgagatct    660
gaggacactg ccgtgtatta ctgtgcgcgc tcttcttacg gttcttacta cggtacttac    720
gattactggg gtcaaggtac tctggtgacc gtctcctca                          759
```

<210> SEQ ID NO 314
<211> LENGTH: 253
<212> TYPE: PRT
<213> ORGANISM: Artificial Sequence
<220> FEATURE:
<223> OTHER INFORMATION: Synthetic

<400> SEQUENCE: 314

Gln Ser Val Val Thr Gln Pro Pro Ser Val Gly Ala Pro Gly Gln
1               5                   10                  15

Arg Val Thr Ile Ser Cys Thr Gly Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Val Val Phe Gly Gly Gly Thr Lys Leu Thr Val Leu Gly Ser
            100                 105                 110

Arg Gly Gly Gly Ser Gly Gly Gly Gly Ser Gly Gly Gly Gly Ser
        115                 120                 125

Leu Glu Met Ala Gln Val Gln Leu Val Gln Ser Gly Ala Glu Val Lys
    130                 135                 140

Lys Pro Gly Ala Ser Val Lys Val Ser Cys Thr Ala Ser Gly Gly Thr
145                 150                 155                 160

Phe Ser Ser Tyr Ala Ile Ser Trp Val Arg Gln Ala Pro Gly Gln Gly
                165                 170                 175

Leu Glu Trp Met Gly Gly Ile Ile Pro Ile Phe Gly Thr Ala Asn Tyr
            180                 185                 190

Ala Gln Lys Phe Gln Gly Arg Val Thr Ile Thr Ala Asp Lys Ser Thr
        195                 200                 205

Ser Thr Ala Tyr Met Glu Leu Ser Ser Leu Arg Ser Glu Asp Thr Ala
    210                 215                 220

Val Tyr Tyr Cys Ala Arg Ser Ser Tyr Gly Ser Tyr Tyr Gly Thr Tyr
225                 230                 235                 240

Asp Tyr Trp Gly Gln Gly Thr Leu Val Thr Val Ser Ser
                245                 250

<210> SEQ ID NO 315
<211> LENGTH: 333
<212> TYPE: DNA
<213> ORGANISM: Artificial Sequence
<220> FEATURE:
<223> OTHER INFORMATION: Synthetic

<400> SEQUENCE: 315
cagtctgtcg tgacgcagcc gccctcagtg tctggggccc cagggcagag ggtcaccatc      60
tcctgcactg ggagcagctc caacatcggg gcaggttatg atgtacactg gtaccagcag     120
cttccaggaa cagcccccaa actcctcatc tatggtaaca gcaatcggcc ctcaggggtc     180
cctgaccgat tctctggctc caagtctggc acctcagcct ccctggccat cactgggctc     240
caggctgagg atgaggctga ttattactgc cagtcctatg acagcagcct gagtgtggta     300
ttcggcggag ggaccaagct gaccgtccta ggt                                   333

<210> SEQ ID NO 316
<211> LENGTH: 111
<212> TYPE: PRT
<213> ORGANISM: Artificial Sequence
<220> FEATURE:
<223> OTHER INFORMATION: Synthetic

<400> SEQUENCE: 316

Gln Ser Val Val Thr Gln Pro Pro Ser Val Ser Gly Ala Pro Gly Gln
1               5                   10                  15

Arg Val Thr Ile Ser Cys Thr Gly Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Val Val Phe Gly Gly Gly Thr Lys Leu Thr Val Leu Gly
            100                 105                 110

<210> SEQ ID NO 317
<211> LENGTH: 363
<212> TYPE: DNA
<213> ORGANISM: Artificial Sequence
<220> FEATURE:
<223> OTHER INFORMATION: Synthetic

<400> SEQUENCE: 317
caggtgcagc tggtgcagtc tggggctgag gtgaagaagc ctggggcctc agtgaaggtc     60
tcctgcacgg cttctggagg caccttcagc agctatgcta tcagctgggt gcgacaggcc    120
cctggacaag ggcttgagtg gatgggaggg atcatcccta tctttggtac agcaaactac    180
gcacagaagt tccagggcag agtcacgatt accgcggaca atccacgag cacagcctac    240 atggagctga gcagcctgag atctgaggac actgccgtgt attactgtgc gcgctcttct    300
tacggttctt actacggtac ttacgattac tggggtcaag gtactctggt gaccgtctcc    360
tca                                                                  363

<210> SEQ ID NO 318
<211> LENGTH: 121
<212> TYPE: PRT
<213> ORGANISM: Artificial Sequence
<220> FEATURE:
<223> OTHER INFORMATION: Synthetic

<400> SEQUENCE: 318

Gln Val Gln Leu Val Gln Ser Gly Ala Glu Val Lys Lys Pro Gly Ala
1               5                   10                  15

Ser Val Lys Val Ser Cys Thr Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr

```
                 65                  70                  75                  80
Met Glu Leu Ser Ser Leu Arg Ser Glu Asp Thr Ala Val Tyr Tyr Cys
                        85                  90                  95

Ala Arg Ser Ser Tyr Gly Ser Tyr Tyr Gly Thr Tyr Asp Tyr Trp Gly
                100                 105                 110

Gln Gly Thr Leu Val Thr Val Ser Ser
            115                 120
```

<210> SEQ ID NO 319
<211> LENGTH: 747
<212> TYPE: DNA
<213> ORGANISM: Artificial Sequence
<220> FEATURE:
<223> OTHER INFORMATION: Synthetic

<400> SEQUENCE: 319

```
cagtctgtgt tgacgcagcc gccctcagtg tctgcggccc caggacagaa ggtcaccatc    60
tcctgctctg gaagcagctc aacattggg  aataattatg tatcctggta ccagcaactc   120
ccaggaacag cccccaaact cctcatttat gacaataata gcgaccctc  agggattcct   180
gaccgattct ctggctccaa gtctggcacg tcagccaccc tgggcatcac cggactccag   240
actggggacg aggccgatta ttactgcgca acatggcata gcagcctgag tccctcttat   300
gtcttcggaa ctgggaccaa ggtcaccgtc ctaggttcta gaggtggtgg tggtagcggc   360
ggcggcggct ctggtggtgg tggatccctc gagatggccc aggtgcagct ggtgcagtct   420
ggggctgagg tcaagaagcc tggggcctca gtgaaggttt cctgcaaggc atctggatac   480
actttcacca gctactatat gcactgggtg cgacaggccc ctggacaagg gcttgagtgg   540
ttgggaataa tcaaccctac tggtggtagc acattctacg cacagaagtt cagggcaga   600
gtcaccatga ccagagacac gtccacgagc acagtctaca tgcagctgcg caacctgaga   660
tctgaggaca ctgccgtgta ttactgtgcg cgcggttact ctgaaggtga tgtttggggt   720
caaggtactc tggtgaccgt ctcctca                                       747
```

<210> SEQ ID NO 320
<211> LENGTH: 249
<212> TYPE: PRT
<213> ORGANISM: Artificial Sequence
<220> FEATURE:
<223> OTHER INFORMATION: Synthetic

<400> SEQUENCE: 320

```
Gln Ser Val Leu Thr Gln Pro Pro Ser Val Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Ala Thr Trp His Ser Ser Leu
                85                  90                  95

Ser Pro Ser Tyr Val Phe Gly Thr Gly Thr Lys Val Thr Val Leu Gly
            100                 105                 110

Ser Arg Gly Gly Gly Gly Ser Gly Gly Gly Gly Ser Gly Gly Gly Gly
```

|  | 115 |  |  |  | 120 |  |  |  | 125 |  |  |
|---|---|---|---|---|---|---|---|---|---|---|---|

Ser Leu Glu Met Ala Gln Val Gln Leu Val Gln Ser Gly Ala Glu Val
    130                 135                 140

Lys Lys Pro Gly Ala Ser Val Lys Val Ser Cys Lys Ala Ser Gly Tyr
145                 150                 155                 160

Thr Phe Thr Ser Tyr Tyr Met His Trp Val Arg Gln Ala Pro Gly Gln
                165                 170                 175

Gly Leu Glu Trp Leu Gly Ile Ile Asn Pro Thr Gly Gly Ser Thr Phe
            180                 185                 190

Tyr Ala Gln Lys Phe Gln Gly Arg Val Thr Met Thr Arg Asp Thr Ser
        195                 200                 205

Thr Ser Thr Val Tyr Met Gln Leu Arg Asn Leu Arg Ser Glu Asp Thr
    210                 215                 220

Ala Val Tyr Tyr Cys Ala Arg Gly Tyr Ser Glu Gly Asp Val Trp Gly
225                 230                 235                 240

Gln Gly Thr Leu Val Thr Val Ser Ser
            245

<210> SEQ ID NO 321
<211> LENGTH: 336
<212> TYPE: DNA
<213> ORGANISM: Artificial Sequence
<220> FEATURE:
<223> OTHER INFORMATION: Synthetic

<400> SEQUENCE: 321
cagtctgtgt tgacgcagcc gccctcagtg tctgcggccc caggacagaa ggtcaccatc     60
tcctgctctg gaagcagctc aacattggga ataattatg tatcctggta ccagcaactc    120
ccaggaacag cccccaaact cctcatttat gacaataata gcgaccctca gggattcct    180 gaccgattct ctggctccaa gtctggcacg tcagccaccc tgggcatcac cggactccag    240
actggggacg aggccgatta ttactgcgca acatggcata gcagcctgag tccctcttat    300
gtcttcggaa ctgggaccaa ggtcaccgtc ctaggt                              336

<210> SEQ ID NO 322
<211> LENGTH: 112
<212> TYPE: PRT
<213> ORGANISM: Artificial Sequence
<220> FEATURE:
<223> OTHER INFORMATION: Synthetic

<400> SEQUENCE: 322

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Ala Thr Trp His Ser Ser Leu
                85                  90                  95

Ser Pro Ser Tyr Val Phe Gly Thr Gly Thr Lys Val Thr Val Leu Gly
            100                 105                 110

<210> SEQ ID NO 323
<211> LENGTH: 348
<212> TYPE: DNA
<213> ORGANISM: Artificial Sequence
<220> FEATURE:
<223> OTHER INFORMATION: Synthetic

<400> SEQUENCE: 323

```
caggtgcagc tggtgcagtc tggggctgag gtcaagaagc ctggggcctc agtgaaggtt      60
tcctgcaagg catctggata cactttcacc agctactata tgcactgggt gcgacaggcc     120
cctggacaag gcttgagtg gttgggaata atcaaccctaa ctggtggtag cacattctac     180
gcacagaagt tcagggcag agtcaccatg accagagaca cgtccacgag cacagtctac     240
atgcagctgc gcaacctgag atctgaggac actgccgtgt attactgtgc gcgcggttac     300
tctgaaggtg atgtttgggg tcaaggtact ctggtgaccg tctcctca                  348
```

<210> SEQ ID NO 324
<211> LENGTH: 116
<212> TYPE: PRT
<213> ORGANISM: Artificial Sequence
<220> FEATURE:
<223> OTHER INFORMATION: Synthetic

<400> SEQUENCE: 324

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Ser Tyr
            20                  25                  30
Tyr Met His Trp Val Arg Gln Ala Pro Gly Gln Gly Leu Glu Trp Leu
        35                  40                  45
Gly Ile Ile Asn Pro Thr Gly Gly Ser Thr Phe Tyr Ala Gln Lys Phe
    50                  55                  60
Gln Gly Arg Val Thr Met Thr Arg Asp Thr Ser Thr Ser Thr Val Tyr
65                  70                  75                  80
Met Gln Leu Arg Asn Leu Arg Ser Glu Asp Thr Ala Val Tyr Tyr Cys
                85                  90                  95
Ala Arg Gly Tyr Ser Glu Gly Asp Val Trp Gly Gln Gly Thr Leu Val
            100                 105                 110
Thr Val Ser Ser
        115
```

<210> SEQ ID NO 325
<211> LENGTH: 753
<212> TYPE: DNA
<213> ORGANISM: Artificial Sequence
<220> FEATURE:
<223> OTHER INFORMATION: Synthetic

<400> SEQUENCE: 325

```
cagtctgtgg tgactcagcc accctcagcg tctgggaccc ccgggcagag ggtcaccatc      60
tcttgttctg gaagcagctc caacatcgga agtaatactg taaactggta ccagcagctc     120
ccaggaacgg cccccaaact cctcatctat agtaataatc agcggccctc agggtccct      180
gaccgattct ctggctccaa gtctggcacc tcagcctccc tggccatcag tgggctccag     240
tctgaggatg aggctgatta ttactgtgca gcatgggatg acagcctgaa tggtcataat     300
tatgtcttcg gaactgggac caaggtcacc gtcctaggtt ctagaggtgg tggtggtagc     360
ggcggcggcg gctctggtgg tggtggatcc ctcgagatgg cccaggtgca gctggtgcag     420
```

```
tctggggctg aggtgaagaa gcctgggtcc tcggtgaagg tctcctgcaa ggcttctgga    480
ggcaccttca gcagctatgc tatcagctgg gtgcgacagg cccctggaca agggcttgag    540
tggatgggag ggatcatccc tatctttggt acagcaaact acgcacagaa gttccagggc    600
agagtcacga ttaccgcgga caaatccacg agcacagcct acatggagct gagcagcctg    660
agatctgagg acacggccgt gtattactgt gcgcgctact cggtcgtta cgttgattac    720 tggggtcaag gtactctggt gaccgtctcc tca                                 753
```

<210> SEQ ID NO 326
<211> LENGTH: 251
<212> TYPE: PRT
<213> ORGANISM: Artificial Sequence
<220> FEATURE:
<223> OTHER INFORMATION: Synthetic

<400> SEQUENCE: 326

```
Gln Ser Val Val Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly His Asn Tyr Val Phe Gly Thr Gly Thr Lys Val Thr Val Leu
            100                 105                 110

Gly Ser Arg Gly Gly Gly Gly Ser Gly Gly Gly Gly Ser Gly Gly Gly
        115                 120                 125

Gly Ser Leu Glu Met Ala Gln Val Gln Leu Val Gln Ser Gly Ala Glu
    130                 135                 140

Val Lys Lys Pro Gly Ser Ser Val Lys Val Ser Cys Lys Ala Ser Gly
145                 150                 155                 160

Gly Thr Phe Ser Ser Tyr Ala Ile Ser Trp Val Arg Gln Ala Pro Gly
                165                 170                 175

Gln Gly Leu Glu Trp Met Gly Gly Ile Ile Pro Ile Phe Gly Thr Ala
            180                 185                 190

Asn Tyr Ala Gln Lys Phe Gln Gly Arg Val Thr Ile Thr Ala Asp Lys
        195                 200                 205

Ser Thr Ser Thr Ala Tyr Met Glu Leu Ser Ser Leu Arg Ser Glu Asp
    210                 215                 220

Thr Ala Val Tyr Tyr Cys Ala Arg Tyr Phe Gly Arg Tyr Val Asp Tyr
225                 230                 235                 240

Trp Gly Gln Gly Thr Leu Val Thr Val Ser Ser
                245                 250
```

<210> SEQ ID NO 327
<211> LENGTH: 339
<212> TYPE: DNA
<213> ORGANISM: Artificial Sequence
<220> FEATURE:
<223> OTHER INFORMATION: Synthetic -continued

<400> SEQUENCE: 327

```
cagtctgtgg tgactcagcc accctcagcg tctgggaccc ccgggcagag ggtcaccatc      60
tcttgttctg gaagcagctc caacatcgga agtaatactg taaactggta ccagcagctc     120
ccaggaacgg cccccaaact cctcatctat agtaataatc agcggccctc aggggtccct     180
gaccgattct ctggctccaa gtctggcacc tcagcctccc tggccatcag tgggctccag     240
tctgaggatg aggctgatta ttactgtgca gcatgggatg acagcctgaa tggtcataat     300
tatgtcttcg gaactgggac caaggtcacc gtcctaggt                            339
```

<210> SEQ ID NO 328
<211> LENGTH: 113
<212> TYPE: PRT
<213> ORGANISM: Artificial Sequence
<220> FEATURE:
<223> OTHER INFORMATION: Synthetic

<400> SEQUENCE: 328

```
Gln Ser Val Val Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly His Asn Tyr Val Phe Gly Thr Gly Thr Lys Val Thr Val Leu
            100                 105                 110

Gly
```

<210> SEQ ID NO 329
<211> LENGTH: 351
<212> TYPE: DNA
<213> ORGANISM: Artificial Sequence
<220> FEATURE:
<223> OTHER INFORMATION: Synthetic

<400> SEQUENCE: 329

```
caggtgcagc tggtgcagtc tggggctgag gtgaagaagc ctgggtcctc ggtgaaggtc      60
tcctgcaagg cttctggagg caccttcagc agctatgcta tcagctgggt gcgacaggcc     120
cctggacaag gcttgagtg gatgggaggg atcatcccta tctttggtac agcaaactac     180
gcacagaagt tccagggcag agtcacgatt accgcggaca aatccacgag cacagcctac     240
atggagctga gcagcctgag atctgaggac acggccgtgt attactgtgc gcgctacttc     300
ggtcgttacg ttgattactg gggtcaaggt actctggtga ccgtctcctc a              351
```

<210> SEQ ID NO 330
<211> LENGTH: 117
<212> TYPE: PRT
<213> ORGANISM: Artificial Sequence
<220> FEATURE:
<223> OTHER INFORMATION: Synthetic

<400> SEQUENCE: 330

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Phe Gly Arg Tyr Val Asp Tyr Trp Gly Gln Gly Thr Leu
            100                 105                 110

Val Thr Val Ser Ser
            115

<210> SEQ ID NO 331
<211> LENGTH: 747
<212> TYPE: DNA
<213> ORGANISM: Artificial Sequence
<220> FEATURE:
<223> OTHER INFORMATION: Synthetic

<400> SEQUENCE: 331
tcctatgtgc tgactcagcc accctcagcg tctgggaccc ccgggcagag ggtcaccatc      60
tcttgttctg gaagcagctc aacatcggaa gtaatactg taaactggta ccagcagctc     120
ccaggaacgg cccccaaact cctcatctat agtaataatc agcggccctc agggtccct     180
gaccgattct ctggctccaa gtctggcacc tcagcctccc tggccatcag tgggctccag     240
tctgaggatg aggctgatta ttactgtgca gcatgggatg acagcctgaa tggttatgtc     300
ttcggaactg gaccaaggt caccgtccta ggttctagag gtggtggtgg tagcggcggc     360
ggcggctctg gtggtggtgg atccctcgag atggccgagg tccagctggt gcagtctggg     420
gctgaggtga agaagcctgg gtcctcggtg aaggtctcct gcaaggcttc tggaggcacc     480
ttcaacgact atagtgtcag ctgggtgcga cagtcccctg acaagggct gagtggatg      540
ggaaggatca tccccgtcct tgatatgaca accgtcgcac agaaattcca gggcagagtc     600
acaattaacg cggacaaatc gacgagcaca gtgaacatgg agctgagcag cctcagatct     660
gatgacacgg ccgtgtatta ctgtgcgcgc cagtacggtt ctttctggga tcgttggggt     720
caaggtactc tggtgaccgt ctcctca                                          747

<210> SEQ ID NO 332
<211> LENGTH: 249
<212> TYPE: PRT
<213> ORGANISM: Artificial Sequence
<220> FEATURE:
<223> OTHER INFORMATION: Synthetic

<400> SEQUENCE: 332

Ser Tyr Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
 50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Asp Ser Leu
                 85                  90                  95

Asn Gly Tyr Val Phe Gly Thr Gly Thr Lys Val Thr Val Leu Gly Ser
                100                 105                 110

Arg Gly Gly Gly Ser Gly Gly Gly Ser Gly Gly Gly Ser
            115                 120                 125

Leu Glu Met Ala Glu Val Gln Leu Val Gln Ser Gly Ala Glu Val Lys
130                 135                 140

Lys Pro Gly Ser Ser Val Lys Val Ser Cys Lys Ala Ser Gly Gly Thr
145                 150                 155                 160

Phe Asn Asp Tyr Ser Val Ser Trp Val Arg Gln Ser Pro Gly Gln Gly
                165                 170                 175

Leu Glu Trp Met Gly Arg Ile Ile Pro Val Leu Asp Met Thr Thr Val
            180                 185                 190

Ala Gln Lys Phe Gln Gly Arg Val Thr Ile Asn Ala Asp Lys Ser Thr
            195                 200                 205

Ser Thr Val Asn Met Glu Leu Ser Ser Leu Arg Ser Asp Asp Thr Ala
210                 215                 220

Val Tyr Tyr Cys Ala Arg Gln Tyr Gly Ser Phe Trp Asp Arg Trp Gly
225                 230                 235                 240

Gln Gly Thr Leu Val Thr Val Ser Ser
                245

<210> SEQ ID NO 333
<211> LENGTH: 333
<212> TYPE: DNA
<213> ORGANISM: Artificial Sequence
<220> FEATURE:
<223> OTHER INFORMATION: Synthetic

<400> SEQUENCE: 333
tcctatgtgc tgactcagcc accctcagcg tctgggaccc ccgggcagag ggtcaccatc      60
tcttgttctg gaagcagctc caacatcgga agtaatactg taaactggta ccagcagctc     120
ccaggaacgg ccccaaaact cctcatctat agtaataatc agcggccctc aggggtccct     180
gaccgattct ctggctccaa gtctggcacc tcagcctccc tggccatcag tgggctccag     240
tctgaggatg aggctgatta ttactgtgca gcatgggatg acagcctgaa tggttatgtc     300
ttcggaactg ggaccaaggt caccgtccta ggt                                  333

<210> SEQ ID NO 334
<211> LENGTH: 111
<212> TYPE: PRT
<213> ORGANISM: Artificial Sequence
<220> FEATURE:
<223> OTHER INFORMATION: Synthetic

<400> SEQUENCE: 334

Ser Tyr Val Leu Thr Gln Pro Pro Ser Ala Ser Gly Pro Gly Gln
 1               5                  10                  15

Arg Val Thr Ile Ser Cys Ser Gly Ser Ser Asn Ile Gly Ser Asn
                20                  25                  30

Thr Val Asn Trp Tyr Gln Gln Leu Pro Gly Thr Ala Pro Lys Leu Leu
            35                  40                  45

-continued

Ile Tyr Ser Asn Asn Gln Arg Pro Ser Gly Val Pro Asp Arg Phe Ser
        50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Asp Ser Leu
                 85                  90                  95

Asn Gly Tyr Val Phe Gly Thr Gly Thr Lys Val Thr Val Leu Gly
            100                 105                 110

<210> SEQ ID NO 335
<211> LENGTH: 351
<212> TYPE: DNA
<213> ORGANISM: Artificial Sequence
<220> FEATURE:
<223> OTHER INFORMATION: Synthetic

<400> SEQUENCE: 335
gaggtccagc tggtgcagtc tggggctgag gtgaagaagc ctgggtcctc ggtgaaggtc      60
tcctgcaagg cttctggagg caccttcaac gactatagtg tcagctgggt gcgacagtcc    120
cctggacaag ggcttgagtg gatgggaagg atcatccccg tccttgatat gacaaccgtc    180
gcacagaaat tccagggcag agtcacaatt aacgcggaca atcgacgag cacagtgaac     240 atggagctga gcagcctcag atctgatgac acggccgtgt attactgtgc gccagtac     300 ggttctttct gggatcgttg gggtcaaggt actctggtga ccgtctcctc a            351

<210> SEQ ID NO 336
<211> LENGTH: 117
<212> TYPE: PRT
<213> ORGANISM: Artificial Sequence
<220> FEATURE:
<223> OTHER INFORMATION: Synthetic

<400> SEQUENCE: 336

Glu Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Asn Asp Tyr
            20                  25                  30

Ser Val Ser Trp Val Arg Gln Ser Pro Gly Gln Gly Leu Glu Trp Met
        35                  40                  45

Gly Arg Ile Ile Pro Val Leu Asp Met Thr Thr Val Ala Gln Lys Phe
    50                  55                  60

Gln Gly Arg Val Thr Ile Asn Ala Asp Lys Ser Thr Ser Thr Val Asn
 65                  70                  75                  80

Met Glu Leu Ser Ser Leu Arg Ser Asp Asp Thr Ala Val Tyr Tyr Cys
                 85                  90                  95

Ala Arg Gln Tyr Gly Ser Phe Trp Asp Arg Trp Gly Gln Gly Thr Leu
            100                 105                 110

Val Thr Val Ser Ser
        115

<210> SEQ ID NO 337
<211> LENGTH: 747
<212> TYPE: DNA
<213> ORGANISM: Artificial Sequence
<220> FEATURE:
<223> OTHER INFORMATION: Synthetic

<400> SEQUENCE: 337

```
cagtctgtgt tgacgcagcc gccctcagtg tctggggccc tagggcagag ggtgaccatc    60
tcctgcactg ggggccgctc aacatcggg gcagcctttg atgtgcactg gtaccagaaa    120
cttccaggga gagcccccac agtcgtcatc tctggtgaca ataggcgacc ctcaggggtc    180
cctgaccgat tctctgcctc caagtctggc gtctcagcct cactggccat cactgggctc    240
caggctgcgg atgaggctga ttactactgc caatcctatg acaccagtct gaatgtgttg    300
ttcggcggcg ggaccaagct gaccgtccta ggttctagag gtggtggtgg tagcggcggc    360
ggcggctctg gtggtggtgg atccctcgag atggccgagg tgcagctggt ggagtctggg    420
gctgaggtga agaagcctgg ggcctcagtg aaggtttcct gcaaggcatc tggatacacc    480
ttcaccagct actatatgca ctgggtgcga caggcccctg gacaagggct tgagtggatg    540
ggaataatca accctagtgg tggtagcaca agctacgcac agaagttcca gggcagagtc    600
accatgacca gggacacgtc cacgagcaca gtctacatgg agctgagcag cctgagatct    660
gaggacacgg ccgtgtatta ctgtgcggca gggagctact actcgcttga tatctggggc    720
caagggacaa tggtcaccgt ctcttca                                       747
```

<210> SEQ ID NO 338
<211> LENGTH: 249
<212> TYPE: PRT
<213> ORGANISM: Artificial Sequence
<220> FEATURE:
<223> OTHER INFORMATION: Synthetic

<400> SEQUENCE: 338

```
Gln Ser Val Leu Thr Gln Pro Pro Ser Val Ser Gly Ala Leu Gly Gln
1               5                   10                  15

Arg Val Thr Ile Ser Cys Thr Gly Gly Arg Ser Asn Ile Gly Ala Ala
            20                  25                  30

Phe Asp Val His Trp Tyr Gln Lys Leu Pro Gly Arg Ala Pro Thr Val
        35                  40                  45

Val Ile Ser Gly Asp Asn Arg Arg Pro Ser Gly Val Pro Asp Arg Phe
    50                  55                  60

Ser Ala Ser Lys Ser Gly Val Ser Ala Ser Leu Ala Ile Thr Gly Leu
65                  70                  75                  80

Gln Ala Ala Asp Glu Ala Asp Tyr Tyr Cys Gln Ser Tyr Asp Thr Ser
                85                  90                  95

Leu Asn Val Leu Phe Gly Gly Gly Thr Lys Leu Thr Val Leu Gly Ser
            100                 105                 110

Arg Gly Gly Gly Gly Ser Gly Gly Gly Gly Ser Gly Gly Gly Gly Ser
        115                 120                 125

Leu Glu Met Ala Glu Val Gln Leu Val Glu Ser Gly Ala Glu Val Lys
    130                 135                 140

Lys Pro Gly Ala Ser Val Lys Val Ser Cys Lys Ala Ser Gly Tyr Thr
145                 150                 155                 160

Phe Thr Ser Tyr Tyr Met His Trp Val Arg Gln Ala Pro Gly Gln Gly
                165                 170                 175

Leu Glu Trp Met Gly Ile Ile Asn Pro Ser Gly Gly Ser Thr Ser Tyr
            180                 185                 190

Ala Gln Lys Phe Gln Gly Arg Val Thr Met Thr Arg Asp Thr Ser Thr
        195                 200                 205

Ser Thr Val Tyr Met Glu Leu Ser Ser Leu Arg Ser Glu Asp Thr Ala
    210                 215                 220

Val Tyr Tyr Cys Ala Ala Gly Ser Tyr Tyr Ser Leu Asp Ile Trp Gly
```

```
                225                 230                 235                 240

Gln Gly Thr Met Val Thr Val Ser Ser
                245

<210> SEQ ID NO 339
<211> LENGTH: 333
<212> TYPE: DNA
<213> ORGANISM: Artificial Sequence
<220> FEATURE:
<223> OTHER INFORMATION: Synthetic

<400> SEQUENCE: 339
cagtctgtgt tgacgcagcc gccctcagtg tctggggccc tagggcagag ggtgaccatc      60
tcctgcactg ggggccgctc aacatcgggg gcagcctttg atgtgcactg gtaccagaaa     120
cttccaggga gacccccac agtcgtcatc tctggtgaca ataggcgacc ctcaggggtc      180
cctgaccgat tctctgcctc caagtctggc gtctcagcct cactggccat cactgggctc     240
caggctgcgg atgaggctga ttactactgc caatcctatg acaccagtct gaatgtgttg     300
ttcggcggcg ggaccaagct gaccgtccta ggt                                  333

<210> SEQ ID NO 340
<211> LENGTH: 111
<212> TYPE: PRT
<213> ORGANISM: Artificial Sequence
<220> FEATURE:
<223> OTHER INFORMATION: Synthetic

<400> SEQUENCE: 340

Gln Ser Val Leu Thr Gln Pro Pro Ser Val Ser Gly Ala Leu Gly Gln
1               5                   10                  15

Arg Val Thr Ile Ser Cys Thr Gly Gly Arg Ser Asn Ile Gly Ala Ala
            20                  25                  30

Phe Asp Val His Trp Tyr Gln Lys Leu Pro Gly Arg Ala Pro Thr Val
        35                  40                  45

Val Ile Ser Gly Asp Asn Arg Arg Pro Ser Gly Val Pro Asp Arg Phe
    50                  55                  60

Ser Ala Ser Lys Ser Gly Val Ser Ala Ser Leu Ala Ile Thr Gly Leu
65                  70                  75                  80

Gln Ala Ala Asp Glu Ala Asp Tyr Tyr Cys Gln Ser Tyr Asp Thr Ser
                85                  90                  95

Leu Asn Val Leu Phe Gly Gly Gly Thr Lys Leu Thr Val Leu Gly
            100                 105                 110

<210> SEQ ID NO 341
<211> LENGTH: 351
<212> TYPE: DNA
<213> ORGANISM: Artificial Sequence
<220> FEATURE:
<223> OTHER INFORMATION: Synthetic

<400> SEQUENCE: 341
gaggtgcagc tggtggagtc tggggctgag gtgaagaagc ctggggcctc agtgaaggtt      60
tcctgcaagg catctggata caccttcacc agctactata tgcactgggt gcgacaggcc     120
cctggacaag gcttgagtg gatgggaata atcaaccta gtggtggtag cacaagctac       180
gcacagaagt tccagggcag agtcaccatg accagggaca cgtccacgag cacagtctac     240
atggagctga gcagcctgag atctgaggac acggccgtgt attactgtgc ggcagggagc     300
tactactcgc ttgatatctg gggccaaggg acaatggtca ccgtctcttc a              351
```

<210> SEQ ID NO 342
<211> LENGTH: 117
<212> TYPE: PRT
<213> ORGANISM: Artificial Sequence
<220> FEATURE:
<223> OTHER INFORMATION: Synthetic

<400> SEQUENCE: 342

```
Glu Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Ala Gly Ser Tyr Tyr Ser Leu Asp Ile Trp Gly Gln Gly Thr Met
            100                 105                 110

Val Thr Val Ser Ser
        115
```

<210> SEQ ID NO 343
<211> LENGTH: 741
<212> TYPE: DNA
<213> ORGANISM: Artificial Sequence
<220> FEATURE:
<223> OTHER INFORMATION: Synthetic

<400> SEQUENCE: 343

```
cagtctgtgt tgactcagcc accctcagtg tcagtggccc caggaaagac ggccagcatt      60
acctgtgggg gaaacaacat tgaaagtaaa agtgtgcact ggtaccagca gaagccaggc     120
caggcccctg tactggtcat ctattttgat agcgaccggc cctcagggat ccctgagcga     180
ttctctggct ccaactctgg gaacacggcc accctgacca tcagcagggt cgaagccggg     240
gatgaggccg actattactg tcaggtgtgg atagtagta gtgatcatta tgtcttcgga     300
actgggacca aggtcaccgt cctaggttct agaggtggtg gtggtagcgg cggcggcggc     360
tctggtggtg gtggatccct cgagatggcc gaggtccagc tggtgcagtc tggggctgag     420
gtgaagaagc ctggggcctc agtgaaggtt tcctgcaagg catctggata caccttcacc     480
agctactata tgcactgggt gcgacaggcc cctggacaag gcttgagtg atgggaata      540 atcaaccta gtggtggtag cacaagctac gcacagaagt tccagggcag agtcaccatg     600
accagggaca cgtccacgag cacagtctac atggagctga gcagcctgag atctgaggac     660
acggccgtgt attactgtgc gagtgggagc cgatatgctt ttgatatctg gggccaaggg     720
acaatggtca ccgtctcttc a                                               741
```

<210> SEQ ID NO 344
<211> LENGTH: 247
<212> TYPE: PRT
<213> ORGANISM: Artificial Sequence
<220> FEATURE:
<223> OTHER INFORMATION: Synthetic

<400> SEQUENCE: 344

```
Gln Ser Val Leu Thr Gln Pro Pro Ser Val Ser Val Ala Pro Gly Lys
1               5                   10                  15

Thr Ala Ser Ile Thr Cys Gly Gly Asn Asn Ile Glu Ser Lys Ser Val
            20                  25                  30

His Trp Tyr Gln Gln Lys Pro Gly Gln Ala Pro Val Leu Val Ile Tyr
        35                  40                  45

Phe Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Asp His
                85                  90                  95

Tyr Val Phe Gly Thr Gly Thr Lys Val Thr Val Leu Gly Ser Arg Gly
            100                 105                 110

Gly Gly Gly Ser Gly Gly Gly Gly Ser Gly Gly Gly Gly Ser Leu Glu
        115                 120                 125

Met Ala Glu Val Gln Leu Val Gln Ser Gly Ala Glu Val Lys Lys Pro
130                 135                 140

Gly Ala Ser Val Lys Val Ser Cys Lys Ala Ser Gly Tyr Thr Phe Thr
145                 150                 155                 160

Ser Tyr Tyr Met His Trp Val Arg Gln Ala Pro Gly Gln Gly Leu Glu
                165                 170                 175

Trp Met Gly Ile Ile Asn Pro Ser Gly Gly Ser Thr Ser Tyr Ala Gln
            180                 185                 190

Lys Phe Gln Gly Arg Val Thr Met Thr Arg Asp Thr Ser Thr Ser Thr
        195                 200                 205

Val Tyr Met Glu Leu Ser Ser Leu Arg Ser Glu Asp Thr Ala Val Tyr
    210                 215                 220

Tyr Cys Ala Ser Gly Ser Arg Tyr Ala Phe Asp Ile Trp Gly Gln Gly
225                 230                 235                 240

Thr Met Val Thr Val Ser Ser
                245
```

<210> SEQ ID NO 345
<211> LENGTH: 327
<212> TYPE: DNA
<213> ORGANISM: Artificial Sequence
<220> FEATURE:
<223> OTHER INFORMATION: Synthetic

<400> SEQUENCE: 345

```
cagtctgtgt tgactcagcc accctcagtg tcagtggccc caggaaagac ggccagcatt    60
acctgtgggg gaaacaacat tgaaagtaaa agtgtgcact ggtaccagca gaagccaggc   120
caggcccctg tactggtcat ctattttgat agcgaccggc cctcagggat ccctgagcga   180
ttctctggct ccaactctgg gaacacggcc accctgacca tcagcagggt cgaagccggg   240
gatgaggccg actattactg tcaggtgtgg gatagtagta gtgatcatta tgtcttcgga   300
actgggacca aggtcaccgt cctaggt                                       327
```

<210> SEQ ID NO 346
<211> LENGTH: 109
<212> TYPE: PRT
<213> ORGANISM: Artificial Sequence
<220> FEATURE:
<223> OTHER INFORMATION: Synthetic

<400> SEQUENCE: 346

Gln Ser Val Leu Thr Gln Pro Pro Ser Val Ser Val Ala Pro Gly Lys
1               5                   10                  15

Thr Ala Ser Ile Thr Cys Gly Gly Asn Asn Ile Glu Ser Lys Ser Val
            20                  25                  30

His Trp Tyr Gln Gln Lys Pro Gly Gln Ala Pro Val Leu Val Ile Tyr
        35                  40                  45

Phe Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Tyr Val Phe Gly Thr Gly Thr Lys Val Thr Val Leu Gly
            100                 105

<210> SEQ ID NO 347
<211> LENGTH: 351
<212> TYPE: DNA
<213> ORGANISM: Artificial Sequence
<220> FEATURE:
<223> OTHER INFORMATION: Synthetic

<400> SEQUENCE: 347
gaggtccagc tggtgcagtc tggggctgag gtgaagaagc ctggggcctc agtgaaggtt        60
tcctgcaagg catctggata caccttcacc agctactata tgcactgggt gcgacaggcc       120
cctggacaag gcttgagtg gatgggaata atcaacccta gtggtggtag cacaagctac        180
gcacagaagt tccagggcag agtcaccatg accaggaca cgtccacgag cacagtctac        240
atggagctga gcagcctgag atctgaggac acggccgtgt attactgtgc gagtgggagc       300
cgatatgctt ttgatatctg gggccaaggg acaatggtca ccgtctcttc a                351

<210> SEQ ID NO 348
<211> LENGTH: 117
<212> TYPE: PRT
<213> ORGANISM: Artificial Sequence
<220> FEATURE:
<223> OTHER INFORMATION: Synthetic

<400> SEQUENCE: 348

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Ser Gly Ser Arg Tyr Ala Phe Asp Ile Trp Gly Gln Gly Thr Met
            100                 105                 110

Val Thr Val Ser Ser
            115

<210> SEQ ID NO 349
<211> LENGTH: 747
<212> TYPE: DNA
<213> ORGANISM: Artificial Sequence
<220> FEATURE:
<223> OTHER INFORMATION: Synthetic

<400> SEQUENCE: 349

```
caggctgtgc tgactcagcc accctcagtg tcagtggccc aggaaagac ggccaggatt      60
acctgtgggg gaaacaacat tggaagtaaa agtgtgcact ggtaccagca gaagccaggc    120
caggcccctg tgctggtcat ctattatgat agcgaccggc cctcagggat ccctgagcga    180
ttctctggct ccaactctgg gaacacggcc accctgacca tcagcagggt cgaagccggg    240
gatgaggccg actattactg tcaggtgtgg gatagtagta gtgatcatcc ggtgttcggc    300
ggagggacca agctgaccgt cctaggttct agaggtggtg gtggtagcgg cggcggcggc    360
tctggtggtg gtggatccct cgagatggcc gaggtgcagc tggtggagtc tgggggctgag   420
gtgaagaagc ctggggcctc agtgaaggtt tcctgcaagg catctggata caccttcacc    480
agctactata tgcactgggt gcgacaggcc cctggacaag gcttgagtg gatgggaata    540
atcaaccctr gtggtggtag cacaagctac gcacagaagt tccagggcag agtcaccatg    600
accagggaca cgtccacgag cacagtctac atggagctga gcagcctgag atctgaggac    660
acggccgtgt attactgtgc gagggctatt actgcccttg atgcttttga tatctggggc    720
caagggacaa tggtcaccgt ctcttca                                         747
```

<210> SEQ ID NO 350
<211> LENGTH: 249
<212> TYPE: PRT
<213> ORGANISM: Artificial Sequence
<220> FEATURE:
<223> OTHER INFORMATION: Synthetic

<400> SEQUENCE: 350

```
Gln Ala Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Pro Val Phe Gly Gly Gly Thr Lys Leu Thr Val Leu Gly Ser Arg Gly
            100                 105                 110

Gly Gly Gly Ser Gly Gly Gly Gly Ser Gly Gly Gly Ser Leu Glu
        115                 120                 125

Met Ala Glu Val Gln Leu Val Glu Ser Gly Ala Glu Val Lys Lys Pro
    130                 135                 140

Gly Ala Ser Val Lys Val Ser Cys Lys Ala Ser Gly Tyr Thr Phe Thr
145                 150                 155                 160

Ser Tyr Tyr Met His Trp Val Arg Gln Ala Pro Gly Gln Gly Leu Glu
                165                 170                 175
```

```
Trp Met Gly Ile Ile Asn Pro Ser Gly Gly Ser Thr Ser Tyr Ala Gln
            180                 185                 190

Lys Phe Gln Gly Arg Val Thr Met Thr Arg Asp Thr Ser Thr Ser Thr
        195                 200                 205

Val Tyr Met Glu Leu Ser Ser Leu Arg Ser Glu Asp Thr Ala Val Tyr
    210                 215                 220

Tyr Cys Ala Arg Ala Ile Thr Ala Leu Asp Ala Phe Asp Ile Trp Gly
225                 230                 235                 240

Gln Gly Thr Met Val Thr Val Ser Ser
                245
```

<210> SEQ ID NO 351
<211> LENGTH: 327
<212> TYPE: DNA
<213> ORGANISM: Artificial Sequence
<220> FEATURE:
<223> OTHER INFORMATION: Synthetic

<400> SEQUENCE: 351

```
caggctgtgc tgactcagcc accctcagtg tcagtggccc caggaaagac ggccaggatt    60
acctgtgggg gaaacaacat tggaagtaaa agtgtgcact ggtaccagca gaagccaggc   120
caggcccctg tgctggtcat ctattatgat agcgaccggc cctcagggat ccctgagcga   180
ttctctggct ccaactctgg gaacacggcc accctgacca tcagcagggt cgaagccggg   240
gatgaggccg actattactg tcaggtgtgg gatagtagta gtgatcatcc ggtgttcggc   300
ggagggacca agctgaccgt cctaggt                                       327
```

<210> SEQ ID NO 352
<211> LENGTH: 109
<212> TYPE: PRT
<213> ORGANISM: Artificial Sequence
<220> FEATURE:
<223> OTHER INFORMATION: Synthetic

<400> SEQUENCE: 352

```
Gln Ala Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Pro Val Phe Gly Gly Gly Thr Lys Leu Thr Val Leu Gly
            100                 105
```

<210> SEQ ID NO 353
<211> LENGTH: 357
<212> TYPE: DNA
<213> ORGANISM: Artificial Sequence
<220> FEATURE:
<223> OTHER INFORMATION: Synthetic

<400> SEQUENCE: 353

```
gaggtgcagc tggtggagtc tggggctgag gtgaagaagc tggggcctc agtgaaggtt      60 tcctgcaagg catctggata caccttcacc agctactata tgcactgggt gcgacaggcc    120
cctggacaag ggcttgagtg gatgggaata atcaaccta gtggtggtag cacaagctac    180
gcacagaagt tccagggcag agtcaccatg accaggaca cgtccacgag cacagtctac    240
atggagctga gcagcctgag atctgaggac acggccgtgt attactgtgc gagggctatt    300
actgcccttg atgcttttga tatctggggc caagggacaa tggtcaccgt ctcttca       357
```

<210> SEQ ID NO 354
<211> LENGTH: 119
<212> TYPE: PRT
<213> ORGANISM: Artificial Sequence
<220> FEATURE:
<223> OTHER INFORMATION: Synthetic

<400> SEQUENCE: 354

```
Glu Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ala Ile Thr Ala Leu Asp Ala Phe Asp Ile Trp Gly Gln Gly
            100                 105                 110

Thr Met Val Thr Val Ser Ser
        115
```

<210> SEQ ID NO 355
<211> LENGTH: 756
<212> TYPE: DNA
<213> ORGANISM: Artificial Sequence
<220> FEATURE:
<223> OTHER INFORMATION: Synthetic

<400> SEQUENCE: 355

```
ctgcctgtgc tgactcagcc accctcggtg tcagtggccc caggacagac ggccaggatt     60
acctgtgggg gaaacaacat tggaagtaaa agtgtgcact ggtaccagca gaagccaggc    120
caggcccctg tgctggtcgt ctatgatgat agcgaccggc cctcaggat ccctgagcga    180 ttctctggct ccaactctgg gaacacggcc accctgacca tcagcagggt cgaagccggg    240
gatgaggccg actattactg tcaggtgtgg gatagtagta gtgatcatgg ggtattcggc    300
ggagggacca agctgaccgt cctaggttct agaggtggtg gtggtagcgg cggcggcggc    360
tctggtggtg gtggatccct cgagatggcc caggtccagc tggtacagtc tggggctgag    420
gtgaagaagc tggggcctc agtgaaggtt tcctgcaagg catctgaata caccctcacc    480
acctattata tgcactgggt gcgacaggcc cctggacaag ggcttgagtg gatgggaata    540
atcaatcctg gtagtggtag cacaagttac gcacagaagt tccagggcag actcaccatg    600
accagcgaca cgtccacgag cacagtctac atggagctga gcagcctgag atctgaggac    660
acggccatgt attactgtgc tagagcgttt ggttacgggg actacttcta cggtatggac    720
```

```
gtctggggcc aagggaccac ggtcaccgtc tcctca                                756
```

<210> SEQ ID NO 356
<211> LENGTH: 252
<212> TYPE: PRT
<213> ORGANISM: Artificial Sequence
<220> FEATURE:
<223> OTHER INFORMATION: Synthetic

<400> SEQUENCE: 356

```
Leu Pro Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Gly Val Phe Gly Gly Gly Thr Lys Leu Thr Val Leu Gly Ser Arg Gly
            100                 105                 110

Gly Gly Gly Ser Gly Gly Gly Ser Gly Gly Gly Ser Leu Glu
        115                 120                 125

Met Ala Gln Val Gln Leu Val Gln Ser Gly Ala Glu Val Lys Lys Pro
    130                 135                 140

Gly Ala Ser Val Lys Val Ser Cys Lys Ala Ser Glu Tyr Thr Leu Thr
145                 150                 155                 160

Thr Tyr Tyr Met His Trp Val Arg Gln Ala Pro Gly Gln Gly Leu Glu
                165                 170                 175

Trp Met Gly Ile Ile Asn Pro Gly Ser Gly Ser Thr Ser Tyr Ala Gln
            180                 185                 190

Lys Phe Gln Gly Arg Leu Thr Met Thr Ser Asp Thr Ser Thr Ser Thr
        195                 200                 205

Val Tyr Met Glu Leu Ser Ser Leu Arg Ser Glu Asp Thr Ala Met Tyr
    210                 215                 220

Tyr Cys Ala Arg Ala Phe Gly Tyr Gly Asp Tyr Phe Tyr Gly Met Asp
225                 230                 235                 240

Val Trp Gly Gln Gly Thr Thr Val Thr Val Ser Ser
                245                 250
```

<210> SEQ ID NO 357
<211> LENGTH: 327
<212> TYPE: DNA
<213> ORGANISM: Artificial Sequence
<220> FEATURE:
<223> OTHER INFORMATION: Synthetic

<400> SEQUENCE: 357

```
ctgcctgtgc tgactcagcc accctcggtg tcagtggccc caggacagac ggccaggatt    60
acctgtgggg gaaacaacat tggaagtaaa agtgtgcact ggtaccagca gaagccaggc   120
caggcccctg tgctggtcgt ctatgatgat agcgaccggc cctcagggat ccctgagcga   180
ttctctggct ccaactctgg gaacacggcc accctgacca tcagcagggt cgaagccggg   240
```

```
gatgaggccg actattactg tcaggtgtgg gatagtagta gtgatcatgg ggtattcggc    300
ggagggacca agctgaccgt cctaggt                                        327
```

<210> SEQ ID NO 358
<211> LENGTH: 109
<212> TYPE: PRT
<213> ORGANISM: Artificial Sequence
<220> FEATURE:
<223> OTHER INFORMATION: Synthetic

<400> SEQUENCE: 358

```
Leu Pro Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Gly Val Phe Gly Gly Gly Thr Lys Leu Thr Val Leu Gly
            100                 105
```

<210> SEQ ID NO 359
<211> LENGTH: 366
<212> TYPE: DNA
<213> ORGANISM: Artificial Sequence
<220> FEATURE:
<223> OTHER INFORMATION: Synthetic

<400> SEQUENCE: 359

```
caggtccagc tggtacagtc tggggctgag gtgaagaagc ctggggcctc agtgaaggtt     60
tcctgcaagg catctgaata cacccctcacc acctattata tgcactgggt gcgacaggcc   120
cctggacaag ggcttgagtg gatgggaata atcaatcctg gtagtggtag cacaagttac   180
gcacagaagt tccagggcag actcaccatg accagcgaca cgtccacgag cacagtctac   240
atggagctga gcagcctgag atctgaggac acggccatgt attactgtgc tagagcgttt   300
ggttacgggg actacttcta cggtatggac gtctggggcc aagggaccac ggtcaccgtc   360
tcctca                                                               366
```

<210> SEQ ID NO 360
<211> LENGTH: 122
<212> TYPE: PRT
<213> ORGANISM: Artificial Sequence
<220> FEATURE:
<223> OTHER INFORMATION: Synthetic

<400> SEQUENCE: 360

```
Gln Val Gln Leu Val Gln Ser Gly Ala Glu Val Lys Lys Pro Gly Ala
1               5                   10                  15

Ser Val Lys Val Ser Cys Lys Ala Ser Glu Tyr Thr Leu Thr Thr Tyr
            20                  25                  30

Tyr Met His Trp Val Arg Gln Ala Pro Gly Gln Gly Leu Glu Trp Met
        35                  40                  45

Gly Ile Ile Asn Pro Gly Ser Gly Ser Thr Ser Tyr Ala Gln Lys Phe
```

| 50 | | | 55 | | | | 60 | | |

Gln Gly Arg Leu Thr Met Thr Ser Asp Thr Ser Thr Ser Thr Val Tyr
65                    70                    75                    80

Met Glu Leu Ser Ser Leu Arg Ser Glu Asp Thr Ala Met Tyr Tyr Cys
                    85                    90                    95

Ala Arg Ala Phe Gly Tyr Gly Asp Tyr Phe Tyr Gly Met Asp Val Trp
              100                  105                  110

Gly Gln Gly Thr Thr Val Thr Val Ser Ser
        115                  120

<210> SEQ ID NO 361
<211> LENGTH: 768
<212> TYPE: DNA
<213> ORGANISM: Artificial Sequence
<220> FEATURE:
<223> OTHER INFORMATION: Synthetic

<400> SEQUENCE: 361
caggctgtgc tgactcagcc gccctcagtg tctggggccc cagggcagag ggtcaccatc        60
tcctgcactg ggagcagctc aacatcgggg gcaggtcatg atgtacattg gtatcaccaa       120
cttccaggaa cagcccccaa actcctcatc tatagtaatg gcaatcggcc ctcagggatc       180
cctgaccgat tctctggctc caagtctggc acctcagcct ccctggccat cactgggctc       240
caggctgagg atgagggtga ttattattgc agtcctatg acagcagcct gagtggtgat       300
gtggtcttcg gcggagggac caaggtcacc gtcctaggtt ctagaggtgg tggtggtagc       360
ggcggcggcg gctctggtgg tggtggatcc ctcgagatgg ccgaggtgca gctggtggag       420
tctggggggag gcttggtcca gcctgggggg tccctgagac tctcctgtgc agcctctgga       480
ttcaggttca gtggctatag catgaactgg gtccgccagg ctccagggaa ggggctggag       540
tgggtttcat acattagaag tagtagtgat cttataacct acgcagactc tgtgaagggc       600
cgattcacca tctccagaga caatgccaag aactcactgt atctgcagat gaacagcctg       660
agagacgagg acacggctgt ctattattgt gcgagagata tgggcagcac tggtaccga        720
ggtgctttg atttttgggg ccaagggaca atggtcaccg tctcttca                     768

<210> SEQ ID NO 362
<211> LENGTH: 256
<212> TYPE: PRT
<213> ORGANISM: Artificial Sequence
<220> FEATURE:
<223> OTHER INFORMATION: Synthetic

<400> SEQUENCE: 362

Gln Ala Val Leu Thr Gln Pro Pro Ser Val Ser Gly Ala Pro Gly Gln
1                    5                    10                    15

Arg Val Thr Ile Ser Cys Thr Gly Ser Ser Ser Asn Ile Gly Ala Gly
                    20                    25                    30

His Asp Val His Trp Tyr His Gln Leu Pro Gly Thr Ala Pro Lys Leu
              35                    40                    45

Leu Ile Tyr Ser Asn Gly Asn Arg Pro Ser Gly Ile Pro Asp Arg Phe
     50                    55                    60

Ser Gly Ser Lys Ser Gly Thr Ser Ala Ser Leu Ala Ile Thr Gly Leu
65                    70                    75                    80

Gln Ala Glu Asp Glu Gly Asp Tyr Tyr Cys Gln Ser Tyr Asp Ser Ser
              85                    90                    95

Leu Ser Gly Asp Val Val Phe Gly Gly Gly Thr Lys Val Thr Val Leu

```
                100             105             110
Gly Ser Arg Gly Gly Gly Ser Gly Gly Gly Ser Gly Gly
        115                 120             125
Gly Ser Leu Glu Met Ala Glu Val Gln Leu Val Glu Ser Gly Gly Gly
        130                 135             140
Leu Val Gln Pro Gly Gly Ser Leu Arg Leu Ser Cys Ala Ala Ser Gly
145                 150             155                 160
Phe Arg Phe Ser Gly Tyr Ser Met Asn Trp Val Arg Gln Ala Pro Gly
                165                 170             175
Lys Gly Leu Glu Trp Val Ser Tyr Ile Arg Ser Ser Asp Leu Ile
            180                 185             190
Thr Tyr Ala Asp Ser Val Lys Gly Arg Phe Thr Ile Ser Arg Asp Asn
            195                 200             205
Ala Lys Asn Ser Leu Tyr Leu Gln Met Asn Ser Leu Arg Asp Glu Asp
        210                 215             220
Thr Ala Val Tyr Tyr Cys Ala Arg Asp Met Gly Ser Thr Trp Tyr Arg
225                 230             235                 240
Gly Ala Phe Asp Phe Trp Gly Gln Gly Thr Met Val Thr Val Ser Ser
                245                 250             255
```

<210> SEQ ID NO 363
<211> LENGTH: 339
<212> TYPE: DNA
<213> ORGANISM: Artificial Sequence
<220> FEATURE:
<223> OTHER INFORMATION: Synthetic

<400> SEQUENCE: 363

```
caggctgtgc tgactcagcc gccctcagtg tctggggccc cagggcagag ggtcaccatc      60
tcctgcactg ggagcagctc caacatcggg gcaggtcatg atgtacattg gtatcaccaa     120
cttccaggaa cagcccccaa actcctcatc tatagtaatg gcaatcggcc ctcagggatc     180
cctgaccgat tctctggctc caagtctggc acctcagcct ccctggccat cactgggctc     240
caggctgagg atgagggtga ttattattgc cagtcctatg acagcagcct gagtggtgat     300
gtggtcttcg gcggagggac caaggtcacc gtcctaggt                            339
```

<210> SEQ ID NO 364
<211> LENGTH: 113
<212> TYPE: PRT
<213> ORGANISM: Artificial Sequence
<220> FEATURE:
<223> OTHER INFORMATION: Synthetic

<400> SEQUENCE: 364

```
Gln Ala Val Leu Thr Gln Pro Pro Ser Val Ser Gly Ala Pro Gly Gln
1               5                   10                  15
Arg Val Thr Ile Ser Cys Thr Gly Ser Ser Ser Asn Ile Gly Ala Gly
            20                  25                  30
His Asp Val His Trp Tyr His Gln Leu Pro Gly Thr Ala Pro Lys Leu
        35                  40                  45
Leu Ile Tyr Ser Asn Gly Asn Arg Pro Ser Gly Ile Pro Asp Arg Phe
    50                  55                  60
Ser Gly Ser Lys Ser Gly Thr Ser Ala Ser Leu Ala Ile Thr Gly Leu
65                  70                  75                  80
Gln Ala Glu Asp Glu Gly Asp Tyr Tyr Cys Gln Ser Tyr Asp Ser Ser
                85                  90                  95
```

Leu Ser Gly Asp Val Val Phe Gly Gly Gly Thr Lys Val Thr Val Leu
            100                 105                 110

Gly

<210> SEQ ID NO 365
<211> LENGTH: 366
<212> TYPE: DNA
<213> ORGANISM: Artificial Sequence
<220> FEATURE:
<223> OTHER INFORMATION: Synthetic

<400> SEQUENCE: 365
gaggtgcagc tggtggagtc tgggggaggc ttggtccagc ctggggggtc cctgagactc     60
tcctgtgcag cctctggatt caggttcagt ggctatagca tgaactgggt ccgccaggct    120
ccagggaagg ggctggagtg ggtttcatac attagaagta gtagtgatct tataacctac    180
gcagactctg tgaagggccg attcaccatc tccagagaca atgccaagaa ctcactgtat    240
ctgcagatga acagcctgag agacgaggac acggctgtct attattgtgc gagagatatg    300
ggcagcacct ggtaccgagg tgcttttgat ttttggggcc aagggacaat ggtcaccgtc    360
tcttca                                                               366

<210> SEQ ID NO 366
<211> LENGTH: 122
<212> TYPE: PRT
<213> ORGANISM: Artificial Sequence
<220> FEATURE:
<223> OTHER INFORMATION: Synthetic

<400> SEQUENCE: 366

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Arg Phe Ser Gly Tyr
            20                  25                  30

Ser Met Asn Trp Val Arg Gln Ala Pro Gly Lys Gly Leu Glu Trp Val
        35                  40                  45

Ser Tyr Ile Arg Ser Ser Ser Asp Leu Ile Thr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Asp Met Gly Ser Thr Trp Tyr Arg Gly Ala Phe Asp Phe Trp
            100                 105                 110

Gly Gln Gly Thr Met Val Thr Val Ser Ser
        115                 120

<210> SEQ ID NO 367
<211> LENGTH: 747
<212> TYPE: DNA
<213> ORGANISM: Artificial Sequence
<220> FEATURE:
<223> OTHER INFORMATION: Synthetic

<400> SEQUENCE: 367
ctgcctgtgc tgactcagcc accctcagtg tcagtggccc caggagagac ggccagcatt     60
acctgtgggg gaaacaatat tggacgtcaa agtgtgcact ggtaccagca gaagccaggc    120
caggcccctt tgttagtcat ctattatgat gccgaccggc cctctgggat ccctgagcga    180

-continued

```
ttctctggct ccaactctgg gaacacggcc accctgaccc tcagcagggt cgaagccggg      240
gatgaggccg actattattg tcaggtgtgg gatagtagta gtgatcatta tgtcttcgga      300
actgggacca aggtcaccgt cctaggttct agaggtggtg gtggtagcgg cggcggcggc      360
tctggtggtg gtggatccct cgagatggcc gaggtccagc tggtgcagtc tggggctgag      420
gtgaagaagc tgggggcctc agtgaaggtt tcctgcaagg catctggata caccttcacc      480
agctactata tacactgggt gcgacaggcc cctggacaag gcttgagtg gatgggagta       540 atcaacccta gtggtggtag cacaagctac gcacagaagt tccagggcag agtcaccatg      600
accagggaca cgtccacgag cacagtctac atggagctca gcagcctgag atctgaggac      660
acggccgtat attactgtgc gcgctctccg ggtggtggtt acggtcagga tggttggggt      720
caaggtactc tggtgaccgt ctcctca                                          747
```

<210> SEQ ID NO 368  
<211> LENGTH: 249  
<212> TYPE: PRT  
<213> ORGANISM: Artificial Sequence  
<220> FEATURE:  
<223> OTHER INFORMATION: Synthetic

<400> SEQUENCE: 368

```
Leu Pro Val Leu Thr Gln Pro Pro Ser Val Ser Val Ala Pro Gly Glu
1               5                   10                  15

Thr Ala Ser Ile Thr Cys Gly Gly Asn Asn Ile Gly Arg Gln Ser Val
            20                  25                  30

His Trp Tyr Gln Gln Lys Pro Gly Gln Ala Pro Leu Leu Val Ile Tyr
        35                  40                  45

Tyr Asp Ala Asp Arg Pro Ser Gly Ile Pro Glu Arg Phe Ser Gly Ser
    50                  55                  60

Asn Ser Gly Asn Thr Ala Thr Leu Thr Leu Ser Arg Val Glu Ala Gly
65                  70                  75                  80

Asp Glu Ala Asp Tyr Tyr Cys Gln Val Trp Asp Ser Ser Ser Asp His
                85                  90                  95

Tyr Val Phe Gly Thr Gly Thr Lys Val Thr Val Leu Gly Ser Arg Gly
            100                 105                 110

Gly Gly Gly Ser Gly Gly Gly Gly Ser Gly Gly Gly Gly Ser Leu Glu
        115                 120                 125

Met Ala Glu Val Gln Leu Val Gln Ser Gly Ala Glu Val Lys Lys Pro
    130                 135                 140

Gly Ala Ser Val Lys Val Ser Cys Lys Ala Ser Gly Tyr Thr Phe Thr
145                 150                 155                 160

Ser Tyr Tyr Ile His Trp Val Arg Gln Ala Pro Gly Gln Gly Leu Glu
                165                 170                 175

Trp Met Gly Val Ile Asn Pro Ser Gly Gly Ser Thr Ser Tyr Ala Gln
            180                 185                 190

Lys Phe Gln Gly Arg Val Thr Met Thr Arg Asp Thr Ser Thr Ser Thr
        195                 200                 205

Val Tyr Met Glu Leu Ser Ser Leu Arg Ser Glu Asp Thr Ala Val Tyr
    210                 215                 220

Tyr Cys Ala Arg Ser Pro Gly Gly Gly Tyr Gly Gln Asp Gly Trp Gly
225                 230                 235                 240

Gln Gly Thr Leu Val Thr Val Ser Ser
                245
```

```
<210> SEQ ID NO 369
<211> LENGTH: 327
<212> TYPE: DNA
<213> ORGANISM: Artificial Sequence
<220> FEATURE:
<223> OTHER INFORMATION: Synthetic

<400> SEQUENCE: 369
ctgcctgtgc tgactcagcc accctcagtg tcagtggccc caggagagac ggccagcatt    60
acctgtgggg gaaacaatat tggacgtcaa agtgtgcact ggtaccagca gaagccaggc   120
caggccccct tgttagtcat ctattatgat gccgaccggc cctctgggat ccctgagcga   180
ttctctggct ccaactctgg gaacacggcc accctgaccc tcagcagggt cgaagccggg   240
gatgaggccg actattattg tcaggtgtgg gatagtagta gtgatcatta tgtcttcgga   300
actgggacca aggtcaccgt cctaggt                                       327

<210> SEQ ID NO 370
<211> LENGTH: 109
<212> TYPE: PRT
<213> ORGANISM: Artificial Sequence
<220> FEATURE:
<223> OTHER INFORMATION: Synthetic

<400> SEQUENCE: 370

Leu Pro Val Leu Thr Gln Pro Pro Ser Val Ser Val Ala Pro Gly Glu
1               5                   10                  15

Thr Ala Ser Ile Thr Cys Gly Gly Asn Asn Ile Gly Arg Gln Ser Val
            20                  25                  30

His Trp Tyr Gln Gln Lys Pro Gly Gln Ala Pro Leu Leu Val Ile Tyr
        35                  40                  45

Tyr Asp Ala Asp Arg Pro Ser Gly Ile Pro Glu Arg Phe Ser Gly Ser
    50                  55                  60

Asn Ser Gly Asn Thr Ala Thr Leu Thr Leu Ser Arg Val Glu Ala Gly
65                  70                  75                  80

Asp Glu Ala Asp Tyr Tyr Cys Gln Val Trp Asp Ser Ser Ser Asp His
                85                  90                  95

Tyr Val Phe Gly Thr Gly Thr Lys Val Thr Val Leu Gly
            100                 105

<210> SEQ ID NO 371
<211> LENGTH: 357
<212> TYPE: DNA
<213> ORGANISM: Artificial Sequence
<220> FEATURE:
<223> OTHER INFORMATION: Synthetic

<400> SEQUENCE: 371
gaggtccagc tggtgcagtc tggggctgag gtgaagaagc ctggggcctc agtgaaggtt    60
tcctgcaagg catctggata caccttcacc agctactata tacactgggt gcgacaggcc   120
cctggacaag ggcttgagtg gatgggagta atcaaccctg tggtggtagc acaagctac    180 gcacagaagt tccagggcag agtcaccatg accagggaca cgtccacgag cacagtctac   240
atggagctca gcagcctgag atctgaggac acggccgtat attactgtgc cgctctccg    300 ggtggtggtt acggtcagga tgttggggt caaggtactc tggtgaccgt ctcctca       357

<210> SEQ ID NO 372
<211> LENGTH: 119
<212> TYPE: PRT
<213> ORGANISM: Artificial Sequence
```

<220> FEATURE:
<223> OTHER INFORMATION: Synthetic

<400> SEQUENCE: 372

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Met
        35                  40                  45

Gly Val Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Pro Gly Gly Gly Tyr Gly Gln Asp Gly Trp Gly Gln Gly
            100                 105                 110

Thr Leu Val Thr Val Ser Ser
        115

<210> SEQ ID NO 373
<211> LENGTH: 741
<212> TYPE: DNA
<213> ORGANISM: Artificial Sequence
<220> FEATURE:
<223> OTHER INFORMATION: Synthetic

<400> SEQUENCE: 373
gatgttgtga tgactcagtc tccatcctcc ctgtctgcat ctgtaggaga cagagtcacc      60
atcacttgcc gggcaagtca gagcattagc agctatttaa attggtatca gcagaaacca     120
gggaaagccc ctaagctcct gatctatgct gcatccagtt tgcaaagtgg ggtcccatca     180
aggttcagtg gcagtggatc tgggacagat ttcactctca ccatcagcag tctgcaacct     240
gaagattttg caacttacta ctgtcaacag agttacagta ccccttcac cttcggccaa      300 gggacacgac tggagattaa acgttctaga ggtggtggtg gtagcggcgg cggcggctct     360
ggtggtggtg gatccctcga gatggcccag gtgcagctgg tgcaatctgg ggctgaggtg     420
aaggagcctg gagcctcagt taaggtttcc tgcaaggcgt ctggatacac cttcagcagc     480
ttctatatgc actgggtgcg acaggcccct ggacaagggc ttgagtggat gggaataatc     540
gaccctaatt ctggtttcac aagctacgca cagaacttcc aggccagact caccatgacc     600
agggacccgt ccactaacac agtctacatg gaactcagca acctgagatc tgacgacact     660
gccgtgtatt actgtgcgcg ctacatctac tacatgggtt acgatgaatg gggtcaaggt     720
actctggtga ccgtctcctc a                                                741

<210> SEQ ID NO 374
<211> LENGTH: 247
<212> TYPE: PRT
<213> ORGANISM: Artificial Sequence
<220> FEATURE:
<223> OTHER INFORMATION: Synthetic

<400> SEQUENCE: 374

Asp Val Val Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr

```
            20                  25                  30
Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Phe
                85                  90                  95

Thr Phe Gly Gln Gly Thr Arg Leu Glu Ile Lys Arg Ser Arg Gly Gly
            100                 105                 110

Gly Gly Ser Gly Gly Gly Ser Gly Gly Gly Ser Leu Glu Met
            115                 120                 125

Ala Gln Val Gln Leu Val Gln Ser Gly Ala Glu Val Lys Glu Pro Gly
            130                 135                 140

Ala Ser Val Lys Val Ser Cys Lys Ala Ser Gly Tyr Thr Phe Ser Ser
145                 150                 155                 160

Phe Tyr Met His Trp Val Arg Gln Ala Pro Gly Gln Gly Leu Glu Trp
                165                 170                 175

Met Gly Ile Ile Asp Pro Asn Ser Gly Phe Thr Ser Tyr Ala Gln Asn
            180                 185                 190

Phe Gln Ala Arg Leu Thr Met Thr Arg Asp Pro Ser Thr Asn Thr Val
            195                 200                 205

Tyr Met Glu Leu Ser Asn Leu Arg Ser Asp Asp Thr Ala Val Tyr Tyr
        210                 215                 220

Cys Ala Arg Tyr Ile Tyr Tyr Met Gly Tyr Asp Glu Trp Gly Gln Gly
225                 230                 235                 240

Thr Leu Val Thr Val Ser Ser
            245

<210> SEQ ID NO 375
<211> LENGTH: 324
<212> TYPE: DNA
<213> ORGANISM: Artificial Sequence
<220> FEATURE:
<223> OTHER INFORMATION: Synthetic

<400> SEQUENCE: 375
gatgttgtga tgactcagtc tccatcctcc ctgtctgcat ctgtaggaga cagagtcacc       60
atcacttgcc gggcaagtca gagcattagc agctatttaa attggtatca gcagaaacca      120
gggaaagccc ctaagctcct gatctatgct gcatccagtt tgcaaagtgg ggtcccatca      180
aggttcagtg gcagtggatc tgggacagat ttcactctca ccatcagcag tctgcaacct      240
gaagattttg caacttacta ctgtcaacag agttacagta ccccccttca cttcggccaa      300
gggacacgac tggagattaa acgt                                             324

<210> SEQ ID NO 376
<211> LENGTH: 108
<212> TYPE: PRT
<213> ORGANISM: Artificial Sequence
<220> FEATURE:
<223> OTHER INFORMATION: Synthetic

<400> SEQUENCE: 376

Asp Val Val Met Thr Gln Ser Pro Ser Ser Leu Ser Ala Ser Val Gly
1               5                   10                  15
```

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Phe
                 85                  90                  95

Thr Phe Gly Gln Gly Thr Arg Leu Glu Ile Lys Arg
            100                 105

<210> SEQ ID NO 377
<211> LENGTH: 354
<212> TYPE: DNA
<213> ORGANISM: Artificial Sequence
<220> FEATURE:
<223> OTHER INFORMATION: Synthetic

<400> SEQUENCE: 377
caggtgcagc tggtgcaatc tggggctgag gtgaaggagc ctggagcctc agttaaggtt     60
tcctgcaagg cgtctggata caccttcagc agcttctata tgcactgggt gcgacaggcc    120
cctggacaag gcttgagtg gatgggaata atcgaccta attctggttt cacaagctac      180
gcacagaact tccaggccag actcaccatg accagggacc cgtccactaa cacagtctac    240
atggaactca gcaacctgag atctgacgac actgccgtgt attactgtgc gcgctacatc    300
tactacatgg gttacgatga atggggtcaa ggtactctgg tgaccgtctc ctca          354

<210> SEQ ID NO 378
<211> LENGTH: 118
<212> TYPE: PRT
<213> ORGANISM: Artificial Sequence
<220> FEATURE:
<223> OTHER INFORMATION: Synthetic

<400> SEQUENCE: 378

Gln Val Gln Leu Val Gln Ser Gly Ala Glu Val Lys Glu Pro Gly Ala
1                5                  10                  15

Ser Val Lys Val Ser Cys Lys Ala Ser Gly Tyr Thr Phe Ser Ser Phe
            20                  25                  30

Tyr Met His Trp Val Arg Gln Ala Pro Gly Gln Gly Leu Glu Trp Met
         35                  40                  45

Gly Ile Ile Asp Pro Asn Ser Gly Phe Thr Ser Tyr Ala Gln Asn Phe
 50                  55                  60

Gln Ala Arg Leu Thr Met Thr Arg Asp Pro Ser Thr Asn Thr Val Tyr
 65                  70                  75                  80

Met Glu Leu Ser Asn Leu Arg Ser Asp Asp Thr Ala Val Tyr Tyr Cys
                 85                  90                  95

Ala Arg Tyr Ile Tyr Tyr Met Gly Tyr Asp Glu Trp Gly Gln Gly Thr
            100                 105                 110

Leu Val Thr Val Ser Ser
         115

<210> SEQ ID NO 379
<211> LENGTH: 741
<212> TYPE: DNA
<213> ORGANISM: Artificial Sequence
<220> FEATURE:
<223> OTHER INFORMATION: Synthetic

<400> SEQUENCE: 379

```
caggctgtgc tgactcagcc accctcagtg tcagtggccc caggaaagac ggcccggatc    60
acctgtggtg agacaacat tgaaactaaa agtgtgcact ggtaccagca gaggccaggc   120
caggccctg tactggtcat ctattatgat aacgaccggc cctcagggat ccctgagcgg   180
ttctctggct ccaactctgg ggacacgccc accctgacca tcagcagggt cgaagccggg   240
gacgaggccg actattactg tcaggtgtgg gataaaagta atgatcacat ggtgtttggc   300
ggagggacca gctgaccgt cctaggttct agaggtggtg gtggtagcgg cggcggcggc   360
tctggtggtg gtggatccct cgagatggcc gaagtgcagc tggtgcagtc tggggctgag   420
gtgaagaagc tgggggcctc agtgaagatt tcctgcaagg catctggata caccttcacc   480
agctactata tgcactgggt gcgacaggcc cctggacaag gcttgagtg gatgggaata   540
atcaacccta gtggtggtta cacaagctac gcacagaagt tccagggcag agtcaccatg   600
accagggaca cgtccacgag cacagtctac atggagctga gcagcctgag atctgaggac   660
accgccatgt attactgtgc gcgcggtatg ctgacttacc tggattcttg gggtcaaggt   720
actctggtga ccgtctcctc a                                              741
```

<210> SEQ ID NO 380
<211> LENGTH: 247
<212> TYPE: PRT
<213> ORGANISM: Artificial Sequence
<220> FEATURE:
<223> OTHER INFORMATION: Synthetic

<400> SEQUENCE: 380

```
Gln Ala Val Leu Thr Gln Pro Pro Ser Val Ser Val Ala Pro Gly Lys
1               5                   10                  15

Thr Ala Arg Ile Thr Cys Gly Gly Asp Asn Ile Glu Thr Lys Ser Val
            20                  25                  30

His Trp Tyr Gln Gln Arg Pro Gly Gln Ala Pro Val Leu Val Ile Tyr
        35                  40                  45

Tyr Asp Asn Asp Arg Pro Ser Gly Ile Pro Glu Arg Phe Ser Gly Ser
    50                  55                  60

Asn Ser Gly Asp Thr Pro Thr Leu Thr Ile Ser Arg Val Glu Ala Gly
65                  70                  75                  80

Asp Glu Ala Asp Tyr Tyr Cys Gln Val Trp Asp Lys Ser Asn Asp His
                85                  90                  95

Met Val Phe Gly Gly Gly Thr Lys Leu Thr Val Leu Gly Ser Arg Gly
            100                 105                 110

Gly Gly Gly Ser Gly Gly Gly Gly Ser Gly Gly Gly Gly Ser Leu Glu
        115                 120                 125

Met Ala Glu Val Gln Leu Val Gln Ser Gly Ala Glu Val Lys Lys Pro
    130                 135                 140

Gly Ala Ser Val Lys Ile Ser Cys Lys Ala Ser Gly Tyr Thr Phe Thr
145                 150                 155                 160

Ser Tyr Tyr Met His Trp Val Arg Gln Ala Pro Gly Gln Gly Leu Glu
                165                 170                 175

Trp Met Gly Ile Ile Asn Pro Ser Gly Gly Tyr Thr Ser Tyr Ala Gln
            180                 185                 190

Lys Phe Gln Gly Arg Val Thr Met Thr Arg Asp Thr Ser Thr Ser Thr
        195                 200                 205
```

```
Val Tyr Met Glu Leu Ser Ser Leu Arg Ser Glu Asp Thr Ala Met Tyr
    210                 215                 220
Tyr Cys Ala Arg Gly Met Leu Thr Tyr Leu Asp Ser Trp Gly Gln Gly
225                 230                 235                 240
Thr Leu Val Thr Val Ser Ser
                245
```

<210> SEQ ID NO 381
<211> LENGTH: 327
<212> TYPE: DNA
<213> ORGANISM: Artificial Sequence
<220> FEATURE:
<223> OTHER INFORMATION: Synthetic

<400> SEQUENCE: 381

```
caggctgtgc tgactcagcc accctcagtg tcagtggccc caggaaagac ggcccggatc     60
acctgtggtg agacaacat tgaaactaaa agtgtgcact ggtaccagca gaggccaggc    120
caggcccctg tactggtcat ctattatgat aacgaccggc cctcagggat ccctgagcgg    180
ttctctggct ccaactctgg ggacacgccc accctgacca tcagcagggt cgaagccggg    240
gacgaggccg actattactg tcaggtgtgg ataaaagta atgatcacat ggtgtttggc    300
ggagggacca agctgaccgt cctaggt                                        327
```

<210> SEQ ID NO 382
<211> LENGTH: 109
<212> TYPE: PRT
<213> ORGANISM: Artificial Sequence
<220> FEATURE:
<223> OTHER INFORMATION: Synthetic

<400> SEQUENCE: 382

```
Gln Ala Val Leu Thr Gln Pro Pro Ser Val Ser Val Ala Pro Gly Lys
1               5                   10                  15
Thr Ala Arg Ile Thr Cys Gly Gly Asp Asn Ile Glu Thr Lys Ser Val
            20                  25                  30
His Trp Tyr Gln Gln Arg Pro Gly Gln Ala Pro Val Leu Val Ile Tyr
        35                  40                  45
Tyr Asp Asn Asp Arg Pro Ser Gly Ile Pro Glu Arg Phe Ser Gly Ser
    50                  55                  60
Asn Ser Gly Asp Thr Pro Thr Leu Thr Ile Ser Arg Val Glu Ala Gly
65                  70                  75                  80
Asp Glu Ala Asp Tyr Tyr Cys Gln Val Trp Asp Lys Ser Asn Asp His
                85                  90                  95
Met Val Phe Gly Gly Gly Thr Lys Leu Thr Val Leu Gly
            100                 105
```

<210> SEQ ID NO 383
<211> LENGTH: 351
<212> TYPE: DNA
<213> ORGANISM: Artificial Sequence
<220> FEATURE:
<223> OTHER INFORMATION: Synthetic

<400> SEQUENCE: 383

```
gaagtgcagc tggtgcagtc tggggctgag gtgaagaagc ctggggcctc agtgaagatt     60
tcctgcaagg catctggata caccttcacc agctactata tgcactgggt gcgacaggcc    120
cctggacaag gcttgagtg gatgggaata atcaacccta gtggtggtta cacaagctac    180
```

```
gcacagaagt tccagggcag agtcaccatg accagggaca cgtccacgag cacagtctac    240
atggagctga gcagcctgag atctgaggac accgccatgt attactgtgc gcgcggtatg    300
ctgacttacc tggattcttg gggtcaaggt actctggtga ccgtctcctc a             351
```

```
<210> SEQ ID NO 384
<211> LENGTH: 117
<212> TYPE: PRT
<213> ORGANISM: Artificial Sequence
<220> FEATURE:
<223> OTHER INFORMATION: Synthetic

<400> SEQUENCE: 384
```

```
Glu Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Tyr Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Met Tyr Tyr Cys
                85                  90                  95

Ala Arg Gly Met Leu Thr Tyr Leu Asp Ser Trp Gly Gln Gly Thr Leu
            100                 105                 110

Val Thr Val Ser Ser
        115
```

```
<210> SEQ ID NO 385
<211> LENGTH: 753
<212> TYPE: DNA
<213> ORGANISM: Artificial Sequence
<220> FEATURE:
<223> OTHER INFORMATION: Synthetic

<400> SEQUENCE: 385
```

```
caatctgccc tgactcagcc tccctccgcg tccgggtctc ctggacagtc agtcaccatc    60
tcctgcactg gagccagcag tcacgttggt gcttacagct atgtctcctg gtaccaacag    120
cacccaggca aagcccccaa actcataatt tatgacgtca ataagcggcc ctcaggggtc    180
cctgatcgct tctctggctc caagtctggc aacacggcct ccctgaccgt ctctgggctc    240
caggctgagg atgaggctga ttattactgc agctcatatg caagcagcaa caattatgtg    300
cttttcggcg gagggaccaa gctgaccgtc ctaggttcta gaggtggtgg tggtagcggc    360
ggcggcggct ctggtggtgg tggatcctc gagatggccc aggtgcagct ggtgcagtct    420
ggggctgagg tgaagaagcc tggggcctca gtgaaggtct cctgcaaggc ttctggatac    480
accttcagca gcttctatat gcactgggtg cgacaggccc tggacaaggg cttgagtgg    540 atgggaataa tcgaccctaa ttctggtttc acaagctacg cacagaactt ccaggccaga    600
ctcaccatga ccagggaccc gtccactaac acagtctaca tggaactcag caacctgaga    660
tctgacgaca cggccgtgta ttactgtgcg cgctacatct acgcttctgg tatcgatact    720
tggggtcaag gtactctggt gaccgtctcc tca                                 753
```

```
<210> SEQ ID NO 386
<211> LENGTH: 251
```

```
<212> TYPE: PRT
<213> ORGANISM: Artificial Sequence
<220> FEATURE:
<223> OTHER INFORMATION: Synthetic

<400> SEQUENCE: 386
```

| | | | | | | | | | | | | | | | |
|---|---|---|---|---|---|---|---|---|---|---|---|---|---|---|---|
| Gln | Ser | Ala | Leu | Thr | Gln | Pro | Pro | Ser | Ala | Ser | Gly | Ser | Pro | Gly | Gln |
| 1 | | | | 5 | | | | | 10 | | | | | 15 | |
| Ser | Val | Thr | Ile | Ser | Cys | Thr | Gly | Ala | Ser | Ser | His | Val | Gly | Ala | Tyr |
| | | | 20 | | | | | 25 | | | | | 30 | | |
| Ser | Tyr | Val | Ser | Trp | Tyr | Gln | Gln | His | Pro | Gly | Lys | Ala | Pro | Lys | Leu |
| | | 35 | | | | | 40 | | | | | 45 | | | |
| Ile | Ile | Tyr | Asp | Val | Asn | Lys | Arg | Pro | Ser | Gly | Val | Pro | Asp | Arg | Phe |
| 50 | | | | | 55 | | | | | 60 | | | | | |
| Ser | Gly | Ser | Lys | Ser | Gly | Asn | Thr | Ala | Ser | Leu | Thr | Val | Ser | Gly | Leu |
| 65 | | | | | 70 | | | | | 75 | | | | | 80 |
| Gln | Ala | Glu | Asp | Glu | Ala | Asp | Tyr | Tyr | Cys | Ser | Ser | Tyr | Ala | Ser | Ser |
| | | | | 85 | | | | | 90 | | | | | 95 | |
| Asn | Asn | Tyr | Val | Leu | Phe | Gly | Gly | Gly | Thr | Lys | Leu | Thr | Val | Leu | Gly |
| | | | 100 | | | | | 105 | | | | | 110 | | |
| Ser | Arg | Gly | Gly | Gly | Gly | Ser | Gly | Gly | Gly | Ser | Gly | Gly | Gly | Gly | |
| | | 115 | | | | | 120 | | | | | 125 | | | |
| Ser | Leu | Glu | Met | Ala | Gln | Val | Gln | Leu | Val | Gln | Ser | Gly | Ala | Glu | Val |
| 130 | | | | | 135 | | | | | 140 | | | | | |
| Lys | Lys | Pro | Gly | Ala | Ser | Val | Lys | Val | Ser | Cys | Lys | Ala | Ser | Gly | Tyr |
| 145 | | | | | 150 | | | | | 155 | | | | | 160 |
| Thr | Phe | Ser | Ser | Phe | Tyr | Met | His | Trp | Val | Arg | Gln | Ala | Pro | Gly | Gln |
| | | | 165 | | | | | 170 | | | | | 175 | | |
| Gly | Leu | Glu | Trp | Met | Gly | Ile | Ile | Asp | Pro | Asn | Ser | Gly | Phe | Thr | Ser |
| | | 180 | | | | | 185 | | | | | 190 | | | |
| Tyr | Ala | Gln | Asn | Phe | Gln | Ala | Arg | Leu | Thr | Met | Thr | Arg | Asp | Pro | Ser |
| | | 195 | | | | | 200 | | | | | 205 | | | |
| Thr | Asn | Thr | Val | Tyr | Met | Glu | Leu | Ser | Asn | Leu | Arg | Ser | Asp | Asp | Thr |
| 210 | | | | | 215 | | | | | 220 | | | | | |
| Ala | Val | Tyr | Tyr | Cys | Ala | Arg | Tyr | Ile | Tyr | Ala | Ser | Gly | Ile | Asp | Thr |
| 225 | | | | | 230 | | | | | 235 | | | | | 240 |
| Trp | Gly | Gln | Gly | Thr | Leu | Val | Thr | Val | Ser | Ser | | | | | |
| | | | | 245 | | | | | 250 | | | | | | |

```
<210> SEQ ID NO 387
<211> LENGTH: 336
<212> TYPE: DNA
<213> ORGANISM: Artificial Sequence
<220> FEATURE:
<223> OTHER INFORMATION: Synthetic
<400> SEQUENCE: 387
caatctgccc tgactcagcc tccctccgcg tccgggtctc ctggacagtc agtcaccatc      60
tcctgcactg gagccagcag tcacgttggt gcttacagct atgtctcctg gtaccaacag     120
cacccaggca agccccccaa actcataatt tatgacgtca ataagcggcc ctcaggggtc     180
cctgatcgct tctctggctc caagtctggc aacacggcct ccctgaccgt ctctgggctc     240
caggctgagg atgaggctga ttattactgc agctcatatg caagcagcaa caattatgtg     300
cttttcggcg gagggaccaa gctgaccgtc ctaggt                               336

<210> SEQ ID NO 388
```

```
<211> LENGTH: 112
<212> TYPE: PRT
<213> ORGANISM: Artificial Sequence
<220> FEATURE:
<223> OTHER INFORMATION: Synthetic

<400> SEQUENCE: 388

Gln Ser Ala Leu Thr Gln Pro Pro Ser Ala Ser Gly Ser Pro Gly Gln
1               5                   10                  15

Ser Val Thr Ile Ser Cys Thr Gly Ala Ser Ser His Val Gly Ala Tyr
            20                  25                  30

Ser Tyr Val Ser Trp Tyr Gln Gln His Pro Gly Lys Ala Pro Lys Leu
        35                  40                  45

Ile Ile Tyr Asp Val Asn Lys Arg Pro Ser Gly Val Pro Asp Arg Phe
50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Ser Ser
                85                  90                  95

Asn Asn Tyr Val Leu Phe Gly Gly Gly Thr Lys Leu Thr Val Leu Gly
            100                 105                 110

<210> SEQ ID NO 389
<211> LENGTH: 354
<212> TYPE: DNA
<213> ORGANISM: Artificial Sequence
<220> FEATURE:
<223> OTHER INFORMATION: Synthetic

<400> SEQUENCE: 389
caggtgcagc tggtgcagtc tggggctgag gtgaagaagc ctggggcctc agtgaaggtc      60
tcctgcaagg cttctggata caccttcagc agcttctata tgcactgggt gcgacaggcc    120
cctggacaag gcttgagtg gatgggaata atcgaccta attctggttt cacaagctac      180
gcacagaact tccaggccag actcaccatg accaggacc cgtccactaa cacagtctac      240
atggaactca gcaacctgag atctgacgac acggccgtgt attactgtgc gcgctacatc    300
tacgcttctg gtatcgatac ttggggtcaa ggtactctgg tgaccgtctc ctca          354

<210> SEQ ID NO 390
<211> LENGTH: 118
<212> TYPE: PRT
<213> ORGANISM: Artificial Sequence
<220> FEATURE:
<223> OTHER INFORMATION: Synthetic

<400> SEQUENCE: 390

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Ser Phe
            20                  25                  30

Tyr Met His Trp Val Arg Gln Ala Pro Gly Gln Gly Leu Glu Trp Met
        35                  40                  45

Gly Ile Ile Asp Pro Asn Ser Gly Phe Thr Ser Tyr Ala Gln Asn Phe
50                  55                  60

Gln Ala Arg Leu Thr Met Thr Arg Asp Pro Ser Thr Asn Thr Val Tyr
65                  70                  75                  80

Met Glu Leu Ser Asn Leu Arg Ser Asp Asp Thr Ala Val Tyr Tyr Cys
                85                  90                  95
```

Ala Arg Tyr Ile Tyr Ala Ser Gly Ile Asp Thr Trp Gly Gln Gly Thr
            100                 105                 110

Leu Val Thr Val Ser Ser
        115

<210> SEQ ID NO 391
<211> LENGTH: 750
<212> TYPE: DNA
<213> ORGANISM: Artificial Sequence
<220> FEATURE:
<223> OTHER INFORMATION: Synthetic

<400> SEQUENCE: 391
gacatccagt tgacccagtc tccatcctcc ctgtctgcat ctgtaggaga cagagtcacc      60
atcacttgtc gggcaagtca gagcattagc agctatttaa attggtatca gcagaaacca     120
gggaaagccc ctaagctcct gatctatgct gcatccagtt tgcaaagtgg ggtcccatca     180
aggttcagtg gcagtggatc tgggacagat ttcactctca ccatcagcag tctgcaacct     240
gaagattttg caacttacta ctgtcaacag agttacagta ccccgctcac tttcggcgga     300
gggaccaagg tggagatcaa acgttctaga ggtggtggtg gtagcggcgg cggcggctct     360
ggtggtggtg gatccctcga gatggcccag gtgcagctgg tgcagtctgg ggctgaggtg     420
aagaagcctg ggcctcagt gaaggtttcc tgcaaggcat ctggatacac cttcaccagc     480
tactatatgc actgggtgcg acaggcccct ggacaagggc ttgagtggat gggaataatc     540
aaccctagtg gtggtagcac aagctacgca cagaagttcc agggcagagt caccatgacc     600
agggacacgt ccacgagcac agtctacatg gagctgagca gcctgagatc tgacgacacg     660
gccgtgtatt actgtgcgcg ctcttactac tctgttggta ctcagtggct ggattcttgg     720
ggtcaaggta ctctggtgac cgtctcctca                                       750

<210> SEQ ID NO 392
<211> LENGTH: 250
<212> TYPE: PRT
<213> ORGANISM: Artificial Sequence
<220> FEATURE:
<223> OTHER INFORMATION: Synthetic

<400> SEQUENCE: 392

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys Arg Ser Arg Gly Gly
            100                 105                 110

Gly Gly Ser Gly Gly Gly Gly Ser Gly Gly Gly Gly Ser Leu Glu Met
        115                 120                 125

Ala Gln Val Gln Leu Val Gln Ser Gly Ala Glu Val Lys Lys Pro Gly
    130                 135                 140

```
Ala Ser Val Lys Val Ser Cys Lys Ala Ser Gly Tyr Thr Phe Thr Ser
145                 150                 155                 160

Tyr Tyr Met His Trp Val Arg Gln Ala Pro Gln Gly Leu Glu Trp
            165                 170                 175

Met Gly Ile Ile Asn Pro Ser Gly Gly Ser Thr Ser Tyr Ala Gln Lys
            180                 185                 190

Phe Gln Gly Arg Val Thr Met Thr Arg Asp Thr Ser Thr Ser Thr Val
        195                 200                 205

Tyr Met Glu Leu Ser Ser Leu Arg Ser Asp Asp Thr Ala Val Tyr Tyr
    210                 215                 220

Cys Ala Arg Ser Tyr Tyr Ser Val Gly Thr Gln Trp Leu Asp Ser Trp
225                 230                 235                 240

Gly Gln Gly Thr Leu Val Thr Val Ser Ser
                245                 250
```

<210> SEQ ID NO 393
<211> LENGTH: 324
<212> TYPE: DNA
<213> ORGANISM: Artificial Sequence
<220> FEATURE:
<223> OTHER INFORMATION: Synthetic

<400> SEQUENCE: 393

```
gacatccagt tgacccagtc tccatcctcc ctgtctgcat ctgtaggaga cagagtcacc      60
atcacttgtc gggcaagtca gagcattagc agctatttaa attggtatca gcagaaacca     120
gggaaagccc ctaagctcct gatctatgct gcatccagtt tgcaaagtgg ggtcccatca     180
aggttcagtg gcagtggatc tgggacagat ttcactctca ccatcagcag tctgcaacct     240
gaagattttg caacttacta ctgtcaacag agttacagta ccccgctcac tttcggcgga     300
gggaccaagg tggagatcaa acgt                                            324
```

<210> SEQ ID NO 394
<211> LENGTH: 108
<212> TYPE: PRT
<213> ORGANISM: Artificial Sequence
<220> FEATURE:
<223> OTHER INFORMATION: Synthetic

<400> SEQUENCE: 394

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys Arg
            100                 105
```

<210> SEQ ID NO 395
<211> LENGTH: 363
<212> TYPE: DNA
<213> ORGANISM: Artificial Sequence
<220> FEATURE:
<223> OTHER INFORMATION: Synthetic

<400> SEQUENCE: 395

```
caggtgcagc tggtgcagtc tggggctgag gtgaagaagc ctggggcctc agtgaaggtt    60
tcctgcaagg catctggata caccttcacc agctactata tgcactgggt gcgacaggcc   120
cctggacaag gcttgagtg gatgggaata atcaacccta gtggtggtag cacaagctac   180
gcacagaagt tccagggcag agtcaccatg accaggaca cgtccacgag cacagtctac   240
atggagctga gcagcctgag atctgacgac acggccgtgt attactgtgc gcgctcttac   300
tactctgttg gtactcagtg gctggattct tggggtcaag gtactctggt gaccgtctcc   360
tca                                                                  363
```

<210> SEQ ID NO 396
<211> LENGTH: 121
<212> TYPE: PRT
<213> ORGANISM: Artificial Sequence
<220> FEATURE:
<223> OTHER INFORMATION: Synthetic

<400> SEQUENCE: 396

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Ser Tyr
            20                  25                  30
Tyr Met His Trp Val Arg Gln Ala Pro Gly Gln Gly Leu Glu Trp Met
        35                  40                  45
Gly Ile Ile Asn Pro Ser Gly Gly Ser Thr Ser Tyr Ala Gln Lys Phe
    50                  55                  60
Gln Gly Arg Val Thr Met Thr Arg Asp Thr Ser Thr Ser Thr Val Tyr
65                  70                  75                  80
Met Glu Leu Ser Ser Leu Arg Ser Asp Asp Thr Ala Val Tyr Tyr Cys
                85                  90                  95
Ala Arg Ser Tyr Tyr Ser Val Gly Thr Gln Trp Leu Asp Ser Trp Gly
            100                 105                 110
Gln Gly Thr Leu Val Thr Val Ser Ser
        115                 120
```

<210> SEQ ID NO 397
<211> LENGTH: 744
<212> TYPE: DNA
<213> ORGANISM: Artificial Sequence
<220> FEATURE:
<223> OTHER INFORMATION: Synthetic

<400> SEQUENCE: 397

```
tcctatgagc tgactcagcc accctcgatg tcagtggccc caggacagac ggccaggatt    60
acctgtgggg gaaacaacgt tggcagaaaa agtgtgcact ggtaccagca gaagccaggc   120
caggcccctg tgctggtcgt ctatgatgat agcgtccggc cctcagggat ccctgagcga   180
ttctctggct ccaactctgg gaacacggcc accctgacca tcagcagggt cgaagccggg   240
gatgaggccg actatttctg tcaggtgtgg gataattttc gtgatcaggt gttcggcgga   300
gggaccaagc tgaccgtcct aggttctaga ggtggtggtg gtagcggcgg cggcggctct   360
ggtggtggtg gatccctcga gatggccgag gtgcagctgg tggagtctgg ggctgaggtg   420
aagaagcctg ggcctcagt gaaggtttcc tgcaaggcat ctggatacac cttcaccagc   480
```

```
tactatatgc actgggtgcg acaggcccct ggacaagggc ttgagtggat gggaataatc      540
aaccctagtg gtggtagcac aagctacgca cagaagttcc agggcagagt caccatgacc      600
agggacacgt ccacgagcac agtctacatg gcgctgagca gcctgagatc tgaggacacg      660
gccgtatatt actgtgcgcg cggtgtttct ttcatgtctg ctatggattc ttggggtcaa      720
ggtactctgg tgaccgtctc ctca                                             744
```

<210> SEQ ID NO 398
<211> LENGTH: 248
<212> TYPE: PRT
<213> ORGANISM: Artificial Sequence
<220> FEATURE:
<223> OTHER INFORMATION: Synthetic

<400> SEQUENCE: 398

```
Ser Tyr Glu Leu Thr Gln Pro Pro Ser Met Ser Val Ala Pro Gly Gln
1               5                   10                  15

Thr Ala Arg Ile Thr Cys Gly Gly Asn Asn Val Gly Arg Lys Ser Val
            20                  25                  30

His Trp Tyr Gln Gln Lys Pro Gly Gln Ala Pro Val Leu Val Val Tyr
        35                  40                  45

Asp Asp Ser Val Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Phe Cys Gln Val Trp Asp Asn Phe Arg Asp Gln
                85                  90                  95

Val Phe Gly Gly Gly Thr Lys Leu Thr Val Leu Gly Ser Arg Gly Gly
            100                 105                 110

Gly Gly Ser Gly Gly Gly Ser Gly Gly Gly Ser Leu Glu Met
            115                 120                 125

Ala Glu Val Gln Leu Val Glu Ser Gly Ala Glu Val Lys Lys Pro Gly
        130                 135                 140

Ala Ser Val Lys Val Ser Cys Lys Ala Ser Gly Tyr Thr Phe Thr Ser
145                 150                 155                 160

Tyr Tyr Met His Trp Val Arg Gln Ala Pro Gly Gln Gly Leu Glu Trp
                165                 170                 175

Met Gly Ile Ile Asn Pro Ser Gly Gly Ser Thr Ser Tyr Ala Gln Lys
            180                 185                 190

Phe Gln Gly Arg Val Thr Met Thr Arg Asp Thr Ser Thr Ser Thr Val
        195                 200                 205

Tyr Met Ala Leu Ser Ser Leu Arg Ser Glu Asp Thr Ala Val Tyr Tyr
    210                 215                 220

Cys Ala Arg Gly Val Ser Phe Met Ser Ala Met Asp Ser Trp Gly Gln
225                 230                 235                 240

Gly Thr Leu Val Thr Val Ser Ser
                245
```

<210> SEQ ID NO 399
<211> LENGTH: 324
<212> TYPE: DNA
<213> ORGANISM: Artificial Sequence
<220> FEATURE:
<223> OTHER INFORMATION: Synthetic

<400> SEQUENCE: 399

```
tcctatgagc tgactcagcc accctcgatg tcagtggccc caggacagac ggccaggatt      60
```
acctgtgggg gaaacaacgt tggcagaaaa agtgtgcact ggtaccagca gaagccaggc    120
caggcccctg tgctggtcgt ctatgatgat agcgtccggc cctcaggat ccctgagcga     180 ttctctggct ccaactctgg gaacacggcc accctgacca tcagcagggt cgaagccggg    240
gatgaggccg actatttctg tcaggtgtgg gataattttc gtgatcaggt gttcggcgga    300
gggaccaagc tgaccgtcct aggt                                           324

<210> SEQ ID NO 400
<211> LENGTH: 108
<212> TYPE: PRT
<213> ORGANISM: Artificial Sequence
<220> FEATURE:
<223> OTHER INFORMATION: Synthetic

<400> SEQUENCE: 400

Ser Tyr Glu Leu Thr Gln Pro Pro Ser Met Ser Val Ala Pro Gly Gln
1               5                   10                  15

Thr Ala Arg Ile Thr Cys Gly Gly Asn Asn Val Gly Arg Lys Ser Val
            20                  25                  30

His Trp Tyr Gln Gln Lys Pro Gly Gln Ala Pro Val Leu Val Val Tyr
        35                  40                  45

Asp Asp Ser Val Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Phe Cys Gln Val Trp Asp Asn Phe Arg Asp Gln
                85                  90                  95

Val Phe Gly Gly Gly Thr Lys Leu Thr Val Leu Gly
            100                 105

<210> SEQ ID NO 401
<211> LENGTH: 357
<212> TYPE: DNA
<213> ORGANISM: Artificial Sequence
<220> FEATURE:
<223> OTHER INFORMATION: Synthetic

<400> SEQUENCE: 401
gaggtgcagc tggtggagtc tggggctgag gtgaagaagc ctggggcctc agtgaaggtt    60
tcctgcaagg catctggata caccttcacc agctactata tgcactgggt gcgacaggcc    120
cctggacaag gcttgagtg gatgggaata atcaaccca gtggtggtag cacaagctac     180
gcacagaagt tccagggcag agtcaccatg accagggaca cgtccacgag cacagtctac    240
atggcgctga gcagcctgag atctgaggac acggccgtat attactgtgc gcgcggtgtt    300
tctttcatgt ctgctatgga ttcttgggt caaggtactc tggtgaccgt ctcctca       357

<210> SEQ ID NO 402
<211> LENGTH: 119
<212> TYPE: PRT
<213> ORGANISM: Artificial Sequence
<220> FEATURE:
<223> OTHER INFORMATION: Synthetic

<400> SEQUENCE: 402

Glu Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Ala Leu Ser Ser Leu Arg Ser Glu Asp Thr Ala Val Tyr Tyr Cys
                85                  90                  95

Ala Arg Gly Val Ser Phe Met Ser Ala Met Asp Ser Trp Gly Gln Gly
            100                 105                 110

Thr Leu Val Thr Val Ser Ser
        115

<210> SEQ ID NO 403
<211> LENGTH: 747
<212> TYPE: DNA
<213> ORGANISM: Artificial Sequence
<220> FEATURE:
<223> OTHER INFORMATION: Synthetic

<400> SEQUENCE: 403
gacatccagt tgacccagtc tccttccacc ctggctgcat ctgtcggaga aagagtcacc      60
atcacttgcc gggccagtca gaatattggt aactggttgg cctggtatca gcagaaacca     120
gggaaagccc ctaaggtcct gatgtttcag gcatctaatt tagaagctgg ggtcccatca     180
aggttcagcg gcagtggatt tgggacagaa ttcactctta ccatcagcag cctgcagcct     240
gatgattttg caacttatta ctgtcaacag tattatggta cccctctcac tttcggcgga     300
gggaccaagg tggagatcaa acgttctaga ggtggtggtg gtagcggcgg cggcggctct     360
ggtggtggtg gatccctcga gatggccgag gtccagctgg tgcagtctgg ggctgaggtg     420
aagaagcctg ggcctcagt gaaggtctcc tgcaaggctt ctggatacac cttcaccggc     480
tactatatgc actgggtgcg acaggcccct ggacaagggc ttgagtggat gggacggatc     540
aaccctaaca gtggtggcac aaactatgca cagaagtttc agggcagggt caccatgacc     600
agggacacgt ccatcagcac agcctacatg gagctgagca ggctgagatc tgacgacacg     660
gccgtgtatt actgtgcgcg cgactggtct tcttacgact ctgttatgga ttcttggggt     720
caaggtactc tggtgaccgt ctcctca                                         747

<210> SEQ ID NO 404
<211> LENGTH: 249
<212> TYPE: PRT
<213> ORGANISM: Artificial Sequence
<220> FEATURE:
<223> OTHER INFORMATION: Synthetic

<400> SEQUENCE: 404

Asp Ile Gln Leu Thr Gln Ser Pro Ser Thr Leu Ala Ala Ser Val Gly
1               5                   10                  15

Glu Arg Val Thr Ile Thr Cys Arg Ala Ser Gln Asn Ile Gly Asn Trp
            20                  25                  30

Leu Ala Trp Tyr Gln Gln Lys Pro Gly Lys Ala Pro Lys Val Leu Met
        35                  40                  45

Phe Gln Ala Ser Asn Leu Glu Ala Gly Val Pro Ser Arg Phe Ser Gly
    50                  55                  60

Ser Gly Phe Gly Thr Glu Phe Thr Leu Thr Ile Ser Ser Leu Gln Pro
65                  70                  75                  80

Asp Asp Phe Ala Thr Tyr Tyr Cys Gln Gln Tyr Tyr Gly Thr Pro Leu
                85                  90                  95

Thr Phe Gly Gly Gly Thr Lys Val Glu Ile Lys Arg Ser Arg Gly Gly
            100                 105                 110

Gly Gly Ser Gly Gly Gly Gly Ser Gly Gly Gly Ser Leu Glu Met
        115                 120                 125

Ala Glu Val Gln Leu Val Gln Ser Gly Ala Glu Val Lys Lys Pro Gly
130                 135                 140

Ala Ser Val Lys Val Ser Cys Lys Ala Ser Gly Tyr Thr Phe Thr Gly
145                 150                 155                 160

Tyr Tyr Met His Trp Val Arg Gln Ala Pro Gly Gln Gly Leu Glu Trp
                165                 170                 175

Met Gly Arg Ile Asn Pro Asn Ser Gly Gly Thr Asn Tyr Ala Gln Lys
            180                 185                 190

Phe Gln Gly Arg Val Thr Met Thr Arg Asp Thr Ser Ile Ser Thr Ala
        195                 200                 205

Tyr Met Glu Leu Ser Arg Leu Arg Ser Asp Asp Thr Ala Val Tyr Tyr
    210                 215                 220

Cys Ala Arg Asp Trp Ser Ser Tyr Asp Ser Val Met Asp Ser Trp Gly
225                 230                 235                 240

Gln Gly Thr Leu Val Thr Val Ser Ser
                245

<210> SEQ ID NO 405
<211> LENGTH: 324
<212> TYPE: DNA
<213> ORGANISM: Artificial Sequence
<220> FEATURE:
<223> OTHER INFORMATION: Synthetic

<400> SEQUENCE: 405
gacatccagt tgacccagtc tccttccacc ctggctgcat ctgtcggaga aagagtcacc     60
atcacttgcc gggccagtca gaatattggt aactggttgg cctggtatca gcagaaacca    120
gggaaagccc ctaaggtcct gatgtttcag gcatctaatt tagaagctgg ggtcccatca    180
aggttcagcg gcagtggatt tgggacagaa ttcactctta ccatcagcag cctgcagcct    240
gatgattttg caacttatta ctgtcaacag tattatggta cccctctcac tttcggcgga    300
gggaccaagg tggagatcaa acgt                                           324

<210> SEQ ID NO 406
<211> LENGTH: 108
<212> TYPE: PRT
<213> ORGANISM: Artificial Sequence
<220> FEATURE:
<223> OTHER INFORMATION: Synthetic

<400> SEQUENCE: 406

Asp Ile Gln Leu Thr Gln Ser Pro Ser Thr Leu Ala Ala Ser Val Gly
1               5                   10                  15

Glu Arg Val Thr Ile Thr Cys Arg Ala Ser Gln Asn Ile Gly Asn Trp
            20                  25                  30

Leu Ala Trp Tyr Gln Gln Lys Pro Gly Lys Ala Pro Lys Val Leu Met
        35                  40                  45

Phe Gln Ala Ser Asn Leu Glu Ala Gly Val Pro Ser Arg Phe Ser Gly
    50                  55                  60

Ser Gly Phe Gly Thr Glu Phe Thr Leu Thr Ile Ser Ser Leu Gln Pro

```
                65                  70                  75                  80
Asp Asp Phe Ala Thr Tyr Tyr Cys Gln Gln Tyr Tyr Gly Thr Pro Leu
                    85                  90                  95

Thr Phe Gly Gly Gly Thr Lys Val Glu Ile Lys Arg
                100                 105

<210> SEQ ID NO 407
<211> LENGTH: 360
<212> TYPE: DNA
<213> ORGANISM: Artificial Sequence
<220> FEATURE:
<223> OTHER INFORMATION: Synthetic

<400> SEQUENCE: 407
gaggtccagc tggtgcagtc tggggctgag gtgaagaagc ctggggcctc agtgaaggtc    60
tcctgcaagg cttctggata caccttcacc ggctactata tgcactgggt gcgacaggcc   120
cctggacaag gcttgagtg gatgggacgg atcaacccta acagtggtgg cacaaactat    180
gcacagaagt tcagggcag ggtcaccatg accaggaca cgtccatcag cacagcctac     240
atggagctga gcaggctgag atctgacgac acggccgtgt attactgtgc gcgcgactgg   300
tcttcttacg actctgttat ggattcttgg ggtcaaggta ctctggtgac cgtctcctca   360

<210> SEQ ID NO 408
<211> LENGTH: 120
<212> TYPE: PRT
<213> ORGANISM: Artificial Sequence
<220> FEATURE:
<223> OTHER INFORMATION: Synthetic

<400> SEQUENCE: 408

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Arg Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Trp Ser Ser Tyr Asp Ser Val Met Asp Ser Trp Gly Gln
            100                 105                 110

Gly Thr Leu Val Thr Val Ser Ser
        115                 120

<210> SEQ ID NO 409
<211> LENGTH: 744
<212> TYPE: DNA
<213> ORGANISM: Artificial Sequence
<220> FEATURE:
<223> OTHER INFORMATION: Synthetic

<400> SEQUENCE: 409
tcttctgagc tgactcagga ccctgctgtg tctgtggcct tgggacagac agtcaggatc    60
acatgccagg gagacagcct cagagacttt tatgcaacct ggtaccagca gaagccagga   120
caggcccctg tacttgtcat ctatggtgaa aattaccggc cctcagggat cccagaccgg   180
```

-continued

```
ttctctggct ccaggtcagg aaatacagct tccttgacca tcagtggggc tcaggcggag    240
gatgaggctg actattactg taagtcccgc gacagcaatg tttaccattg ggtattcggc    300
ggcgggacca agctgaccgt cctaggttct agaggtggtg gtggtagcgg cggcggcggc    360
tctggtggtg gtggatccct cgagatggcc caggtccagc tggtgcagtc tggagctgag    420
gtgaagaagc tgggggcctc agtgaaggtc tcctgcaagg cttctggtta cacctttacc    480
agctacggta tcagctgggt gcgacaggcc cctggacaag gcttgagtg gatgggatgg    540 atcagcgctt acaatggtaa cacaaactat gcacagaagc tccagggcag agtcaccatg    600
accacagaca catccacgag cacagcctac atggagctga ggagcctgag atctgacgac    660
acggccgtgt attactgtgc gcgctgggtt ggtatggaag aagaagatca ttggggtcaa    720
ggtactctgg tgaccgtctc ctca                                          744
```

<210> SEQ ID NO 410
<211> LENGTH: 248
<212> TYPE: PRT
<213> ORGANISM: Artificial Sequence
<220> FEATURE:
<223> OTHER INFORMATION: Synthetic

<400> SEQUENCE: 410

```
Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Asp Phe Tyr Ala
            20                  25                  30

Thr Trp Tyr Gln Gln Lys Pro Gly Gln Ala Pro Val Leu Val Ile Tyr
        35                  40                  45

Gly Glu Asn Tyr Arg Pro Ser Gly Ile Pro Asp Arg Phe Ser Gly Ser
    50                  55                  60

Arg Ser Gly Asn Thr Ala Ser Leu Thr Ile Ser Gly Ala Gln Ala Glu
65                  70                  75                  80

Asp Glu Ala Asp Tyr Tyr Cys Lys Ser Arg Asp Ser Asn Val Tyr His
                85                  90                  95

Trp Val Phe Gly Gly Gly Thr Lys Leu Thr Val Leu Gly Ser Arg Gly
            100                 105                 110

Gly Gly Gly Ser Gly Gly Gly Gly Ser Gly Gly Gly Gly Ser Leu Glu
        115                 120                 125

Met Ala Gln Val Gln Leu Val Gln Ser Gly Ala Glu Val Lys Lys Pro
130                 135                 140

Gly Ala Ser Val Lys Val Ser Cys Lys Ala Ser Gly Tyr Thr Phe Thr
145                 150                 155                 160

Ser Tyr Gly Ile Ser Trp Val Arg Gln Ala Pro Gly Gln Gly Leu Glu
                165                 170                 175

Trp Met Gly Trp Ile Ser Ala Tyr Asn Gly Asn Thr Asn Tyr Ala Gln
            180                 185                 190

Lys Leu Gln Gly Arg Val Thr Met Thr Thr Asp Thr Ser Thr Ser Thr
        195                 200                 205

Ala Tyr Met Glu Leu Arg Ser Leu Arg Ser Asp Asp Thr Ala Val Tyr
    210                 215                 220

Tyr Cys Ala Arg Trp Val Gly Met Glu Glu Glu Asp His Trp Gly Gln
225                 230                 235                 240

Gly Thr Leu Val Thr Val Ser Ser
            245
```

<210> SEQ ID NO 411
<211> LENGTH: 327
<212> TYPE: DNA
<213> ORGANISM: Artificial Sequence
<220> FEATURE:
<223> OTHER INFORMATION: Synthetic

<400> SEQUENCE: 411

```
tcttctgagc tgactcagga ccctgctgtg tctgtggcct tgggacagac agtcaggatc      60
acatgccagg gagacagcct cagagacttt tatgcaacct ggtaccagca gaagccagga     120
caggcccctg tacttgtcat ctatggtgaa aattaccggc cctcagggat cccagaccgg     180
ttctctggct ccaggtcagg aaatacagct tccttgacca tcagtggggc tcaggcggag     240
gatgaggctg actattactg taagtcccgc gacagcaatg tttaccattg ggtattcggc     300
ggcgggacca agctgaccgt cctaggt                                          327
```

<210> SEQ ID NO 412
<211> LENGTH: 109
<212> TYPE: PRT
<213> ORGANISM: Artificial Sequence
<220> FEATURE:
<223> OTHER INFORMATION: Synthetic

<400> SEQUENCE: 412

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Asp Phe Tyr Ala
            20                  25                  30

Thr Trp Tyr Gln Gln Lys Pro Gly Gln Ala Pro Val Leu Val Ile Tyr
        35                  40                  45

Gly Glu Asn Tyr Arg Pro Ser Gly Ile Pro Asp Arg Phe Ser Gly Ser
    50                  55                  60

Arg Ser Gly Asn Thr Ala Ser Leu Thr Ile Ser Gly Ala Gln Ala Glu
65                  70                  75                  80

Asp Glu Ala Asp Tyr Tyr Cys Lys Ser Arg Asp Ser Asn Val Tyr His
                85                  90                  95

Trp Val Phe Gly Gly Gly Thr Lys Leu Thr Val Leu Gly
            100                 105

<210> SEQ ID NO 413
<211> LENGTH: 354
<212> TYPE: DNA
<213> ORGANISM: Artificial Sequence
<220> FEATURE:
<223> OTHER INFORMATION: Synthetic

<400> SEQUENCE: 413

```
caggtccagc tggtgcagtc tggagctgag gtgaagaagc ctggggcctc agtgaaggtc      60
tcctgcaagg cttctggtta cacctttacc agctacggta tcagctgggt gcgacaggcc     120
cctggacaag gcttgagtg gatgggatgg atcagcgctt acaatggtaa cacaaactat     180
gcacagaagc tccagggcag agtcaccatg accacagaca catccacgag cacagcctac     240
atggagctga ggagcctgag atctgacgac acggccgtgt attactgtgc gcgctgggtt     300
ggtatggaag aagaagatca ttggggtcaa ggtactctgg tgaccgtctc ctca            354
```

<210> SEQ ID NO 414
<211> LENGTH: 118
<212> TYPE: PRT

<210> ORGANISM: Artificial Sequence
<220> FEATURE:
<223> OTHER INFORMATION: Synthetic

<400> SEQUENCE: 414

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Trp Val Gly Met Glu Glu Glu Asp His Trp Gly Gln Gly Thr
            100                 105                 110

Leu Val Thr Val Ser Ser
        115
```

<210> SEQ ID NO 415
<211> LENGTH: 759
<212> TYPE: DNA
<213> ORGANISM: Artificial Sequence
<220> FEATURE:
<223> OTHER INFORMATION: Synthetic

<400> SEQUENCE: 415

```
cagtctgtcg tgacgcagcc gccctcagtg tctggggccc cagggcagag ggtcaccatg      60
tcctgcactg ggagcagctc caacatcggg gcaggtcatg atgtacactg gtaccaacaa     120
tttccagaga cagcccccaa actcctcatc tctggtaacg cgatcggccc tctggggtc      180
cctgaccgct tctctggctc caagtctggc acctcagcct ccctggccat cgctggactc     240
caggctgagg atgaggctga ttattactgc cagtcctatg acagcagcct gagtggttat     300
gtcttcggca gtgggaccaa ggtcaccgtc ctaggttcta gaggtggtgg tggtagcggc     360
ggcggcggct ctggtggtgg tggatccctc gagatggccg aggtgcagct ggtggagact     420
ggggctgagg tgaagaagcc tggggcctcc gtgaagattt cctgcaaggc atctggatac     480
accttcagta gttactatct acattggctg cgacaggccc ctggacaagg cctcagtgg      540
atgggagtaa tcaacccgag cggtggttac acaagctacg cacagagatt ccagggcaga     600
gtcaccatga ccagggacac gtccacagaa acaatctaca tggagctgag cagcctgacg     660
tctgatgaca cggccgtata ttactgtgcg cgctctgtta ctcattcttc ttctgctttc     720
gattactggg gtcaaggtac tctggtgacc gtctcctca                           759
```

<210> SEQ ID NO 416
<211> LENGTH: 253
<212> TYPE: PRT
<213> ORGANISM: Artificial Sequence
<220> FEATURE:
<223> OTHER INFORMATION: Synthetic

<400> SEQUENCE: 416

```
Gln Ser Val Val Thr Gln Pro Pro Ser Val Ser Gly Ala Pro Gly Gln
1               5                   10                  15
```

```
Arg Val Thr Met Ser Cys Thr Gly Ser Ser Asn Ile Gly Ala Gly
             20                  25                  30

His Asp Val His Trp Tyr Gln Gln Phe Pro Glu Thr Ala Pro Lys Leu
         35                  40                  45

Leu Ile Ser Gly Asn Gly Asp Arg Pro Ser Gly Val Pro Asp Arg Phe
 50                  55                  60

Ser Gly Ser Lys Ser Gly Thr Ser Ala Ser Leu Ala Ile Ala Gly Leu
65                  70                  75                  80

Gln Ala Glu Asp Glu Ala Asp Tyr Tyr Cys Gln Ser Tyr Asp Ser Ser
                 85                  90                  95

Leu Ser Gly Tyr Val Phe Gly Ser Gly Thr Lys Val Thr Val Leu Gly
            100                 105                 110

Ser Arg Gly Gly Gly Gly Ser Gly Gly Gly Ser Gly Gly Gly Gly
            115                 120                 125

Ser Leu Glu Met Ala Glu Val Gln Leu Val Glu Thr Gly Ala Glu Val
            130                 135                 140

Lys Lys Pro Gly Ala Ser Val Lys Ile Ser Cys Lys Ala Ser Gly Tyr
145                 150                 155                 160

Thr Phe Ser Ser Tyr Tyr Leu His Trp Leu Arg Gln Ala Pro Gly Gln
                165                 170                 175

Gly Pro Gln Trp Met Gly Val Ile Asn Pro Ser Gly Gly Tyr Thr Ser
            180                 185                 190

Tyr Ala Gln Arg Phe Gln Gly Arg Val Thr Met Thr Arg Asp Thr Ser
                195                 200                 205

Thr Glu Thr Ile Tyr Met Glu Leu Ser Ser Leu Thr Ser Asp Asp Thr
            210                 215                 220

Ala Val Tyr Tyr Cys Ala Arg Ser Val Thr His Ser Ser Ser Ala Phe
225                 230                 235                 240

Asp Tyr Trp Gly Gln Gly Thr Leu Val Thr Val Ser Ser
                245                 250

<210> SEQ ID NO 417
<211> LENGTH: 336
<212> TYPE: DNA
<213> ORGANISM: Artificial Sequence
<220> FEATURE:
<223> OTHER INFORMATION: Synthetic

<400> SEQUENCE: 417
cagtctgtcg tgacgcagcc gccctcagtg tctggggccc cagggcagag ggtcaccatg      60
tcctgcactg ggagcagctc caacatcggg gcaggtcatg atgtacactg gtaccaacaa     120
tttccagaga cagcccccaa actcctcatc tctggtaacg gcgatcggcc ctctggggtc     180
cctgaccgct tctctggctc caagtctggc acctcagcct ccctggccat cgctggactc     240
caggctgagg atgaggctga ttattactgc cagtcctatg acagcagcct gagtggttat     300
gtcttcggca gtgggaccaa ggtcaccgtc ctaggt                               336

<210> SEQ ID NO 418
<211> LENGTH: 112
<212> TYPE: PRT
<213> ORGANISM: Artificial Sequence
<220> FEATURE:
<223> OTHER INFORMATION: Synthetic

<400> SEQUENCE: 418

Gln Ser Val Val Thr Gln Pro Pro Ser Val Ser Gly Ala Pro Gly Gln
1               5                  10                  15
```

```
Arg Val Thr Met Ser Cys Thr Gly Ser Ser Asn Ile Gly Ala Gly
         20                  25                  30

His Asp Val His Trp Tyr Gln Gln Phe Pro Glu Thr Ala Pro Lys Leu
         35                  40                  45

Leu Ile Ser Gly Asn Gly Asp Arg Pro Ser Gly Val Pro Asp Arg Phe
 50                  55                  60

Ser Gly Ser Lys Ser Gly Thr Ser Ala Ser Leu Ala Ile Ala Gly Leu
 65                  70                  75                  80

Gln Ala Glu Asp Glu Ala Asp Tyr Tyr Cys Gln Ser Tyr Asp Ser Ser
                 85                  90                  95

Leu Ser Gly Tyr Val Phe Gly Ser Gly Thr Lys Val Thr Val Leu Gly
                100                 105                 110
```

<210> SEQ ID NO 419
<211> LENGTH: 360
<212> TYPE: DNA
<213> ORGANISM: Artificial Sequence
<220> FEATURE:
<223> OTHER INFORMATION: Synthetic

<400> SEQUENCE: 419

```
gaggtgcagc tggtggagac tgggcctgag gtgaagaagc ctggggcctc cgtgaagatt    60
tcctgcaagg catctggata caccttcagt agttactatc tacattggct gcgacaggcc   120
cctggacaag ggcctcagtg gatgggagta atcaacccga gcggtggtta cacaagctac   180
gcacagagat tccagggcag agtcaccatg accagggaca cgtccacaga aacaatctac   240
atggagctga gcagcctgac gtctgatgac acggccgtat attactgtgc gcgctctgtt   300
actcattctt cttctgcttt cgattactgg ggtcaaggta ctctggtgac cgtctcctca   360
```

<210> SEQ ID NO 420
<211> LENGTH: 120
<212> TYPE: PRT
<213> ORGANISM: Artificial Sequence
<220> FEATURE:
<223> OTHER INFORMATION: Synthetic

<400> SEQUENCE: 420

```
Glu Val Gln Leu Val Glu Thr Gly Ala Glu Val Lys Lys Pro Gly Ala
  1               5                  10                  15

Ser Val Lys Ile Ser Cys Lys Ala Ser Gly Tyr Thr Phe Ser Ser Tyr
             20                  25                  30

Tyr Leu His Trp Leu Arg Gln Ala Pro Gly Gln Gly Pro Gln Trp Met
         35                  40                  45

Gly Val Ile Asn Pro Ser Gly Gly Tyr Thr Ser Tyr Ala Gln Arg Phe
 50                  55                  60

Gln Gly Arg Val Thr Met Thr Arg Asp Thr Ser Thr Glu Thr Ile Tyr
 65                  70                  75                  80

Met Glu Leu Ser Ser Leu Thr Ser Asp Asp Thr Ala Val Tyr Tyr Cys
                 85                  90                  95

Ala Arg Ser Val Thr His Ser Ser Ser Ala Phe Asp Tyr Trp Gly Gln
                100                 105                 110

Gly Thr Leu Val Thr Val Ser Ser
            115                 120
```

<210> SEQ ID NO 421
<211> LENGTH: 741
<212> TYPE: DNA

<213> ORGANISM: Artificial Sequence
<220> FEATURE:
<223> OTHER INFORMATION: Synthetic

<400> SEQUENCE: 421

```
cagtctgtgt tgactcagcc accctcagtg tcagtggccc caggacagac ggccaggatt    60
acctgtgggg gaaacaacat tggaactaaa actgttcact ggtaccagca gaagtcaggc   120
caggccctg tgctggtcat ctattatgat atcgaccggc cctcagggat ccctgagcgg    180
ttctctggct ccacctctgg aaatacggcc accctgacca tcagcagggt cgaagccggg   240
gatgaggccg actatcactg tcaggtgtgg gatagtggca gttatcaggg ggtgttcggc   300
ggagggacca agctgaccgt cctaggttct agaggtggtg gtggtagcgg cggcggcggc   360
tctggtggtg gtggatccct cgagatggcc cagatgcagc tggtgcagtc tggggctgag   420
gtgaagaagc ctggggcctc agtgaaggtt tcctgcaagg catctggata caccttcacc   480
agctactata tgcactgggt gcgacaggcc cctggacaag gcttgagtg gatgggaata   540
atcaacccta gtggtggtag cacaagctac gcacagaagt tccagggcag agtcaccatg   600
accagggaca cgtccacgag cacagtctac atggagctga gcagcctgag atctgaggac   660
actgccgtgt attactgtgc gcgcggtcag tctggtgttg tttacgattg gggtcaaggt   720
actctggtga ccgtctcctc a                                             741
```

<210> SEQ ID NO 422
<211> LENGTH: 247
<212> TYPE: PRT
<213> ORGANISM: Artificial Sequence
<220> FEATURE:
<223> OTHER INFORMATION: Synthetic

<400> SEQUENCE: 422

```
Gln Ser Val Leu Thr Gln Pro Pro Ser Val Ser Val Ala Pro Gly Gln
1               5                   10                  15

Thr Ala Arg Ile Thr Cys Gly Gly Asn Asn Ile Gly Thr Lys Thr Val
            20                  25                  30

His Trp Tyr Gln Gln Lys Ser Gly Gln Ala Pro Val Leu Val Ile Tyr
        35                  40                  45

Tyr Asp Ile Asp Arg Pro Ser Gly Ile Pro Glu Arg Phe Ser Gly Ser
    50                  55                  60

Thr Ser Gly Asn Thr Ala Thr Leu Thr Ile Ser Arg Val Glu Ala Gly
65                  70                  75                  80

Asp Glu Ala Asp Tyr His Cys Gln Val Trp Asp Ser Gly Ser Tyr Gln
                85                  90                  95

Gly Val Phe Gly Gly Gly Thr Lys Leu Thr Val Leu Gly Ser Arg Gly
            100                 105                 110

Gly Gly Gly Ser Gly Gly Gly Gly Ser Gly Gly Gly Gly Ser Leu Glu
        115                 120                 125

Met Ala Gln Met Gln Leu Val Gln Ser Gly Ala Glu Val Lys Lys Pro
    130                 135                 140

Gly Ala Ser Val Lys Val Ser Cys Lys Ala Ser Gly Tyr Thr Phe Thr
145                 150                 155                 160

Ser Tyr Tyr Met His Trp Val Arg Gln Ala Pro Gly Gln Gly Leu Glu
                165                 170                 175

Trp Met Gly Ile Ile Asn Pro Ser Gly Gly Ser Thr Ser Tyr Ala Gln
            180                 185                 190

Lys Phe Gln Gly Arg Val Thr Met Thr Arg Asp Thr Ser Thr Ser Thr
```

195                 200                 205
Val Tyr Met Glu Leu Ser Ser Leu Arg Ser Glu Asp Thr Ala Val Tyr
            210                 215                 220

Tyr Cys Ala Arg Gly Gln Ser Gly Val Val Tyr Asp Trp Gly Gln Gly
225                 230                 235                 240

Thr Leu Val Thr Val Ser Ser
                245

<210> SEQ ID NO 423
<211> LENGTH: 327
<212> TYPE: DNA
<213> ORGANISM: Artificial Sequence
<220> FEATURE:
<223> OTHER INFORMATION: Synthetic

<400> SEQUENCE: 423
cagtctgtgt tgactcagcc accctcagtg tcagtggccc caggacagac ggccaggatt    60
acctgtgggg gaaacaacat tggaactaaa actgttcact ggtaccagca gaagtcaggc   120
caggcccctg tgctggtcat ctattatgat atcgaccggc cctcagggat ccctgagcgg   180
ttctctggct ccacctctgg aaatacggcc accctgacca tcagcagggt cgaagccggg   240
gatgaggccg actatcactg tcaggtgtgg gatagtggca gttatcaggg ggtgttcggc   300
ggagggacca agctgaccgt cctaggt                                        327

<210> SEQ ID NO 424
<211> LENGTH: 109
<212> TYPE: PRT
<213> ORGANISM: Artificial Sequence
<220> FEATURE:
<223> OTHER INFORMATION: Synthetic

<400> SEQUENCE: 424

Gln Ser Val Leu Thr Gln Pro Pro Ser Val Ser Val Ala Pro Gly Gln
1               5                   10                  15

Thr Ala Arg Ile Thr Cys Gly Gly Asn Asn Ile Gly Thr Lys Thr Val
            20                  25                  30

His Trp Tyr Gln Gln Lys Ser Gly Gln Ala Pro Val Leu Val Ile Tyr
        35                  40                  45

Tyr Asp Ile Asp Arg Pro Ser Gly Ile Pro Glu Arg Phe Ser Gly Ser
    50                  55                  60

Thr Ser Gly Asn Thr Ala Thr Leu Thr Ile Ser Arg Val Glu Ala Gly
65                  70                  75                  80

Asp Glu Ala Asp Tyr His Cys Gln Val Trp Asp Ser Gly Ser Tyr Gln
                85                  90                  95

Gly Val Phe Gly Gly Gly Thr Lys Leu Thr Val Leu Gly
            100                 105

<210> SEQ ID NO 425
<211> LENGTH: 351
<212> TYPE: DNA
<213> ORGANISM: Artificial Sequence
<220> FEATURE:
<223> OTHER INFORMATION: Synthetic

<400> SEQUENCE: 425
cagatgcagc tggtgcagtc tggggctgag gtgaagaagc ctggggcctc agtgaaggtt    60
tcctgcaagg catctggata caccttcacc agctactata tgcactgggt gcgacaggcc   120
cctggacaag gcttgagtg gatgggaata atcaacccta gtggtggtag cacaagctac   180

```
gcacagaagt tccagggcag agtcaccatg accagggaca cgtccacgag cacagtctac    240
atggagctga gcagcctgag atctgaggac actgccgtgt attactgtgc gcgcggtcag    300
tctggtgttg tttacgattg gggtcaaggt actctggtga ccgtctcctc a             351
```

<210> SEQ ID NO 426
<211> LENGTH: 117
<212> TYPE: PRT
<213> ORGANISM: Artificial Sequence
<220> FEATURE:
<223> OTHER INFORMATION: Synthetic

<400> SEQUENCE: 426

Gln Met Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gln Ser Gly Val Val Tyr Asp Trp Gly Gln Gly Thr Leu
            100                 105                 110

Val Thr Val Ser Ser
        115

<210> SEQ ID NO 427
<211> LENGTH: 753
<212> TYPE: DNA
<213> ORGANISM: Artificial Sequence
<220> FEATURE:
<223> OTHER INFORMATION: Synthetic

<400> SEQUENCE: 427

```
gaaattgtgt tgacacagtc tccaggcacc ctgtctttgt ctccagggga aagagcatcc    60
ctctcctgca gggccagtca gagtattacc gacaacttct tagcctggta ccagcagaaa    120
cctggccagg ctcccaggct cctcttctat ggggcatcct acagggccaa tggcatccca    180
gacaggttca gtggcagtgg gtctgggaca gacttcactc tcaccatcag cagactggag    240
cctgaagatt ttgccgtgta ttactgtcac cagtatggca gctcacctcc gggcactttc    300
ggccctggga ccaaagtgga tatcaaacgt tctagaggtg gtggtggtag cggcggcggc    360
ggctctggtg gtggtggatc cctcgagatg gccgaggtcc agctggtaca gtctggggct    420
gaggtgaaga agcctggggc ctcagtgaag ctttcctgca aggcatctgg atacaccttc    480
accagttact acatgcactg ggtgcgacag gcccctggac aagggcttga gtggatggga    540
ataattaacc ctactggtgg ttacacaacc tacgcacaga gttccaggca cagagtcgcc    600
attaccaggg acacgtccat gagcacagtc tacatggagc tgagcaacct gagatctgaa    660
gacacggccg tgtattactg tgcgcgcggt actacttaca tgtggtctgg ttacgattct    720
tggggtcaag gtactctggt gaccgtctcc tca                                 753
```

<210> SEQ ID NO 428

<211> LENGTH: 275
<212> TYPE: PRT
<213> ORGANISM: Artificial Sequence
<220> FEATURE:
<223> OTHER INFORMATION: Synthetic

<400> SEQUENCE: 428

```
Met Lys Tyr Leu Leu Pro Thr Ala Ala Ala Gly Leu Leu Leu Leu Ala
1               5                   10                  15
Ala Gln Pro Ala Met Ala Glu Leu Glu Ile Val Leu Thr Gln Ser Pro
                20                  25                  30
Gly Thr Leu Ser Leu Ser Pro Gly Glu Arg Ala Ser Leu Ser Cys Arg
            35                  40                  45
Ala Ser Gln Ser Ile Thr Asp Asn Phe Leu Ala Trp Tyr Gln Gln Lys
        50                  55                  60
Pro Gly Gln Ala Pro Arg Leu Leu Phe Tyr Gly Ala Ser Tyr Arg Ala
65                  70                  75                  80
Asn Gly Ile Pro Asp Arg Phe Ser Gly Ser Gly Ser Gly Thr Asp Phe
                85                  90                  95
Thr Leu Thr Ile Ser Arg Leu Glu Pro Glu Asp Phe Ala Val Tyr Tyr
            100                 105                 110
Cys His Gln Tyr Gly Ser Ser Pro Pro Gly Thr Phe Gly Pro Gly Thr
        115                 120                 125
Lys Val Asp Ile Lys Arg Ser Arg Gly Gly Gly Ser Gly Gly Gly
    130                 135                 140
Gly Ser Gly Gly Gly Ser Leu Glu Met Ala Glu Val Gln Leu Val
145                 150                 155                 160
Gln Ser Gly Ala Glu Val Lys Lys Pro Gly Ala Ser Val Lys Leu Ser
                165                 170                 175
Cys Lys Ala Ser Gly Tyr Thr Phe Thr Ser Tyr Tyr Met His Trp Val
            180                 185                 190
Arg Gln Ala Pro Gly Gln Gly Leu Glu Trp Met Gly Ile Ile Asn Pro
        195                 200                 205
Thr Gly Gly Tyr Thr Thr Tyr Ala Gln Lys Phe Gln Asp Arg Val Ala
    210                 215                 220
Ile Thr Arg Asp Thr Ser Met Ser Thr Val Tyr Met Glu Leu Ser Asn
225                 230                 235                 240
Leu Arg Ser Glu Asp Thr Ala Val Tyr Tyr Cys Ala Arg Gly Thr Thr
                245                 250                 255
Tyr Met Trp Ser Gly Tyr Asp Ser Trp Gly Gln Gly Thr Leu Val Thr
            260                 265                 270
Val Ser Ser
        275
```

<210> SEQ ID NO 429
<211> LENGTH: 330
<212> TYPE: DNA
<213> ORGANISM: Artificial Sequence
<220> FEATURE:
<223> OTHER INFORMATION: Synthetic

<400> SEQUENCE: 429

```
gaaattgtgt tgacacagtc tccaggcacc ctgtctttgt ctccagggga aagagcatcc      60
ctctcctgca gggccagtca gagtattacc gacaacttct tagcctggta ccagcagaaa     120
cctggccagg ctcccaggct cctcttctat ggggcatcct acagggccaa tggcatccca     180
gacaggttca gtggcagtgg gtctgggaca gacttcactc tcaccatcag cagactggag     240
```

```
cctgaagatt tgccgtgta ttactgtcac cagtatggca gctcacctcc gggcactttc    300
ggccctggga ccaaagtgga tatcaaacgt                                    330
```

<210> SEQ ID NO 430
<211> LENGTH: 110
<212> TYPE: PRT
<213> ORGANISM: Artificial Sequence
<220> FEATURE:
<223> OTHER INFORMATION: Synthetic

<400> SEQUENCE: 430

```
Glu Ile Val Leu Thr Gln Ser Pro Gly Thr Leu Ser Leu Ser Pro Gly
1               5                   10                  15

Glu Arg Ala Ser Leu Ser Cys Arg Ala Ser Gln Ser Ile Thr Asp Asn
            20                  25                  30

Phe Leu Ala Trp Tyr Gln Gln Lys Pro Gly Gln Ala Pro Arg Leu Leu
        35                  40                  45

Phe Tyr Gly Ala Ser Tyr Arg Ala Asn Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys His Gln Tyr Gly Ser Ser Pro
                85                  90                  95

Pro Gly Thr Phe Gly Pro Gly Thr Lys Val Asp Ile Lys Arg
            100                 105                 110
```

<210> SEQ ID NO 431
<211> LENGTH: 360
<212> TYPE: DNA
<213> ORGANISM: Artificial Sequence
<220> FEATURE:
<223> OTHER INFORMATION: Synthetic

<400> SEQUENCE: 431

```
gaggtccagc tggtacagtc tggggctgag gtgaagaagc ctggggcctc agtgaagctt    60
tcctgcaagg catctggata caccttcacc agttactaca tgcactgggt gcgacaggcc   120
cctggacaag gcttgagtg gatgggaata attaacccta ctggtggtta cacaacctac    180
gcacagaagt tccaggacag agtcgccatt accagggaca cgtccatgag cacagtctac   240
atggagctga gcaacctgag atctgaagac acggccgtgt attactgtgc gcgcggtact   300
acttacatgt ggtctggtta cgattcttgg ggtcaaggta ctctggtgac cgtctcctca   360
```

<210> SEQ ID NO 432
<211> LENGTH: 120
<212> TYPE: PRT
<213> ORGANISM: Artificial Sequence
<220> FEATURE:
<223> OTHER INFORMATION: Synthetic

<400> SEQUENCE: 432

```
Glu Val Gln Leu Val Gln Ser Gly Ala Glu Val Lys Lys Pro Gly Ala
1               5                   10                  15

Ser Val Lys Leu Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Thr Gly Gly Tyr Thr Thr Tyr Ala Gln Lys Phe
    50                  55                  60
```

Gln Asp Arg Val Ala Ile Thr Arg Asp Thr Ser Met Ser Thr Val Tyr
65                  70                  75                  80

Met Glu Leu Ser Asn Leu Arg Ser Glu Asp Thr Ala Val Tyr Tyr Cys
                85                  90                  95

Ala Arg Gly Thr Thr Tyr Met Trp Ser Gly Tyr Asp Ser Trp Gly Gln
            100                 105                 110

Gly Thr Leu Val Thr Val Ser Ser
        115                 120

<210> SEQ ID NO 433
<211> LENGTH: 756
<212> TYPE: DNA
<213> ORGANISM: Artificial Sequence
<220> FEATURE:
<223> OTHER INFORMATION: Synthetic

<400> SEQUENCE: 433
caggctgtgc tgactcagcc tgcctccgtg tctgggtctc ctggacagtc gatcaccgtc      60
tcctgcactg gaaccagcag tgacgttggt ggttataact atgtctcctg gtaccaacag     120
cacccaggca agcccccaa actcatgatt tatgatgtca gtcagcggcc ctcagggggtt     180 tctcatcgct tctctggctc caagtctggc aacacggcct ccctgaccat ctctgggctc     240
caggctgagg acgaggctga ttattactgc agttcatata aagcaccag tgtttatgtc      300 ttcggaactg ggaccaaggt caccgtccta ggttctagag tggtggtgg tagcggcggc     360 ggcggctctg gtggtggtgg atccctcgag atggcccagg tgcagctggt gcagtctgga     420
cctgaggtga agaagcctgg ggcctcagtg aaggtttcct gcaaggcatc tggatacacc     480
ttcaccagtt actatatgca ctgggtgcga caggcccctg gacaagggct gagtggatg     540 ggaataatca accctagtgg tggtagcaca acctacgcac agaagttcca gggcagagtc     600
accatgacca gggacacgtc cacgagcaca gtctacatgg agctgagcag cctgagatct     660
gaggacactg ccgtgtatta ctgtgcgcgc tctgttatgc attactacga cttcttcgat     720
ggttggggtc aaggtactct ggtgaccgtc tcctca                              756

<210> SEQ ID NO 434
<211> LENGTH: 252
<212> TYPE: PRT
<213> ORGANISM: Artificial Sequence
<220> FEATURE:
<223> OTHER INFORMATION: Synthetic

<400> SEQUENCE: 434

Gln Ala Val Leu Thr Gln Pro Ala Ser Val Ser Gly Ser Pro Gly Gln
1               5                   10                  15

Ser Ile Thr Val Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Gln Arg Pro Ser Gly Val Ser His Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Thr
                85                  90                  95

Ser Val Tyr Val Phe Gly Thr Gly Thr Lys Val Thr Val Leu Gly Ser
            100                 105                 110

Arg Gly Gly Gly Gly Ser Gly Gly Gly Ser Gly Gly Gly Ser
          115                 120                 125

Leu Glu Met Ala Gln Val Gln Leu Val Gln Ser Gly Pro Glu Val Lys
        130                 135                 140

Lys Pro Gly Ala Ser Val Lys Val Ser Cys Lys Ala Ser Gly Tyr Thr
145                 150                 155                 160

Phe Thr Ser Tyr Tyr Met His Trp Val Arg Gln Ala Pro Gly Gln Gly
                165                 170                 175

Leu Glu Trp Met Gly Ile Ile Asn Pro Ser Gly Gly Ser Thr Thr Tyr
            180                 185                 190

Ala Gln Lys Phe Gln Gly Arg Val Thr Met Thr Arg Asp Thr Ser Thr
        195                 200                 205

Ser Thr Val Tyr Met Glu Leu Ser Ser Leu Arg Ser Glu Asp Thr Ala
    210                 215                 220

Val Tyr Tyr Cys Ala Arg Ser Val Met His Tyr Tyr Asp Phe Phe Asp
225                 230                 235                 240

Gly Trp Gly Gln Gly Thr Leu Val Thr Val Ser Ser
                245                 250

<210> SEQ ID NO 435
<211> LENGTH: 333
<212> TYPE: DNA
<213> ORGANISM: Artificial Sequence
<220> FEATURE:
<223> OTHER INFORMATION: Synthetic

<400> SEQUENCE: 435
caggctgtgc tgactcagcc tgcctccgtg tctgggtctc ctggacagtc gatcaccgtc     60
tcctgcactg gaaccagcag tgacgttggt ggttataact atgtctcctg gtaccaacag    120
cacccaggca agcccccaa actcatgatt tatgatgtca gtcagcggcc ctcaggggtt     180
tctcatcgct tctctggctc caagtctggc aacacggcct ccctgaccat ctctgggctc    240
caggctgagg acgaggctga ttattactgc agttcatata caagcaccag tgtttatgtc    300
ttcggaactg ggaccaaggt caccgtccta ggt                                 333

<210> SEQ ID NO 436
<211> LENGTH: 111
<212> TYPE: PRT
<213> ORGANISM: Artificial Sequence
<220> FEATURE:
<223> OTHER INFORMATION: Synthetic

<400> SEQUENCE: 436

Gln Ala Val Leu Thr Gln Pro Ala Ser Val Ser Gly Ser Pro Gly Gln
1               5                   10                  15

Ser Ile Thr Val Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Gln Arg Pro Ser Gly Val Ser His Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Thr
                85                  90                  95

Ser Val Tyr Val Phe Gly Thr Gly Thr Lys Val Thr Val Leu Gly

<210> SEQ ID NO 437
<211> LENGTH: 360
<212> TYPE: DNA
<213> ORGANISM: Artificial Sequence
<220> FEATURE:
<223> OTHER INFORMATION: Synthetic

<400> SEQUENCE: 437

```
caggtgcagc tggtgcagtc tggacctgag gtgaagaagc ctggggcctc agtgaaggtt      60
tcctgcaagg catctggata caccttcacc agttactata tgcactgggt gcgacaggcc     120
cctggacaag ggcttgagtg gatgggaata atcaaccctc gtggtggtag cacaacctac     180
gcacagaagt tccagggcag agtcaccatg accagggaca cgtccacgag cacagtctac     240
atggagctga gcagcctgag atctgaggac actgccgtgt attactgtgc gcgctctgtt     300
atgcattact acgacttctt cgatggttgg ggtcaaggta ctctggtgac cgtctcctca     360
```

<210> SEQ ID NO 438
<211> LENGTH: 120
<212> TYPE: PRT
<213> ORGANISM: Artificial Sequence
<220> FEATURE:
<223> OTHER INFORMATION: Synthetic

<400> SEQUENCE: 438

Gln Val Gln Leu Val Gln Ser Gly Pro Glu Val Lys Lys Pro Gly Ala
1               5                   10                  15
Ser Val Lys Val Ser Cys Lys Ala Ser Gly Tyr Thr Phe Thr Ser Tyr
            20                  25                  30
Tyr Met His Trp Val Arg Gln Ala Pro Gly Gln Gly Leu Glu Trp Met
        35                  40                  45
Gly Ile Ile Asn Pro Ser Gly Gly Ser Thr Thr Tyr Ala Gln Lys Phe
    50                  55                  60
Gln Gly Arg Val Thr Met Thr Arg Asp Thr Ser Thr Ser Thr Val Tyr
65                  70                  75                  80
Met Glu Leu Ser Ser Leu Arg Ser Glu Asp Thr Ala Val Tyr Tyr Cys
                85                  90                  95
Ala Arg Ser Val Met His Tyr Tyr Asp Phe Phe Asp Gly Trp Gly Gln
            100                 105                 110
Gly Thr Leu Val Thr Val Ser Ser
        115                 120

<210> SEQ ID NO 439
<211> LENGTH: 753
<212> TYPE: DNA
<213> ORGANISM: Artificial Sequence
<220> FEATURE:
<223> OTHER INFORMATION: Synthetic

<400> SEQUENCE: 439

```
caatctgccc tgactcagcc tgcctccgtg tctgggtctc ctggacagtc gatcaccatc      60
tcctgcagtg gaaccagcag tgacgttggt gcatataact atgtctcctg gtaccaacaa     120
cacccaggca aagcccccaa actcatgatc tatgatgtca ctaagcggcc ctcaggggtt     180
tctcatcgct tctctggctc caagtctggc aacacggcct ccctgaccat ctctgggctc     240
caggctgagg acgaggctga ttattactgc agctcgttta cagccatcgg cacttgggtg     300
ttcggcggag ggaccaagct gaccgtccta ggttctagag gtggtggtgg tagcggcggc     360
```

```
ggcggctctg gtggtggtgg atccctcgag atggcccagg tccagctggt gcagtctggg     420
gctgaggtgg agaagcctgg ggcctcagtg aaagtttcct gcaaggcatc tggatacacc     480
ttcaccagct cctatctgca ctgggtgcga caggcccctg acaaggact tgagtggatg      540 ggaataatca accctactgc tggtagcaca agctacgcac agaagttcca ggacagagtc     600
accatgacca gggacacgtc gacgagcaca gtctacatgg agctgagcag gctgagatct     660
gacgacacgg ccgtgtatta ctgtgcgcgc ggttactctt tcgctggtta ctacgattgg     720
tggggtcaag gtactctggt gaccgtctcc tca                                  753
```

```
<210> SEQ ID NO 440
<211> LENGTH: 251
<212> TYPE: PRT
<213> ORGANISM: Artificial Sequence
<220> FEATURE:
<223> OTHER INFORMATION: Synthetic

<400> SEQUENCE: 440
```

Gln Ser Ala Leu Thr Gln Pro Ala Ser Val Ser Gly Ser Pro Gly Gln
1               5                   10                  15

Ser Ile Thr Ile Ser Cys Ser Gly Thr Ser Ser Asp Val Gly Ala Tyr
            20                  25                  30

Asn Tyr Val Ser Trp Tyr Gln Gln His Pro Gly Lys Ala Pro Lys Leu
        35                  40                  45

Met Ile Tyr Asp Val Thr Lys Arg Pro Ser Gly Val Ser His Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Phe Thr Ala Ile
                85                  90                  95

Gly Thr Trp Val Phe Gly Gly Gly Thr Lys Leu Thr Val Leu Gly Ser
            100                 105                 110

Arg Gly Gly Gly Gly Ser Gly Gly Gly Gly Ser Gly Gly Gly Gly Ser
        115                 120                 125

Leu Glu Met Ala Gln Val Gln Leu Val Gln Ser Gly Ala Glu Val Glu
    130                 135                 140

Lys Pro Gly Ala Ser Val Lys Val Ser Cys Lys Ala Ser Gly Tyr Thr
145                 150                 155                 160

Phe Thr Ser Ser Tyr Leu His Trp Val Arg Gln Ala Pro Gly Gln Gly
                165                 170                 175

Leu Glu Trp Met Gly Ile Ile Asn Pro Thr Ala Gly Ser Thr Ser Tyr
            180                 185                 190

Ala Gln Lys Phe Gln Asp Arg Val Thr Met Thr Arg Asp Thr Ser Thr
        195                 200                 205

Ser Thr Val Tyr Met Glu Leu Ser Arg Leu Arg Ser Asp Asp Thr Ala
    210                 215                 220

Val Tyr Tyr Cys Ala Arg Gly Tyr Ser Phe Ala Gly Tyr Tyr Asp Trp
225                 230                 235                 240

Trp Gly Gln Gly Thr Leu Val Thr Val Ser Ser
                245                 250

```
<210> SEQ ID NO 441
<211> LENGTH: 333
<212> TYPE: DNA
<213> ORGANISM: Artificial Sequence
<220> FEATURE:
```

<223> OTHER INFORMATION: Synthetic

<400> SEQUENCE: 441

```
caatctgccc tgactcagcc tgcctccgtg tctgggtctc ctggacagtc gatcaccatc    60
tcctgcagtg gaaccagcag tgacgttggt gcatataact atgtctcctg gtaccaacaa   120
cacccaggca aagcccccaa actcatgatc tatgatgtca ctaagcggcc ctcagggggtt  180
tctcatcgct ctctctggctc caagtctggc aacacggcct ccctgaccat ctctgggctc   240
caggctgagg acgaggctga ttattactgc agctcgttta cagccatcgg cacttgggtg   300
ttcggcggag ggaccaagct gaccgtccta ggt                                333
```

<210> SEQ ID NO 442
<211> LENGTH: 111
<212> TYPE: PRT
<213> ORGANISM: Artificial Sequence
<220> FEATURE:
<223> OTHER INFORMATION: Synthetic

<400> SEQUENCE: 442

```
Gln Ser Ala Leu Thr Gln Pro Ala Ser Val Ser Gly Ser Pro Gly Gln
1               5                   10                  15
Ser Ile Thr Ile Ser Cys Ser Gly Thr Ser Ser Asp Val Gly Ala Tyr
            20                  25                  30
Asn Tyr Val Ser Trp Tyr Gln Gln His Pro Gly Lys Ala Pro Lys Leu
        35                  40                  45
Met Ile Tyr Asp Val Thr Lys Arg Pro Ser Gly Val Ser His Arg Phe
    50                  55                  60
Ser Gly Ser Lys Ser Gly Asn Thr Ala Ser Leu Thr Ile Ser Gly Leu
65                  70                  75                  80
Gln Ala Glu Asp Glu Ala Asp Tyr Tyr Cys Ser Ser Phe Thr Ala Ile
                85                  90                  95
Gly Thr Trp Val Phe Gly Gly Gly Thr Lys Leu Thr Val Leu Gly
            100                 105                 110
```

<210> SEQ ID NO 443
<211> LENGTH: 357
<212> TYPE: DNA
<213> ORGANISM: Artificial Sequence
<220> FEATURE:
<223> OTHER INFORMATION: Synthetic

<400> SEQUENCE: 443

```
caggtccagc tggtgcagtc tggggctgag gtgagaagc ctggggcctc agtgaaagtt     60
tcctgcaagg catctggata caccttcacc agctcctatc tgcactgggt gcgacaggcc   120
cctggacaag gacttgagtg gatgggaata atcaaccct ctgctggtag cacaagctac    180
gcacagaagt tccaggacag agtcaccatg accagggaca cgtcgacgag cacagtctac   240
atggagctga gcaggctgag atctgacgac acggccgtgt attactgtgc gcgcggttac   300
tctttcgctg gttactacga ttggtgggggt caaggtactc tggtgaccgt ctcctca     357
```

<210> SEQ ID NO 444
<211> LENGTH: 119
<212> TYPE: PRT
<213> ORGANISM: Artificial Sequence
<220> FEATURE:
<223> OTHER INFORMATION: Synthetic

<400> SEQUENCE: 444

Gln Val Gln Leu Val Gln Ser Gly Ala Glu Val Lys Pro Gly Ala
1               5                   10                  15

Ser Val Lys Val Ser Cys Lys Ala Ser Gly Tyr Thr Phe Thr Ser Ser
            20                  25                  30

Tyr Leu His Trp Val Arg Gln Ala Pro Gly Gln Gly Leu Glu Trp Met
        35                  40                  45

Gly Ile Ile Asn Pro Thr Ala Gly Ser Thr Ser Tyr Ala Gln Lys Phe
    50                  55                  60

Gln Asp Arg Val Thr Met Thr Arg Asp Thr Ser Thr Ser Thr Val Tyr
65                  70                  75                  80

Met Glu Leu Ser Arg Leu Arg Ser Asp Asp Thr Ala Val Tyr Tyr Cys
            85                  90                  95

Ala Arg Gly Tyr Ser Phe Ala Gly Tyr Tyr Asp Trp Trp Gly Gln Gly
            100                 105                 110

Thr Leu Val Thr Val Ser Ser
            115

<210> SEQ ID NO 445
<211> LENGTH: 753
<212> TYPE: DNA
<213> ORGANISM: Artificial Sequence
<220> FEATURE:
<223> OTHER INFORMATION: Synthetic

<400> SEQUENCE: 445
cagtctgtgt tgacgcagcc gccctcagtg tctggggccc cagggcagag ggtcaccatc      60
tcctgcactg ggagcagctc caacatcggg gcaggttatg atgtacactg gtaccaacaa     120
cttccgggaa gagcccccaa agtcctcatc tatggtaaca acaatcggcc ctcgggggtc     180
cctgaccgat tctctggctc caagtctggc acctcagcct ccctggccat cactggtctc     240
cgggttgagg atgaggctga ttattactgc cagtcctatg acaacaacct gagtggggta     300
ttcggcggag ggaccaagct gaccgtccta ggttctagag gtggtggtgg tagcggcggc     360
ggcggctctg gtggtggtgg atccctcgag atggcccaga tgcagctggt gcagtctggg     420
gctgaggtga agaagcctgg ggcctcactg aaggtttcct gcaaggcatc tggatacacc     480
ttcaccagtt actatatgca ctgggtgcga caggcccctg gcaagggct tgagtggatg     540
ggaataatca accctactgg tggtagcaca agctacgcac agaagttcca gggcagagtc     600
accatgacca gggacacgtc cacgagcaca gtctacatgg agctgagcag cctgagatct     660
gaggacacgg ccgtgtatta ctgtgcgcgc tctatcactt actggtctgc ttacgattac     720
tggggtcaag gtactctggt gaccgtctcc tca                                  753

<210> SEQ ID NO 446
<211> LENGTH: 251
<212> TYPE: PRT
<213> ORGANISM: Artificial Sequence
<220> FEATURE:
<223> OTHER INFORMATION: Synthetic

<400> SEQUENCE: 446

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Arg Ala Pro Lys Val
            35                  40                  45

Leu Ile Tyr Gly Asn Asn Arg Pro Ser Gly Val Pro Asp Arg Phe
        50                  55                  60

Ser Gly Ser Lys Ser Gly Thr Ser Ala Ser Leu Ala Ile Thr Gly Leu
 65                  70                  75                  80

Arg Val Glu Asp Glu Ala Asp Tyr Tyr Cys Gln Ser Tyr Asp Asn Asn
                85                  90                  95

Leu Ser Gly Val Phe Gly Gly Thr Lys Leu Thr Val Leu Gly Ser
            100                 105                 110

Arg Gly Gly Gly Ser Gly Gly Gly Ser Gly Gly Gly Ser
            115                 120                 125

Leu Glu Met Ala Gln Met Gln Leu Val Gln Ser Gly Ala Glu Val Lys
130                 135                 140

Lys Pro Gly Ala Ser Leu Lys Val Ser Cys Lys Ala Ser Gly Tyr Thr
145                 150                 155                 160

Phe Thr Ser Tyr Tyr Met His Trp Val Arg Gln Ala Pro Gly Gln Gly
                165                 170                 175

Leu Glu Trp Met Gly Ile Ile Asn Pro Thr Gly Gly Ser Thr Ser Tyr
            180                 185                 190

Ala Gln Lys Phe Gln Gly Arg Val Thr Met Thr Arg Asp Thr Ser Thr
            195                 200                 205

Ser Thr Val Tyr Met Glu Leu Ser Ser Leu Arg Ser Glu Asp Thr Ala
210                 215                 220

Val Tyr Tyr Cys Ala Arg Ser Ile Thr Tyr Trp Ser Ala Tyr Asp Tyr
225                 230                 235                 240

Trp Gly Gln Gly Thr Leu Val Thr Val Ser Ser
            245                 250

<210> SEQ ID NO 447
<211> LENGTH: 333
<212> TYPE: DNA
<213> ORGANISM: Artificial Sequence
<220> FEATURE:
<223> OTHER INFORMATION: Synthetic

<400> SEQUENCE: 447
cagtctgtgt tgacgcagcc gccctcagtg tctggggccc cagggcagag ggtcaccatc    60
tcctgcactg ggagcagctc caacatcggg gcaggttatg atgtacactg gtaccaacaa   120
cttccgggaa gagcccccaa agtcctcatc tatggtaaca acaatcggcc ctcgggggtc   180
cctgaccgat tctctggctc caagtctggc acctcagcct ccctggccat cactggtctc   240
cgggttgagg atgaggctga ttattactgc cagtcctatg acaacaacct gagtggggta   300
ttcggcggag ggaccaagct gaccgtccta ggt                                333

<210> SEQ ID NO 448
<211> LENGTH: 111
<212> TYPE: PRT
<213> ORGANISM: Artificial Sequence
<220> FEATURE:
<223> OTHER INFORMATION: Synthetic

<400> SEQUENCE: 448

Gln Ser Val Leu Thr Gln Pro Pro Ser Val Ser Gly Ala Pro Gly Gln
 1               5                  10                  15

Arg Val Thr Ile Ser Cys Thr Gly Ser Ser Ser Asn Ile Gly Ala Gly
                20                  25                  30

Tyr Asp Val His Trp Tyr Gln Gln Leu Pro Gly Arg Ala Pro Lys Val
            35                  40                  45

-continued

```
Leu Ile Tyr Gly Asn Asn Arg Pro Ser Gly Val Pro Asp Arg Phe
        50                  55                  60
Ser Gly Ser Lys Ser Gly Thr Ser Ala Ser Leu Ala Ile Thr Gly Leu
 65                  70                  75                  80
Arg Val Glu Asp Glu Ala Asp Tyr Tyr Cys Gln Ser Tyr Asp Asn Asn
                 85                  90                  95
Leu Ser Gly Val Phe Gly Gly Gly Thr Lys Leu Thr Val Leu Gly
            100                 105                 110

<210> SEQ ID NO 449
<211> LENGTH: 357
<212> TYPE: DNA
<213> ORGANISM: Artificial Sequence
<220> FEATURE:
<223> OTHER INFORMATION: Synthetic

<400> SEQUENCE: 449
cagatgcagc tggtgcagtc tggggctgag gtgaagaagc ctggggcctc actgaaggtt    60
tcctgcaagg catctggata caccttcacc agttactata tgcactgggt gcgacaggcc   120
cctgggcaag gcttgagtg gatgggaata atcaaccctaa ctggtggtag cacaagctac   180
gcacagaagt tccagggcag agtcaccatg accagggaca cgtccacgag cacagtctac   240
atggagctga gcagcctgag atctgaggac acggccgtgt attactgtgc gcgctctatc   300
acttactggt ctgcttacga ttactggggt caaggtactc tggtgaccgt ctcctca     357

<210> SEQ ID NO 450
<211> LENGTH: 119
<212> TYPE: PRT
<213> ORGANISM: Artificial Sequence
<220> FEATURE:
<223> OTHER INFORMATION: Synthetic

<400> SEQUENCE: 450

Gln Met Gln Leu Val Gln Ser Gly Ala Glu Val Lys Lys Pro Gly Ala
 1               5                  10                  15
Ser Leu Lys Val Ser Cys Lys Ala Ser Gly Tyr Thr Phe Thr Ser Tyr
            20                  25                  30
Tyr Met His Trp Val Arg Gln Ala Pro Gly Gln Gly Leu Glu Trp Met
        35                  40                  45
Gly Ile Ile Asn Pro Thr Gly Gly Ser Thr Ser Tyr Ala Gln Lys Phe
    50                  55                  60
Gln Gly Arg Val Thr Met Thr Arg Asp Thr Ser Thr Ser Thr Val Tyr
 65                  70                  75                  80
Met Glu Leu Ser Ser Leu Arg Ser Glu Asp Thr Ala Val Tyr Tyr Cys
                 85                  90                  95
Ala Arg Ser Ile Thr Tyr Trp Ser Ala Tyr Asp Tyr Trp Gly Gln Gly
            100                 105                 110
Thr Leu Val Thr Val Ser Ser
        115

<210> SEQ ID NO 451
<211> LENGTH: 756
<212> TYPE: DNA
<213> ORGANISM: Artificial Sequence
<220> FEATURE:
<223> OTHER INFORMATION: Synthetic

<400> SEQUENCE: 451
```

```
cagtctgtgt tgacgcagcc gccctcagtg tctgcggccc caggacagaa ggtcaccatc      60
tcctgctctg gaagcagctc caacattggg aataattatg tatcctggta ccagcagctc     120
ccaggaacag cccccaaact cctcatttat gacaataata gcgaccctca gggattcct      180
gaccgattct ctggctccaa gtctggcacg tcagccaccc tgggcatcac cggactccag     240
actggggacg aggccgatta ttactgcggc atatgggata gcagcctgag tgctggctct     300
tatgtcttcg gaaatgggac caaggtcacc gtcctaggtt ctagaggtgg tgtggtagc     360
ggcggcggcg gctctggtgg tggtggatcc ctcgagatgg cccagatgca gctggtgcag     420
tctggggctg aggtgaagaa gcctggggcc tcagtgaagg tttcctgcaa ggcgtctgga     480
tacaccttca ccagctacta tatacactgg gtgcgacagg cccctggaca agggcttgag     540
tggatgggaa tgatcaatcc tactgctggt accacaaact acacacagaa ctttcaggac     600
agagtcacca tgaccaggga cacgtccacg accacagtct catggagct gaccagcctg      660
agatctgagg acacggccgt gtattactgt gcgcgctacg ttttcggttc tggtcaggat     720
tcttggggtc aaggtactct ggtgaccgtc tcctca                               756
```

<210> SEQ ID NO 452
<211> LENGTH: 252
<212> TYPE: PRT
<213> ORGANISM: Artificial Sequence
<220> FEATURE:
<223> OTHER INFORMATION: Synthetic

<400> SEQUENCE: 452

```
Gln Ser Val Leu Thr Gln Pro Pro Ser Val Ser Ala Ala Pro Gly Gln
1               5                   10                  15

Lys Val Thr Ile Ser Cys Ser Gly Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Ile Trp Asp Ser Ser Leu
                85                  90                  95

Ser Ala Gly Ser Tyr Val Phe Gly Asn Gly Thr Lys Val Thr Val Leu
            100                 105                 110

Gly Ser Arg Gly Gly Gly Gly Ser Gly Gly Gly Ser Gly Gly Gly
        115                 120                 125

Gly Ser Leu Glu Met Ala Gln Met Gln Leu Val Gln Ser Gly Ala Glu
    130                 135                 140

Val Lys Lys Pro Gly Ala Ser Val Lys Val Ser Cys Lys Ala Ser Gly
145                 150                 155                 160

Tyr Thr Phe Thr Ser Tyr Tyr Ile His Trp Val Arg Gln Ala Pro Gly
                165                 170                 175

Gln Gly Leu Glu Trp Met Gly Met Ile Asn Pro Thr Ala Gly Thr Thr
            180                 185                 190

Asn Tyr Thr Gln Asn Phe Gln Asp Arg Val Thr Met Thr Arg Asp Thr
        195                 200                 205

Ser Thr Thr Thr Val Phe Met Glu Leu Thr Ser Leu Arg Ser Glu Asp
    210                 215                 220

Thr Ala Val Tyr Tyr Cys Ala Arg Tyr Val Phe Gly Ser Gly Gln Asp
```

```
                225                 230                 235                 240
Ser Trp Gly Gln Gly Thr Leu Val Thr Val Ser Ser
                245                 250

<210> SEQ ID NO 453
<211> LENGTH: 339
<212> TYPE: DNA
<213> ORGANISM: Artificial Sequence
<220> FEATURE:
<223> OTHER INFORMATION: Synthetic

<400> SEQUENCE: 453
cagtctgtgt tgacgcagcc gccctcagtg tctgcggccc caggacagaa ggtcaccatc      60
tcctgctctg gaagcagctc caacattggg aataattatg tatcctggta ccagcagctc     120
ccaggaacag cccccaaact cctcatttat gacaataata gcgaccctc agggattcct      180 gaccgattct ctggctccaa gtctggcacg tcagccaccc tgggcatcac cggactccag     240 actgggacg aggccgatta ttactgcggc atatgggata gcagcctgag tgctggctct      300
tatgtcttcg gaaatgggac caaggtcacc gtcctaggt                            339

<210> SEQ ID NO 454
<211> LENGTH: 113
<212> TYPE: PRT
<213> ORGANISM: Artificial Sequence
<220> FEATURE:
<223> OTHER INFORMATION: Synthetic

<400> SEQUENCE: 454

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Ile Trp Asp Ser Ser Leu
                85                  90                  95

Ser Ala Gly Ser Tyr Val Phe Gly Asn Gly Thr Lys Val Thr Val Leu
                100                 105                 110

Gly

<210> SEQ ID NO 455
<211> LENGTH: 354
<212> TYPE: DNA
<213> ORGANISM: Artificial Sequence
<220> FEATURE:
<223> OTHER INFORMATION: Synthetic

<400> SEQUENCE: 455
cagatgcagc tggtgcagtc tggggctgag gtgaagaagc ctggggcctc agtgaaggtt      60
tcctgcaagg cgtctggata caccttcacc agctactata cactgggt gcgacaggcc      120 cctggacaag gcttgagtg gatgggaatg atcaatccta ctgctggtac cacaaactac     180
acacagaact tcaggacag agtcaccatg accaggaca cgtccacgac cacagtcttc      240
atggagctga ccagcctgag atctgaggac acggccgtgt attactgtgc gcgctacgtt      300
```

```
ttcggttctg gtcaggattc ttggggtcaa ggtactctgg tgaccgtctc ctca          354
```

<210> SEQ ID NO 456
<211> LENGTH: 118
<212> TYPE: PRT
<213> ORGANISM: Artificial Sequence
<220> FEATURE:
<223> OTHER INFORMATION: Synthetic

<400> SEQUENCE: 456

```
Gln Met Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Met
        35                  40                  45

Gly Met Ile Asn Pro Thr Ala Gly Thr Thr Asn Tyr Thr Gln Asn Phe
    50                  55                  60

Gln Asp Arg Val Thr Met Thr Arg Asp Thr Ser Thr Thr Thr Val Phe
65                  70                  75                  80

Met Glu Leu Thr Ser Leu Arg Ser Glu Asp Thr Ala Val Tyr Tyr Cys
                85                  90                  95

Ala Arg Tyr Val Phe Gly Ser Gly Gln Asp Ser Trp Gly Gln Gly Thr
            100                 105                 110

Leu Val Thr Val Ser Ser
        115
```

<210> SEQ ID NO 457
<211> LENGTH: 741
<212> TYPE: DNA
<213> ORGANISM: Artificial Sequence
<220> FEATURE:
<223> OTHER INFORMATION: Synthetic

<400> SEQUENCE: 457

```
cagtctgtgt tgactcagcc accctcggtg tcagtggccc caggaaagac ggccaggatt    60
acctgtgggg gaaacaacat tggaagtaaa agtgtgcact ggtaccagca gaagccaggc   120
caggcccctg tgctggtcgt ctatgatgat agcgaccggc cctcagggat ccctgagcga   180
ttctctggct ccaactctgg gaacacggcc accctgacca tcagcagggt cgaagccggg   240
gatgaggccg actattactg tcaggtgtgg gatagtagta gtgatcatgt ggtattcggc   300
ggagggacca agctgaccgt cctaggttct agaggtggtg gtggtagcgg cggcggcggc   360
tctggtggtg gtggatccct cgagatggcc gaggtgcagc tggtggagtc tggggctgag   420
gtgaagaagc ctggggcctc agtgaaagtt tctgcaagg catctggata cgccttcacc   480
agctactata ttcactgggt gcgacaggcc cctggacaag tcttgagtg atgggagta    540 atcaaccta ctggtggtta cacaacctac gcacagaagt tccagggcag agtcaccatg   600
accagtgaca cgtccacgaa cacagtctac atggaactga gcagcctgag atctgaggac   660
acggccgtgt attactgtgc gcgcggtgtt tacggttctc tggattcttg gggtcaaggt   720
actctggtga ccgtctcctc a                                              741
```

<210> SEQ ID NO 458
<211> LENGTH: 247
<212> TYPE: PRT
<213> ORGANISM: Artificial Sequence
<220> FEATURE:

<223> OTHER INFORMATION: Synthetic

<400> SEQUENCE: 458

Gln Ser Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Val Val Phe Gly Gly Gly Thr Lys Leu Thr Val Leu Gly Ser Arg Gly
            100                 105                 110

Gly Gly Gly Ser Gly Gly Gly Ser Gly Gly Gly Ser Leu Glu
        115                 120                 125

Met Ala Glu Val Gln Leu Val Glu Ser Gly Ala Glu Val Lys Lys Pro
    130                 135                 140

Gly Ala Ser Val Lys Val Phe Cys Lys Ala Ser Gly Tyr Ala Phe Thr
145                 150                 155                 160

Ser Tyr Tyr Ile His Trp Val Arg Gln Ala Pro Gly Gln Gly Leu Glu
                165                 170                 175

Trp Met Gly Val Ile Asn Pro Thr Gly Gly Tyr Thr Thr Tyr Ala Gln
            180                 185                 190

Lys Phe Gln Gly Arg Val Thr Met Thr Ser Asp Thr Ser Thr Asn Thr
        195                 200                 205

Val Tyr Met Glu Leu Ser Ser Leu Arg Ser Glu Asp Thr Ala Val Tyr
    210                 215                 220

Tyr Cys Ala Arg Gly Val Tyr Gly Ser Leu Asp Ser Trp Gly Gln Gly
225                 230                 235                 240

Thr Leu Val Thr Val Ser Ser
                245

<210> SEQ ID NO 459
<211> LENGTH: 327
<212> TYPE: DNA
<213> ORGANISM: Artificial Sequence
<220> FEATURE:
<223> OTHER INFORMATION: Synthetic

<400> SEQUENCE: 459
cagtctgtgt tgactcagcc accctcggtg tcagtggccc caggaaagac ggccaggatt      60
acctgtgggg gaaacaacat tggaagtaaa agtgtgcact ggtaccagca gaagccaggc     120
caggcccctg tgctggtcgt ctatgatgat agcgaccggc cctcaggat ccctgagcga      180 ttctctggct ccaactctgg gaacacggcc accctgacca tcagcagggt cgaagccggg     240
gatgaggccg actattactg tcaggtgtgg gatagtagta gtgatcatgt ggtattcggc     300
ggagggacca agctgaccgt cctaggt                                          327

<210> SEQ ID NO 460
<211> LENGTH: 109
<212> TYPE: PRT
<213> ORGANISM: Artificial Sequence

```
<220> FEATURE:
<223> OTHER INFORMATION: Synthetic

<400> SEQUENCE: 460

Gln Ser Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Asp His
                85                  90                  95

Val Val Phe Gly Gly Gly Thr Lys Leu Thr Val Leu Gly
            100                 105

<210> SEQ ID NO 461
<211> LENGTH: 351
<212> TYPE: DNA
<213> ORGANISM: Artificial Sequence
<220> FEATURE:
<223> OTHER INFORMATION: Synthetic

<400> SEQUENCE: 461
gaggtgcagc tggtggagtc tgggggctgag gtgaagaagc ctgggggcctc agtgaaagtt     60 ttctgcaagg catctggata cgccttcacc agctactata ttcactgggt gcgacaggcc    120
cctggacaag gtcttgagtg gatgggagta atcaaccccta ctggtggtta cacaacctac    180
gcacagaagt tccagggcag agtcaccatg accagtgaca cgtccacgaa cacagtctac    240
atggaactga gcagcctgag atctgaggac acggccgtgt attactgtgc gcgcggtgtt    300
tacggttctc tggattcttg ggtcaaggt actctggtga ccgtctcctc a              351

<210> SEQ ID NO 462
<211> LENGTH: 117
<212> TYPE: PRT
<213> ORGANISM: Artificial Sequence
<220> FEATURE:
<223> OTHER INFORMATION: Synthetic

<400> SEQUENCE: 462

Glu Val Gln Leu Val Glu Ser Gly Ala Glu Val Lys Lys Pro Gly Ala
1               5                   10                  15

Ser Val Lys Val Phe Cys Lys Ala Ser Gly Tyr Ala Phe Thr Ser Tyr
            20                  25                  30

Tyr Ile His Trp Val Arg Gln Ala Pro Gly Gln Gly Leu Glu Trp Met
        35                  40                  45

Gly Val Ile Asn Pro Thr Gly Gly Tyr Thr Thr Tyr Ala Gln Lys Phe
    50                  55                  60

Gln Gly Arg Val Thr Met Thr Ser Asp Thr Ser Thr Asn Thr Val Tyr
65                  70                  75                  80

Met Glu Leu Ser Ser Leu Arg Ser Glu Asp Thr Ala Val Tyr Tyr Cys
                85                  90                  95

Ala Arg Gly Val Tyr Gly Ser Leu Asp Ser Trp Gly Gln Gly Thr Leu
            100                 105                 110
```

Val Thr Val Ser Ser
        115

<210> SEQ ID NO 463
<211> LENGTH: 747
<212> TYPE: DNA
<213> ORGANISM: Artificial Sequence
<220> FEATURE:
<223> OTHER INFORMATION: Synthetic

<400> SEQUENCE: 463

```
caggctgtgc tgactcagcc accctcggtg tcagtggccc caggaaagac ggccaggatt      60
acctgtgcgg gaaacaaaat tgaaagtaaa agtgtgcatt ggtaccagaa gaagccaggc     120
caggcccctg tgttggtcgt ctatgatgat agtgaccggc cctcagggat ccctgagcga     180
ttctctggct ccaactctgg gaacacggcc accctgacca tcagcggggt cgaagccggg     240
gatgaggccg actattactg tcaggtgtgg atagtagta atgatgtcca ggtgttcggc      300
ggagggacca agctgaccgt cctaggttct agaggtggtg gtggtagcgg cggcggcggc     360
tctggtggtg gtggatccct cgagatggcc caggtccagc tggtgcagtc tggggctgag     420
gtgaagaagc ctggggcctc agtgcaggtt tcctgcaggg catctggata cacaatcacc     480
tcctactata tgcactgggt gcgacaggcc cctggacaag gcttgagtg gatgggagta      540
atcaacccta tgctggcag cacaagatac gcacagaaat tccagggcag agtcaccatg      600
agcactgaca cgtccacgag cacagtctac atggcgctga gtagtctgag atctgacgac     660
acggccgtgt attactgtgc gcgccagtct tctggtcgtg acggtttcga ttcttggggt     720
caaggtactc tggtgaccgt ctcctca                                         747
```

<210> SEQ ID NO 464
<211> LENGTH: 249
<212> TYPE: PRT
<213> ORGANISM: Artificial Sequence
<220> FEATURE:
<223> OTHER INFORMATION: Synthetic

<400> SEQUENCE: 464

Gln Ala Val Leu Thr Gln Pro Pro Ser Val Ser Val Ala Pro Gly Lys
1               5                   10                  15

Thr Ala Arg Ile Thr Cys Ala Gly Asn Lys Ile Glu Ser Lys Ser Val
            20                  25                  30

His Trp Tyr Gln Lys Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Gly Val Glu Ala Gly
65                  70                  75                  80

Asp Glu Ala Asp Tyr Tyr Cys Gln Val Trp Asp Ser Ser Asn Asp Val
                85                  90                  95

Gln Val Phe Gly Gly Gly Thr Lys Leu Thr Val Leu Gly Ser Arg Gly
            100                 105                 110

Gly Gly Gly Ser Gly Gly Gly Gly Ser Gly Gly Gly Gly Ser Leu Glu
        115                 120                 125

Met Ala Gln Val Gln Leu Val Gln Ser Gly Ala Glu Val Lys Lys Pro
    130                 135                 140

Gly Ala Ser Val Gln Val Ser Cys Arg Ala Ser Gly Tyr Thr Ile Thr
145                 150                 155                 160

Ser Tyr Tyr Met His Trp Val Arg Gln Ala Pro Gly Gln Gly Leu Glu
            165                 170                 175

Trp Met Gly Val Ile Asn Pro Asn Ala Gly Ser Thr Arg Tyr Ala Gln
        180                 185                 190

Lys Phe Gln Gly Arg Val Thr Met Ser Thr Asp Thr Ser Thr Ser Thr
            195                 200                 205

Val Tyr Met Ala Leu Ser Ser Leu Arg Ser Asp Asp Thr Ala Val Tyr
    210                 215                 220

Tyr Cys Ala Arg Gln Ser Ser Gly Arg Asp Gly Phe Asp Ser Trp Gly
225                 230                 235                 240

Gln Gly Thr Leu Val Thr Val Ser Ser
                245

<210> SEQ ID NO 465
<211> LENGTH: 327
<212> TYPE: DNA
<213> ORGANISM: Artificial Sequence
<220> FEATURE:
<223> OTHER INFORMATION: Synthetic

<400> SEQUENCE: 465
caggctgtgc tgactcagcc accctcggtg tcagtggccc caggaaagac ggccaggatt     60
acctgtgcgg gaaacaaaat tgaaagtaaa agtgtgcatt ggtaccagaa gaagccaggc    120
caggcccctg tgttggtcgt ctatgatgat agtgaccggc cctcaggat  ccctgagcga    180 ttctctggct ccaactctgg gaacacggcc accctgacca tcagcggggt cgaagccggg    240
gatgaggccg actattactg tcaggtgtgg gatagtagta tgatgtccca ggtgttcggc    300
ggagggacca agctgaccgt cctaggt                                        327

<210> SEQ ID NO 466
<211> LENGTH: 109
<212> TYPE: PRT
<213> ORGANISM: Artificial Sequence
<220> FEATURE:
<223> OTHER INFORMATION: Synthetic

<400> SEQUENCE: 466

Gln Ala Val Leu Thr Gln Pro Pro Ser Val Ser Val Ala Pro Gly Lys
1               5                   10                  15

Thr Ala Arg Ile Thr Cys Ala Gly Asn Lys Ile Glu Ser Lys Ser Val
            20                  25                  30

His Trp Tyr Gln Lys Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Gly Val Glu Ala Gly
65                  70                  75                  80

Asp Glu Ala Asp Tyr Tyr Cys Gln Val Trp Asp Ser Ser Asn Asp Val
                85                  90                  95

Gln Val Phe Gly Gly Gly Thr Lys Leu Thr Val Leu Gly
            100                 105

<210> SEQ ID NO 467
<211> LENGTH: 357
<212> TYPE: DNA
<213> ORGANISM: Artificial Sequence
<220> FEATURE:
<223> OTHER INFORMATION: Synthetic

<400> SEQUENCE: 467

```
caggtccagc tggtgcagtc tggggctgag gtgaagaagc ctggggcctc agtgcaggtt      60
tcctgcaggg catctggata cacaatcacc tcctactata tgcactgggt gcgacaggcc     120
cctggacaag gcttgagtg gatgggagta atcaaccta atgctggcag cacaagatac       180
gcacagaaat ccagggcag agtcaccatg agcactgaca cgtccacgag cacagtctac      240
atggcgctga gtagtctgag atctgacgac acggccgtgt attactgtgc gcgccagtct     300
tctggtcgtg acggtttcga ttcttggggt caaggtactc tggtgaccgt ctcctca        357
```

<210> SEQ ID NO 468
<211> LENGTH: 119
<212> TYPE: PRT
<213> ORGANISM: Artificial Sequence
<220> FEATURE:
<223> OTHER INFORMATION: Synthetic

<400> SEQUENCE: 468

```
Gln Val Gln Leu Val Gln Ser Gly Ala Glu Val Lys Lys Pro Gly Ala
1               5                   10                  15

Ser Val Gln Val Ser Cys Arg Ala Ser Gly Tyr Thr Ile Thr Ser Tyr
            20                  25                  30

Tyr Met His Trp Val Arg Gln Ala Pro Gly Gln Gly Leu Glu Trp Met
        35                  40                  45

Gly Val Ile Asn Pro Asn Ala Gly Ser Thr Arg Tyr Ala Gln Lys Phe
    50                  55                  60

Gln Gly Arg Val Thr Met Ser Thr Asp Thr Ser Thr Ser Thr Val Tyr
65                  70                  75                  80

Met Ala Leu Ser Ser Leu Arg Ser Asp Asp Thr Ala Val Tyr Tyr Cys
                85                  90                  95

Ala Arg Gln Ser Ser Gly Arg Asp Gly Phe Asp Ser Trp Gly Gln Gly
            100                 105                 110

Thr Leu Val Thr Val Ser Ser
        115
```

<210> SEQ ID NO 469
<211> LENGTH: 744
<212> TYPE: DNA
<213> ORGANISM: Artificial Sequence
<220> FEATURE:
<223> OTHER INFORMATION: Synthetic

<400> SEQUENCE: 469

```
tcctatgtgc tgactcagcc accctcagtg tcagtggccc caggaaagac ggccaggatt      60
acctgtgggg gaaacaacat tggaagtaaa agtgtgcact ggtaccagca gaagccaggc     120
caggcccctg tgctggtcat ctattatgat agcgaccggc cctcagggat ccctgagcga     180
ttctctggct ccaactctgg gaacacggcc accctgacca tcagcagggt cgaagccggg     240
gatgaggccg actattactg tcaggtgtgg gatagtagta gtgatcttcc ttatgtcttc     300
ggaactggga ccaaggtcac cgtcctaggt tctagaggtg gtggtggtag cggcggcggc     360
ggctctggtg gtggtggatc cctcgagatg gcccagatgc ggctggtgca gtctgggct     420
gaggtgaaga agcctggggc ctcagtgaag gtttcctgca aggcatctgg ataccacttc     480
accagctact atatgcactg ggtgcgacag gcccctggac aagggcttga gtggatggga     540
ataatcaacc ctactagtgg taccacaagc ttcgcacaga gttccagggg cagagtcacc     600
atgaccaggg acacgtccac gagcacagtc tacatggagc tgagcagcct gagatctgag     660
```

```
gacactgccg tgtattactg tgcgcgctct ccgtctttct actacgatgg ttggggtcaa    720
ggtactctgg tgaccgtctc ctca                                           744
```

<210> SEQ ID NO 470
<211> LENGTH: 248
<212> TYPE: PRT
<213> ORGANISM: Artificial Sequence
<220> FEATURE:
<223> OTHER INFORMATION: Synthetic

<400> SEQUENCE: 470

```
Ser Tyr Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp Leu
                85                  90                  95

Pro Tyr Val Phe Gly Thr Gly Thr Lys Val Thr Val Leu Gly Ser Arg
            100                 105                 110

Gly Gly Gly Gly Ser Gly Gly Gly Ser Gly Gly Gly Gly Ser Leu
        115                 120                 125

Glu Met Ala Gln Met Arg Leu Val Gln Ser Gly Ala Glu Val Lys Lys
130                 135                 140

Pro Gly Ala Ser Val Lys Val Ser Cys Lys Ala Ser Gly Tyr Thr Phe
145                 150                 155                 160

Thr Ser Tyr Tyr Met His Trp Val Arg Gln Ala Pro Gly Gln Gly Leu
                165                 170                 175

Glu Trp Met Gly Ile Ile Asn Pro Thr Ser Gly Thr Thr Ser Phe Ala
            180                 185                 190

Gln Lys Phe Gln Gly Arg Val Thr Met Thr Arg Asp Thr Ser Thr Ser
        195                 200                 205

Thr Val Tyr Met Glu Leu Ser Ser Leu Arg Ser Glu Asp Thr Ala Val
    210                 215                 220

Tyr Tyr Cys Ala Arg Ser Pro Ser Phe Tyr Tyr Asp Gly Trp Gly Gln
225                 230                 235                 240

Gly Thr Leu Val Thr Val Ser Ser
                245
```

<210> SEQ ID NO 471
<211> LENGTH: 330
<212> TYPE: DNA
<213> ORGANISM: Artificial Sequence
<220> FEATURE:
<223> OTHER INFORMATION: Synthetic

<400> SEQUENCE: 471

```
tcctatgtgc tgactcagcc accctcagtg tcagtggccc caggaaagac ggccaggatt    60
acctgtgggg gaaacaacat tggaagtaaa agtgtgcact ggtaccagca gaagccaggc   120
caggcccctg tgctggtcat ctattatgat agcgaccggc cctcagggat ccctgagcga   180
```

```
ttctctggct ccaactctgg gaacacggcc accctgacca tcagcagggt cgaagccggg    240
gatgaggccg actattactg tcaggtgtgg gatagtagta gtgatcttcc ttatgtcttc    300
ggaactggga ccaaggtcac cgtcctaggt                                     330
```

<210> SEQ ID NO 472
<211> LENGTH: 110
<212> TYPE: PRT
<213> ORGANISM: Artificial Sequence
<220> FEATURE:
<223> OTHER INFORMATION: Synthetic

<400> SEQUENCE: 472

```
Ser Tyr Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp Leu
                85                  90                  95

Pro Tyr Val Phe Gly Thr Gly Thr Lys Val Thr Val Leu Gly
            100                 105                 110
```

<210> SEQ ID NO 473
<211> LENGTH: 351
<212> TYPE: DNA
<213> ORGANISM: Artificial Sequence
<220> FEATURE:
<223> OTHER INFORMATION: Synthetic

<400> SEQUENCE: 473

```
cagatgcggc tggtgcagtc tggggctgag gtgaagaagc ctggggcctc agtgaaggtt     60
tcctgcaagg catctggata caccttcacc agctactata tgcactgggt gcgacaggcc    120
cctggacaag gcttgagtg gatgggaata atcaaccta ctagtggtac cacaagcttc      180
gcacagaagt tccagggcag agtcaccatg accaggaca cgtccacgag cacagtctac     240
atggagctga gcagcctgag atctgaggac actgccgtgt attactgtgc gcgctctccg    300
tctttctact acgatggttg gggtcaaggt actctggtga ccgtctcctc a             351
```

<210> SEQ ID NO 474
<211> LENGTH: 117
<212> TYPE: PRT
<213> ORGANISM: Artificial Sequence
<220> FEATURE:
<223> OTHER INFORMATION: Synthetic

<400> SEQUENCE: 474

```
Gln Met Arg Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Thr Ser Gly Thr Thr Ser Phe Ala Gln Lys Phe
```

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Pro Ser Phe Tyr Tyr Asp Gly Trp Gly Gln Gly Thr Leu
            100                 105                 110

Val Thr Val Ser Ser
        115

<210> SEQ ID NO 475
<211> LENGTH: 780
<212> TYPE: DNA
<213> ORGANISM: Artificial Sequence
<220> FEATURE:
<223> OTHER INFORMATION: Synthetic

<400> SEQUENCE: 475
cagtctgtgt tgacgcagcc gccctcagtg tctggggccc cagggcagag ggtcaccatc    60
tcctgcactg ggagcagctc aacatcgggg gcaggttatg atgtacactg gtaccagcag   120
cttccaggaa cagcccccaa actcctcatc cagggtaaca gcaatcggcc ctcaggggtc   180
cctgatcgat tctctggctc caagtctggc gcctcagcct ccctggccat cactgggctc   240
caggctgagg atgaggctga ttattactgc cagtcctatg acgacaggtt gagtggctct   300
tatgtctttg gaactgggac caaggtcacc gtcctaggtt ctagaggtgg tggtggtagc   360
ggcggcggcg gctctggtgg tggtggatcc ctcgagatgg cccaggtgca gctggtgcag   420 tctgggggctg aggtgaagag gcctgggggcc tcagtgaagg tttcctgcaa ggcatctgga   480
tacagcttca ccaactacta tatgcactgg gtgcgacagg cccctggaca cgggcttgag   540
tggatgggtt taatcacccc tactaatggt ggcgccaact acgcacagaa gttccgggga   600
agagtctcct tgaccaggga cacgtccacg gacacagtct acatggagtt gagcagcctg   660
acttctgagg acacggccgt gtattactgt gcgcgccagt ggtcttacac ttctttctct   720
ctgtctggtt acatctctta cgattcttgg ggtcaaggta ctctggtgac cgtctcctca   780

<210> SEQ ID NO 476
<211> LENGTH: 260
<212> TYPE: PRT
<213> ORGANISM: Artificial Sequence
<220> FEATURE:
<223> OTHER INFORMATION: Synthetic

<400> SEQUENCE: 476

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Gln Gly Asn Ser Asn Arg Pro Ser Gly Val Pro Asp Arg Phe
    50                  55                  60

Ser Gly Ser Lys Ser Gly Ala Ser Ala Ser Leu Ala Ile Thr Gly Leu
65                  70                  75                  80

Gln Ala Glu Asp Glu Ala Asp Tyr Tyr Cys Gln Ser Tyr Asp Asp Arg
                85                  90                  95

Leu Ser Gly Ser Tyr Val Phe Gly Thr Gly Thr Lys Val Thr Val Leu

```
                    100                 105                 110
Gly Ser Arg Gly Gly Gly Ser Gly Gly Gly Ser Gly Gly Gly
            115                 120                 125

Gly Ser Leu Glu Met Ala Gln Val Gln Leu Val Gln Ser Gly Ala Glu
130                 135                 140

Val Lys Arg Pro Gly Ala Ser Val Lys Val Ser Cys Lys Ala Ser Gly
145                 150                 155                 160

Tyr Ser Phe Thr Asn Tyr Tyr Met His Trp Val Arg Gln Ala Pro Gly
                165                 170                 175

His Gly Leu Glu Trp Met Gly Leu Ile Thr Pro Thr Asn Gly Gly Ala
            180                 185                 190

Asn Tyr Ala Gln Lys Phe Arg Gly Arg Val Ser Leu Thr Arg Asp Thr
        195                 200                 205

Ser Thr Asp Thr Val Tyr Met Glu Leu Ser Ser Leu Thr Ser Glu Asp
    210                 215                 220

Thr Ala Val Tyr Tyr Cys Ala Arg Gln Trp Ser Tyr Thr Ser Phe Ser
225                 230                 235                 240

Leu Ser Gly Tyr Ile Ser Tyr Asp Ser Trp Gly Gln Gly Thr Leu Val
                245                 250                 255

Thr Val Ser Ser
            260

<210> SEQ ID NO 477
<211> LENGTH: 339
<212> TYPE: DNA
<213> ORGANISM: Artificial Sequence
<220> FEATURE:
<223> OTHER INFORMATION: Synthetic

<400> SEQUENCE: 477
cagtctgtgt tgacgcagcc gccctcagtg tctggggccc cagggcagag ggtcaccatc      60
tcctgcactg ggagcagctc caacatcggg gcaggttatg atgtacactg gtaccagcag     120
cttccaggaa cagcccccaa actcctcatc agggtaaca gcaatcggcc ctcaggggtc      180
cctgatcgat tctctggctc caagtctggc gcctcagcct ccctggccat cactgggctc     240
caggctgagg atgaggctga ttattactgc cagtcctatg acgacaggtt gagtggctct     300
tatgtctttg gaactgggac caaggtcacc gtcctaggt                            339

<210> SEQ ID NO 478
<211> LENGTH: 113
<212> TYPE: PRT
<213> ORGANISM: Artificial Sequence
<220> FEATURE:
<223> OTHER INFORMATION: Synthetic

<400> SEQUENCE: 478

Gln Ser Val Leu Thr Gln Pro Pro Ser Val Ser Gly Ala Pro Gly Gln
1               5                   10                  15

Arg Val Thr Ile Ser Cys Thr Gly Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Gln Gly Asn Ser Asn Arg Pro Ser Gly Val Pro Asp Arg Phe
    50                  55                  60

Ser Gly Ser Lys Ser Gly Ala Ser Ala Ser Leu Ala Ile Thr Gly Leu
65                  70                  75                  80
```

Gln Ala Glu Asp Glu Ala Asp Tyr Tyr Cys Gln Ser Tyr Asp Asp Arg
            85                  90                  95

Leu Ser Gly Ser Tyr Val Phe Gly Thr Gly Thr Lys Val Thr Val Leu
            100                 105                 110

Gly

<210> SEQ ID NO 479
<211> LENGTH: 378
<212> TYPE: DNA
<213> ORGANISM: Artificial Sequence
<220> FEATURE:
<223> OTHER INFORMATION: Synthetic

<400> SEQUENCE: 479
caggtgcagc tggtgcagtc tggggctgag gtgaagaggc ctggggcctc agtgaaggtt      60
tcctgcaagg catctggata cagcttcacc aactactata tgcactgggt gcgacaggcc    120
cctggacacg ggcttgagtg gatgggttta atcaccccta ctaatggtgg cgccaactac    180
gcacagaagt tccggggaag agtctccttg accaggggaca cgtccacgga cacagtctac    240
atggagttga gcagcctgac ttctgaggac acggccgtgt attactgtgc gcgccagtgg    300
tcttacactt ctttctctct gtctggttac atctcttacg attcttgggg tcaaggtact    360
ctggtgaccg tctcctca                                                   378

<210> SEQ ID NO 480
<211> LENGTH: 126
<212> TYPE: PRT
<213> ORGANISM: Artificial Sequence
<220> FEATURE:
<223> OTHER INFORMATION: Synthetic

<400> SEQUENCE: 480

Gln Val Gln Leu Val Gln Ser Gly Ala Glu Val Lys Arg Pro Gly Ala
1               5                   10                  15

Ser Val Lys Val Ser Cys Lys Ala Ser Gly Tyr Ser Phe Thr Asn Tyr
            20                  25                  30

Tyr Met His Trp Val Arg Gln Ala Pro Gly His Gly Leu Glu Trp Met
        35                  40                  45

Gly Leu Ile Thr Pro Thr Asn Gly Gly Ala Asn Tyr Ala Gln Lys Phe
    50                  55                  60

Arg Gly Arg Val Ser Leu Thr Arg Asp Thr Ser Thr Asp Thr Val Tyr
65                  70                  75                  80

Met Glu Leu Ser Ser Leu Thr Ser Glu Asp Thr Ala Val Tyr Tyr Cys
                85                  90                  95

Ala Arg Gln Trp Ser Tyr Thr Ser Phe Ser Leu Ser Gly Tyr Ile Ser
            100                 105                 110

Tyr Asp Ser Trp Gly Gln Gly Thr Leu Val Thr Val Ser Ser
        115                 120                 125

<210> SEQ ID NO 481
<211> LENGTH: 768
<212> TYPE: DNA
<213> ORGANISM: Artificial Sequence
<220> FEATURE:
<223> OTHER INFORMATION: Synthetic

<400> SEQUENCE: 481
tcctatgtgc tgactcagcc accctcagtg tcagtggccc caggaaagac ggccaggatt      60
acctgtgggg gaaacaacat tggaagtaaa agtgtgcact ggtaccagca gaagccaggc    120

-continued

```
caggcccctg tgctggtcat ctattatgat agcgaccggc cctcaggat ccctgagcga      180 ttctctggct ccaactctgg gaacacggcc accctgacca tcagcagggt cgaagccggg      240
gatgaggccg actattactg tcaggtgtgg gatagtagta gtgatcaagg ggtgttcggc      300
ggagggacca agctgaccgt cctaggttct agaggtggtg gtggtagcgg cggcggcggc      360
tctggtggtg gtggatccct cgagatggcc gaggtgcagc tggtgcagtc tggggaggc      420 ttggtacagc ctaggggtc cctgagactc tcctgtgcag gctctggatt caccttcagt      480
agctatgcta tgcactgggt tcgccaggct ccaggcaagg ggctggagtg ggtggcagtt      540
atatcatatg atggaagcaa taaatactac gcagactccg tgaagggccg attcaccatc      600
tccagagaca attccaagaa cacgctgtat ctgcaaatga acagcctgag agctgaggac      660
acggccgtgt attactgtgc gcgcaacggt tactggtact ggggttctgg tgaacatggt      720
tcttggtacg attcttgggg tcaaggtact ctggtgaccg tctcctca                   768
```

<210> SEQ ID NO 482
<211> LENGTH: 256
<212> TYPE: PRT
<213> ORGANISM: Artificial Sequence
<220> FEATURE:
<223> OTHER INFORMATION: Synthetic

<400> SEQUENCE: 482

```
Ser Tyr Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp Gln
                85                  90                  95

Gly Val Phe Gly Gly Gly Thr Lys Leu Thr Val Leu Gly Ser Arg Gly
            100                 105                 110

Gly Gly Gly Ser Gly Gly Gly Gly Ser Gly Gly Gly Gly Ser Leu Glu
        115                 120                 125

Met Ala Glu Val Gln Leu Val Gln Ser Gly Gly Gly Leu Val Gln Pro
    130                 135                 140

Arg Gly Ser Leu Arg Leu Ser Cys Ala Gly Ser Gly Phe Thr Phe Ser
145                 150                 155                 160

Ser Tyr Ala Met His Trp Val Arg Gln Ala Pro Gly Lys Gly Leu Glu
                165                 170                 175

Trp Val Ala Val Ile Ser Tyr Asp Gly Ser Asn Lys Tyr Tyr Ala Asp
            180                 185                 190

Ser Val Lys Gly Arg Phe Thr Ile Ser Arg Asp Asn Ser Lys Asn Thr
        195                 200                 205

Leu Tyr Leu Gln Met Asn Ser Leu Arg Ala Glu Asp Thr Ala Val Tyr
    210                 215                 220

Tyr Cys Ala Arg Asn Gly Tyr Trp Tyr Trp Gly Ser Gly Glu His Gly
225                 230                 235                 240

Ser Trp Tyr Asp Ser Trp Gly Gln Gly Thr Leu Val Thr Val Ser Ser
```

<210> SEQ ID NO 483
<211> LENGTH: 327
<212> TYPE: DNA
<213> ORGANISM: Artificial Sequence
<220> FEATURE:
<223> OTHER INFORMATION: Synthetic

<400> SEQUENCE: 483

```
tcctatgtgc tgactcagcc accctcagtg tcagtggccc caggaaagac ggccaggatt    60
acctgtgggg gaaacaacat tggaagtaaa agtgtgcact ggtaccagca gaagccaggc   120
caggcccctg tgctggtcat ctattatgat agcgaccggc cctcagggat ccctgagcga   180
ttctctggct ccaactctgg gaacacggcc accctgacca tcagcagggt cgaagccggg   240
gatgaggccg actattactg tcaggtgtgg gatagtagta gtgatcaagg ggtgttcggc   300
ggagggacca agctgaccgt cctaggt                                       327
```

<210> SEQ ID NO 484
<211> LENGTH: 109
<212> TYPE: PRT
<213> ORGANISM: Artificial Sequence
<220> FEATURE:
<223> OTHER INFORMATION: Synthetic

<400> SEQUENCE: 484

Ser Tyr Val Leu Thr Gln Pro Pro Ser Val Ser Val Ala Pro Gly Lys
1               5                   10                  15
Thr Ala Arg Ile Thr Cys Gly Gly Asn Asn Ile Gly Ser Lys Ser Val
            20                  25                  30
His Trp Tyr Gln Gln Lys Pro Gly Gln Ala Pro Val Leu Val Ile Tyr
        35                  40                  45
Tyr Asp Ser Asp Arg Pro Ser Gly Ile Pro Glu Arg Phe Ser Gly Ser
    50                  55                  60
Asn Ser Gly Asn Thr Ala Thr Leu Thr Ile Ser Arg Val Glu Ala Gly
65                  70                  75                  80
Asp Glu Ala Asp Tyr Tyr Cys Gln Val Trp Asp Ser Ser Ser Asp Gln
                85                  90                  95
Gly Val Phe Gly Gly Gly Thr Lys Leu Thr Val Leu Gly
            100                 105

<210> SEQ ID NO 485
<211> LENGTH: 378
<212> TYPE: DNA
<213> ORGANISM: Artificial Sequence
<220> FEATURE:
<223> OTHER INFORMATION: Synthetic

<400> SEQUENCE: 485

```
gaggtgcagc tggtgcagtc tggggggaggc ttggtacagc ctaggggtc cctgagactc    60 tcctgtgcag gctctggatt caccttcagt agctatgcta tgcactgggt tcgccaggct   120
ccaggcaagg gctggagtg gtggcagtt atatcatatg atggaagcaa taaatactac   180
gcagactccg tgaagggccg attcaccatc tccagagaca attccaagaa cacgctgtat   240
ctgcaaatga acagcctgag agctgaggac acggccgtgt attactgtgc gcgaacggt   300 tactggtact ggggttctgg tgaacatggt tcttggtacg attcttgggg tcaaggtact   360
ctggtgaccg tctcctca                                                 378
```

<210> SEQ ID NO 486
<211> LENGTH: 126
<212> TYPE: PRT
<213> ORGANISM: Artificial Sequence
<220> FEATURE:
<223> OTHER INFORMATION: Synthetic

<400> SEQUENCE: 486

```
Glu Val Gln Leu Val Gln Ser Gly Gly Gly Leu Val Gln Pro Arg Gly
1               5                   10                  15

Ser Leu Arg Leu Ser Cys Ala Gly Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Gly Tyr Trp Tyr Trp Gly Ser Gly Glu His Gly Ser Trp
            100                 105                 110

Tyr Asp Ser Trp Gly Gln Gly Thr Leu Val Thr Val Ser Ser
        115                 120                 125
```

<210> SEQ ID NO 487
<211> LENGTH: 741
<212> TYPE: DNA
<213> ORGANISM: Artificial Sequence
<220> FEATURE:
<223> OTHER INFORMATION: Synthetic

<400> SEQUENCE: 487

| | | |
|---|---|---|
| tcctatgtgc tgactcagcc actctcagtg tcagtggccc caggaacgcc ggccaggatt | 60 |
| acctgtgagg gaaacaacat tggaagtaat agcgtgcact ggtaccagca gaaggcaggc | 120 |
| caggccctg tgttggtcat ctattatgat agcgaccggc cctcagggat ccctgagcga | 180 |
| ttctctggct ccacctctgg gaacacggcc accctgacca tcagcagggt cgaaggcggg | 240 |
| gatgaggccg actatttctg tcaggtgtgg gatagtgcta taaatcatgt ggtcttcggc | 300 |
| ggagggacca agctgaccgt cctaggttct agaggtggtg gtggtagcgg cggcggcggc | 360 |
| tctggtggtg gtggatccct cgagatggcc caggtgcagc tggtgcagtc tggggctgag | 420 |
| gagaagaagc ctgggacctc agtgagggtt tcctgcaagg catctggata caccttcacc | 480 |
| agttactata tgcactgggt gcgacaggcc cctggacaag gcttgagtg gatgggaata | 540 |
| atcaacccta gtggtggtag cacaagctac gcacagaagt tccagggcag agtcaccatg | 600 |
| accagggaca cgtccacgag cacagtctac atggagctga gcagcctgag atctgaggac | 660 |
| actgccgtgt attactgtgc gcgcggtatg ccggacgttg ttgatgactg gggtcaaggt | 720 |
| actctggtga ccgtctcctc a | 741 |

<210> SEQ ID NO 488
<211> LENGTH: 247
<212> TYPE: PRT
<213> ORGANISM: Artificial Sequence
<220> FEATURE:
<223> OTHER INFORMATION: Synthetic

<400> SEQUENCE: 488

```
Ser Tyr Val Leu Thr Gln Pro Leu Ser Val Ser Val Ala Pro Gly Thr
1               5                   10                  15

Pro Ala Arg Ile Thr Cys Glu Gly Asn Asn Ile Gly Ser Asn Ser Val
                20                  25                  30

His Trp Tyr Gln Gln Lys Ala Gly Gln Ala Pro Val Leu Val Ile Tyr
            35                  40                  45

Tyr Asp Ser Asp Arg Pro Ser Gly Ile Pro Glu Arg Phe Ser Gly Ser
        50                  55                  60

Thr Ser Gly Asn Thr Ala Thr Leu Thr Ile Ser Arg Val Glu Gly Gly
65                  70                  75                  80

Asp Glu Ala Asp Tyr Phe Cys Gln Val Trp Asp Ser Ala Ile Asn His
                85                  90                  95

Val Val Phe Gly Gly Gly Thr Lys Leu Thr Val Leu Gly Ser Arg Gly
            100                 105                 110

Gly Gly Gly Ser Gly Gly Gly Ser Gly Gly Gly Ser Leu Glu
        115                 120                 125

Met Ala Gln Val Gln Leu Val Gln Ser Gly Ala Glu Glu Lys Lys Pro
    130                 135                 140

Gly Thr Ser Val Arg Val Ser Cys Lys Ala Ser Gly Tyr Thr Phe Thr
145                 150                 155                 160

Ser Tyr Tyr Met His Trp Val Arg Gln Ala Pro Gly Gln Gly Leu Glu
                165                 170                 175

Trp Met Gly Ile Ile Asn Pro Ser Gly Gly Ser Thr Ser Tyr Ala Gln
            180                 185                 190

Lys Phe Gln Gly Arg Val Thr Met Thr Arg Asp Thr Ser Thr Ser Thr
        195                 200                 205

Val Tyr Met Glu Leu Ser Ser Leu Arg Ser Glu Asp Thr Ala Val Tyr
    210                 215                 220

Tyr Cys Ala Arg Gly Met Pro Asp Val Asp Asp Trp Gly Gln Gly
225                 230                 235                 240

Thr Leu Val Thr Val Ser Ser
                245

<210> SEQ ID NO 489
<211> LENGTH: 327
<212> TYPE: DNA
<213> ORGANISM: Artificial Sequence
<220> FEATURE:
<223> OTHER INFORMATION: Synthetic

<400> SEQUENCE: 489
tcctatgtgc tgactcagcc actctcagtg tcagtggccc caggaacgcc ggccaggatt      60
acctgtgagg gaaacaacat tggaagtaat agcgtgcact ggtaccagca gaaggcaggc     120
caggcccctg tgttggtcat ctattatgat agcgaccggc cctcagggat ccctgagcga     180
ttctctggct ccacctctgg gaacacggcc accctgacca tcagcagggt cgaaggcggg     240
gatgaggccg actatttctg tcaggtgtgg gatagtgcta taaatcatgt ggtcttcggc     300
ggagggacca agctgaccgt cctaggt                                         327

<210> SEQ ID NO 490
<211> LENGTH: 109
<212> TYPE: PRT
<213> ORGANISM: Artificial Sequence
<220> FEATURE:
<223> OTHER INFORMATION: Synthetic
```

<400> SEQUENCE: 490

Ser Tyr Val Leu Thr Gln Pro Leu Ser Val Ser Val Ala Pro Gly Thr
1               5                   10                  15

Pro Ala Arg Ile Thr Cys Glu Gly Asn Asn Ile Gly Ser Asn Ser Val
            20                  25                  30

His Trp Tyr Gln Gln Lys Ala Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Thr Ser Gly Asn Thr Ala Thr Leu Thr Ile Ser Arg Val Glu Gly Gly
65                  70                  75                  80

Asp Glu Ala Asp Tyr Phe Cys Gln Val Trp Asp Ser Ala Ile Asn His
                85                  90                  95

Val Val Phe Gly Gly Gly Thr Lys Leu Thr Val Leu Gly
            100                 105

<210> SEQ ID NO 491
<211> LENGTH: 351
<212> TYPE: DNA
<213> ORGANISM: Artificial Sequence
<220> FEATURE:
<223> OTHER INFORMATION: Synthetic

<400> SEQUENCE: 491
caggtgcagc tggtgcagtc tggggctgag gagaagaagc ctgggacctc agtgagggtt      60
tcctgcaagg catctggata caccttcacc agttactata tgcactgggt gcgacaggcc     120
cctggacaag gcttgagtg gatgggaata atcaaccta gtggtggtag cacaagctac      180
gcacagaagt tccagggcag agtcaccatg accagggaca cgtccacgag cacagtctac     240
atggagctga gcagcctgag atctgaggac actgccgtgt attactgtgc gcgcggtatg     300
ccggacgttg ttgatgactg gggtcaaggt actctggtga ccgtctcctc a              351

<210> SEQ ID NO 492
<211> LENGTH: 117
<212> TYPE: PRT
<213> ORGANISM: Artificial Sequence
<220> FEATURE:
<223> OTHER INFORMATION: Synthetic

<400> SEQUENCE: 492

Gln Val Gln Leu Val Gln Ser Gly Ala Glu Glu Lys Lys Pro Gly Thr
1               5                   10                  15

Ser Val Arg Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Met Pro Asp Val Val Asp Asp Trp Gly Gln Gly Thr Leu
            100                 105                 110

Val Thr Val Ser Ser
        115

<210> SEQ ID NO 493
<211> LENGTH: 747
<212> TYPE: DNA
<213> ORGANISM: Artificial Sequence
<220> FEATURE:
<223> OTHER INFORMATION: Synthetic

<400> SEQUENCE: 493

```
caggctgtgc tgactcagcc accctcagtg tcagtggccc caggaaagac ggccaggatt     60
acctgtgggg gaaacaacat tggaagtaaa agtgtgcact ggtaccagca gaagccaggc    120
caggcccctg tgctggtcat ctattatgat agcgaccggc cctcagggat ccctgagcga    180
ttctctggct ccaactctgg gaacacggcc accctgacca tcagcagggt cgaagccggg    240
gatgaggccg actattactg tcaggtgtgg gatagtagta gtgatcattg ggtgttcggc    300
ggagggacca agctgaccgt cctaggttct agaggtggtg gtggtagcgg cggcggcggc    360
tctggtggtg gtggatccct cgagatggcc gaggtccagc tggtgcagtc tggggctgag    420
gtgaagaagc ctggggcctc agtgaaggtt tcctgcaagg catctggata cacctthacc    480
agctactata tgcactgggt gcgacaggcc cctggacaag gcttgagtg atgggagta     540
atcaaccta gtggtggtta cacaagctac gcacagaagt tccagggcag agtcaccatg    600
accagggaca cgtccacgag cacagtctac atggagctga gcagcctgag atctgaggac    660
acggccgtgt attactgtgc gcgctcttct tctggtggta acggtgctga ttcttggggt    720
caaggtactc tggtgaccgt ctcctca                                        747
```

<210> SEQ ID NO 494
<211> LENGTH: 249
<212> TYPE: PRT
<213> ORGANISM: Artificial Sequence
<220> FEATURE:
<223> OTHER INFORMATION: Synthetic

<400> SEQUENCE: 494

```
Gln Ala Val Leu Thr Gln Pro Pro Ser Val Ser Val Ala Pro Gly Lys
  1               5                  10                  15

Thr Ala Arg Ile Thr Cys Gly Gly Asn Asn Ile Gly Ser Lys Ser Val
             20                  25                  30

His Trp Tyr Gln Gln Lys Pro Gly Gln Ala Pro Val Leu Val Ile Tyr
         35                  40                  45

Tyr Asp Ser Asp Arg Pro Ser Gly Ile Pro Glu Arg Phe Ser Gly Ser
     50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Ser Ser Ser Asp His
                 85                  90                  95

Trp Val Phe Gly Gly Gly Thr Lys Leu Thr Val Leu Gly Ser Arg Gly
            100                 105                 110

Gly Gly Gly Ser Gly Gly Gly Gly Ser Gly Gly Gly Gly Ser Leu Glu
        115                 120                 125

Met Ala Glu Val Gln Leu Val Gln Ser Gly Ala Glu Val Lys Lys Pro
    130                 135                 140

Gly Ala Ser Val Lys Val Ser Cys Lys Ala Ser Gly Tyr Thr Phe Thr
145                 150                 155                 160

Ser Tyr Tyr Met His Trp Val Arg Gln Ala Pro Gly Gln Gly Leu Glu
                165                 170                 175
```

```
Trp Met Gly Val Ile Asn Pro Ser Gly Gly Tyr Thr Ser Tyr Ala Gln
            180                 185                 190

Lys Phe Gln Gly Arg Val Thr Met Thr Arg Asp Thr Ser Thr Ser Thr
        195                 200                 205

Val Tyr Met Glu Leu Ser Ser Leu Arg Ser Glu Asp Thr Ala Val Tyr
    210                 215                 220

Tyr Cys Ala Arg Ser Ser Ser Gly Asn Gly Ala Asp Ser Trp Gly
225                 230                 235                 240

Gln Gly Thr Leu Val Thr Val Ser Ser
                245
```

<210> SEQ ID NO 495
<211> LENGTH: 327
<212> TYPE: DNA
<213> ORGANISM: Artificial Sequence
<220> FEATURE:
<223> OTHER INFORMATION: Synthetic

<400> SEQUENCE: 495

```
caggctgtgc tgactcagcc accctcagtg tcagtggccc caggaaagac ggccaggatt     60
acctgtgggg gaaacaacat tggaagtaaa agtgtgcact ggtaccagca gaagccaggc    120
caggcccctg tgctggtcat ctattatgat agcgaccggc cctcagggat ccctgagcga    180
ttctctggct ccaactctgg gaacacggcc accctgacca tcagcagggt cgaagccggg    240
gatgaggccg actattactg tcaggtgtgg gatagtagta gtgatcattg ggtgttcggc    300
ggagggacca agctgaccgt cctaggt                                        327
```

<210> SEQ ID NO 496
<211> LENGTH: 109
<212> TYPE: PRT
<213> ORGANISM: Artificial Sequence
<220> FEATURE:
<223> OTHER INFORMATION: Synthetic

<400> SEQUENCE: 496

```
Gln Ala Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Trp Val Phe Gly Gly Gly Thr Lys Leu Thr Val Leu Gly
            100                 105
```

<210> SEQ ID NO 497
<211> LENGTH: 357
<212> TYPE: DNA
<213> ORGANISM: Artificial Sequence
<220> FEATURE:
<223> OTHER INFORMATION: Synthetic

<400> SEQUENCE: 497

```
gaggtccagc tggtgcagtc tggggctgag gtgaagaagc ctggggcctc agtgaaggtt     60
```

```
tcctgcaagg catctggata caccttcacc agctactata tgcactgggt gcgacaggcc      120
cctggacaag ggcttgagtg gatgggagta atcaaccta gtggtggtta cacaagctac       180
gcacagaagt tccagggcag agtcaccatg accagggaca cgtccacgag cacagtctac      240
atggagctga gcagcctgag atctgaggac acggccgtgt attactgtgc gcgctcttct      300
tctggtggta acggtgctga ttcttggggt caaggtactc tggtgaccgt ctcctca         357
```

<210> SEQ ID NO 498
<211> LENGTH: 119
<212> TYPE: PRT
<213> ORGANISM: Artificial Sequence
<220> FEATURE:
<223> OTHER INFORMATION: Synthetic

<400> SEQUENCE: 498

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Val Ile Asn Pro Ser Gly Gly Tyr Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Ser Ser Gly Gly Asn Gly Ala Asp Ser Trp Gly Gln Gly
            100                 105                 110

Thr Leu Val Thr Val Ser Ser
        115
```

<210> SEQ ID NO 499
<211> LENGTH: 771
<212> TYPE: DNA
<213> ORGANISM: Artificial Sequence
<220> FEATURE:
<223> OTHER INFORMATION: Synthetic

<400> SEQUENCE: 499

```
cagtctgtgt tgactcagcc accctcaacg tctgggaccc cgggcagag ggtcaccatc        60 tcttgttctg gaagcagctc caacatcgga agaaatactg caaactggta ccagcagctc      120
ccaggaacgg cccccaaact cctcatctat agtaataatc accggccctc agggtccct       180 gaccgattct ctggctccaa gtctggcacc tcagcctccc tggccatcag tgggctccag      240
tctgaggatg aggctgatta ttactgtgca gcatgggatg acagcctgaa tggtccggtg      300
ttcggcggag ggaccaagct gaccgtccta ggttctagag gtggtggtgg tagcggcggc      360
ggcggctctg gtggtggtgg atccctcgag atggccgagg tccagctggt gcagtctgga      420
gctgaggtga agaagcctgg ggcctcagtg aaggtctcct gcaaggcttc tggttacacc      480
tttaccagct atggtatcag ctgggtgcga caggcccctg acaagggct tgagtggatg       540 ggatggatca gcgcttacaa tggtaacaca aactatgcac agaagctcca gggcagagtc      600
accatgacca cagacacatc cacgagcaca gcctacatgg agctgaggag cctgagatct      660
gacgacactg ccgtgtatta ctgtgcgcgc tcttactacg ctgctgactg gtggtggcat      720
```
gctactatga tggatatgtg gggtcaaggt actctggtga ccgtctcctc a          771

<210> SEQ ID NO 500
<211> LENGTH: 257
<212> TYPE: PRT
<213> ORGANISM: Artificial Sequence
<220> FEATURE:
<223> OTHER INFORMATION: Synthetic

<400> SEQUENCE: 500

Gln Ser Val Leu Thr Gln Pro Pro Ser Thr Ser Gly Thr Pro Gly Gln
1               5                   10                  15

Arg Val Thr Ile Ser Cys Ser Gly Ser Ser Asn Ile Gly Arg Asn
            20                  25                  30

Thr Ala Asn Trp Tyr Gln Gln Leu Pro Gly Thr Ala Pro Lys Leu Leu
        35                  40                  45

Ile Tyr Ser Asn Asn His Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Pro Val Phe Gly Gly Gly Thr Lys Leu Thr Val Leu Gly Ser
            100                 105                 110

Arg Gly Gly Gly Gly Ser Gly Gly Gly Gly Ser Gly Gly Gly Gly Ser
        115                 120                 125

Leu Glu Met Ala Glu Val Gln Leu Val Gln Ser Gly Ala Glu Val Lys
    130                 135                 140

Lys Pro Gly Ala Ser Val Lys Val Ser Cys Lys Ala Ser Gly Tyr Thr
145                 150                 155                 160

Phe Thr Ser Tyr Gly Ile Ser Trp Val Arg Gln Ala Pro Gly Gln Gly
                165                 170                 175

Leu Glu Trp Met Gly Trp Ile Ser Ala Tyr Asn Gly Asn Thr Asn Tyr
            180                 185                 190

Ala Gln Lys Leu Gln Gly Arg Val Thr Met Thr Thr Asp Thr Ser Thr
        195                 200                 205

Ser Thr Ala Tyr Met Glu Leu Arg Ser Leu Arg Ser Asp Asp Thr Ala
    210                 215                 220

Val Tyr Tyr Cys Ala Arg Ser Tyr Tyr Ala Ala Asp Trp Trp Trp His
225                 230                 235                 240

Ala Thr Met Met Asp Met Trp Gly Gln Gly Thr Leu Val Thr Val Ser
                245                 250                 255

Ser

<210> SEQ ID NO 501
<211> LENGTH: 333
<212> TYPE: DNA
<213> ORGANISM: Artificial Sequence
<220> FEATURE:
<223> OTHER INFORMATION: Synthetic

<400> SEQUENCE: 501
cagtctgtgt tgactcagcc accctcaacg tctgggaccc ccgggcagag ggtcaccatc     60
tcttgttctg gaagcagctc aaacatcgga agaaatactg caaactggta ccagcagctc    120
ccaggaacgg ccccaaaact cctcatctat agtaataatc accggccctc agggtccct    180 gaccgattct ctggctccaa gtctggcacc tcagcctccc tggccatcag tgggctccag    240

```
tctgaggatg aggctgatta ttactgtgca gcatgggatg acagcctgaa tggtccggtg     300
ttcggcggag ggaccaagct gaccgtccta ggt                                 333
```

<210> SEQ ID NO 502
<211> LENGTH: 111
<212> TYPE: PRT
<213> ORGANISM: Artificial Sequence
<220> FEATURE:
<223> OTHER INFORMATION: Synthetic

<400> SEQUENCE: 502

```
Gln Ser Val Leu Thr Gln Pro Pro Ser Thr Gly Thr Pro Gly Gln
1               5                   10                  15

Arg Val Thr Ile Ser Cys Ser Gly Ser Ser Asn Ile Gly Arg Asn
            20                  25                  30

Thr Ala Asn Trp Tyr Gln Gln Leu Pro Gly Thr Ala Pro Lys Leu Leu
        35                  40                  45

Ile Tyr Ser Asn Asn His Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Pro Val Phe Gly Gly Gly Thr Lys Leu Thr Val Leu Gly
            100                 105                 110
```

<210> SEQ ID NO 503
<211> LENGTH: 375
<212> TYPE: DNA
<213> ORGANISM: Artificial Sequence
<220> FEATURE:
<223> OTHER INFORMATION: Synthetic

<400> SEQUENCE: 503

```
gaggtccagc tggtgcagtc tggagctgag gtgaagaagc ctggggcctc agtgaaggtc     60
tcctgcaagg cttctggtta cacctttacc agctatggta tcagctgggt gcgacaggcc    120
cctggacaag ggcttgagtg gatgggatgg atcagcgctt acaatggtaa cacaaactat    180
gcacagaagc tccagggcag agtcaccatg accacagaca catccacgag cacagcctac    240
atggagctga ggagcctgag atctgacgac actgccgtgt attactgtgc gcgctcttac    300
tacgctgctg actggtggtg gcatgctact atgatggata tgtggggtca aggtactctg    360
gtgaccgtct cctca                                                     375
```

<210> SEQ ID NO 504
<211> LENGTH: 125
<212> TYPE: PRT
<213> ORGANISM: Artificial Sequence
<220> FEATURE:
<223> OTHER INFORMATION: Synthetic

<400> SEQUENCE: 504

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45
```

Gly Trp Ile Ser Ala Tyr Asn Gly Asn Thr Asn Tyr Ala Gln Lys Leu
 50                  55                  60

Gln Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Ser Tyr Tyr Ala Ala Asp Trp Trp His Ala Thr Met Met
            100                 105                 110

Asp Met Trp Gly Gln Gly Thr Leu Val Thr Val Ser Ser
            115                 120                 125

<210> SEQ ID NO 505
<211> LENGTH: 741
<212> TYPE: DNA
<213> ORGANISM: Artificial Sequence
<220> FEATURE:
<223> OTHER INFORMATION: Synthetic

<400> SEQUENCE: 505
gacatccaga tgacccagtc tccatcctcc ctgtctgcat ctgtaggaga cagagtcacc      60
atcacttgcc gggcgagtca gggcattggc aattatttag cctggtatca gcagaaacca     120
gggaaagttc ctaagctcct gatctattct gtatccactc tgcaatcagg ggtcccatct     180
cggttcagcg gcagtggatc tgggacagat ttcgctctca ccatcagcag cctgcagcct     240
gatgattttg caacttatta ctgtcaaaag tataacagtg ccccgggac tttcggccct      300
gggaccaaag tggatatcaa acgttctaga ggtggtggtg gtagcggcgg cggcggctct     360
ggtggtggtg gatccctcga gatggcccag gtccagctgg tgcagtctgg ggctgaggtg     420
aagaagcctg ggcctcagt gaaggtctcc tgcaagactt ctggatacac cttcaccacc      480
tatgatttca ctgggtgcg acaggccgct ggacaagggc ttgagtggat gggatggatg      540
aaccctaaca gtggtaacac aggctatgca aagaagttcc agggcagagt caccatgacc     600
agggacacct ccataaacac agcctacatg gagctgagca gcctgacatc tgaagacacg     660
gccgtgtatt actgtgcgcg cggttacggt gttttccatt acgattcttg gggtcaaggt     720
actctggtga ccgtctcctc a                                               741

<210> SEQ ID NO 506
<211> LENGTH: 248
<212> TYPE: PRT
<213> ORGANISM: Artificial Sequence
<220> FEATURE:
<223> OTHER INFORMATION: Synthetic

<400> SEQUENCE: 506

Leu Pro Val Leu Thr Gln Pro Pro Ser Val Ser Val Ala Pro Gly Lys
 1               5                  10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
 50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Ser Ser Ser Asp His
                 85                  90                  95

```
Tyr Val Phe Gly Thr Gly Thr Lys Val Thr Leu Gly Ser Arg Gly
                100                 105                 110

Gly Gly Gly Ser Gly Gly Gly Gly Ser Gly Gly Gly Ser Leu Glu
            115                 120                 125

Met Ala Gln Met Gln Leu Val Gln Ser Gly Ala Glu Val Lys Lys Pro
        130                 135                 140

Gly Ala Ser Val Lys Val Ser Cys Lys Ala Ser Gly Tyr Thr Phe Thr
145                 150                 155                 160

Ser Tyr Tyr Met His Trp Val Arg Gln Ala Pro Gly Gln Gly Leu Glu
                165                 170                 175

Trp Met Gly Ile Ile Asn Pro Ser Gly Gly Ser Thr Ser Tyr Ala Gln
            180                 185                 190

Lys Phe Gln Gly Arg Val Thr Met Thr Arg Asp Thr Ser Thr Ser Thr
        195                 200                 205

Val Tyr Met Glu Leu Ser Ser Leu Arg Ser Glu Asp Thr Ala Val Tyr
    210                 215                 220

Tyr Cys Ala Arg Ser Gly Ser Tyr Gly Asp Ser Asp Ser Trp Gly Gln
225                 230                 235                 240

Gly Thr Leu Val Thr Val Ser Ser
                245
```

<210> SEQ ID NO 507
<211> LENGTH: 327
<212> TYPE: DNA
<213> ORGANISM: Artificial Sequence
<220> FEATURE:
<223> OTHER INFORMATION: Synthetic

<400> SEQUENCE: 507

```
ctgcctgtgc tgactcagcc accctcagtg tcagtggccc caggaaagac ggccaggatt     60
acctgtgggg gaaacaacat tggaagtaaa agtgtgcact ggtaccagca gaagccaggc    120
caggcccctg tgctggtcat ctattatgat agcgaccggc cctcagggat ccctgagcga    180
ttctctggct ccaactctgg gaacacggcc accctgacca tcagcagggt cgaagccggg    240
gatgaggccg actattactg tcaggtgtgg gatagtagta gtgatcatta tgtcttcgga    300
actgggacca aggtcaccgt cctaggt                                       327
```

<210> SEQ ID NO 508
<211> LENGTH: 109
<212> TYPE: PRT
<213> ORGANISM: Artificial Sequence
<220> FEATURE:
<223> OTHER INFORMATION: Synthetic

<400> SEQUENCE: 508

```
Leu Pro Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95
```

-continued

Tyr Val Phe Gly Thr Gly Thr Lys Val Thr Val Leu Gly
            100                 105

<210> SEQ ID NO 509
<211> LENGTH: 354
<212> TYPE: DNA
<213> ORGANISM: Artificial Sequence
<220> FEATURE:
<223> OTHER INFORMATION: Synthetic

<400> SEQUENCE: 509
cagatgcagc tggtgcagtc tggggctgag gtgaagaagc ctggggcctc agtgaaggtt    60
tcctgcaagg catctggata caccttcacc agctactata tgcactgggt gcgacaggcc   120
cctggacaag gcttgagtg gatgggaata atcaaccta gtggtggtag cacaagctac   180
gcacagaagt tccagggcag agtcaccatg accaggaca cgtccacgag cacagtctac   240
atggagctga gcagcctgag atctgaggac actgccgtgt attactgtgc gcgctctggt   300
tcttacggtg actctgattc ttggggtcaa ggtactctgg tgaccgtctc ctca         354

<210> SEQ ID NO 510
<211> LENGTH: 118
<212> TYPE: PRT
<213> ORGANISM: Artificial Sequence
<220> FEATURE:
<223> OTHER INFORMATION: Synthetic

<400> SEQUENCE: 510

Gln Met Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Gly Ser Tyr Gly Asp Ser Asp Ser Trp Gly Gln Gly Thr
            100                 105                 110

Leu Val Thr Val Ser Ser
        115

<210> SEQ ID NO 511
<211> LENGTH: 744
<212> TYPE: DNA
<213> ORGANISM: Artificial Sequence
<220> FEATURE:
<223> OTHER INFORMATION: Synthetic

<400> SEQUENCE: 511
cagcctgtgc tgactcagcc accctcggtg tcagtggccc caagacagac ggccaggatt    60
acctgtgggg gagacaacgt tggaagtaaa agtgtgcact ggtaccagca gaagccaggt   120
caggcccctg tactggtcgt ctatgatgat agcgaccggc cctcagggat ccctgagcga   180
ttctctggct ccaactctgg gaacacagcc actctgacca tcagcgggac ccaggctatg   240
gatgaggctg actattactg tcaggcgtgg gacagcagca ctgtggtatt cggcggaggg   300

```
accaagctga ccgtcctagg ttctagaggt ggtggtggta gcggcggcgg cggctctggt    360
ggtggtggat ccctcgagat ggcccagctg cagctgcagg agtcgggccc aggactggtg    420
aagccttcgg agaccctgtc cctcacctgc actgtctctg gtgcctccat cagcagtact    480
tattactact ggagctggat ccggcagtcc ccagggaagg gactggagtg gattgggtat    540
atcggttaca gtgggatcac caactacaac ccctccctcc agagtcgagt caccatatca    600
gtagacacgt ccaagaacca gttctccctg aagctgacct ctgtgaccgc cgcagacacg    660
gccgtgtatt actgtgcgcg cggttcttgg tggtactctt actacgatca ttggggtcaa    720
ggtactctgg tgaccgtctc ctca                                          744
```

<210> SEQ ID NO 512
<211> LENGTH: 248
<212> TYPE: PRT
<213> ORGANISM: Artificial Sequence
<220> FEATURE:
<223> OTHER INFORMATION: Synthetic

<400> SEQUENCE: 512

```
Gln Pro Val Leu Thr Gln Pro Pro Ser Val Ser Val Ala Pro Arg Gln
1               5                   10                  15

Thr Ala Arg Ile Thr Cys Gly Gly Asp Asn Val Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr Val Val
                85                  90                  95

Phe Gly Gly Gly Thr Lys Leu Thr Val Leu Gly Ser Arg Gly Gly Gly
            100                 105                 110

Gly Ser Gly Gly Gly Gly Ser Gly Gly Gly Gly Ser Leu Glu Met Ala
        115                 120                 125

Gln Leu Gln Leu Gln Glu Ser Gly Pro Gly Leu Val Lys Pro Ser Glu
    130                 135                 140

Thr Leu Ser Leu Thr Cys Thr Val Ser Gly Ala Ser Ile Ser Ser Thr
145                 150                 155                 160

Tyr Tyr Tyr Trp Ser Trp Ile Arg Gln Ser Pro Gly Lys Gly Leu Glu
                165                 170                 175

Trp Ile Gly Tyr Ile Gly Tyr Ser Gly Ile Thr Asn Tyr Asn Pro Ser
            180                 185                 190

Leu Gln Ser Arg Val Thr Ile Ser Val Asp Thr Ser Lys Asn Gln Phe
        195                 200                 205

Ser Leu Lys Leu Thr Ser Val Thr Ala Ala Asp Thr Ala Val Tyr Tyr
    210                 215                 220

Cys Ala Arg Gly Ser Trp Trp Tyr Ser Tyr Tyr Asp His Trp Gly Gln
225                 230                 235                 240

Gly Thr Leu Val Thr Val Ser Ser
                245
```

<210> SEQ ID NO 513
<211> LENGTH: 321
<212> TYPE: DNA

<213> ORGANISM: Artificial Sequence
<220> FEATURE:
<223> OTHER INFORMATION: Synthetic

<400> SEQUENCE: 513

```
cagcctgtgc tgactcagcc accctcggtg tcagtggccc caagacagac ggccaggatt      60
acctgtgggg agacaacgt tggaagtaaa agtgtgcact ggtaccagca gaagccaggt     120
caggcccctg tactggtcgt ctatgatgat agcgaccggc cctcaggat ccctgagcga      180
ttctctggct ccaactctgg gaacacagcc actctgacca tcagcgggac ccaggctatg     240
gatgaggctg actattactg tcaggcgtgg gacagcagca ctgtggtatt cggcggaggg     300
accaagctga ccgtcctagg t                                              321
```

<210> SEQ ID NO 514
<211> LENGTH: 107
<212> TYPE: PRT
<213> ORGANISM: Artificial Sequence
<220> FEATURE:
<223> OTHER INFORMATION: Synthetic

<400> SEQUENCE: 514

```
Gln Pro Val Leu Thr Gln Pro Pro Ser Val Ser Val Ala Pro Arg Gln
1               5                   10                  15
Thr Ala Arg Ile Thr Cys Gly Gly Asp Asn Val Gly Ser Lys Ser Val
            20                  25                  30
His Trp Tyr Gln Gln Lys Pro Gly Gln Ala Pro Val Leu Val Val Tyr
        35                  40                  45
Asp Asp Ser Asp Arg Pro Gly Ile Pro Glu Arg Phe Ser Gly Ser
    50                  55                  60
Asn Ser Gly Asn Thr Ala Thr Leu Thr Ile Ser Gly Thr Gln Ala Met
65                  70                  75                  80
Asp Glu Ala Asp Tyr Tyr Cys Gln Ala Trp Asp Ser Ser Thr Val Val
                85                  90                  95
Phe Gly Gly Gly Thr Lys Leu Thr Val Leu Gly
            100                 105
```

<210> SEQ ID NO 515
<211> LENGTH: 360
<212> TYPE: DNA
<213> ORGANISM: Artificial Sequence
<220> FEATURE:
<223> OTHER INFORMATION: Synthetic

<400> SEQUENCE: 515

```
cagctgcagc tgcaggagtc gggcccagga ctggtgaagc cttcggagac cctgtccctc      60
acctgcactg tctctggtgc ctccatcagc agtacttatt actactggag ctggatccgg     120
cagtccccag ggaagggact ggagtggatt gggtatatcg ttacagtgg atcaccaac      180
tacaacccct ccctcagag tcgagtcacc atatcagtag acacgtccaa gaaccagttc     240
tccctgaagc tgacctctgt gaccgccgca gacacggccg tgtattactg tgcgcgcggt     300
tcttggtggt actcttacta cgatcattgg ggtcaaggta ctctggtgac cgtctcctca     360
```

<210> SEQ ID NO 516
<211> LENGTH: 120
<212> TYPE: PRT
<213> ORGANISM: Artificial Sequence
<220> FEATURE:
<223> OTHER INFORMATION: Synthetic

<400> SEQUENCE: 516

Gln Leu Gln Leu Gln Glu Ser Gly Pro Gly Leu Val Lys Pro Ser Glu
1               5                   10                  15

Thr Leu Ser Leu Thr Cys Thr Val Ser Gly Ala Ser Ile Ser Ser Thr
            20                  25                  30

Tyr Tyr Tyr Trp Ser Trp Ile Arg Gln Ser Pro Gly Lys Gly Leu Glu
        35                  40                  45

Trp Ile Gly Tyr Ile Gly Tyr Ser Gly Ile Thr Asn Tyr Asn Pro Ser
    50                  55                  60

Leu Gln Ser Arg Val Thr Ile Ser Val Asp Thr Ser Lys Asn Gln Phe
65                  70                  75                  80

Ser Leu Lys Leu Thr Ser Val Thr Ala Ala Asp Thr Ala Val Tyr Tyr
                85                  90                  95

Cys Ala Arg Gly Ser Trp Trp Tyr Ser Tyr Tyr Asp His Trp Gly Gln
            100                 105                 110

Gly Thr Leu Val Thr Val Ser Ser
        115                 120

<210> SEQ ID NO 517
<211> LENGTH: 741
<212> TYPE: DNA
<213> ORGANISM: Artificial Sequence
<220> FEATURE:
<223> OTHER INFORMATION: Synthetic

<400> SEQUENCE: 517
gacatccaga tgacccagtc tccatcctcc ctgtctgcat ctgtaggaga cagagtcacc      60
atcacttgcc gggcgagtca gggcattggc aattatttag cctggtatca gcagaaacca    120
gggaaagttc ctaagctcct gatctattct gtatccactc tgcaatcagg ggtcccatct    180
cggttcagcg gcagtggatc tgggacagat ttcgctctca ccatcagcag cctgcagcct    240
gatgattttg caacttatta ctgtcaaaag tataacagtg ccccggggac tttcggccct    300
gggaccaaag tggatatcaa acgttctaga ggtggtggtg gtagcggcgg cggcggctct    360
ggtggtggtg gatccctcga gatggcccag gtccagctgg tgcagtctgg ggctgaggtg    420
aagaagcctg ggcctcagt gaaggtctcc tgcaagactt ctggatacac cttcaccacc    480
tatgatttca ctgggtgcg acaggccgct ggacaagggc ttgagtggat gggatggatg    540
aaccctaaca gtggtaacac aggctatgca aagaagttcc agggcagagt caccatgacc    600
agggacacct ccataaacac agcctacatg gagctgagca gcctgacatc tgaagacacg    660
gccgtgtatt actgtgcgcg cggttacggt gttttccatt acgattcttg gggtcaaggt    720
actctggtga ccgtctcctc a                                              741

<210> SEQ ID NO 518
<211> LENGTH: 247
<212> TYPE: PRT
<213> ORGANISM: Artificial Sequence
<220> FEATURE:
<223> OTHER INFORMATION: Synthetic

<400> SEQUENCE: 518

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Gly Asn Tyr
            20                  25                  30

Leu Ala Trp Tyr Gln Gln Lys Pro Gly Lys Val Pro Lys Leu Leu Ile

```
            35                  40                  45
Tyr Ser Val Ser Thr Leu Gln Ser Gly Val Pro Ser Arg Phe Ser Gly
 50                  55                  60
Ser Gly Ser Gly Thr Asp Phe Ala Leu Thr Ile Ser Ser Leu Gln Pro
 65                  70                  75                  80
Asp Asp Phe Ala Thr Tyr Tyr Cys Gln Lys Tyr Asn Ser Ala Pro Gly
                 85                  90                  95
Thr Phe Gly Pro Gly Thr Lys Val Asp Ile Lys Arg Ser Arg Gly Gly
            100                 105                 110
Gly Gly Ser Gly Gly Gly Gly Ser Gly Gly Gly Ser Leu Glu Met
                115                 120                 125
Ala Gln Val Gln Leu Val Gln Ser Gly Ala Glu Val Lys Lys Pro Gly
130                 135                 140
Ala Ser Val Lys Val Ser Cys Lys Thr Ser Gly Tyr Thr Phe Thr
145                 150                 155                 160
Tyr Asp Phe Asn Trp Val Arg Gln Ala Ala Gly Gln Gly Leu Glu Trp
                165                 170                 175
Met Gly Trp Met Asn Pro Asn Ser Gly Asn Thr Gly Tyr Ala Lys Lys
                180                 185                 190
Phe Gln Gly Arg Val Thr Met Thr Arg Asp Thr Ser Ile Asn Thr Ala
            195                 200                 205
Tyr Met Glu Leu Ser Ser Leu Thr Ser Glu Asp Thr Ala Val Tyr Tyr
210                 215                 220
Cys Ala Arg Gly Tyr Gly Val Phe His Tyr Asp Ser Trp Gly Gln Gly
225                 230                 235                 240
Thr Leu Val Thr Val Ser Ser
                245

<210> SEQ ID NO 519
<211> LENGTH: 324
<212> TYPE: DNA
<213> ORGANISM: Artificial Sequence
<220> FEATURE:
<223> OTHER INFORMATION: Synthetic

<400> SEQUENCE: 519
gacatccaga tgacccagtc tccatcctcc ctgtctgcat ctgtaggaga cagagtcacc      60
atcacttgcc gggcgagtca gggcattggc aattatttag cctggtatca gcagaaacca     120
gggaaagttc ctaagctcct gatctattct gtatccactc tgcaatcagg ggtcccatct     180
cggttcagcg gcagtggatc tgggacagat ttcgctctca ccatcagcag cctgcagcct     240
gatgattttg caacttatta ctgtcaaaag tataacagtg ccccgggac tttcggccct     300 gggaccaaag tggatatcaa acgt                                            324

<210> SEQ ID NO 520
<211> LENGTH: 108
<212> TYPE: PRT
<213> ORGANISM: Artificial Sequence
<220> FEATURE:
<223> OTHER INFORMATION: Synthetic

<400> SEQUENCE: 520

Asp Ile Gln Met Thr Gln Ser Pro Ser Ser Leu Ser Ala Ser Val Gly
  1               5                  10                  15
Asp Arg Val Thr Ile Thr Cys Arg Ala Ser Gln Gly Ile Gly Asn Tyr
             20                  25                  30
```

Leu Ala Trp Tyr Gln Gln Lys Pro Gly Lys Val Pro Lys Leu Leu Ile
              35                  40                  45

Tyr Ser Val Ser Thr Leu Gln Ser Gly Val Pro Ser Arg Phe Ser Gly
 50                  55                  60

Ser Gly Ser Gly Thr Asp Phe Ala Leu Thr Ile Ser Ser Leu Gln Pro
 65                  70                  75                  80

Asp Asp Phe Ala Thr Tyr Tyr Cys Gln Lys Tyr Asn Ser Ala Pro Gly
                 85                  90                  95

Thr Phe Gly Pro Gly Thr Lys Val Asp Ile Lys Arg
            100                 105

<210> SEQ ID NO 521
<211> LENGTH: 354
<212> TYPE: DNA
<213> ORGANISM: Artificial Sequence
<220> FEATURE:
<223> OTHER INFORMATION: Synthetic

<400> SEQUENCE: 521
caggtccagc tggtgcagtc tggggctgag gtgaagaagc ctggggcctc agtgaaggtc     60
tcctgcaaga cttctggata caccttcacc acctatgatt tcaactgggt gcgacaggcc    120
gctggacaag ggcttgagtg gatgggatgg atgaacccta acagtggtaa cacaggctat    180
gcaaagaagt tccagggcag agtcaccatg accagggaca cctccataaa cacagcctac    240
atggagctga gcagcctgac atctgaagac acggccgtgt attactgtgc gcgcggttac    300
ggtgttttcc attacgattc ttggggtcaa ggtactctgg tgaccgtctc ctca          354

<210> SEQ ID NO 522
<211> LENGTH: 118
<212> TYPE: PRT
<213> ORGANISM: Artificial Sequence
<220> FEATURE:
<223> OTHER INFORMATION: Synthetic

<400> SEQUENCE: 522

Gln Val Gln Leu Val Gln Ser Gly Ala Glu Val Lys Lys Pro Gly Ala
 1               5                  10                  15

Ser Val Lys Val Ser Cys Lys Thr Ser Gly Tyr Thr Phe Thr Thr Tyr
             20                  25                  30

Asp Phe Asn Trp Val Arg Gln Ala Ala Gly Gln Gly Leu Glu Trp Met
         35                  40                  45

Gly Trp Met Asn Pro Asn Ser Gly Asn Thr Gly Tyr Ala Lys Lys Phe
     50                  55                  60

Gln Gly Arg Val Thr Met Thr Arg Asp Thr Ser Ile Asn Thr Ala Tyr
 65                  70                  75                  80

Met Glu Leu Ser Ser Leu Thr Ser Glu Asp Thr Ala Val Tyr Tyr Cys
                 85                  90                  95

Ala Arg Gly Tyr Gly Val Phe His Tyr Asp Ser Trp Gly Gln Gly Thr
            100                 105                 110

Leu Val Thr Val Ser Ser
        115

<210> SEQ ID NO 523
<211> LENGTH: 8
<212> TYPE: PRT
<213> ORGANISM: Artificial Sequence
<220> FEATURE:
<223> OTHER INFORMATION: Synthetic

```
<400> SEQUENCE: 523

Gly Tyr Thr Phe Thr Ser Tyr Tyr
1               5

<210> SEQ ID NO 524
<211> LENGTH: 8
<212> TYPE: PRT
<213> ORGANISM: Artificial Sequence
<220> FEATURE:
<223> OTHER INFORMATION: Synthetic

<400> SEQUENCE: 524

Glu Tyr Thr Leu Thr Thr Tyr Tyr
1               5

<210> SEQ ID NO 525
<211> LENGTH: 8
<212> TYPE: PRT
<213> ORGANISM: Artificial Sequence
<220> FEATURE:
<223> OTHER INFORMATION: Synthetic

<400> SEQUENCE: 525

Gly Phe Arg Phe Ser Gly Tyr Ser
1               5

<210> SEQ ID NO 526
<211> LENGTH: 8
<212> TYPE: PRT
<213> ORGANISM: Artificial Sequence
<220> FEATURE:
<223> OTHER INFORMATION: Synthetic

<400> SEQUENCE: 526

Gly Tyr Thr Phe Ser Ser Phe Tyr
1               5

<210> SEQ ID NO 527
<211> LENGTH: 8
<212> TYPE: PRT
<213> ORGANISM: Artificial Sequence
<220> FEATURE:
<223> OTHER INFORMATION: Synthetic

<400> SEQUENCE: 527

Gly Tyr Thr Phe Ser Ser Phe Tyr
1               5

<210> SEQ ID NO 528
<211> LENGTH: 8
<212> TYPE: PRT
<213> ORGANISM: Artificial Sequence
<220> FEATURE:
<223> OTHER INFORMATION: Synthetic

<400> SEQUENCE: 528

Gly Tyr Thr Phe Thr Gly Tyr Tyr
1               5

<210> SEQ ID NO 529
<211> LENGTH: 8
<212> TYPE: PRT
<213> ORGANISM: Artificial Sequence
<220> FEATURE:
<223> OTHER INFORMATION: Synthetic

<400> SEQUENCE: 529
```

```
Gly Tyr Thr Phe Thr Ser Tyr Gly
1               5

<210> SEQ ID NO 530
<211> LENGTH: 8
<212> TYPE: PRT
<213> ORGANISM: Artificial Sequence
<220> FEATURE:
<223> OTHER INFORMATION: Synthetic

<400> SEQUENCE: 530

Gly Tyr Thr Phe Ser Ser Tyr Tyr
1               5

<210> SEQ ID NO 531
<211> LENGTH: 8
<212> TYPE: PRT
<213> ORGANISM: Artificial Sequence
<220> FEATURE:
<223> OTHER INFORMATION: Synthetic

<400> SEQUENCE: 531

Gly Tyr Thr Phe Thr Ser Ser Tyr
1               5

<210> SEQ ID NO 532
<211> LENGTH: 8
<212> TYPE: PRT
<213> ORGANISM: Artificial Sequence
<220> FEATURE:
<223> OTHER INFORMATION: Synthetic

<400> SEQUENCE: 532

Gly Tyr Ala Phe Thr Ser Tyr Tyr
1               5

<210> SEQ ID NO 533
<211> LENGTH: 8
<212> TYPE: PRT
<213> ORGANISM: Artificial Sequence
<220> FEATURE:
<223> OTHER INFORMATION: Synthetic

<400> SEQUENCE: 533

Gly Tyr Thr Ile Thr Ser Tyr Tyr
1               5

<210> SEQ ID NO 534
<211> LENGTH: 8
<212> TYPE: PRT
<213> ORGANISM: Artificial Sequence
<220> FEATURE:
<223> OTHER INFORMATION: Synthetic

<400> SEQUENCE: 534

Gly Tyr Ser Phe Thr Asn Tyr Tyr
1               5

<210> SEQ ID NO 535
<211> LENGTH: 8
<212> TYPE: PRT
<213> ORGANISM: Artificial Sequence
<220> FEATURE:
<223> OTHER INFORMATION: Synthetic

<400> SEQUENCE: 535
```

```
Gly Phe Thr Phe Ser Ser Tyr Ala
1               5

<210> SEQ ID NO 536
<211> LENGTH: 8
<212> TYPE: PRT
<213> ORGANISM: Artificial Sequence
<220> FEATURE:
<223> OTHER INFORMATION: Synthetic

<400> SEQUENCE: 536

Gly Tyr Thr Phe Thr Ser Tyr Gly
1               5

<210> SEQ ID NO 537
<211> LENGTH: 10
<212> TYPE: PRT
<213> ORGANISM: Artificial Sequence
<220> FEATURE:
<223> OTHER INFORMATION: Synthetic

<400> SEQUENCE: 537

Gly Ala Ser Ile Ser Ser Thr Tyr Tyr Tyr
1               5                   10

<210> SEQ ID NO 538
<211> LENGTH: 8
<212> TYPE: PRT
<213> ORGANISM: Artificial Sequence
<220> FEATURE:
<223> OTHER INFORMATION: Synthetic

<400> SEQUENCE: 538

Gly Tyr Thr Phe Thr Thr Tyr Asp
1               5

<210> SEQ ID NO 539
<211> LENGTH: 8
<212> TYPE: PRT
<213> ORGANISM: Artificial Sequence
<220> FEATURE:
<223> OTHER INFORMATION: Synthetic

<400> SEQUENCE: 539

Ile Asn Pro Ser Gly Gly Ser Thr
1               5

<210> SEQ ID NO 540
<211> LENGTH: 8
<212> TYPE: PRT
<213> ORGANISM: Artificial Sequence
<220> FEATURE:
<223> OTHER INFORMATION: Synthetic

<400> SEQUENCE: 540

Ile Asn Pro Gly Ser Gly Ser Thr
1               5

<210> SEQ ID NO 541
<211> LENGTH: 8
<212> TYPE: PRT
<213> ORGANISM: Artificial Sequence
<220> FEATURE:
<223> OTHER INFORMATION: Synthetic

<400> SEQUENCE: 541

Ile Arg Ser Ser Ser Asp Leu Ile
```

```
<210> SEQ ID NO 542
<211> LENGTH: 8
<212> TYPE: PRT
<213> ORGANISM: Artificial Sequence
<220> FEATURE:
<223> OTHER INFORMATION: Synthetic

<400> SEQUENCE: 542

Ile Asp Pro Asn Ser Gly Phe Thr
1               5

<210> SEQ ID NO 543
<211> LENGTH: 8
<212> TYPE: PRT
<213> ORGANISM: Artificial Sequence
<220> FEATURE:
<223> OTHER INFORMATION: Synthetic

<400> SEQUENCE: 543

Ile Asn Pro Ser Gly Gly Tyr Thr
1               5

<210> SEQ ID NO 544
<211> LENGTH: 8
<212> TYPE: PRT
<213> ORGANISM: Artificial Sequence
<220> FEATURE:
<223> OTHER INFORMATION: Synthetic

<400> SEQUENCE: 544

Ile Asp Pro Asn Ser Gly Phe Thr
1               5

<210> SEQ ID NO 545
<211> LENGTH: 8
<212> TYPE: PRT
<213> ORGANISM: Artificial Sequence
<220> FEATURE:
<223> OTHER INFORMATION: Synthetic

<400> SEQUENCE: 545

Ile Asn Pro Asn Ser Gly Gly Thr
1               5

<210> SEQ ID NO 546
<211> LENGTH: 8
<212> TYPE: PRT
<213> ORGANISM: Artificial Sequence
<220> FEATURE:
<223> OTHER INFORMATION: Synthetic

<400> SEQUENCE: 546

Ile Ser Ala Tyr Asn Gly Asn Thr
1               5

<210> SEQ ID NO 547
<211> LENGTH: 8
<212> TYPE: PRT
<213> ORGANISM: Artificial Sequence
<220> FEATURE:
<223> OTHER INFORMATION: Synthetic

<400> SEQUENCE: 547

Ile Asn Pro Ser Gly Gly Tyr Thr
1               5
```

```
<210> SEQ ID NO 548
<211> LENGTH: 8
<212> TYPE: PRT
<213> ORGANISM: Artificial Sequence
<220> FEATURE:
<223> OTHER INFORMATION: Synthetic

<400> SEQUENCE: 548

Ile Asn Pro Thr Gly Gly Tyr Thr
1               5

<210> SEQ ID NO 549
<211> LENGTH: 8
<212> TYPE: PRT
<213> ORGANISM: Artificial Sequence
<220> FEATURE:
<223> OTHER INFORMATION: Synthetic

<400> SEQUENCE: 549

Ile Asn Pro Thr Ala Gly Ser Thr
1               5

<210> SEQ ID NO 550
<211> LENGTH: 8
<212> TYPE: PRT
<213> ORGANISM: Artificial Sequence
<220> FEATURE:
<223> OTHER INFORMATION: Synthetic

<400> SEQUENCE: 550

Ile Asn Pro Thr Gly Gly Ser Thr
1               5

<210> SEQ ID NO 551
<211> LENGTH: 8
<212> TYPE: PRT
<213> ORGANISM: Artificial Sequence
<220> FEATURE:
<223> OTHER INFORMATION: Synthetic

<400> SEQUENCE: 551

Ile Asn Pro Thr Ala Gly Thr Thr
1               5

<210> SEQ ID NO 552
<211> LENGTH: 8
<212> TYPE: PRT
<213> ORGANISM: Artificial Sequence
<220> FEATURE:
<223> OTHER INFORMATION: Synthetic

<400> SEQUENCE: 552

Ile Asn Pro Thr Gly Gly Tyr Thr
1               5

<210> SEQ ID NO 553
<211> LENGTH: 8
<212> TYPE: PRT
<213> ORGANISM: Artificial Sequence
<220> FEATURE:
<223> OTHER INFORMATION: Synthetic

<400> SEQUENCE: 553

Ile Asn Pro Asn Ala Gly Ser Thr
1               5
```

```
<210> SEQ ID NO 554
<211> LENGTH: 8
<212> TYPE: PRT
<213> ORGANISM: Artificial Sequence
<220> FEATURE:
<223> OTHER INFORMATION: Synthetic

<400> SEQUENCE: 554

Ile Asn Pro Thr Ser Gly Thr Thr
1               5

<210> SEQ ID NO 555
<211> LENGTH: 8
<212> TYPE: PRT
<213> ORGANISM: Artificial Sequence
<220> FEATURE:
<223> OTHER INFORMATION: Synthetic

<400> SEQUENCE: 555

Ile Thr Pro Thr Asn Gly Gly Ala
1               5

<210> SEQ ID NO 556
<211> LENGTH: 8
<212> TYPE: PRT
<213> ORGANISM: Artificial Sequence
<220> FEATURE:
<223> OTHER INFORMATION: Synthetic

<400> SEQUENCE: 556

Ile Ser Tyr Asp Gly Ser Asn Lys
1               5

<210> SEQ ID NO 557
<211> LENGTH: 8
<212> TYPE: PRT
<213> ORGANISM: Artificial Sequence
<220> FEATURE:
<223> OTHER INFORMATION: Synthetic

<400> SEQUENCE: 557

Ile Asn Pro Ser Gly Gly Tyr Thr
1               5

<210> SEQ ID NO 558
<211> LENGTH: 8
<212> TYPE: PRT
<213> ORGANISM: Artificial Sequence
<220> FEATURE:
<223> OTHER INFORMATION: Synthetic

<400> SEQUENCE: 558

Ile Ser Ala Tyr Asn Gly Asn Thr
1               5

<210> SEQ ID NO 559
<211> LENGTH: 7
<212> TYPE: PRT
<213> ORGANISM: Artificial Sequence
<220> FEATURE:
<223> OTHER INFORMATION: Synthetic

<400> SEQUENCE: 559

Ile Gly Tyr Ser Gly Ile Thr
1               5
```

```
<210> SEQ ID NO 560
<211> LENGTH: 8
<212> TYPE: PRT
<213> ORGANISM: Artificial Sequence
<220> FEATURE:
<223> OTHER INFORMATION: Synthetic

<400> SEQUENCE: 560

Met Asn Pro Asn Ser Gly Asn Thr
1               5

<210> SEQ ID NO 561
<211> LENGTH: 10
<212> TYPE: PRT
<213> ORGANISM: Artificial Sequence
<220> FEATURE:
<223> OTHER INFORMATION: Synthetic

<400> SEQUENCE: 561

Ala Ala Gly Ser Tyr Tyr Ser Leu Asp Ile
1               5                   10

<210> SEQ ID NO 562
<211> LENGTH: 10
<212> TYPE: PRT
<213> ORGANISM: Artificial Sequence
<220> FEATURE:
<223> OTHER INFORMATION: Synthetic

<400> SEQUENCE: 562

Ala Ser Gly Ser Arg Tyr Ala Phe Asp Ile
1               5                   10

<210> SEQ ID NO 563
<211> LENGTH: 12
<212> TYPE: PRT
<213> ORGANISM: Artificial Sequence
<220> FEATURE:
<223> OTHER INFORMATION: Synthetic

<400> SEQUENCE: 563

Ala Arg Ala Ile Thr Ala Leu Asp Ala Phe Asp Ile
1               5                   10

<210> SEQ ID NO 564
<211> LENGTH: 15
<212> TYPE: PRT
<213> ORGANISM: Artificial Sequence
<220> FEATURE:
<223> OTHER INFORMATION: Synthetic

<400> SEQUENCE: 564

Ala Arg Ala Phe Gly Tyr Gly Asp Tyr Phe Tyr Gly Met Asp Val
1               5                   10                  15

<210> SEQ ID NO 565
<211> LENGTH: 15
<212> TYPE: PRT
<213> ORGANISM: Artificial Sequence
<220> FEATURE:
<223> OTHER INFORMATION: Synthetic

<400> SEQUENCE: 565

Ala Arg Asp Met Gly Ser Thr Trp Tyr Arg Gly Ala Phe Asp Phe
1               5                   10                  15

<210> SEQ ID NO 566
```

```
<211> LENGTH: 12
<212> TYPE: PRT
<213> ORGANISM: Artificial Sequence
<220> FEATURE:
<223> OTHER INFORMATION: Synthetic

<400> SEQUENCE: 566

Ala Arg Ser Pro Gly Gly Gly Tyr Gly Gln Asp Gly
1               5                   10

<210> SEQ ID NO 567
<211> LENGTH: 11
<212> TYPE: PRT
<213> ORGANISM: Artificial Sequence
<220> FEATURE:
<223> OTHER INFORMATION: Synthetic

<400> SEQUENCE: 567

Ala Arg Tyr Ile Tyr Tyr Met Gly Tyr Asp Glu
1               5                   10

<210> SEQ ID NO 568
<211> LENGTH: 10
<212> TYPE: PRT
<213> ORGANISM: Artificial Sequence
<220> FEATURE:
<223> OTHER INFORMATION: Synthetic

<400> SEQUENCE: 568

Ala Arg Gly Met Leu Thr Tyr Leu Asp Ser
1               5                   10

<210> SEQ ID NO 569
<211> LENGTH: 11
<212> TYPE: PRT
<213> ORGANISM: Artificial Sequence
<220> FEATURE:
<223> OTHER INFORMATION: Synthetic

<400> SEQUENCE: 569

Ala Arg Tyr Ile Tyr Ala Ser Gly Ile Asp Thr
1               5                   10

<210> SEQ ID NO 570
<211> LENGTH: 14
<212> TYPE: PRT
<213> ORGANISM: Artificial Sequence
<220> FEATURE:
<223> OTHER INFORMATION: Synthetic

<400> SEQUENCE: 570

Ala Arg Ser Tyr Tyr Ser Val Gly Thr Gln Trp Leu Asp Ser
1               5                   10

<210> SEQ ID NO 571
<211> LENGTH: 12
<212> TYPE: PRT
<213> ORGANISM: Artificial Sequence
<220> FEATURE:
<223> OTHER INFORMATION: Synthetic

<400> SEQUENCE: 571

Ala Arg Gly Val Ser Phe Met Ser Ala Met Asp Ser
1               5                   10

<210> SEQ ID NO 572
<211> LENGTH: 13
```

```
<212> TYPE: PRT
<213> ORGANISM: Artificial Sequence
<220> FEATURE:
<223> OTHER INFORMATION: Synthetic

<400> SEQUENCE: 572

Ala Arg Asp Trp Ser Ser Tyr Asp Ser Val Met Asp Ser
1               5                   10

<210> SEQ ID NO 573
<211> LENGTH: 11
<212> TYPE: PRT
<213> ORGANISM: Artificial Sequence
<220> FEATURE:
<223> OTHER INFORMATION: Synthetic

<400> SEQUENCE: 573

Ala Arg Trp Val Gly Met Glu Glu Glu Asp His
1               5                   10

<210> SEQ ID NO 574
<211> LENGTH: 13
<212> TYPE: PRT
<213> ORGANISM: Artificial Sequence
<220> FEATURE:
<223> OTHER INFORMATION: Synthetic

<400> SEQUENCE: 574

Ala Arg Ser Val Thr His Ser Ser Ser Ala Phe Asp Tyr
1               5                   10

<210> SEQ ID NO 575
<211> LENGTH: 10
<212> TYPE: PRT
<213> ORGANISM: Artificial Sequence
<220> FEATURE:
<223> OTHER INFORMATION: Synthetic

<400> SEQUENCE: 575

Ala Arg Gly Gln Ser Gly Val Val Tyr Asp
1               5                   10

<210> SEQ ID NO 576
<211> LENGTH: 13
<212> TYPE: PRT
<213> ORGANISM: Artificial Sequence
<220> FEATURE:
<223> OTHER INFORMATION: Synthetic

<400> SEQUENCE: 576

Ala Arg Gly Thr Thr Tyr Met Trp Ser Gly Tyr Asp Ser
1               5                   10

<210> SEQ ID NO 577
<211> LENGTH: 13
<212> TYPE: PRT
<213> ORGANISM: Artificial Sequence
<220> FEATURE:
<223> OTHER INFORMATION: Synthetic

<400> SEQUENCE: 577

Ala Arg Ser Val Met His Tyr Tyr Asp Phe Phe Asp Gly
1               5                   10

<210> SEQ ID NO 578
<211> LENGTH: 12
<212> TYPE: PRT
```

```
<213> ORGANISM: Artificial Sequence
<220> FEATURE:
<223> OTHER INFORMATION: Synthetic

<400> SEQUENCE: 578

Ala Arg Gly Tyr Ser Phe Ala Gly Tyr Tyr Asp Trp
1               5                   10

<210> SEQ ID NO 579
<211> LENGTH: 12
<212> TYPE: PRT
<213> ORGANISM: Artificial Sequence
<220> FEATURE:
<223> OTHER INFORMATION: Synthetic

<400> SEQUENCE: 579

Ala Arg Ser Ile Thr Tyr Trp Ser Ala Tyr Asp Tyr
1               5                   10

<210> SEQ ID NO 580
<211> LENGTH: 11
<212> TYPE: PRT
<213> ORGANISM: Artificial Sequence
<220> FEATURE:
<223> OTHER INFORMATION: Synthetic

<400> SEQUENCE: 580

Ala Arg Tyr Val Phe Gly Ser Gly Gln Asp Ser
1               5                   10

<210> SEQ ID NO 581
<211> LENGTH: 10
<212> TYPE: PRT
<213> ORGANISM: Artificial Sequence
<220> FEATURE:
<223> OTHER INFORMATION: Synthetic

<400> SEQUENCE: 581

Ala Arg Gly Val Tyr Gly Ser Leu Asp Ser
1               5                   10

<210> SEQ ID NO 582
<211> LENGTH: 12
<212> TYPE: PRT
<213> ORGANISM: Artificial Sequence
<220> FEATURE:
<223> OTHER INFORMATION: Synthetic

<400> SEQUENCE: 582

Ala Arg Gln Ser Ser Gly Arg Asp Gly Phe Asp Ser
1               5                   10

<210> SEQ ID NO 583
<211> LENGTH: 10
<212> TYPE: PRT
<213> ORGANISM: Artificial Sequence
<220> FEATURE:
<223> OTHER INFORMATION: Synthetic

<400> SEQUENCE: 583

Ala Arg Ser Pro Ser Phe Tyr Tyr Asp Gly
1               5                   10

<210> SEQ ID NO 584
<211> LENGTH: 19
<212> TYPE: PRT
<213> ORGANISM: Artificial Sequence
```

```
<220> FEATURE:
<223> OTHER INFORMATION: Synthetic

<400> SEQUENCE: 584

Ala Arg Gln Trp Ser Tyr Thr Ser Phe Ser Leu Ser Gly Tyr Ile Ser
1               5                   10                  15

Tyr Asp Ser

<210> SEQ ID NO 585
<211> LENGTH: 19
<212> TYPE: PRT
<213> ORGANISM: Artificial Sequence
<220> FEATURE:
<223> OTHER INFORMATION: Synthetic

<400> SEQUENCE: 585

Ala Arg Asn Gly Tyr Trp Tyr Trp Gly Ser Gly Glu His Gly Ser Trp
1               5                   10                  15

Tyr Asp Ser

<210> SEQ ID NO 586
<211> LENGTH: 10
<212> TYPE: PRT
<213> ORGANISM: Artificial Sequence
<220> FEATURE:
<223> OTHER INFORMATION: Synthetic

<400> SEQUENCE: 586

Ala Arg Gly Met Pro Asp Val Val Asp Asp
1               5                   10

<210> SEQ ID NO 587
<211> LENGTH: 12
<212> TYPE: PRT
<213> ORGANISM: Artificial Sequence
<220> FEATURE:
<223> OTHER INFORMATION: Synthetic

<400> SEQUENCE: 587

Ala Arg Ser Ser Ser Gly Gly Asn Gly Ala Asp Ser
1               5                   10

<210> SEQ ID NO 588
<211> LENGTH: 18
<212> TYPE: PRT
<213> ORGANISM: Artificial Sequence
<220> FEATURE:
<223> OTHER INFORMATION: Synthetic

<400> SEQUENCE: 588

Ala Arg Ser Tyr Tyr Ala Ala Asp Trp Trp Trp His Ala Thr Met Met
1               5                   10                  15

Asp Met

<210> SEQ ID NO 589
<211> LENGTH: 11
<212> TYPE: PRT
<213> ORGANISM: Artificial Sequence
<220> FEATURE:
<223> OTHER INFORMATION: Synthetic

<400> SEQUENCE: 589

Ala Arg Ser Gly Ser Tyr Gly Asp Ser Asp Ser
1               5                   10
```

```
<210> SEQ ID NO 590
<211> LENGTH: 12
<212> TYPE: PRT
<213> ORGANISM: Artificial Sequence
<220> FEATURE:
<223> OTHER INFORMATION: Synthetic

<400> SEQUENCE: 590

Ala Arg Gly Ser Trp Trp Tyr Ser Tyr Tyr Asp His
1               5                   10

<210> SEQ ID NO 591
<211> LENGTH: 11
<212> TYPE: PRT
<213> ORGANISM: Artificial Sequence
<220> FEATURE:
<223> OTHER INFORMATION: Synthetic

<400> SEQUENCE: 591

Ala Arg Gly Tyr Gly Val Phe His Tyr Asp Ser
1               5                   10

<210> SEQ ID NO 592
<211> LENGTH: 9
<212> TYPE: PRT
<213> ORGANISM: Artificial Sequence
<220> FEATURE:
<223> OTHER INFORMATION: Synthetic

<400> SEQUENCE: 592

Arg Ser Asn Ile Gly Ala Ala Phe Asp
1               5

<210> SEQ ID NO 593
<211> LENGTH: 6
<212> TYPE: PRT
<213> ORGANISM: Artificial Sequence
<220> FEATURE:
<223> OTHER INFORMATION: Synthetic

<400> SEQUENCE: 593

Asn Ile Glu Ser Lys Ser
1               5

<210> SEQ ID NO 594
<211> LENGTH: 6
<212> TYPE: PRT
<213> ORGANISM: Artificial Sequence
<220> FEATURE:
<223> OTHER INFORMATION: Synthetic

<400> SEQUENCE: 594

Asn Ile Gly Ser Lys Ser
1               5

<210> SEQ ID NO 595
<211> LENGTH: 6
<212> TYPE: PRT
<213> ORGANISM: Artificial Sequence
<220> FEATURE:
<223> OTHER INFORMATION: Synthetic

<400> SEQUENCE: 595

Asn Ile Gly Ser Lys Ser
1               5
```

```
<210> SEQ ID NO 596
<211> LENGTH: 9
<212> TYPE: PRT
<213> ORGANISM: Artificial Sequence
<220> FEATURE:
<223> OTHER INFORMATION: Synthetic

<400> SEQUENCE: 596

Ser Ser Asn Ile Gly Ala Gly His Asp
1               5

<210> SEQ ID NO 597
<211> LENGTH: 6
<212> TYPE: PRT
<213> ORGANISM: Artificial Sequence
<220> FEATURE:
<223> OTHER INFORMATION: Synthetic

<400> SEQUENCE: 597

Asn Ile Gly Arg Gln Ser
1               5

<210> SEQ ID NO 598
<211> LENGTH: 6
<212> TYPE: PRT
<213> ORGANISM: Artificial Sequence
<220> FEATURE:
<223> OTHER INFORMATION: Synthetic

<400> SEQUENCE: 598

Gln Ser Ile Ser Ser Tyr
1               5

<210> SEQ ID NO 599
<211> LENGTH: 6
<212> TYPE: PRT
<213> ORGANISM: Artificial Sequence
<220> FEATURE:
<223> OTHER INFORMATION: Synthetic

<400> SEQUENCE: 599

Asn Ile Glu Thr Lys Ser
1               5

<210> SEQ ID NO 600
<211> LENGTH: 9
<212> TYPE: PRT
<213> ORGANISM: Artificial Sequence
<220> FEATURE:
<223> OTHER INFORMATION: Synthetic

<400> SEQUENCE: 600

Ser Ser His Val Gly Ala Tyr Ser Tyr
1               5

<210> SEQ ID NO 601
<211> LENGTH: 6
<212> TYPE: PRT
<213> ORGANISM: Artificial Sequence
<220> FEATURE:
<223> OTHER INFORMATION: Synthetic

<400> SEQUENCE: 601

Asn Val Gly Arg Lys Ser
1               5

<210> SEQ ID NO 602
```

```
<211> LENGTH: 6
<212> TYPE: PRT
<213> ORGANISM: Artificial Sequence
<220> FEATURE:
<223> OTHER INFORMATION: Synthetic

<400> SEQUENCE: 602

Gln Asn Ile Gly Asn Trp
1               5

<210> SEQ ID NO 603
<211> LENGTH: 6
<212> TYPE: PRT
<213> ORGANISM: Artificial Sequence
<220> FEATURE:
<223> OTHER INFORMATION: Synthetic

<400> SEQUENCE: 603

Ser Leu Arg Asp Phe Tyr
1               5

<210> SEQ ID NO 604
<211> LENGTH: 9
<212> TYPE: PRT
<213> ORGANISM: Artificial Sequence
<220> FEATURE:
<223> OTHER INFORMATION: Synthetic

<400> SEQUENCE: 604

Ser Ser Asn Ile Gly Ala Gly His Asp
1               5

<210> SEQ ID NO 605
<211> LENGTH: 6
<212> TYPE: PRT
<213> ORGANISM: Artificial Sequence
<220> FEATURE:
<223> OTHER INFORMATION: Synthetic

<400> SEQUENCE: 605

Asn Ile Gly Thr Lys Thr
1               5

<210> SEQ ID NO 606
<211> LENGTH: 7
<212> TYPE: PRT
<213> ORGANISM: Artificial Sequence
<220> FEATURE:
<223> OTHER INFORMATION: Synthetic

<400> SEQUENCE: 606

Gln Ser Ile Thr Asp Asn Phe
1               5

<210> SEQ ID NO 607
<211> LENGTH: 9
<212> TYPE: PRT
<213> ORGANISM: Artificial Sequence
<220> FEATURE:
<223> OTHER INFORMATION: Synthetic

<400> SEQUENCE: 607

Ser Ser Asp Val Gly Gly Tyr Asn Tyr
1               5

<210> SEQ ID NO 608
<211> LENGTH: 9
```

```
<212> TYPE: PRT
<213> ORGANISM: Artificial Sequence
<220> FEATURE:
<223> OTHER INFORMATION: Synthetic

<400> SEQUENCE: 608

Ser Ser Asp Val Gly Ala Tyr Asn Tyr
1               5

<210> SEQ ID NO 609
<211> LENGTH: 9
<212> TYPE: PRT
<213> ORGANISM: Artificial Sequence
<220> FEATURE:
<223> OTHER INFORMATION: Synthetic

<400> SEQUENCE: 609

Ser Ser Asn Ile Gly Ala Gly Tyr Asp
1               5

<210> SEQ ID NO 610
<211> LENGTH: 8
<212> TYPE: PRT
<213> ORGANISM: Artificial Sequence
<220> FEATURE:
<223> OTHER INFORMATION: Synthetic

<400> SEQUENCE: 610

Ser Ser Asn Ile Gly Asn Asn Tyr
1               5

<210> SEQ ID NO 611
<211> LENGTH: 6
<212> TYPE: PRT
<213> ORGANISM: Artificial Sequence
<220> FEATURE:
<223> OTHER INFORMATION: Synthetic

<400> SEQUENCE: 611

Asn Ile Gly Ser Lys Ser
1               5

<210> SEQ ID NO 612
<211> LENGTH: 6
<212> TYPE: PRT
<213> ORGANISM: Artificial Sequence
<220> FEATURE:
<223> OTHER INFORMATION: Synthetic

<400> SEQUENCE: 612

Lys Ile Glu Ser Lys Ser
1               5

<210> SEQ ID NO 613
<211> LENGTH: 6
<212> TYPE: PRT
<213> ORGANISM: Artificial Sequence
<220> FEATURE:
<223> OTHER INFORMATION: Synthetic

<400> SEQUENCE: 613

Asn Ile Gly Ser Lys Ser
1               5

<210> SEQ ID NO 614
<211> LENGTH: 9
<212> TYPE: PRT
```

```
<213> ORGANISM: Artificial Sequence
<220> FEATURE:
<223> OTHER INFORMATION: Synthetic

<400> SEQUENCE: 614

Ser Ser Asn Ile Gly Ala Gly Tyr Asp
1               5

<210> SEQ ID NO 615
<211> LENGTH: 6
<212> TYPE: PRT
<213> ORGANISM: Artificial Sequence
<220> FEATURE:
<223> OTHER INFORMATION: Synthetic

<400> SEQUENCE: 615

Asn Ile Gly Ser Lys Ser
1               5

<210> SEQ ID NO 616
<211> LENGTH: 6
<212> TYPE: PRT
<213> ORGANISM: Artificial Sequence
<220> FEATURE:
<223> OTHER INFORMATION: Synthetic

<400> SEQUENCE: 616

Asn Ile Gly Ser Asn Ser
1               5

<210> SEQ ID NO 617
<211> LENGTH: 6
<212> TYPE: PRT
<213> ORGANISM: Artificial Sequence
<220> FEATURE:
<223> OTHER INFORMATION: Synthetic

<400> SEQUENCE: 617

Asn Ile Gly Ser Lys Ser
1               5

<210> SEQ ID NO 618
<211> LENGTH: 8
<212> TYPE: PRT
<213> ORGANISM: Artificial Sequence
<220> FEATURE:
<223> OTHER INFORMATION: Synthetic

<400> SEQUENCE: 618

Ser Ser Asn Ile Gly Arg Asn Thr
1               5

<210> SEQ ID NO 619
<211> LENGTH: 6
<212> TYPE: PRT
<213> ORGANISM: Artificial Sequence
<220> FEATURE:
<223> OTHER INFORMATION: Synthetic

<400> SEQUENCE: 619

Asn Ile Gly Ser Lys Ser
1               5

<210> SEQ ID NO 620
<211> LENGTH: 6
<212> TYPE: PRT
<213> ORGANISM: Artificial Sequence
```

```
<220> FEATURE:
<223> OTHER INFORMATION: Synthetic

<400> SEQUENCE: 620

Asn Val Gly Ser Lys Ser
1               5

<210> SEQ ID NO 621
<211> LENGTH: 6
<212> TYPE: PRT
<213> ORGANISM: Artificial Sequence
<220> FEATURE:
<223> OTHER INFORMATION: Synthetic

<400> SEQUENCE: 621

Gln Gly Ile Gly Asn Tyr
1               5

<210> SEQ ID NO 622
<211> LENGTH: 3
<212> TYPE: PRT
<213> ORGANISM: Artificial Sequence
<220> FEATURE:
<223> OTHER INFORMATION: Synthetic

<400> SEQUENCE: 622

Gly Asp Asn
1

<210> SEQ ID NO 623
<211> LENGTH: 3
<212> TYPE: PRT
<213> ORGANISM: Artificial Sequence
<220> FEATURE:
<223> OTHER INFORMATION: Synthetic

<400> SEQUENCE: 623

Phe Asp Ser
1

<210> SEQ ID NO 624
<211> LENGTH: 3
<212> TYPE: PRT
<213> ORGANISM: Artificial Sequence
<220> FEATURE:
<223> OTHER INFORMATION: Synthetic

<400> SEQUENCE: 624

Tyr Asp Ser
1

<210> SEQ ID NO 625
<211> LENGTH: 3
<212> TYPE: PRT
<213> ORGANISM: Artificial Sequence
<220> FEATURE:
<223> OTHER INFORMATION: Synthetic

<400> SEQUENCE: 625

Asp Asp Ser
1

<210> SEQ ID NO 626
<211> LENGTH: 3
<212> TYPE: PRT
<213> ORGANISM: Artificial Sequence
<220> FEATURE:
```

<223> OTHER INFORMATION: Synthetic

<400> SEQUENCE: 626

Ser Asn Gly
1

<210> SEQ ID NO 627
<211> LENGTH: 3
<212> TYPE: PRT
<213> ORGANISM: Artificial Sequence
<220> FEATURE:
<223> OTHER INFORMATION: Synthetic

<400> SEQUENCE: 627

Tyr Asp Ala
1

<210> SEQ ID NO 628
<211> LENGTH: 3
<212> TYPE: PRT
<213> ORGANISM: Artificial Sequence
<220> FEATURE:
<223> OTHER INFORMATION: Synthetic

<400> SEQUENCE: 628

Ala Ala Ser
1

<210> SEQ ID NO 629
<211> LENGTH: 3
<212> TYPE: PRT
<213> ORGANISM: Artificial Sequence
<220> FEATURE:
<223> OTHER INFORMATION: Synthetic

<400> SEQUENCE: 629

Tyr Asp Asn
1

<210> SEQ ID NO 630
<211> LENGTH: 3
<212> TYPE: PRT
<213> ORGANISM: Artificial Sequence
<220> FEATURE:
<223> OTHER INFORMATION: Synthetic

<400> SEQUENCE: 630

Asp Val Asn
1

<210> SEQ ID NO 631
<211> LENGTH: 3
<212> TYPE: PRT
<213> ORGANISM: Artificial Sequence
<220> FEATURE:
<223> OTHER INFORMATION: Synthetic

<400> SEQUENCE: 631

Gln Ala Ser
1

<210> SEQ ID NO 632
<211> LENGTH: 3
<212> TYPE: PRT
<213> ORGANISM: Artificial Sequence
<220> FEATURE:
<223> OTHER INFORMATION: Synthetic

<400> SEQUENCE: 632

Gly Glu Asn
1

<210> SEQ ID NO 633
<211> LENGTH: 3
<212> TYPE: PRT
<213> ORGANISM: Artificial Sequence
<220> FEATURE:
<223> OTHER INFORMATION: Synthetic

<400> SEQUENCE: 633

Gly Asn Gly
1

<210> SEQ ID NO 634
<211> LENGTH: 3
<212> TYPE: PRT
<213> ORGANISM: Artificial Sequence
<220> FEATURE:
<223> OTHER INFORMATION: Synthetic

<400> SEQUENCE: 634

Tyr Asp Ile
1

<210> SEQ ID NO 635
<211> LENGTH: 3
<212> TYPE: PRT
<213> ORGANISM: Artificial Sequence
<220> FEATURE:
<223> OTHER INFORMATION: Synthetic

<400> SEQUENCE: 635

Gly Ala Ser
1

<210> SEQ ID NO 636
<211> LENGTH: 3
<212> TYPE: PRT
<213> ORGANISM: Artificial Sequence
<220> FEATURE:
<223> OTHER INFORMATION: Synthetic

<400> SEQUENCE: 636

Asp Val Ser
1

<210> SEQ ID NO 637
<211> LENGTH: 3
<212> TYPE: PRT
<213> ORGANISM: Artificial Sequence
<220> FEATURE:
<223> OTHER INFORMATION: Synthetic

<400> SEQUENCE: 637

Asp Val Thr
1

<210> SEQ ID NO 638
<211> LENGTH: 3
<212> TYPE: PRT
<213> ORGANISM: Artificial Sequence
<220> FEATURE:
<223> OTHER INFORMATION: Synthetic

```
<400> SEQUENCE: 638

Gly Asn Asn
1

<210> SEQ ID NO 639
<211> LENGTH: 3
<212> TYPE: PRT
<213> ORGANISM: Artificial Sequence
<220> FEATURE:
<223> OTHER INFORMATION: Synthetic

<400> SEQUENCE: 639

Asp Asn Asn
1

<210> SEQ ID NO 640
<211> LENGTH: 3
<212> TYPE: PRT
<213> ORGANISM: Artificial Sequence
<220> FEATURE:
<223> OTHER INFORMATION: Synthetic

<400> SEQUENCE: 640

Tyr Asp Ser
1

<210> SEQ ID NO 641
<211> LENGTH: 3
<212> TYPE: PRT
<213> ORGANISM: Artificial Sequence
<220> FEATURE:
<223> OTHER INFORMATION: Synthetic

<400> SEQUENCE: 641

Gly Asn Ser
1

<210> SEQ ID NO 642
<211> LENGTH: 3
<212> TYPE: PRT
<213> ORGANISM: Artificial Sequence
<220> FEATURE:
<223> OTHER INFORMATION: Synthetic

<400> SEQUENCE: 642

Tyr Asp Ser
1

<210> SEQ ID NO 643
<211> LENGTH: 3
<212> TYPE: PRT
<213> ORGANISM: Artificial Sequence
<220> FEATURE:
<223> OTHER INFORMATION: Synthetic

<400> SEQUENCE: 643

Ser Asn Asn
1

<210> SEQ ID NO 644
<211> LENGTH: 3
<212> TYPE: PRT
<213> ORGANISM: Artificial Sequence
<220> FEATURE:
<223> OTHER INFORMATION: Synthetic

<400> SEQUENCE: 644
```

```
Tyr Asp Ser
1

<210> SEQ ID NO 645
<211> LENGTH: 3
<212> TYPE: PRT
<213> ORGANISM: Artificial Sequence
<220> FEATURE:
<223> OTHER INFORMATION: Synthetic

<400> SEQUENCE: 645

Ser Val Ser
1

<210> SEQ ID NO 646
<211> LENGTH: 10
<212> TYPE: PRT
<213> ORGANISM: Artificial Sequence
<220> FEATURE:
<223> OTHER INFORMATION: Synthetic

<400> SEQUENCE: 646

Gln Ser Tyr Asp Thr Ser Leu Asn Val Leu
1               5                   10

<210> SEQ ID NO 647
<211> LENGTH: 11
<212> TYPE: PRT
<213> ORGANISM: Artificial Sequence
<220> FEATURE:
<223> OTHER INFORMATION: Synthetic

<400> SEQUENCE: 647

Gln Val Trp Asp Ser Ser Ser Asp His Tyr Val
1               5                   10

<210> SEQ ID NO 648
<211> LENGTH: 11
<212> TYPE: PRT
<213> ORGANISM: Artificial Sequence
<220> FEATURE:
<223> OTHER INFORMATION: Synthetic

<400> SEQUENCE: 648

Gln Val Trp Asp Ser Ser Ser Asp His Pro Val
1               5                   10

<210> SEQ ID NO 649
<211> LENGTH: 11
<212> TYPE: PRT
<213> ORGANISM: Artificial Sequence
<220> FEATURE:
<223> OTHER INFORMATION: Synthetic

<400> SEQUENCE: 649

Gln Val Trp Asp Ser Ser Ser Asp His Gly Val
1               5                   10

<210> SEQ ID NO 650
<211> LENGTH: 12
<212> TYPE: PRT
<213> ORGANISM: Artificial Sequence
<220> FEATURE:
<223> OTHER INFORMATION: Synthetic

<400> SEQUENCE: 650
```

```
Gln Ser Tyr Asp Ser Ser Leu Ser Gly Asp Val Val
1               5                   10
```

<210> SEQ ID NO 651
<211> LENGTH: 11
<212> TYPE: PRT
<213> ORGANISM: Artificial Sequence
<220> FEATURE:
<223> OTHER INFORMATION: Synthetic

<400> SEQUENCE: 651

```
Gln Val Trp Asp Ser Ser Ser Asp His Tyr Val
1               5                   10
```

<210> SEQ ID NO 652
<211> LENGTH: 9
<212> TYPE: PRT
<213> ORGANISM: Artificial Sequence
<220> FEATURE:
<223> OTHER INFORMATION: Synthetic

<400> SEQUENCE: 652

```
Gln Gln Ser Tyr Ser Thr Pro Phe Thr
1               5
```

<210> SEQ ID NO 653
<211> LENGTH: 11
<212> TYPE: PRT
<213> ORGANISM: Artificial Sequence
<220> FEATURE:
<223> OTHER INFORMATION: Synthetic

<400> SEQUENCE: 653

```
Gln Val Trp Asp Lys Ser Asn Asp His Met Val
1               5                   10
```

<210> SEQ ID NO 654
<211> LENGTH: 11
<212> TYPE: PRT
<213> ORGANISM: Artificial Sequence
<220> FEATURE:
<223> OTHER INFORMATION: Synthetic

<400> SEQUENCE: 654

```
Ser Ser Tyr Ala Ser Ser Asn Asn Tyr Val Leu
1               5                   10
```

<210> SEQ ID NO 655
<211> LENGTH: 9
<212> TYPE: PRT
<213> ORGANISM: Artificial Sequence
<220> FEATURE:
<223> OTHER INFORMATION: Synthetic

<400> SEQUENCE: 655

```
Gln Gln Ser Tyr Ser Thr Pro Leu Thr
1               5
```

<210> SEQ ID NO 656
<211> LENGTH: 10
<212> TYPE: PRT
<213> ORGANISM: Artificial Sequence
<220> FEATURE:
<223> OTHER INFORMATION: Synthetic

<400> SEQUENCE: 656

```
Gln Val Trp Asp Asn Phe Arg Asp Gln Val
```

-continued

```
1               5                   10
```

<210> SEQ ID NO 657
<211> LENGTH: 9
<212> TYPE: PRT
<213> ORGANISM: Artificial Sequence
<220> FEATURE:
<223> OTHER INFORMATION: Synthetic

<400> SEQUENCE: 657

```
Gln Gln Tyr Tyr Gly Thr Pro Leu Thr
1               5
```

<210> SEQ ID NO 658
<211> LENGTH: 11
<212> TYPE: PRT
<213> ORGANISM: Artificial Sequence
<220> FEATURE:
<223> OTHER INFORMATION: Synthetic

<400> SEQUENCE: 658

```
Lys Ser Arg Asp Ser Asn Val Tyr His Trp Val
1               5                   10
```

<210> SEQ ID NO 659
<211> LENGTH: 11
<212> TYPE: PRT
<213> ORGANISM: Artificial Sequence
<220> FEATURE:
<223> OTHER INFORMATION: Synthetic

<400> SEQUENCE: 659

```
Gln Ser Tyr Asp Ser Ser Leu Ser Gly Tyr Val
1               5                   10
```

<210> SEQ ID NO 660
<211> LENGTH: 11
<212> TYPE: PRT
<213> ORGANISM: Artificial Sequence
<220> FEATURE:
<223> OTHER INFORMATION: Synthetic

<400> SEQUENCE: 660

```
Gln Val Trp Asp Ser Gly Ser Tyr Gln Gly Val
1               5                   10
```

<210> SEQ ID NO 661
<211> LENGTH: 10
<212> TYPE: PRT
<213> ORGANISM: Artificial Sequence
<220> FEATURE:
<223> OTHER INFORMATION: Synthetic

<400> SEQUENCE: 661

```
His Gln Tyr Gly Ser Ser Pro Pro Gly Thr
1               5                   10
```

<210> SEQ ID NO 662
<211> LENGTH: 10
<212> TYPE: PRT
<213> ORGANISM: Artificial Sequence
<220> FEATURE:
<223> OTHER INFORMATION: Synthetic

<400> SEQUENCE: 662

```
Ser Ser Tyr Thr Ser Thr Ser Val Tyr Val
1               5                   10
```

```
<210> SEQ ID NO 663
<211> LENGTH: 10
<212> TYPE: PRT
<213> ORGANISM: Artificial Sequence
<220> FEATURE:
<223> OTHER INFORMATION: Synthetic

<400> SEQUENCE: 663

Ser Ser Phe Thr Ala Ile Gly Thr Trp Val
1               5                   10

<210> SEQ ID NO 664
<211> LENGTH: 10
<212> TYPE: PRT
<213> ORGANISM: Artificial Sequence
<220> FEATURE:
<223> OTHER INFORMATION: Synthetic

<400> SEQUENCE: 664

Gln Ser Tyr Asp Asn Asn Leu Ser Gly Val
1               5                   10

<210> SEQ ID NO 665
<211> LENGTH: 13
<212> TYPE: PRT
<213> ORGANISM: Artificial Sequence
<220> FEATURE:
<223> OTHER INFORMATION: Synthetic

<400> SEQUENCE: 665

Gly Ile Trp Asp Ser Ser Leu Ser Ala Gly Ser Tyr Val
1               5                   10

<210> SEQ ID NO 666
<211> LENGTH: 11
<212> TYPE: PRT
<213> ORGANISM: Artificial Sequence
<220> FEATURE:
<223> OTHER INFORMATION: Synthetic

<400> SEQUENCE: 666

Gln Val Trp Asp Ser Ser Ser Asp His Val Val
1               5                   10

<210> SEQ ID NO 667
<211> LENGTH: 11
<212> TYPE: PRT
<213> ORGANISM: Artificial Sequence
<220> FEATURE:
<223> OTHER INFORMATION: Synthetic

<400> SEQUENCE: 667

Gln Val Trp Asp Ser Ser Asn Asp Val Gln Val
1               5                   10

<210> SEQ ID NO 668
<211> LENGTH: 12
<212> TYPE: PRT
<213> ORGANISM: Artificial Sequence
<220> FEATURE:
<223> OTHER INFORMATION: Synthetic

<400> SEQUENCE: 668

Gln Val Trp Asp Ser Ser Ser Asp Leu Pro Tyr Val
1               5                   10
```

<210> SEQ ID NO 669
<211> LENGTH: 12
<212> TYPE: PRT
<213> ORGANISM: Artificial Sequence
<220> FEATURE:
<223> OTHER INFORMATION: Synthetic

<400> SEQUENCE: 669

Gln Ser Tyr Asp Asp Arg Leu Ser Gly Ser Tyr Val
1               5                   10

<210> SEQ ID NO 670
<211> LENGTH: 11
<212> TYPE: PRT
<213> ORGANISM: Artificial Sequence
<220> FEATURE:
<223> OTHER INFORMATION: Synthetic

<400> SEQUENCE: 670

Gln Val Trp Asp Ser Ser Ser Asp Gln Gly Val
1               5                   10

<210> SEQ ID NO 671
<211> LENGTH: 11
<212> TYPE: PRT
<213> ORGANISM: Artificial Sequence
<220> FEATURE:
<223> OTHER INFORMATION: Synthetic

<400> SEQUENCE: 671

Gln Val Trp Asp Ser Ala Ile Asn His Val Val
1               5                   10

<210> SEQ ID NO 672
<211> LENGTH: 11
<212> TYPE: PRT
<213> ORGANISM: Artificial Sequence
<220> FEATURE:
<223> OTHER INFORMATION: Synthetic

<400> SEQUENCE: 672

Gln Val Trp Asp Ser Ser Ser Asp His Trp Val
1               5                   10

<210> SEQ ID NO 673
<211> LENGTH: 11
<212> TYPE: PRT
<213> ORGANISM: Artificial Sequence
<220> FEATURE:
<223> OTHER INFORMATION: Synthetic

<400> SEQUENCE: 673

Ala Ala Trp Asp Asp Ser Leu Asn Gly Pro Val
1               5                   10

<210> SEQ ID NO 674
<211> LENGTH: 11
<212> TYPE: PRT
<213> ORGANISM: Artificial Sequence
<220> FEATURE:
<223> OTHER INFORMATION: Synthetic

<400> SEQUENCE: 674

Gln Val Trp Asp Ser Ser Ser Asp His Tyr Val
1               5                   10

```
<210> SEQ ID NO 675
<211> LENGTH: 9
<212> TYPE: PRT
<213> ORGANISM: Artificial Sequence
<220> FEATURE:
<223> OTHER INFORMATION: Synthetic

<400> SEQUENCE: 675

Gln Ala Trp Asp Ser Ser Thr Val Val
1               5

<210> SEQ ID NO 676
<211> LENGTH: 9
<212> TYPE: PRT
<213> ORGANISM: Artificial Sequence
<220> FEATURE:
<223> OTHER INFORMATION: Synthetic

<400> SEQUENCE: 676

Gln Lys Tyr Asn Ser Ala Pro Gly Thr
1               5

<210> SEQ ID NO 677
<211> LENGTH: 117
<212> TYPE: PRT
<213> ORGANISM: Artificial Sequence
<220> FEATURE:
<223> OTHER INFORMATION: Synthetic

<400> SEQUENCE: 677

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Asn Glu Leu Ser Ser Leu Arg Ser Glu Asp Thr Ala Val Tyr Tyr Cys
                85                  90                  95

Ala Arg Ser Met Gly Ala Trp Trp Asp Pro Trp Gly Gln Gly Thr Leu
            100                 105                 110

Val Thr Val Ser Ser
        115

<210> SEQ ID NO 678
<211> LENGTH: 10
<212> TYPE: PRT
<213> ORGANISM: Artificial Sequence
<220> FEATURE:
<223> OTHER INFORMATION: Synthetic

<400> SEQUENCE: 678

Ala Leu Tyr Val Asp Ser Leu Phe Phe Leu
1               5                   10

<210> SEQ ID NO 679
<211> LENGTH: 10
<212> TYPE: PRT
<213> ORGANISM: Artificial Sequence
<220> FEATURE:
<223> OTHER INFORMATION: Synthetic
```

<400> SEQUENCE: 679

Ala Leu Ala Val Asp Ser Leu Phe Phe Leu
1               5                   10

<210> SEQ ID NO 680
<211> LENGTH: 10
<212> TYPE: PRT
<213> ORGANISM: Artificial Sequence
<220> FEATURE:
<223> OTHER INFORMATION: Synthetic

<400> SEQUENCE: 680

Ala Leu Tyr Ala Asp Ser Leu Phe Phe Leu
1               5                   10

<210> SEQ ID NO 681
<211> LENGTH: 10
<212> TYPE: PRT
<213> ORGANISM: Artificial Sequence
<220> FEATURE:
<223> OTHER INFORMATION: Synthetic

<400> SEQUENCE: 681

Ala Leu Tyr Val Ala Ser Leu Phe Phe Leu
1               5                   10

<210> SEQ ID NO 682
<211> LENGTH: 10
<212> TYPE: PRT
<213> ORGANISM: Artificial Sequence
<220> FEATURE:
<223> OTHER INFORMATION: Synthetic

<400> SEQUENCE: 682

Ala Leu Tyr Val Asp Ala Leu Phe Phe Leu
1               5                   10

<210> SEQ ID NO 683
<211> LENGTH: 10
<212> TYPE: PRT
<213> ORGANISM: Artificial Sequence
<220> FEATURE:
<223> OTHER INFORMATION: Synthetic

<400> SEQUENCE: 683

Ala Leu Tyr Val Asp Ser Ala Phe Phe Leu
1               5                   10

<210> SEQ ID NO 684
<211> LENGTH: 10
<212> TYPE: PRT
<213> ORGANISM: Artificial Sequence
<220> FEATURE:
<223> OTHER INFORMATION: Synthetic

<400> SEQUENCE: 684

Ala Leu Tyr Val Asp Ser Leu Ala Phe Leu
1               5                   10

<210> SEQ ID NO 685
<211> LENGTH: 10
<212> TYPE: PRT
<213> ORGANISM: Artificial Sequence
<220> FEATURE:
<223> OTHER INFORMATION: Synthetic

```
<400> SEQUENCE: 685

Ala Leu Tyr Val Asp Ser Leu Phe Ala Leu
1               5                   10

<210> SEQ ID NO 686
<211> LENGTH: 10
<212> TYPE: PRT
<213> ORGANISM: Artificial Sequence
<220> FEATURE:
<223> OTHER INFORMATION: Synthetic

<400> SEQUENCE: 686

Ala Leu Tyr Val Asp Ser Leu Phe Phe Leu
1               5                   10

<210> SEQ ID NO 687
<211> LENGTH: 10
<212> TYPE: PRT
<213> ORGANISM: Artificial Sequence
<220> FEATURE:
<223> OTHER INFORMATION: Synthetic

<400> SEQUENCE: 687

Ala Ala Tyr Val Asp Ser Leu Phe Phe Leu
1               5                   10

<210> SEQ ID NO 688
<211> LENGTH: 10
<212> TYPE: PRT
<213> ORGANISM: Artificial Sequence
<220> FEATURE:
<223> OTHER INFORMATION: Synthetic

<400> SEQUENCE: 688

Ala Leu Ala Val Asp Ser Leu Phe Phe Leu
1               5                   10

<210> SEQ ID NO 689
<211> LENGTH: 10
<212> TYPE: PRT
<213> ORGANISM: Artificial Sequence
<220> FEATURE:
<223> OTHER INFORMATION: Synthetic

<400> SEQUENCE: 689

Ala Leu Tyr Ala Asp Ser Leu Phe Phe Leu
1               5                   10

<210> SEQ ID NO 690
<211> LENGTH: 10
<212> TYPE: PRT
<213> ORGANISM: Artificial Sequence
<220> FEATURE:
<223> OTHER INFORMATION: Synthetic

<400> SEQUENCE: 690

Ala Leu Tyr Val Ala Ser Leu Phe Phe Leu
1               5                   10

<210> SEQ ID NO 691
<211> LENGTH: 10
<212> TYPE: PRT
<213> ORGANISM: Artificial Sequence
<220> FEATURE:
<223> OTHER INFORMATION: Synthetic

<400> SEQUENCE: 691
```

```
Ala Leu Tyr Val Asp Ala Leu Phe Phe Leu
1               5                   10

<210> SEQ ID NO 692
<211> LENGTH: 10
<212> TYPE: PRT
<213> ORGANISM: Artificial Sequence
<220> FEATURE:
<223> OTHER INFORMATION: Synthetic

<400> SEQUENCE: 692

Ala Leu Tyr Val Asp Ser Ala Phe Phe Leu
1               5                   10

<210> SEQ ID NO 693
<211> LENGTH: 10
<212> TYPE: PRT
<213> ORGANISM: Artificial Sequence
<220> FEATURE:
<223> OTHER INFORMATION: Synthetic

<400> SEQUENCE: 693

Ala Leu Tyr Val Asp Ser Leu Ala Phe Leu
1               5                   10

<210> SEQ ID NO 694
<211> LENGTH: 10
<212> TYPE: PRT
<213> ORGANISM: Artificial Sequence
<220> FEATURE:
<223> OTHER INFORMATION: Synthetic

<400> SEQUENCE: 694

Ala Leu Tyr Val Asp Ser Leu Phe Ala Leu
1               5                   10

<210> SEQ ID NO 695
<211> LENGTH: 10
<212> TYPE: PRT
<213> ORGANISM: Artificial Sequence
<220> FEATURE:
<223> OTHER INFORMATION: Synthetic

<400> SEQUENCE: 695

Ala Leu Tyr Val Asp Ser Leu Phe Phe Ala
1               5                   10

<210> SEQ ID NO 696
<211> LENGTH: 10
<212> TYPE: PRT
<213> ORGANISM: Artificial Sequence
<220> FEATURE:
<223> OTHER INFORMATION: Synthetic

<400> SEQUENCE: 696

Ala Leu Tyr Ala Ala Ala Ala Phe Phe Leu
1               5                   10
```